(12) United States Patent
Crews et al.

(10) Patent No.: US 11,028,088 B2
(45) Date of Patent: Jun. 8, 2021

(54) MODULATORS OF BTK PROTEOLYSIS AND METHODS OF USE

(71) Applicant: Yale University, New Haven, CT (US)

(72) Inventors: Craig M. Crews, New Haven, CT (US); Saul Jaime-Figueroa, Morris Plains, NJ (US); Momar Toure, Billerica, MA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/297,282

(22) Filed: Mar. 8, 2019

(65) Prior Publication Data
US 2019/0276459 A1   Sep. 12, 2019

Related U.S. Application Data

(60) Provisional application No. 62/641,276, filed on Mar. 10, 2018, provisional application No. 62/678,157, filed on May 30, 2018.

(51) Int. Cl.
| | | |
|---|---|---|
| *C07D 487/04* | (2006.01) | |
| *C07D 401/14* | (2006.01) | |
| *A61P 35/02* | (2006.01) | |
| *A61K 47/10* | (2017.01) | |
| *A61K 47/14* | (2017.01) | |
| *A61K 47/54* | (2017.01) | |

(52) U.S. Cl.
CPC ............ *C07D 487/04* (2013.01); *A61K 47/10* (2013.01); *A61K 47/14* (2013.01); *A61K 47/545* (2017.08); *A61P 35/02* (2018.01); *C07D 401/14* (2013.01)

(58) Field of Classification Search
CPC .. A61K 47/55; A61K 31/427; A61K 31/4439; A61K 31/4706; A61K 31/519; A61K 45/06; A61K 47/10; A61K 47/14; A61K 47/545; A61P 35/02; C07D 401/14; C07D 487/04
See application file for complete search history.

(56) References Cited

U.S. PATENT DOCUMENTS

| | | |
|---|---|---|
| 7,345,081 B2 | 3/2008 | Cohen et al. |
| 7,419,975 B2 | 9/2008 | Palermo et al. |
| 9,447,070 B2 | 9/2016 | Muller et al. |
| 2014/0302523 A1 | 10/2014 | Crews et al. |
| 2014/0356322 A1 | 12/2014 | Crews et al. |
| 2015/0291562 A1 | 10/2015 | Crew et al. |
| 2016/0058872 A1 | 3/2016 | Crew et al. |
| 2016/0272639 A1 | 9/2016 | Crew et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2018/0099940 A1 | 4/2018 | Crew et al. |

FOREIGN PATENT DOCUMENTS

| | | | |
|---|---|---|---|
| WO | 2007101347 A1 | 9/2007 | |
| WO | 2008014236 A1 | 1/2008 | |
| WO | 2008128171 A2 | 10/2008 | |
| WO | 2013071035 A1 | 5/2013 | |
| WO | 2013071039 A1 | 5/2013 | |
| WO | 2013152135 A1 | 10/2013 | |
| WO | 2014011712 A1 | 1/2014 | |
| WO | 2014025759 A1 | 2/2014 | |
| WO | 2014047024 A1 | 3/2014 | |
| WO | 2014055461 A1 | 4/2014 | |
| WO | 2014074658 A1 | 5/2014 | |
| WO | 2016149668 A1 | 9/2016 | |
| WO | WO 2017/117473 * | 7/2017 | ........... C07D 471/14 |
| WO | 2017197055 A1 | 11/2017 | |
| WO | 2017211924 A1 | 12/2017 | |
| WO | 2018033556 A1 | 2/2018 | |
| WO | 2018144649 A1 | 8/2018 | |

OTHER PUBLICATIONS

International Search Report and Written Opinion for PCT/US2019/021428 dated May 24, 2019.
Ardecky, et al., "Design, synthesis and evaluation of inhibitor of apoptosis protein (IAP) antagonists that are highly selective for the BIR2 domain of XIAP", Bioorg Med Chem Lett. 23(14), Jul. 2013, 4253-4257.
Asano, et al., "Design, stereoselective synthesis, and biological evaluation of novel tri-cyclic compounds as inhibitor of apoptosis proteins (IAP) antagonists", Bioorg Med Chem. Sep. 15, 2013;21(18), Sep. 2013, 5725-2737.
Cohen, et al., "Antagonists of inhibitor of apoptosis proteins based on thiazole amide isosteres", Bioorg Med Chem Lett. 20(7), Apr. 2010, 2229-2233.
Cohen, et al., "Orally bioavailable antagonists of inhibitor of apoptosis proteins based on an azabicyclooctane scaffold", J Med Chem. 52(6), Mar. 2009, 1723-1730.
Flygare, et al., "Small-molecule pan-IAP antagonists: a patent review", Expert Opin Ther Pat. 20(2), Feb. 2010, 251-267.
Hennessy, et al., "Discovery of aminopiperidine-based Smac mimetics as IAP antagonists", Bioorg Med Chem Lett. 22(4), Feb. 2012, 1690-1694.

(Continued)

*Primary Examiner* — Erich A Leeser
(74) *Attorney, Agent, or Firm* — Saul Ewing Arnstein & Lehr LLP; Kathryn Doyle; Domingos J. Silva

(57) ABSTRACT

The present disclosure relates to bifunctional compounds, which find utility as modulators of Burton's Tyrosine Kinase (BTK). In particular, the present disclosure is directed to bifunctional compounds. One end of a bifunctional compound includes a Von Hippel-Lindau, Cereblon, Inhibitors of Apoptosis Proteins, or Mouse Double-Minute Homolog 2 ligand that binds to the respective E3 ubiquitin ligase. The other end of a bifunctional compound includes a moiety that binds a target protein, such that the target protein is placed in proximity to the ubiquitin ligase to effect degradation (and inhibition) of target protein. Diseases or disorders that result from aggregation, accumulation, and/or overactivation of the target protein can be treated or prevented with compounds and compositions of the present disclosure.

35 Claims, 14 Drawing Sheets
Specification includes a Sequence Listing.

(56) References Cited

OTHER PUBLICATIONS

Hird, et al., "Structure-based design and synthesis of tricyclic IAP (Inhibitors of Apoptosis Proteins) inhibitors", Bioorg Med Chem Lett. 24(7), Apr. 2014, 1820-1824.

Kim, et al., "Discovery of tetrahydroisoquinoline-based bivalent heterodimeric IAP antagonists", Bioorg Med Chem Lett. 24(21), Nov. 2014, 5022-5029.

Mannhold, et al., "IAP antagonists: promising candidates for cancer therapy", Drug Discov Today. 15(5-6), Mar. 2010, 210-219.

Ndubaku, et al., "Antagonism of c-IAP and XIAP proteins is required for efficient induction of cell death by small-molecule IAP antagonists", ACS Chem Biol. 4(7), Jul. 2009, 557-566.

Perez, et al., "Discovery of potent heterodimeric antagonists of inhibitor of apoptosis proteins (IAPs) with sustained antitumor activity", J Med Chem. 58(3), Feb. 2015, 1556-1562.

Schneekloth, et al., "Targeted intracellular protein degradation induced by a small molecule: En route to chemical proteomics", Bioorg Med Chem Lett. 18(22), Nov. 2008, 5904-5908.

Vamos, et al., "Expedient synthesis of highly potent antagonists of inhibitor of apoptosis proteins (IAPs) with unique selectivity for ML-IAP", ACS Chem Biol. 8(4), Apr. 2013, 725-732.

Vassilev, et al., "In vivo activation of the p53 pathway by small-molecule antagonists of MDM2", Science 303, Feb. 6, 2004, 844-848.

Buhimschi, et al., "Targeting the C481S Ibrutinib-Resistance Mutation in Bruton's Tyrosine Kinase Using PROTAC-Mediated Degradation", Biochemistry 57(26), Jul. 2018, 3564-3575 (Abstract only).

* cited by examiner

FIG. 3A

| Level of Cpd. 102 Inhibition | Kinase | Cpd. 102 % Control | Ibrutinib % Control |
|---|---|---|---|
| Low (>80%) | ITK | 96 | 6.8 |
|  | JAK3 | 81 | 0 |
|  | MKK7 | 86 | 0.7 |
| High (<10%) | BTK | 0.25 | 0 |
|  | BLK | 0.35 | 0.1 |
|  | TEC | 3.6 | 1.9 |
|  | ERBB2 | 6.6 | 0 |
|  | ERBB3 | 0 | 0 |

FIG. 3B

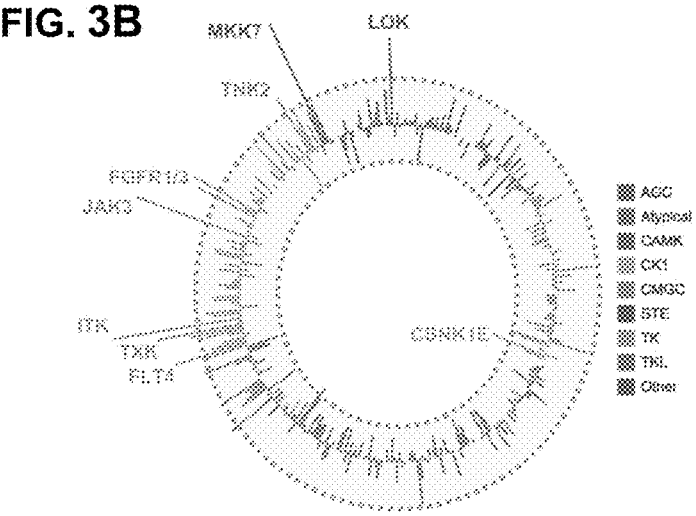

FIG. 3C

```
                    474     481              (BTK Numbering)
BTK     HEKLVQLYGVCTKQ--RPIFIITEYMANGCLLNYLREMRH-RFQTQQLLEMCKDVCEAME
BLK     HERLVRLYAVVTK---EPIYIVTEYMARGCLLDFLKTDEGSRLSLPRLIDMSAQIAEGMA
TEC     HPKLVQLYGVCTQQ--KPIYIVTEFMERGCLLNFLRQRQG-HFSRDVLLSMCQDVCEGME
ERBB2   SPYVSRLLGICLTS---TVQLVTQLMPYGCLLDHVRENRG-RLGSQDLLNWCMQIAKGMS
ERBB3   HAHIVRLLGLCPGS---SLQLVTQYLPLGSLLDHVRQHRG-ALGPQLLLNWGVQIAKGMY
ITK     HPKLVQLYGVCLEQ--APICLVFEFMEHGCLSDYLRTQRG-LFAAETLLGMCLDVCEGMA
JAK3    SDFIVKYRGVSYGPGRQSLRLVMEYLPSGCLRDFLQRHRA-RLDASRLLLYSSQICKGME
MKK7    CPYIVQCFGTFITN--TDVFIAMELMG-TCAEKLKKRMQG-PIPERILGKMTVAIVKALY
```

FIG. 3D

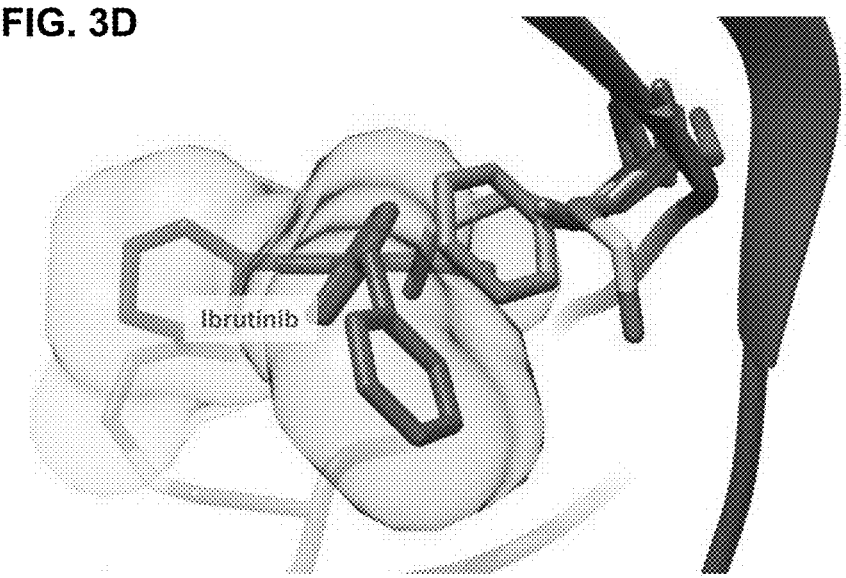

BTK: Thr
ITK: Phe
MKK7: Met
JAK3: Met

| Compound | IC$_{50}$ (WT BTK) | IC$_{50}$ (C481S BTK) |
|---|---|---|
| Ibrutinib | <50 pM | 1.86 nM |
| Compound 1 | 51.0 nM | 30.7 nM |
| Compound 102 | 46.9 nM | 20.9 nM |

Ibrutinib

Cpd 102

FIG. 11A
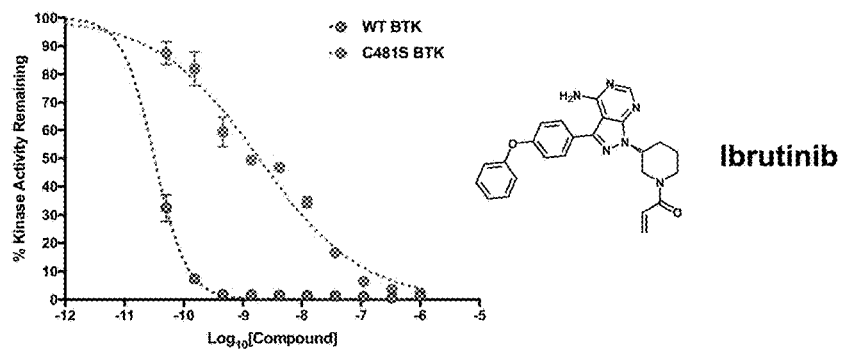
FIG. 11B
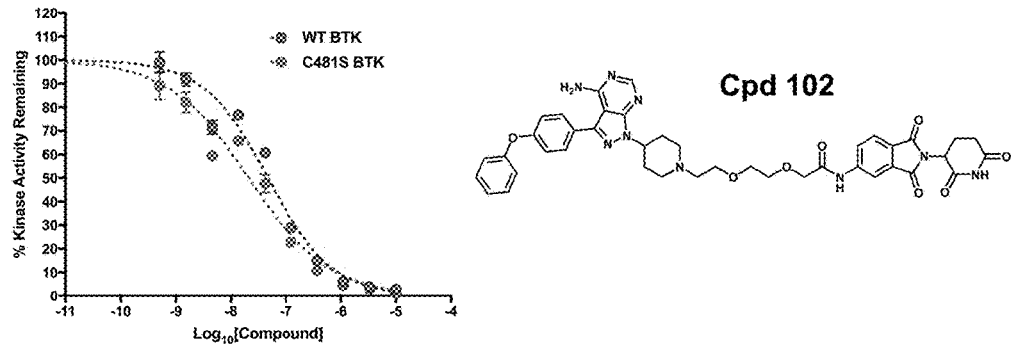
FIG. 11C
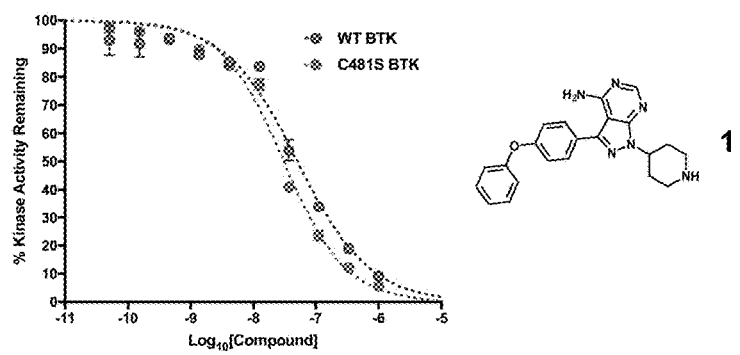
FIG. 11D
| Compound | IC$_{50}$ (WT BTK) | IC$_{50}$ (C481S BTK) |
|---|---|---|
| Ibrutinib | <50 pM | 1.86 nM |
| Cpd 102 | 46.88 nM | 20.89 nM |
| Compound 1 | 50.96 nM | 30.68 nM |

FIG. 12A
Ibrutinib
FIG. 12B
Cpd 102 Warhead
(Compound1)
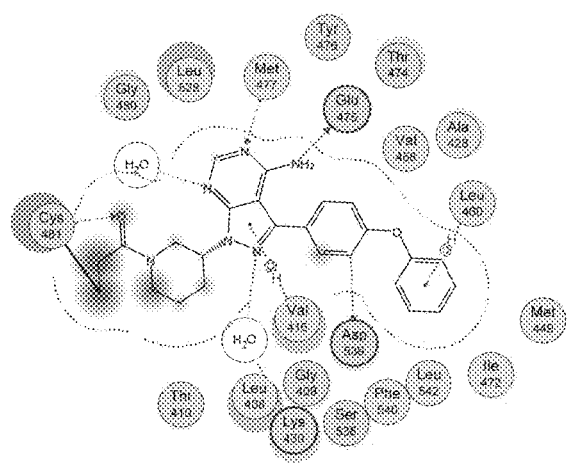
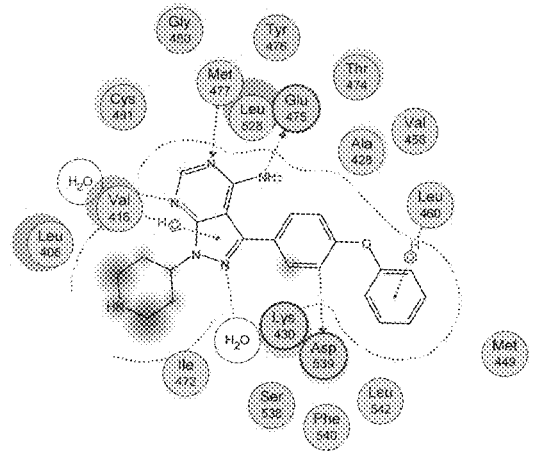
FIG. 12C
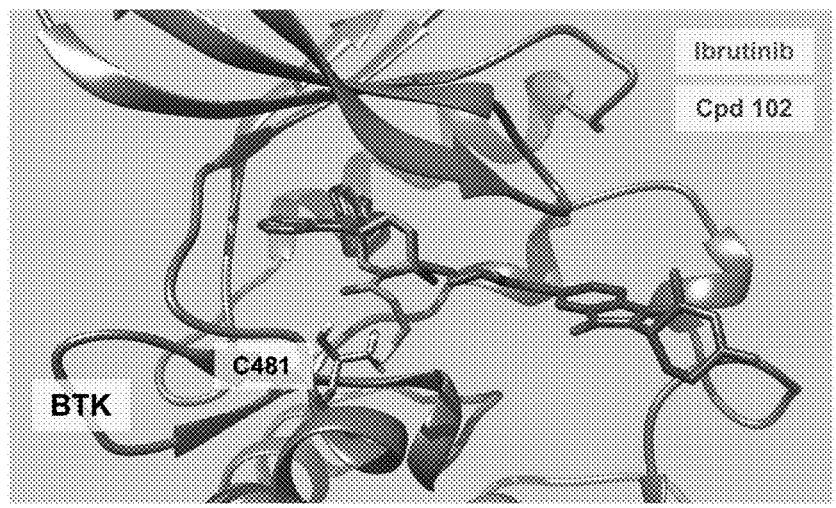

MODULATORS OF BTK PROTEOLYSIS AND METHODS OF USE

CROSS-REFERENCE TO RELATED APPLICATIONS

This application claims priority under 35 U.S.C. § 119(e) to U.S. Provisional Application Ser. No. 62/641,276, filed Mar. 10, 2018, and U.S. Provisional Application Ser. No. 62/678,157, filed May 30, 2018, all of which applications are hereby incorporated by reference in their entirety herein.

STATEMENT REGARDING FEDERALLY FUNDED RESEARCH

This invention was made with government support under grant number NIH CA197589, as issued by the National Institutes of Health. The government has certain rights in the invention.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds that target E3 ligases have been reported, but the field remains underdeveloped.

One E3 ligase with therapeutic potential is the von Hippel-Lindau (VHL) tumor suppressor, the substrate recognition subunit of the E3 ligase complex VCB, which also consists of elongins B and C, Cul2 and Rbxl. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. Small molecule ligands of Von Hippel Lindau (VHL) capable of binding to the substrate recognition subunit of the E3 ligase were synthesized, and their crystal structures confirmed that the compounds mimic the binding mode of the transcription factor HIF-1α, the major substrate of VHL.

Cereblon is a protein that is encoded by the CRBN gene in humans. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism that has not yet been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspase-9) that promote apoptosis. The binding of IAPs to caspases inhibits cell death. However, pro-apoptotic stimuli can result in the release of mitochondrial proteins DIABLO (also known as second mitochondria-derived activator of caspases or SMAC) and HTRA2 (also known as Omi). SMAC interacts with essentially all known IAPs including XIAP, c-IAP1, c-IAP2, NIL-IAP, Bruce, and survivin. The first four amino acids (AVPI) of mature SMAC bind to a portion of IAPs, which is believed to be essential for blocking the anti-apoptotic effects of IAPs.

Bifunctional or proteolysis targeting chimeric (PROTAC) compounds such as those described in U.S. Patent Application Publications Nos. 2015/0291562 and 2014/0356322, function to recruit endogenous proteins to an E3 ubiquitin ligase for degradation. These PROTACs can find utility as modulators of targeted ubiquitination of a variety of polypeptides and other proteins, which are then degraded and/or otherwise inhibited by the bifunctional compounds.

Targeted cancer therapy directed at inhibition of kinases has been successful for a multitude of diseases where mutated or fusion transcript proteins are present. Recently, kinases relevant to pathway dependency in select cancers have been exploited. Specifically, B-cell receptor (BCR) signaling has been shown to be constitutively active in compartments of chronic lymphocytic leukemia (CLL) proliferation (bone marrow, spleen, and lymph node) among all CLL patients and enhanced further among patients with aggressive disease bearing ZAP-70 overexpression. A variety of kinases involved in both proximal BCR signaling, including spleen tyrosine kinase, phosphatidylinositide 3-kinase-5 (PI3K-δ), and Bruton's Tyrosine Kinase (BTK) are potentially targetable with small molecule inhibitors.

BTK has emerged as an important drug target in CLL. BTK is a Tec family kinase of hematopoietic origin found in B-cells throughout their development, with the exception of plasma B-cells. Although it is expressed in a variety of hematopoietic cells, in many cases there is functional redundancy with other family members. In the B-cell, little redundancy with BTK exists and its function is to propagate proximal B-cell receptor (BCR) signaling. Upon BCR stimulation by antigen, syk is first activated to induce BTK phosphorylation. BTK then drives multiple pro-survival and proliferative pathways, including the activation of PLCγ-2 phosphorylation, which furthers the Ras/Raf/MEK/ERK kinase pathway and culminates in release of intracellular calcium stores. In turn, factors such as NFκB localize to the nucleus and induce transcription of growth factors and anti-apoptotic proteins that enhance CLL proliferation and survival.

The predominant approach for targeting BTK has been via small-molecule mediated inhibition. To date, the most successful clinical implementation of a direct BTK inhibitor has been observed with ibrutinib, which irreversibly binds cysteine 481 in the kinase domain of BTK. Inhibition of BTK in this manner is prolonged and has resulted in both dramatic and durable responses across virtually all patients treated with ibrutinib. However, a subset of patients receiving prolonged ibrutinib therapy experience disease relapse, which has been attributed to mutations in BTK that only allow reversible inhibition of the kinase when the drug is actively present at inhibitory levels in the cell. Specifically, the most commonly observed resistance mutation is substitution of cysteine 481 for serine, abolishing ibrutinib's ability to covalently modify BTK. As ibrutinib has a relatively short terminal half-life, function of BTK within the tumor cell is generally partially restored, facilitating tumor growth and eventual clinical relapse. Encouragingly, C481S mutant tumors are still responsive to BTK-targeted therapy, indicating that an agent with retained efficacy in this mutational setting could control disease and continue to exploit the aforementioned benefits of BTK susceptibility in CLL. Evidence of these C481S mutant tumors continued dependence on BTK is best exemplified by 1) tumor developing this direct mutation that partially impairs ibrutinib's mechanism of action and 2) the ability of ibrutinib to still partially control disease when administered even in the presence of C481S mutant CLL; and 3) that withdrawal of ibrutinib in this setting results in even more rapid tumor proliferation and clinical demise of the patient that can be reversed, if only temporarily, with re-initiation of ibrutinib.

The outcomes of CLL patients developing the C481S mutation CLL are poor. This emphasizes the need for developing new therapeutic approaches for these patients.

There is a need in the art for effective treatments for disease associated with activation of BTKs, including both wild-type and C481S mutant forms of Bruton's Tyrosine Kinase (BTK). However, relapse due to resistance from prolonged therapy, and the inability to target and modulate mutant BTKs, remain obstacles to the development of effective treatments. As such, small-molecule therapeutic agents that target BTKs and that leverage or potentiate VHL's, cereblon's, MDM2's, and IAPs' substrate specificity would be very useful as therapeutic agents.

SUMMARY OF THE INVENTION

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. In various embodiments, a non-limiting advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., pancreatic cancer, colon cancer, colorectal cancer, lung cancer, non-small cell lung cancer, biliary tract malignancies, endometrial cancer, cervical cancer, bladder cancer, liver cancer, myeloid leukemia, and breast cancer.

As such, in one embodiment the disclosure provides bifunctional or PROTAC compounds, which comprise an E3 ubiquitin ligase binding moiety (i.e., a ligand for an E3 ubiquitin ligase or "ULM" group), and a moiety that binds a target protein (i.e., a protein/polypeptide targeting ligand or "PTM" group) such that the target protein/polypeptide (e.g., Bruton's tyrosine kinase (BTK)) is placed in proximity to the ubiquitin ligase to effect degradation (and inhibition) of that protein. In a certain embodiment, the ULM (ubiquitination ligase modulator) can be Von Hippel-Lindau E3 ubiquitin ligase (VEIL) binding moiety (VLM), or a cereblon E3 ubiquitin ligase binding moiety (CLM), or a mouse double miniute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

PTM-ULM

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

PTM-L-ULM where PTM is a protein/polypeptide targeting moiety, L is a linker, e.g., a bond or a chemical group coupling PTM to ULM, and ULM is a IAP E3 ubiquitin ligase binding moiety (ILM), or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

PTM-L-(VLM or CLM or MLM or ILM)

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety that binds to MDM2; and ILM is an IAP binding moiety that binds to IAP.

In certain embodiments, the ILM is an AVPI tetrapeptide fragment. As such, in certain additional embodiments, the ILM of the bifunctional compound includes the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(=O)NH— or —NHC(=O)—).

In certain embodiments, the compounds as described herein comprise multiple independently selected ULMs, multiple PTMs, multiple chemical linkers or a combination thereof.

In certain embodiments, ILM includes chemical moieties such as those described herein.

In additional embodiments, VLM can be hydroxyproline or a derivative thereof. Furthermore, other contemplated VLMs are described in U.S. Patent Application Publication No. US2014/03022523.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. US2015/0291562, which is incorporated herein by reference in its entirety.

In certain embodiments, MLM can be nutlin or a derivative thereof. Furthermore, other contemplated MLMs are included in U.S. Patent Application Publication No. US2017/0008904, which as discussed above, is incorporated herein in its entirety. In certain additional embodiments, the MLM of the bifunctional compound includes chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM includes the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The linker "L" can include, but is not limited to, functional groups such as ether, amide, alkane, alkene, alkyne, ketone, hydroxyl, carboxylic acid, thioether, sulfoxide, and sulfone, and combinations thereof. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides. In certain embodiments, CLM is a derivative of piperidine-2,6-dione, where piperidine-2,6-dione can be substituted at the 3-position, and the 3-substitution can be bicyclic heteroaromatics with the linkage as C—N bond or C—C bond. Examples of CLM can be, but not limited to, pomalidomide, lenalidomide and thalidomide and their derivatives.

In an additional embodiment, the description provides therapeutic compositions comprising an effective amount of any compound described herein or salt form thereof, and a pharmaceutically acceptable carrier. The therapeutic compositions modulate protein degradation and/or inhibition in a patient or subject, for example, an animal such as a human, and can be used for treating or ameliorating disease states or conditions that are modulated through the degraded/inhibited protein. In certain embodiments, the therapeutic compositions as described herein can be used to effectuate the degradation of proteins of interest for the treatment or amelioration of a disease, e.g., cancer (such as pancreatic cancer, colon cancer, colorectal cancer, lung cancer, or non-small cell lung cancer). In yet another embodiment, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another embodiment, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject. In another embodiment, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various embodiments and embodiments of the disclosure may be utilized in numerous combinations, all of which are expressly contemplated by the present description. These additional embodiments and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure.

FIG. 3A illustrates the results of a KINOMEscan™ for selected kinases when screened at 1 µM Compound 102 and ibrutinib. Kinases were classified according to the level of inhibition by Compound 102 ("High" inhibition is a % of control <10% and "Low" inhibition is a % of control >80%).

FIG. 3B shows the Bland-Altman difference analysis expressed as a radial bar chart with kinases ordered according to their group. Bars pointing outwards represent kinases inhibited more strongly by ibrutinib than Compound 102. Those pointing inwards represent kinases inhibited more strongly by Compound 102 than ibrutinib. The shaded gray area represents the interval formed by the 95% limits of agreement (−36.9 to 28.1% of control).

FIG. 3C illustrates a kinase alignment by sequence identity using the CLUSTALW algorithm, and the kinases are grouped according to their level of inhibition by Compound 102 (Upper="high inhibition" and lower="low inhibition"). Amino acids homologous to positions 481 and 474 in BTK are highlighted in light color and underlined for all kinases. Sequence listings are SEQ ID NOs: 1-8 from top to bottom.

FIG. 3D depicts crystal structures for BTK in complex with ibrutinib (PDB code: 5P9J), ITK (PDB code: 3QGW), MKK7 (PDB code: 3WZU), and JAK3 (PDB code: 3PJC) were aligned. The space-filling cloud of ibrutinib (marked as "Ibrutinib") is shown to sterically clash with the gatekeeper residues in ITK, MKK7, and JAK3.

FIG. 11A illustrates a duplicate 10-point dose response curve of ibrutinib with recombinant wild-type and C481S BTK in the presence of 10 µM ATP.

FIG. 11B illustrates a duplicate 10-point dose response curve of Compound 102 with recombinant wild-type and C481S BTK in the presence of 10 µM ATP.

FIG. 11C illustrates a duplicate 10-point dose response curve of SJF-4676 with recombinant wild-type and C481S BTK in the presence of 10 µM ATP.

FIG. 11D is a table of calculated IC50 values obtained from the dose response curves in FIGS. 11A-11C.

FIG. 12A illustrates the interactions between BTK and ibrutinib in the kinase binding pocket.

FIG. 12B illustrates the interactions between BTK and SJF-4676, the warhead used for BTK PROTACs, according to various embodiments.

FIG. 12C illustrates that docking Compound 102 into the kinase pocket of BTK shows a key interaction between the backbone amide of C481 and ibrutinib is absent with PROTAC. This may explain some of the enhanced BTK inhibition observed with ibrutinib compared to the reversible warhead, SJF-4676.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

U.S. patent application Ser. No. 15/230,354, U.S. patent application Ser. No. 15/206,497, U.S. patent application Ser. No. 15/209,648, U.S. patent application Ser. No. 15/730,728, U.S. patent application Ser. No. 14/686,640, U.S. Patent Application Publication No. 2015/0291562, U.S. patent application Ser. No. 14/792,414, U.S. Patent Application Publication No. 2016/0058872, U.S. patent application Ser. No. 14/371,956, and U.S. patent application Ser. No. 15/074,820, and U.S. Provisional Patent Application Ser. No. 62/452,972, and International Patent Application No. PCT/US2016/023258, are incorporated herein by reference in their entireties.

Figure 1A:
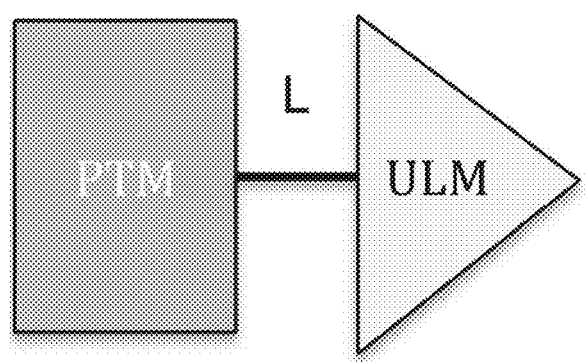
FIG. 1A is a schematic illustration of a PROTAC that includes a protein targeting moiety (PTM; darkly shaded rectangle), a ubiquitin ligase binding moiety (ULM; lightly shaded triangle), and optionally a linker moiety (L; black line) coupling or tethering the PTM to the ULM.
Figure 1B:
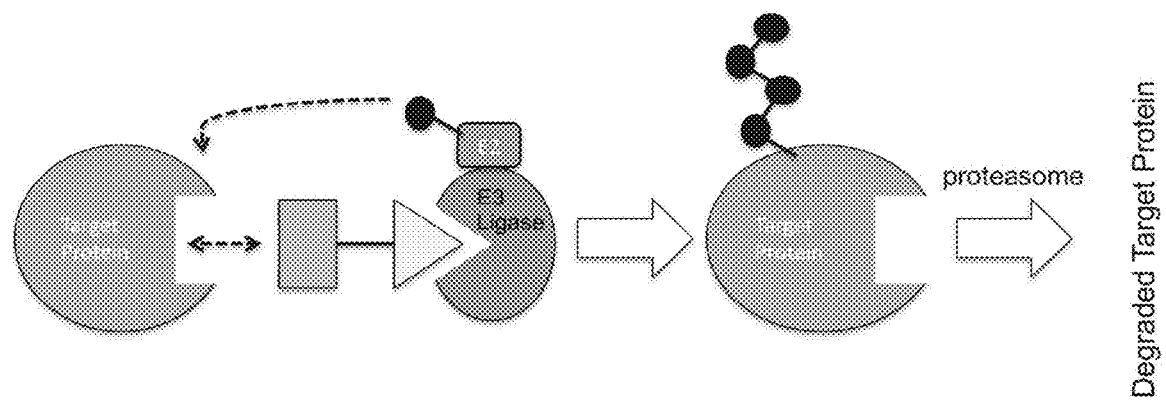
FIG. 1B illustrates a functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome (see FIGS. 1A-1B). The present disclosure also provides a library of compositions and the use thereof.

In certain embodiments, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VEIL, MDM2, or cereblon. The compounds also comprise a moiety that is capable of binding to a target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

Definitions

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred embodiments, one or more of the present compounds described herein, are coadministered in combination with at least one additional bioactive agent, especially including an anticancer agent, such as a chemotherapy or biological therapy that targets epidermal growth factor receptors (e.g., epidermal growth factor receptor inhibitors, such as at least one of gefitinib, erlotinib, neratinib, lapatinib, cetuximab, vandetanib, necitumamab, osimertinib, or a combination thereof). In particularly preferred embodiments, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (At, Br, Cl, F, or I). In certain non-limiting embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "alkenyl" refers to linear, branch-chained or cyclic $C_2$-$C_{10}$ (preferably $C_2$-$C_6$) hydrocarbon radicals containing at least one C=C bond.

The term "alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halogen groups, preferably from 1 to 3 halogen groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" means substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" means independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_{66}$ dialkyl amine which alkyl groups may be substituted with one or two hydroxyl groups) or an optionally substituted —N($C_0$-$C_6$ alkyl)C(=O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a O—$C_6$ alkyl group, preferably $R_1$, $R_2$, $R_3$ in this context is a $C_1$-$C_6$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain.

Non-limiting substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halogen groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents.

The term "substituted" (each substituent being independent of any other substituent also means within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(=O)—$NR_1R_2$ or —N($R_1$)—C(=O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, non-limiting substituents will include for example, —NH—, —NHC(=O)—, —O—, =O, —(CH$_2$)$_m$— (here, m and n are in context, 1, 2, 3, 4, 5 or 6), —S—, —S(=O)—, SO$_2$— or —NH—C(=O)—NH—, —(CH$_2$)$_n$OH, —(CH$_2$)$_n$SH, —(CH$_2$)$_n$COOH, C$_1$-C$_6$ alkyl, —(CH$_2$)$_n$O—(C$_1$-C$_6$ alkyl), —(CH$_2$)$_n$C(=O)—(C$_1$-C$_6$ alkyl), —(CH$_2$)$_n$OC(=O)—(C$_1$-C$_6$ alkyl), —(CH$_2$)$_n$C(=O)O—(C$_1$-C$_6$ alkyl), —(CH$_2$)$_n$NHC(=O)—R$_1$, —(CH$_2$)$_n$C(=O)—NR$_1$R$_2$, —(OCH$_2$)$_n$OH, —(CH$_2$O)$_n$COOH, C$_1$-C$_6$ alkyl, —(OCH$_2$)$_n$O—(C$_1$-C$_6$ alkyl), —(CH$_2$O)$_n$C(=O)—(C$_1$-C$_6$ alkyl), —(OCH$_2$)$_n$NHC(=O)—R$_1$, —(CH$_2$O)$_n$C(=O)—NR$_1$R$_2$, —S(=O)$_2$—R$_S$, —S(=O)—R$_S$ (R$_S$ is C$_1$-C$_6$ alkyl or a —(CH$_2$)$_m$—NR$_1$R$_2$ group), NO$_2$, CN or halogen (F, Cl, Br, I, preferably F or Cl), depending on the context of the use of the substituent. R$_1$ and R$_2$ are each, within context, H or a C$_1$-C$_6$ alkyl group (which may be optionally substituted with one or two hydroxyl groups or up to three halogen groups, preferably fluorine).

The term "substituted" also means, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted C$_1$-C$_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(=O)—NR$_1$R$_2$ group where R$_1$ and R$_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—(C$_1$-C$_6$)alkyl, —(CH$_2$)$_n$—O—(CH$_2$)$_n$—(C$_1$-C$_6$)alkyl, —(CH$_2$)$_n$—C(=O)(C$_0$-C$_6$) alkyl, —(CH$_2$)$_n$—C(O)O(C$_0$-C$_6$)alkyl, —(CH$_2$)$_n$—OC(=O)(C$_0$-C$_6$)alkyl, amine, mono- or di-(C$_1$-C$_6$ alkyl) amine wherein the alkyl group on the amine is optionally substituted with 1 or 2 hydroxyl groups or up to three halogen (preferably F, Cl) groups, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably connected/attached to a PTM group, including a ULM group, via a linker group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

The term "carboxyl" denotes the group —C(=O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" means, but is not limited to, an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(=O)—O—C$_1$-C$_6$ alkyl group), an optionally substituted pyridine (2-, 3-, or 4-pyridine) or a group according to the chemical structure:

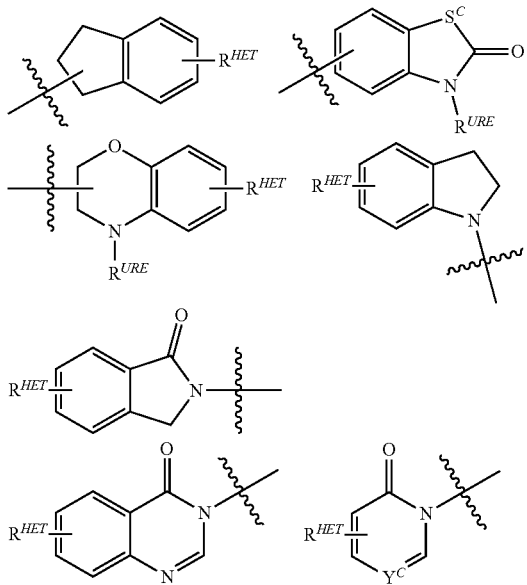

wherein:

S$^c$ is CHR$^{SS}$, NR$^{URE}$, or O;

R$^{HET}$ is H, CN, NO$_2$, halogen (preferably Cl or F), optionally substituted C$_1$-C$_6$ alkyl (preferably substituted with one or two hydroxyl groups or up to three halogen groups (e.g. CF$_3$), optionally substituted O(C$_1$-C$_6$ alkyl) (preferably substituted with one or two hydroxyl groups or up to three halogen groups) or an optionally substituted acetylenic group —C≡C—R$_a$ where R$_a$ is H or a C$_1$-C$_6$ alkyl group (preferably C$_1$-C$_3$ alkyl);

R$^{SS}$ is H, CN, NO$_2$, halogen (preferably F or Cl), optionally substituted C$_1$-C$_6$ alkyl (preferably substituted with one or two hydroxyl groups or up to three halogen groups), optionally substituted O—(C$_1$-C$_6$ alkyl) (preferably substituted with one or two hydroxyl groups or up to three halogen groups) or an optionally substituted —C(=O)(C$_1$-C$_6$ alkyl) (preferably substituted with one or two hydroxyl groups or up to three halogen groups);

R$^{URE}$ is H, a C$_1$-C$_6$ alkyl (preferably H or C$_1$-C$_3$ alkyl) or a —C(=O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and Y$^c$ is N or C—R$^{YC}$, where R$^{YC}$ is H, OH, CN, NO$_2$, halogen (preferably Cl or F), optionally substituted C$_1$-C$_6$ alkyl (preferably substituted with one or two hydroxyl groups or up to three halogen groups (e.g. CF$_3$), optionally substituted O(C$_1$-C$_6$ alkyl) (preferably substituted with one or two hydroxyl groups or up to three halogen groups) or an optionally substituted acetylenic group —C≡C—R$_a$ where R$_a$ is H or a C$_1$-C$_6$ alkyl group (preferably C$_1$-C$_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove. Non-limiting examples of heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO—heteroaryl, —SO$_2$-alkyl, —SO$_2$-substituted alkyl, —SO$_2$-aryl, oxo (=O), and —SO$_2$-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defnied herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

The term "heterocycloalkyl" refers to a monocyclic or polycyclic alkyl group in which at least one ring carbon atom of its cyclic structure being replaced with a heteroatom selected from the group consisting of N, O, S or P.

The term "substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" means a compound that contains carbon and hydrogen and which may be fully saturated, partially unsaturated or aromatic and includes aryl groups, alkyl groups, alkenyl groups and alkynyl groups.

The term "lower alkyl" means methyl, ethyl, propyl, or iso-propyl.

The term "lower alkoxy" means methoxy, ethoxy, propoxy, or isopropoxy.

The term "unnatural mimetic" refers to a synthetic moiety that can, for example, mimic the shape, conformational space, charge, and/or hydrogen bonding interactions of a particular naturally occurring amino acid. Non-limiting examples of unnatural mimetics include, α-guanidino acids as arginine mimetics, and β-amino acid analogs of natural α-amino acids.

Compounds and Compositions

In one embodiment, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindau E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

PTM-L-ULM     (A)

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another embodiment, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. In various embodiments, a bifunctional compound can be depicted as:

PTM-ILM     (B)

PTM-CLM     (C)

PTM-VLM     (D)

PTM-MLM     (E)

In certain embodiments, the bifunctional compound further includes a chemical linker ("L"). For example, the bifunctional compound can be depicted as:

PTM-L-ILM     (F)

PTM-L-CLM     (G)

PTM-L-VLM     (H)

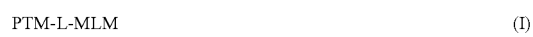

PTM-L-MLM     (I)

wherein the PTM is a protein/polypeptide targeting moiety, the Lisa chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 μM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the embodiments or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquitin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound includes multiple ULMs, the ULMs are identical. In additional embodiments, the compound including a plurality of ULMs (e.g., ULM, ULM', etc.), at least one PTM coupled to a ULM directly or via a chemical linker (L) or both. In certain additional embodiments, the compound including a plurality of ULMs further includes multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

IAP E3 Ubiquitin Ligase Binding Moieties

AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

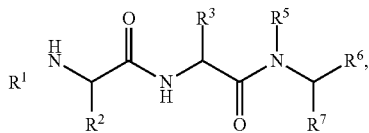

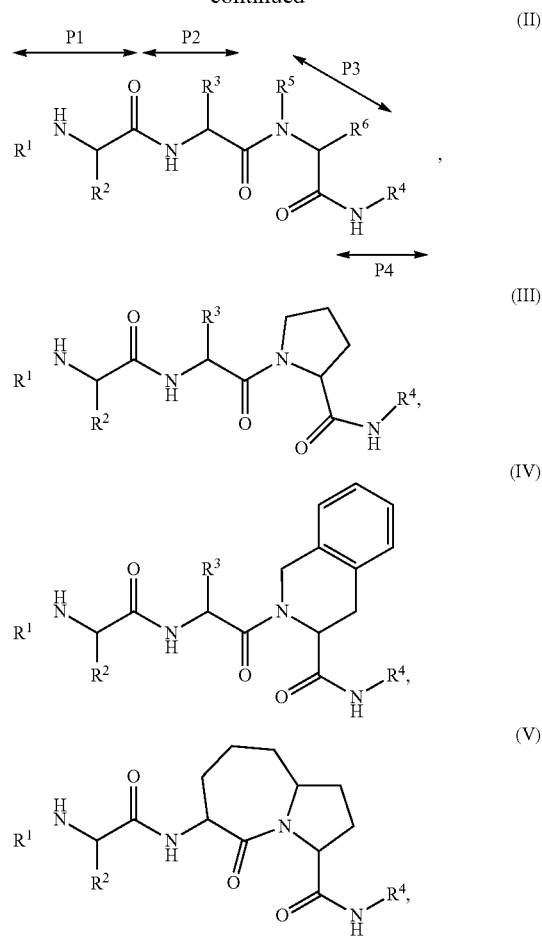

wherein:
each occurrence of $R^1$ in compounds of Formulas (I), (II), (III), (IV), and (V) is independently selected from the group consisting of H and alkyl;
each occurrence of $R^2$ in compounds of Formulas (I), (II), (III), (IV), and (V) is independently selected from the group consisting of H and alkyl;
each occurrence of $R^3$ in compounds of Formulas (I), (II), (III), (IV), and (V) is independently selected from the group consisting of H, alkyl, cycloalkyl and heterocycloalkyl;
each occurrence of $R^5$ and $R^6$ in compounds of Formulas (I), (II), (III), (IV), and (V) are independently selected from the group consisting of H, alkyl, cycloalkyl, and heterocycloalkyl; or
$R^5$ and $R^6$ taken together independently in compounds of Formulas (I), (II), (III), (IV), and (V) form a pyrrolidine or a piperidine ring further optionally fused to 1-2 cycloalkyl, heterocycloalkyl, aryl, or heteroaryl rings, each of which is optionally fused to an additional cycloalkyl, heterocycloalkyl, aryl, or heteroaryl ring;
each occurrence of $R^3$ and $R^5$ in compounds of Formulas (I), (II), (III), (IV), and (V) are independently taken together can form a 5-8-membered ring and further optionally fused to 1-2 cycloalkyl, heterocycloalkyl, aryl, or heteroaryl rings;
each occurrence of $R^7$ in compounds of Formulas (I), (II), (III), (IV), and (V) is independently selected from the group consisting of cycloalkyl, cycloalkylalkyl, heterocycloalkyl, aryl, arylalkyl, heteroaryl or heteroarylalkyl, each of which can be optionally substituted; and
R⁴ is selected from alkyl, cycloalkyl, heterocycloalkyl, cycloalkylalkyl, heterocycloalkylalkyl, aryl, arylalkyl, heteroaryl, heteroarylalkyl, further optionally substituted.

In various embodiments, P1, P2, P3, and P4 in the compound of Formula (II) correspond to the A, V, P, and I residues, respectively, of the AVPI tetrapeptide fragment or an unnatural mimetic thereof. Similarly, each compound of Formulas (I) and (III) through (V) have portions corresponding to the A, V, P, and I residues of the AVPI tetrapeptide fragment or an unnatural mimetic thereof.

In various embodiments, the ILM moiety can have the structure of Formula (VI), as described in WO Pub. No. 2008/014236, or an unnatural mimetic thereof:

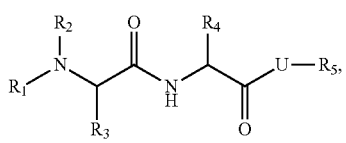

(VI)

wherein:
each occurrence of $R_1$ in the compound of Formula (VI) is independently selected from the group consisting of H, $C_1$-$C_4$-alkyl, $C_1$-$C_4$-alkenyl, $C_1$-$C_4$-alkynyl, and $C_3$-$C_{10}$-cycloalkyl,
each of which can be optionally substituted with 1-3 substituents selected from the group consisting of halogen, alkyl, haloalkyl, hydroxyl, alkoxy, cyano, heterocycloalkyl, and heteroaryl;
each occurrence of $R_2$ in the compound of Formula (VI) is independently selected from the group consisting of H, $C_1$-$C_4$-alkyl, $C_1$-$C_4$-alkenyl, $C_1$-$C_4$-alkynyl, and $C_3$-$C_{10}$-cycloalkyl,
each of which can be optionally substituted with 1-3 substituents selected from the group consisting of halogen, alkyl, haloalkyl, hydroxyl, alkoxy, cyano, heterocycloalkyl, and heteroaryl;
each occurrence of $R_3$ in the compound of Formula (VI) is independently selected from the group consisting of H, —$CF_3$, —$C_2H_5$, $C_1$-$C_4$-alkyl, $C_1$-$C_4$-alkenyl, $C_1$-$C_4$-alkynyl, —$CH_2$—Z, and any $R_2$ and $R_3$ together form a heterocyclic ring, each of which can be optionally substituted with 1-3 substituents selected from the group consisting of halogen, alkyl, haloalkyl, hydroxyl, alkoxy, cyano, heterocycloalkyl, and heteroaryl;
each occurrence of Z in the compound of Formula (VI) is independently selected from the group consisting of H, —OH, F, Cl, —$CH_3$, —$CF_3$, —$CH_2Cl$, —$CH_2F$, and —$CH_2OH$;
each occurrence of $R_4$ in the compound of Formula (VI) is independently selected from the group consisting of $C_1$-$C_{16}$ straight or branched alkyl, $C_1$-$C_{16}$-alkenyl, $C_1$-$C_{16}$-alkynyl, $C_3$-$C_{10}$-cycloalkyl, —$(CH_2)_{0-6}$—$Z_1$, —$(CH_2)_{0-6}$-aryl, and —$(CH_2)_{0-6}$-het, each of which can be optionally substituted with 1-3 substituents selected from the group consisting of halogen, alkyl, haloalkyl, hydroxyl, alkoxy, cyano, heterocycloalkyl, and heteroaryl;
each occurrence of $R_5$ in the compound of Formula (VI) is independently selected from the group consisting of H, $C_{1-10}$-alkyl, aryl, phenyl, $C_{3-7}$-cycloalkyl, —$(CH_2)_{1-6}$—$C_{3-7}$-cycloalkyl, —$C_{1-10}$-alkyl-aryl, —$(CH_2)_{1-6}$—$C_{3-7}$-cycloalkyl-$(CH_2)_{0-6}$-phenyl, —$(CH_2)_{0-4}$—CH[$(CH_2)_{1-4}$-phenyl]$_2$, indanyl, —C(=O)—$C_{1-10}$-alkyl, —C(=O)—$(CH_2)_{1-6}$—$C_{3-7}$-cycloalkyl, —C(=O)—$(CH_2)_{0-6}$-phenyl, —$(CH_2)_{0-6}$—C(=O)-phenyl, —$(CH_2)_{0-6}$-het, —C(=O)—$(CH_2)_{1-6}$-het, and a residue of an amino acid, each of which can be optionally substituted with 1-3 substituents selected from the group consisting of halogen, alkyl, haloalkyl, hydroxyl, alkoxy, cyano, heterocycloalkyl, and heteroaryl;
each occurrence of $Z_1$ in the compound of Formula (VI) is independently selected from the group consisting of —N($R_{10}$)—C(=O)—$C_{1-10}$-alkyl, —N($R_{10}$)—C(=O)—$(CH_2)_{0-6}$—$C_{3-7}$-cycloalkyl, —N($R_{10}$)—C(=O)—$(CH_2)_{0-6}$-phenyl, —N($R_{10}$)—C(=O)($CH_2)_{1-6}$-het, —C(=O)—N($R_{11}$)($R_{12}$), —C(=O)—O—$C_{1-10}$-alkyl, —C(=O)—O—$(CH_2)_{1-6}$—$C_{3-7}$-cycloalkyl, —C(=O)—O—$(CH_2)_{0-6}$-phenyl, —C(=O)—O—$(CH_2)_{1-6}$-het, —O—C(=O)—$C_{1-10}$-alkyl, —O—C(=O)—$(CH_2)_{1-6}$—$C_{3-7}$-cycloalkyl, —O—C(=O)—$(CH_2)_{0-6}$-phenyl, and —O—C(=O)—$(CH_2)_{1-6}$-het, each of which can be optionally substituted with 1-3 substituents selected from the group consisting of halogen, alkyl, haloalkyl, hydroxyl, alkoxy, cyano, heterocycloalkyl, and heteroaryl;
each occurrence of het in the compound of Formula (VI) is independently selected from the group consisting of a 5-7 member heterocyclic ring containing 1-4 N, O, or S heteroatoms, and an 8-12 member fused ring system including at least one 5-7 member heterocyclic ring containing 1-3 N, O, or S heteroatoms, which heterocyclic ring or fused ring system is optionally substituted with 1-3 substituents selected from the group consisting of halogen, alkyl, haloalkyl, hydroxyl, alkoxy, cyano, heterocycloalkyl, and heteroaryl on a carbon or nitrogen atom in the heterocyclic ring or fused ring system;
each occurrence of $R_{10}$ in the compound of Formula (VI) is selected from the group consisting of H, —$CH_3$, —$CF_3$, —$CH_2OH$, and —$CH_2C_1$;
each occurrence of $R_{11}$ and $R_{12}$ in the compound of Formula (VI) is independently selected from the group consisting of H, $C_{1-4}$-alkyl, $C_{3-7}$-cycloalkyl, —$(CH_2)_{1-6}$—$C_{3-7}$-cycloakyl, $(CH_2)_{0-6}$-phenyl, each of which can be optionally substituted with 1-3 substituents selected from the group consisting of halogen, alkyl, haloalkyl, hydroxyl, alkoxy, cyano, heterocycloalkyl, and heteroaryl; or $R_{11}$ and $R_{12}$ together with the nitrogen form het, and each occurrence of U in the compound of Formula (VI) is independently of Formula (VII):

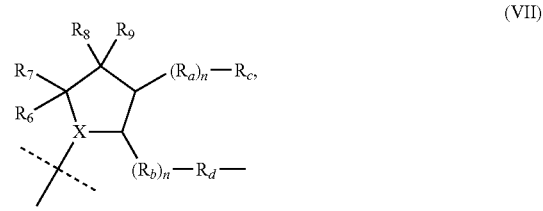

(VII)

wherein:
each occurrence of n in the compound of Formula (VII) is independently selected from a whole number from 0 to 5;

each occurrence of X in the compound of Formula (VII) is independently selected from the group consisting of —CH and N;

each occurrence of $R_a$ and Rb in the compound of Formula (VII) is independently selected from the group consisting of an O atom, a S atom, an N atom, and $C_{0-8}$-alkyl, wherein one or more of the carbon atoms in the $C_{0-8}$-alkyl is optionally replaced by a heteroatom selected from the group consisting of O, S, and N, and wherein each occurrence of $C_{0-8}$-alkyl is independently optionally substituted with 1-3 substituents selected from the group consisting of halogen, alkyl, haloalkyl, hydroxyl, alkoxy, cyano, heterocycloalkyl, and heteroaryl;

each occurrence of Rd in the compound of Formula (VII) is independently selected from the group consisting of $R_e$-Q-$(R_f)_p(R_g)_q$, and $Ar_1$-D-$Ar_2$;

each occurrence of $R_c$ in the compound of Formula (VII) is independently selected from the group consisting of H and any $R_c$ and $R_d$ taken together form a cycloalkyl or het; with the proviso that if $R_c$ and $R_d$ form a cycloalkyl or het, $R_5$ is attached to the formed ring at a C or N atom;

each occurrence of p and q in the compound of Formula (VII) is independently 0 or 1;

each occurrence of $R_e$ in the compound of Formula (VII) is selected from the group consisting of $C_{1-8}$-alkyl and alkylidene, each of which is optionally substituted with 1-3 substituents selected from the group consisting of halogen, alkyl, haloalkyl, hydroxyl, alkoxy, cyano, heterocycloalkyl, and heteroaryl;

each occurrence of Q is independently selected from the group consisting of N, O, S, S(=O), and S(=O)$_2$;

each occurrence of $Ar_1$ and $Ar_2$ in the compound of Formula (VII) is independently selected from the group consisting of aryl and het, each of which is optionally substituted with 1-3 substituents selected from the group consisting of halogen, alkyl, haloalkyl, hydroxyl, alkoxy, cyano, heterocycloalkyl, and heteroaryl;

each occurrence of $R_f$ and $R_g$ in the compound of Formula (VII) is independently selected from the group consisting of H, —$C_{1-10}$-alkyl, $C_{1-10}$-alkylaryl, —OH, —O—$C_{1-10}$-alkyl, —(CH$_2$)$_{0-6}$—$C_{3-7}$-cycloalky, —O—(CH$_2$)$_{0-6}$-aryl, phenyl, aryl, phenyl-phenyl, —(CH$_2$)$_{1-6}$-het, —O—(CH$_2$)$_{1-6}$-het, —OR$_{13}$, —C(=O)—R$_{13}$, —C(=O)—N(R$_{13}$)(R$_{14}$), —N(R$_{13}$)(R$_{14}$), —S—R$_{13}$, —S(=O)—R$_{13}$, —S(=O)$_2$—R$_{13}$, —S(=O)$_2$—NR$_{13}$R$_{14}$, —NR$_{13}$—S(=O)$_2$—R$_{14}$; —S—$C_{1-10}$-alkyl, aryl-$C_{1-4}$-alkyl, or het-$C_{1-4}$-alkyl, —SO$_2$—$C_{1-2}$-alkyl, —SO$_2$—$C_{1-2}$-alkylphenyl, —O—$C_{1-4}$-alkyl, and any $R_g$ and $R_f$ together form a ring selected from het or aryl, each of which is optionally substituted with 1-3 substituents selected from the group consisting of halogen, alkyl, haloalkyl, hydroxyl, alkoxy, cyano, heterocycloalkyl, and heteroaryl;

each occurrence of D in the compound of Formula (VII) is independently selected from the group consisting of —CO—, —C(=O)—$C_{1-7}$-alkylene, —C(=O)—$C_{1-7}$-arylene, —CF$_2$—, —O—, —S(=O)$_r$, where r is a whole number from 0-2, 1,3-dioxalane, $C_{1-7}$-alkyl-OH, and N(R$_h$), each of which is optionally substituted with one or more of halogen, OH, —O—$C_{1-6}$-alkyl, —S—$C_{1-6}$-alkyl, or —CF$_3$;

each occurrence of $R_h$ in the compound of Formula (VII) is independently selected from the group consisting of H, unsubstituted or substituted $C_{1-7}$-alkyl, aryl, unsubstituted or substituted —O—($C_{1-7}$-cycloalkyl), —C(=O)—$C_{1-10}$-alkyl, —C(=O)—$C_{0-10}$-alkyl-aryl, —C—O—$C_{0-10}$-alkyl, —C—O—$C_{0-10}$-alkyl-aryl, —SO$_2$—$C_{1-10}$-alkyl, and —SO$_2$—(C$_{0-10}$-alkylaryl);

each occurrence of $R_6$, $R_7$, $R_8$, and $R_9$ in the compound of Formula (VII) is independently selected from the group consisting of H, —$C_{1-10}$-alkyl, —$C_{1-10}$-alkoxy, aryl-$C_{1-10}$-alkoxy, —OH, —O—$C_{1-10}$-alkyl, —(CH$_2$)$_{0-6}$—$C_{3-7}$-cycloalkyl, —O—(CH$_2$)$_{0-6}$-aryl, phenyl, —(CH$_2$)$_{1-6}$-het, —O—(CH$_2$)$_{1-6}$-het, —OR$_{13}$, —C(=O)—R$_{13}$, —C(=O)—N(R$_{13}$)(R$_{14}$), —N(R$_{13}$)(R$_{14}$), —S—R$_{13}$, —S(=O)—R$_{13}$, —S(=O)$_2$—R$_{13}$, —S(=O)$_2$—NR$_{13}$R$_{14}$, and —NR$_{13}$—S(=O)$_2$—R$_{14}$, each of which is optionally substituted with 1-3 substituents selected from the group consisting of halogen, alkyl, haloalkyl, hydroxyl, alkoxy, cyano, heterocycloalkyl, and heteroaryl; or any occurrence of $R_6$, $R_7$, $R_8$, and $R_9$ together optionally form a ring system;

each occurrence of $R_{13}$ and $R_{14}$ in the compound of Formula (VII) is independently selected from the group consisting of H, $C_{1-10}$-alkyl, —(CH$_2$)$_{0-6}$—$C_{3-7}$-cycloalkyl, —(CH$_2$)$_{0-6}$—(CH)$_{0-1}$-(aryl)$_{1-2}$, —C(=O)—$C_{1-10}$-alkyl, —C(=O)—(CH$_2$)$_{1-6}$—$C_{3-7}$-cycloalkyl, —C(=O)—O—(CH$_2$)$_{0-6}$-aryl, —C(=O)—(CH$_2$)$_{0-6}$—O-fluorenyl, —C(=O)—NH—(CH$_2$)$_{0-6}$-aryl, —C(=O)—(CH$_2$)$_{0-6}$-aryl, —C(=O)—(CH$_2$)$_{0-6}$-het, —C(=S)—$C_{1-10}$-alkyl, —C(=S)—(CH$_2$)$_{1-6}$—$C_{3-7}$-cycloalkyl, —C(=S)—O—(CH$_2$)$_{0-6}$-aryl, —C(=S)—(CH$_2$)$_{0-6}$—O-fluorenyl, —C(=S)—NH—(CH$_2$)$_{0-6}$-aryl, —C(=S)—(CH$_2$)$_{0-6}$-aryl, and —C(=S)—(CH$_2$)$_{1-6}$-het, each of which is optionally substituted with one or more substituents selected from the group consisting of $C_{1-10}$-alkyl, halogen, OH, —O—$C_{1-6}$-alkyl, —S—$C_{1-6}$-alkyl, —CF$_3$, halogen, hydroxyl, $C_{1-4}$-alkyl, $C_{1-4}$-alkoxy, nitro, —CN, —O—C(=O)—$C_{1-4}$-alkyl, and —C(=O)—O—$C_{1-4}$-aryl; or any $R_{13}$ and $R_{14}$ can join together with a nitrogen atom to form a het.

In certain embodiments, the compound further comprises an independently selected second ILM attached to the ILM of Formula (VI), or an unnatural mimetic thereof, by way of at least one additional independently selected linker group L. In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM, $L_1$ and $L_2$. In an embodiment, the at least one additional linker group for an ILM of Formula (VI), or an unnatural mimetic thereof, chemically links groups selected from $R_4$ and $R_5$. In a non-limiting example, an ILM of Formula (VI) and a second ILM of Formula (VI), or an unnatural mimetic thereof, can be linked as shown below:

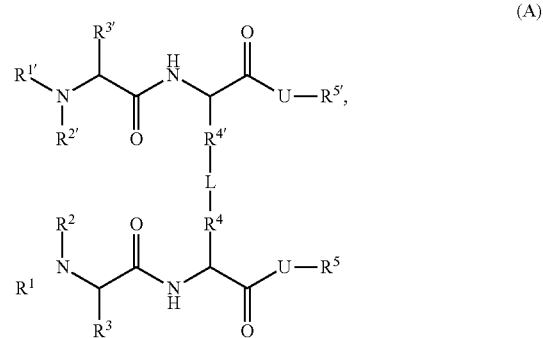

(A)

(B) 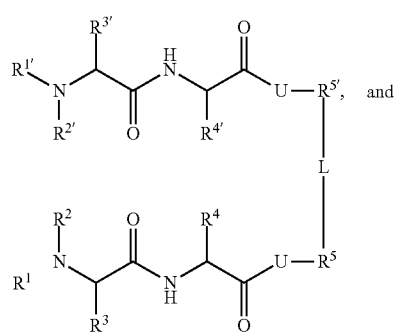, and
(C) 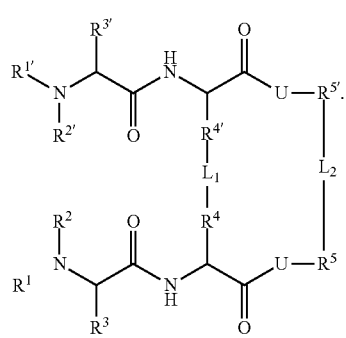
In certain embodiments, the ILM, the at least one additional independently selected linker group L, and the second ILM has a structure selected from the group consisting of:
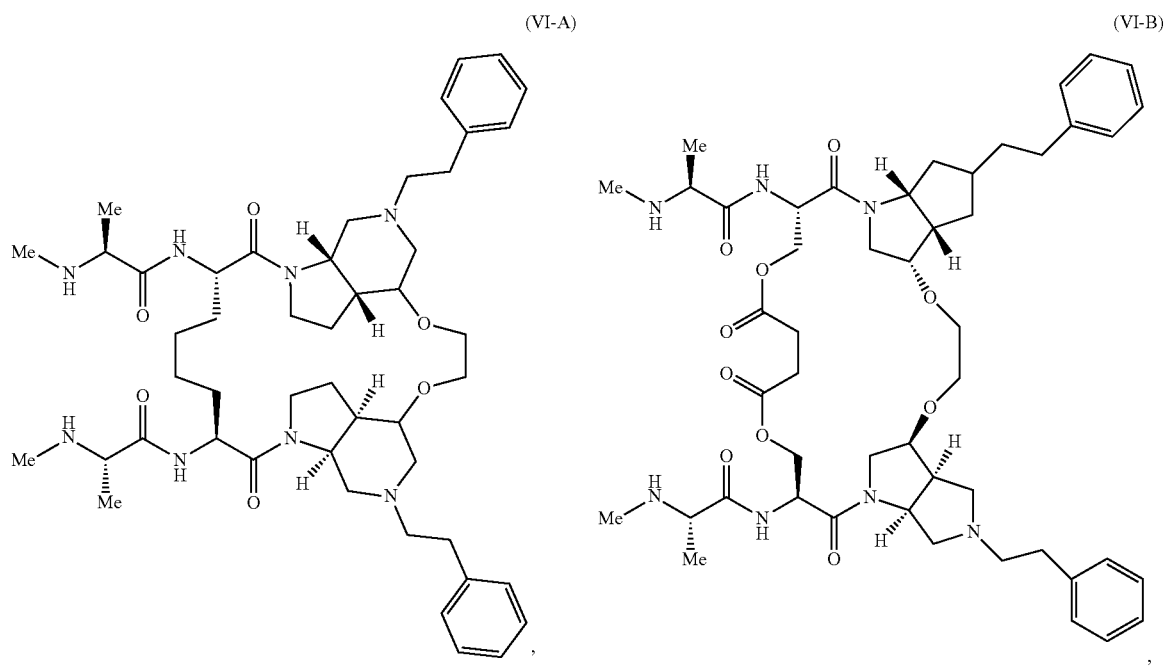
(VI-A) , (VI-B) ,

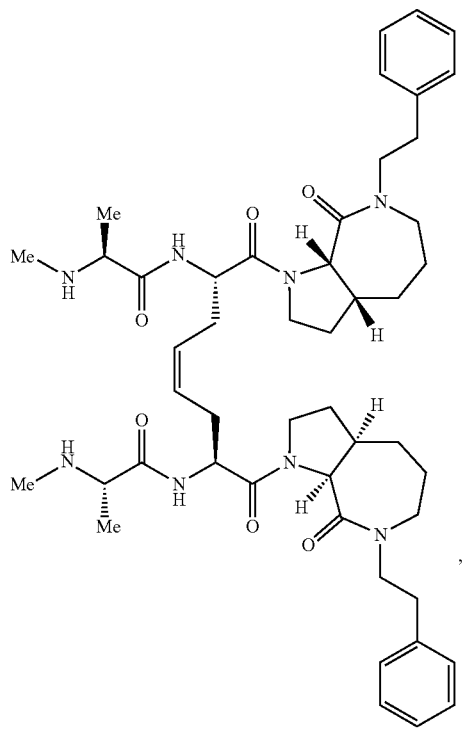
(VI-C)
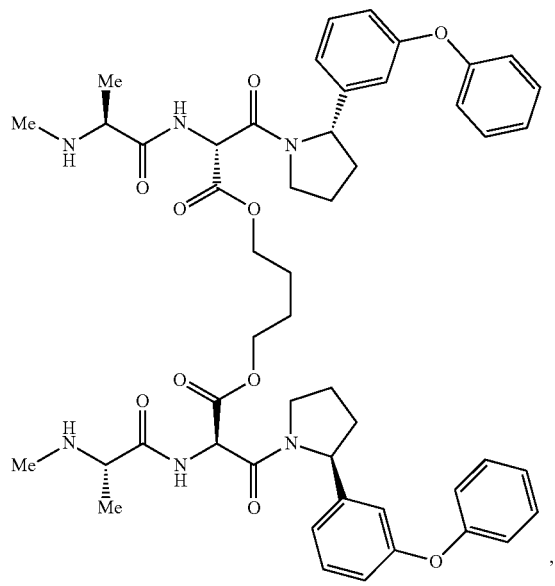
(VI-D)
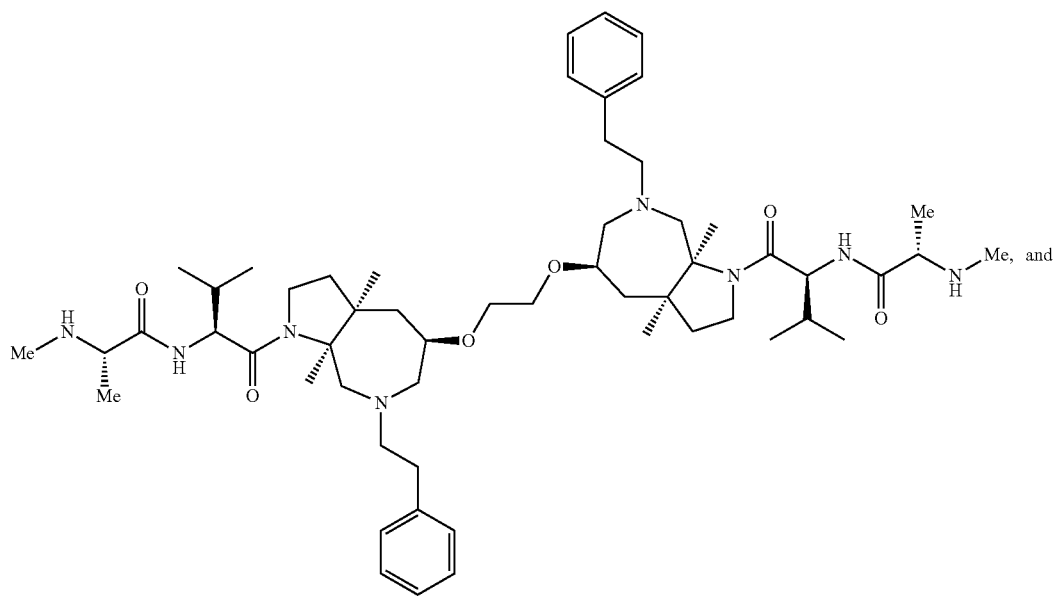
(VI-E)

-continued (VI-F)

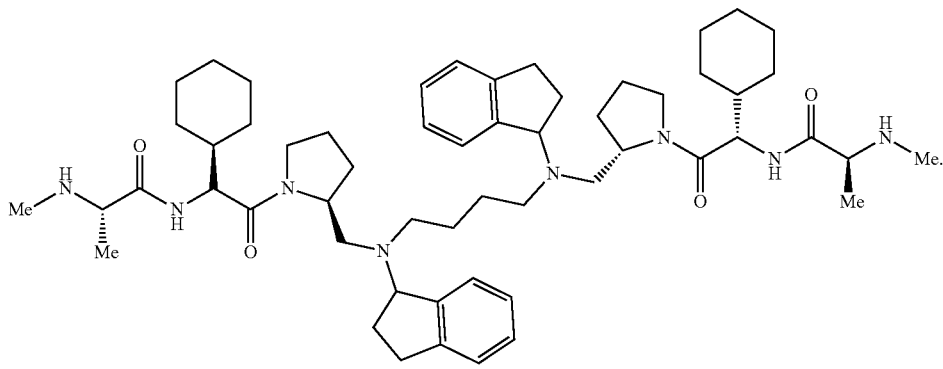

In various embodiments, the ILM can have the structure of Formula (VIII), as described in *ACS Chem. Biol.*, 557-566, 4 (7) (2009), or an unnatural mimetic thereof:

(VIII)

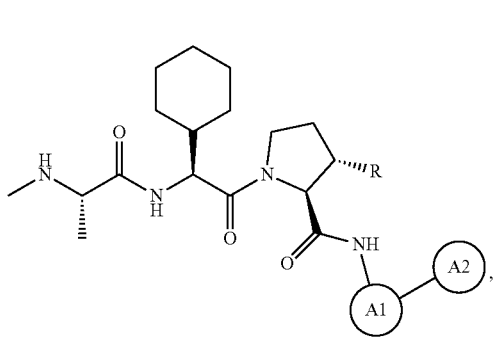

wherein each occurrence of A1 and A2 in the compound of Formula (VIII) is independently selected from the group consisting of a monocyclic ring, a fused ring, an aryl, and a heteroaryl, each of which is optionally substituted with 1-3 substituents selected from the group consisting of halogen, alkyl, haloalkyl, hydroxyl, alkoxy, cyano, heterocycloalkyl, and heteroaryl; and each occurrence of R in the compound of Formula (VIII) is independently H or Me.

In a certain embodiment, the linker group L is attached to A1 of Formula (VIII). In another embodiment, the linker group L is attached to A2 of Formula (VIII).

In various embodiments, the ILM is selected from the group consisting of (VIII-A)

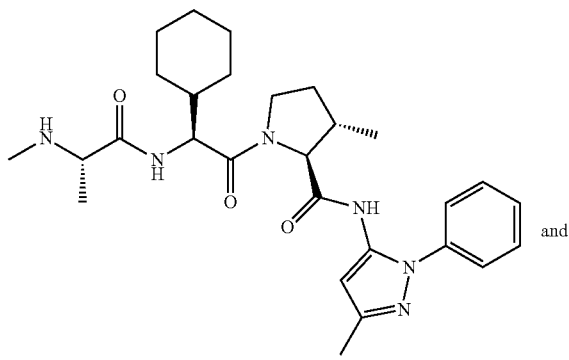

and

-continued (VIII-B)

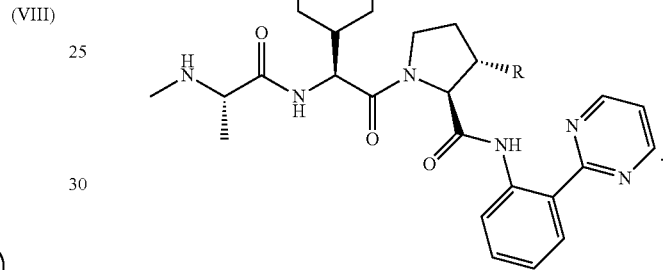

In various embodiments, the ILM can have the structure of Formula (IX), as described in *Drug Discov. Today*, 15 (5-6), 210-9 (2010), or an unnatural mimetic thereof:

(IX)

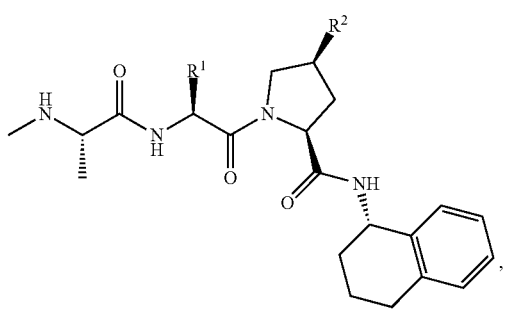

wherein each occurrence $R^1$ in the compound of Formula (IX) is independently selected from the group consisting of alkyl, cycloalkyl, heterocycloalkyl. In various embodiments, R1 in the compound of Formula (IX) is independently selected from the group consisting of isopropyl, tert-butyl, cyclohexyl, and tetrahydropyranyl. In various embodiments, each occurrence of $R^2$ in the compound of Formula (IX) is selected from —OPh or H.

In various embodiments, the ILM can have the structure of Formula (X), as described in *Drug Discov. Today*, 15 (5-6), 210-9 (2010), or an unnatural mimetic thereof:

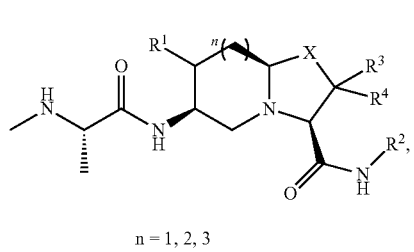

n = 1, 2, 3 wherein:
each occurrence of $R^1$ in the compound of Formula (X) is independently selected from the group consisting of H, —CH$_2$OH, —CH$_2$CH$_2$OH, —CH$_2$NH$_2$, and —CH$_2$CH$_2$NH$_2$;
each occurrence of X in the compound of Formula (X) is independently selected from S and CH$_2$;
each occurrence of $R^2$ in the compound of Formula (X) is independently selected from the group consisting of:

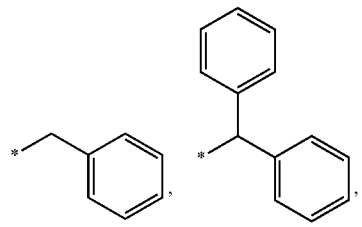

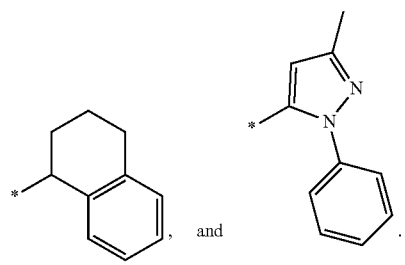

each occurrence of $R^3$ and $R^4$ in the compound of Formula (X) is independently selected from H and Me.

In various embodiments, the ILM can have the structure of Formula (XI), as described in *Drug Discov. Today*, 15 (5-6), 210-9 (2010), or an unnatural mimetic thereof:

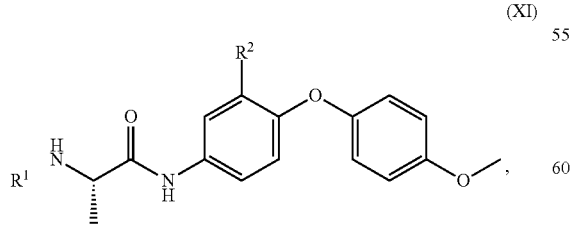

(XI)

wherein each occurrence of $R^1$ in the compound of Formula (XI) is independently selected from H and Me, and each occurrence of $R^2$ in the compound of Formula (XI) is independently selected from H and

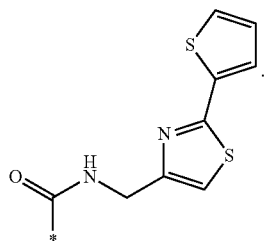 [SMILES: *C(=O)NCc1csc(-c2cccs2)n1]

In various embodiments, the ILM can have the structure of Formula (XII), as described in *Drug Discov. Today*, 15 (5-6), 210-9 (2010), or an unnatural mimetic thereof:

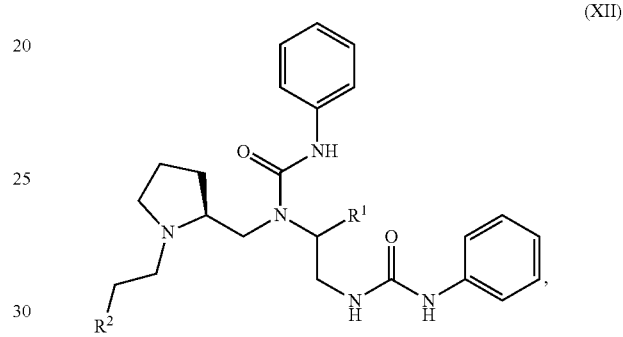

(XII)

wherein:
each occurrence of $R^1$ in the compound of Formula (XII) is independently selected from the group consisting of:

and each occurrence of $R^2$ in the compound of Formula (XII) is independently selected from the group consisting of:

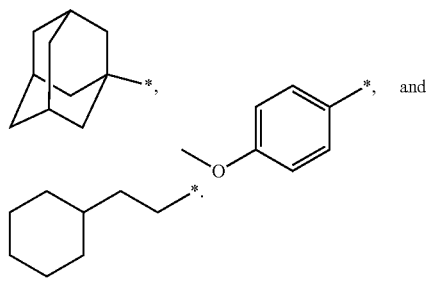

In various embodiments, the ILM moiety is selected from the group consisting of:

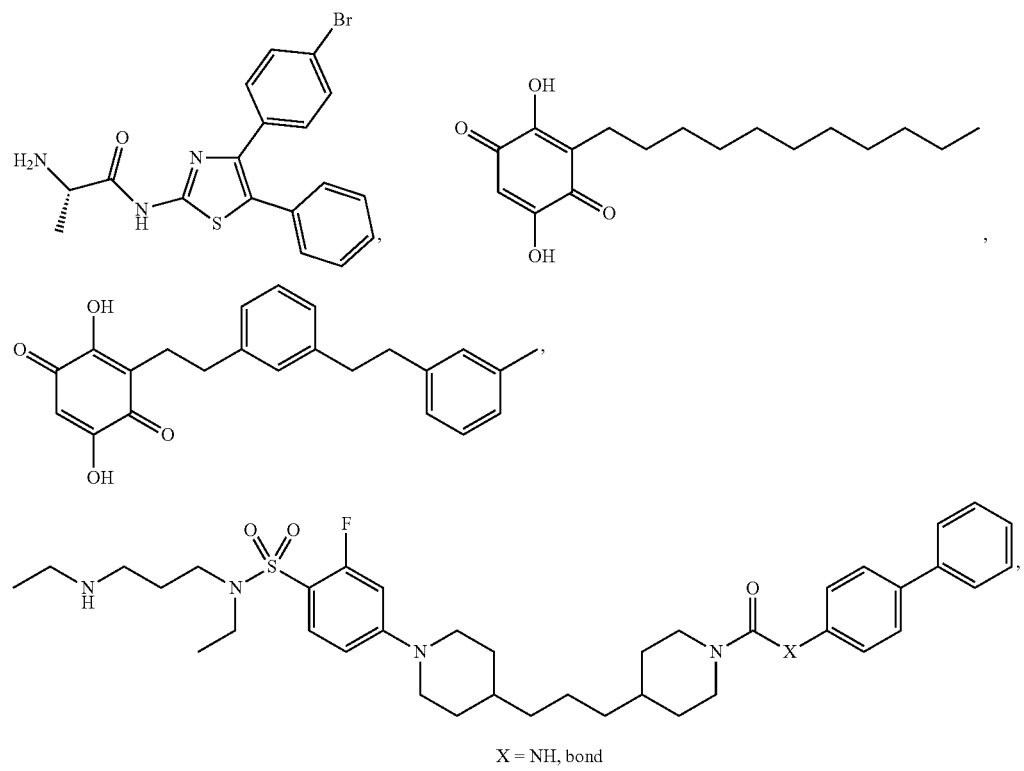
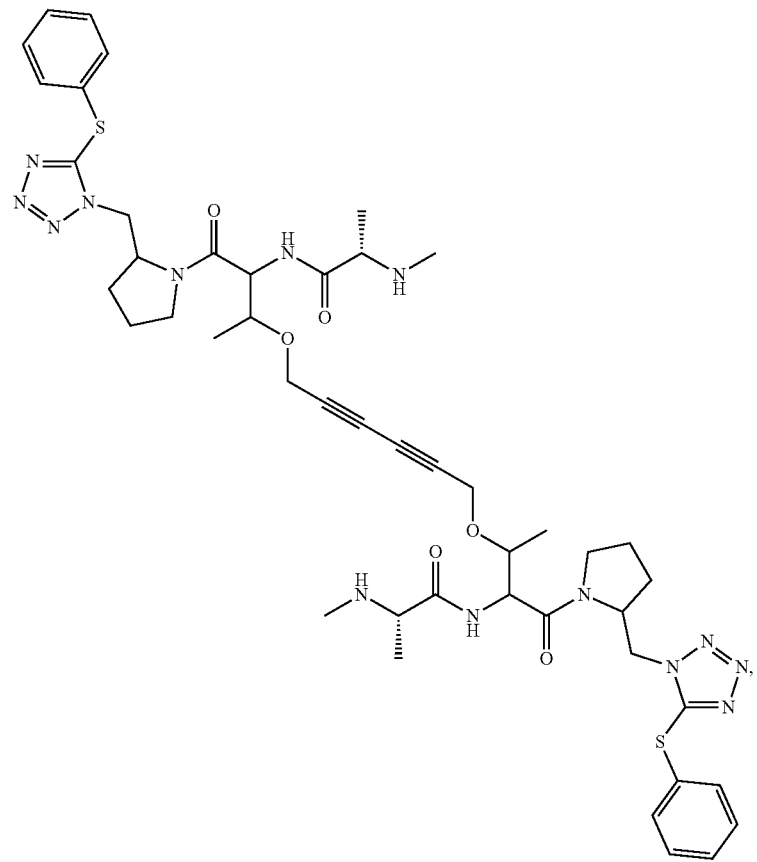
X = NH, bond

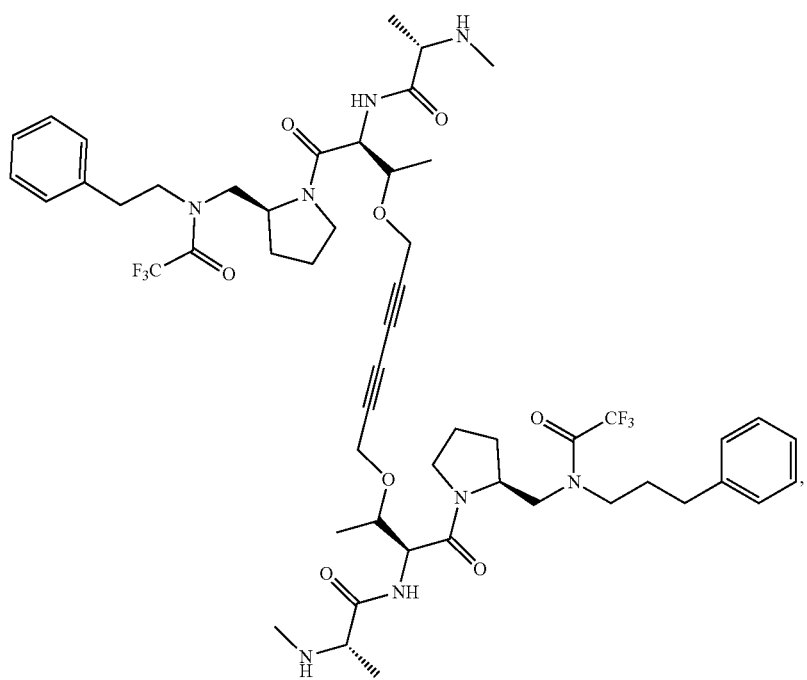
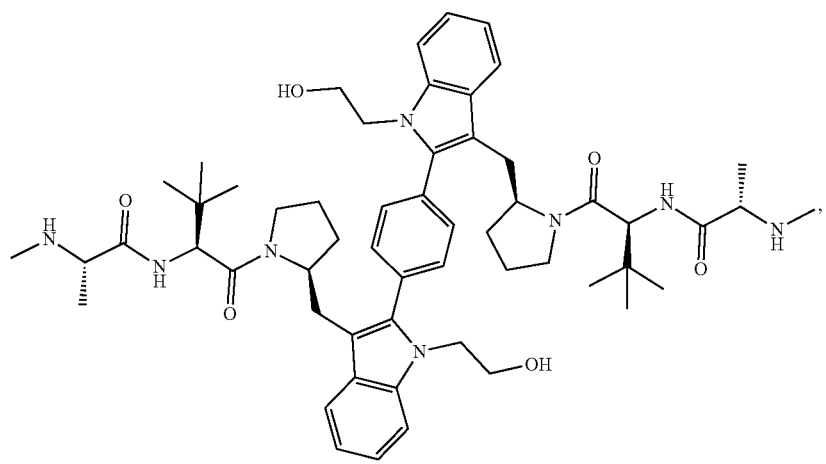
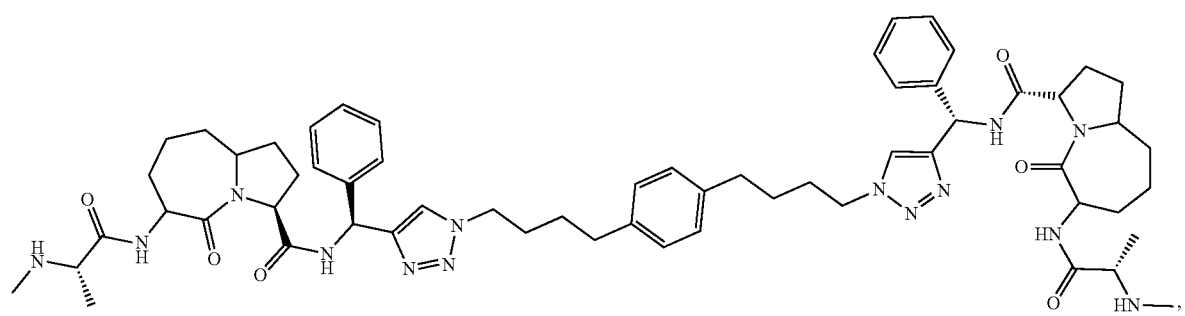

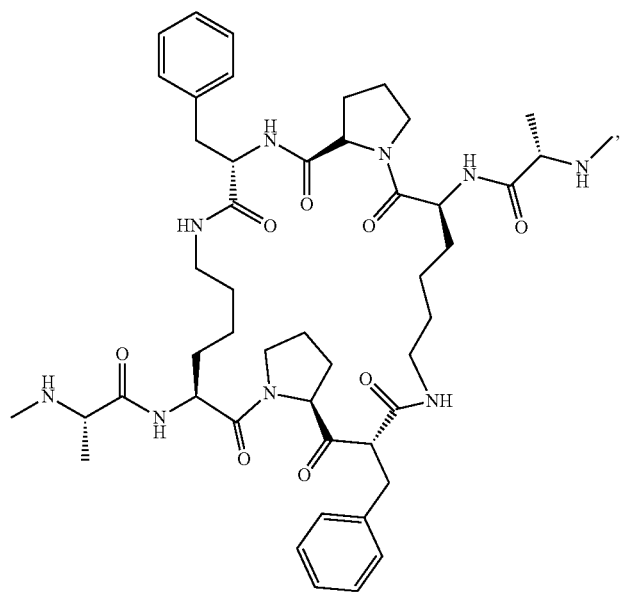
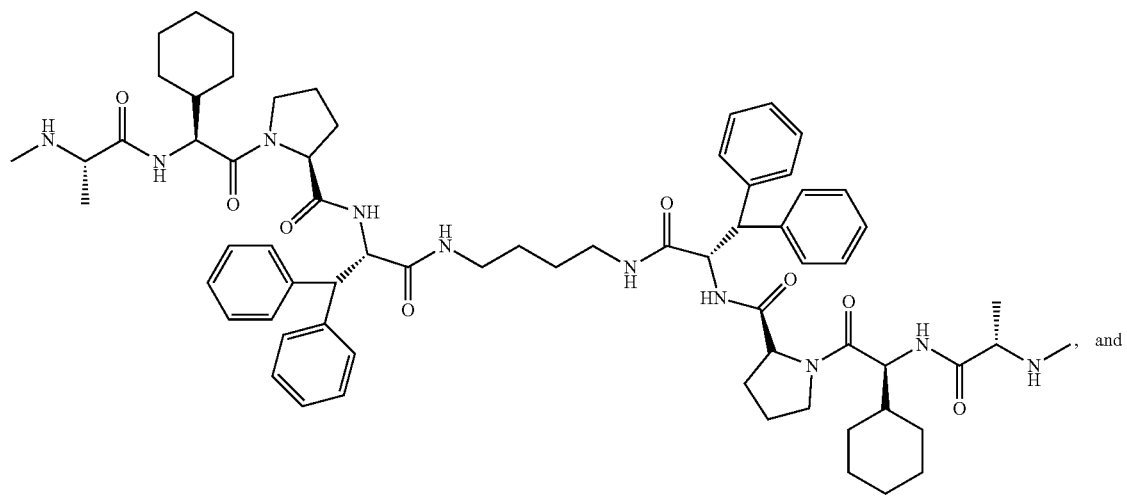
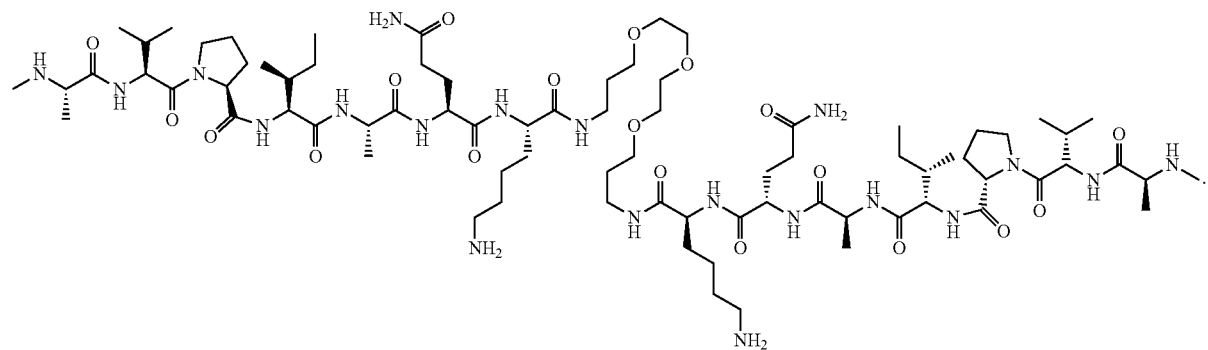

In various embodiments, the ILM can have the structure of Formula (XIII) as described in *Expert Opin. Ther. Pat.,* 20 (2), 251-67 (2010), or an unnatural mimetic thereof:

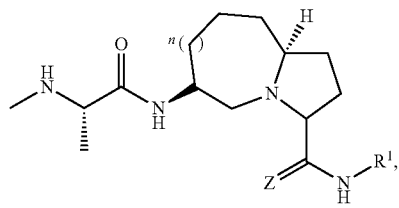

(XIII)

n = 0, 2 or, preferably, 1 wherein:
at each occurrence, Z in the compound of Formula (XIII) is independently absent or O;
each occurrence of $R^1$ in the compound of Formula (XIII) is independently selected from the group consisting of:

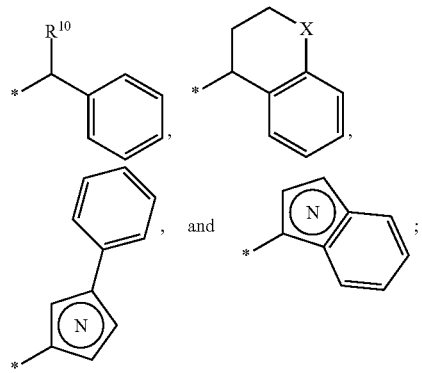

each occurrence of $R^{10}$ in the compound of Formula (XIII) is selected from the group consisting of H, alkyl, and aryl;
each occurrence of X in the compound of Formula (XIII) is selected from $CH_2$ and O; and

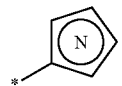

is a nitrogen-containing heteroaryl containing from 1-3 nitrogen atoms in the ring.

In various embodiments, the ILM can have the structure of Formula (XIV) as described in *Expert Opin. Ther. Pat.,* 20 (2), 251-67 (2010), or an unnatural mimetic thereof:

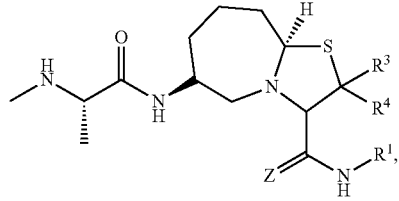

(XIV)

wherein:
at each occurrence, Z in the compound of Formula (XIV) is independently absent or O;
each occurrence of $R^1$ in the compound of Formula (XIV) is independently selected from the group consisting of:

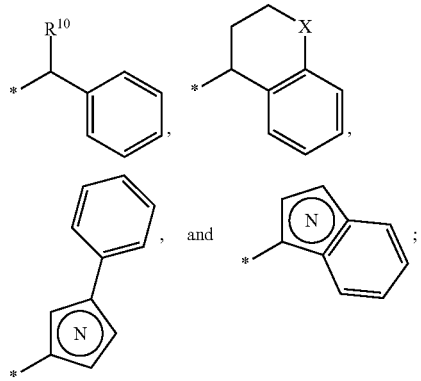

each occurrence of $R^3$ and $R^4$ in the compound of Formula (XIV) is independently selected from H and Me;
each occurrence of $R^{10}$ in the compound of Formula (XIV) is selected from the group consisting of H, alkyl, and aryl;
each occurrence of X in the compound of Formula (XIV) is selected from the group consisting of $CH_2$ and O; and
each

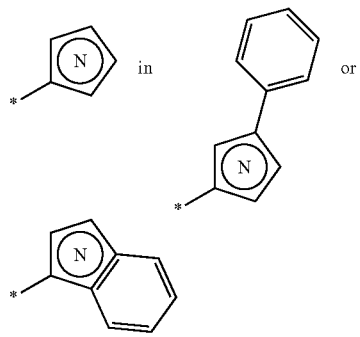

is a nitrogen-containing heteroaryl containing from 1-3 nitrogen atoms in the ring.

In various embodiments, the ILM is selected from the group consisting of:

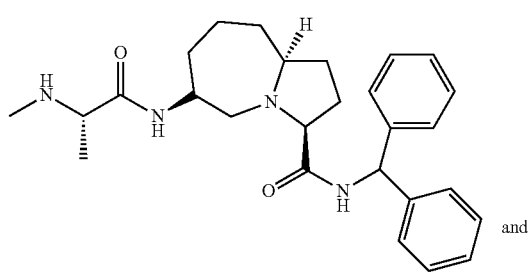

and

-continued

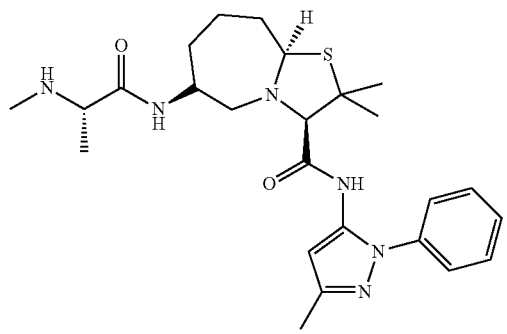

In various, the ILM can have the structure of Formula (XV), as described in WO Pub. No. 2008/128171, or an unnatural mimetic thereof:

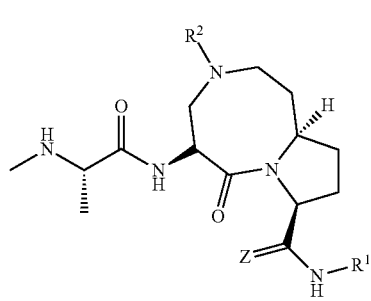 (XV)

wherein:
at each occurrence Z in the compound of Formula (XV) is absent or O;
each occurrence of $R^1$ in the compound of Formula (XV) is independently selected from the group consisting of:

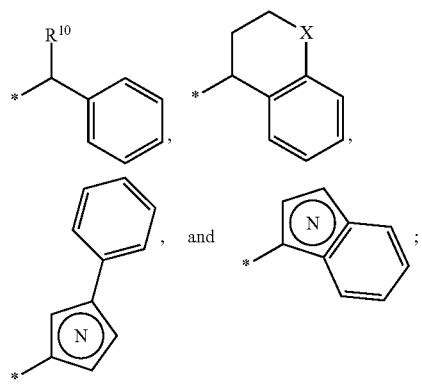

each occurrence of $R^2$ in the compound of Formula (XV) is independently selected from the group consisting of H, alkyl, and acyl;
each occurrence of $R^{10}$ in the compound of Formula (XV) is selected from the group consisting of H, alkyl, and aryl;
each occurrence of X in the compound of Formula (XV) is selected from CH$_2$ and O; and each

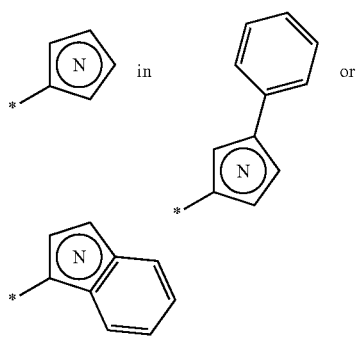

is a nitrogen-containing heteroaryl containing from 1-3 nitrogen atoms in the ring.

In a particular embodiment, the ILM has the structure:

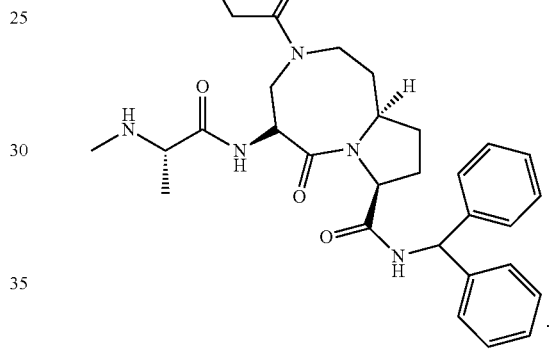

In various embodiments, the ILM can have the structure of Formula (XVI), as described in WO Pub. No. 2006/069063, or an unnatural mimetic thereof:

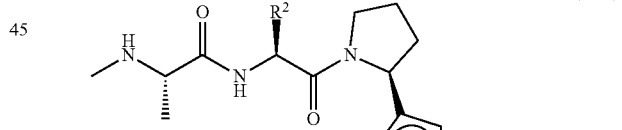 (XVI)

wherein:
each occurrence of $R^2$ in the compound of Formula (XVI) is independently selected from the group consisting of alkyl, cycloalkyl, heterocycloalkyl, isopropyl, tert-butyl, cyclohexyl, and tetrahydropyranyl. In various embodiments, $R^2$ in the compound of Formula (XVI) is independently selected from the group consisting of isopropyl, tert-butyl, and cyclohexyl.
each occurrence of

in the compound of Formula (XVI) is independently a 5- or 6-membered nitrogen-containing heteroaryl. In various embodiments,

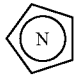

is a 5-membered nitrogen-containing heteroaryl. In various embodiments,

is thiazole. In various embodiments, each occurrence of Ar in the compound of Formula (XVI) is independently an aryl or a heteroaryl.

In various embodiments, the ILM can have the structure of Formula (XVII), as described in Bioorg. Med. Chem. Lett., 20(7), 2229-33 (2010), or an unnatural mimetic thereof:

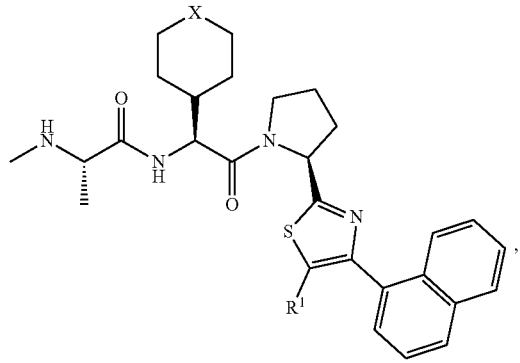
(XVII)

wherein each occurrence of $R^1$ in the compound of Formula (XVII) is independently selected from the group consisting of halogen, cyano, —C≡CH, —C≡CCH$_3$, —C≡CCH$_2$OCH$_3$, and —C≡CCH$_2$OH; and each occurrence of X in the compound of Formula (XVII) is independently selected from the group consisting of O and CH$_2$.

In various embodiments, the ILM can have the structure of Formula (XVIII), as described in Bioorg. Med. Chem. Lett., 20(7), 2229-33 (2010), or an unnatural mimetic thereof:

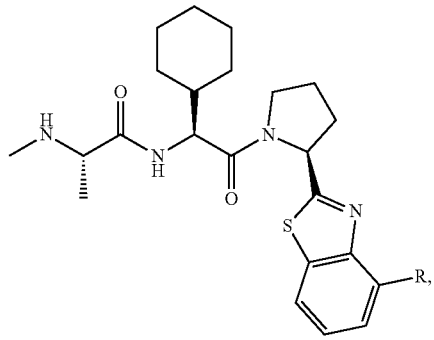
(XVIII)

wherein each occurrence of R in the compound of Formula (XVIII) is independently selected from the group consisting of alkyl, aryl, heteroaryl, arylalkyl, heteroarylalkyl, and halogen (in variable substitution position).

In various embodiments, the ILM can have the structure of Formula (XIX) as described in Bioorg. Med. Chem. Lett., 20(7), 2229-33 (2010), or an unnatural mimetic thereof:

(XIX)

wherein

is a 6-member nitrogen heteroaryl.

In a certain embodiment, the ILM of the composition is selected from the group consisting of:

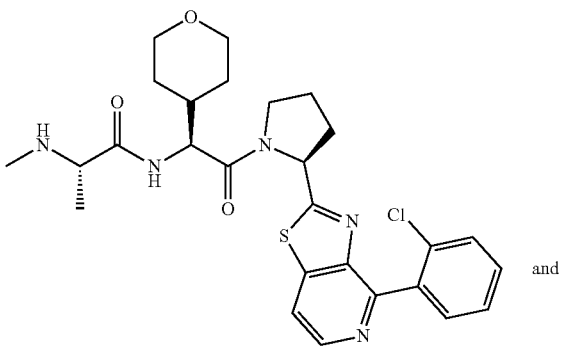

and

-continued

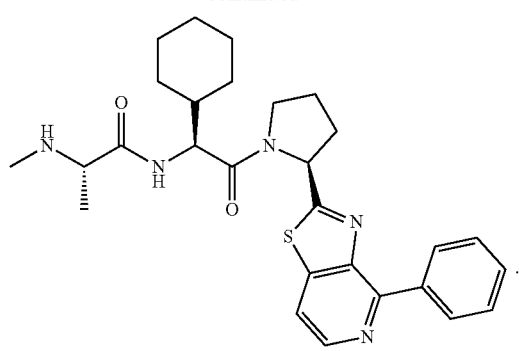

In certain embodiments, the ILM of the composition is selected from the group consisting of:

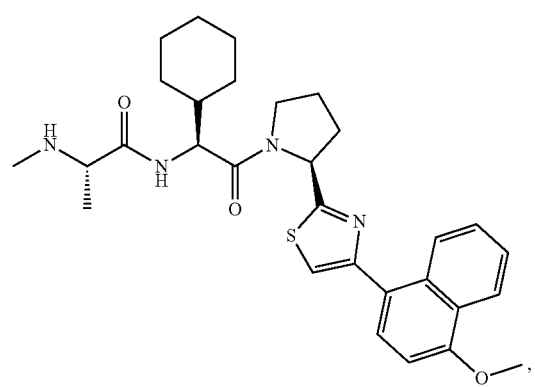

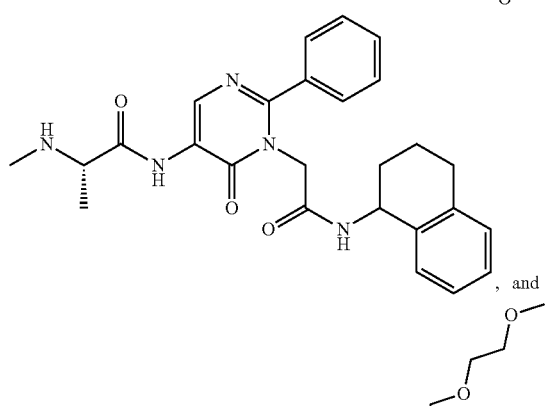

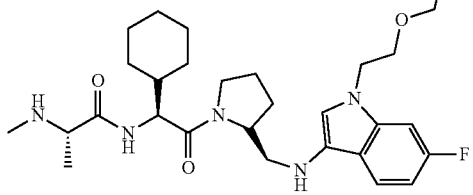

In various embodiments, the ILM can have the structure of Formula (XX), as described in WO Pub. No. 2007/101347, or an unnatural mimetic thereof:

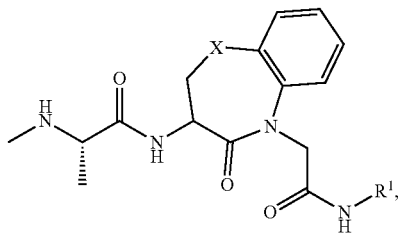

wherein each occurrence of X in the compound of Formula (XX) is independently selected from the group consisting of CH$_2$, O, NH, and S.

In certain embodiments, the ILM can have the structure of Formula (XXI), as described in U.S. Pat. Nos. 7,345,081 and 7,419,975, or an unnatural mimetic thereof:

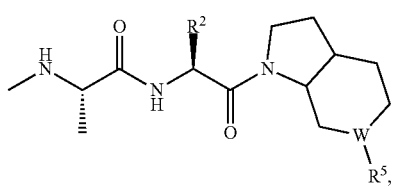

wherein:
each occurrence of R$^2$ in the compound of Formula (XXI) is independently selected from the group consisting of tert-butyl, iso-propyl, and cyclohexyl;
each occurrence of R$^5$ in the compound of Formula (XXI) is independently selected from

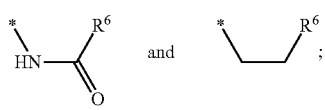

each occurrence of W in the compound of Formula (XXI) is independently selected from CH and N; and
each occurrence of R$^6$ in the compound of Formula (XXI) is independently selected from the group consisting of a mono-cyclic fused aryl, a bicyclic fused aryl, and heteroaryl.

In certain embodiments, the ILM of the compound is selected from the group consisting of:

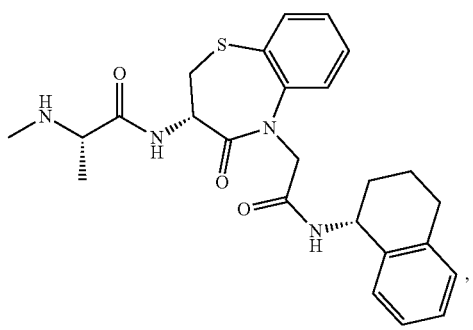

49
-continued
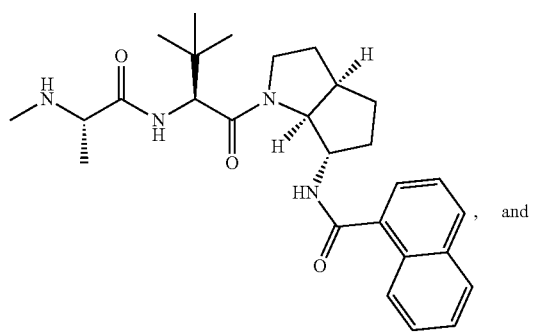
, and
50
-continued
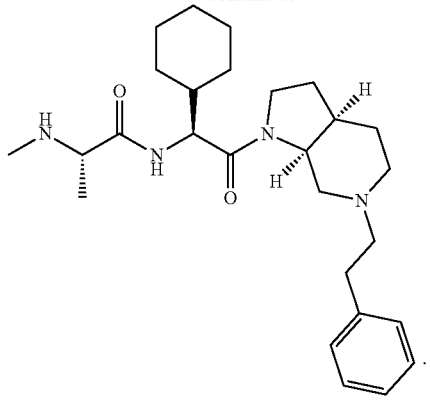
.
In certain embodiments, the ILM of the compound is selected from the group consisting of:
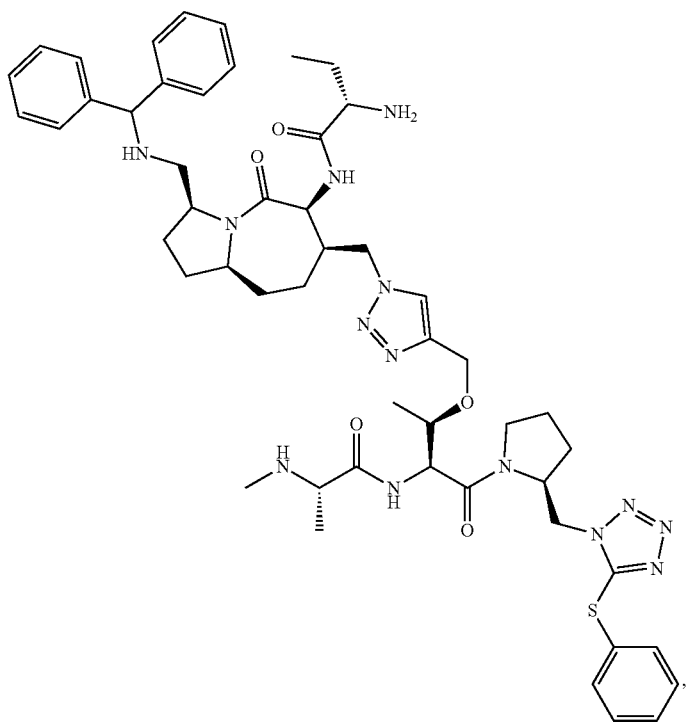
,
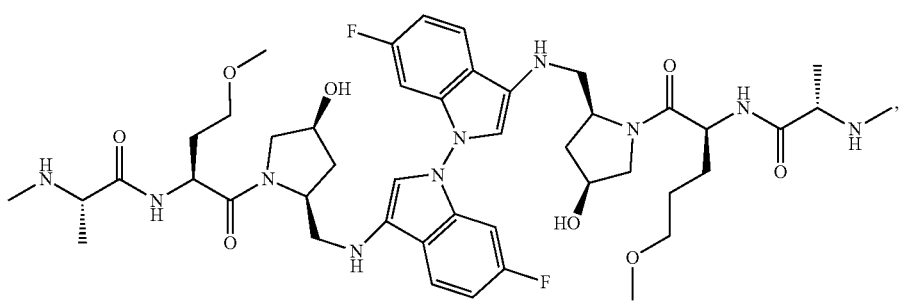
,

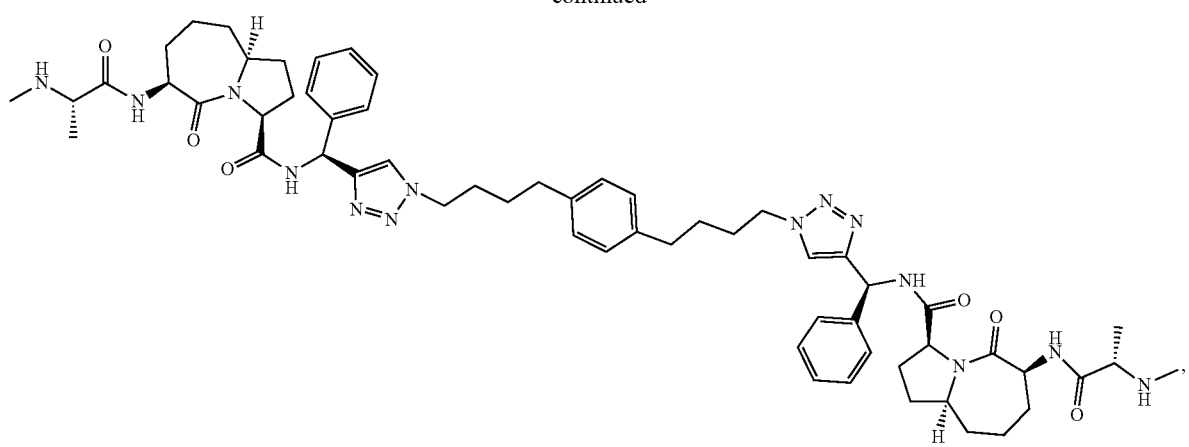
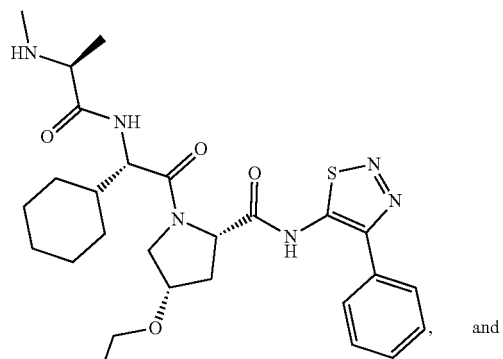, and
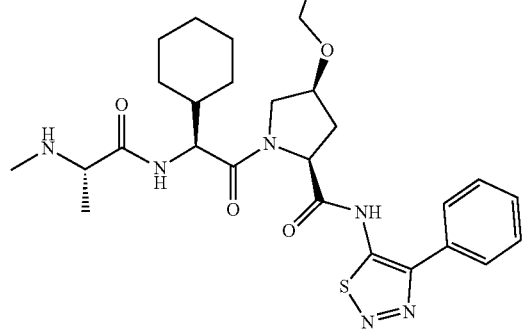

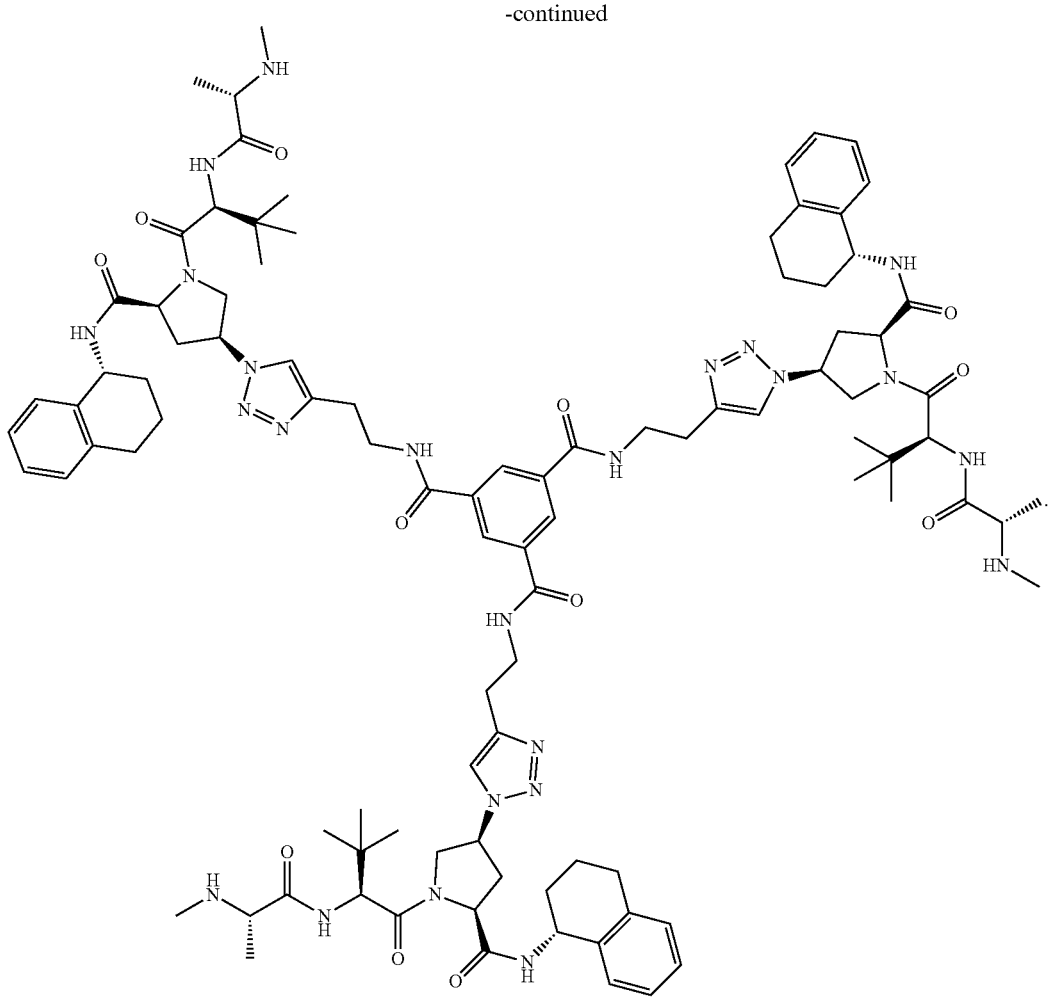
40
In various embodiments, the ILM can have the structure of Formula (XXII) or (XXIII) as described in J. Med. Chem. 58(3), 1556-62 (2015), or an unnatural mimetic thereof:
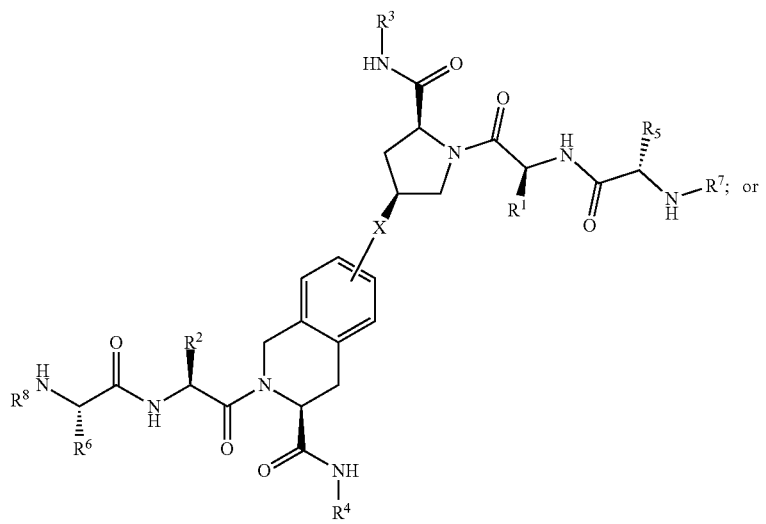
(XXII)

-continued

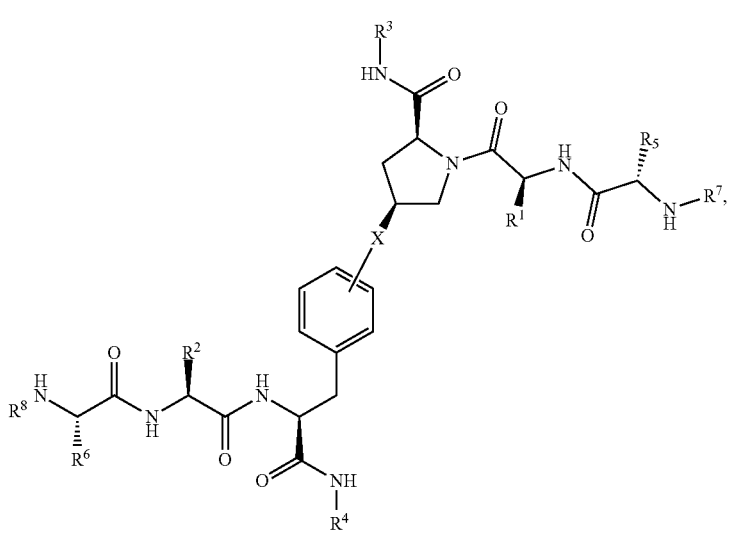

(XXIII)

wherein:
- each occurrence of $R^1$ and $R^2$ in the compounds of Formula (XXII) or (XXIII) is independently selected from the group consisting of alkyl, cycloalkyl, cycloalkylalkyl, heterocyclyl, arylalkyl, and aryl, each of which is optionally substituted;
- or alternatively, each occurrence of $R^1$ and $R^2$ in the compounds of Formula (XXII) or (XXIII) is independently an optionally substituted thioalkyl, wherein the substituents attached to the S atom of the thioalkyl are selected from the group consisting of alkyl, branched alkyl, heterocyclyl, —$(CH_2)_vCOR^{20}$, —$CH_2CFR^{21}COR^{22}$, and —$CH_2R^{23}$, each of which is optionally substituted;
- at each occurrence in the compounds of Formula (XXII) or (XXIII), v is independently an integer from 1-3;
- each occurrence of $R^{20}$ and $R^{22}$ in the compounds of Formula (XXII) or (XXIII) is independently selected from the group consisting of OH, $NR^{24}R^{25}$, and $OR^{26}$;
- each occurrence of $R^{21}$ in the compounds of Formula (XXII) or (XXIII) is independently the group $NR^{24}R^{25}$;
- each occurrence of $R^{23}$ in the compounds of Formula (XXII) or (XXIII) is independently selected from the group consisting of aryl and heterocyclyl, each of which is optionally substituted by one or more of alkyl or halogen;
- each occurrence of $R^{24}$ in the compounds of Formula (XXII) or (XXIII) is independently hydrogen or optionally substituted alkyl;
- each occurrence of $R^{25}$ in the compounds of Formula (XXII) or (XXIII) is independently selected from the group consisting of hydrogen, alkyl, branched alkyl, arylalkyl, heterocyclyl, —$CH_2(OCH_2CH_2O)_mCH_3$, and —$[CH_2CH_2(CH_2)_\delta NH]_\psi CH_2CH_2(CH_2)_\omega NH_2$, each of which is optionally substituted, wherein δ is a whole number from 0-2, ψ is an integer from 1-3, and ω is a whole number from 0-2. In various embodiments, $R^{25}$ in the compounds of Formula (XXII) or (XXIII) is spermine or spermidine.
- Each occurrence of $R^{26}$ in the compounds of Formula (XXII) or (XXIII) is independently alkyl, optionally substituted by one or more of OH, halogen, or $NH_2$;
- at each occurrence in the compounds of Formula (XXII) or (XXIII) m is independently an integer from 1-8;
- each occurrence of $R^3$ and $R^4$ in the compounds of Formula (XXII) or (XXIII) is independently selected from the group consisting of alkyl, cycloalkyl, aryl, arylalkyl, arylalkoxy, heteroaryl, heterocyclyl, heteroarylalkyl, and heterocycloalkyl, each of which is optionally substituted by one or more of alkyl, halogen, or OH;
- each occurrence of $R^5$, $R^6$, $R^7$ and $R^8$ in the compounds of Formula (XXII) or (XXIII) is independently selected from the group consisting of hydrogen, alkyl, and cycloalkyl, each of which is optionally substituted; and
- each occurrence of X in the compounds of Formula (XXII) or (XXIII) is independently a bond or a chemical linker group.

In certain embodiments, X is a bond or is selected from the group consisting of:

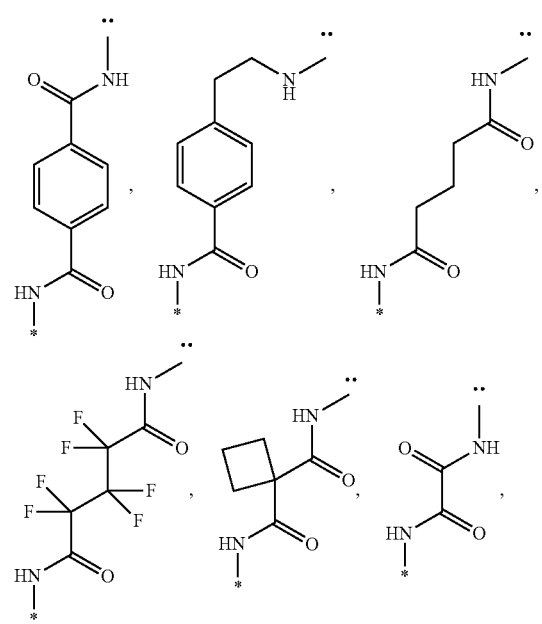

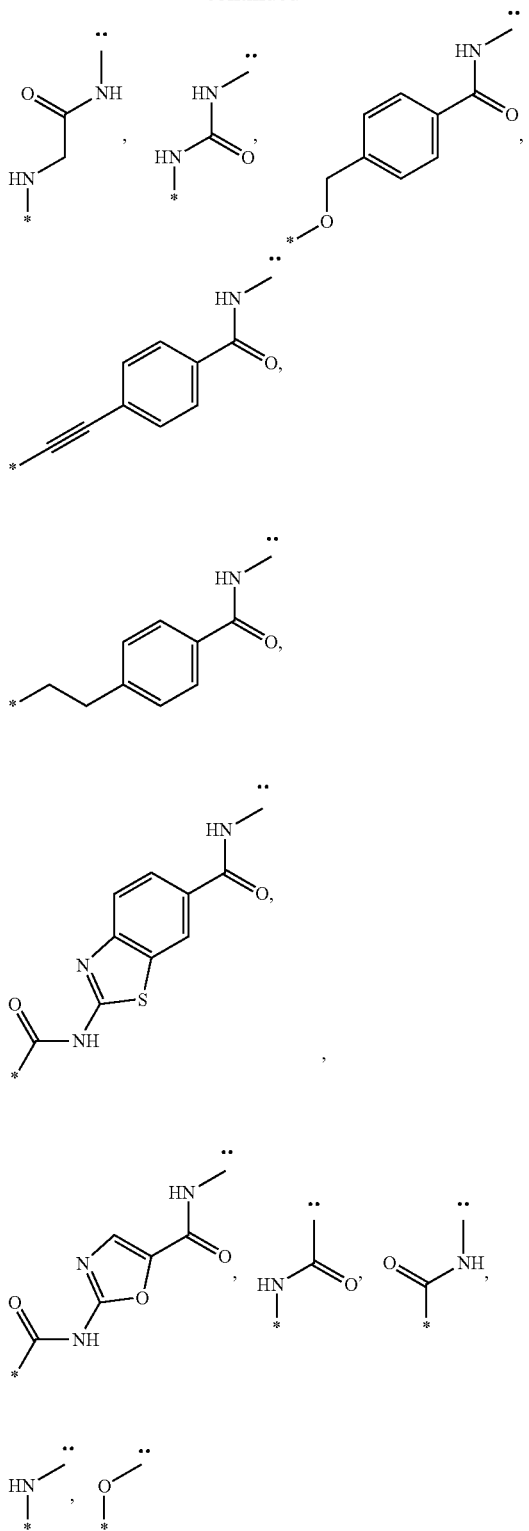

wherein "*" is a point of attachment to a PTM, L, or any ULM described herein.

In various embodiments, the ILM can have the structure of Formula (XXIV), (XXV), or (XXVI), as described in J. Med. Chem. 58(3), 1556-62 (2015), or an unnatural mimetic thereof, and the chemical linker to linker group L as shown:

wherein:
each occurrence of $R^1$ and $R^2$ in the compounds of Formula (XXIV), (XXV), or (XXVI) is independently selected from the group consisting of alkyl, cycloalkyl, cycloalkylalkyl, heterocyclyl, arylalkyl, and aryl, each of which is optionally substituted;
or alternatively, each occurrence of $R^1$ and $R^2$ in the compounds of Formula (XXIV), (XXV), or (XXVI) is independently an optionally substituted thioalkyl, wherein the substituents attached to the S atom of the thioalkyl are selected from the group consisting of alkyl, branched alkyl, heterocyclyl, —$(CH_2)_vCOR^{20}$, —$CH_2CHR^{21}COR^{22}$, and —$CH_2R^{23}$, each of which is optionally substituted;
at each occurrence in the compounds of Formula (XXIV), (XXV), or (XXVI), v is independently an integer from 1-3;
each occurrence of $R^{20}$ and $R^{22}$ in the compounds of Formula (XXIV), (XXV), or (XXVI), is independently selected from the group consisting of OH, $NR^{24}R^{25}$, and $OR^{26}$;

each occurrence of $R^{21}$ in the compounds of Formula (XXIV), (XXV), or (XXVI), is independently the group $NR^{24}R^{25}$;

each occurrence of $R^{23}$ in the compounds of Formula (XXIV), (XXV), or (XXVI) is independently selected from the group consisting of aryl and heterocyclyl, each of which is optionally substituted by one or more of alkyl or halogen;

each occurrence of $R^{24}$ in the compounds of Formula (XXIV), (XXV), or (XXVI) is independently hydrogen or optionally substituted alkyl;

each occurrence of $R^{25}$ in the compounds of Formula (XXIV), (XXV), or (XXVI) is independently selected from the group consisting of hydrogen, alkyl, branched alkyl, arylalkyl, heterocyclyl, —$CH_2(OCH_2CH_2O)_mCH_3$, and —$[CH_2CH_2(CH_2)_\delta NH]_\psi CH_2CH_2(CH_2)\overline{\omega}NH_2$, each of which is optionally substituted, wherein $\delta$ is a whole number from 0-2, $\psi$ is an integer from 1-3, and $\overline{\omega}$ is a whole number from 0-2. In various embodiments, $R^{25}$ in the compounds of Formula (XXIV), (XXV), or (XXVI) is spermine or spermidine.

Each occurrence of $R^{26}$ in the compounds of Formula (XXIV), (XXV), or (XXVI) is independently alkyl, optionally substituted by one or more of OH, halogen, or $NH_2$;

at each occurrence in the compounds of Formula (XXIV), (XXV), or (XXVI) m is independently an integer from 1-8;

each occurrence of $R^3$ and $R^4$ in the compounds of Formula (XXIV), (XXV), or (XXVI) is independently selected from the group consisting of alkyl, cycloalkyl, aryl, arylalkyl, arylalkoxy, heteroaryl, heterocyclyl, heteroarylalkyl, and heterocycloalkyl, each of which is optionally substituted by one or more of alkyl, halogen, or OH;

each occurrence of $R^5$, $R^6$, $R^7$ and $R^8$ in the compounds of Formula (XXIV), (XXV), or (XXVI) is independently selected from the group consisting of hydrogen, alkyl, and cycloalkyl, each of which is optionally substituted.

In various embodiments, the ILM has the structure according to Formulas (XXII) through (XXVI), wherein each occurrence of $R^7$ and $R^8$ in the compounds of Formulas (XXII) through (XXVI) is independently selected from H or Me;

each occurrence of $R^5$ and $R^6$ in the compounds of Formulas (XXII) through (XXVI) is independently selected from the group consisting of

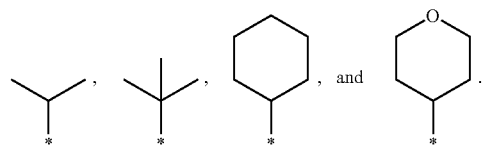

each occurrence of $R^3$ and $R^4$ in the compounds Formulas (XXII) through (XXVI) is independently selected from the group consisting of:

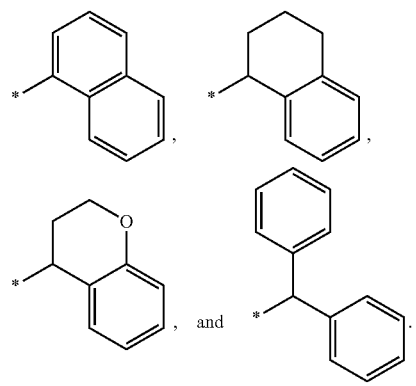

In various embodiments, the ILM can have the structure of Formula (XXVII) or (XXVII), as described in WO Pub. No. 2014/055461 and Bioorg. Med. Chem. Lett. 24(21), 5022-9 (2014), or an unnatural mimetics thereof:

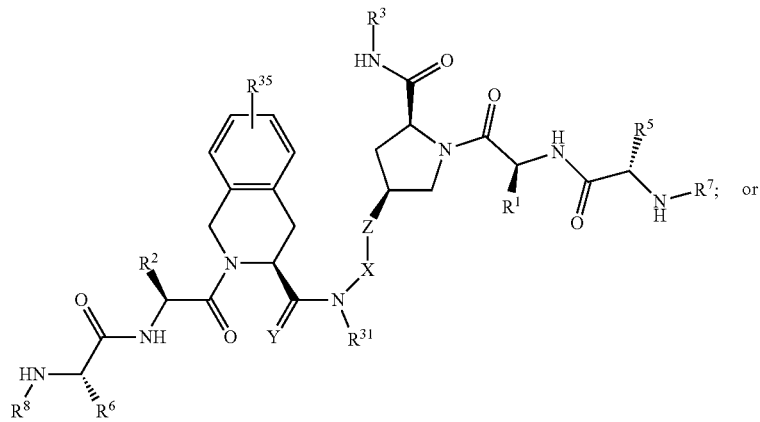

(XXVII)

(XXVIII)

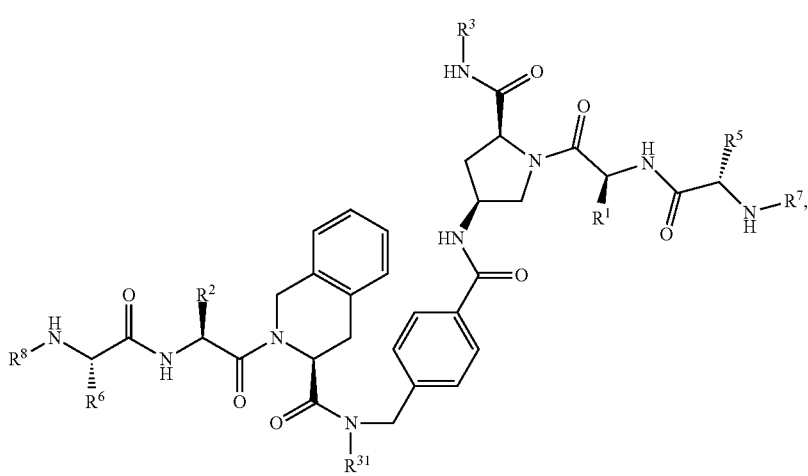

wherein:
each $R^{35}$ in the compounds of Formula (XXVII) or (XXVIII) represents 1 or 2 substituents independently selected from the group consisting of alkyl, halogen, alkoxy, cyano, and haloalkoxy;

each occurrence of $R^1$ and $R^2$ of in the compounds of Formula (XXVII) or (XXVIII) is selected from the group consisting of H alkyl, cycloalkyl, cycloalkylalkyl, heterocyclyl, arylalkyl, aryl, each of which is optionally substituted;

or alternatively, each occurrence of $R^1$ and $R^2$ in the compounds of Formula (XXVII) or (XXVIII) is independently —$CR^{60}R^{61}SR^{70}$, wherein each occurrence of $R^{60}$ and $R^{61}$ is independently H or methyl, and each occurrence of $R^{70}$ is independently selected from the group consisting of alkyl, branched alkyl, heterocyclyl, —$(CH_2)_vCOR^{20}$, —$CH_2CHR^{21}COR^{22}$ or —$CH_2R^{23}$, each of which is optionally substituted, at each occurrence in the compounds of Formula (XXVII) or (XXVIII), v is independently an integer from 1-3;

each occurrence of $R^{20}$ and $R^{22}$ in the compounds of Formula (XXVII) or (XXVIII) is independently selected from the group consisting of OH, $NR^{24}R^{25}$, and $OR^{26}$;

each occurrence of $R^{21}$ in the compounds of Formula (XXVII) or (XXVIII) is independently the group $NR^{24}R^{25}$;

each occurrence of $R^{23}$ in the compounds of Formula (XXVII) or (XXVIII) is independently selected from the group consisting of aryl and heterocyclyl, each of which is optionally substituted by one or more of alkyl or halogen;

each occurrence of $R^{24}$ in the compounds of Formula (XXVII) or (XXVIII) is independently hydrogen or optionally substituted alkyl;

each occurrence of $R^{25}$ in the compounds of Formula (XXVII) or (XXVIII) is independently selected from the group consisting of hydrogen, alkyl, branched alkyl, arylalkyl, heterocyclyl, —$CH_2(OCH_2CH_2O)_mCH_3$, and —$[CH_2CH_2(CH_2)_\delta NH]_\psi CH_2CH_2(CH_2)_{\overline{\omega}}NH_2$, each of which is optionally substituted, wherein δ is a whole number from 0-2, ψ is an integer from 1-3, and $\overline{\omega}$ is a whole number from 0-2. In various embodiments, $R^{25}$ in the compounds of Formula (XXII) or (XXIII) is spermine or spermidine.

Each occurrence of $R^{26}$ in the compounds of Formula (XXVII) or (XXVIII) is independently alkyl, optionally substituted by one or more of OH, halogen, or $NH_2$;

at each occurrence in the compounds of Formula (XXVII) or (XXVIII) m is independently an integer from 1-8;

each occurrence of $R^3$ and $R^4$ in the compounds of Formula (XXVII) or (XXVIII) is independently selected from the group consisting of alkyl, cycloalkyl, aryl, arylalkyl, arylalkoxy, heteroaryl, heterocyclyl, heteroarylalkyl, and heterocycloalkyl, each of which is optionally substituted by one or more of alkyl, halogen, or OH;

each occurrence of $R^5$, $R^6$, $R^7$ and $R^8$ in the compounds of Formula (XXVII) or (XXVIII) is independently selected from the group consisting of hydrogen, alkyl, and cycloalkyl, each of which is optionally substituted;

each occurrence of $R^{31}$ in the compounds of Formulas (XXVII) or (XXVIII) is independently selected from the group consisting of alkyl, aryl, arylalkyl, heteroaryl, and heteroarylalkyl, each of which is optionally further substituted. In various embodiments, $R^{31}$ in the compounds of Formulas (XXVII) or (XXVIII) is selected form the group consisting of:

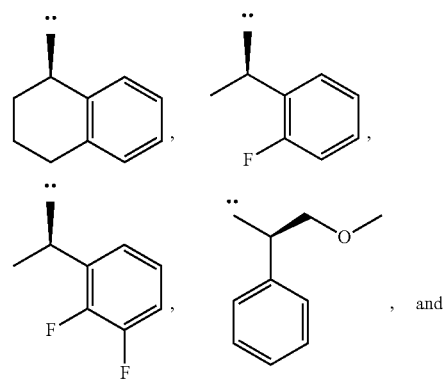

, and

-continued

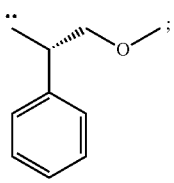

each occurrence of X in the compounds of Formulas (XXVII) or (XXVIII) is selected from —(CR$^{81}$R$^{82}$)$_m$—, optionally substituted heteroaryl or heterocyclyl,

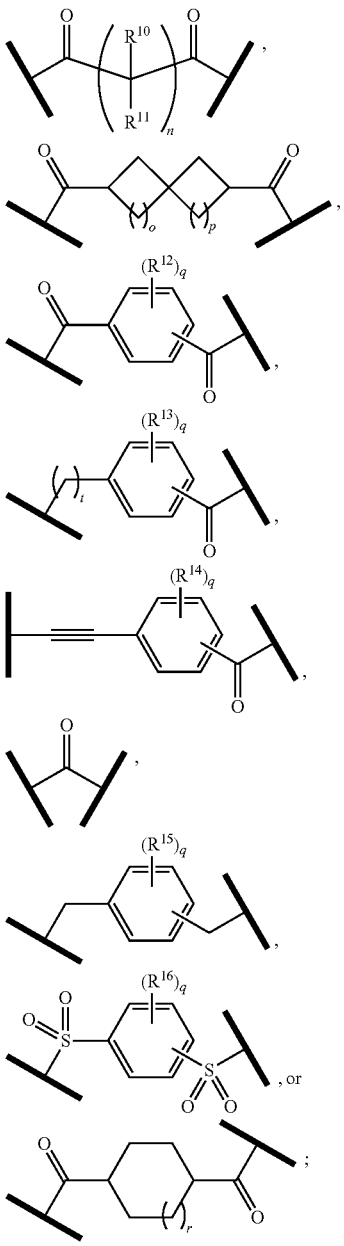

each occurrence of Z in the compound of Formula (XXVII) is absent or independently selected from the group consisting of C=O, —O—, —NR, —CONH—, and —NHCO—;

each occurrence of R$^{81}$ and R$^{82}$ in the compounds of Formulas (XXVII) or (XXVIII) is independently selected from the group consisting of hydrogen, halogen, alkyl, and cycloalkyl, or R$^{81}$ and R$^{82}$ can be taken together to form a carbocyclic ring;

each occurrence of R$^{10}$ and R$^{11}$ in

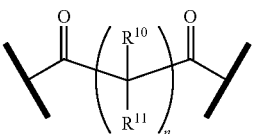

in the compounds of Formulas (XXVII) or (XXVIII) is independently selected from the group consisting of hydrogen, halogen and alkyl;

each occurrence of R$^{12}$, R$^{13}$, R$^{14}$, R$^{15}$ and R$^{16}$ in

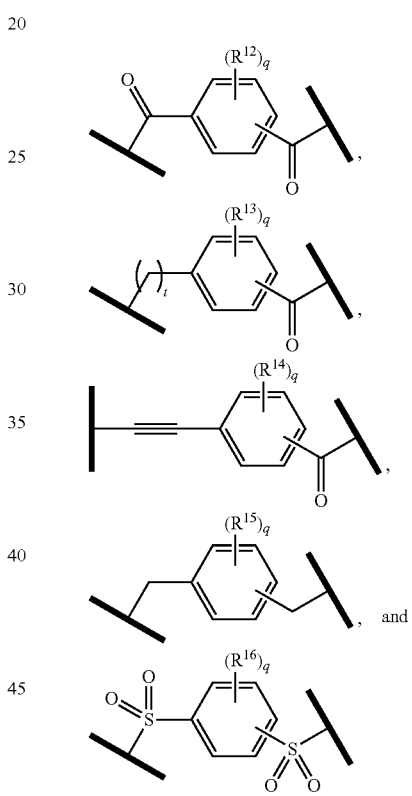

in the compounds of Formulas (XXVII) or (XXVIII) is independently selected from the group consisting of hydrogen, halogen, optionally substituted alkyl, and OR$^{17}$;

each occurrence of R$^{17}$ in the compounds of Formulas (XXVII) or (XXVIII) is independently selected from the group consisting of hydrogen, optionally substituted alkyl, and optionally substituted cycloalkyl;

each occurrence of m and n in —(CR$^{21}$R$^{22}$)$_m$— and

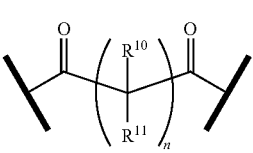

in the compounds of Formulas (XXVII) or (XXVIII) is independently 0, 1, 2, 3, or 4;

each occurrence of o and p in

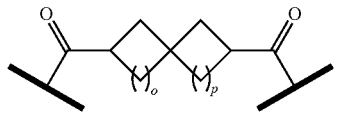

in the compounds of Formulas (XXVII) or (XXVIII) is independently 0, 1, 2 or 3;

each occurrence of q and t in

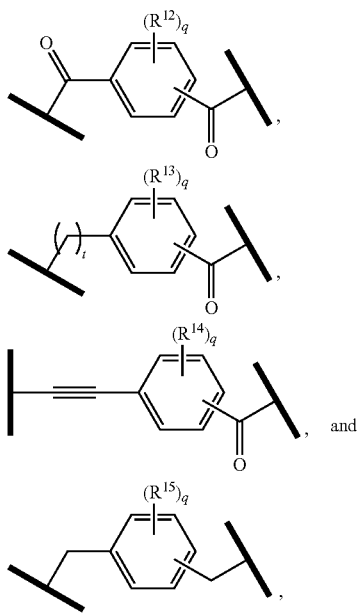

in the compounds of Formulas (XXVII) or (XXVIII) is independently 0, 1, 2, 3, or 4;

each occurrence of r in

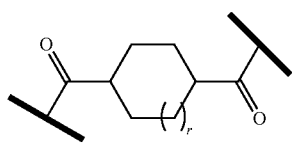

in the compounds of Formulas (XXVII) or (XXVIII) is 0 or 1.

In various embodiments, the ILM can have the structure of Formula (XXIX), (XXX), (XXXI), or (XXXII), as described in WO Pub. No. 2014/055461 and Bioorg. Med. Chem. Lett. 24(21), 5022-9 (2014), or an unnatural mimetic thereof, and the chemical linker to linker group L as shown:

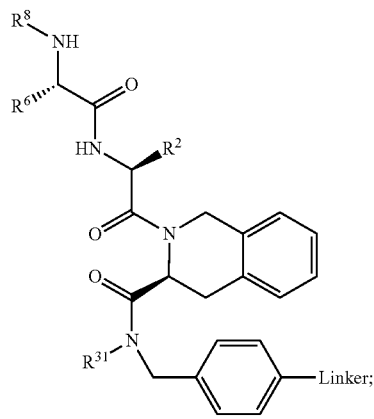
(XXIX)

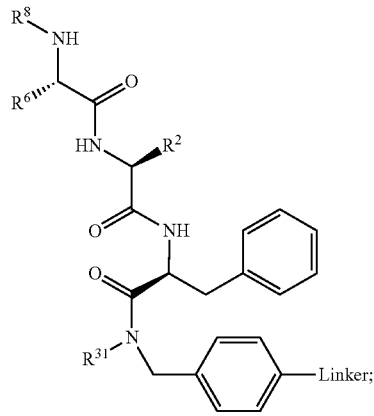
(XXX)

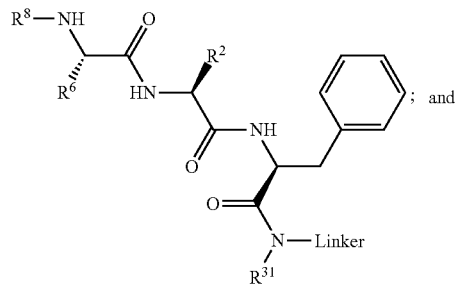
(XXXI)

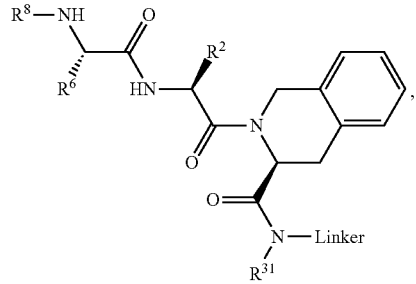
(XXXII)

wherein:

each occurrence of $R^2$ in the compounds of Formula (XXIX) through (XXXII) independently selected from the group consisting of alkyl, cycloalkyl, cycloalkylalkyl, heterocyclyl, arylalkyl, and aryl, each of which is optionally substituted;

or alternatively;

each occurrence $R^1$ and $R^2$ in the compounds of Formula (XXIX) through (XXXII) are independently selected from H, an optionally substituted thioalkyl —CR$^{60}$R$^{61}$SR$^{70}$ wherein R$^{60}$ and R$^{61}$ are selected from H or methyl, and R$^{70}$ is an optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$;

wherein:

at each occurrence in the compounds of Formula (XXIX) through (XXXII), v is independently an integer from 1-3;

each occurrence of R$^{20}$ and R$^{22}$ in the compounds of Formula (XXIX) through (XXXII) is independently selected from the group consisting of OH, NR$^{24}$R$^{25}$, and OR$^{26}$;

each occurrence of R$^{21}$ in the compounds of Formula (XXIX) through (XXXII) is independently the group NR$^{24}$R$^{25}$;

each occurrence of R$^{23}$ in the compounds of Formula (XXIX) through (XXXII) is independently selected from the group consisting of aryl and heterocyclyl, each of which is optionally substituted by one or more of alkyl or halogen;

each occurrence of R$^{24}$ in the compounds of Formula (XXIX) through (XXXII) is independently hydrogen or optionally substituted alkyl;

each occurrence of R$^{25}$ in the compounds of Formula (XXIX) through (XXXII) is independently selected from the group consisting of hydrogen, alkyl, branched alkyl, arylalkyl, heterocyclyl, —CH$_2$(OCH$_2$CH$_2$O)$_m$CH$_3$, and —[CH$_2$CH$_2$(CH$_2$)$_\delta$NH]$_\psi$CH$_2$CH$_2$(CH$_2$)$_{\overline{\omega}}$NH$_2$, each of which is optionally substituted, wherein δ is a whole number from 0-2, $\overline{\psi}$ is an integer from 1-3, and $\overline{\omega}$ is a whole number from 0-2. In various embodiments, R$^{25}$ in the compounds of Formula (XXII) or (XXIII) is spermine or spermidine.

Each occurrence of R$^{26}$ in the compounds of Formula (XXIX) through (XXXII) is independently alkyl, optionally substituted by one or more of OH, halogen, or NH$_2$;

at each occurrence in the compounds of Formula (XXIX) through (XXXII) m is independently an integer from 1-8;

each occurrence of R$^6$ and R$^8$ in the compounds of Formula (XXIX) through (XXXII) is independently selected from the group consisting of hydrogen, optionally substituted alkyl, and optionally substituted cycloalkyl; and each occurrence of R$^{31}$ in the compounds of Formulas (XXIX) through (XXXII) is independently selected from the group consisting of alkyl, aryl, arylalkyl, heteroaryl or heteroarylalkyl, each of which is optionally substituted. In various embodiments, R$^{31}$ in the compounds of Formulas (XXIX) through (XXXII) is independently selected from the group consisting of

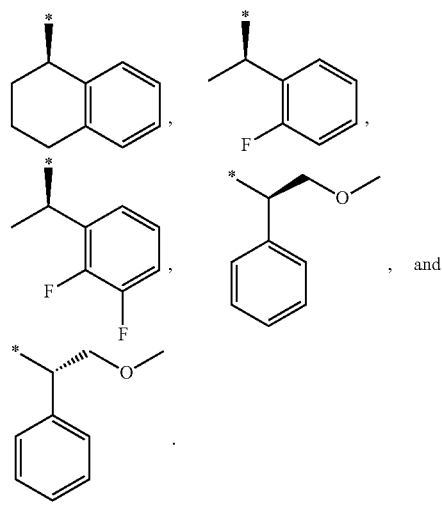

In certain embodiments, the ILM of the compound is:

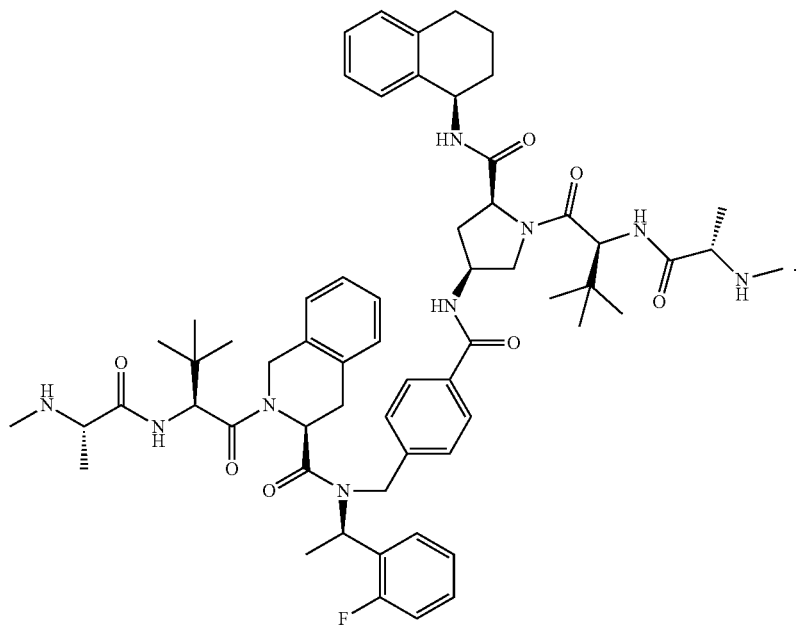

In various embodiments, the ILM can have the structure of Formula (XXXIII), as described in WO Pub. No. 2014/074658 and WO Pub. No. 2013/071035, or an unnatural mimetic thereof:

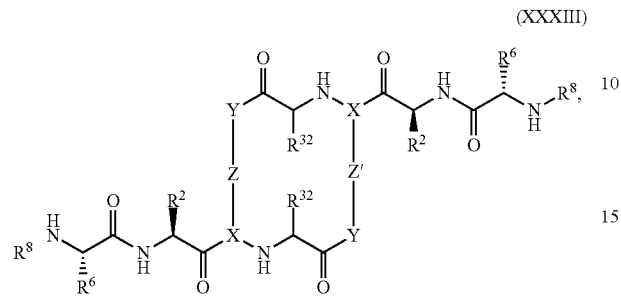
(XXXIII)

wherein:

each occurrence of $R^2$ in the compound of Formula (XXXIII) is independently selected from H, alkyl, cycloalkyl, cycloalkylalkyl, heterocyclyl, arylalkyl, and aryl, each of which is optionally substituted;

each occurrence of $R^6$ and $R^8$ in the compound of Formula (XXXIII) is independently selected from the group consisting of hydrogen, optionally substituted alkyl, and optionally substituted cycloalkyl;

each occurrence of $R^{32}$ in the compound of Formula (XXXIII) is selected from $(C_1$-$C_4$ alkylene)-$R^{33}$ wherein $R^{33}$ is selected from the group consisting of hydrogen, aryl, heteroaryl, and cycloalkyl, each of which is optionally further substituted;

each occurrence of X in the compound of Formula (XXXIII) is independently selected from the group consisting of:

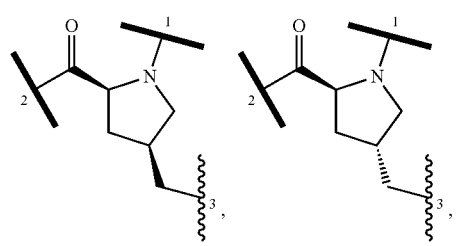

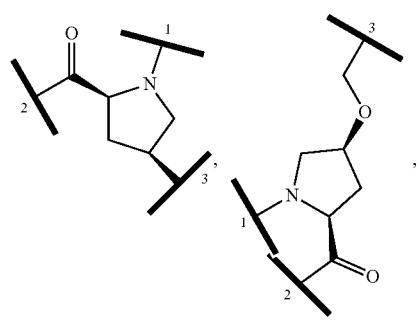

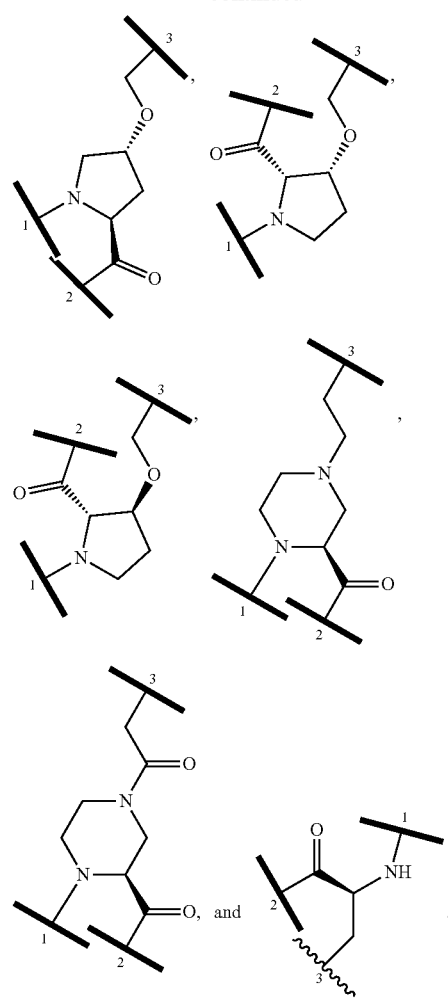

Each occurrence of Z and Z' in the compound of Formula (XXXIII) is independently selected from the group consisting of:

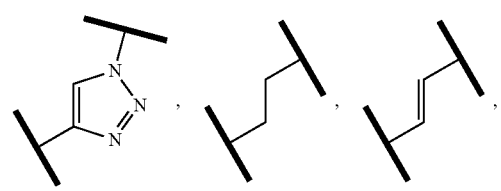

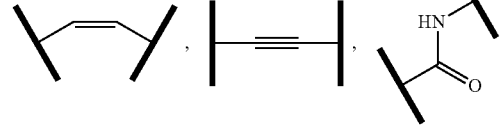

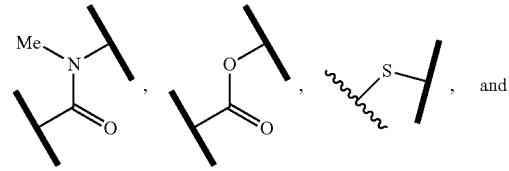
and

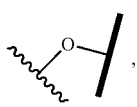

wherein each

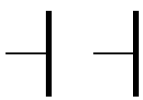

represents a point of attachment to the compound, with the proviso that Z and Z' cannot both be

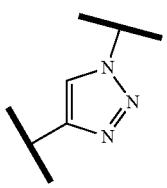

in any given compound;

each occurrence of Y in the compound of Formula (XXXIII) is independently selected from the group consisting of:

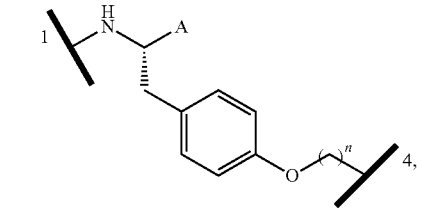

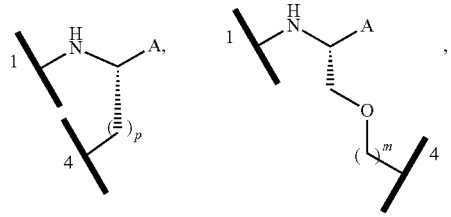

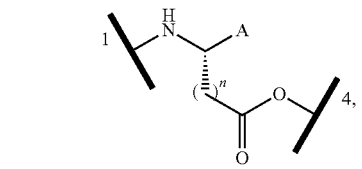

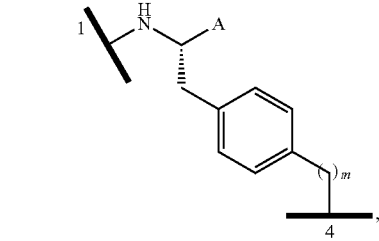

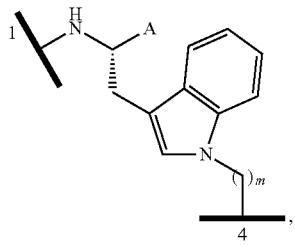

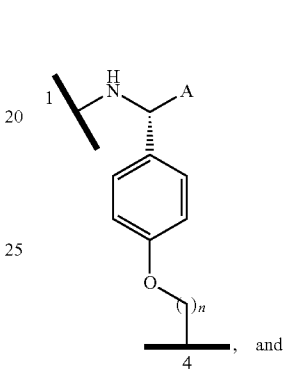

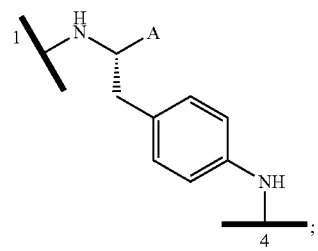

and wherein Z and Z' in the compound of Formula (XXXIII) are the same and Z is

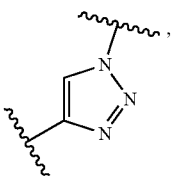 [SMILES: *c1cn(*)nn1]

wherein each

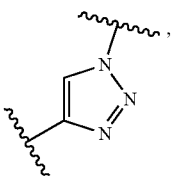 [SMILES: *c1cn(*)nn1]

represents a point of attachment to the compound, and each occurrence of X in the compound of Formula (XXXIII) is selected from the group consisting of:

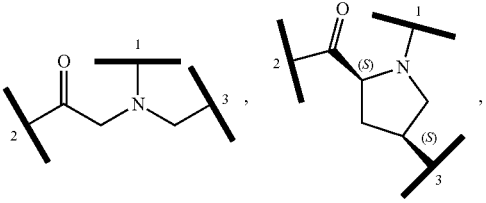

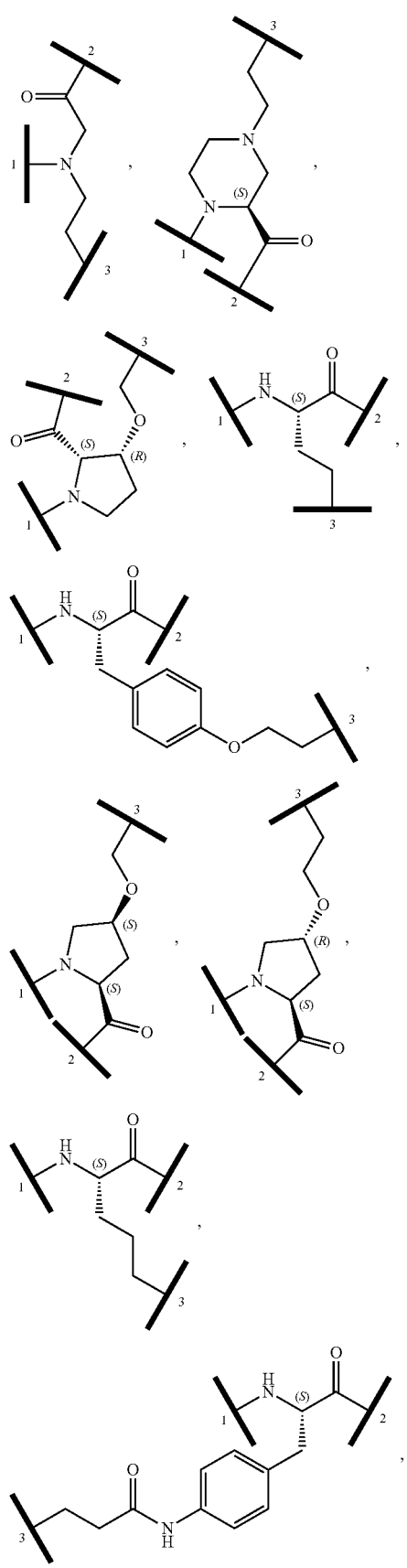
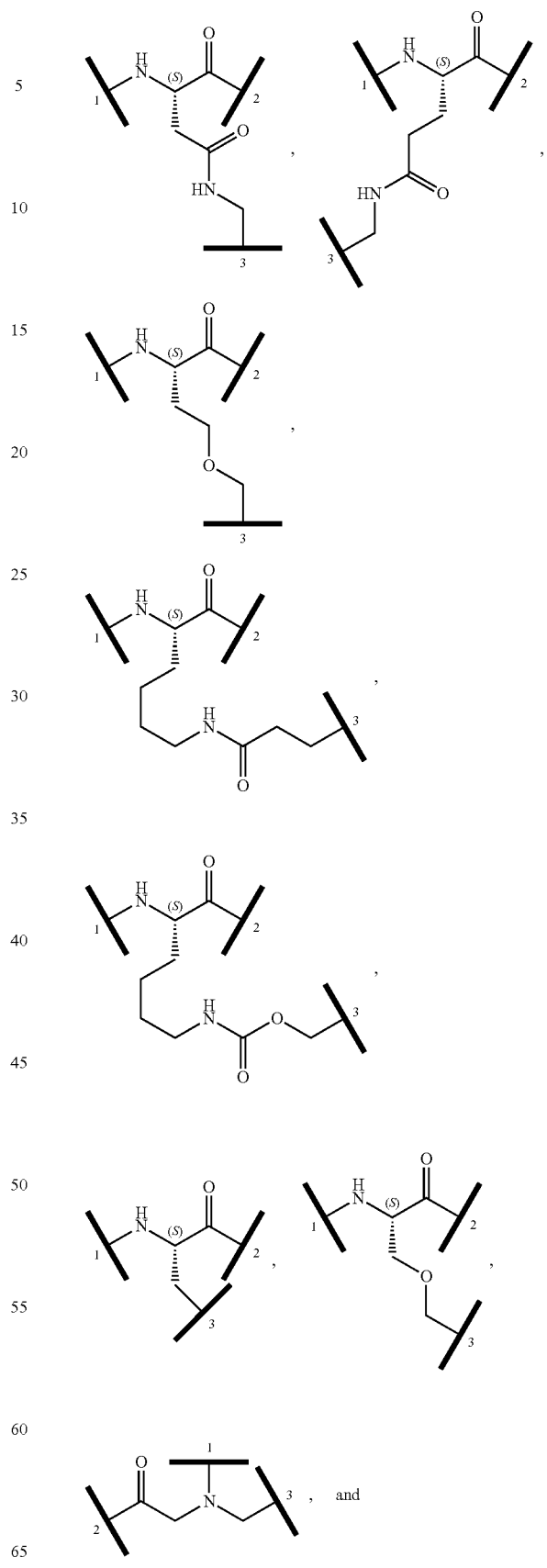

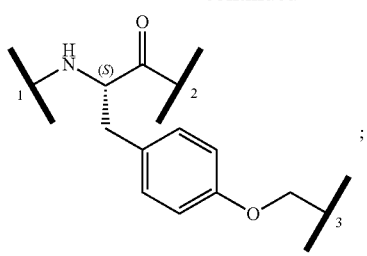
each occurrence of Y in the compound of Formula (XXXIII) is independently selected from the group consisting of:
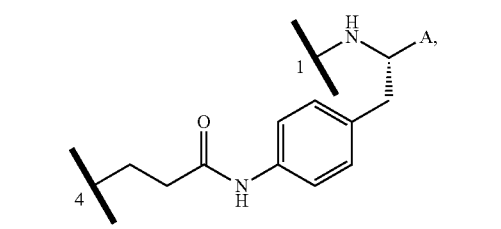
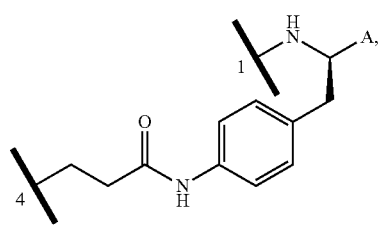
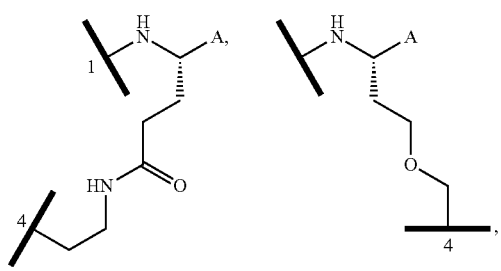
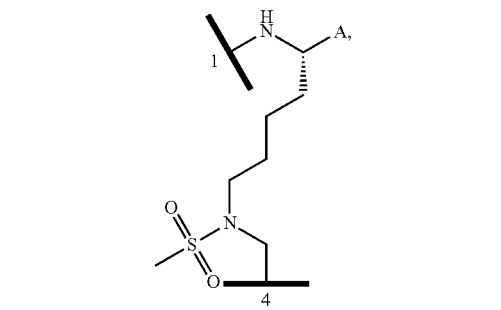
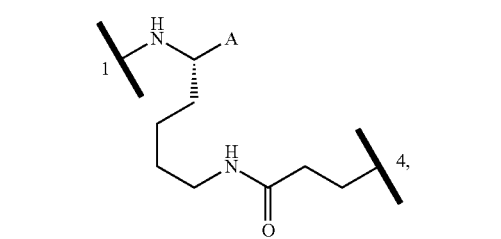
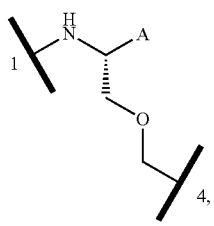
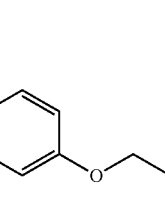
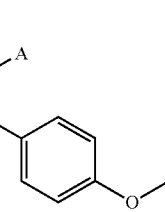
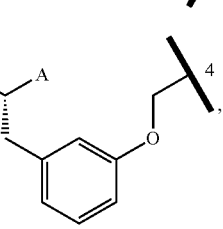
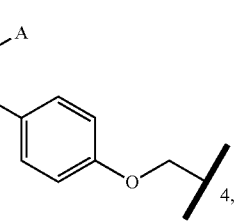

-continued

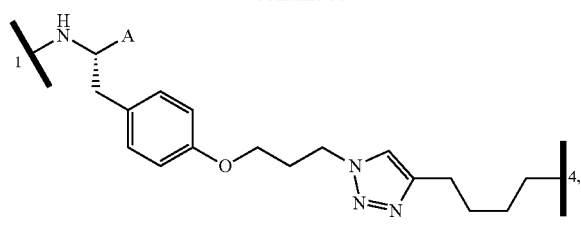

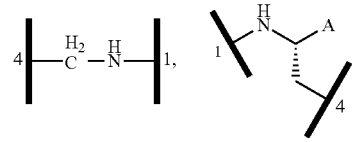

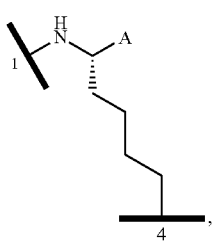

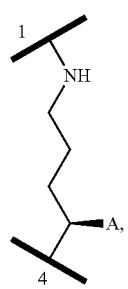

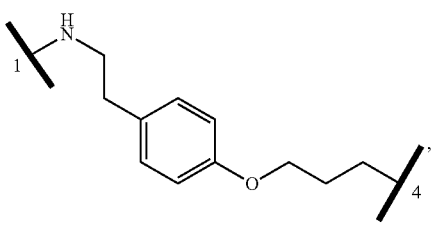

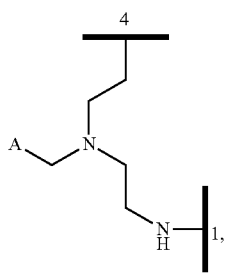

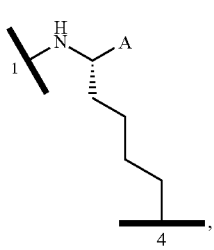

-continued

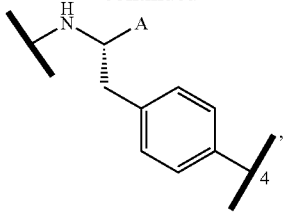

and

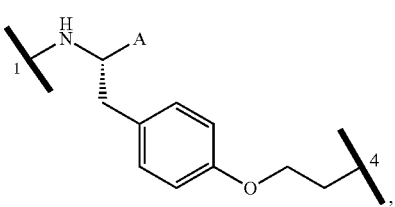

wherein:

represents a point of attachment to a —C=O portion of the compound;

represents a point of attachment to a —NH portion of the compound;

represents a first point of attachment to Z;

represents a second point of attachment to Z;
at each occurrence in the compound of Formula (XXXIII), m is independently an integer from 0-3;
at each occurrence in the compound of Formula (XXXIII), n is independently an integer from 1-3;
at each occurrence in the compound of Formula (XXXIII), p is independently an integer from 0-4; and
A in the compound of Formula (XXXIII) is —C(=O)R$^3$.
Each occurrence of R$^3$ in the compound of Formula (XXXIII) is independently selected from the group consisting of OH, NHCN, NHSO$_2$R$^{10}$, NHOR$^{11}$, and N(R$^{12}$)(R$^{13}$);
each occurrence of R$^{10}$ and R$^{11}$ in the compound of Formula (XXXIII) is independently selected from the group consisting of hydrogen, optionally substituted —C$_1$-C$_4$ alkyl, cycloalkyl, aryl, heteroaryl, heterocyclyl, and heterocycloalkyl;

each occurrence of R$^{12}$ and R$^{13}$ in the compound of Formula (XXXIII) is independently selected from the group consisting of hydrogen, —C$_1$-C$_4$ alkyl, —(C$_1$-C$_4$) alkylene)-NH—(C$_1$-C$_4$ alkyl), and —(C$_1$-C$_4$ alkylene)-O—(C$_1$-C$_4$ hydroxyalkyl), or R$^{12}$ and R$^{13}$ taken together with the nitrogen atom to which they are commonly bound form a saturated heterocyclyl optionally comprising one additional heteroatom selected from N, O and S, and wherein the saturated heterocycle is optionally substituted with methyl.

In various embodiments, the ILM can have the structure of Formula (XXXIV) or (XXXV), as described in WO Pub. No. 2014/047024, or an unnatural mimetic thereof:

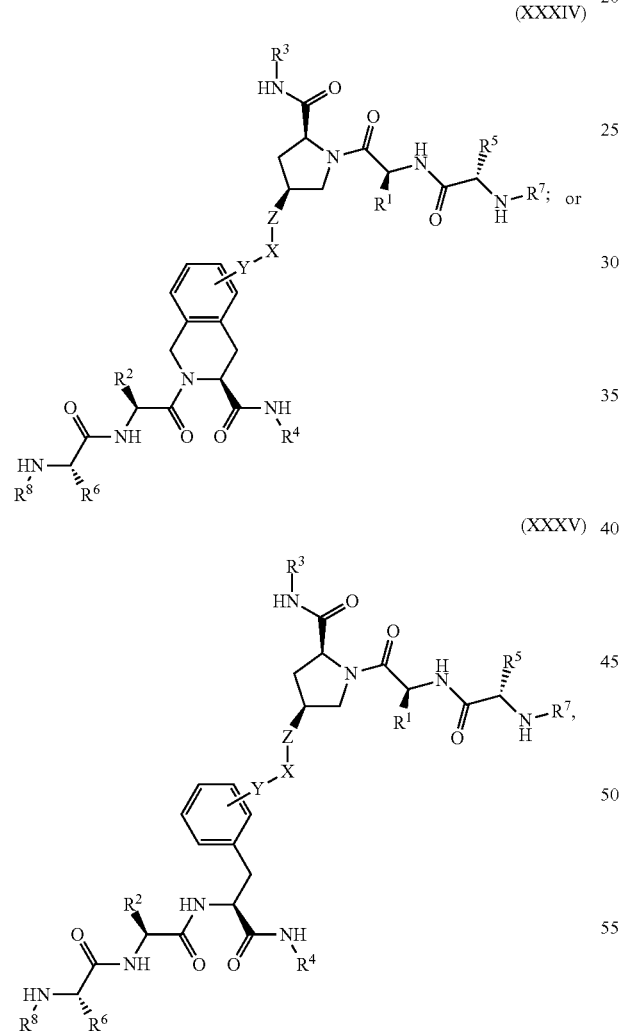

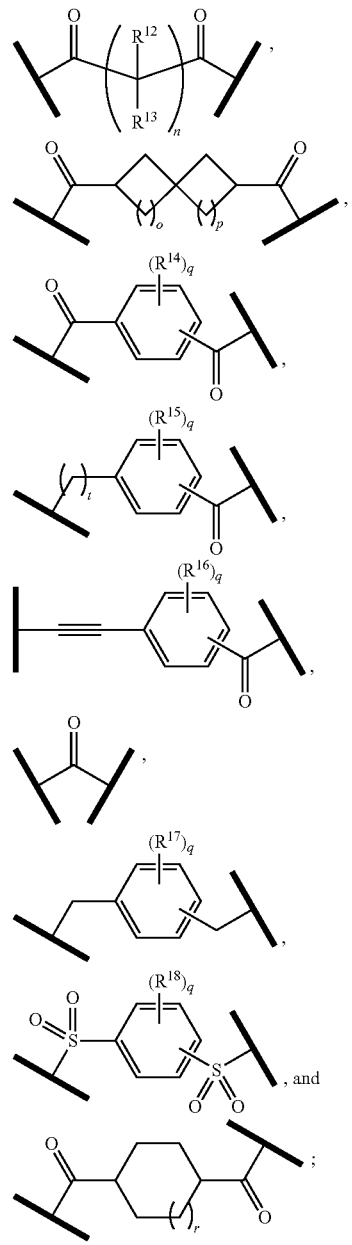

wherein:

each occurrence of X in the compound of Formula (XXXIV) or (XXXV) is absent or a independently selected from the group consisting of —(CR$^{10}$R$^{11}$)$_m$—, optionally substituted heteroaryl, optionally substituted heterocyclyl, each occurrence of Y and Z in the compounds of Formula (XXXIV) or (XXXV) is absent or independently selected from the group consisting of C(=O), —O—, —NR$^9$—, —CONH—, and —NHCO—;

each occurrence of R$^1$ and R$^2$ in the compounds of Formula (XXXIV) or (XXXV) is independently selected from the group consisting of alkyl, cycloalkyl, cycloalkylalkyl, arylalkyl, aryl, each of which is optionally substituted; or each occurrence of R$^1$ and R$^2$ in the compounds of Formula (XXXIV) or (XXXV) is an optionally substituted thioalkyl wherein the substituents attached to the S atom of the thioalkyl are independently selected from the group consisting of optionally substituted alkyl, optionally substituted branched alkyl, optionally substituted heterocyclyl, —(CH$_2$)$_v$COR$^{20}$, —CH$_2$CHR$^{21}$COR$^{22}$, and —CH$_2$R$^{23}$; wherein at each occurrence in the compounds of Formula (XXXIV) or (XXXV), v is independently an integer from 1-3;

each occurrence of $R^{20}$ and $R^{22}$ in the compounds of Formula (XXXIV) or (XXXV) is independently selected from the group consisting of OH, $NR^{24}R^{25}$, and $OR^{26}$;

each occurrence of $R^{21}$ in the compounds of Formula (XXXIV) or (XXXV) is independently the group $NR^{24}R^{25}$;

each occurrence of $R^{23}$ in the compounds of Formula (XXXIV) or (XXXV) is independently selected from the group consisting of aryl and heterocyclyl, each of which is optionally substituted by one or more of alkyl or halogen;

each occurrence of $R^{24}$ in the compounds of Formula (XXXIV) or (XXXV) is independently hydrogen or optionally substituted alkyl;

each occurrence of $R^{25}$ in the compounds of Formula (XXXIV) or (XXXV) is independently selected from the group consisting of hydrogen, alkyl, branched alkyl, arylalkyl, heterocyclyl, $-CH_2(OCH_2CH_2O)_mCH_3$, and $-[CH_2CH_2(CH_2)_\S NH]_\psi CH_2CH_2(CH_2)_{\overline{\omega}}NH_2$, each of which is optionally substituted, wherein § is a whole number from 0-2, ψ is an integer from 1-3, and $\overline{\omega}$ is a whole number from 0-2. In various embodiments, $R^{25}$ in the compounds of Formula (XXII) or (XXIII) is spermine or spermidine.

Each occurrence of $R^{26}$ in the compounds of Formula (XXXIV) or (XXXV) is independently alkyl, optionally substituted by one or more of OH, halogen, or $NH_2$;

at each occurrence in the compounds of Formula (XXXIV) or (XXXV) m is independently an integer from 1-8;

each occurrence of $R^3$ and $R^4$ in the compounds of Formula (XXXIV) or (XXXV) is independently selected from the group consisting of alkyl, cycloalkyl, aryl, arylalkyl, arylalkoxy, heteroaryl, heterocyclyl, heteroarylalkyl, and heterocycloalkyl, each of which is optionally substituted by one or more of alkyl, halogen, or OH;

each occurrence of $R^5$, $R^6$, $R^7$ and $R^8$ in the compounds of Formula (XXXIV) or (XXXV) is independently selected from the group consisting of hydrogen, optionally substituted alkyl, and optionally substituted cycloalkyl;

each occurrence of $R^{10}$ and $R^{11}$ in the compounds of Formula (XXXIV) or (XXXV) is independently selected from the group consisting of hydrogen, halogen, and optionally substituted alkyl;

each occurrence $R^{12}$ and $R^{13}$ in the compounds of Formula (XXXIV) or (XXXV) is independently selected from hydrogen, halogen or optionally substituted alkyl, or $R^{12}$ and $R^{13}$ can be taken together to form a carbocyclic ring;

$R^{14}$, $R^{15}$, $R^{16}$, $R^{17}$ and $R^{18}$ of

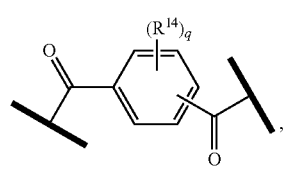

-continued

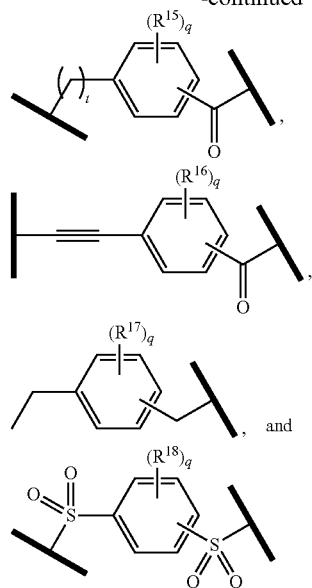

are independently selected from hydrogen, halogen, optionally substituted alkyl or $OR^{19}$;

each occurrence of $R^{19}$ in the compounds of Formula (XXXIV) or (XXXV) is independently selected from hydrogen, optionally substituted alkyl or optionally substituted cycloalkyl;

each occurrence of m and n in the compounds of Formula (XXXIV) or (XXXV) is independently 0, 1, 2, 3, or 4;

each occurrence of o and p in the compounds of Formula (XXXIV) or (XXXV) is independently 0, 1, 2 or 3;

each occurrence of q in the compounds of Formula (XXXIV) or (XXXV) is independently 0, 1, 2, 3, or 4;

at each occurrence in the compounds of Formula (XXXIV) or (XXXV), r is independently 0 or 1;

each occurrence of t in the compounds of Formula (XXXIV) or (XXXV) is independently 1, 2, or 3.

In various embodiments, the ILM can have the structure of Formula (XXXVI), as described in WO Pub. No. 2014/025759, or an unnatural mimetic thereof:

(XXXVI)

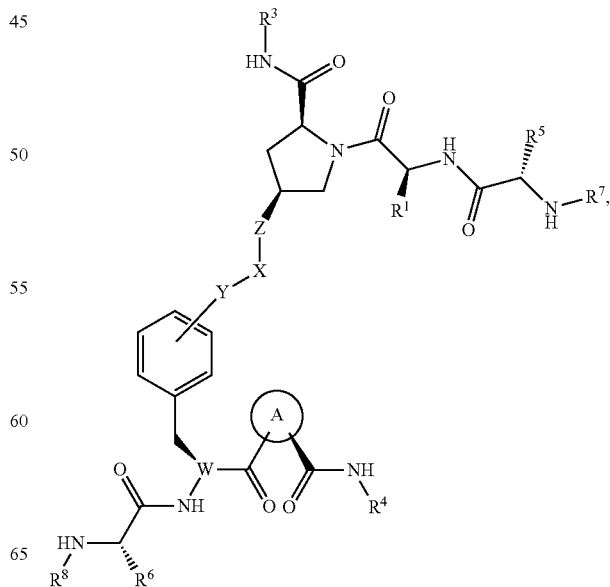

where:
each occurrence of A of Formula (XXXVI) is independently selected from:

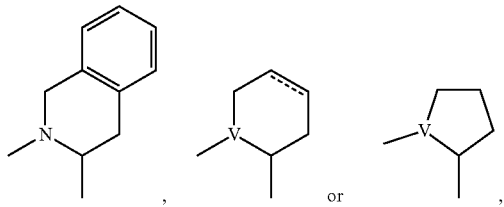

where the dotted line represents an optional double bond;
each occurrence of X of Formula (XXXVI) is independently selected from: —(CR²¹R²²)$_m$—,

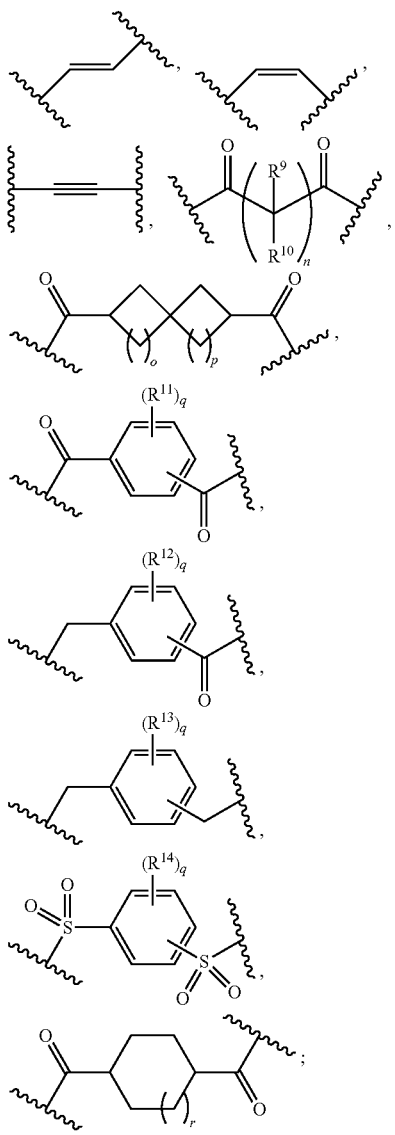

each occurrence of Y and Z of Formula (XXXVI) is independently selected from —O—, —NR⁶— or are absent;

each occurrence of V of Formula (XXXVI) is independently selected from —N— or —CH—;
each occurrence of W of Formula (XXXVI) is independently selected from —CH— or —N—;
each occurrence of R¹ of Formula (XXXVI) is independently selected from an optionally substituted alkyl, optionally substituted cycloalkyl, optionally substituted cycloalkylalkyl, optionally substituted arylalkyl or optionally substituted aryl;
each occurrence of R³ and R⁴ of Formula (XXXVI) is independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;
each occurrence of R⁵, R⁶, R⁷ and R⁸ of Formula (XXXVI) is independently selected from hydrogen, optionally substituted alkyl or optionally substituted cycloalkyl, or preferably methyl;
each occurrence of R⁹ and R¹⁰ of

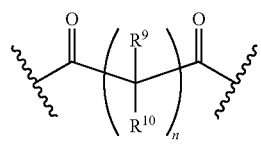

of Formula (XXXVI) is independently selected from hydrogen, halogen or optionally substituted alkyl, or R⁹ and R¹⁰ can be taken together to form a ring;
each occurrence of R¹¹, R¹², R¹³ and R¹⁴ of

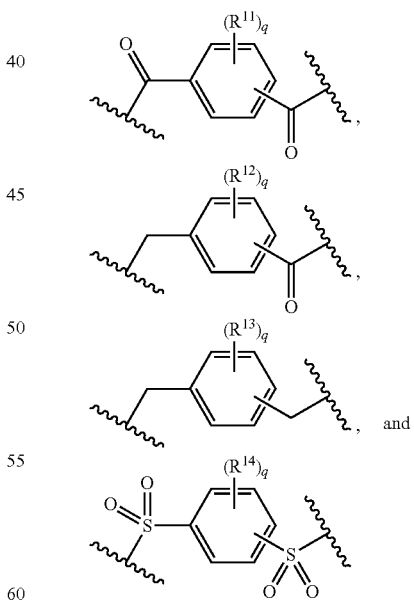

of Formula (XXXVI) is independently selected from hydrogen, halogen, optionally substituted alkyl or OR¹⁵;
each occurrence of R¹⁵ of OR¹⁵ of Formula (XXXVI) is independently selected from hydrogen, optionally substituted alkyl or optionally substituted cycloalkyl;

each occurrence of m and n of —(CR²¹R²²)ₘ— and

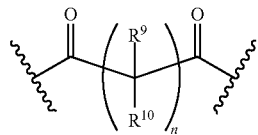

of Formula (XXXVI) is independently selected from 0, 1, 2, 3, or 4;

each occurrence of o and p of

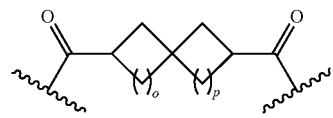

of Formula (XXXVI) is independently selected from 0, 1, 2 or 3;

each occurrence of q of

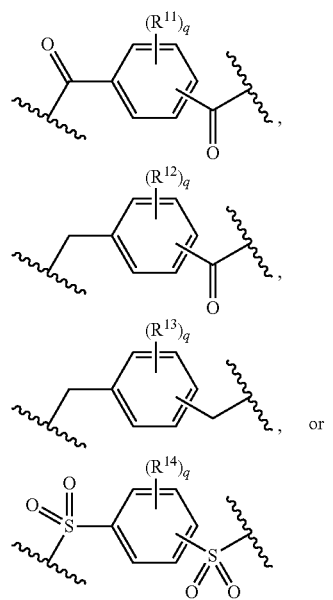

of Formula (XXXVI) is independently selected from 0, 1, 2, 3, or 4;

each occurrence of r of

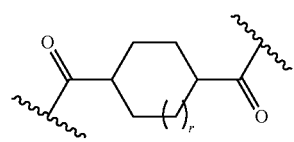

of Formula (XXXVI) is independently selected from 0 or 1.

In various embodiments, the ILM can have the structure of Formula (XXXVII) or (XXXVIII), as described in WO Pub. No. 2014/011712, or an unnatural mimetic thereof:

(XXXVII)

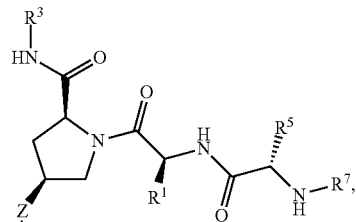

(XXXVIII)

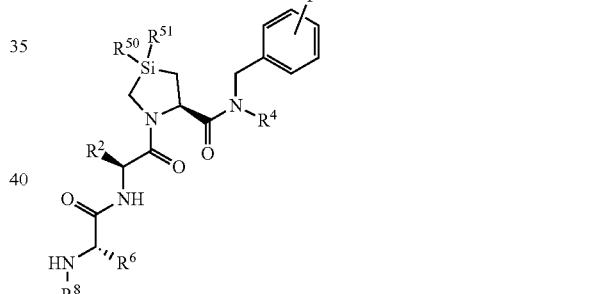

wherein:

each occurrence of X of Formulas (XXXVII) and (XXXVIII) is independently —(CR¹⁶R¹⁷)ₘ—,

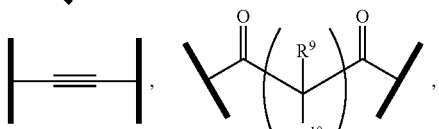

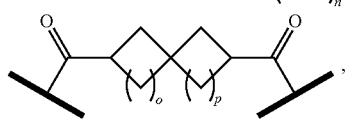

-continued

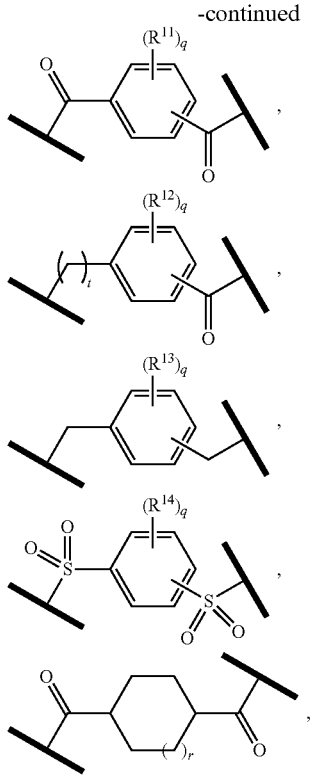

or absent;

each occurrence of Y and Z of Formula (XXXVII) and (XXXVIII) is independently selected from —O—, C=O, $NR^6$ or are absent;

each occurrence of $R^1$ and $R^2$ of Formula (XXXVII) and (XXXVIII) is independently selected from optionally substituted alkyl, optionally substituted cycloalkyl, optionally substituted alkylaryl or optionally substituted aryl;

each occurrence of $R^3$ and $R^4$ of Formula (XXXVII) and (XXXVIII) is independently selected from optionally substituted alkyl, optionally substituted cycloalkyl, optionally substituted cycloalkylalkyl, optionally substituted arylalkyl or optionally substituted aryl;

each occurrence of $R^5$ and $R^6$ of Formula (XXXVII) and (XXXVIII) is independently selected from optionally substituted alkyl or optionally substituted cycloalkyl;

each occurrence of $R^7$ and $R^8$ of Formula (XXXVII) and (XXXVIII) is independently selected from hydrogen, optionally substituted alkyl or optionally substituted cycloalkyl, or preferably methyl;

each occurrence of $R^9$ and $R^{10}$ of

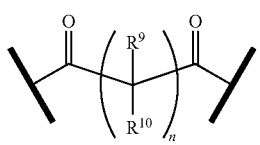

of Formula (XXXVII) and (XXXVIII) is independently selected from hydrogen, optionally substituted alkyl, or $R^9$ and $R^{10}$ may be taken together to form a ring;

each occurrence $R^{11}$ to $R^{14}$ of

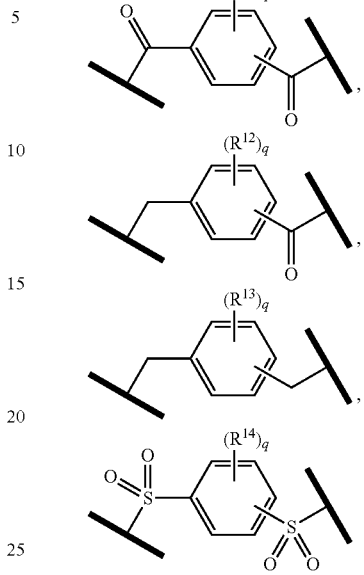

of Formula (XXXVII) and (XXXVIII) is independently selected from hydrogen, halogen, optionally substituted alkyl or $OR^{15}$;

each occurrence of $R^{15}$ of $OR^{15}$ of Formula (XXXVII) and (XXXVIII) is independently selected from hydrogen, optionally substituted alkyl or optionally substituted cycloalkyl;

each occurrence of $R^{16}$ and $R^{17}$ of $—(CR^{16}R^{17})_m—$ of Formula (XXXVII) and (XXXVIII) is independently selected from hydrogen, halogen or optionally substituted alkyl;

each occurrence of $R^{50}$ and $R^{51}$ of Formula (XXXVII) and (XXXVIII) is independently selected from optionally substituted alkyl, or $R^{50}$ and $R^{51}$ are taken together to form a ring;

each occurrence of m and n of $—(CR^{16}R^{17})_m—$ and

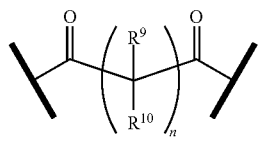

of Formula (XXXVII) and (XXXVIII) is independently an integer from 0-4;

each occurrence of o and p of

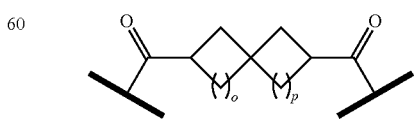

of Formula (XXXVII) and (XXXVIII) is independently an integer from 0-3;

each occurrence of q of

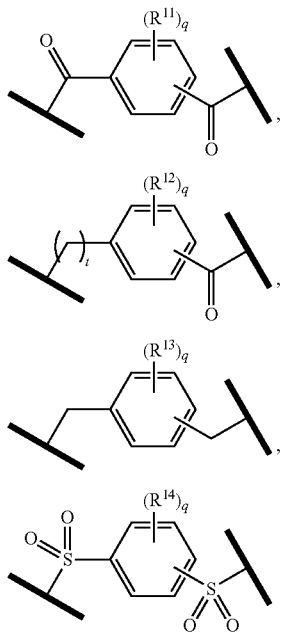

of Formula (XXXVII) and (XXXVIII) is independently an integer from 0-4; and each occurrence of r of

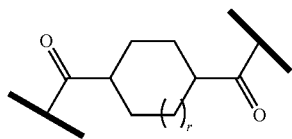

of Formula (XXXVII) and (XXXVIII) is independently an integer from 0-1.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In various embodiments, the ILM can have the structure of Formula (XXXIX) or (XL), as described in WO Pub. No. 2013/071039, or an unnatural mimetic thereof:

(XXXIX)

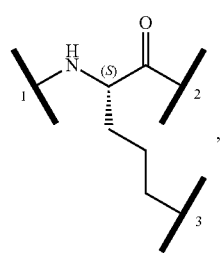

(XL)

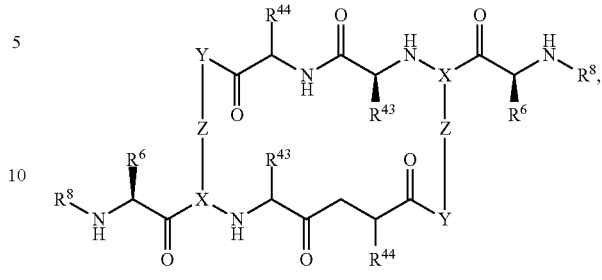

wherein:

each occurrence of $R^{43}$ and $R^{44}$ of Formulas (XXXIX) and (XL) is independently selected from hydrogen, alkyl, aryl, arylalkyl, heteroaryl, heteroarylalkyl, cycloalkyl, cycloalkylalkyl further optionally substituted, and each occurrence of $R^6$ and $R^8$ of Formula (XXXIX) and (XL) is independently selected from hydrogen, optionally substituted alkyl or optionally substituted cycloalkyl.

each occurrence of X of Formulas (XXXIX) and (XL) is independently selected from:

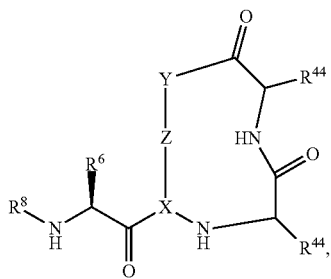

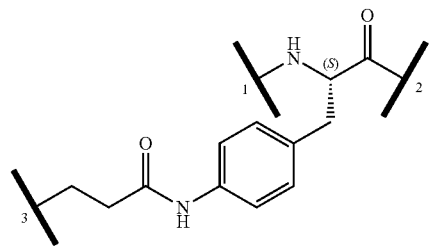

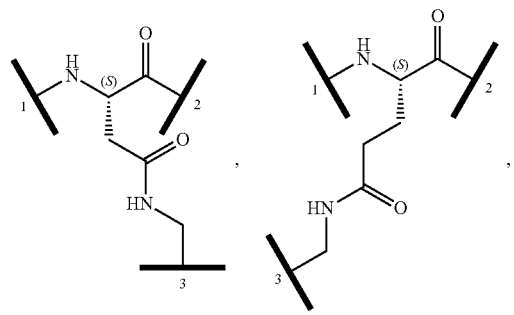

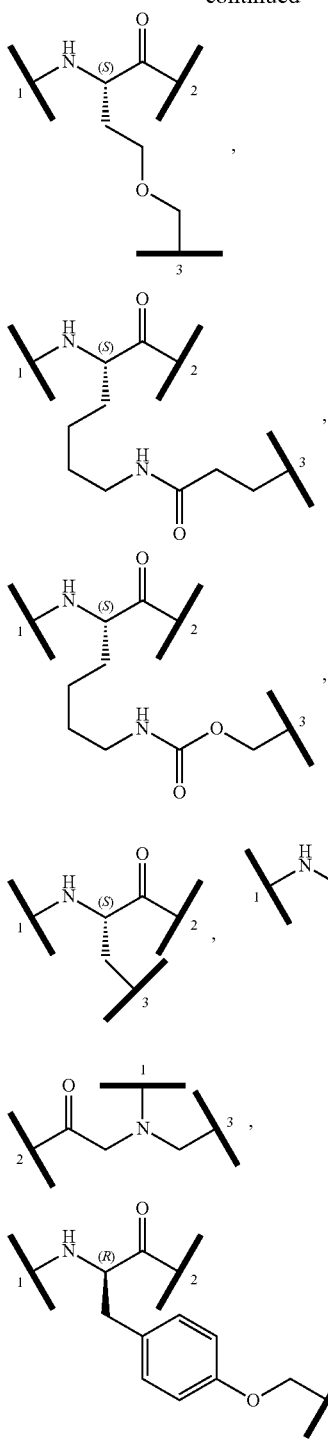
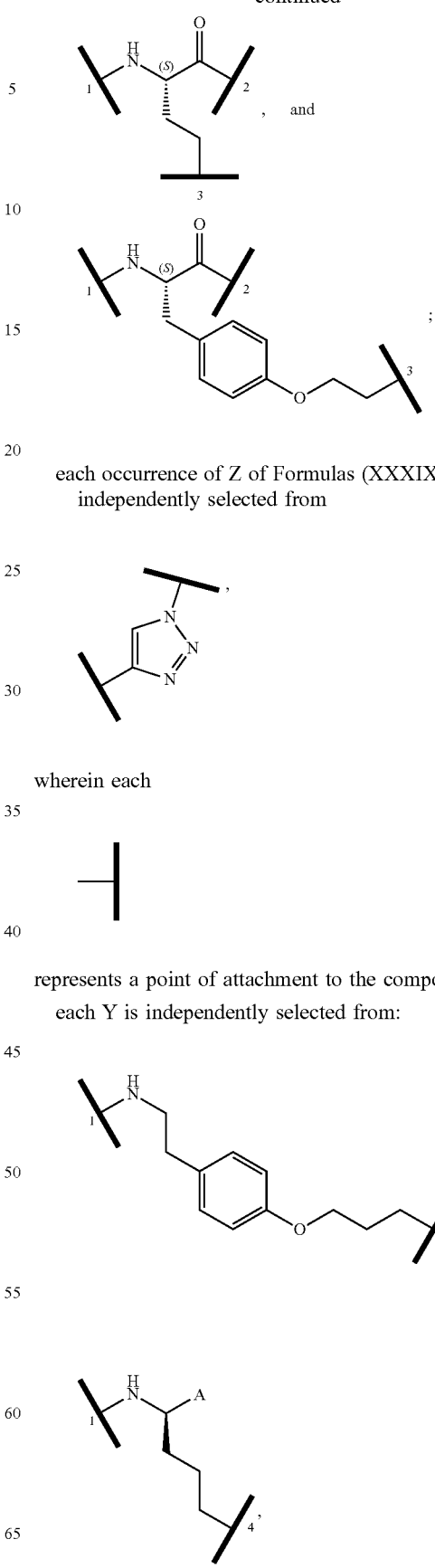
each occurrence of Z of Formulas (XXXIX) and (XL) is independently selected from
wherein each
represents a point of attachment to the compound; and each Y is independently selected from:

93
-continued
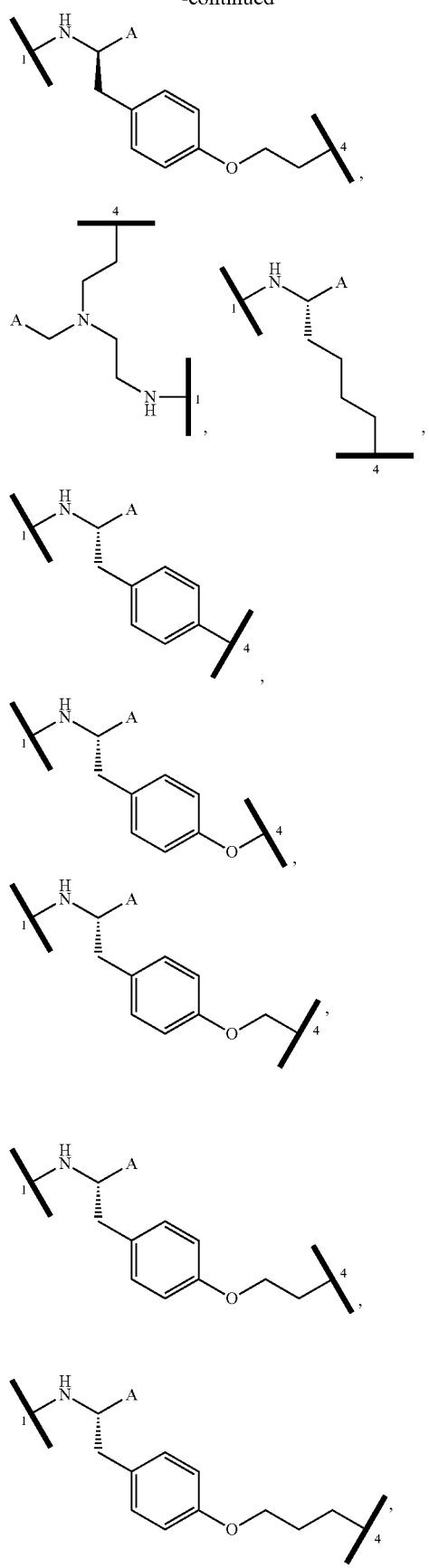
94
-continued
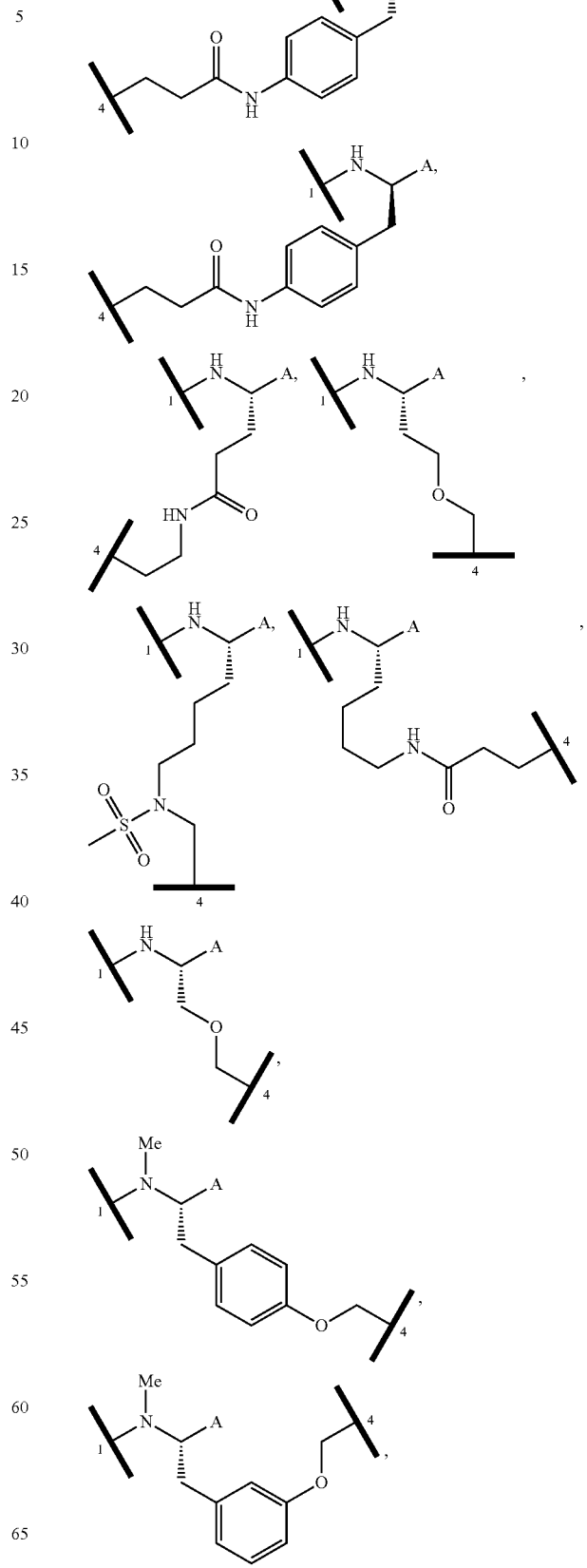

-continued

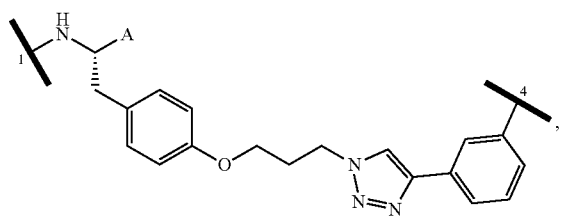

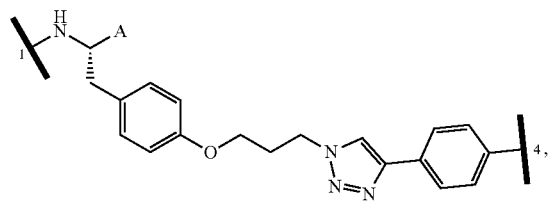

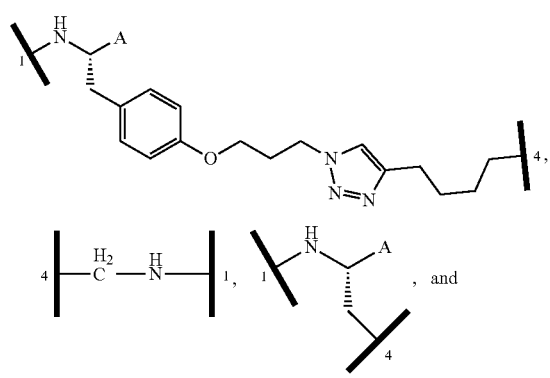

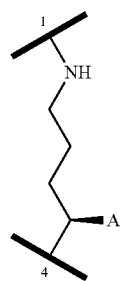

wherein:

represents a point of attachment to a —C(=O) portion of the compound;

represents a point of attachment to an amino portion of the compound;

represents a first point of attachment to Z;

represents a second point of attachment to Z; and
each occurrence of A of Formulas (XXXIX) and (XL) is independently selected from —C(=O)R³ or

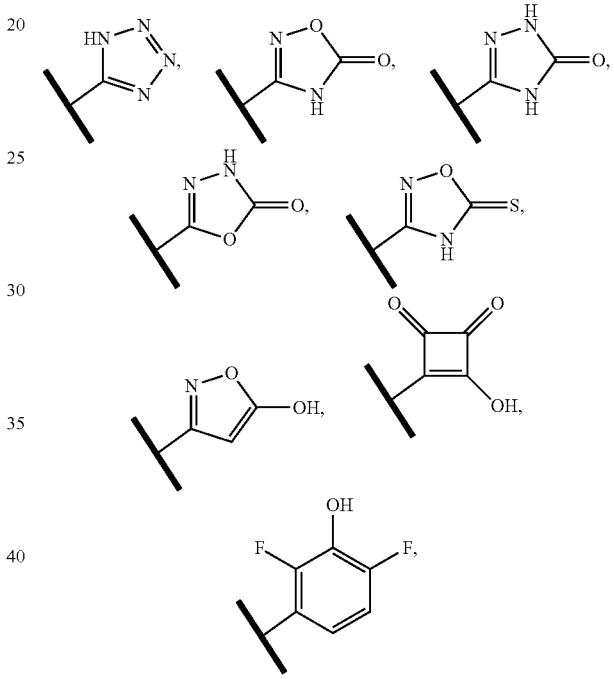

or a tautomeric form of any of the foregoing, wherein:
each occurrence of R³ of —C(=O)R³ of Formulas (XXXIX) and (XL) is selected from OH, NHCN, NHSO₂R¹⁰, NHOR¹¹ or N(R¹²)(R¹³);
each occurrence of R¹⁰ and R¹¹ of NHSO₂R¹⁰ and NHOR¹¹ of Formulas (XXXIX) and (XL) is independently selected from —C₁-C₄ alkyl, cycloalkyl, aryl, heteroaryl, or heterocycloalkyl, any of which are optionally substituted, and hydrogen;
each occurrence of R¹² and R¹³ of N(R¹²)(R¹³) of Formulas (XXXIX) and (XL) is independently selected from hydrogen, —C₁-C₄ alkyl, —(C₁-C₄ alkylene)-NH—(C₁-C₄ alkyl), benzyl, —(C₁-C₄ alkylene)-C(=O)OH, —(C₁-C₄ alkylene)-C(=O)CH₃, —CH(benzyl)-COOH, —C₁-C₄ alkoxy, and (C₁-C₄ alkylene)-O—(C₁-C₄ hydroxy alkyl); or R¹² and R¹³ of N(R¹²)(R¹³) are taken together with the nitrogen atom to which they are commonly bound to form a saturated heterocyclyl optionally comprising one additional heteroatom selected from N, O and S, and wherein the saturated heterocycle is optionally substituted with methyl.

In various embodiments, the ILM can have the structure of Formula (XLI) as described in WO Pub. No. 2013/071039, or an unnatural mimetic thereof:

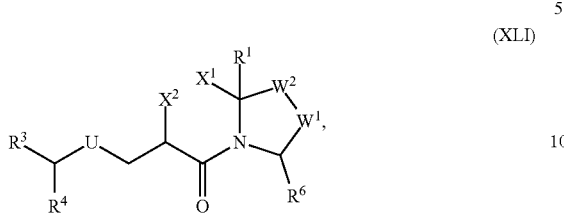

(XLI)

wherein:
each occurrence of $W^1$ of Formula (XLI) is independently selected from O, S, N—$R^A$, or $C(R^{8a})(R^{8b})$;
each occurrence of $W^2$ of Formula (XLI) is independently selected from O, S, N—$R^A$, or $C(R^{8c})(R^{8d})$; provided that $W^1$ and $W^2$ are not both O, or both S;
each occurrence of $R^1$ of Formula (XLI) is independently selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
when each occurrence of $X^1$ of Formula (XLI) is independently selected from O, N—$R^A$, S, S(=O), or S(=O)$_2$, then $X^2$ is $C(R^{2a}R^{2b})$;
or:
each occurrence of $X^1$ of Formula (XLI) is independently selected from $CR^{2c}R^{2d}$ and $X^2$ is $CR^{2a}R^{2b}$, and $R^{2c}$ and $R^{2a}$ together form a bond;
or:
each occurrence of $X^1$ and $X^2$ of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;
or:
each occurrence of $X^1$ of Formula (XLI) is independently selected from $CH_2$ and $X^2$ is C(=O), C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
each occurrence of $R^A$ of N—$R^A$ of Formula (XLI) is independently selected from H, $C_1$-$C_6$alkyl, —C(=O) $C_1$-$C_2$alkyl, substituted or unsubstituted aryl, or substituted or unsubstituted heteroaryl;
each occurrence of $R^{2a}$, $R^{2b}$, $R^{2c}$, $R^{2d}$ of $CR^{2c}R^{2d}$ and $CR^{2a}R^{2b}$ of Formula (XLI) is independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
each occurrence of $R^B$ of —C(=O)$R^B$ of Formula (XLI) is independently selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;
each occurrence of RD and $R^E$ of NR$^D$R$^E$ of Formula (XLI) is independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
each occurrence of m of Formula (XLI) is independently selected from 0, 1 or 2;
each occurrence of —U— of Formula (XLI) is independently selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
each occurrence of $R^3$ of Formula (XLI) is independently selected from $C_1$-$C_3$alkyl, or $C_1$-$C_3$fluoroalkyl;
each occurrence of $R^4$ of Formula (XLI) is independently selected from —NHR$^5$, —N(R$^5$)2, —N+(R$^5$)3 or —OR$^5$;
each occurrence of each $R^5$ of —NHR$^5$, —N(R$^5$)$_2$, —N(R$^5$)$_3^+$ and —OR$^5$ of Formula (XLI) is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
or:
each occurrence of $R^3$ and $R^5$ of Formula (XLI) together with the atoms to which they are attached form a substituted or unsubstituted 5-7 membered ring;
or:
of Formula (XLI) $R^3$ of Formula (XLI) is bonded to a nitrogen atom of U to form a substituted or unsubstituted 5-7 membered ring;
each occurrence of $R^6$ of Formula (XLI) is independently selected from —NHC(=O)$R^7$, —C(=O)NHR$^7$, —NHS(=O)$_2$R$^7$, —S(=O)$_2$NHR$^7$, —NHC(=O)NHR$^7$, —NHS(=O)$_2$NHR$^7$, —($C_1$-$C_3$alkyl)-NHC(=O)$R^7$, —($C_1$-$C_3$alkyl)-C(=O)NHR$^7$, —($C_1$-$C_3$alkyl)-NHS(=O)$_2$R$^7$, —($C_1$-$C_3$alkyl)-S(=O)$_2$NHR$^7$, —($C_1$-$C_3$alkyl)-NHC(=O)NHR$^7$, —($C_1$-$C_3$alkyl)-NHS(=O)$_2$NHR$^7$, substituted or unsubstituted $C_2$-$C_{10}$heterocycloalkyl, or substituted or unsubstituted heteroaryl;
each occurrence of $R^7$ of —NHC(=O)$R^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —($C_1$-$C_3$alkyl)-

$NHC(=O)R^7$, $-(C_1\text{-}C_3\text{alkyl})\text{-}C(=O)NHR^7$, $-(C_1\text{-}C_3\text{alkyl})\text{-}NHS(=O)_2R^7$, $-(C_1\text{-}C_3\text{alkyl})\text{-}S(=O)_2NHR^7$, $-(C_1\text{-}C_3\text{alkyl})\text{-}NHC(=O)NHR^7$, $-(C_1\text{-}C_3\text{alkyl})\text{-}NHS(=O)_2NHR^7$ of Formula (XLI) is independently selected from $C_1\text{-}C_6$alkyl, $C_1\text{-}C_6$haloalkyl, $C_1\text{-}C_6$heteroalkyl, a substituted or unsubstituted $C_3\text{-}C_{10}$cycloalkyl, a substituted or unsubstituted $C_2\text{-}C_{10}$heterocycloalkyl, a substituted or unsubstituted aryl, a substituted or unsubstituted heteroaryl, $-C_1\text{-}C_6$alkyl-(substituted or unsubstituted $C_3\text{-}C_{10}$cycloalkyl), $-C_1\text{-}C_6$alkyl-(substituted or unsubstituted $C_2\text{-}C_{10}$heterocycloalkyl, $-C_1\text{-}C_6$alkyl-(substituted or unsubstituted aryl), $-C_1\text{-}C_6$alkyl-(substituted or unsubstituted heteroaryl), $-(CH_2)_p\text{-}CH$(substituted or unsubstituted aryl)$_2$, $-(CH_2)_p\text{-}CH$(substituted or unsubstituted heteroaryl)$_2$, $-(CH_2)_p\text{-}CH$(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

each occurrence of p of $R^7$ of Formula (XLI) is independently selected from 0, 1 or 2;

each occurrence of $R^{8a}$, $R^{8b}$, $R^{8c}$, and $R^{8d}$ of $C(R^{8a})(R^{8b})$ and $C(R^{8c})(R^{8d})$ of Formula (XLI) is independently selected from H, $C_1\text{-}C_6$alkyl, $C_1\text{-}C_6$fluoroalkyl, $C_1\text{-}C_6$ alkoxy, $C_1\text{-}C_6$heteroalkyl, and substituted or unsubstituted aryl;

or:

each occurrence of $R^{8a}$ and $R^{8d}$ of Formula (XLI) are as defined above, and $R^{8b}$ and $R^{8c}$ together form a bond;

or:

each occurrence of $R^{8a}$ and $R^{8d}$ of Formula (XLI) are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

each occurrence of $R^{8c}$ and $R^{8d}$ of Formula (XLI) are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

each occurrence of $R^{8a}$ and $R^{8b}$ of Formula (XLI) are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocloalkyl, aryl or heteroaryl is substituted with 1-3 $R^9$; and each occurrence of $R^9$ of $R^{8a}$, $R^{8b}$, $R^{8c}$ and $R^{8d}$ of Formula (XLI) is independently selected from halogen, —OH, —SH, (C=O), CN, $C_1\text{-}C_4$alkyl, $C_1\text{-}C_4$fluoroalkyl, $C_1\text{-}C_4$ alkoxy, $C_1\text{-}C_4$ fluoroalkoxy, $-NH_2$, $-NH(C_1\text{-}C_4\text{alkyl})$, $-NH(C_1\text{-}C_4\text{alkyl})_2$, $-C(=O)OH$, $-C(=O)NH_2$, $-C(=O)C_1\text{-}C_3\text{alkyl}$, $-S(=O)_2CH_3$, $-NH(C_1\text{-}C_4\text{alkyl})\text{-}OH$, $-NH(C_1\text{-}C_4\text{alkyl})\text{-}O\text{-}(C_1\text{-}C_4\text{alkyl})$, $-O(C_1\text{-}C_4\text{alkyl})\text{-}NH_2$, $O(C_1\text{-}C_4\text{alkyl})\text{-}NH\text{-}(C_1\text{-}C_4\text{alkyl})$, and $-O(C_1\text{-}C_4\text{alkyl})\text{-}N\text{-}(C_1\text{-}C_4\text{alkyl})_2$, or two $R^9$ together with the atoms to which they are attached form a methylene dioxy or ethylene dioxy ring substituted or unsubstituted with halogen, —OH, or $C_1\text{-}C_3$alkyl.

In various embodiments, the ILM can have the structure of Formula (XLII), as described in WO Pub. No. 2013/071039, or an unnatural mimetic thereof:

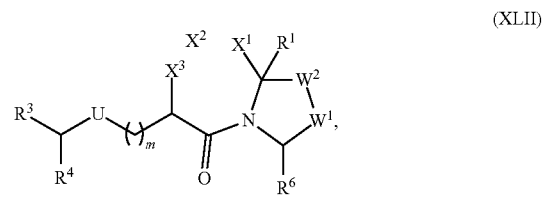

(XLII)

wherein:

each occurrence of $W^1$ in Formula (XLII) is independently O, S, N—$R^A$, or $C(R^{8a})(R^{8b})$;

each occurrence of $W^2$ in Formula (XLII) is independently O, S, N—$R^A$, or $C(R^{8c})(R^{8d})$; provided that $W^1$ and $W^2$ are not both O, or both S;

each occurrence of $R^1$ in Formula (XLII) is independently selected from H, $C_1\text{-}C_6$alkyl, $C_3\text{-}C_6$cycloalkyl, $-C_1\text{-}C_6$alkyl-(substituted or unsubstituted $C_3\text{-}C_6$cycloalkyl), substituted or unsubstituted aryl, substituted or unsubstituted heteroaryl, $-C_1\text{-}C_6$alkyl-(substituted or unsubstituted aryl), or $-C_1\text{-}C_6$alkyl-(substituted or unsubstituted heteroaryl);

when $X^1$ of Formula (XLII) is N—$R^A$, then $X^2$ is C=O, or $CR^{2c}R^{2d}$, and $X^3$ is $CR^{2a}R^{2b}$;

or:

when $X^1$ of Formula (XLII) is selected from S, S(=O), or S(=O)$_2$, then $X^2$ is $CR^{2c}R^{2d}$, and $X^3$ is $CR^{2a}R^{2b}$;

or:

when $X^1$ of Formula (XLII) is O, then $X^2$ is $CR^{2c}R^{2d}$ or N—$R^A$ and $X^3$ is $CR^{2a}R^{2b}$;

or:

when $X^1$ of Formula (XLII) is $CH_3$, then $X^2$ is independently selected from O, N—$R^A$, S, S(=O), or S(=O)$_2$, and $X^3$ is $CR^{2a}R^{2b}$;

when $X^1$ of Formula (XLII) is $CR^{2e}R^{2f}$ then $X_2$ is $CR^{2c}R^{2d}$, and $R^{2e}$ and $R^{2c}$ together form a bond, and $X^3$ of Formula (VLII) is $CR^{2a}R^{2b}$;

or:

when $X^1$ and $X^3$ of Formula (XLII) are both $CH_2$ and $X^2$ of Formula (XLII) is C—O, C=C($R^C$)$_2$, or C=N$R^C$; where each $R^C$ is independently selected from H, —CN, —OH, alkoxy, substituted or unsubstituted $C_1\text{-}C_6$alkyl, substituted or unsubstituted $C_3\text{-}C_6$cycloalkyl, substituted or unsubstituted $C_2\text{-}C_5$heterocycloalkyl, substituted or unsubstituted aryl, substituted or unsubstituted heteroaryl, $-C_1\text{-}C_6$alkyl-(substituted or unsubstituted $C_3\text{-}C_6$cycloalkyl), $-C_1\text{-}C_6$alkyl-(substituted or unsubstituted $C_2\text{-}C_5$heterocycloalkyl), $-C_1\text{-}C_6$alkyl-(substituted or unsubstituted aryl), or $-C_1\text{-}C_6$alkyl-(substituted or unsubstituted heteroaryl);

or:

$X^1$ and $X^2$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (XLII) is $CR^{2e}R^{2f}$;

Each occurrence of $R^A$ of $N-R^A$ of Formula (XLII) is independently selected from H, $C_1$-$C_6$alkyl, —C(=O) $C_1$-$C_2$alkyl, substituted or unsubstituted aryl, or substituted or unsubstituted heteroaryl;

at each occurrence $R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ of Formula (XLII) are independently selected from Fl, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

at each occurrence $R^B$ of —C(=O)$R^B$ of Formula (XLII) is independently selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alky(-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

at each occurrence RD and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl); at each occurrence m of Formula (XLII) is independently selected from 0, 1 or 2;

at each occurrence —U— of Formula (XLII) is independently selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

at each occurrence $R^3$ of Formula (XLII) is independently selected from $C_1$-$C_3$alkyl, or $C_1$-$C_3$fluoroalkyl;

at each occurrence $R^4$ of Formula (XLII) is independently selected from —$NHR^5$, —$N(R^5)_2$, —$N(R^5)_3^+$ or —$OR^5$;

at each occurrence each $R^5$ of —$NHR^5$, —$N(R^5)_2$, —$N(R^5)_3^+$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

at each occurrence $R^3$ and $R^5$ of Formula (XLII) together with the atoms to which they are attached form a substituted or unsubstituted 5-7 membered ring;

or:

at each occurrence $R^3$ of Formula (XLII) is bonded to a nitrogen atom of U to form a substituted or unsubstituted 5-7 membered ring;

at each occurrence $R^6$ of Formula (XLII) is independently selected from —NHC(=O)$R^7$, —C(=O)$NHR^7$, —NHS(=O)$_2R^7$, —S(=O)$_2NHR^7$, —NHC(=O)$NHR^7$, —NHS(=O)$_2NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)$_2R^7$, —($C_1$-$C_3$alkyl)-S(=O)$_2NHR^7$, —($C_1$-$C_3$alkyl)-NHC(=O)$NHR^7$, —($C_1$-$C_3$alkyl)-NHS(=O)$_2NHR^7$, substituted or unsubstituted $C_2$-$C_{10}$heterocycloalkyl, or substituted or unsubstituted heteroaryl; at each occurrence $R^7$ of —NHC(=O)$R^7$, —C(=O)$NHR^7$, —NHS(=O)$_2R^7$, —S(=O)$_2NHR^7$, NHC(=O)$NHR^7$, —NHS(=O)$_2NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)$_2R^7$, —($C_1$-$C_3$alkyl)-S(=O)$_2NHR^7$, —($C_1$-$C_3$alkyl)-NHC(=O)$NHR^7$, —($C_1$-$C_3$alkyl)-NHS(=O)$_2NHR^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)p-CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

at each occurrence p of $R^7$ is independently selected from 0, 1 or 2;

at each occurrence $R^{8a}$, $R^{8b}$, $R^{8c}$, and $R^{8d}$ of C($R^{8a}$)($R^{8b}$) and C($R^{8c}$)($R^{8d}$) of Formula (XLII) are independently selected from H, $C_1$-$C_6$alkyl, $C_1$-$C_6$fluoroalkyl, $C_1$-$C_6$alkoxy, $C_1$-$C_6$heteroalkyl, and substituted or unsubstituted aryl;

or:

at each occurrence $R^{8a}$ and $R^{8d}$ of Formula (XLII) are as defined above, and $R^{8b}$ and $R^{8c}$ together form a bond;

or:

at each occurrence $R^{8a}$ and $R^{8d}$ of Formula (XLII) are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

at each occurrence $R^{8c}$ and $R^{8d}$ of Formula (XLII) are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

at each occurrence $R^{8a}$ and $R^{8b}$ of Formula (XLII) are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and at each occurrence $R^9$ of $R^{8a}$, $R^{8b}$, $R^{8c}$ and $R^{8d}$ is independently selected from halogen, —OH, —SH, C(=O), CN, $C_1$-$C_4$alkyl, $C_1$-$C_4$fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ taken together with the atoms to which they are attached form a methylene dioxy or ethylene dioxy ring substituted or unsubstituted with halogen, —OH, or $C_1$-$C_3$alkyl.

In various embodiments, the ILM can have the structure of Formula (XLIII), as described in WO Pub. No. 2013/071039, or an unnatural mimetic thereof:

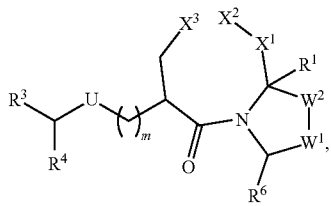

(XLIII)

wherein:

at each occurrence $W^1$ of Formula (XLIII) is independently selected from O, S, N—$R^A$, or C($R^{8a}$)($R^{8b}$);

at each occurrence $W^2$ of Formula (XLIII) is independently selected from O, S, N—$R^A$, or C($R^{8c}$)($R^{8d}$); provided that $W^1$ and $W^2$ are not both O, or both S;

at each occurrence $R^1$ of Formula (XLIII) is independently selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XLIII) is independently selected from N—$R^A$, S, S(=O), or S(=O)$_2$, then $X^2$ of Formula (XLIII) is $CR^{2c}R^{2d}$, and $X^3$ of Formula (XLIII) is $CR^{2a}R^{2b}$;

or:

when $X^1$ of Formula (XLIII) is O, then $X^2$ of Formula (XLIII) is independently selected from O, N—R S, S(=O), or S(=O)$_2$, and $X^3$ of Formula (XLIII) is $CR^{2a}R^{2b}$;

or:

when $X^1$ of Formula (XLIII) is $CR^{2e}R^{2f}$, then $X^2$ of Formula (XLIII) is $CR^{2c}R^{2d}$, and $R^{2e}$ and $R^{2c}$ together form a bond, and $X^3$ of Formula (XLIII) is $CR^{2a}R^{2b}$;

or:

at each occurrence $X^1$ and $X^2$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIII) is $CR^{2a}R^{2b}$;

or:

at each occurrence $X^2$ and $X^3$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;

at each occurrence $R^A$ of N—$R^A$ of Formula (XLIII) is independently H, $C_1$-$C_6$alkyl, —C(=O)$C_1$-$C_2$alkyl, substituted or unsubstituted aryl, or substituted or unsubstituted heteroaryl;

at each occurrence $R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ of Formula (XLIII) are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alky(-(substituted or unsubstituted aryl), —$C_1$-$C_6$alkyl-(substituted or unsubstituted heteroaryl) and —C(=O)$R^B$;

at each occurrence $R^B$ of —C(=O)$R^B$ of Formula (XLIII) is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;

at each occurrence $R^D$ and $R^E$ of NR$^D$R$^E$ of Formula (XLIII) are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

at each occurrence m of Formula (XLIII) is independently 0, 1 or 2;

at each occurrence —U— of Formula (XLIII) is independently —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

at each occurrence $R^3$ of Formula (XLIII) is independently $C_1$-$C_3$alkyl, or $C_1$-$C_3$fluoroalkyl;

at each occurrence $R^4$ of Formula (XLIII) is independently —NHR$^5$, —N(R$^5$)$_2$, —N+(R$^5$)$_3$ or —OR$^5$;

at each occurrence $R^5$ of —NHR$^5$, —N(R$^5$)$_2$, —N+(R$^5$)$_3$ and —OR$^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl); or:

at each occurrence $R^3$ and $R^5$ of Formula (XLIII) together with the atoms to which they are attached form a substituted or unsubstituted 5-7 membered ring; or:

at each occurrence $R^3$ of Formula (XLIII) is bonded to a nitrogen atom of U to form a substituted or unsubstituted 5-7 membered ring;

at each occurrence $R^6$ of Formula (XLIII) is independently selected from —NHC(=O)R$^7$, —C(=O)NHR$^7$, —NHS(=O)$_2$R$^7$, —S(=O)$_2$NHR$^7$, —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^7$, —($C_1$-$C_3$alkyl)-NHS(=O)$_2$R$^7$, —($C_1$-$C_3$alkyl)-S(=O)$_2$NHR$^7$, —($C_1$-$C_3$alkyl)-NHC(=O)NHR$^7$, —($C_1$-$C_3$alkyl)-NHS(=O)$_2$NHR$^7$, substituted or unsubstituted $C_2$-$C_{10}$heterocycloalkyl, or substituted or unsubstituted heteroaryl;

at each occurrence $R^7$ of —NHC(=O)R$^7$, —C(=O)NHR$^7$, —NHS(=O)$_2$R$^7$, —S(=O)$_2$NHR$^7$, —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^7$, —($C_1$-$C_3$alkyl)-NHS(=O)$_2$R$^7$, —($C_1$-$C_3$alkyl)-S(=O)$_2$NHR$^7$, —($C_1$-$C_3$alkyl)-NHC(=O)NHR$^7$, —($C_1$-$C_3$alkyl)-NHS(=O)$_2$NHR$^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)p-CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

at each occurrence p of R$^7$ of Formula (XLIII) is independently 0, 1 or 2;

at each occurrence R$^{8a}$, R$^{8b}$, R$^{8c}$, and R$^{8d}$ of C(R$^{8a}$)(R$^{8b}$) and C(R$^{8c}$)(R$^{8d}$) of Formula (XLIII) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:
at each occurrence R$^{8a}$ and R$^{8d}$ of Formula (XLIII) are as defined above, and R$^{8b}$ and R$^{8c}$ together form a bond;

or:
at each occurrence R$^{8a}$ and R$^{8d}$ of Formula (XLIII) are as defined above, and R$^{8b}$ and R$^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
at each occurrence R$^{8c}$ and R$^{8d}$ of Formula (XLIII) are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

or:
at each occurrence R$^{8a}$ and R$^{8b}$ of Formula (XLIII) are as defined above, and R$^{8c}$ and R$^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R$^9$; and at each occurrence R$^9$ of R$^{8a}$, R$^{8b}$, R$^{8c}$ and R$^{8d}$ of Formula (XLIII) is independently selected from halogen, —OH, —SH, C(=O), CN, $C_1$-$C_4$alkyl, $C_1$-$C_4$fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two R$^9$ together with the atoms to which they are attached form a methylene dioxy or ethylene dioxy ring substituted or unsubstituted with halogen, —OH, or $C_1$-$C_3$alkyl.

In various embodiments, the ILM can have the structure of Formula (XLIV), as described in WO Pub. No. 2013/071039, or an unnatural mimetic thereof:

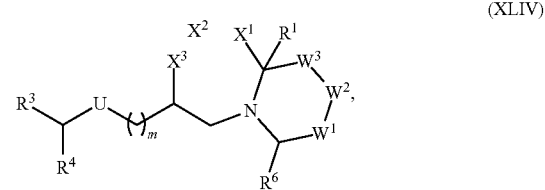

(XLIV)

wherein:
at each occurrence W$^1$ of Formula (XLIV) is independently selected from O, S, N—R$^4$, or C(R$^{8a}$)(R$^{8b}$);

at each occurrence W$^2$ of Formula (XLIV) is independently selected from O, S, N—R$^4$, or C(R$^{8c}$)(R$^{8d}$); provided that W$^1$ and W$^2$ are not both O, or both S;

at each occurrence W$^3$ of Formula (XLIV) is independently selected from O, S, N—R$^4$, or C(R$^{8e}$)(R$^{8f}$), providing that the ring comprising $W^1$, $W^2$, and $W^3$ does not comprise two adjacent oxygen atoms or sulfur atoms;

at each occurrence $R^1$ of Formula (XLIV) is independently selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XLIV) is O, then $X^2$ of Formula (XLIV) is independently selected from $CR^{2c}R^{2d}$ and N—$R^A$, and $X^3$ of Formula (XLIV) is $CR^{2a}R^{2b}$;

or:

when $X^1$ of Formula (XLIV) is $CH_2$, then $X^2$ of Formula (XLIV) is independently selected from O, N—$R^A$, S, S(=O), or S(=O)$_2$, and $X^3$ of Formula (XLIV) is $CR^{2a}R^{2b}$;

or:

when $X^1$ of Formula (XLIV) is $CR^{2e}R^{2f}$, then $X^2$ of Formula (XLIV) is $CR^{2c}R^{2d}$, and $R^{2e}$ and $R^{2c}$ together form a bond, and $X^3$ of Formula (VLIV) is $CR^{2a}R^{2b}$;

or:

when $X^1$ and $X^3$ of Formula (XLIV) are both $CH_2$, then $X^2$ of Formula (XLII) is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —O—$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

at each occurrence $X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$;

or:

at each occurrence $X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (XLIV) is $CR^{2e}R^{2f}$;

at each occurrence $R^A$ of N—$R^A$ of Formula (XLIV) is independently selected from H, $C_1$-$C_6$alkyl, —C(=O)$C_1$-$C_2$alkyl, substituted or unsubstituted aryl, or substituted or unsubstituted heteroaryl;

at each occurrence $R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ of Formula (XLIV) are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alky(-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

at each occurrence $R^B$ of —C(=O)$R^B$ of Formula (XLIV) is independently selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;

at each occurrence $R^D$ and $R^E$ of N$R^D R^E$ of Formula (XLIV) are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

at each occurrence m of Formula (XLIV) is independently selected from 0, 1 or 2;

at each occurrence —U— of Formula (XLIV) is independently selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

at each occurrence $R^3$ of Formula (XLIV) is independently selected from $C_1$-$C_3$alkyl, or $C_1$-$C_3$fluoroalkyl;

at each occurrence $R^4$ of Formula (XLIV) is independently selected from —NH$R^5$, —N($R^5$)$_2$, —N+($R^5$)$_3$ or —O$R^5$;

at each occurrence $R^5$ of —NH$R^5$, —N($R^5$)$_2$, —N+($R^5$)$_3$ and —O$R^5$ of Formula (XLIV) is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

at each occurrence $R^3$ and $R^5$ of Formula (XLIV) together with the atoms to which they are attached form a substituted or unsubstituted 5-7 membered ring;

or:

at each occurrence $R^3$ of Formula (XLIV) is bonded to a nitrogen atom of U to form a substituted or unsubstituted 5-7 membered ring;

at each occurrence $R^6$ of Formula (XLIV) is independently selected from —NHC(=O)$R^7$, —C(=O)NH$R^7$, —NHS(=O)$_2 R^7$, —S(=O)$_2$NH$R^7$, —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2 R^7$, —($C_1$-$C_3$alkyl)-S(=O)$_2$NH$R^7$, —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

at each occurrence $R^7$ of —NHC(=O)$R^7$, —C(=O)NH$R^7$, —NHS(=O)$_2 R^7$, —S(=O)$_2$NH$R^7$, NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-

C₃alkyl)-NHS(=O)₂R⁷, —(C₁-C₃alkyl)-S(=O)₂NHR⁷, —(C₁-C₃alkyl)-NHC(=O)NHR⁷, —(C₁-C₃alkyl)-NHS(=O)₂NHR⁷ is independently selected from C₁-C₆alkyl, C₁-C₆haloalkyl, C₁-C₆heteroalkyl, a substituted or unsubstituted C₃-C₁₀cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl-(substituted or unsubstituted C₂-C₁₀heterocycloalkyl, —C₁-C₆alkyl-(substituted or unsubstituted aryl), —C₁-C₆alkyl-(substituted or unsubstituted heteroaryl), —(CH₂)ₚ—CH(substituted or unsubstituted aryl)2, —(CH₂)ₚ—CH(substituted or unsubstituted heteroaryl)2, —(CH₂)ₚ—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

at each occurrence p of R⁷ is independently selected from 0, 1 or 2;

at each occurrence R⁸ᵃ, R⁸ᵇ, R⁸ᶜ, R⁸ᵈ, R⁸ᵉ, and R⁸ᶠ of C(R⁸ᵃ)(R⁸ᵇ), C(R⁸ᶜ)(R⁸ᵈ) and C(R⁸ᵉ)(R⁸ᶠ) of Formula (XLIV) are independently selected from H, C₁-C₆alkyl, C₁-C₆fluoroalkyl, C₁-C₆ alkoxy, C₁-C₆heteroalkyl, and substituted or unsubstituted aryl;

or:

at each occurrence R⁸ᵃ, R⁸ᵈ, R⁸ᵉ, and R⁸ᶠ of C(R⁸ᵃ)(R⁸ᵇ), C(R⁸ᶜ)(R⁸ᵈ) and C(R⁸ᵉ)(R⁸ᶠ) of Formula (XLIV) are as defined above, and R⁸ᵇ and R⁸ᶜ together form a bond;

or:

at each occurrence R⁸ᵃ, R⁸ᵇ, R⁸ᵈ, and R⁸ᶠ of C(R⁸ᵃ)(R⁸ᵇ), C(R⁸ᶜ)(R⁸ᵈ) and C(R⁸ᵉ)(R⁸ᶠ) of Formula (XLIV) are as defined above, and R⁸ᶜ and R⁸ᵉ together form a bond;

or:

at each occurrence R⁸ᵃ, R⁸ᵈ, R⁸ᵉ, and R⁸ᶠ of C(R⁸ᵃ)(R⁸ᵇ), C(R⁸ᶜ)(R⁸ᵈ) and C(R⁸ᵉ)(R⁸ᶠ) of Formula (XLIV) are as defined above, and R⁸ᵇ and R⁸ᶜ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

at each occurrence R⁸ᵃ, R⁸ᵇ, R⁸ᵈ, and R⁸ᶠ of C(R⁸ᵃ)(R⁸ᵇ), C(R⁸ᶜ)(R⁸ᵈ) and C(R⁸ᵉ)(R⁸ᶠ) of Formula (XLIV) are as defined above, and R⁸ᶜ and R⁸ᵉ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

at each occurrence R⁸ᶜ, R⁸ᵈ, R⁸ᵉ, and R⁸ᶠ of C(R⁸ᶜ)(R⁸ᵈ) and C(R⁸ᵉ)(R⁸ᶠ) of Formula (XLIV) are as defined above, and R⁸ᵃ and R⁸ᵇ together with the atoms to which they are attached form a substituted or unsubstituted saturated, or partially saturated 3-7 membered spirocycle or heterospirocycle comprising 1-3 heteroatoms selected from S, O and N;

or:

at each occurrence R⁸ᵃ, R⁸ᵇ, R⁸ᵉ, and R⁸ᶠ of C(R⁸ᵃ)(R⁸ᵇ) and C(R⁸ᵉ)(R⁸ᶠ) of Formula (XLIV) are as defined above, and R⁸ᶜ and R⁸ᵈ together with the atoms to which they are attached form a substituted or unsubstituted saturated, or partially saturated 3-7 membered spirocycle or heterospirocycle comprising 1-3 heteroatoms selected from S, O and N;

or:

at each occurrence R⁸ᵃ, R⁸ᵇ, R⁸ᶜ, and R⁸ᵈ of C(R⁸ᵃ)(R⁸ᵇ) and C(R⁸ᶜ)(R⁸ᵈ) of Formula (XLIV) are as defined above, and R⁸ᵉ and R⁸ᶠ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 R⁹; and at each occurrence R⁹ of R⁸ᵃ, R⁸ᵇ, R⁸ᶜ, R⁸ᵈ, R⁸ᵉ, and R⁸ᶠ is independently selected from halogen, —OH, —SH, C(=O), CN, C₁-C₄alkyl, C₁-C₄fluoroalkyl, C₁-C₄ alkoxy, C₁-C₄ fluoroalkoxy, —NH₂, —NH(C₁-C₄alkyl), —NH(C₁-C₄alkyl)₂, —C(=O)OH, —C(=O)NH₂, —C(=O)C₁-C₃alkyl, —S(=O)₂CH₃, —NH(C₁-C₄alkyl)-OH, —NH(C₁-C₄alkyl)-O—(C₁-C₄alkyl), —O(C₁-C₄alkyl)-NH₂, —O(C₁-C₄alkyl)-NH—(C₁-C₄alkyl), and —O(C₁-C₄alkyl)-N—(C₁-C₄alkyl)₂, or two R⁹ taken together with the atoms to which they are attached form a methylene dioxy or ethylene dioxy ring substituted or unsubstituted with halogen, —OH, or C₁-C₃alkyl.

In various embodiments, the ILM can have the structure of Formula (XLV), (XLVI) or (XLVII), as described in ACS Chem. Biol., 8(4), 725-32 (2013), or an unnatural mimetic thereof:

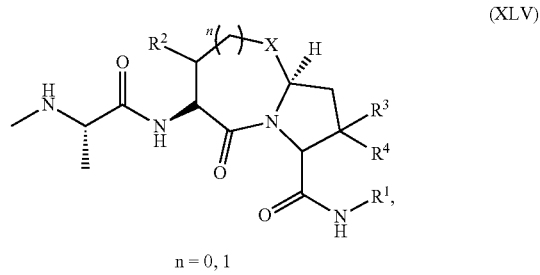

(XLV)

n = 0, 1

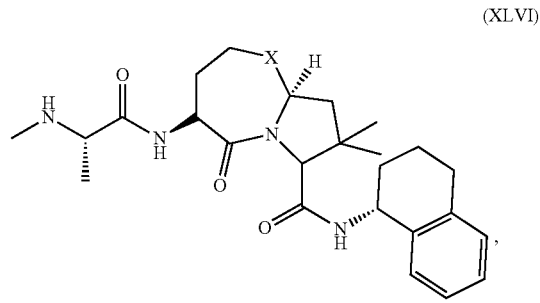

(XLVI)

-continued (XLVII)

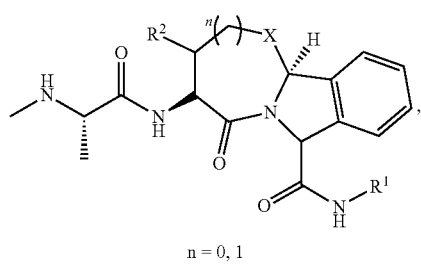

n = 0, 1 wherein:

at each occurrence R², R³ and R⁴ of Formula (XLV) are independently selected from H or Me;

at each occurrence X of Formula (XLV) is independently selected from O or S; and at each occurrence R¹ of Formula (XLV) is independently selected from:

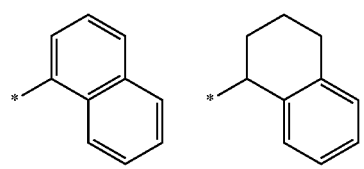

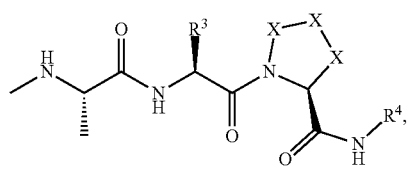

In a particular embodiment, the ILM has a structure according to Formula (XLVIII):

(XLVIII)

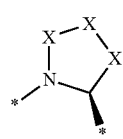

wherein R³ and R⁴ of Formula (XLVIII) are independently selected from H or Me;

is a 5-member heterocycle independently selected from:

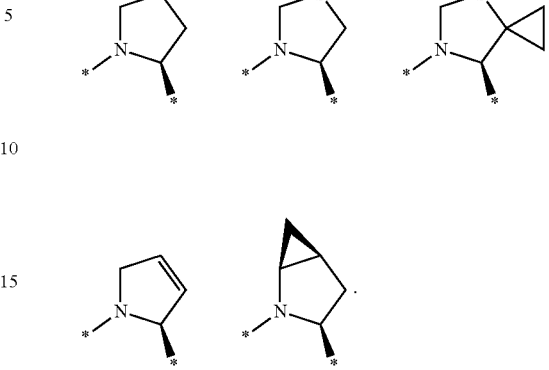

In a particular embodiment, the

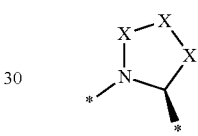

of Formula XLVIII) is

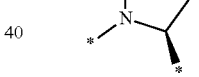

In a particular embodiment, the ILM has a structure and attached to a linker group L as shown below:

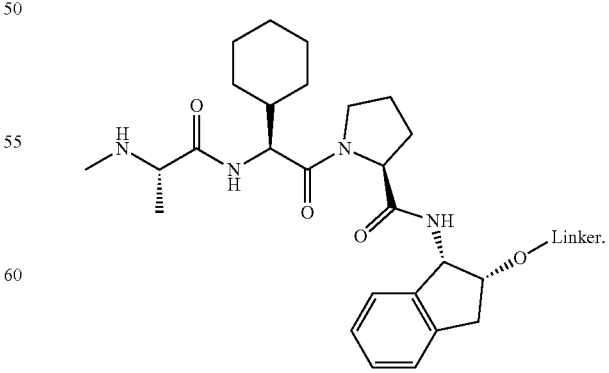

In a particular embodiment, the ILM has a structure according to Formula (XLIX), (L), or (LI):

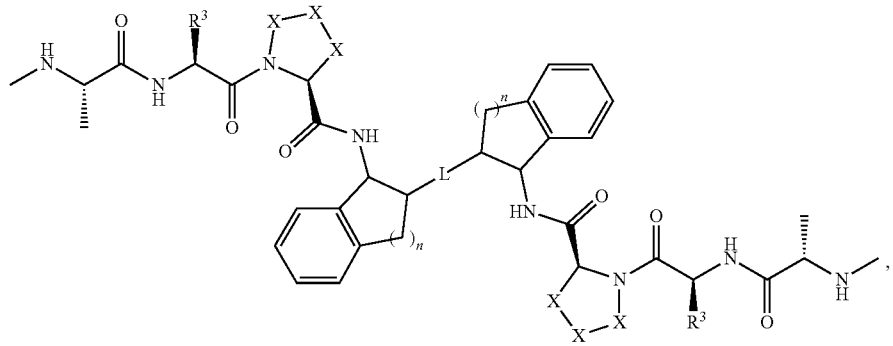
(XLIX)
n = 1, 2
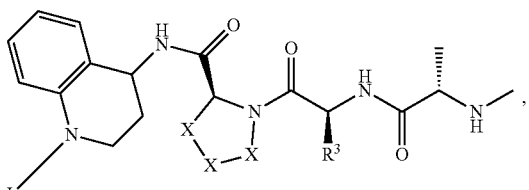
(L)
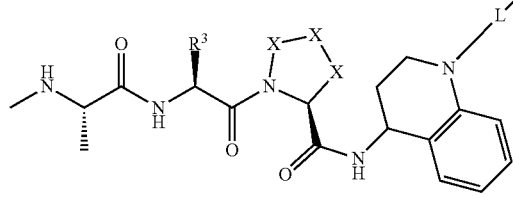
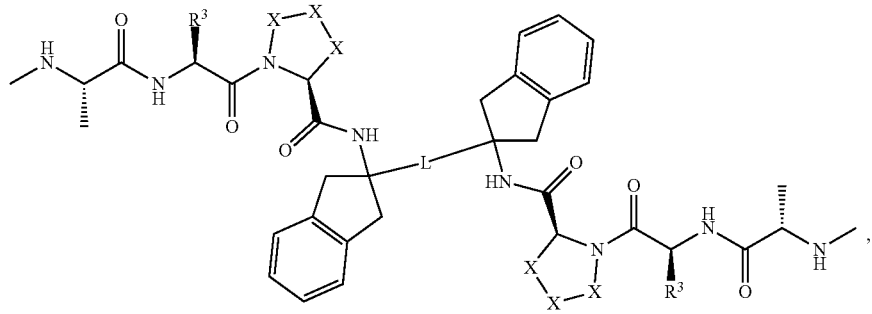
(LI)
wherein:
at each occurrence $R^3$ of Formula (XLIX), (L) or (LI) are independently selected from H or Me;
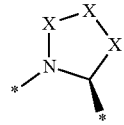
is a 5-member heterocycle independently selected from:
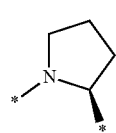 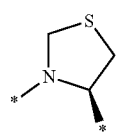 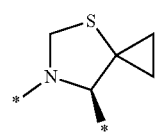
-continued
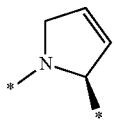 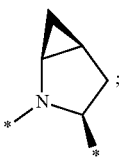
and
L of Formula (XLIX), (L) or (LI) is independently selected from:
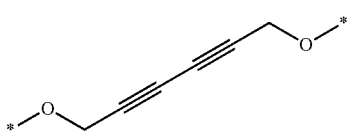

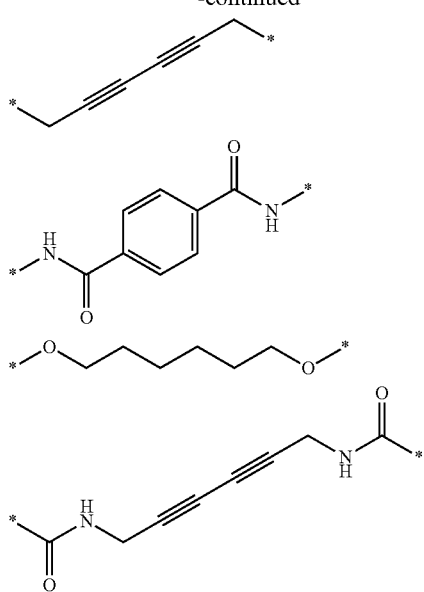
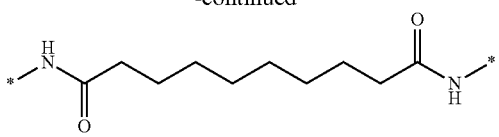
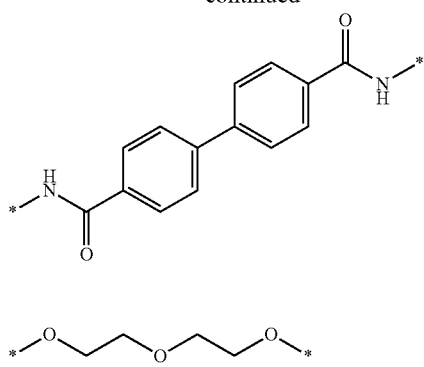
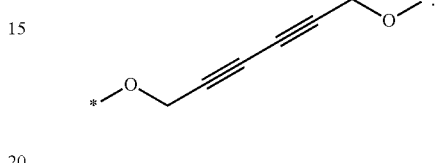
In a particular embodiment, L of Formula (XLIX), (L), or (LI) is
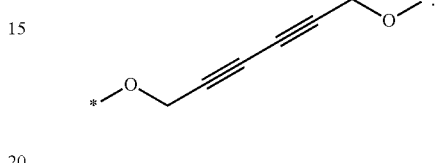
In a particular embodiment, the ILM has a structure according to Formula (LII):
(LII)
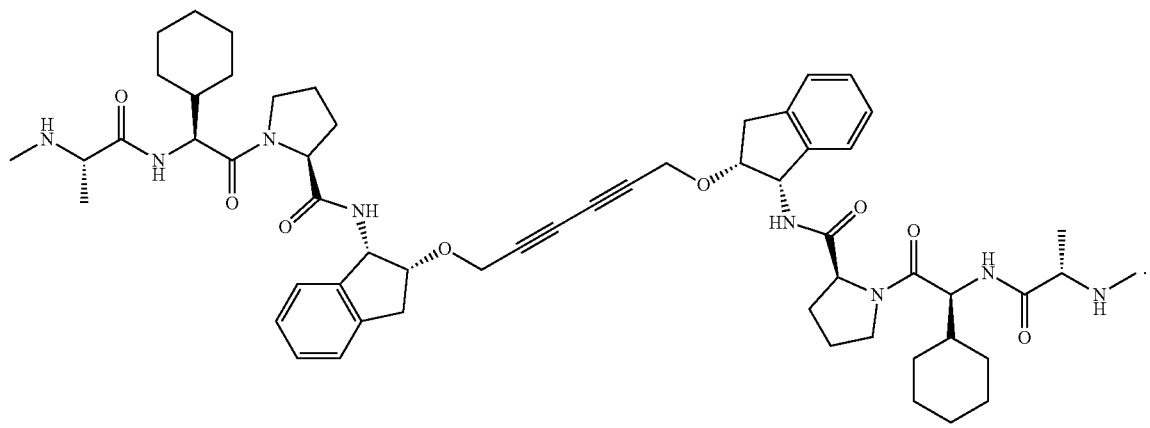
In a particular embodiment, the ILM according to Formula (LII) is chemically linked to the linker group L in the area denoted with
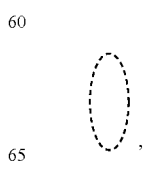

and as shown below:

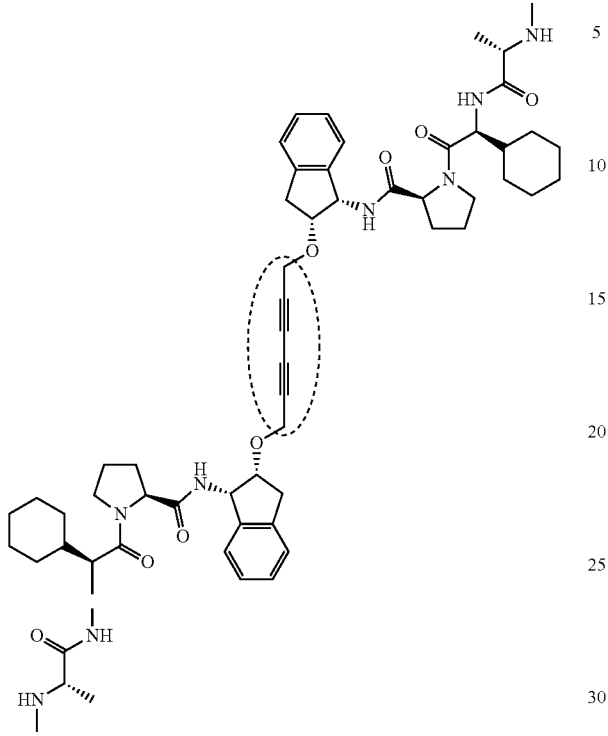

In various embodiments, the ILM can have the structure of Formula (LIII) or (LIV), as described in Bioorg. Med. Chem. Lett., 22(4), 1960-4 (2012), or an unnatural mimetic thereof:

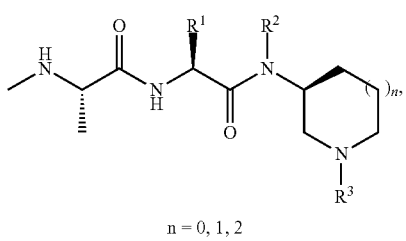

(LIII)

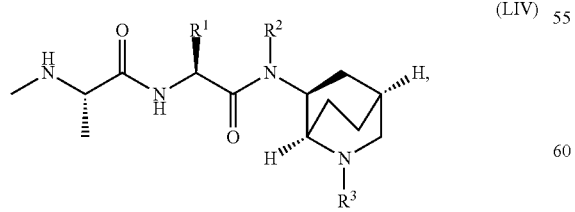

(LIV)

wherein:
at each occurrence $R^1$ of Formulas (LIII) and (LIV) is independently selected from:

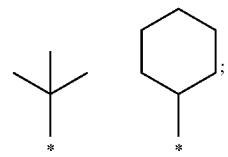

at each occurrence $R^2$ of Formulas (LIII) and (LIV) is independently selected from H or Me;
at each occurrence $R^3$ of Formulas (LIII) and (LIV) is independently selected from:

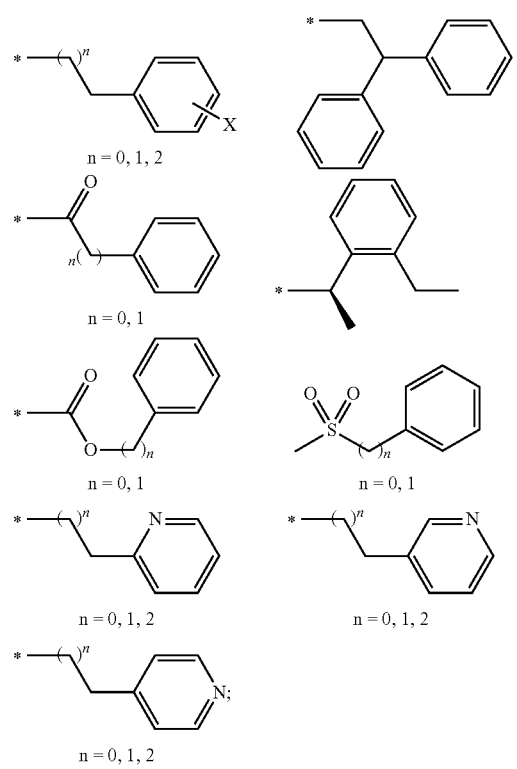

at each occurrence X of Formulas (LIII) and (LIV) is independently selected from H, halogen, methyl, methoxy, hydroxy, nitro or trifluoromethyl.

In various embodiments, the ILM can have the structure shown in Formula (LV) or (LVI), where the linker is as described herein, or an unnatural mimetic thereof:

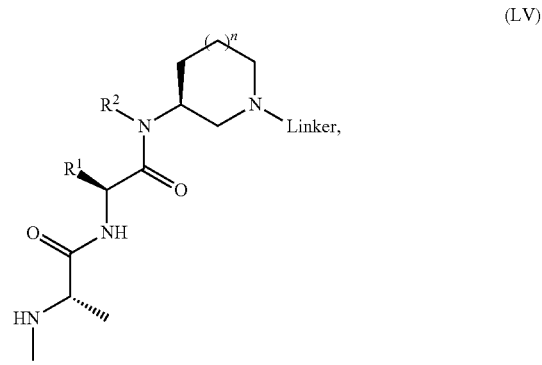

(LV)

-continued (LVI)

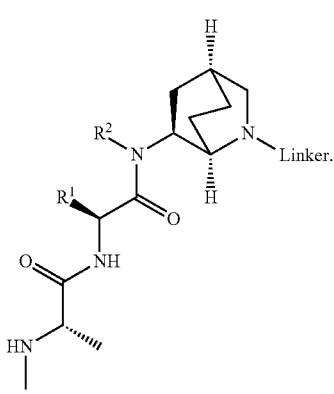

In various embodiments, the ILM can have the structure of Formula (LVII), as described in J. Med. Chem., 52(6), 1723-30 (2009), or an unnatural mimetic thereof:

(LVII)

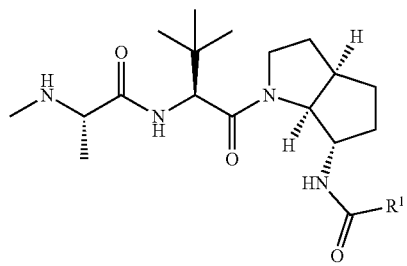

wherein:
at each occurrence $R^1$ of Formula (LVII) is independently selected from:

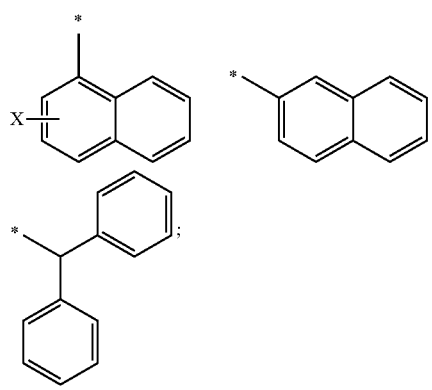

at each occurrence X of

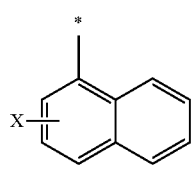

of Formula (LVII) is independently selected from H, fluoro, methyl or methoxy.

In a particular embodiment, the ILM is represented by the following structure:

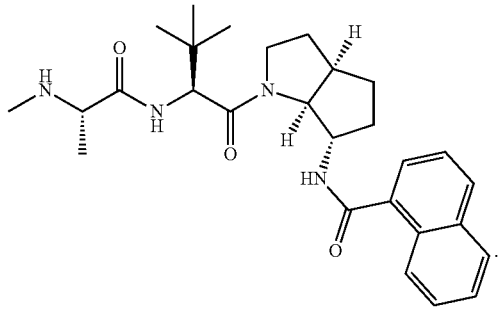 [SMILES: CN[C@@H](C)C(=O)N[C@H](C(=O)N1CC[C@H]2CC[C@H](NC(=O)c3cccc4ccccc34)[C@H]21)C(C)(C)C]

In a particular embodiment, the ILM, which has the chemical link between the ILM and linker group L as shown below, is selected from the group consisting of:

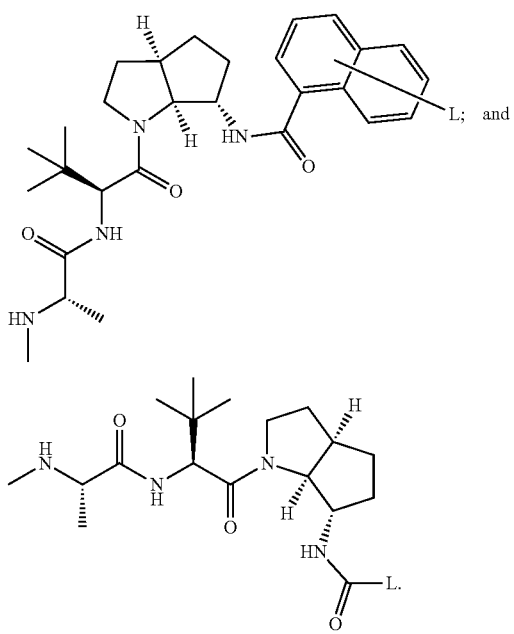

In various embodiments, the ILM is selected from the group consisting of, or an unnatural mimetic thereof:

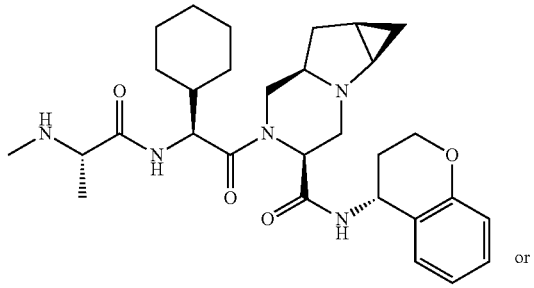

or

-continued

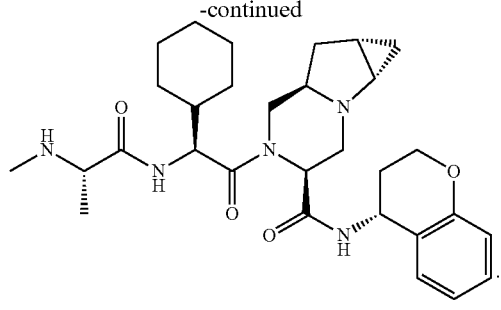

In a particular embodiment, the ILM, in which the chemical link between the ILM and linker group L is shown below, is independently selected from the group consisting of:

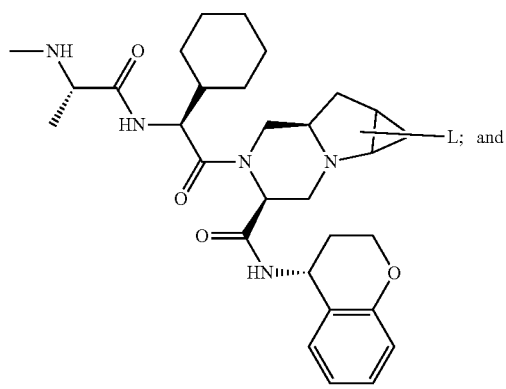

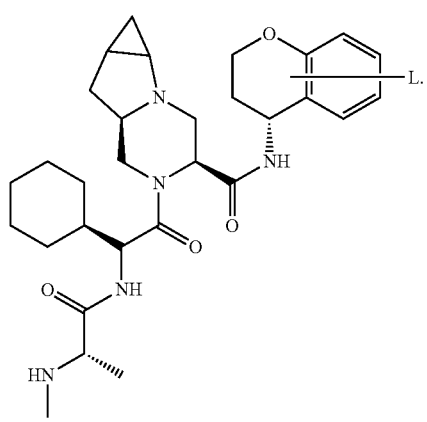

In various embodiments, the ILM can have the structure of Formula (LVIII), as described in Bioorg. Med. Chem., 21(18): 5725-37 (2013), or an unnatural mimetic thereof:

(LVIII)

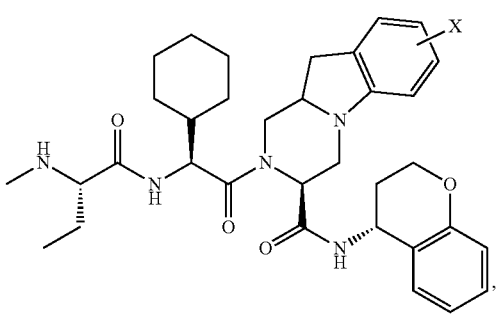

wherein at each occurrence X of Formula (LVIII) is one or two substituents independently selected from H, halogen or cyano.

In various embodiments, the ILM can have the structure of and be chemically linked to the linker group L as shown in Formula (LIX) or (LX), or an unnatural mimetic thereof:

(LIX)

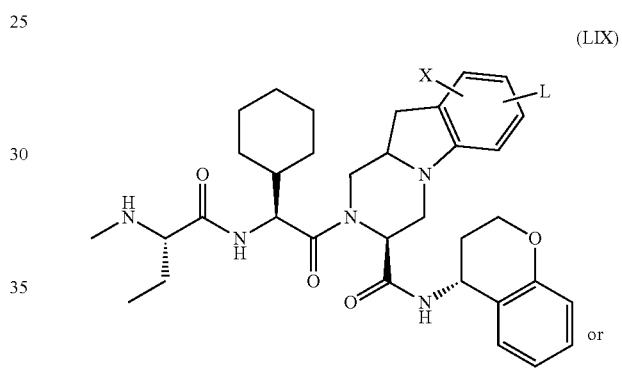

or (LX)

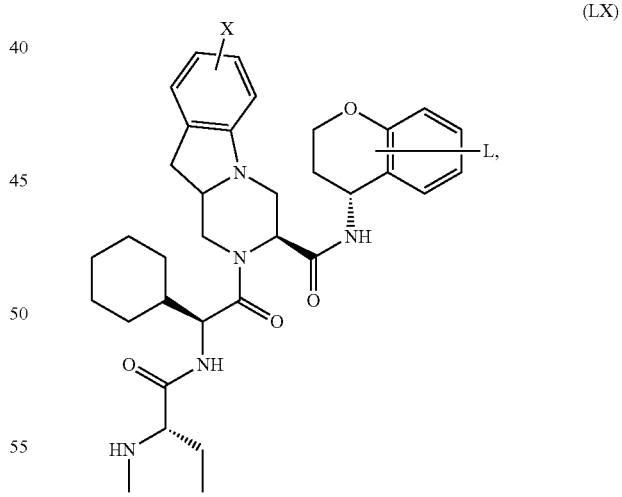

wherein X of Formula (LIX) and (LX) is one or two substituents independently selected from H, halogen or cyano, and L of Formulas (LIX) and (LX) is a linker group as described herein.

In various embodiments, the ILM can have the structure of Formula (LXI) as described in Bioorg. Med. Chem., 23(14): 4253-7 (2013), or an unnatural mimetic thereof:

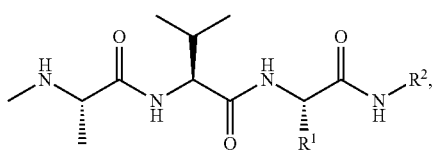  (LXI)

wherein:

at each occurrence

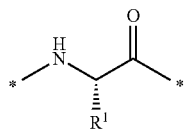

of Formula (LXI) is a natural or unnatural amino acid; and at each occurrence $R^2$ of Formula (LXI) is independently selected from:

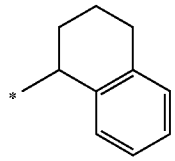 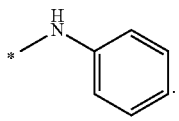

In various embodiments, the ILM can have the structure of and be chemically linked to the linker group L as shown in Formula (LXII) or (LXIII), or an unnatural mimetic thereof:

at each occurrence

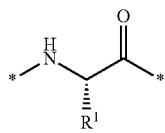

of Formula (LXII) or (LXIII) is a natural or unnatural amino acid; and at each occurrence L of Formula (LXII) or (LXIII) is a linker group as described herein.

In various embodiments, the ILM can have the structure selected from the group consisting of:

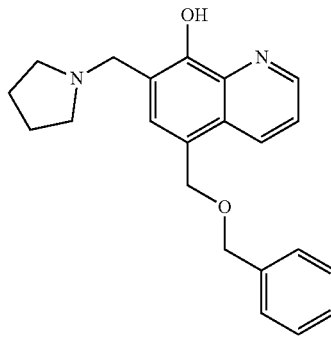

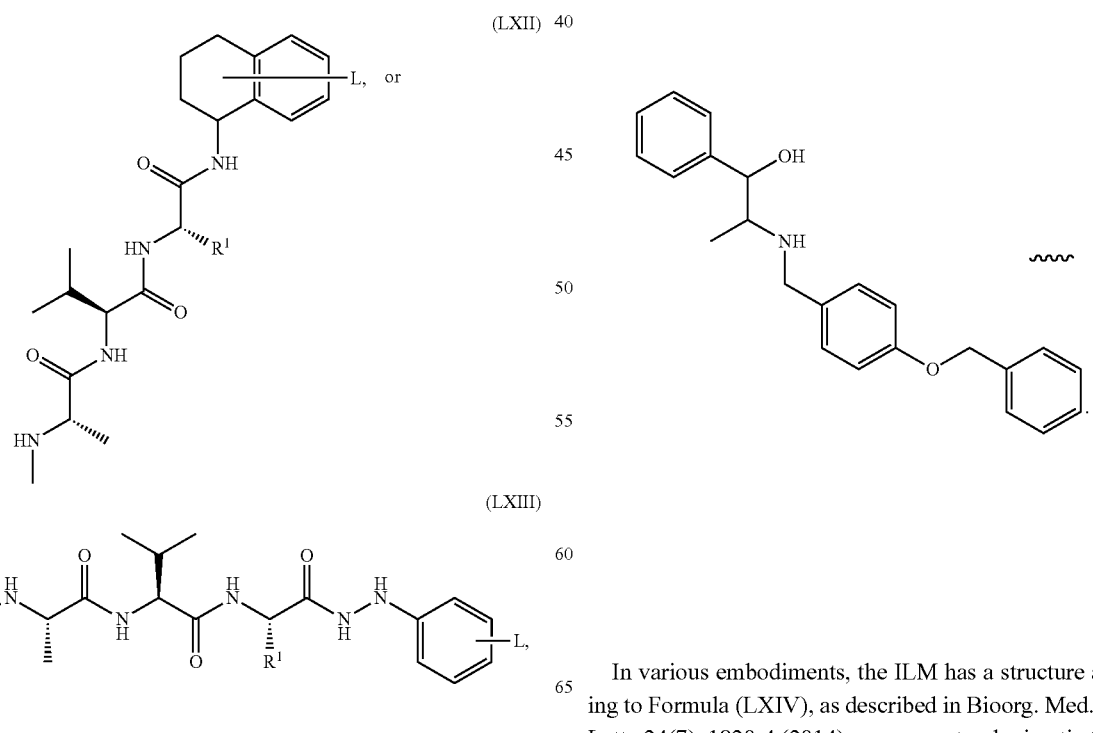

In various embodiments, the ILM has a structure according to Formula (LXIV), as described in Bioorg. Med. Chem. Lett., 24(7): 1820-4 (2014), or an unnatural mimetic thereof:

(LXIV)

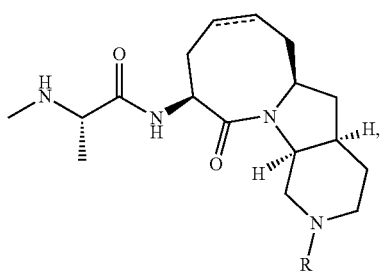

wherein at each occurrence R of Formula (LXIV) is independently selected from the group consisting of:

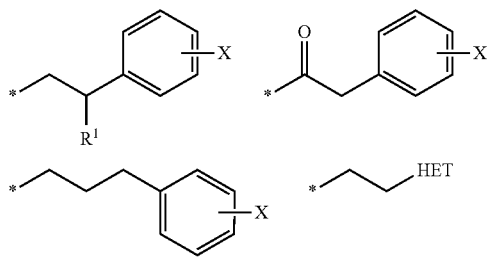

at each occurrence $R^1$ of

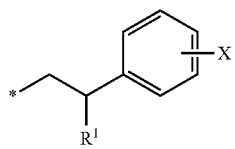

of Formula (LXIV) is independently selected from H or Me;

at each occurrence $R^2$ of

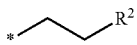

of Formula (LXIV) is independently selected from alkyl or cycloalkyl;

at each occurrence X of

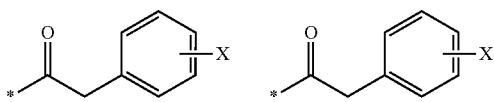

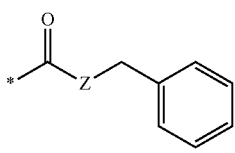

of Formula (LXIV) is 1-2 substitutents independently selected from halogen, hydroxy, methoxy, nitro and trifluoromethyl at each occurrence Z of

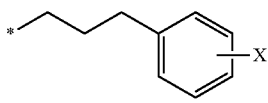

of Formula (LXIV) is O or NH;

at each occurrence HET of

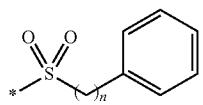

is mono- or fused bicyclic heteroaryl; and at each occurrence - - - of Formula (LXIV) is an optional double bond.

In a particular embodiment, the ILM of the compound has the structure:

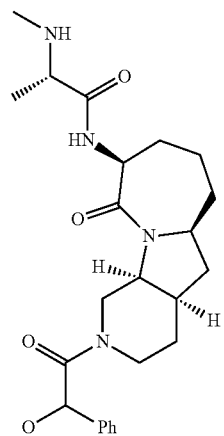
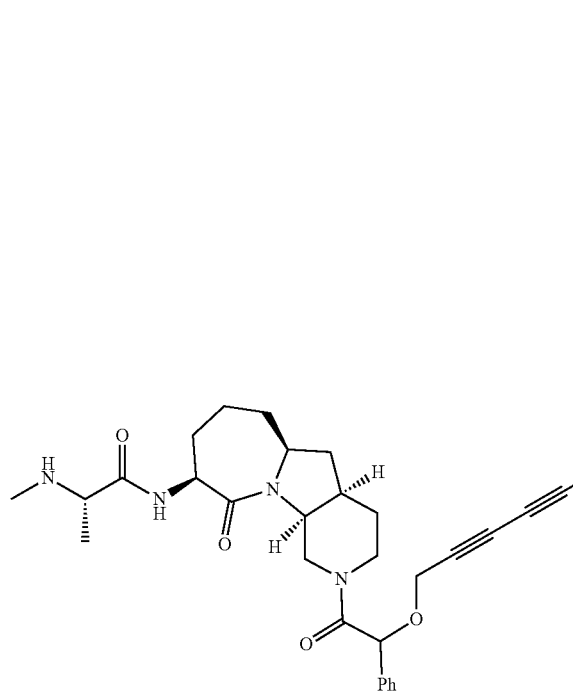
In a particular embodiment, the ILM has a structure selected from the group consisting of:
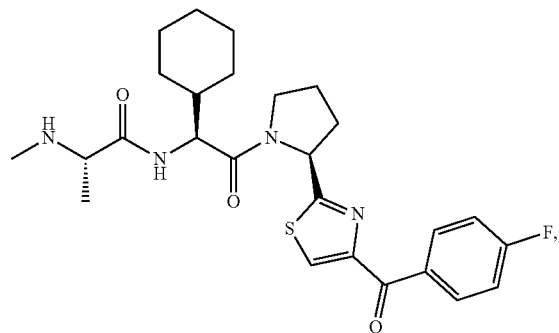
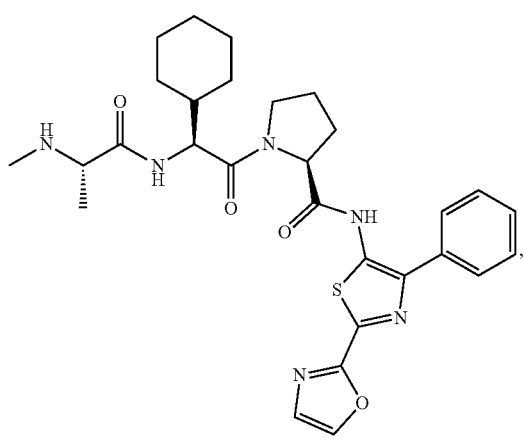
-continued
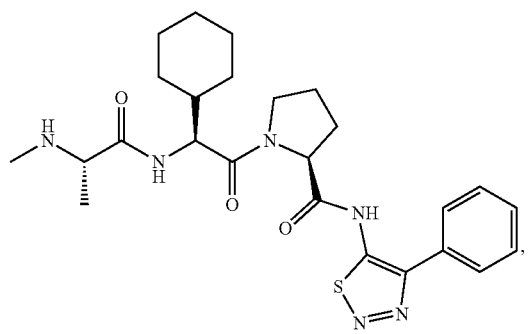
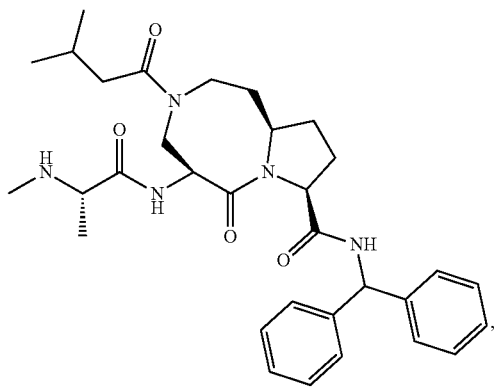

-continued

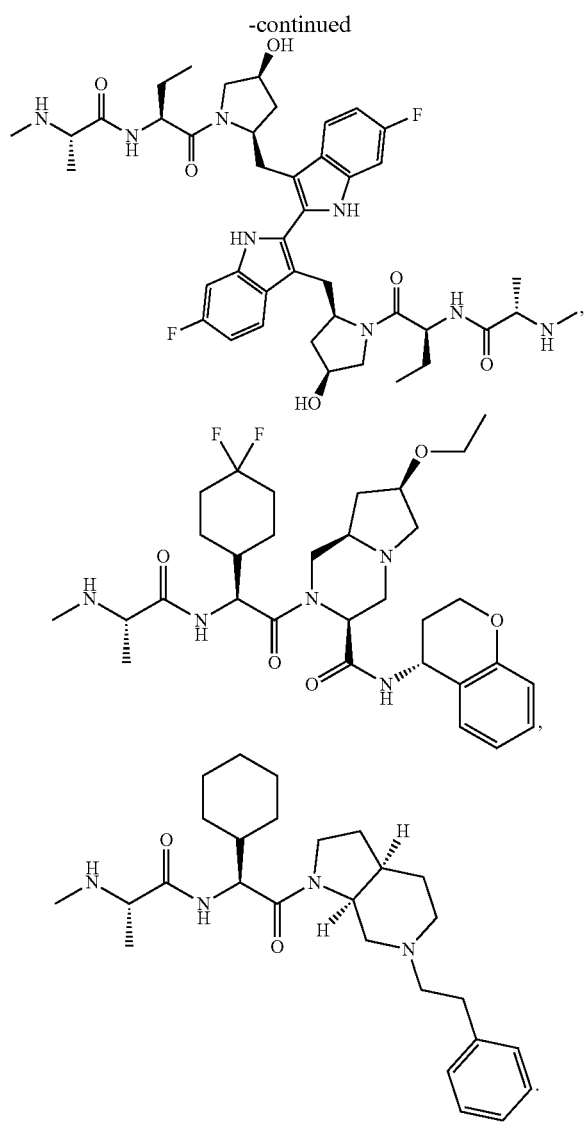

Mouse Double Minute 2 Homolog E3 Ubiquitin Ligase Binding Moieties

In certain embodiments, the MLM of the compound includes chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned in cis- or trans-configurations.

In still additional embodiments, the MLM includes part of the structural features as in compounds RG7112, RG7388, SAR405838, AMG-232, AM-7209, DS-5272, MK-8242, and NVP-CGM-097, and analogs or derivatives thereof.

In certain embodiments, MLM is a compound of Formula (A-1), or thiazoloimidazoline represented as Formula (A-2), or spiro indolinone represented as Formula (A-3), or pyrollidine represented as Formula (A-4), or piperidinone/morpholinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

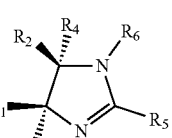

Formula (A-1)

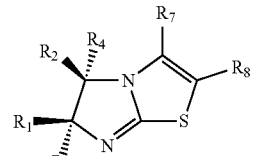

Formula (A-2)

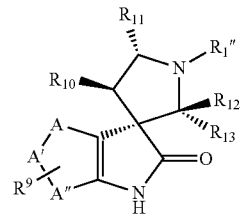

Formula (A-3)

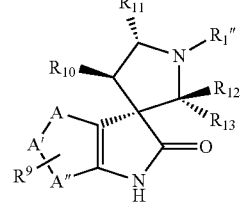

Formula (A-4)

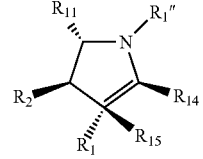

Formula (A-5)

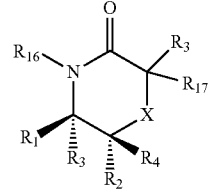

Formula (A-6)

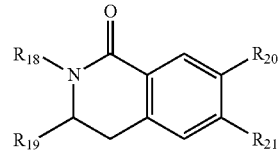

Formula (A-7)

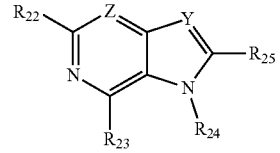

Formula (A-8)

wherein in Formula (A-1) through Formula (A-8), at each occurrence X of Formula (A-1) through Formula (A-8) is independently selected from the group consisting of carbon, oxygen, sulfur, sulfoxide, sulfone, and N—$R^a$;

at each occurrence $R^a$ of Formula (A-1) through Formula (A-8) is independently H or an alkyl group with carbon number 1 to 6;

at each occurrence Y and Z of Formula (A-1) through Formula (A-8) are independently carbon or nitrogen;

at each occurrence A, A' and A" of Formula (A-1) through Formula (A-8) are independently selected from C, N, O or S, can also be one or two atoms forming a fused bicyclic ring, or a 6,5- and 5,5-fused aromatic bicyclic group;

at each occurrence $R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of: halogen, —CN, $C_{1-6}$ alkyl group, $C_{3-6}$ cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

at each occurrence $R_3$, $R_4$ of Formula (A-1) through Formula (A-8) are independently selected from the group consisting of H, methyl and $C_{1-6}$ alkyl;

at each occurrence $R_5$ of Formula (A-1) through Formula (A-8) is independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of: halogen, —CN, $C_{1-6}$ alkyl group, $C_{3-6}$ cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether ($C_{2-6}$), alkyl ketone ($C_{3-6}$), morpholinyl, alkyl ester ($C_{3-6}$), alkyl cyanide ($C_{3-6}$);

at each occurrence $R_6$ of Formula (A-1) through Formula (A-8) is independently H or —C(=O)$R^b$, wherein at each occurrence $R^b$ of Formula (A-1) through Formula (A-8) is independently selected from the group consisting of alkyl, cycloalkyl, mono-, di- or tri-substituted aryl or heteroaryl, 4-morpholinyl, 1-(3-oxopiperazinyl), 1-piperidinyl, 4-N—$R^c$-morpholinyl, 4-$R^c$-1-piperidinyl, and 3-$R^c$-1-piperidinyl, wherein at each occurrence $R^C$ of Formula (A-1) through Formula (A-8) is independently selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, $CH_2CH_2R^d$, and $CH_2CH_2CH_2R^d$, wherein at each occurrence $R^d$ of Formula (A-1) through Formula (A-8) is independently selected from the group consisting of alkoxy, alkyl sulfone, alkyl sulfoxide, N-substituted carboxamide, —NHC(=O)-alkyl, —NH—$SO_2$-alkyl, aryl, substituted aryl, heteroaryl, substituted heteroaryl;

at each occurrence $R_7$ of Formula (A-1) through Formula (A-8) is independently selected from the group consisting of H, $C_{1-6}$ alkyl, cyclic alkyl, fluorine substituted alkyl, cyano substituted alkyl, 5- or 6-membered hetero aryl or aryl, substituted 5- or 6-membered hetero aryl or aryl;

at each occurrence $R_8$ of Formula (A-1) through Formula (A-8) is independently selected from the group consisting of —$R^e$—C(=O)—$R^f$, —$R^e$-alkoxy, —$R^e$-aryl, —$R^e$-heteroaryl, and —$R^e$—C(=O)—$R^f$—C(=O)—$R^g$, wherein:

at each occurrence $R^e$ of Formula (A-1) through Formula (A-8) is an alkylene with 1 to 6 carbons, or a bond;

at each occurrence $R^f$ of Formula (A-1) through Formula (A-8) is a substituted 4- to 7-membered heterocycle;

at each occurrence $R^g$ of Formula (A-1) through Formula (A-8) is independently selected from the group consisting of aryl, hetero aryl, substituted aryl or heteroaryl, and 4- to 7-membered heterocycle;

at each occurrence $R_9$ of Formula (A-1) through Formula (A-8) is independently selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

at each occurrence $R_{10}$ of Formula (A-1) through Formula (A-8) is independently selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, $C_{1-6}$ alkyl group, $C_{1-6}$ cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

at each occurrence $R_{11}$ of Formula (A-1) through Formula (A-8) is —C(=O)—N($R^h$)($R^i$), wherein $R^h$ and $R^i$ are selected from groups consisting of: H, $C_{1-6}$ alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein at each occurrence $R^h$ and $R^i$ of Formula (A-1) through Formula (A-8) are independently selected from the group consisting of H, connected to form a ring, 4-hydroxycyclohehexane, mono- and di-hydroxy substituted alkyl ($C_{3-6}$), 3-hydroxycyclobutane, phenyl-4-carboxylic acid, and substituted phenyl-4-carboxylic acid;

at each occurrence $R_{12}$ and $R_{13}$ of Formula (A-1) through Formula (A-8) are independently selected from H, lower alkyl ($C_{1-6}$), lower alkenyl ($C_{2-6}$), lower alkynyl ($C_{2-6}$), cycloalkyl (4, 5 and 6-membered ring), substituted cycloalkyl, cycloalkenyl, substituted cycloalkenyl, 5- and 6-membered aryl and heteroaryl, $R_{12}$ and $R_{13}$ can be connected to form a 5- and 6-membered ring with or without substitution on the ring;

at each occurrence $R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

at each occurrence $R_{15}$ of Formula (A-1) through Formula (A-8) is CN;

at each occurrence $R_{16}$ of Formula (A-1) through Formula (A-8) is selected from the group consisting of $C_{1-6}$ alkyl, $C_{1-6}$ cycloalkyl, $C_{2-6}$ alkenyl, $C_{1-6}$ alkyl or $C_{3-6}$ cycloalkyl with one or multiple hydrogens replaced by fluorine, alkyl or cycloalkyl with one $CH_2$ replaced by $S(=O)$, —S, or —$S(=O)_2$, alkyl or cycloalkyl with terminal $CH_3$ replaced by $S(=O)_2N(alkyl)(alkyl)$, —$C(=O)N(alkyl)(alkyl)$, —$N(alkyl)S(=O)_2(alkyl)$, —$C(=O)_2(allkyl)$, —O(alkyl), $C_{1-6}$ alkyl or alkyl-cycloalkyl with hydron replaced by hydroxyl group, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, $C_{1-6}$ alkyl groups, hydroxylated $C_{1-6}$ alkyl, $C_{1-6}$ alkyl containing thioether, ether, sulfone, sulfoxide, fluorine substituted ether or cyano group;

at each occurrence $R_{17}$ of Formula (A-1) through Formula (A-8) is independently selected from the group consisting of $(CH_2)_nC(=O)NR^kR^l$, wherein $R^k$ and $R^l$ are independently selected from H, $C_{1-6}$ alkyl, hydroxylated $C_{1-6}$ alkyl, $C_{1-6}$ alkoxy alkyl, $C_{1-6}$ alkyl with one or multiple hydrogens replaced by fluorine, $C_{1-6}$ alkyl with one carbon replaced by $S(=O)$, $S(=O)(0)$, $C_{1-6}$ alkoxyalkyl with one or multiple hydrogens replaced by fluorine, $C_{1-6}$ alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

at each occurrence $R_{18}$ of Formula (A-1) through Formula (A-8) is independently selected from the group consisting of substituted aryl, heteroaryl, alkyl, cycloalkyl, the substitution is preferably —$N(C_{1-4}$ alkyl)(cycloalkyl), —$N(C_{1-4}$ alkyl)alkyl-cycloalkyl, and —$N(C_{1-4}$ alkyl)[(alkyl)-(heterocycle-substituted)-cycloalkyl];

at each occurrence $R_{19}$ of Formula (A-1) through Formula (A-8) is independently selected from the group consisting of aryl, heteroaryl, bicyclic heteroaryl, and these aryl or heteroaryl groups can be substituted with halogen, $C_{1-6}$ alkyl, $C_{1-6}$ cycloalkyl, $CF_3$, F, CN, alkyne, alkyl sulfone, the halogen substitution can be mon- bis- or tri-substituted;

at each occurrence $R_{20}$ and $R_{21}$ of Formula (A-1) through Formula (A-8) are independently selected from $C_{1-6}$ alkyl, $C_{1-6}$ cycloalkyl, $C_{1-6}$ alkoxy, hydroxylated $C_{1-6}$ alkoxy, and fluorine substituted $C_{1-6}$ alkoxy, wherein $R_{20}$ and $R_{21}$ can further be connected to form a 5, 6 and 7-membered cyclic or heterocyclic ring, which can further be substituted;

at each occurrence $R_{22}$ of Formula (A-1) through Formula (A-8) is independently selected from the group consisting of H, $C_{1-6}$ alkyl, $C_{1-6}$ cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with $C_{1-6}$ alkyl, alkoxy, fluorine-substituted alkyl, CN, and alkylsulfone;

at each occurrence $R_{23}$ of Formula (A-1) through Formula (A-8) is independently selected from aryl, heteroaryl, —O-aryl, —O-heteroaryl, —O-alkyl, —O-alkyl-cycloalkyl, —NH-alkyl, —NH— alkyl-cycloalkyl, —N(H)-aryl, —N(H)-heteroaryl, —N(alkyl)-aryl, —N(alkyl)-heteroaryl, the aryl or heteroaryl groups can be substituted with halogen, $C_{1-6}$ alkyl, hydoxylated $C_{1-6}$ alkyl, cycloalkyl, fluorine-substituted $C_{1-6}$ alkyl, CN, alkoxy, alkyl sulfone, amide and sulfonamide;

at each occurrence $R_{24}$ of Formula (A-1) through Formula (A-8) is selected from the group consisting of —$CH_2$—($C_{1-6}$ alkyl), —$CH_2$-cycloalkyl, —$CH_2$-aryl, $CH_2$-heteroaryl, where alkyl, cycloalkyl, aryl and heteroaryl can be substituted with halogen, alkoxy, hydroxylated alkyl, cyano-substituted alkyl, cycloalkyl and substituted cycloalkyl;

at each occurrence $R_{25}$ of Formula (A-1) through Formula (A-8) is independently selected from the group consisting of $C_{1-6}$ alkyl, $C_{1-6}$ alkyl-cycloalkyl, alkoxy-substituted alkyl, hydroxylated alkyl, aryl, heteroaryl, substituted aryl or heteroaryl, 5, 6, and 7-membered nitrogen-containing saturated heterocycles, 5,6-fused and 6,6-fused nitrogen-containing saturated heterocycles and these saturated heterocycles can be substituted with $C_{1-6}$ alkyl, fluorine-substituted $C_{1-6}$ alkyl, alkoxy, aryl and heteroaryl group;

at each occurrence $R_{26}$ of Formula (A-1) through Formula (A-8) is independently selected from the group consisting of $C_{1-6}$ alkyl, $C_{3-6}$ cycloalkyl, the alkyl or cycloalkyl can be substituted with —OH, alkoxy, fluorine-substituted alkoxy, fluorine-substituted alkyl, —$NH_2$, —NH-alkyl, NH—C(=O)alkyl, —NH—S(=O)$_2$-alkyl, and —$S(=O)_2$-alkyl;

at each occurrence $R_{27}$ of Formula (A-1) through Formula (A-8) is independently selected from the group consisting of aryl, heteroaryl, bicyclic heteroaryl, wherein the aryl or heteroaryl groups can be substituted with $C_{1-6}$ alkyl, alkoxy, $NH_2$, NH-alkyl, halogen, or —CN, and the substitution can be independently mono-, bis- and tri-substitution;

at each occurrence $R_{28}$ of Formula (A-1) through Formula (A-8) is independently selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and at each occurrence $R_{1'}$— of Formula (A-1) through Formula (A-8) is independently selected from the group consisting of alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ of Formula (A-1) through Formula (A-8) are independently substituted pyrrolidine, substituted piperidine, substituted piperizine.

In various embodiments, the MLMs of Formula A-1 through A-8, can be used to prepare PROTACs as described herein to target a particular protein for degradation, where L is a linker group, and PTM is a ligand binding to a target protein.

In certain embodiments, the compounds include a molecule with a structure selected from the group consisting of:

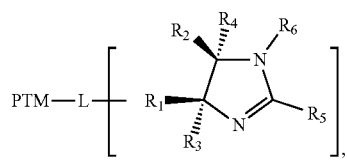

Formula (A-9)

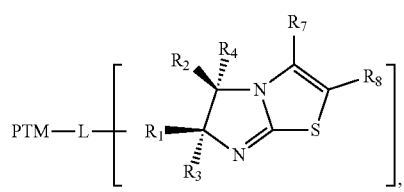

Formula (A-10)

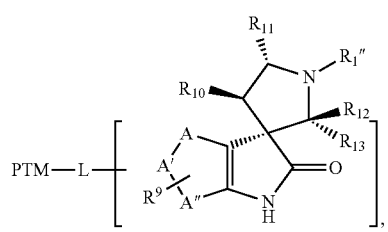

Formula (A-11)

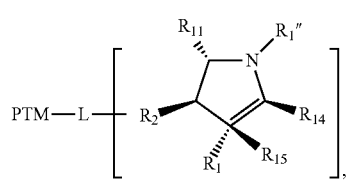

Formula (A-12)

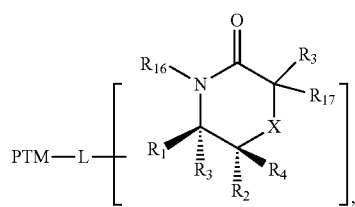

Formula (A-13)

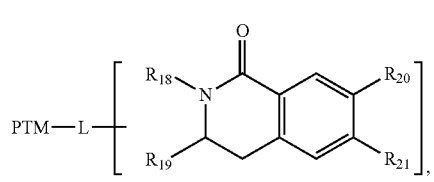

Formula (A-14)

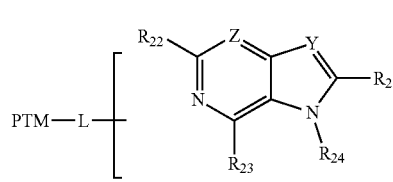

Formula (A-15), and

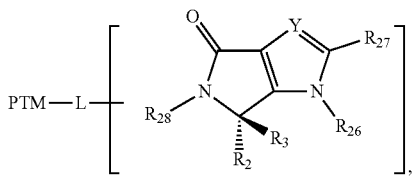

Formula (A-16)

wherein at each occurrence X, $R^a$, Y, Z, A, A', A", $R_1$, $R_2$, $R_3$, $R_4$, $R^5$, $R^6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1''}$ are independently as defined herein with regard to Formulas (A-1) through (A-8).

In certain embodiments, the compound includes molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

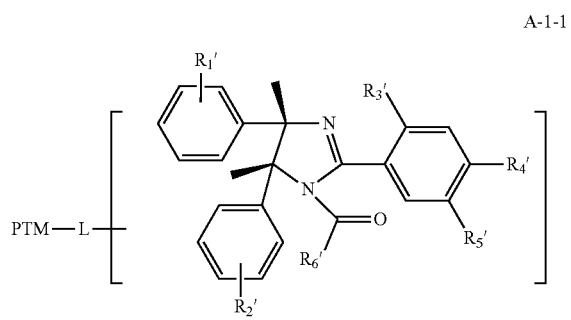

A-1-1

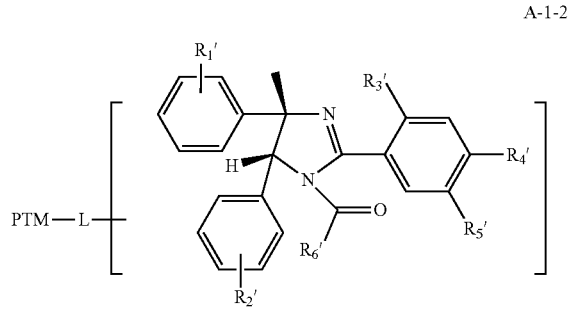

A-1-2

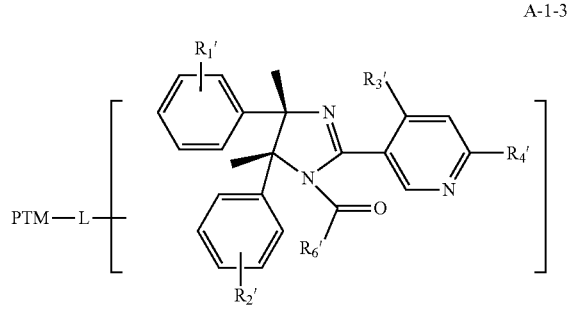

A-1-3

-continued

A-1-4

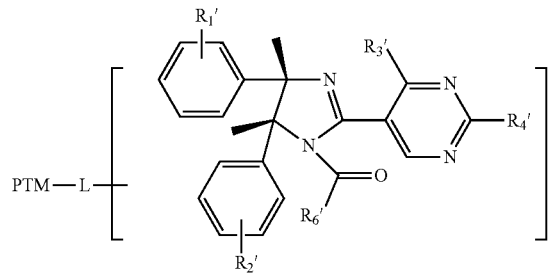

wherein:
at each occurrence $R_{1'}$ and $R_{2'}$ of Formulas A-1-1 through A-1-4 are independently selected from the group consisting of F, Cl, Br, I, ethynyl, CN, $CF_3$ and $NO_2$;

at each occurrence $R_{3'}$ of Formulas A-1-1 through A-1-4 is independently selected from the group consisting of —$OCH_3$, —$OCH_2CH_3$, —$OCH_2CH_2F$, —$OCH_2CH_2OCH_3$, and —$OCH(CH_3)_2$;

at each occurrence $R_{4'}$ of Formulas A-1-1 through A-1-4 is independently selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2OH$, —$C(CH_3)_2OCH_2CH_3$, —$C(CH_3)_2CH_2OH$, —$C(CH_3)_2CH_2OCH_2CH_3$, —$C(CH_3)_2CH_2OCH_2CH_2OH$, —$C(CH_3)_2CH_2OCH_2CH_3$, —$C(CH_3)_2CN$, —$C(CH_3)_2C(=O)CH_3$, —$C(CH_3)_2C(=O)NHCH_3$, —$C(CH_3)_2C(=O)N(CH_3)_2$, —$SCH_3$, —$SCH_2CH_3$, —$S(=O)_2CH_3$, —$S(O_2)CH_2CH_3$, —$NHC(CH_3)_3$, —$N(CH_3)_2$, pyrrolidinyl, and 4-morpholinyl;

at each occurrence $R_{5'}$ of Formulas A-1-1 through A-1-4 is independently selected from the group consisting of halogen, -cyclopropyl, —$S(=O)_2CH_3$, —$S(=O)_2CH_2CH_3$, 1-pyrrolidinyl, —$NH_2$, —$N(CH_3)_2$, and —$NHC(CH_3)_3$; and at each occurrence $R_{6'}$ of Formulas A-1-1 through A-1-4 is independently selected from the group consisting of H,

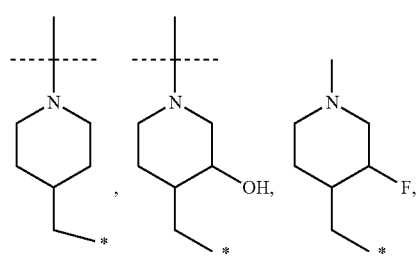

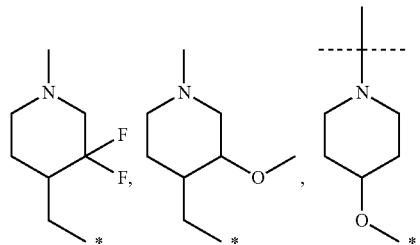

-continued

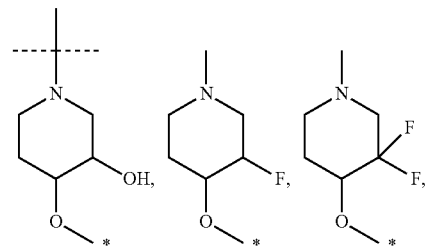

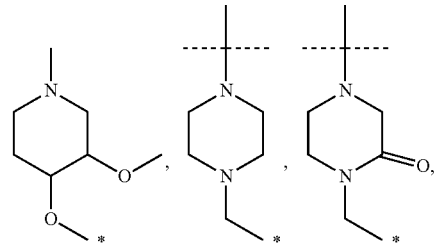

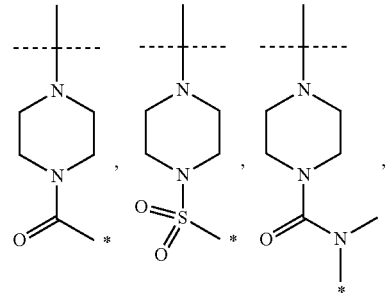

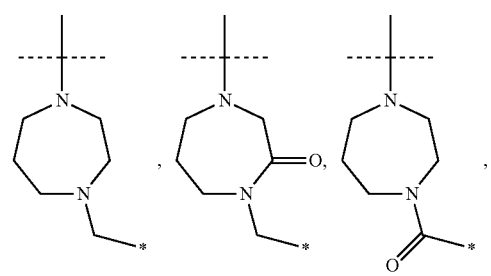

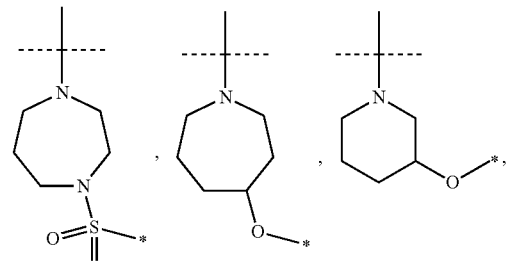

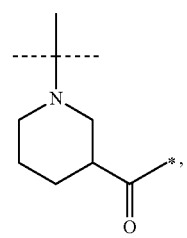

-continued

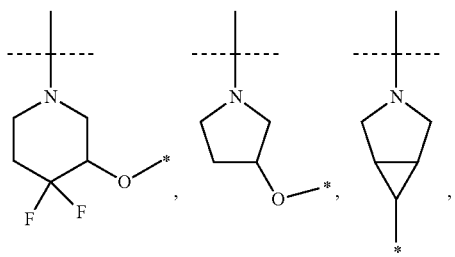

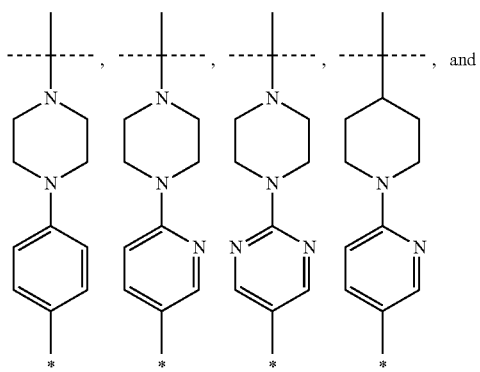

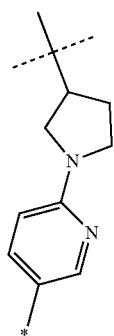

wherein "*" indicates the point of attachment of the linker.

In various embodiments, $R_{4'}$ can also serve as the linker attachment position at any open valance in a terminal atom of any of the $R_{4'}$ groups of Formulas A-1-1 through A-1-4.

In certain embodiments, the linker connection position of Formulas A-1-1 through A-1-4 is at least one of $R_{4'}$ or $R_{6'}$ or both.

In certain embodiments, the linker of Formula A-4-1 through A-4-6 is attached to at least one of $R_{1'}$, $R_{2'}$, $R_{3'}$, $R_{4'}$, $R_{5'}$, $R_{6'}$, or a combination thereof.

In certain embodiments, the description provides bifunctional or chimeric molecules with the structure: PTM-L-MLM, wherein PTM is a protein target binding moiety coupled to an MLM by L, wherein L is a bond or a chemical linker. In certain embodiments, the MLM has a structure selected from the group consisting of A-4-1, A-4-2, A-4-3, A-4-4, A-4-5, and A-4-6:

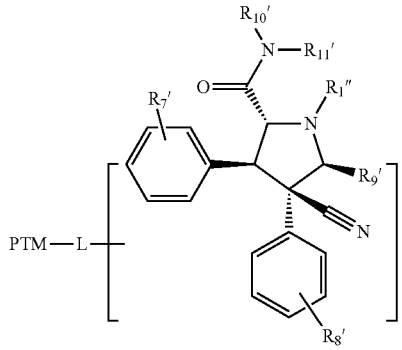
A-4-1

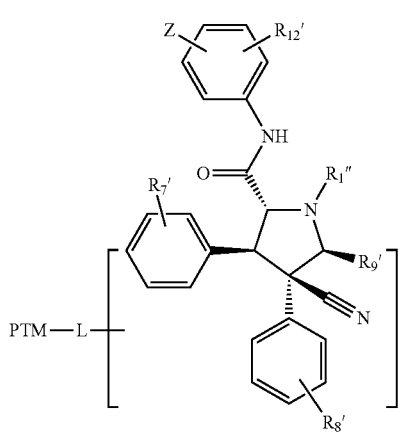
A-4-2

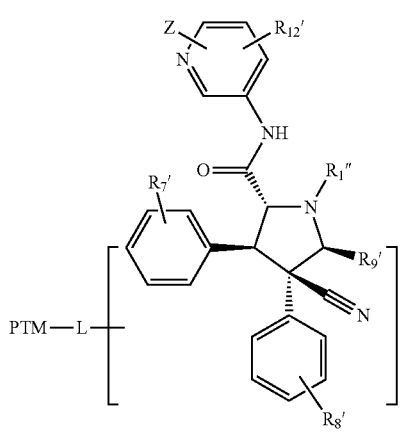
A-4-3

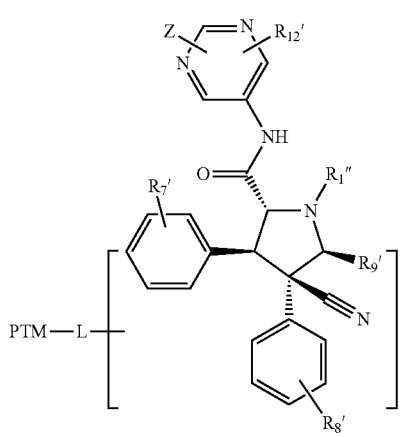
A-4-4

-continued

A-4-5

A-4-6 wherein:
at each occurrence $R_{7'}$ of Formula A-4-1 through A-4-6 is independently selected from the group consisting of halogen, mono-, and di- or tri-substituted halogen;
at each occurrence $R_{8'}$ of Formula A-4-1 through A-4-6 is independently selected from the group consisting of H, —F, —Cl, —Br, —I, —CN, —NO$_2$, ethynyl, cyclopropyl, methyl, ethyl, isopropyl, vinyl, methoxy, ethoxy, isopropoxy, —OH, other C$_{1-6}$ alkyl, other C$_{1-6}$ alkenyl, and C1-6 alkynyl, mono-, di- or tri-substituted;
at each occurrence $R_{9'}$ of Formula A-4-1 through A-4-6 is independently selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;
at each occurrence Z of Formula A-4-1 through A-4-6 is independently selected from the group consisting of H, —OCH$_3$, —OCH$_2$CH$_3$, and halogen;
at each occurrence $R_{10'}$ and $R_{11'}$ of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)m-(CH$_2$)$_n$—NR'COR", (CH$_2$CH$_2$O)$_m$—(CH$_2$)$_n$—NR'SO$_2$R", (CH$_2$CH$_2$O)m(CH$_2$)$_n$—COOH, (CH$_2$CH$_2$O)$_m$(CH$_2$)$_n$—COOR, (CH$_2$CH$_2$O)$_m$—(CH$_2$)$_n$—C$_0$NR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$—(CH$_2$)$_n$R', (CH$_2$)$_p$—(CH$_2$CH$_2$O)$_m$—(CH$_2$)$_n$—OH, (CH$_2$)$_p$—(CH$_2$CH$_2$O)$_m$—(CH$_2$)$_n$—OR', (CH$_2$)$_p$—(CH$_2$CH$_2$O)$_m$—(CH$_2$)n-NR'R", (CH$_2$)$_P$—(CH$_2$CH$_2$O)m-(CH$_2$)$_n$—NR'COR", (CH$_2$)$_p$—(CH$_2$CH$_2$O)m-(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)m-(CH$_2$)$_n$—COOR', (CH$_2$)$_p$—(CH$_2$CH$_2$O)$_m$—(CH$_2$)$_n$—C$_0$NR'R", (CH$_2$)$_p$—(CH$_2$CH$_2$O)m-(CH$_2$)$_n$—SO$_2$R', (CH$_2$)$_P$—(CH$_2$CH$_2$O)$_m$—(CH$_2$)$_n$—COR', (CH$_2$)$_P$—(CH$_2$CH$_2$O)$_m$—(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R" are selected from H, alkyl, alkyl substituted with halogen, hydroxyl, NH$_2$, NH(alkyl), N(alkyl)$_2$, oxo, carboxy, cycloalkyl and heteroaryl;
m, n, and p are independently 0 to 6;
at each occurrence $R_{12'}$ of Formula A-4-1 through A-4-6 is independently selected from the group consisting of —O-(alkyl), —O-(alkyl)-alkoxy, —C(=O)-(alkyl), —C(=O)-alkyl-alkoxy, —C(=O)—NH-(alkyl), —C(=O)—N-(alkyl)$_2$, —S(=O)-(alkyl), S(=O)$_2$-(alkyl), —C(=O)-(cyclic amine), and —O-aryl-(alkyl), —O-aryl-(alkoxy);
at each occurrence $R_{1'}$ of Formula A-4-1 through A-4-6 is independently selected from the group consisting of alkyl, aryl substituted alkyl, alkoxy substituted alkyl, cycloalkyl, ary-substituted cycloalkyl, and alkoxy substituted cycloalkyl.

In various embodiments, the alkyl or alkoxy groups in Formula A-4-1 through A-4-6 can be a lower alkyl or lower alkoxy, respectively.

In certain embodiments, the linker connection position of Formula A-4-1 through A-4-6 is at least one of Z, $R_{8'}$, $R_{9'}$, $R_{10'}$, $R_{11'''}$, $R_{12'''}$, or $R_{1'''}$.

Suitable MDM2 binding moieties include, but are not limited to, the following:

1. The HDM2/MDM2 inhibitors identified in *SCIENCE* vol: 303, page: 844-848 (2004) and *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

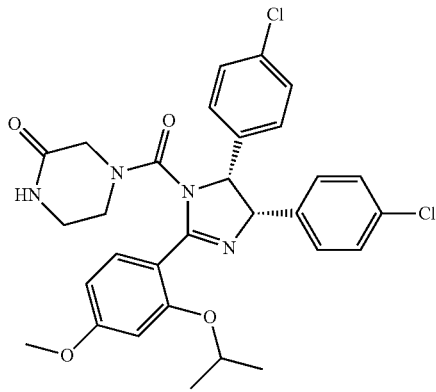 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM)group is attached, for example, at the methoxy group or as a hydroxyl group);

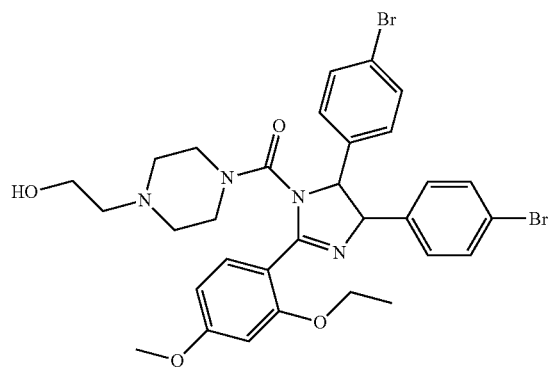 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group);

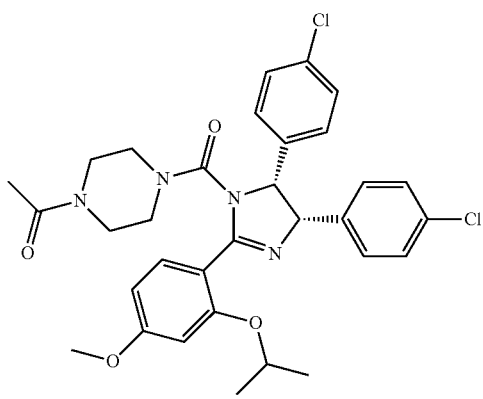 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group).

2. Trans-4-Iodo-4'-Boranyl-Chalcone

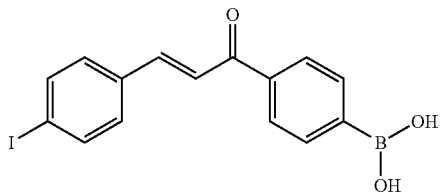 [SMILES: O=C(/C=C/c1ccc(I)cc1)c1ccc(B(O)O)cc1]

(derivatized where a linker group L or a linker group L or a-(L-MLM) group is attached, for example, via a hydroxy group).

Cereblon E3 Ubiquitin Ligase Binding Moieties

Neo-Imide Compounds

In one embodiment the description provides compounds useful for binding to and/or inhibiting cereblon E3 ubiquitin ligase. In certain embodiments, the compound is selected from the group consisting of:

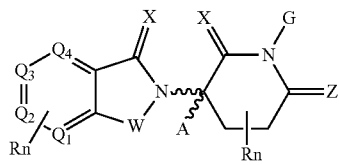 (a)

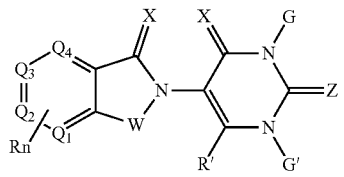 (b)

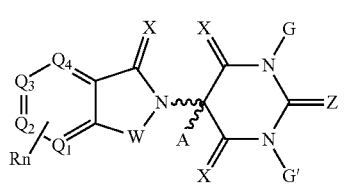 (c)

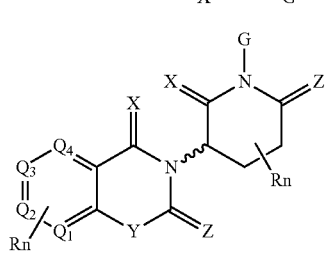 (d)

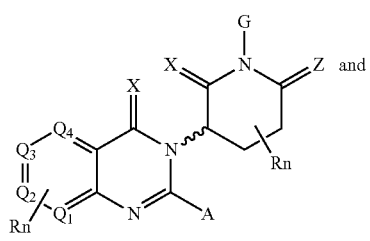 (e) and

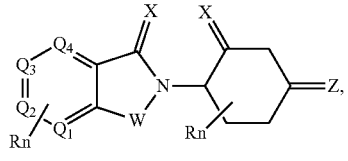 (f)

wherein:
at each occurrence W of Formulas (a) through (f) is independently selected from the group $CH_2$, CHR, C(=O), $SO_2$, NH, and N-alkyl;
at each occurrence X of Formulas (a) through (f) is independently selected from the group O, S and $H_2$;
at each occurrence Y of Formulas (a) through (f) is independently selected from the group $CH_2$, —C=CR', NH, N-alkyl, N-aryl, N-hetaryl, N-cycloalkyl, N-heterocyclyl, O, and S;
at each occurrence Z of Formulas (a) through (f) is independently selected from the group O, and S or $H_2$ except that both X and Z cannot be $H_2$;
at each occurrence G and G' of Formulas (a) through (f) are independently selected from the group H, alkyl (linear, branched, optionally substituted), OH, R'OC(=O)OR, R'OC(=O)NRR", $CH_2$-heterocyclyl optionally substituted with R', and benzyl optionally substituted with R';

at each occurrence $Q_1$-$Q_4$ of Formulas (a) through (f) represent a C substituted with a group independently selected from R', N or N-oxide;

at each occurrence A of Formulas (a) through (f) is independently selected from the group H, alkyl (linear, branched, optionally substituted), cycloalkyl, Cl and F;

at each occurrence R of Formulas (a) through (f) comprises, but is not limited to: —CONR'R", —OR', —NR'R", —SR', —SO$_2$R', —SO$_2$NR'R", —CR'R"—, —CR'NR'R"—, (—CR'O)$_n$R", -aryl, -hetaryl, -alkyl (linear, branched, optionally substituted), -cycloalkyl, -heterocyclyl, —P(=O)(OR')R", —P(=O)R'R", —OP(=O)(OR')R", —OP(=O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —C=CR', —S(C=O)(C=N—R')R", —SF$_5$ and —OCF$_3$ at each occurrence R' and R" of Formulas (a) through (f) are independently selected from a bond, H, alkyl, cycloalkyl, aryl, heteroaryl, heterocyclic, —C(=O)R, heterocyclyl, each of which is optionally substituted;

at each occurrence n of Formulas (a) through (f) is independently an integer from 1-10;

at each occurrence ∼ of Formulas (a) through (f) represents a bond that may be stereospecific ((R) or (S)) or non-stereospecific; and at each occurrence $R_n$ of Formulas (a) through (f) includes from 1 to 4 functional groups or atoms, for example, O, OH, N, $C_{1-6}$ alkyl, $C_{1-6}$ alkoxy, -alkyl-aryl, amine, amide, or carboxy, any of which is optionally modified to be covalently joined to a PTM, a chemical linker group (L), a ULM, CLM (or CLM') or combination thereof.

In various embodiments, the CLM or ULM has the structure:

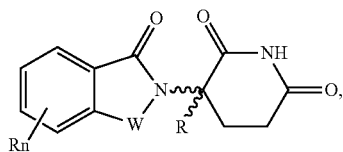

Formula (g)

wherein:
at each occurrence W of Formula (g) is independently selected from the group CH$_2$, C(=O), NH, and N-alkyl;

at each occurrence R of Formula (g) is independently selected from a H, methyl, or optionally substituted alkyl;

at each occurrence ∼ of Formula (g) represents a bond that may be stereospecific ((R) or (S)) or non-stereospecific; and at each occurrence $R_n$ of Formula (g) comprises 1-4 independently selected functional groups or atoms, and optionally, one of which is modified to be covalently joined to a PTM, a chemical linker group (L), a ULM, CLM (or CLM') or combination thereof.

In various embodiments, the W, X, Y, Z, G, G', R, R', R", $Q_1$-$Q_4$, A, and $R_n$ of Formulas (a) through (g) can independently be covalently coupled to a linker and/or a linker to which is attached one or more PTM, ULM, CLM or CLM' groups.

In any of the embodiments or embodiments described herein, $R_n$ of Formulas (a) through (g) includes from 1 to 4 functional groups or atoms, for example, O, OH, N, $C_{1-6}$ alkyl, $C_{1-6}$ alkoxy, amine, amide, or carboxy, and optionally, one of which is modified to be covalently joined to a PTM, a chemical linker group (L), a ULM, CLM (or CLM') or combination thereof.

In various embodiments, the CLMs is selected from the group consisting of

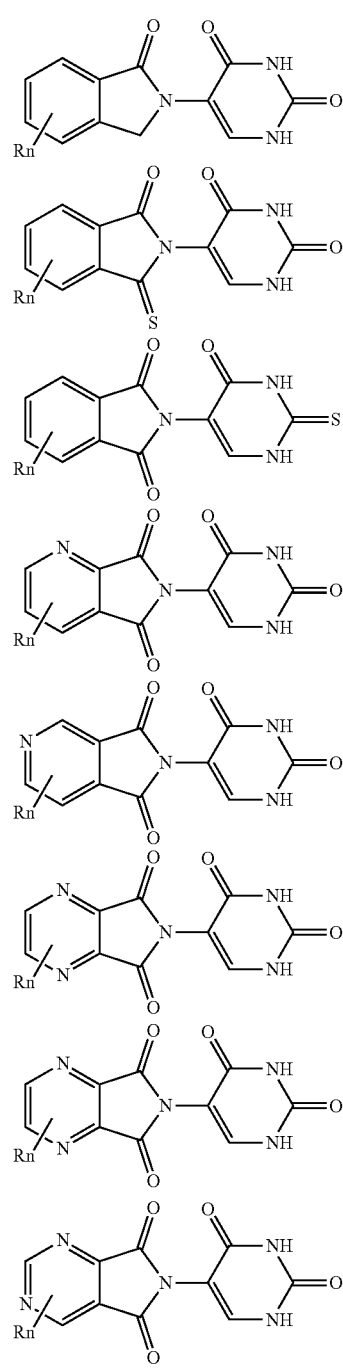

147
-continued
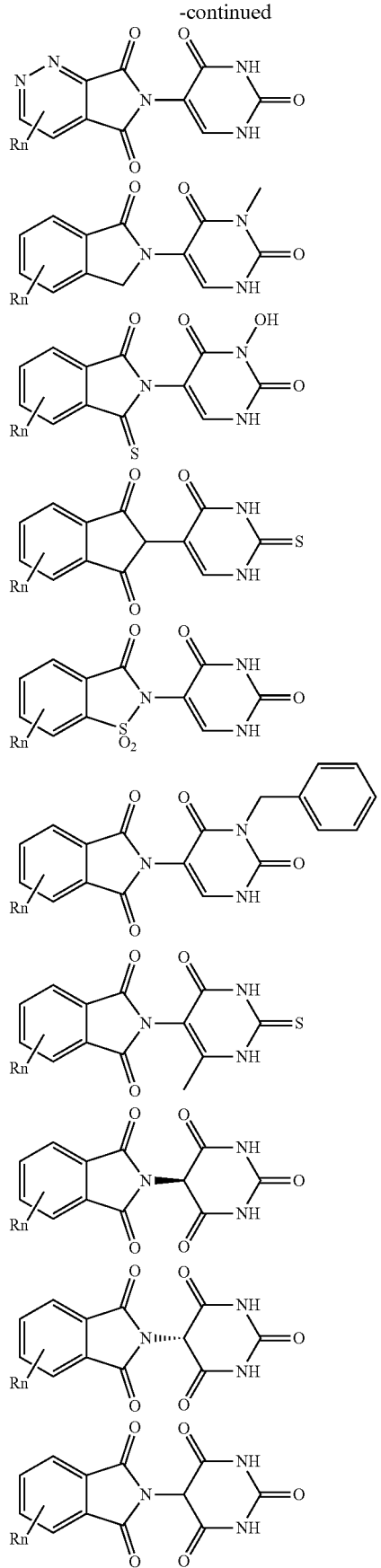
148
-continued
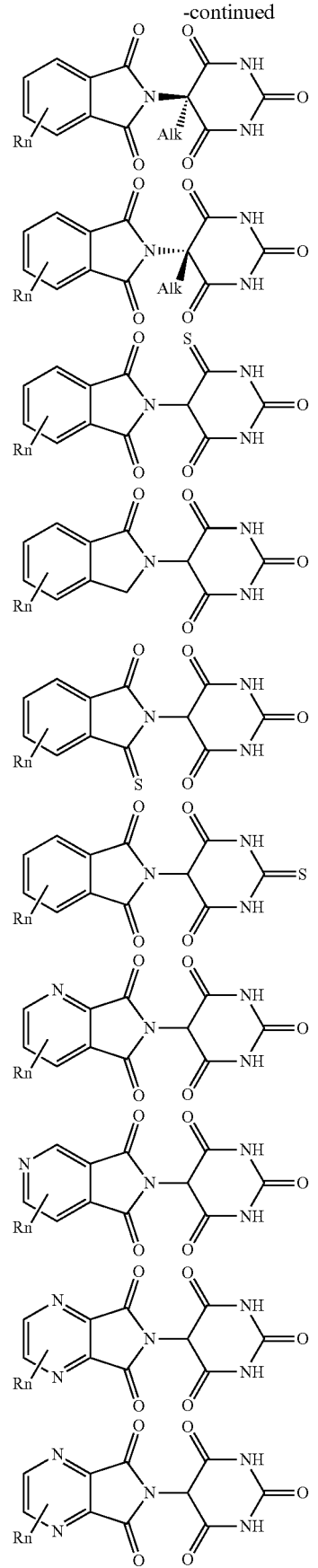

149
-continued
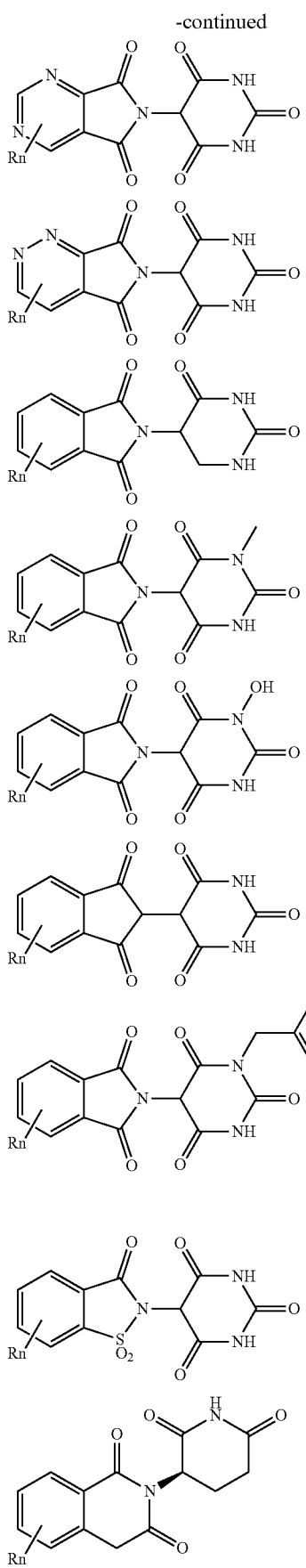
150
-continued
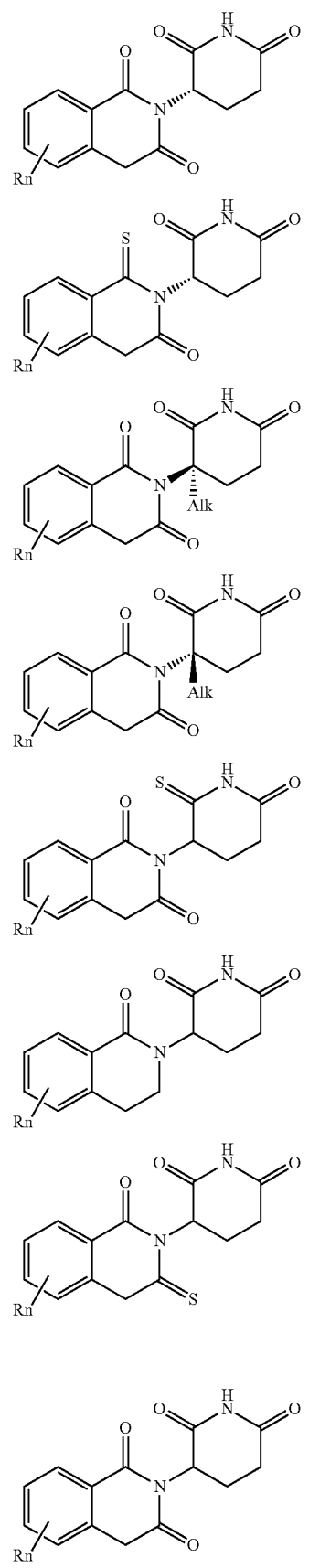

151
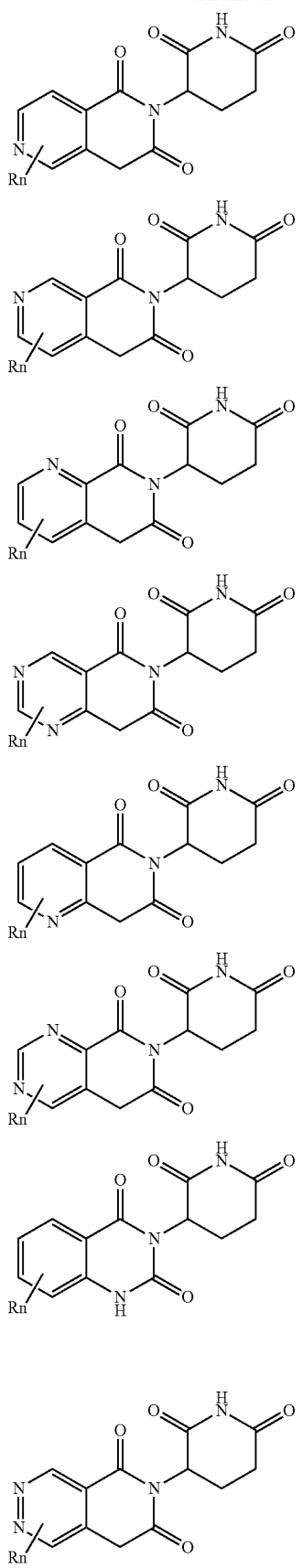
152
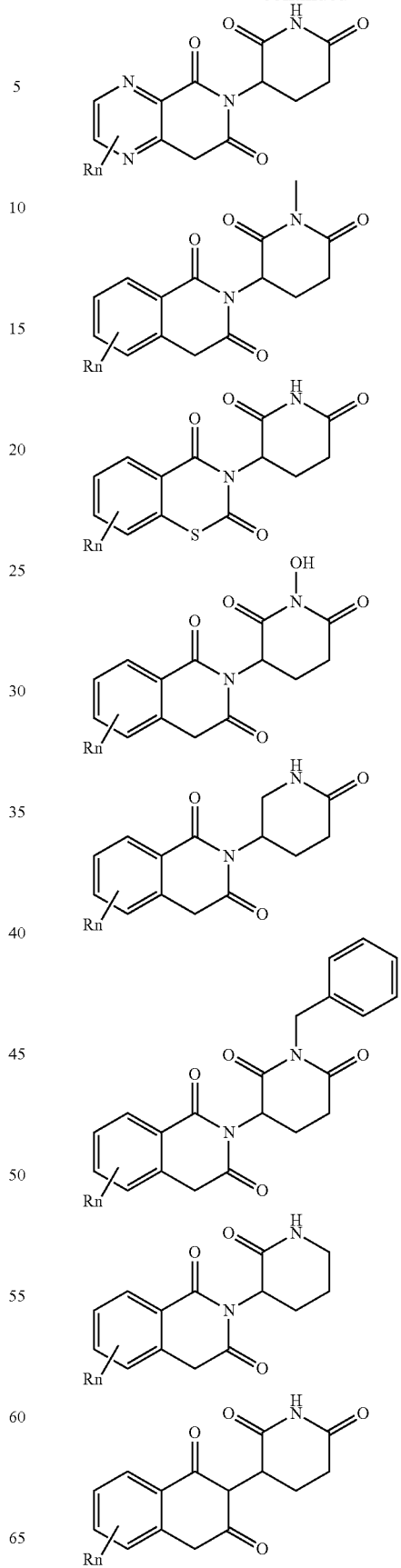

153
-continued
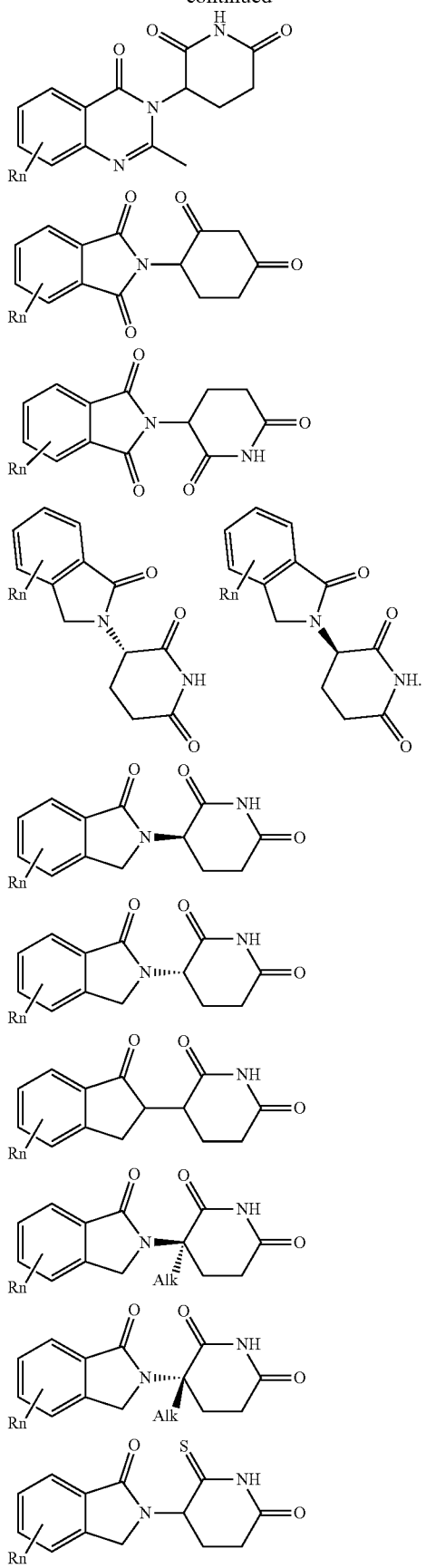
154
-continued
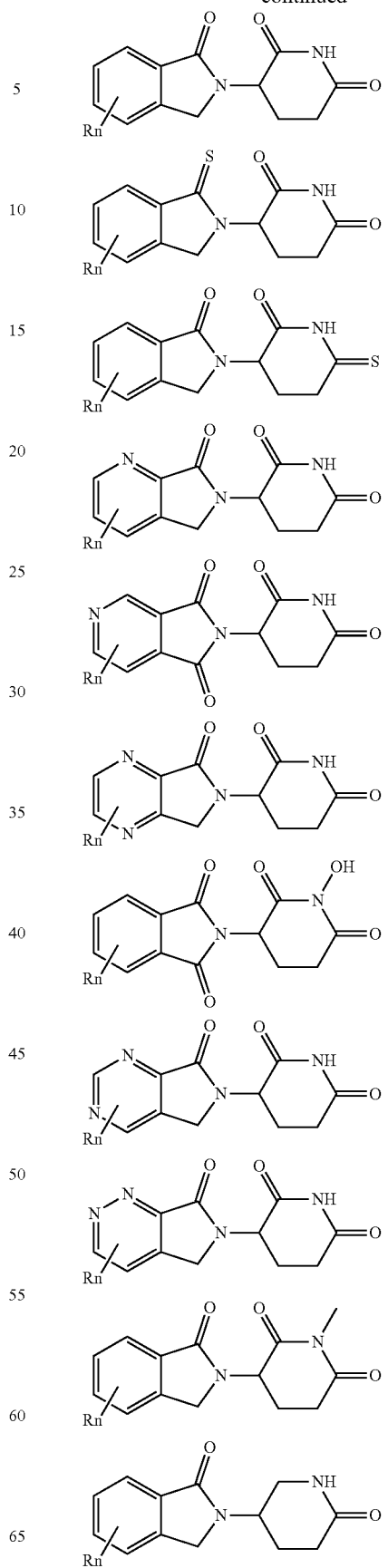

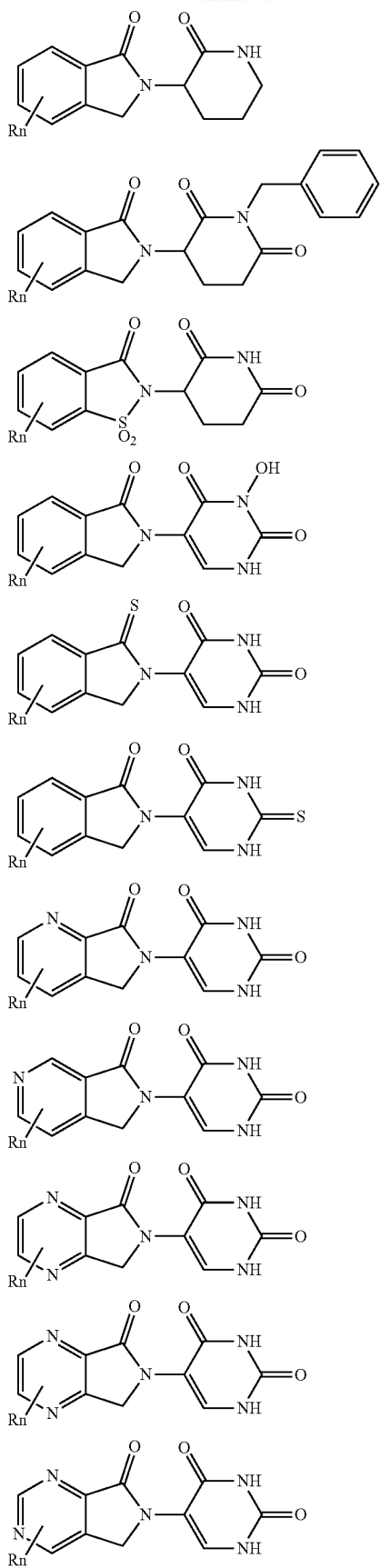
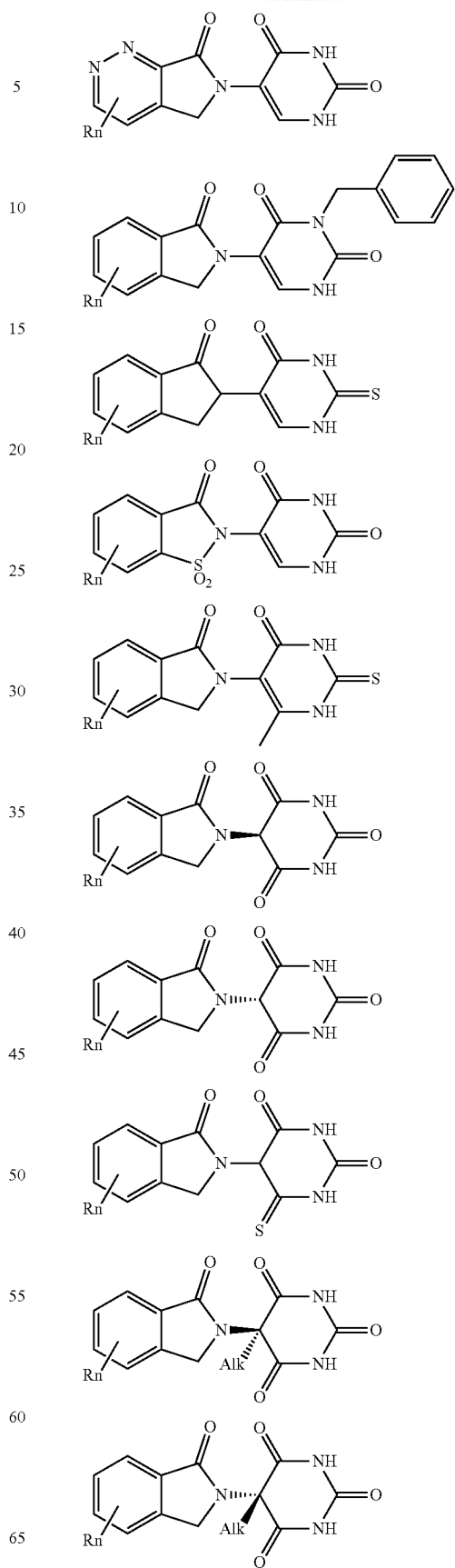

157
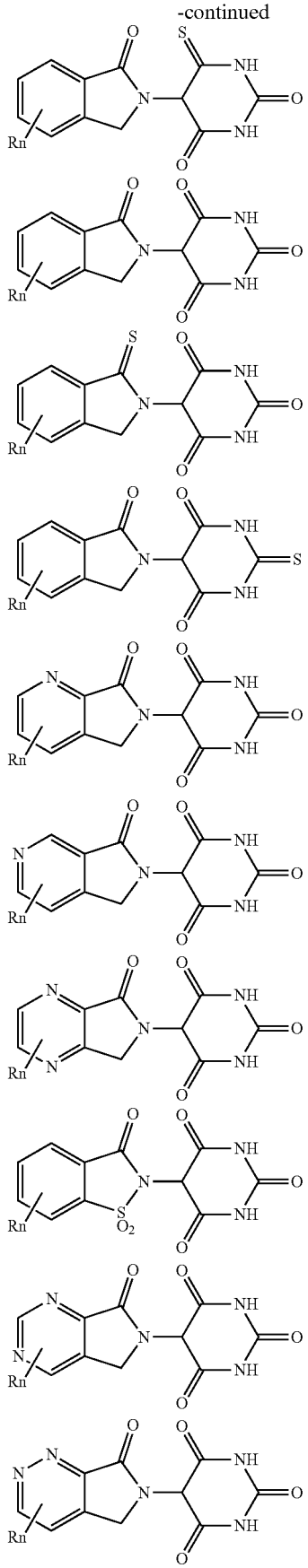
158
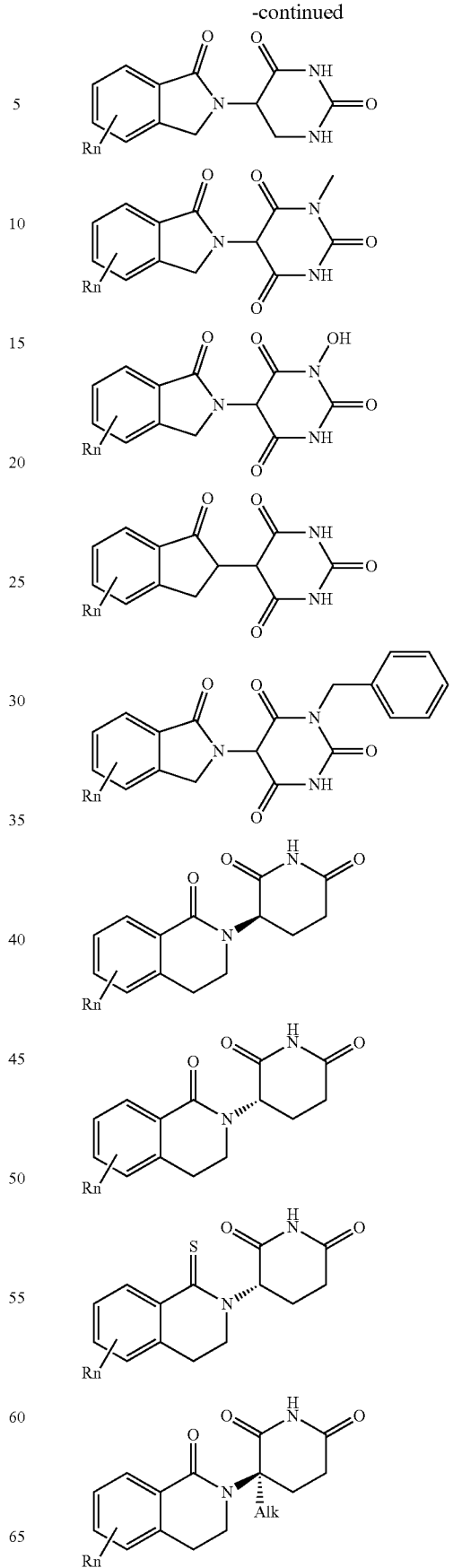

-continued
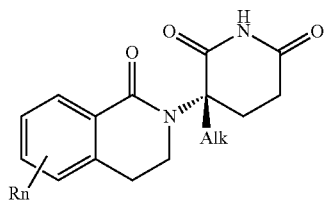
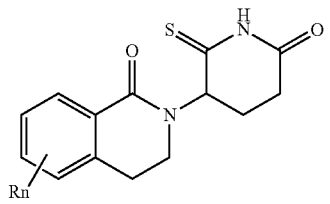
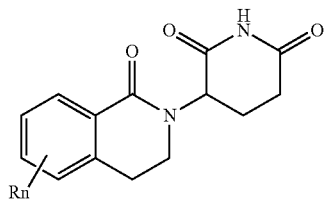
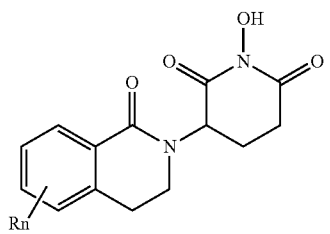
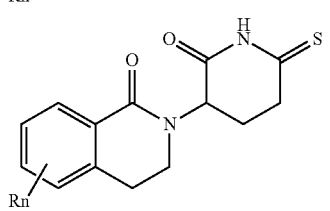
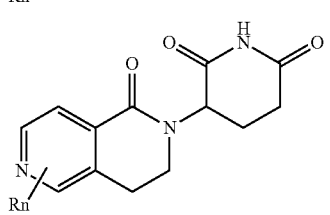
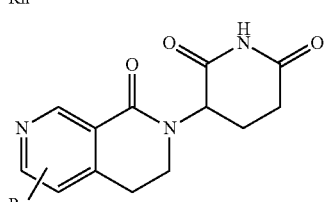
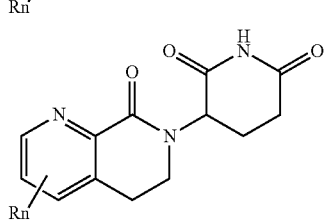
-continued
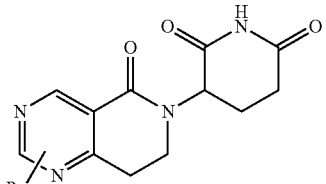
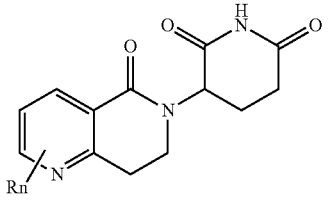
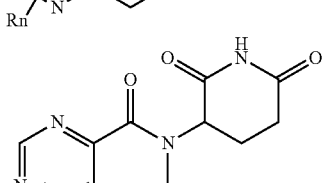
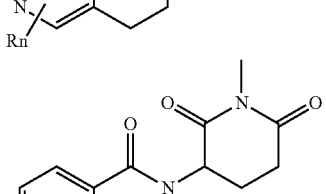
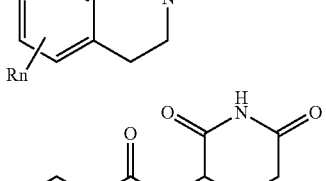
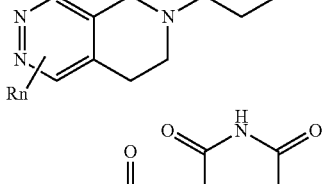
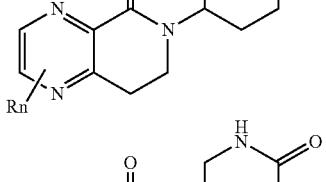
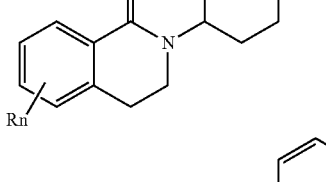
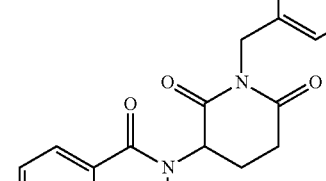

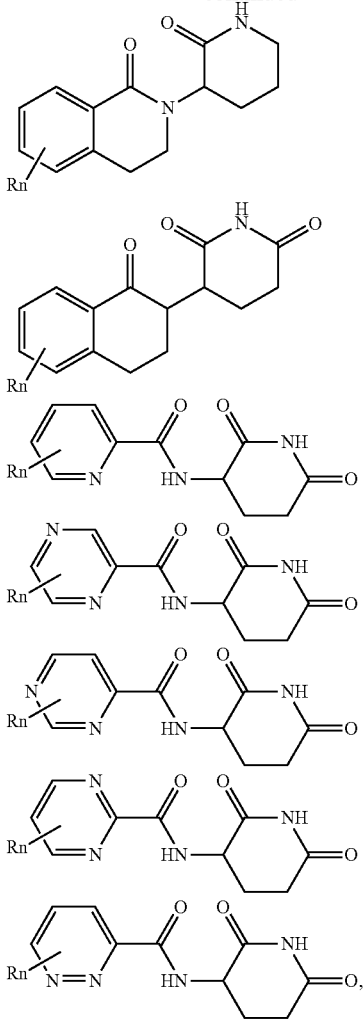

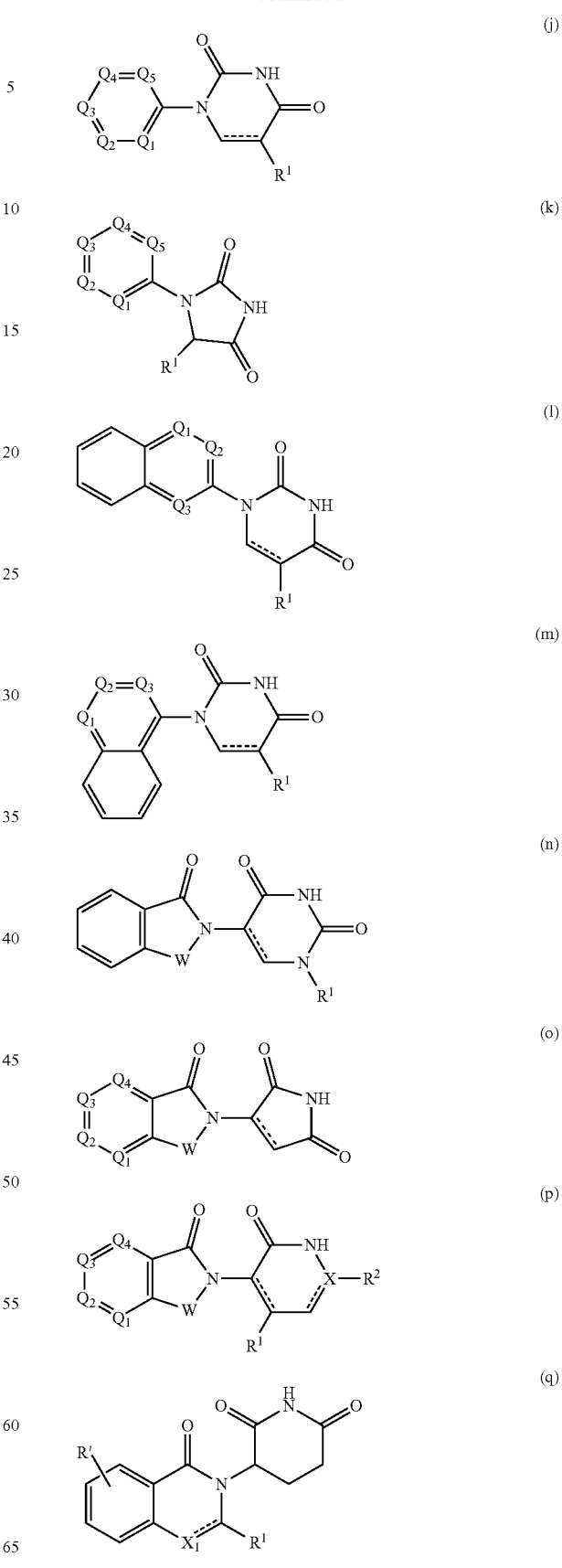

wherein at each occurrence $R_n$ includes from 1 to 4 functional groups or atoms, for example, O, OH, N, $C_{1-6}$ alkyl, $C_{1-6}$ alkoxy, -alkyl-aryl, amine, amide, or carboxy, any of which is optionally modified to be covalently joined to a PTM, a chemical linker group (L), a ULM, CLM (or CLM') or combination thereof; and Alk is an optionally substituted alkyl group.

In various embodiments, the CLM is selected from the group consisting of:

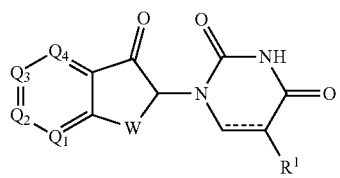

(h)

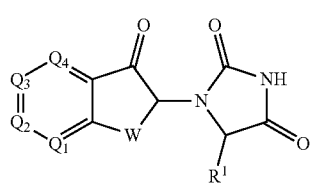

(i)

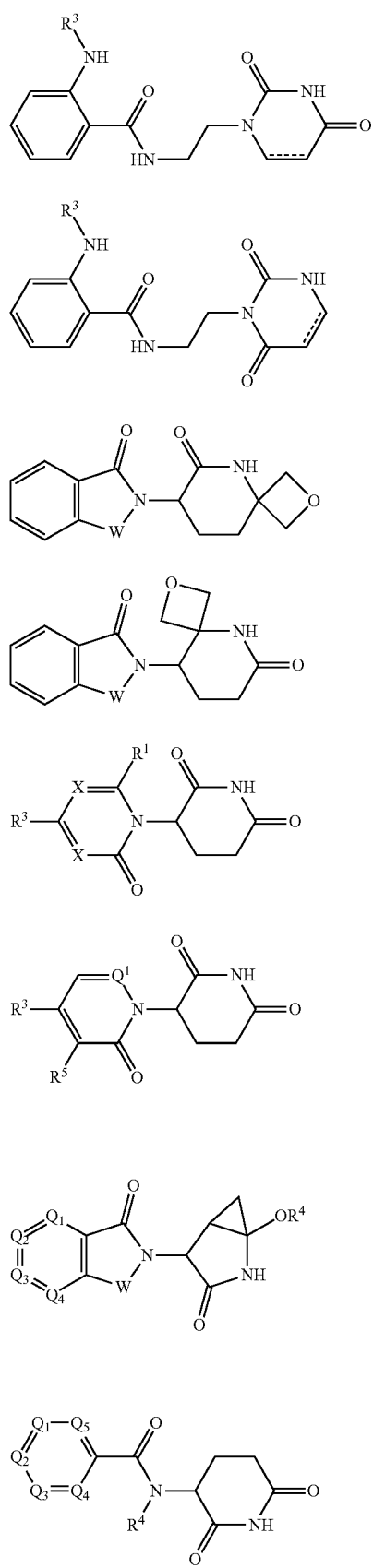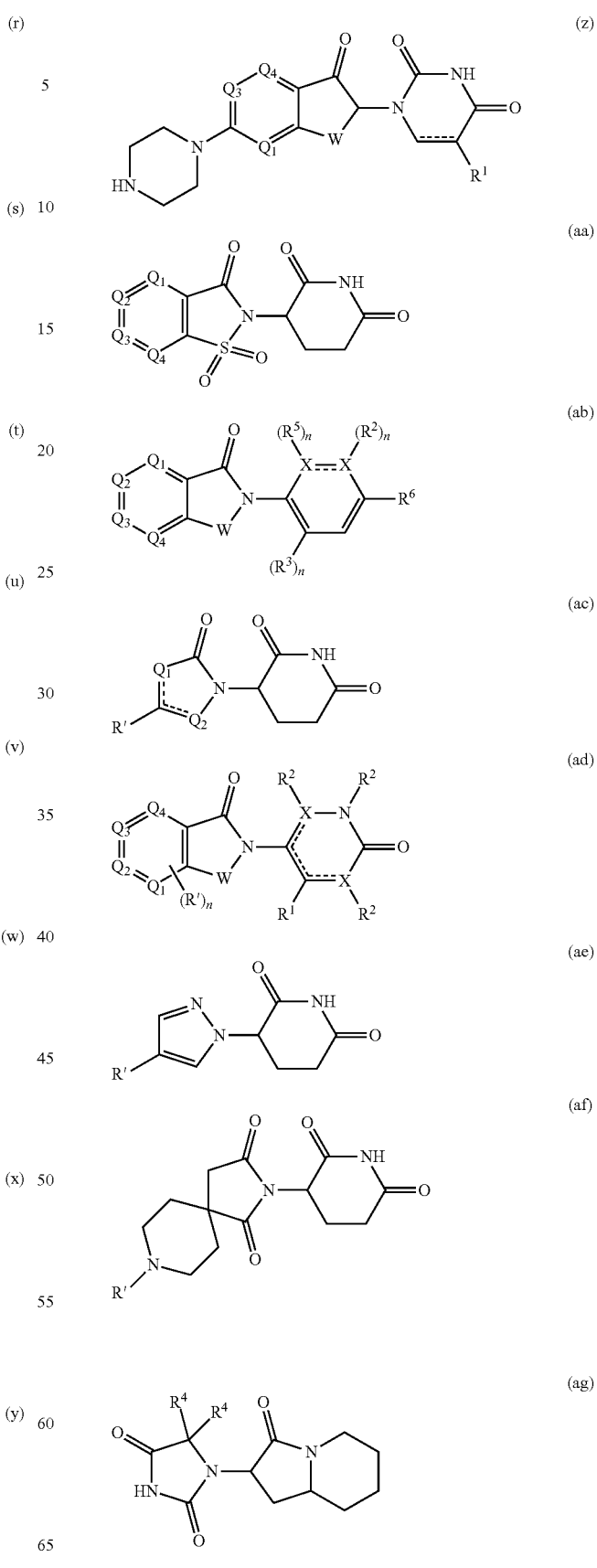

-continued

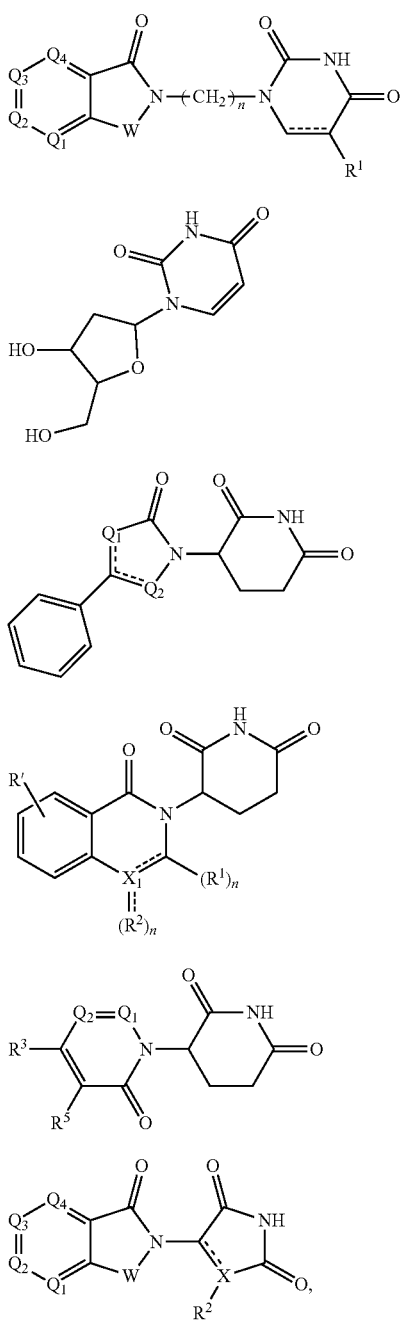

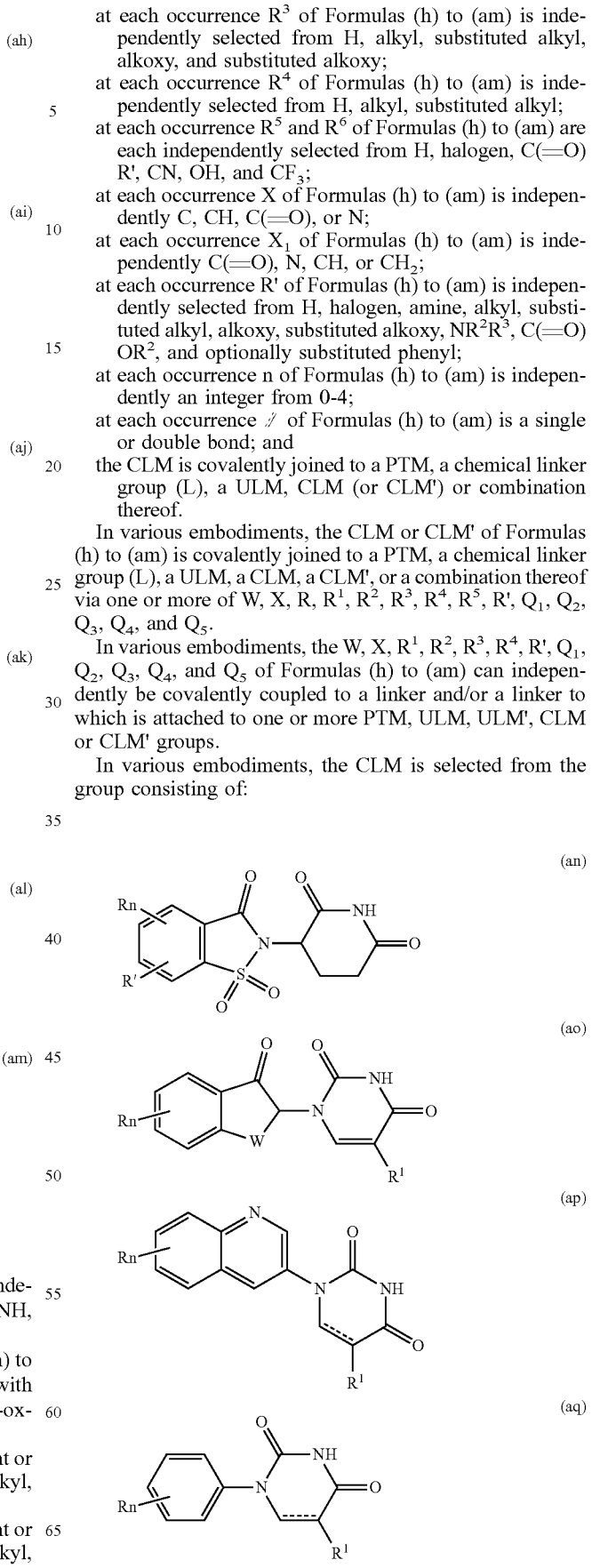

wherein:
at each occurrence W of Formulas (h) to (am) is independently selected from $CH_2$, CHR, C=O, $SO_2$, NH, and N-alkyl;
at each occurrence $Q_1$, $Q_2$, $Q_3$, $Q_4$, $Q_5$ of Formulas (h) to (am) are each independently a C or N substituted with a group independently selected from R', N and N-oxide;
at each occurrence $R^1$ of Formulas (h) to (am) is absent or independently selected from H, OH, CN, $C_{1-3}$ alkyl, and C(=O);
at each occurrence $R^2$ of Formulas (h) to (am) is absent or independently selected from H, OH, CN, $C_{1-3}$ alkyl, $CHF_2$, $CF_3$, CHO, and C(=O)$NH_2$;
at each occurrence $R^3$ of Formulas (h) to (am) is independently selected from H, alkyl, substituted alkyl, alkoxy, and substituted alkoxy;
at each occurrence $R^4$ of Formulas (h) to (am) is independently selected from H, alkyl, substituted alkyl;
at each occurrence $R^5$ and $R^6$ of Formulas (h) to (am) are each independently selected from H, halogen, C(=O) R', CN, OH, and $CF_3$;
at each occurrence X of Formulas (h) to (am) is independently C, CH, C(=O), or N;
at each occurrence $X_1$ of Formulas (h) to (am) is independently C(=O), N, CH, or $CH_2$;
at each occurrence R' of Formulas (h) to (am) is independently selected from H, halogen, amine, alkyl, substituted alkyl, alkoxy, substituted alkoxy, $NR^2R^3$, C(=O) $OR^2$, and optionally substituted phenyl;
at each occurrence n of Formulas (h) to (am) is independently an integer from 0-4;
at each occurrence ⫽ of Formulas (h) to (am) is a single or double bond; and
the CLM is covalently joined to a PTM, a chemical linker group (L), a ULM, CLM (or CLM') or combination thereof.

In various embodiments, the CLM or CLM' of Formulas (h) to (am) is covalently joined to a PTM, a chemical linker group (L), a ULM, a CLM, a CLM', or a combination thereof via one or more of W, X, R, $R^1$, $R^2$, $R^3$, $R^4$, $R^5$, R', $Q_1$, $Q_2$, $Q_3$, $Q_4$, and $Q_5$.

In various embodiments, the W, X, $R^1$, $R^2$, $R^3$, $R^4$, R', $Q_1$, $Q_2$, $Q_3$, $Q_4$, and $Q_5$ of Formulas (h) to (am) can independently be covalently coupled to a linker and/or a linker to which is attached to one or more PTM, ULM, ULM', CLM or CLM' groups.

In various embodiments, the CLM is selected from the group consisting of:

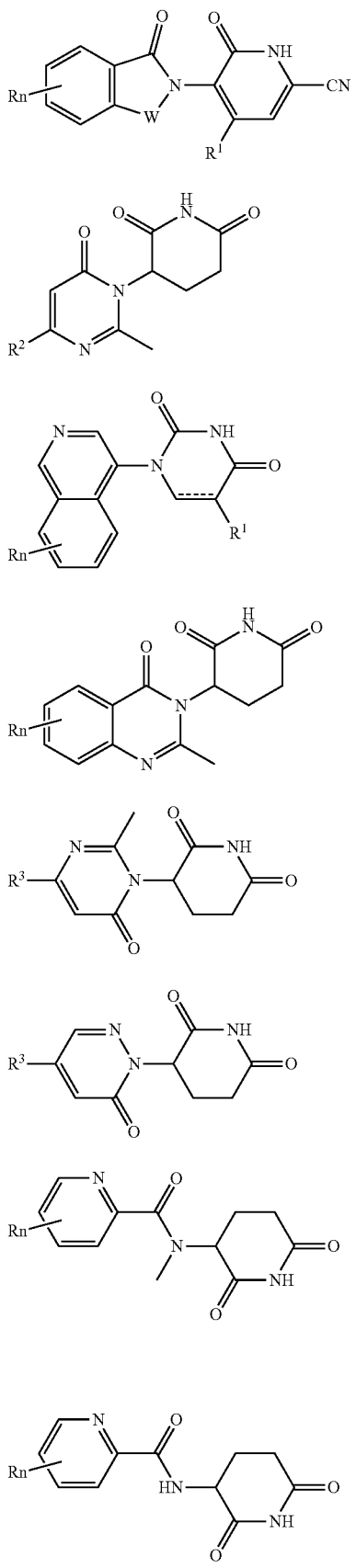
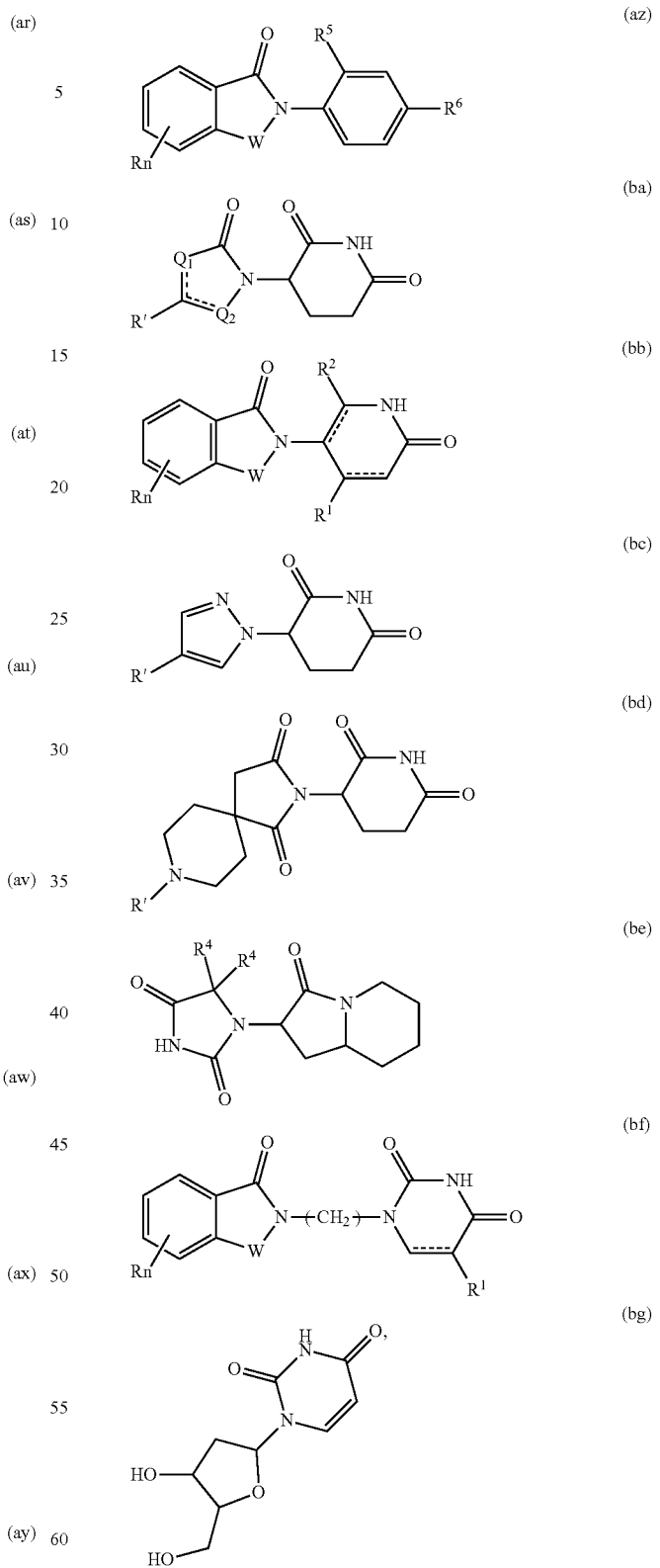
wherein:
at each occurrence W of Formulas (an) through (bg) is independently selected from the group consisting of $CH_2$, CHR, C=O, $SO_2$, NH, and N-alkyl;

at each occurrence $R^1$ of Formulas (an) through (bg) is absent or independently selected from the group consisting of H, CH, CN, and $C_{1-3}$ alkyl;

at each occurrence $R^2$ of Formulas (an) through (bg) is independently H or a $C_{1-3}$ alkyl;

at each occurrence $R^3$ of Formulas (an) through (bg) is independently selected from H, alkyl, substituted alkyl, alkoxy, substituted alkoxy;

at each occurrence $R^4$ of Formulas (an) through (bg) is independently methyl or ethyl;

at each occurrence $R^5$ of Formulas (an) through (bg) is independently H or halogen;

at each occurrence $R^6$ of Formulas (an) through (bg) is independently H or halogen;

at each occurrence R of Formulas (an) through (bg) is H;

at each occurrence R' of Formulas (an) through (bg) is H or an attachment point for a PTM, a PTM', a chemical linker group (L), a ULM, a CLM, a CLM', at each occurrence $Q_1$ and $Q_2$ of Formulas (an) through (bg) are each independently C or N substituted with a group independently selected from H or $C_{1-3}$ alkyl;

at each occurrence $\sim$ of Formulas (an) through (bg) is a single or double bond; and at each occurrence $R_n$ of Formulas (an) through (bg) includes from 1 to 4 functional groups or atoms, for example, O, OH, N, $C_{1-6}$ alkyl, $C_{1-6}$ alkoxy, -alkyl-aryl, amine, amide, or carboxy, any of which is optionally modified to be covalently joined to a PTM, a chemical linker group (L), a ULM, CLM (or CLM') or combination thereof.

In various embodiments, the W, $R^1$, $R^2$, $Q_1$, $Q_2$, $Q_3$, $Q_4$, and $R_n$ of Formulas (an) through (bg) can independently be covalently coupled to a linker and/or a linker to which is attached one or more PTM, ULM, ULM', CLM or CLM' groups.

In various embodiments, the $R^1$, $R^2$, $Q_1$, $Q_2$, $Q_3$, $Q_4$, and $R_n$ of Formulas (an) through (bg) can independently be covalently coupled to a linker and/or a linker to which is attached one or more PTM, ULM, ULM', CLM or CLM' groups.

In various embodiments, the $Q_1$, $Q_2$, $Q_3$, $Q_4$, and $R_n$ of Formulas (an) through (bg) can independently be covalently coupled to a linker and/or a linker to which is attached one or more PTM, ULM, ULM', CLM or CLM' groups.

In various embodiments, $R_n$ of Formulas (an) through (bg) is modified to be covalently joined to the linker group (L), a PTM, a ULM, a second CLM having the same chemical structure as the CLM, a CLM', a second linker, or any multiple or combination thereof.

In various embodiments, the CLM is selected from:

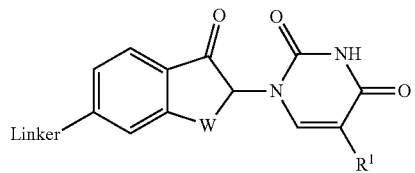

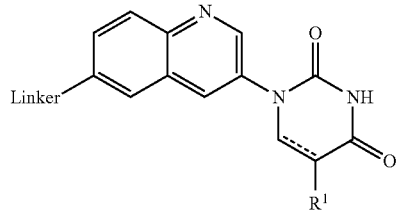

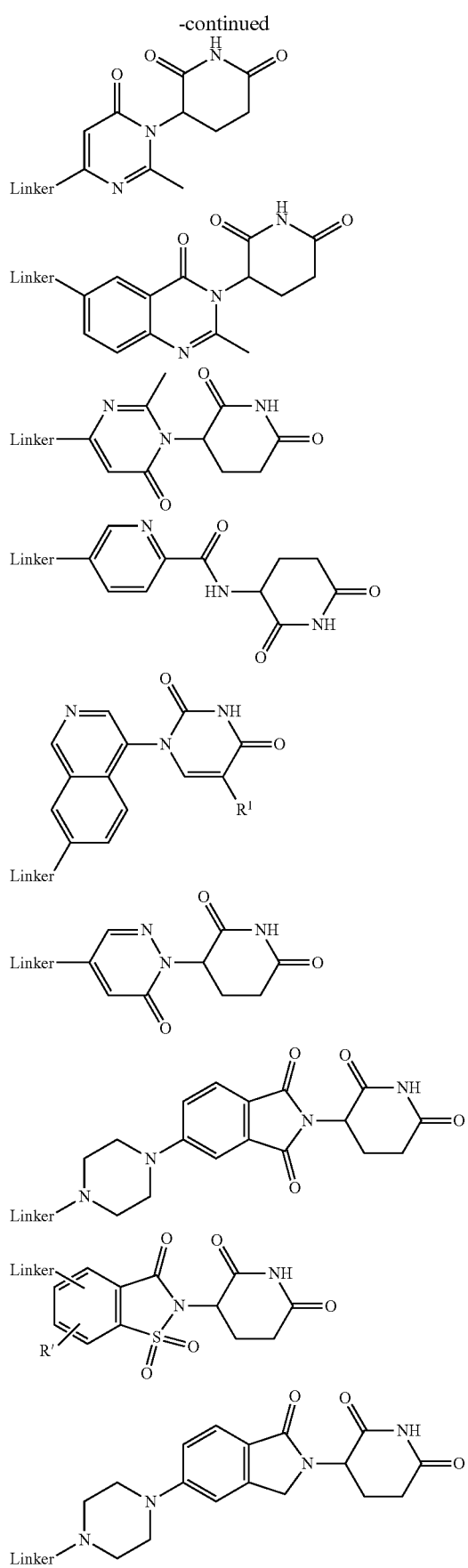

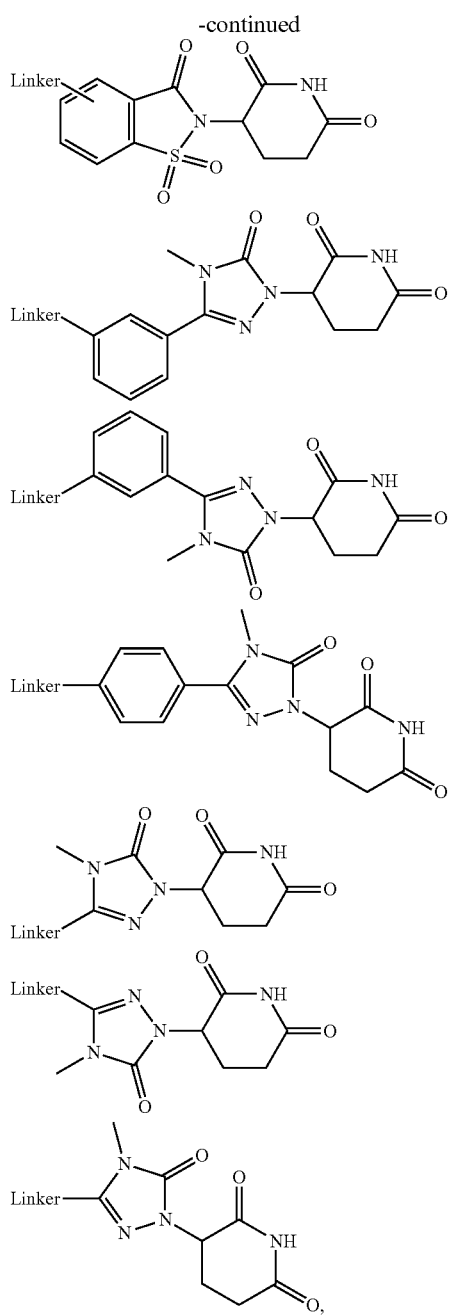
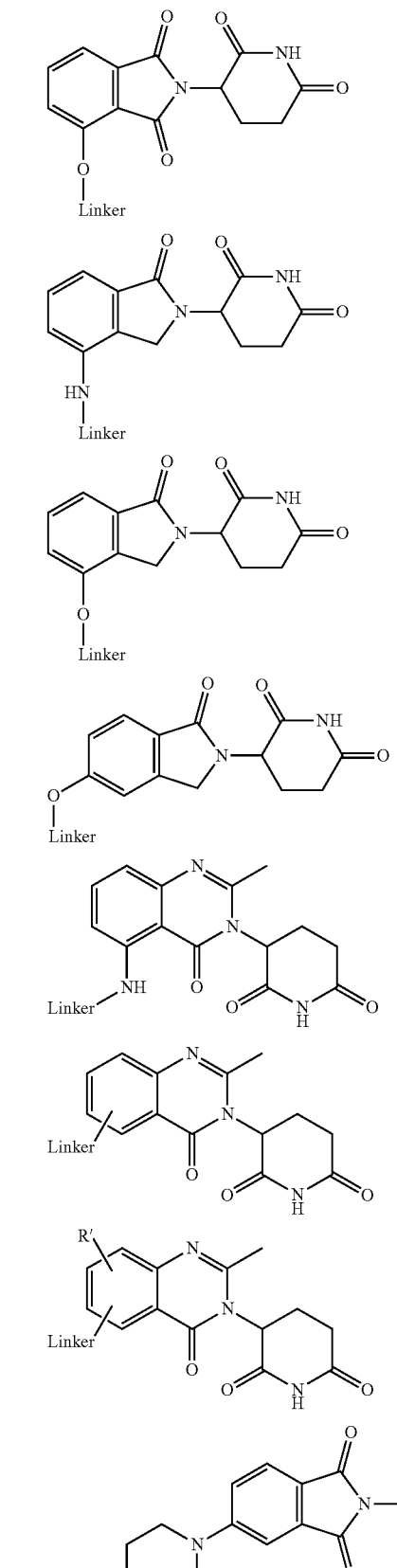
wherein R' is a halogen and $R^1$ is absent or independently selected from the group consisting of H, CH, CN, and $C_{1-3}$ alkyl.
In various embodiments, the CLM is selected from:

-continued

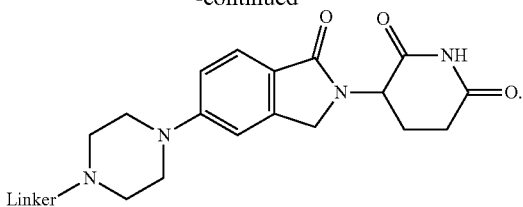

Von Hippel-Lindau E3 Ubiquitin Ligase Binding Moieties

In certain embodiments of the compounds as described herein, ULM is VLM and comprises a chemical structure selected from the group ULM-a:

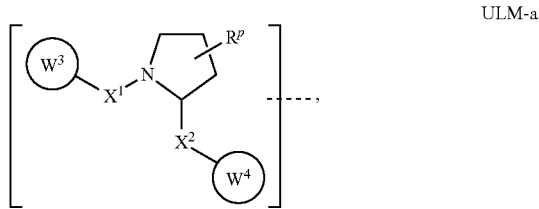

ULM-a wherein:
- at each occurrence a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;
- at each occurrence $X^1$, $X^2$ of Formula ULM-a are each independently selected from the group of a bond, O, $NR^{Y3}$, $CR^{Y3}R^{Y4}$, $C=O$, $C=S$, SO, and $SO_2$;
- at each occurrence $R^{Y3}$, $R^{Y4}$ of Formula ULM-a are each independently selected from the group of Fl, linear or branched $C_{1-6}$ alkyl, optionally substituted by 1 or more halogen, and optionally substituted $C_{1-6}$ alkoxyl;
- at each occurrence $R^P$ of Formula ULM-a is 0, 1, 2, or 3 groups, each independently selected from the group H, halogen, —OH, $C_{1-3}$ alkyl, and $C=O$;
- at each occurrence $W^3$ of Formula ULM-a is selected from the group of an optionally substituted T, an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR^1$-T-Aryl, an optionally substituted —$NR^1$-T-Heteroaryl or an optionally substituted —$NR^1$-T-Heterocycle;
- at each occurrence $X^3$ of Formula ULM-a is $C=O$, $R^1$, $R^{1a}$, $R^{1b}$;
- at each occurrence each of $R^1$, $R^{1a}$, $R^{1b}$ of Formula ULM-a is independently selected from the group consisting of H, linear or branched $C_1$-$C_6$ alkyl group optionally substituted by 1 or more halogen or —OH groups, $R^{Y3}C=O$, $R^{Y3}C=S$, $R^{Y3}SO$, $R^{Y3}SO_2$, $N(R^{Y3}R^{Y4})C=O$, $N(R^{Y3}R^{Y4})C=S$, $N(R^{Y3}R^{Y4})SO$, and $N(R^{Y3}R^{Y4})SO_2$;
- at each occurrence T of Formula ULM-a is independently selected from the group of an optionally substituted alkyl, —(CH$_2$)$_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; or
- at each occurrence T is independently selected from the group of an optionally substituted alkyl, —(CH$_2$)$_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, $C(=O)NR^1R^{1a}$, or $NR^1R^{1a}$ or $R^1$ and $R^{1a}$ are joined to form an optionally substituted heterocycle, or —OH groups or an amino acid side chain optionally substituted; and n is 0 to 6, often 0, 1, 2, or 3, preferably 0 or 1;
- at each occurrence $W^4$ of Formula ULM-a is an optionally substituted —$NR^1$-T-Aryl wherein the aryl group may be optionally substituted with an optionally substituted 5-6 membered heteroaryl, an optionally substituted —$NR^1$-T-Heteroaryl group or an optionally substituted —$NR^1$-T-Heterocycle, where —$NR^1$ is covalently bonded to $X^2$ and $R^1$ is H or $CH_3$, preferably H.

In certain embodiments, at each occurrence $W^4$ of Formula ULM-a is

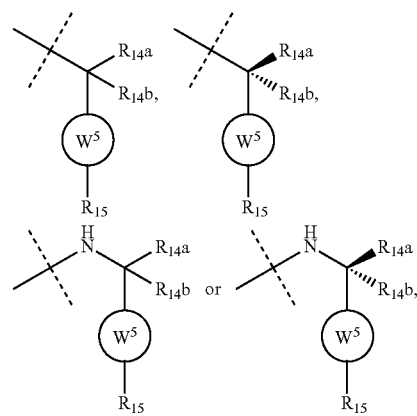

wherein $R_{14a}$, $R_{14b}$, are each independently selected from the group of H, haloalkyl, or optionally substituted alkyl.

In various embodiments, $W^5$ of Formula ULM-a is independently selected from the group of a phenyl or a 5-10 membered heteroaryl,
- at each occurrence $R_{15}$ of Formula ULM-a is independently selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

In additional embodiments, $W^4$ of Formula ULM-a substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halogen, —OH, $C_{1-3}$alkyl, or $C=O$.

In any of the embodiments described herein, the $W^3$, $W^4$ of Formula ULM-a can independently be covalently coupled to a linker which is attached one or more PTM groups, and wherein the dashed line indicates the site of attachment of at least one PTM, another ULM (ULM') or a chemical linker moiety coupling at least one PTM or a ULM' or both to ULM.

In certain embodiments, the VHL has the structure:

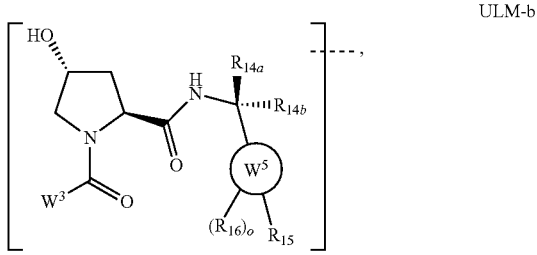

ULM-b wherein:
at each occurrence $W^3$ of Formula ULM-b is independently selected from the group of an optionally substituted aryl, optionally substituted heteroaryl, or

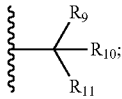

at each occurrence $R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;
at each occurrence $R_{11}$ of Formula ULM-b is independently selected from the group of an optionally substituted heterocyclic, optionally substituted alkoxy, optionally substituted heteroaryl, optionally substituted aryl,

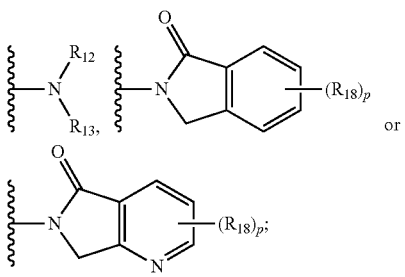

at each occurrence $R_{12}$ of Formula ULM-b is independently selected from the group of H or optionally substituted alkyl;
at each occurrence $R_{13}$ of Formula ULM-b is independently selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
at each occurrence $R_{14a}$, $R_{14b}$ of Formula ULM-b, are each independently selected from the group of Fl, haloalkyl, or optionally substituted alkyl;
at each occurrence $W^5$ of Formula ULM-b is independently selected from the group of a phenyl or a 5-10 membered heteroaryl,
at each occurrence $R_{15}$ of Formula ULM-b is independently selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, aryl, heteroaryl, cycloalkyl, or cycloheteroalkyl (each optionally substituted);
at each occurrence $R_{16}$ of Formula ULM-b is independently selected from the group of halogen, optionally substituted alkyl, optionally substituted haloalkyl, hydroxy, or optionally substituted haloalkoxy;
at each occurrence o of Formula ULM-b is independently 0, 1, 2, 3, or 4;
at each occurrence $R_{18}$ of Formula ULM-b is independently selected from the group of H, halogen, optionally substituted alkoxy, cyano, optionally substituted alkyl, haloalkyl, haloalkoxy or a linker; and
p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ of Formula ULM-b is

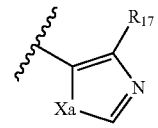

wherein $R_{17}$ is H, halogen, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O. In certain embodiments, $R_{17}$ of Formula ULM-b is selected from the group methyl, ethyl, isopropyl, and cyclopropyl.

In certain embodiments, $R_{15}$ of Formula ULM-b is selected from the group consisting of:

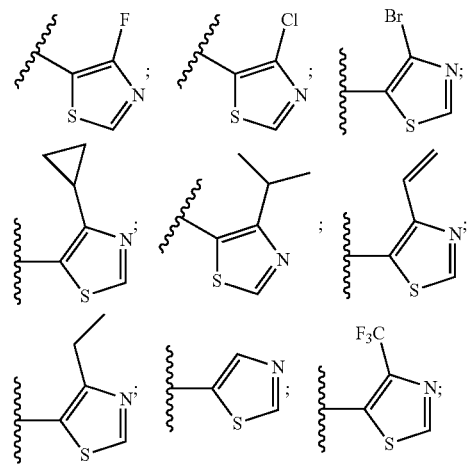

177
-continued
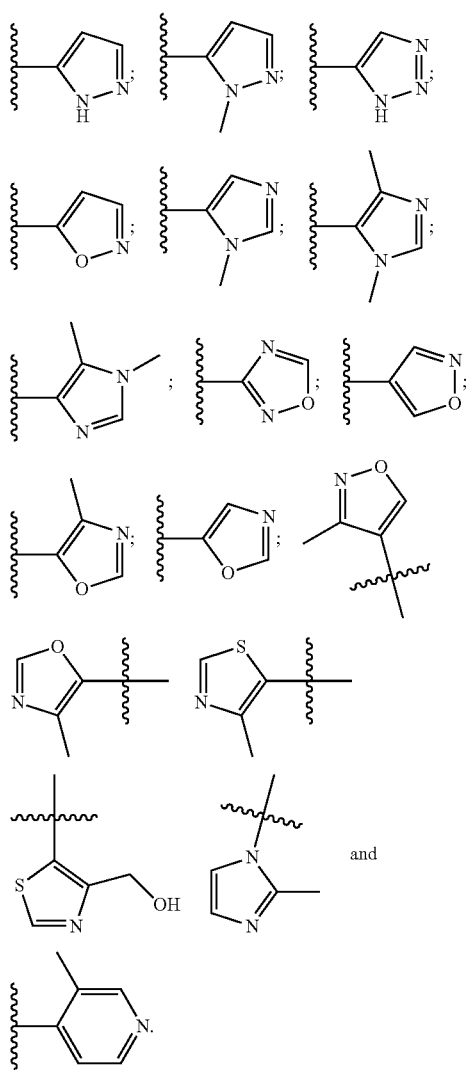
In certain embodiments, $R_{11}$ of Formula ULM-b is selected from the group consisting of:
178
-continued
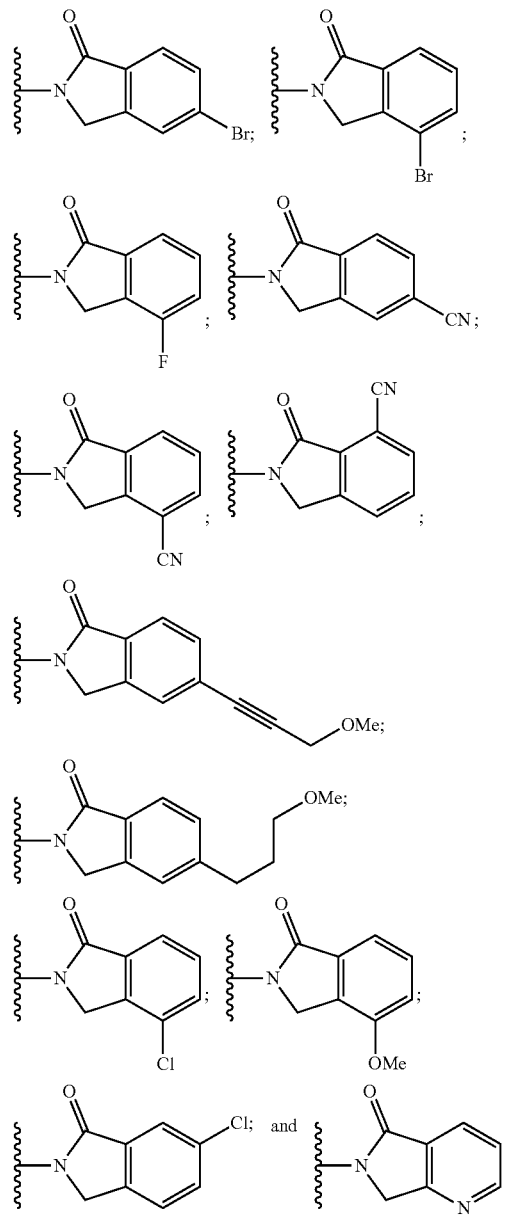
In certain embodiments, the VLM has a structure selected from the group of:
ULM-c
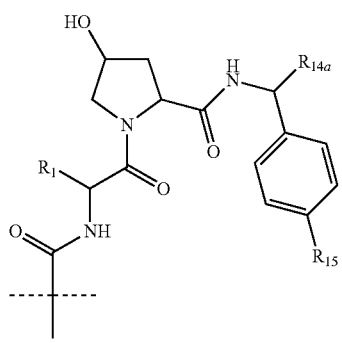

179
-continued

ULM-d

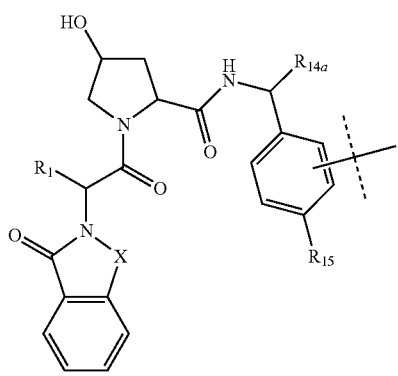

ULM-e

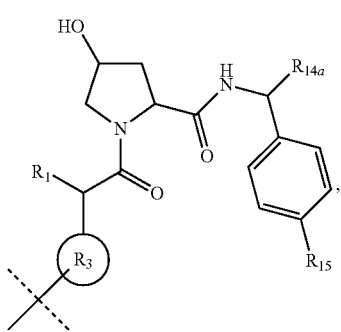

wherein:
at each occurrence $R_1$ of Formulas ULM-c, ULM-d, and ULM-e is independently Fl, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;
at each occurrence $R_{14a}$ of Formulas ULM-c, ULM-d, and ULM-e is independently H, haloalkyl, optionally substituted alkyl, methyl, fluoromethyl, hydroxymethyl, ethyl, isopropyl, or cyclopropyl;
at each occurrence $R_{15}$ of Formulas ULM-c, ULM-d, and ULM-e is independently selected from the group consisting of H, halogen, CN, OH, $NO_2$, optionally substituted heteroaryl, optionally substituted aryl; optionally substituted alkyl, optionally substituted haloalkyl, optionally substituted optionally substituted haloalkoxy, optionally substituted cycloalkyl, and optionally substituted cycloheteroalkyl;
at each occurrence X of Formulas ULM-c, ULM-d, and ULM-e is independently C, $CH_2$, or C=O;
at each occurrence $R_3$ of Formulas ULM-c, ULM-d, and ULM-e is absent or an optionally substituted 5 or 6 membered heteroaryl; and the dashed line of Formulas ULM-c, ULM-d, and ULM-e indicates the site of attachment of at least one PTM, another ULM (ULM') or a chemical linker moiety coupling at least one PTM or a ULM' or both to ULM.

180
In certain embodiments, the VHL has the structure:

ULM-f

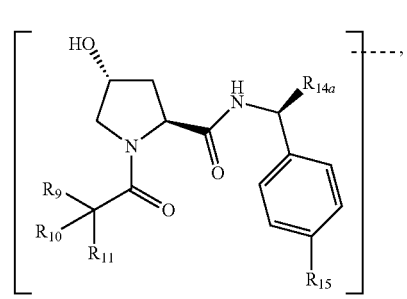

wherein:
at each occurrence $R_{14a}$ of Formula ULM-f is independently H, haloalkyl, optionally substituted alkyl, methyl, fluoromethyl, hydroxymethyl, ethyl, isopropyl, or cyclopropyl;
at each occurrence $R_9$ of Formula ULM-f is independently H;
at each occurrence $R_{10}$ of Formula ULM-f is independently H, ethyl, isopropyl, tert-butyl, sec-butyl, cyclopropyl, cyclobutyl, cyclopentyl, or cyclohexyl;
at each occurrence $R_{11}$ of Formula ULM-f is independently

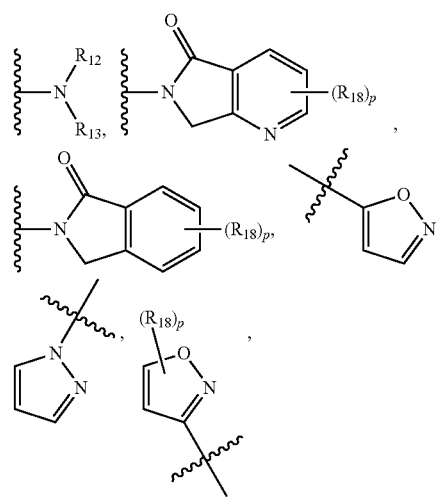

or optionally substituted heteroaryl;
at each occurrence p of Formula ULM-f is independently 0, 1, 2, 3, or 4;
at each occurrence $R_{18}$ of Formula ULM-f is independently halogen, optionally substituted alkoxy, cyano, optionally substituted alkyl, haloalkyl, haloalkoxy or a linker;
$R_{12}$ of Formula ULM-f is H, C=O;
$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
$R_{15}$ of Formula ULM-f is selected from the group consisting of H, halogen, Cl, CN, OH, $NO_2$, optionally substituted heteroaryl, optionally substituted aryl;

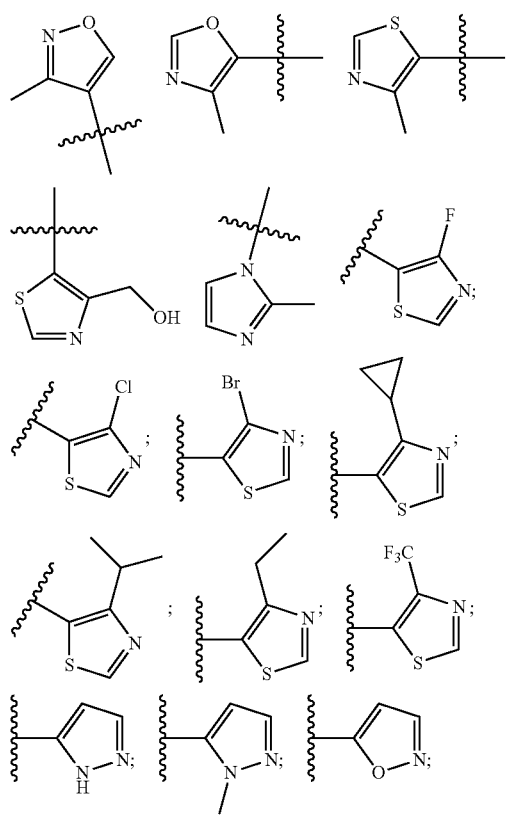
and
wherein the dashed line of Formula ULM-f indicates the site of attachment of at least one PTM, another ULM (ULM') or a chemical linker moiety coupling at least one PTM or a ULM' or both to ULM.
In certain embodiments, the ULM is selected from the following structures:
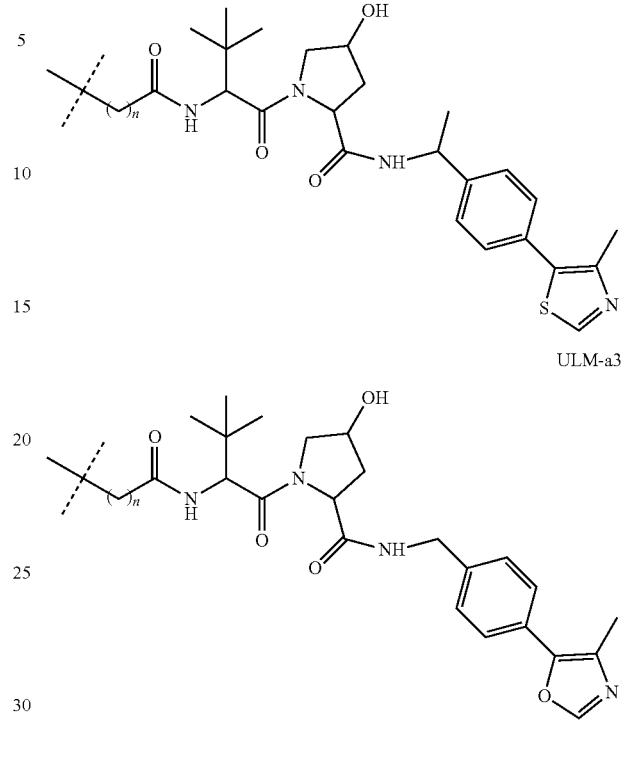
ULM-a2
ULM-a3
ULM-a4
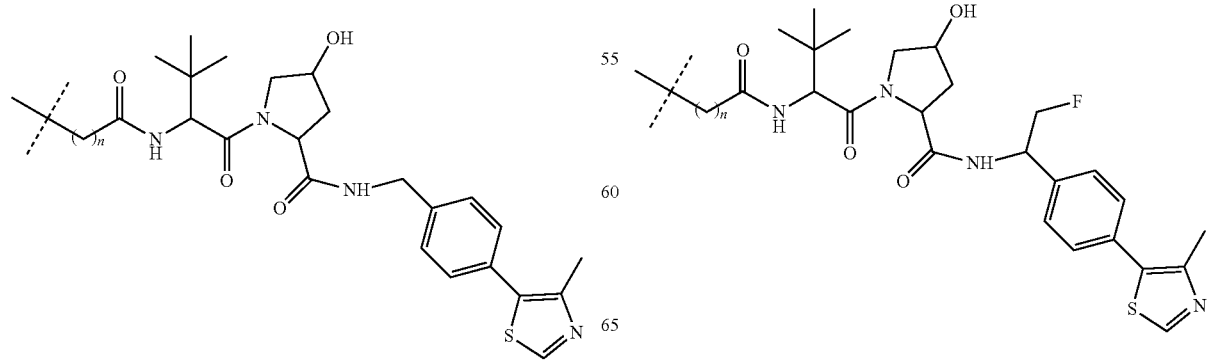
ULM-a5

ULM-a6
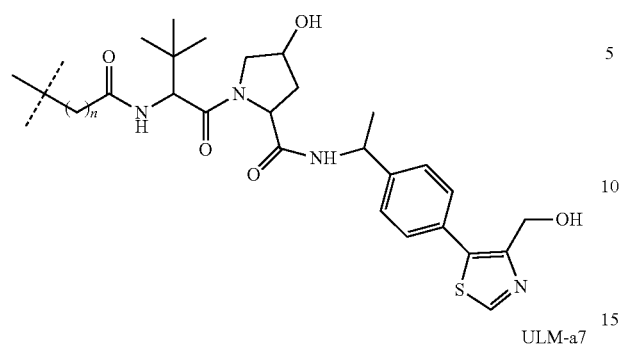
ULM-a7
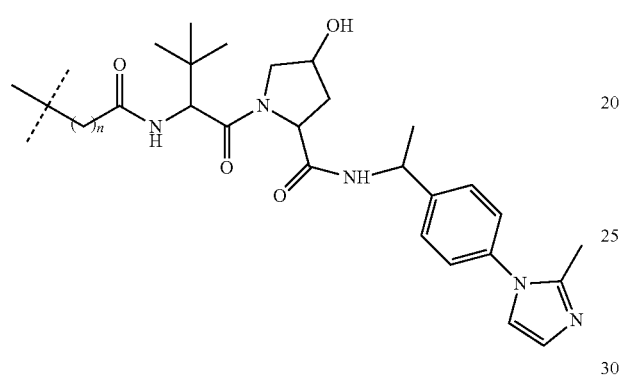
ULM-a8
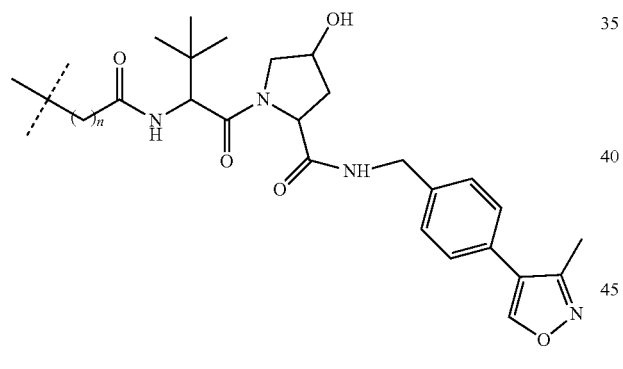
ULM-a9
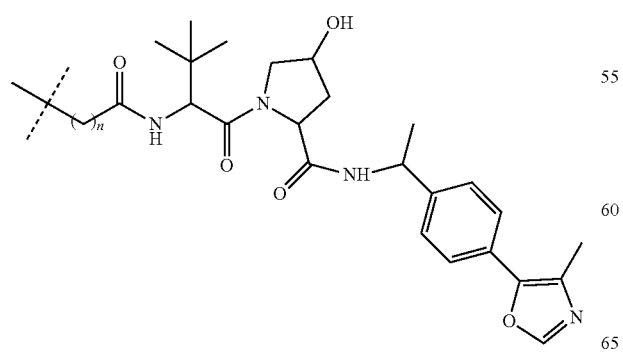
ULM-a10
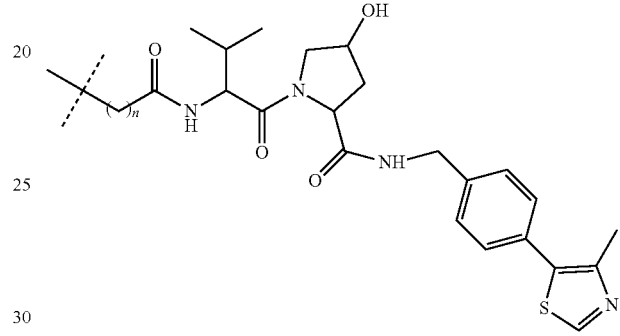
ULM-a11
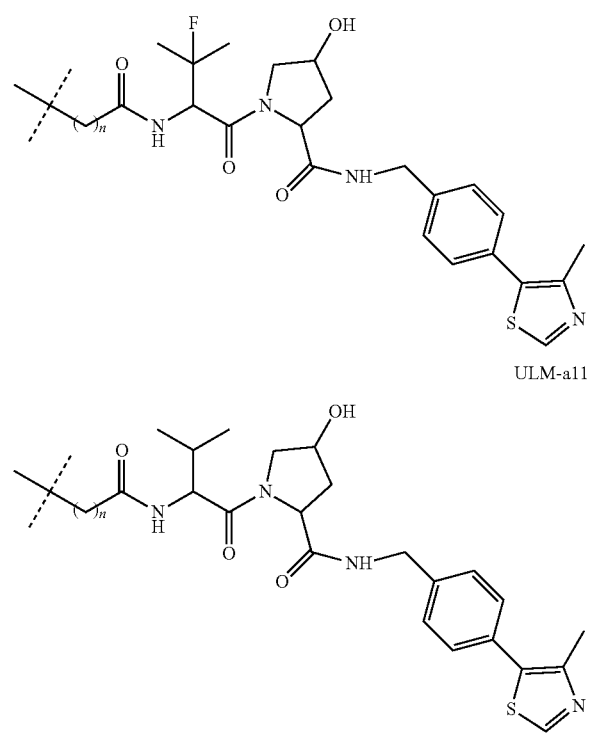
ULM-a12
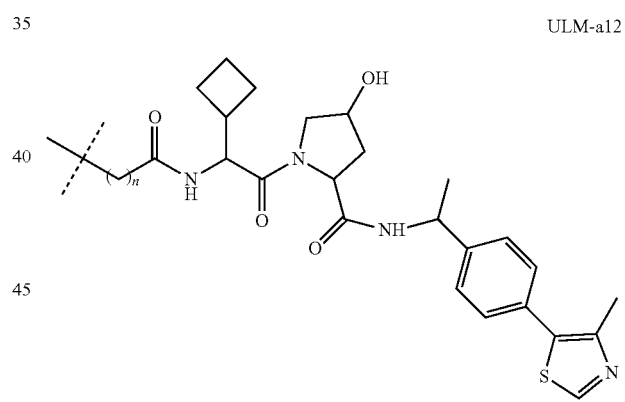
ULM-a13

ULM-a14
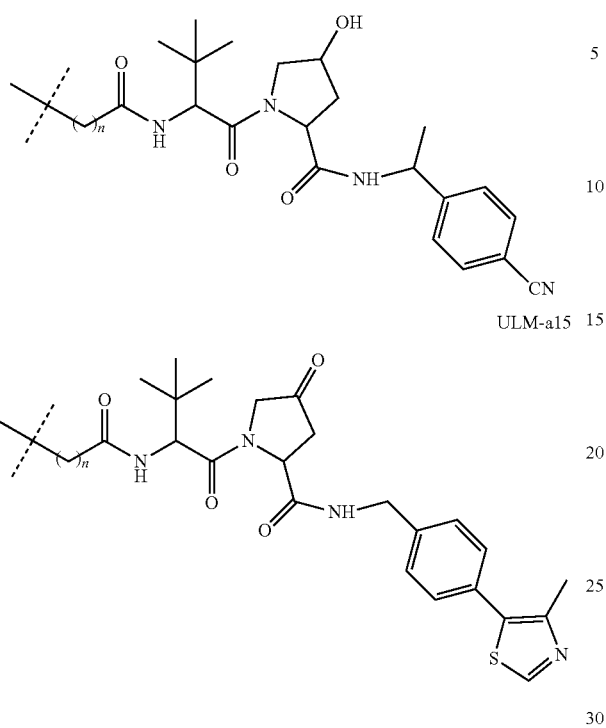
ULM-a15
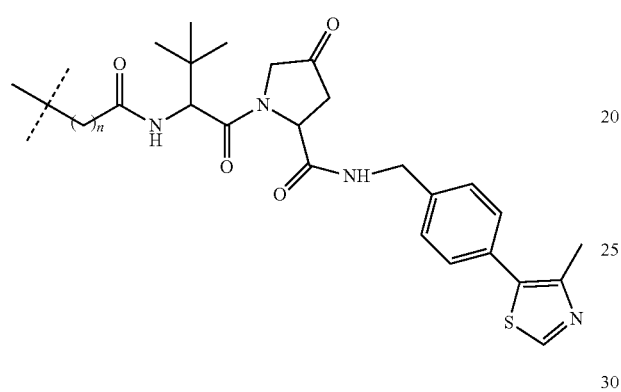
wherein n is 0 or 1.
In certain embodiments, the ULM is selected from the following structures:
ULM-b1
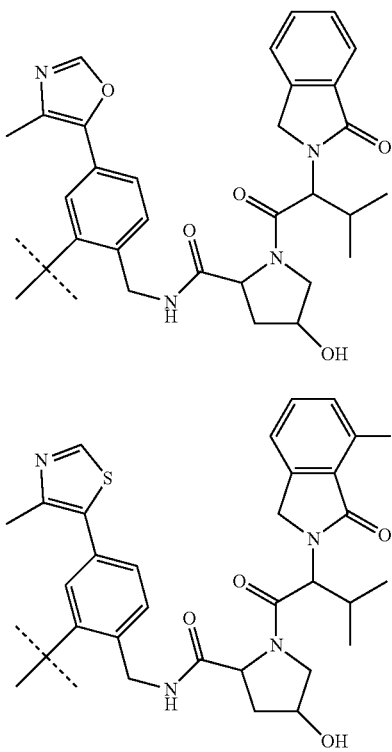
ULM-b2
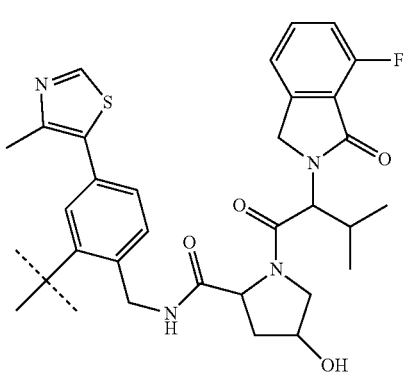
ULM-b3
ULM-b4
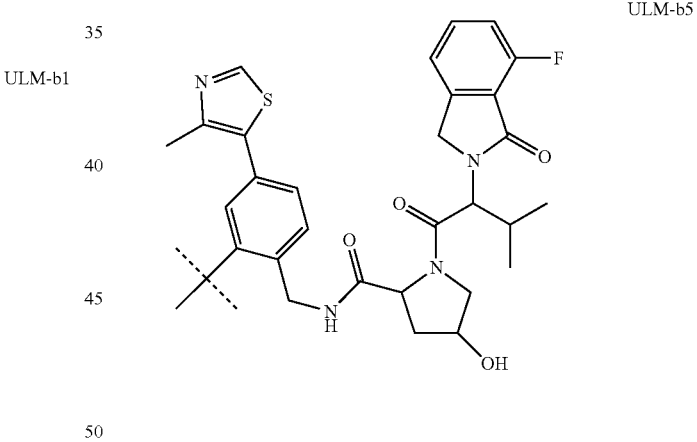
ULM-b5
ULM-b6
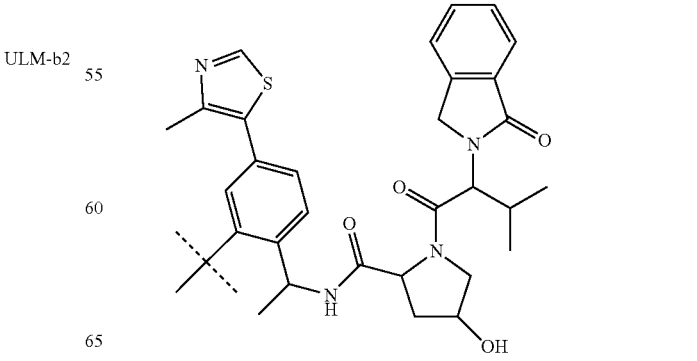

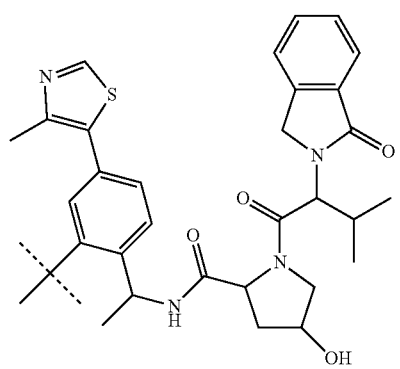
ULM-b7
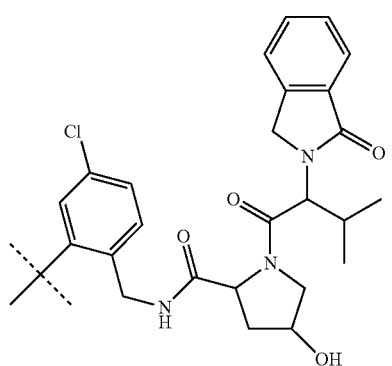
ULM-b8
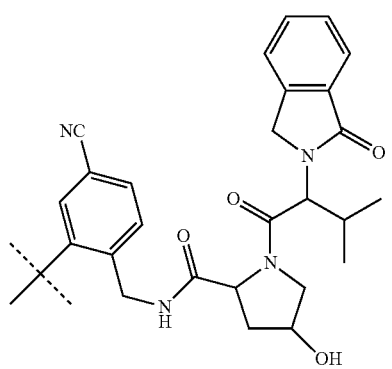
ULM-b9
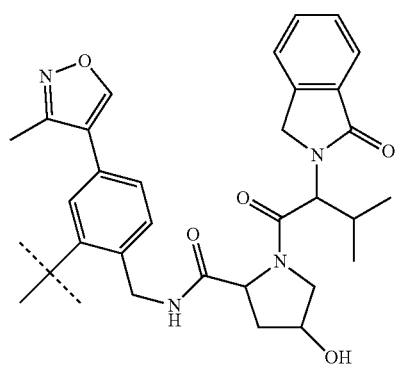
ULM-b10
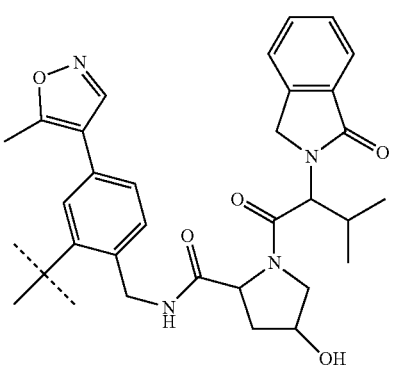
ULM-b11
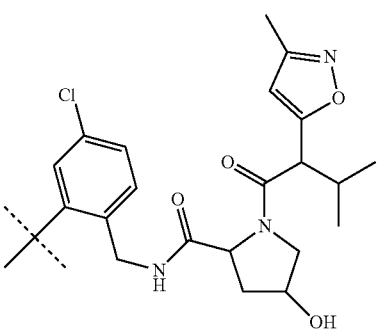
ULM-b12
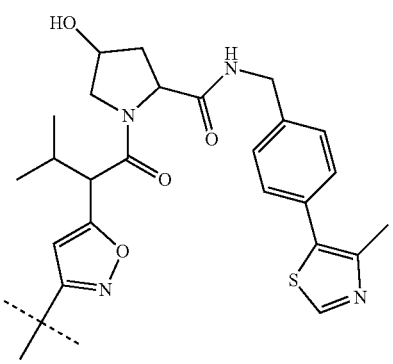
ULM-c1
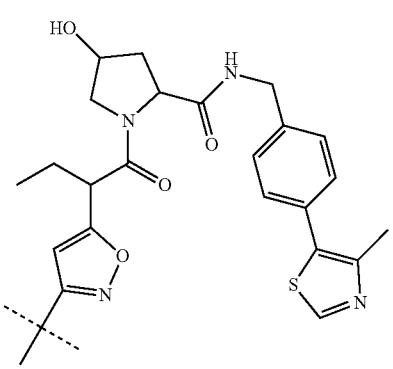
ULM-c2

ULM-c3
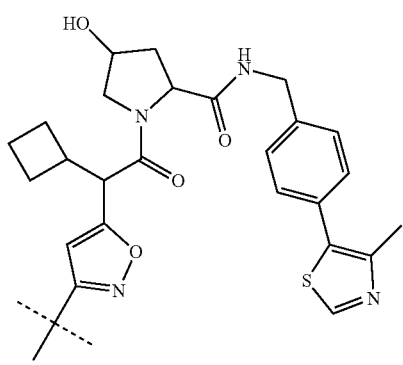
ULM-c4
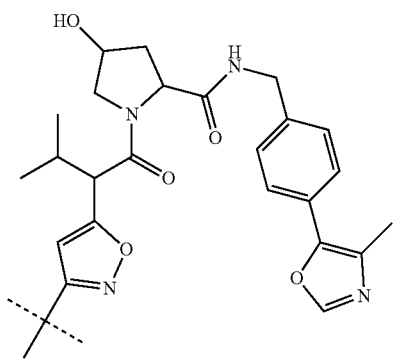
ULM-c5
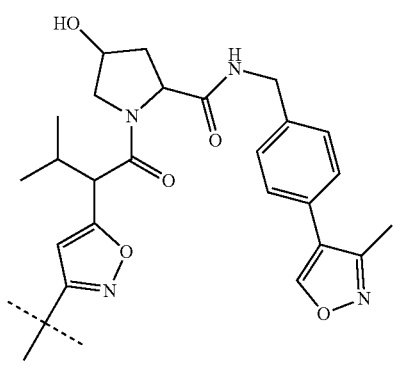
ULM-c6
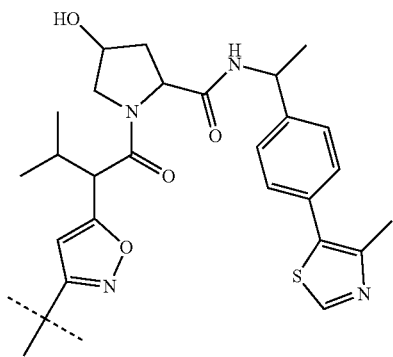
ULM-c7
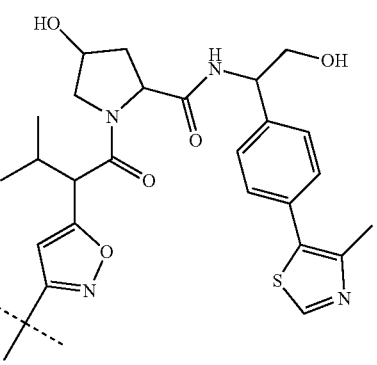
ULM-c8
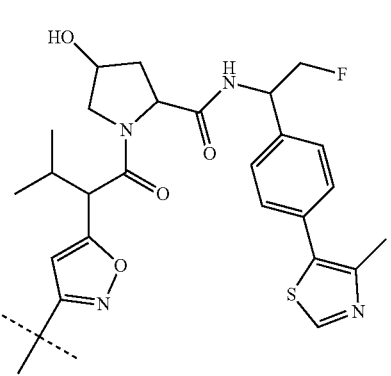
ULM-c9
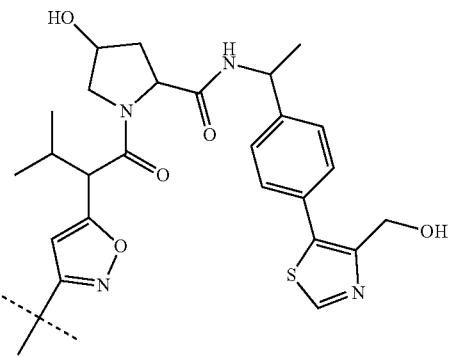
ULM-c10
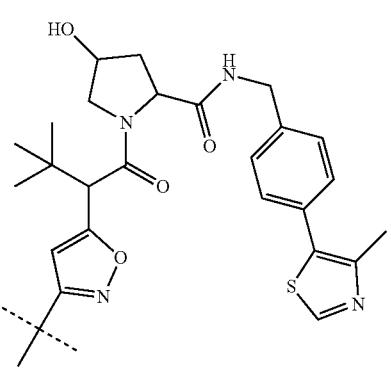

ULM-c11
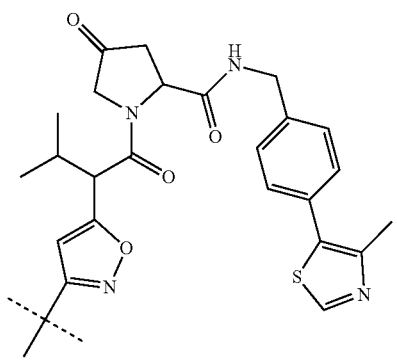
ULM-c12
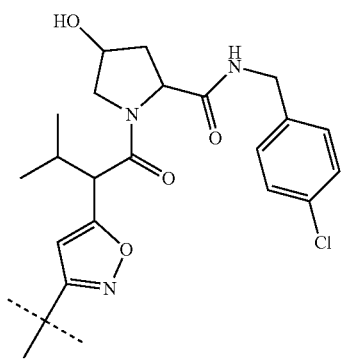
ULM-c13
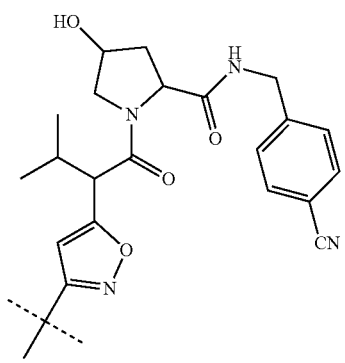
ULM-c14
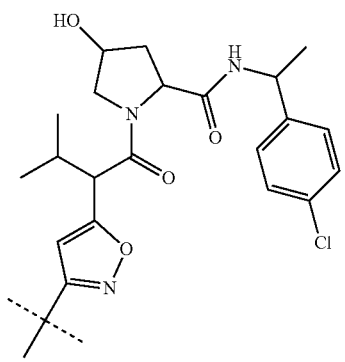
ULM-c15
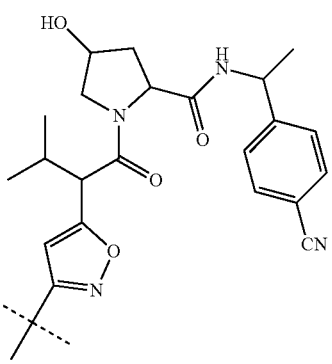
ULM-d1
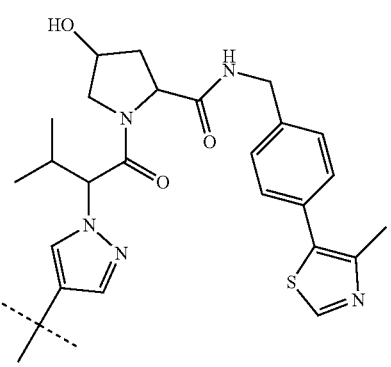
ULM-d2
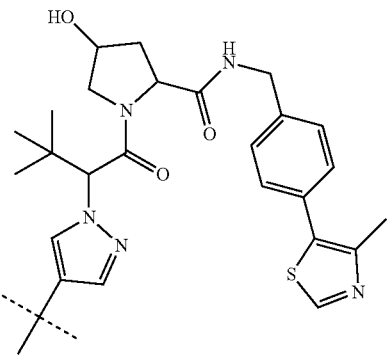
ULM-d3
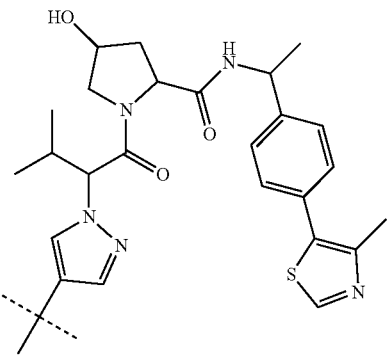

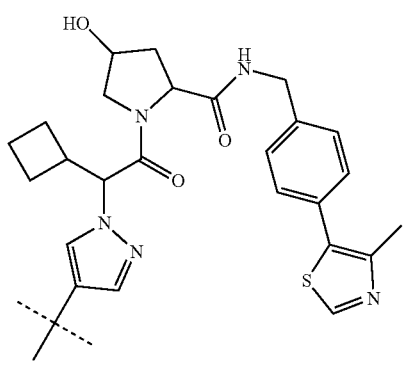
ULM-d4

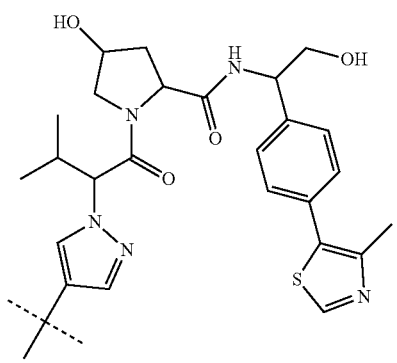
ULM-d5

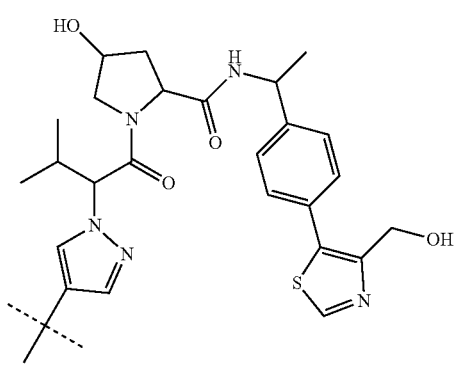
ULM-d6

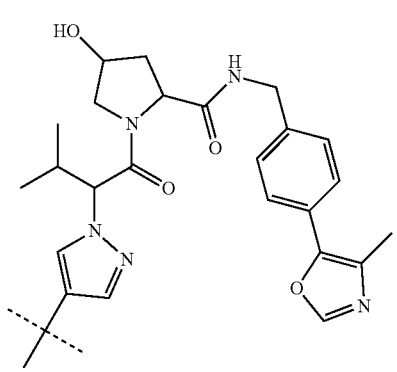
ULM-d7

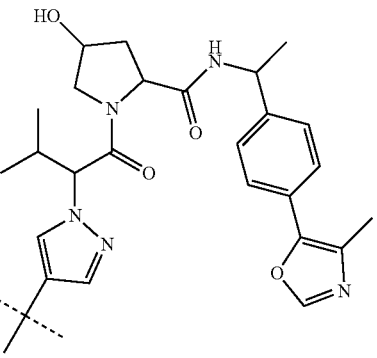
ULM-d8

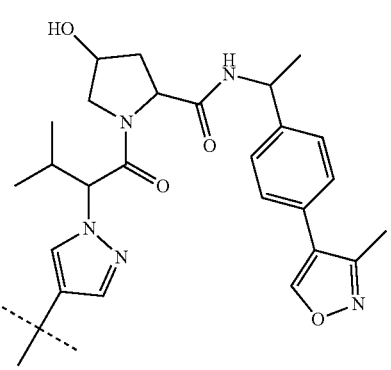
ULM-d9 wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In various embodiments, the ULM and where present, ULM', are each independently a group according to the structure:

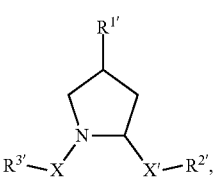
ULM-g wherein:
at each occurrence $R^{1'}$ of ULM-g is independently an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—

WCOCW—($C_0$-$C_6$)alkyl group containing an epoxide moiety WCOCW where each W is independently H or a $C_1$-$C_3$ alkyl group, an optionally substituted —$(CH_2)_n$COOH, an optionally substituted —$(CH_2)_n$C(=O)—($C_1$-$C_6$ alkyl), an optionally substituted —$(CH_2)_n$NHC(=O)—$R_1$, an optionally substituted —$(CH_2)_n$C(=O)—$NR_1R_2$, an optionally substituted —$(CH_2)_n$OC(=O)—$NR_1R_2$, —$(CH_2O)_n$H, an optionally substituted —$(CH_2)_n$OC(=O)—($C_1$-$C_6$ alkyl), an optionally substituted —$(CH_2)_n$C(=O)—O—($C_1$-$C_6$ alkyl), an optionally substituted —$(CH_2O)_n$COOH, an optionally substituted —$(OCH_2)_n$O—($C_1$-$C_6$ alkyl), an optionally substituted —$(CH_2O)_n$C(=O)—($C_1$-$C_6$ alkyl), an optionally substituted —$(OCH_2)_n$NHC(=O)—$R_1$, an optionally substituted —$(CH_2O)_n$C(=O)—$NR_1R_2$, —$(CH_2CH_2O)_n$H, an optionally substituted —$(CH_2CH_2O)_n$COOH, an optionally substituted —$(OCH_2CH_2)_n$O—($C_1$-$C_6$ alkyl), an optionally substituted —$(CH_2CH_2O)_n$C(=O)—($C_1$-$C_6$ alkyl), an optionally substituted —$(OCH_2CH_2)_n$NHC(=O)—$R_1$, an optionally substituted —$(CH_2CH_2O)_n$C(=O)—$NR_1R_2$, an optionally substituted —$SO_2R_S$, an optionally substituted S(=O)$R_S$, $NO_2$, CN or halogen;

at each occurrence $R_1$ and $R_2$ of ULM-g are each independently H or a $C_1$-$C_6$ alkyl group which may be optionally substituted with one or two hydroxyl groups or up to three halogen groups (preferably fluorine);

at each occurrence $R_S$ of ULM-g is a $C_1$-$C_6$ alkyl group, an optionally substituted aryl, heteroaryl or heterocycle group or a —$(CH_2)_m NR_1R_2$ group;

at each occurrence X and X' of ULM-g are each independently C=O, C=S, —S(=O), S(=O)$_2$;

at each occurrence $R^2$ of ULM-g is independently an optionally substituted —$(CH_2)_n$—(C=O)$_u$(NR$_1$)$_v$(SO$_2$)$_w$alkyl group, an optionally substituted —$(CH_2)_n$—(C=O)$_u$(NR$_1$)$_v$(SO$_2$)$_w$NR$_{1N}$R$_{2N}$ group, an optionally substituted —$(CH_2)_n$—(C=O)u(NR$_1$)$_v$(SO$_2$)$_w$-Aryl, an optionally substituted —$(CH_2)_n$—(C=O)$_u$(NR$_1$)$_v$(SO$_2$)$_w$-Heteroaryl, an optionally substituted —$(CH_2)_n$—(C=O)$_v$NR$_1$(SO$_2$)$_w$-Heterocycle, an optionally substituted —NR$^1$—$(CH_2)_n$—C(=O)$_u$(NR$_1$)$_v$(SO$_2$)$_w$-alkyl, an optionally substituted —NR$^1$—$(CH_2)_n$—C(=O)$_u$(NR$_1$)$_v$(SO$_2$)$_w$—NR$_{1N}$R$_{2N}$, an optionally substituted —NR$^1$CH$_2$)$_n$—C(=O)$_u$(NR$_1$)$_v$(SO$_2$)$_w$—NR$_1$C(=O)R$_{1N}$, an optionally substituted —NR$^1$—$(CH_2)_n$—C(=O)$_u$(NR$_1$)$_v$(SO$_2$)$_w$-Aryl, an optionally substituted —NR$^1$—$(CH_2)_n$—C(=O)$_u$(NR$_1$)$_v$(SO$_2$)$_w$-Heteroaryl or an optionally substituted —NR$^1$—$(CH_2)_n$—C(=O)$_v$NR$_1$(SO$_2$)$_w$-Heterocycle, an optionally substituted —$X^{R2'}$-alkyl group; an optionally substituted —$X^{R2'}$— Aryl group; an optionally substituted —$X^{R2'}$— Heteroaryl group; an optionally substituted —$X^{R2'}$— Heterocycle group;

at each occurrence $R^{3'}$ of ULM-g is independently an optionally substituted alkyl, an optionally substituted —$(CH_2)_n$—(O)$_u$(NR$_1$)$_v$(SO$_2$)$_w$-alkyl, an optionally substituted —$(CH_2)_n$—C(=O)$_u$(NR$_1$)$_v$(SO$_2$)$_w$—NR$_{1N}$R$_{2N}$, an optionally substituted —$(CH_2)_n$—C(=O)$_u$(NR$_1$)$_v$(SO$_2$)$_w$—NR$_1$C(=O)R$_{1N}$, an optionally substituted —$(CH_2)_n$—C(=O)$_u$(NR$_1$)$_v$(SO$_2$)$_w$—C(=O)NR$_1$R$_2$, an optionally substituted —$(CH_2)_n$—C(=O)$_u$(NR$_1$)$_v$(SO$_2$)$_w$-Aryl, an optionally substituted —$(CH_2)_n$—C(=O)$_u$(NR$_1$)$_v$(SO$_2$)$_w$-Heteroaryl, an optionally substituted —$(CH_2)_n$—C(=O)$_u$(NR$_1$)$_v$(SO$_2$)$_w$-Heterocycle, an optionally substituted —NR$^1$—$(CH_2)_n$—C(=O)$_u$(NR$_1$)$_v$(SO$_2$)$_w$-alkyl, an optionally substituted —NR$_1$CH$_2$)$_n$—C(=O)$_u$(NR$_1$)$_v$(SO$_2$)$_w$—NR$_{1N}$R$_{2N}$, an optionally substituted —NR$^1$—$(CH_2)_n$—C(=O)$_u$(NR$_1$)$_v$(SO$_2$)$_w$—NR$_1$C(=O)R$_{1N}$, an optionally substituted —NR$^1$—$(CH_2)_n$—C(=O)$_u$(NR$_1$)$_v$(SO$_2$)$_w$-Aryl, an optionally substituted —NR$^1$—$(CH_2)_n$—C(=O)$_u$(NR$_1$)$_v$(SO$_2$)$_w$-Heteroaryl, an optionally substituted —NR$^1$—$(CH_2)_n$—C(=O)$_u$(NR$_1$)$_v$(SO$_2$)$_w$-Heterocycle, an optionally substituted —O—$(CH_2)_n$—(C=O)$_u$(NR$_1$)$_v$(SO$_2$)$_w$-alkyl, an optionally substituted —O—$(CH_2)_n$—(C=O)$_u$(NR$_1$)$_v$(SO$_2$)$_w$—NR$_{1N}$R$_{2N}$, an optionally substituted —O—$(CH_2)_n$—(C=O)$_u$(NR$_1$)$_v$(SO$_2$)$_w$—NR$_1$C(=O)R$_{1N}$, an optionally substituted —O—$(CH_2)_n$—(C=O)$_u$(NR$_1$)$_v$(SO$_2$)$_w$-Aryl, an optionally substituted —O—$(CH_2)_n$—(C=O)$_u$(NR$_1$)$_v$(SO$_2$)$_w$-Heteroaryl or an optionally substituted —O—$(CH_2)_n$—(C=O)$_u$(NR$_1$)$_v$(SO$_2$)$_w$-Heterocycle; —$(CH_2)_n$—(V)$_n$—$(CH_2)_n$—(V)$_{n'}$-alkyl group, an optionally substituted —$(CH_2)_n$—(V)$_{n'}$—$(CH_2)_n$—(V)$_{n'}$-Aryl group, an optionally substituted —$(CH_2)_n$—(V)$_{n'}$—$(CH_2)_n$—(V)$_{n'}$-Heteroaryl group, an optionally substituted —$(CH_2)_n$—(V)$_{n'}$—$(CH_2)_n$—(V)$_{n'}$-Heterocycle group, an optionally substituted —$(CH_2)_n$—N(R$_1$)(C=O)$_{m'}$—(V)$_{n'}$-alkyl group, an optionally substituted —$(CH_2)_n$—N(R$_1$)(C=O)$_{m'}$—(V)$_{n'}$-Aryl group, an optionally substituted —$(CH_2)_n$—N(R$_1$)(C=O)$_{m'}$—(V)$_{n'}$-Heteroaryl group, an optionally substituted —$(CH_2)_n$—N(R$_1$)(C=O)$_{m'}$—(V)$_{n'}$-Heterocycle group, an optionally substituted —$X^{R3'}$— alkyl group; an optionally substituted —$X^{R3'}$— Aryl group; an optionally substituted —$X^{R3'}$— Heteroaryl group; an optionally substituted —$X^{R3'}$— Heterocycle group;

at each occurrence $R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)_n$-Aryl, —$(CH_2)_n$—Heteroaryl or —$(CH_2)_n$-Heterocycle group;

at each occurrence V of ULM-g is independently O, S or NR$_1$;

at each occurrence $R_1$ of ULM-g is independently O, S or NR$_1$;

at each occurrence $R^1$ and $R_{1'}$ of ULM-g are each independently H or a $C_1$-$C_3$ alkyl group;

at each occurrence $X^{R2'}$ and $X^{R3'}$ of ULM-g are each independently an optionally substituted —$(CH_2)_n$—, —$(CH_2)_n$—CH(X$_v$)=CH(X$_v$)— (cis or trans), —$(CH_2)_n$—CH=CH—, —$(CH_2CH_2O)_n$— or a $C_3$-$C_6$ cycloalkyl group, where $X_v$ is H, a halogen or a $C_1$-$C_3$ alkyl group which is optionally substituted;

at each occurrence m of ULM-g is independently 0, 1, 2, 3, 4, 5, 6;

at each occurrence m' of ULM-g is independently 0 or 1;

at each occurrence n of ULM-g is independently 0, 1, 2, 3, 4, 5, 6;

at each occurrence n' of ULM-g is independently 0 or 1;

at each occurrence u of ULM-g is independently 0 or 1;

at each occurrence v of ULM-g is independently 0 or 1;

at each occurrence w of ULM-g is independently 0 or 1; and at each occurrence any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group as described herein.

In various embodiments, the ULM and when present, ULM', each independently have the structure:

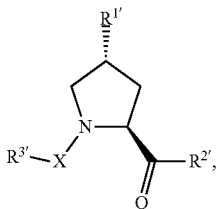

ULM-h wherein:
at each occurrence R¹', R²' and R³'' of ULM-h are defined as in ULM-g and X is selected from C=O, C=S, —S(=O), or S(=O)₂ group, and
at each occurrence R¹', R²' and R³' of ULM-h are optionally modified to bind a linker group as described herein to which is further covalently bonded to the PTM group when PTM is not ULM', or when PTM is ULM', any one or more of R¹', R²', R³' of each of ULM and ULM' are optionally modified to be covalently bonded to each other directly or through a linker group as described herein.

In various embodiments, the ULM, and when present, ULM', each independently have the structure:

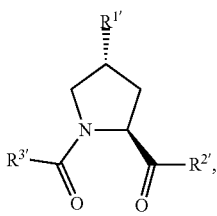

ULM-i wherein:
at each occurrence R¹', R²' and R³' of ULM-I are independently optionally modified to bind a linker group to which is further covalently bonded to the PTM group when PTM is not ULM', or when PTM is ULM', any one or more of R¹', R²', R³' of each of ULM and ULM' are optionally modified to be covalently bonded to each other directly or through a linker group as described herein.

In other embodiments, at each occurrence R¹ of ULM-g through ULM-i is preferably a hydroxyl group or a group which may be metabolized to a hydroxyl or carboxylic group, such that the compound represents a prodrug form of an active compound. For example, non-limiting R¹' groups include, for example, $—(CH_2)_nOH$, $(CH_2)_n—O—(C_1-C_6)$ alkyl group, $—(CH_2)_nCOOH$, $—(CH_2O)_nH$, an optionally substituted $—(CH_2)_nOC(=O)—(C_1-C_6 \text{ alkyl})$, or an optionally substituted $—(CH_2)_nC(=O)—O—(C_1-C_6 \text{ alkyl})$, wherein n is 0 or 1. Where R¹ of ULM-g through ULM-i is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably independently selected from C=O, C=S, —S(=O) or S(=O)₂.

In various embodiments, at each occurrence R² of ULM-g through ULM-i is an optionally substituted —NR¹-T-Aryl, an optionally substituted —NR¹-T-Heteroaryl group or an optionally substituted —NR¹-T-Heterocycle, where R¹ is H or CH₃, preferably H and T is an optionally substituted $—(CH_2)_n—$ group, wherein each one of the methylene groups may be optionally substituted with one or two substituents, preferably selected from halogen, an amino acid sidechain as otherwise described herein or a alkyl group, preferably one or two methyl groups, which may be optionally substituted; and n is 0 to 6, often 0, 1, 2 or 3, preferably 0 or 1. Alternatively, T may also be a $—(CH_2O)_n—$ group, a $—(OCH_2)_n—$ group, a $—(CH_2CH_2O)_n—$ group, a $—(OCH_2CH_2)_n—$ group, all of which groups are optionally substituted.

Suitable aryl groups for R² of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, $C_1-C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methyl imidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halogen, or methyl-substitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), and an optionally substituted quinolone.

In various embodiments, at each occurrence, R¹', R²', and/or R³' of ULM-g through ULM-i is a group independently selected from:

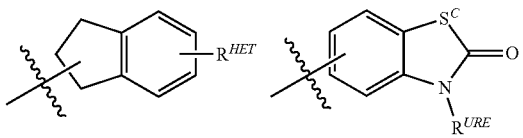

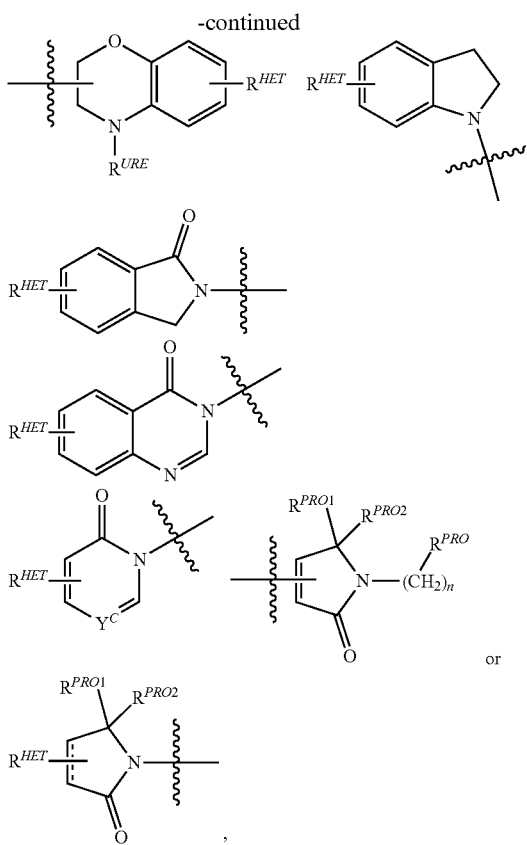

wherein
- at each occurrence $S^c$ of ULM-g through ULM-i is independently $CHR^{SS}$, $NR^{URE}$, or O;
- at each occurrence $R^{HET}$ of ULM-g through ULM-i is independently H, CN, $NO_2$, halogen (preferably Cl or F), optionally substituted $C_1$-$C_6$ alkyl (preferably substituted with one or two hydroxyl groups or up to three halogen groups (e.g. $CF_3$), optionally substituted $O(C_1$-$C_6$ alkyl) (preferably substituted with one or two hydroxyl groups or up to three halogen groups) or an optionally substituted acetylenic group —C≡C—$R_a$ where $R_a$ is H or a $C_1$-$C_6$ alkyl group (preferably $C_1$-$C_3$ alkyl);
- at each occurrence $R^{SS}$ of ULM-g through ULM-i is independently H, CN, $NO_2$, halogen (preferably F or Cl), optionally substituted $C_1$-$C_6$ alkyl (preferably substituted with one or two hydroxyl groups or up to three halogen groups), optionally substituted O—($C_1$-$C_6$ alkyl) (preferably substituted with one or two hydroxyl groups or up to three halogen groups) or an optionally substituted —C(=O)($C_1$-$C_6$ alkyl) (preferably substituted with one or two hydroxyl groups or up to three halogen groups);
- at each occurrence $R^{URE}$ of ULM-g through ULM-i is independently H, a $C_1$-$C_6$ alkyl (preferably H or $C_1$-$C_3$ alkyl) or a —C(=O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
- at each occurrence $Y^c$ of ULM-g through ULM-i is independently N or C—$R^{YC}$, where $R^{YC}$ is H, OH, CN, $NO_2$, halogen (preferably Cl or F), optionally substituted $C_1$-$C_6$ alkyl (preferably substituted with one or two hydroxyl groups or up to three halogen groups (e.g. $CF_3$), optionally substituted $O(C_1$-$C_6$ alkyl) (preferably substituted with one or two hydroxyl groups or up to three halogen groups) or an optionally substituted acetylenic group —C≡C—$R_a$ where $R_a$ is H or a $C_1$-$C_6$ alkyl group (preferably $C_1$-$C_3$ alkyl);
- at each occurrence $R^{PRO}$ of ULM-g through ULM-i is independently H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halogen group, preferably F or Cl), benzofuran, indole, indolizine, azaindolizine;
- at each occurrence $R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6, and
- each of said groups may be optionally connected/attached to a PTM group (including a ULM' group) via a linker group as described herein.

Suitable heteroaryl groups for $R^2$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, and an optionally substituted oximidazole.

Suitable heterocycle groups for $R^{2'}$ of ULM-g through ULM-i also include tetrahydrofuran, tetrahydrothiene, tetrahydroquinoline, piperidine, piperazine, pyrrollidine, morpholine, oxane or thiane, each of which groups may be optionally substituted.

Suitable $R^{2'}$ substituents of ULM-g through ULM-i also include specifically (and without limitation to the specific compound disclosed) the $R^2$ substituents which are found in the identified compounds disclosed herein (which includes the specific compounds which are disclosed in the present specification, and the figures which are attached hereto). Each of these $R^{2'}$ substituents may be used in conjunction with any number of $R^3$ substituents which are also disclosed herein.

In various embodiments, at each occurrence $R^{3'}$ of ULM-g through ULM-i is independently an optionally substituted -T-Aryl, an optionally substituted-T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle, where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —($CH_2O$)$_n$— group, a —($OCH_2$)$_n$— group, a —($CH_2CH_2O$)$_n$— group, a —($OCH_2CH_2$)$_n$— group, each of which groups is optionally substituted.

Suitable aryl groups for $R^3$ of ULM-g through ULM-i include independently optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a —($CH_2$)$_m$—$NR_1C$(=O)$R_2$ group where m, $R_1$ and $R_2$ are the same as above), a halogen (often F or Cl), OH, $CH_3$, $CF_3$, OMe, $OCF_3$, $NO_2$, CN or a S(=O)$_2R_S$ group ($R_S$ is a $C_1$-$C_6$ alkyl group, an optionally substituted aryl, heteroaryl or heterocycle group or a —($CH_2$)$_m$$NR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methyl-substituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo- (preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Suitable heteroaryl groups for $R^3$ of ULM-g through ULM-i also include independently an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —($CH_2$)$_m$—O—$C_1$-$C_6$ alkyl group or an optionally substituted —($CH_2$)$_m$—C(=O)—O—$C_1$-$C_6$ alkyl group), and an optionally substituted pyridine (2-, 3, or 4-pyridine).

Suitable $R^{3'}$ substituents of ULM-g through ULM-i can also any combination of the $R^{3'}$ substituents described herein with respect to ULM-a through ULM-i, and each of these $R^{3'}$ substituents can be bonded to any number of $R^2$ substituents defined in ULM-a through ULM-I herein.

In certain embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, wherein:
at each occurrence $R_1$ of ULM-g through ULM-i is independently H or a $C_1$-$C_3$ alkyl group (preferably H);
at each occurrence $X^{R2'}$ of ULM-g through ULM-i is independently an optionally substituted —($CH_2$)$_n$—, —($CH_2$)$_n$—CH($X_v$)=CH($X_v$)— (cis or trans), —($CH_2$)$_n$—CH=CH—, —($CH_2CH_2O$)$_n$— or a $C_3$-$C_6$ cycloalkyl group; and
at each occurrence $X_v$ of ULM-g through ULM-i is independently H, a halogen or a $C_1$-$C_3$ alkyl group which is optionally substituted with one or two hydroxyl groups or up to three halogen groups;
at each occurrence any alkyl group of ULM-g through ULM-i is independently an optionally substituted $C_1$-$C_{10}$ alkyl (preferably a $C_1$-$C_6$ alkyl) group, or a an optionally substituted $C_1$-$C_{10}$ alkyl having one or more terminal halogens;
at each occurrence any aryl group of ULM-g through ULM-i is an optionally substituted phenyl or naphthyl group (preferably, a phenyl group); and
at each occurrence HET of ULM-g through ULM-i is independently an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinolone, each optionally substituted with a $C_1$-$C_3$ alkyl group or a halogen group, or any group defined for $R^{1'}$, $R^{2'}$, and/or $R^{3'}$ of ULM-g through ULM-i herein.

In certain embodiments, $R^3$ of ULM-g through ULM-i is an optionally substituted —($CH_2$)$_n$—(V)$_{n'}$—($CH_2$)$_n$—(V)n'—$R^{S3'}$ group, an optionally substituted-($CH_2$)$_n$—N($R_{1'}$)(C=O)$_{m'}$—(V)n'—$R^{S3}$ group, an optionally substituted —$X^{R3}$-alkyl group, an optionally substituted —$X^{R3}$-Aryl group; an optionally substituted —$X^{R3}$-HET group, an optionally substituted —$X^{R3}$-Aryl-HET group or an optionally substituted —$X^{R3}$-HET-Aryl group, wherein:
at each occurrence $R^{S3}$ is independently an optionally substituted alkyl group ($C_1$-$C_{10}$, preferably $C_1$-$C_6$ alkyl), an optionally substituted Aryl group or a HET group;
at each occurrence $R_{1'}$ is independently H or a $C_1$-$C_3$ alkyl group (preferably H);
at each occurrence V is independently O, S or $NR_{1'}$;
at each occurrence $X^{R3}$ is independently —($CH_2$)$_n$—, —($CH_2CH_2O$)$_n$—, —$CH_2$)$_n$—CH($X_v$)=CH($X_v$)— (cis or trans), —$CH_2$)$_n$—CH=CH—, or a $C_3$-$C_6$ cycloalkyl group, all optionally substituted;
at each occurrence $X_v$ is independently H, a halogen or a $C_1$-$C_3$ alkyl group which is optionally substituted with 1-2 hydroxyl groups or 0-3 halogen groups;

at each occurrence alkyl is independently an optionally substituted $C_1$-$C_{10}$ alkyl (preferably a $C_1$-$C_6$ alkyl) group (in certain non-limiting embodiments, the alkyl group is end-capped with a halogen group, often a Cl or Br);

at each occurrence aryl is independently an optionally substituted phenyl or napthyl group (preferably, a phenyl group); and at each occurrence HET is independently an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinolone, each optionally substituted with a $C_1$-$C_3$ alkyl group or a halogen group, or any group defined for $R^{1'}$, $R^{2'}$, and/or $R^{3'}$ of ULM-g through ULM-i herein.

In alternative embodiments, $R^{3'}$ of ULM-g through ULM-i is —$(CH_2)_n$-Aryl, —$(CH_2CH_2O)_n$-Aryl, —$(CH_2)_n$—HET or —$(CH_2CH_2O)_n$—HET, wherein:

at each occurrence said Aryl of ULM-g through ULM-i is phenyl which is optionally substituted with one or two substitutents, wherein said substituent(s) is preferably selected from —$(CH_2)_nOH$, $C_1$-$C_6$ alkyl which itself is further optionally substituted with CN, halogen (up to three halogen groups), OH, —$(CH_2)_nO(C_1$-$C_6)$alkyl, amine, mono- or di-($C_1$-$C_6$ alkyl) amine wherein the alkyl group on the amine is optionally substituted with 1 or 2 hydroxyl groups or up to three halogen (preferably F, Cl) groups, or at each occurrence said Aryl group of ULM-g through ULM-i is substituted with —$(CH_2)_nOH$, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(=O)($C_0$-$C_6$) alkyl, —$(CH_2)_n$—C(=O)O($C_0$-$C_6$)alkyl, —$(CH_2)_n$—OC(=O)($C_0$-$C_6$) alkyl, amine, mono- or di-($C_1$-$C_6$ alkyl) amine wherein the alkyl group on the amine is optionally substituted with 1 or 2 hydroxyl groups or up to three halogen (preferably F, Cl) groups, CN, $NO_2$, an optionally substituted —$(CH_2)_n$—$(V)_{m'}$—$CH_2)_n$—$(V)_{m'}$—$(C_1$-$C_6)$alkyl group, a —$(V)_{m'}$—$(CH_2CH_2O)_n$—$R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or at each occurrence said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, each optionally substituted with a $C_1$-$C_3$ alkyl group or a halogen group;

at each occurrence said HET of ULM-g through ULM-i is independently oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, each optionally substituted with a $C_1$-$C_3$ alkyl group or a halogen group, or any group defined for $R^{1'}$, $R^{2'}$, and/or $R^{3'}$ of ULM-g through ULM-i herein.

In additional embodiments, in ULM-I, at each occurrence $R^{1'}$ of ULM-i is independently OH or a group which is metabolized in a patient or subject to OH;

at each occurrence $R^{2'}$ of ULM-i is a —NH—$CH_2$-Aryl-HET (preferably, a phenyl linked directly to a methyl substituted thiazole);

at each occurrence $R^{3'}$ of ULM-i is a —$CHR^{CR3'}$—NH—C(=O)—$R^{3P1}$ group or a —$CHR^{CR3'}$—$R^{3P2}$ group;

at each occurrence $R^{CR3'}$ of ULM-i is a $C_1$-$C_4$ alkyl group, preferably methyl, isopropyl or tert-butyl;

at each occurrence $R^{3P1}$ of ULM-i is $C_1$-$C_3$ alkyl (preferably methyl), an optionally substituted oxetane group (preferably methyl substituted, a —$(CH_2)_nOCH_3$ group where n is 1 or 2 (preferably 2), or a

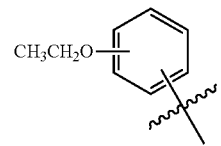

group (the ethyl ether group is preferably meta-substituted on the phenyl moiety), a morpholino group (linked to the carbonyl at the 2- or 3-position;

at each occurrence $R^{3P2}$ of ULM-i is a

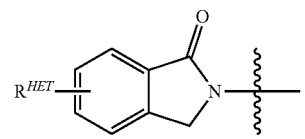

group;

at each occurrence Aryl of ULM-i is phenyl;

at each occurrence HET of ULM-i is an optionally substituted thiazole or isothiazole; and at each occurrence $R^{HET}$ of ULM-i is H or a halogen group (preferably H).

In various embodiments, the ULM has the structure:

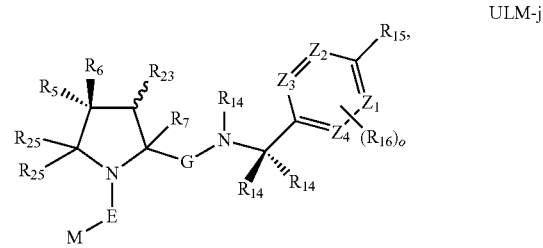

ULM-j wherein:

at each occurrence $R_5$ and $R_6$ of ULM-j is independently OH, SH, or optionally substituted alkyl or $R_5$, $R_6$, and the carbon atom to which they are attached form a carbonyl;

at each occurrence $R_7$ of ULM-j is independently H or optionally substituted alkyl;

at each occurrence E of ULM-j is independently a bond, C=O, or C=S;

at each occurrence G of ULM-j is independently a bond, optionally substituted alkyl, —COOH or C=J;

at each occurrence J of ULM-j is independently O or N—R$_8$;
at each occurrence R$_8$ of ULM-j is independently H, CN, optionally substituted alkyl or optionally substituted alkoxy;
at each occurrence M of ULM-j is independently optionally substituted aryl, optionally substituted heteroaryl, optionally substituted heterocyclic or

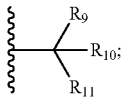

at each occurrence R$_9$ and R$_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or R$_9$, R$_{10}$, and the carbon atom to which they are attached form an optionally substituted cycloalkyl;
at each occurrence R$_{11}$ of ULM-j is independently optionally substituted heterocyclic, optionally substituted alkoxy, optionally substituted heteroaryl, optionally substituted aryl, or

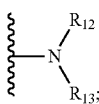

at each occurrence R$_{12}$ of ULM-j is independently H or optionally substituted alkyl;
at each occurrence R$_{13}$ of ULM-j is independently H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate,
at each occurrence R$_{14}$ of ULM-j is independently H, haloalkyl, optionally substituted cycloalkyl, optionally substituted alkyl or optionally substituted heterocyloalkyl;
at each occurrence R$_{15}$ of ULM-j is independently H, optionally substituted heteroaryl, haloalkyl, optionally substituted aryl, optionally substituted alkoxy, or optionally substituted heterocyclyl;
at each occurrence R$_{16}$ of ULM-j is independently halogen, optionally substituted alkyl, optionally substituted haloalkyl, CN, or optionally substituted haloalkoxy;
at each occurrence R$_{25}$ of ULM-j is independently H or optionally substituted alkyl; or both R$_{25}$ groups can be taken together to form an oxo or optionally substituted cycloalkyl group;
at each occurrence R$_{23}$ of ULM-j is independently H or OH;
at each occurrence Z$_1$, Z$_2$, Z$_3$, and Z$_4$ of ULM-j are independently C or N; and
at each occurrence o of ULM-j is 0, 1, 2, 3, or 4.
In certain embodiments, in ULM-j, wherein G of ULM-j is C=J, J is O, R$_7$ is H, each R$_{14}$ is H, and o is 0.
In certain embodiments, in ULM-j, wherein G of ULM-j is C=J, J is O, R$_7$ is H, each R$_{14}$ is H, R$_{15}$ is optionally substituted heteroaryl, and o is 0.

In other embodiments, in ULM-j, E is C=O and M is

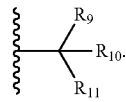

In certain embodiments, if E of ULM-j is C=O, R$_{11}$ is optionally substituted heterocyclic or

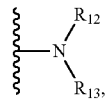

and M is

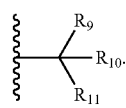

In certain embodiments, if E of ULM-j is

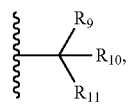

and R$_{11}$ is

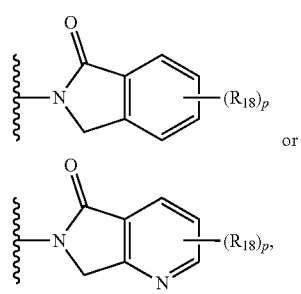

each R$_{18}$ is independently halogen, optionally substituted alkoxy, cyano, optionally substituted alkyl, haloalkyl, or haloalkoxy; and p is 0, 1, 2, 3, or 4.
In certain embodiments, ULM and where present, ULM', have the structure:

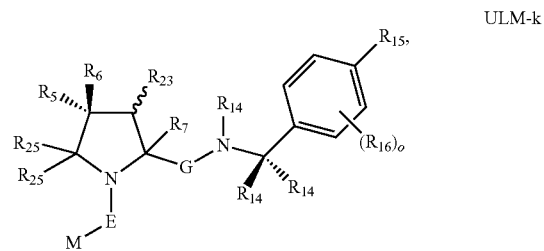

ULM-k wherein:
at each occurrence G of ULM-k is C=J, J is O;
at each occurrence $R_7$ of ULM-k is H;
at each occurrence each $R_{14}$ of ULM-k is H;
at each occurrence o of ULM-k is 0;
at each occurrence $R_{15}$ of ULM-k is

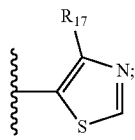

and
at each occurrence $R_{17}$ of ULM-k is H, halogen, optionally substituted cycloalkyl, optionally substituted alkyl, optionally substituted alkenyl, and haloalkyl.

In other embodiments, $R_{17}$ of ULM-k is alkyl or cycloalkyl.

In other embodiments,
at each occurrence G of ULM-k is C=J, J is O;
at each occurrence $R_7$ of ULM-k is H;
at each occurrence $R_{14}$ of ULM-k is H;
at each occurrence ULM-k is 0; and
at each occurrence $R_{15}$ of ULM-k is independently selected from the group consisting of:

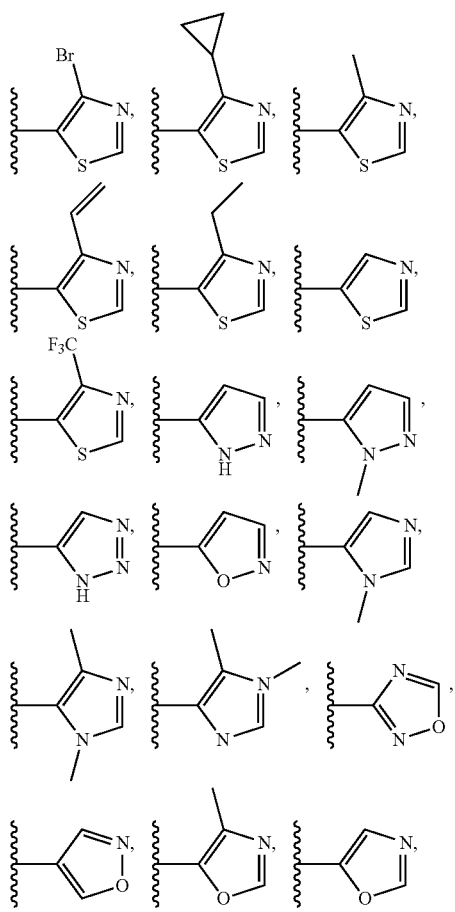

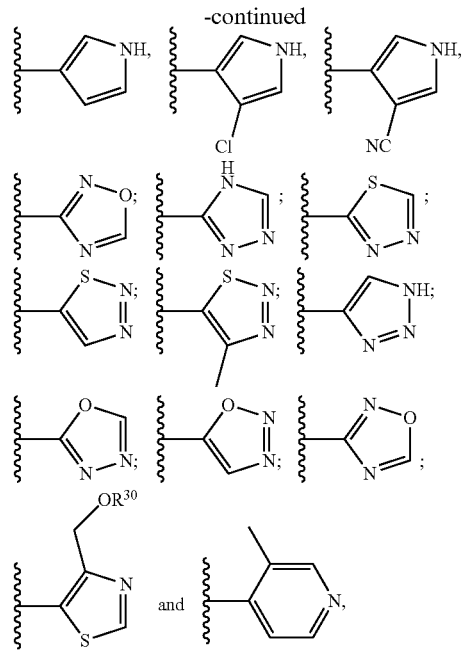

wherein $R_{30}$ of ULM-k is H or an optionally substituted alkyl.

In other embodiments, ULM and where present, ULM' have the structure:

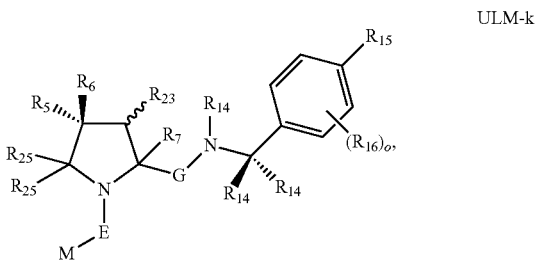

wherein:
at each occurrence E of ULM-k is C=O,
at each occurrence M of ULM-k is

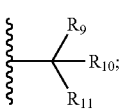

and
at each occurrence $R_{11}$ of ULM-k is selected from the group consisting of:

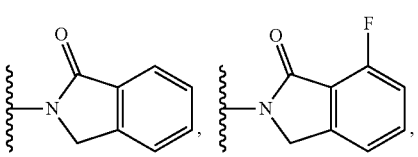

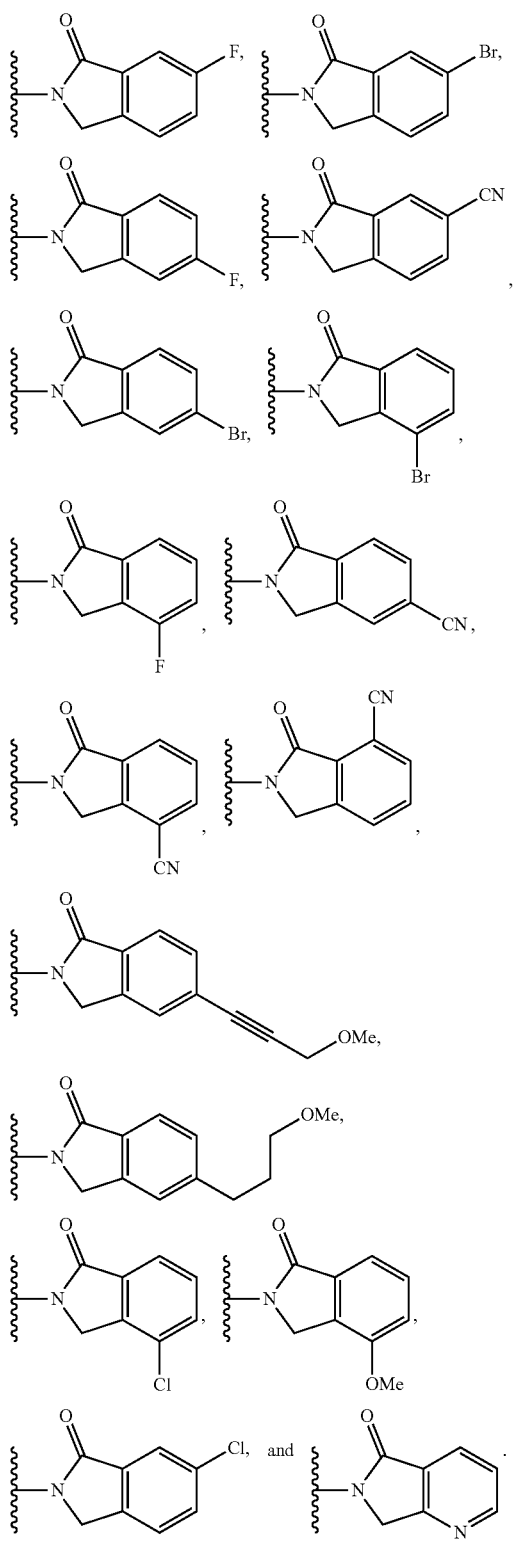

In still other embodiments, in the compound of formula ULM-k,

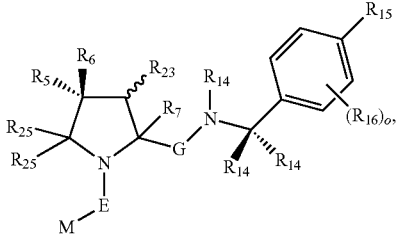

at each occurrence E of ULM-k is C=O;
at each occurrence $R_{11}$ of ULM-k is

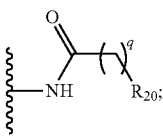

at each occurrence M or ULM-k is

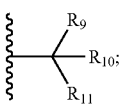

at each occurrence q of ULM-k is 1 or 2;
at each occurrence $R_{20}$ of ULM-k is H, optionally substituted alkyl, optionally substituted cycloalkyl, optionally substituted aryl, or

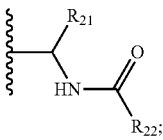

at each occurrence $R_{21}$ of ULM-k is H or optionally substituted alkyl; and
at each occurrence $R_{22}$ of ULM-k is H, optionally substituted alkyl, optionally substituted alkoxy, or haloalkyl.

In various embodiments, $R_{11}$ of ULM-j or ULM-k is independently selected from the group consisting of:

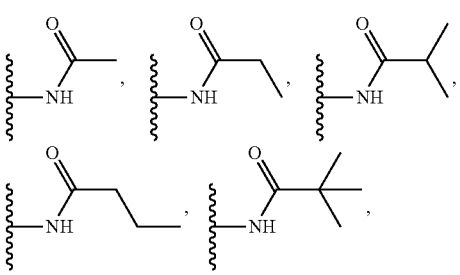

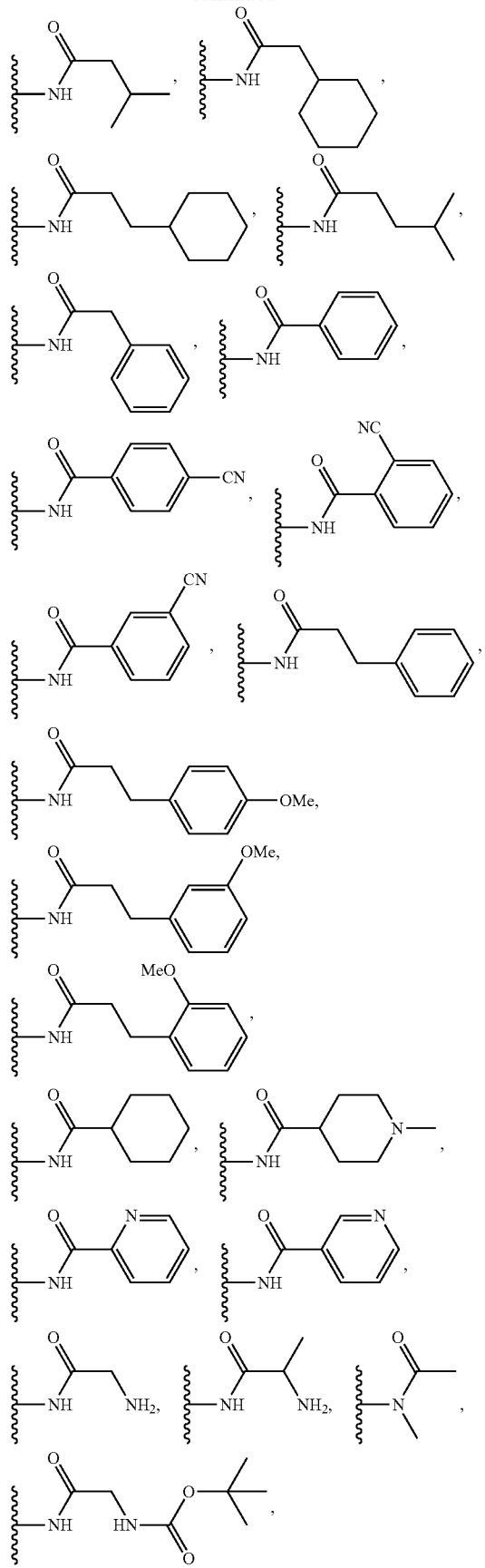
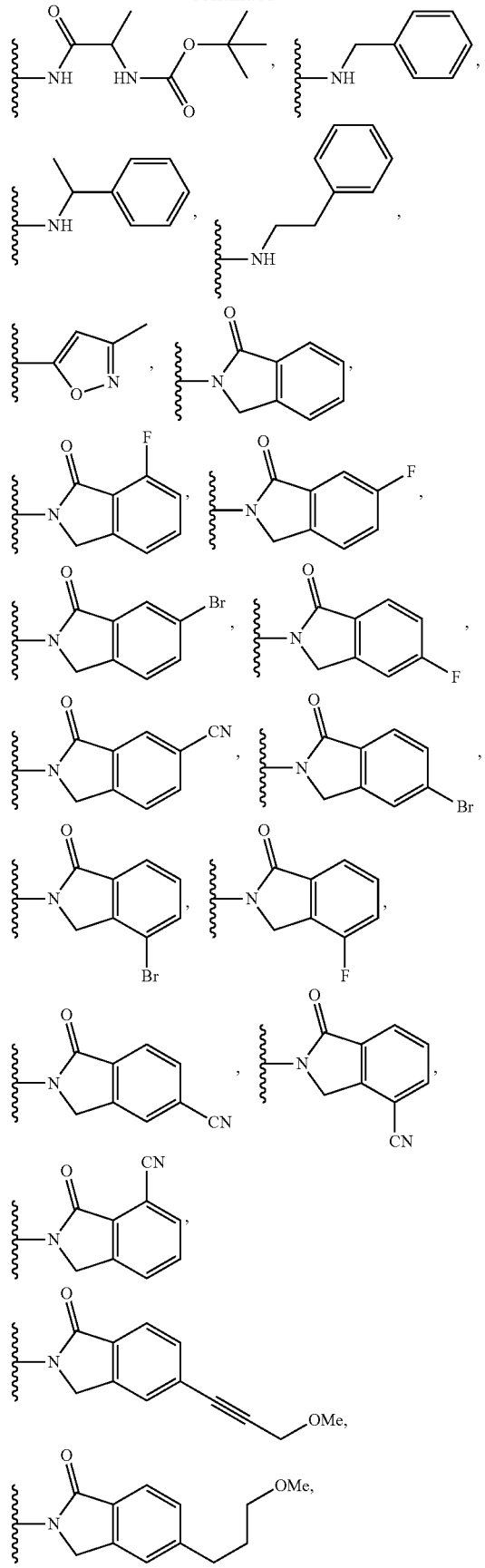

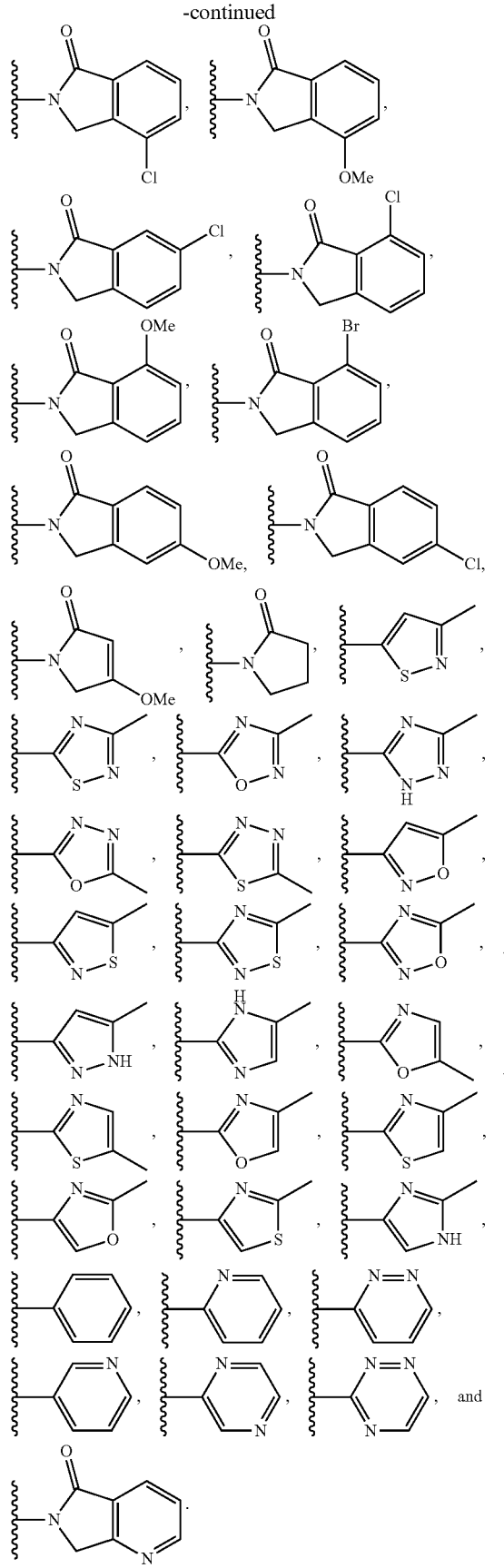
In certain embodiments, $R_{11}$ of ULM-j or ULM-k is independently selected from the group consisting of:
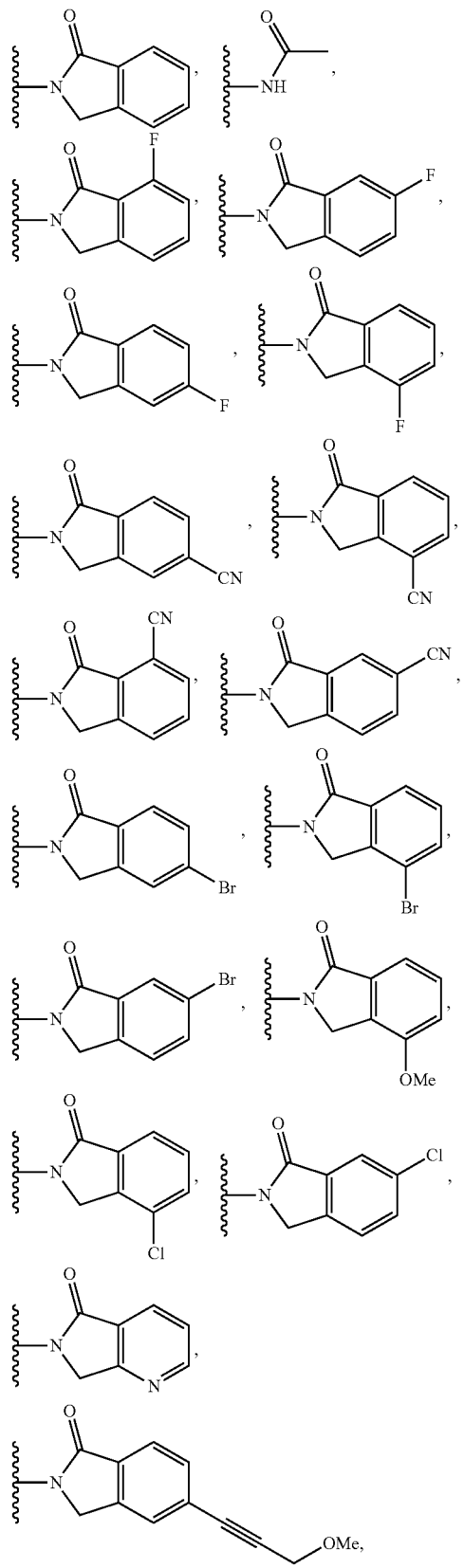

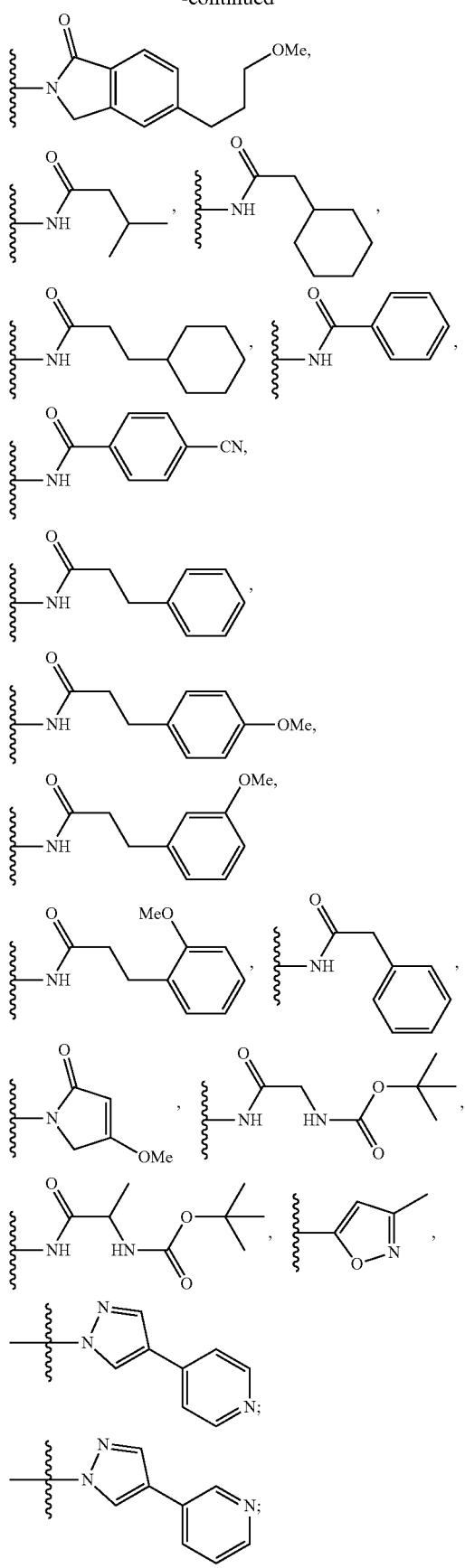

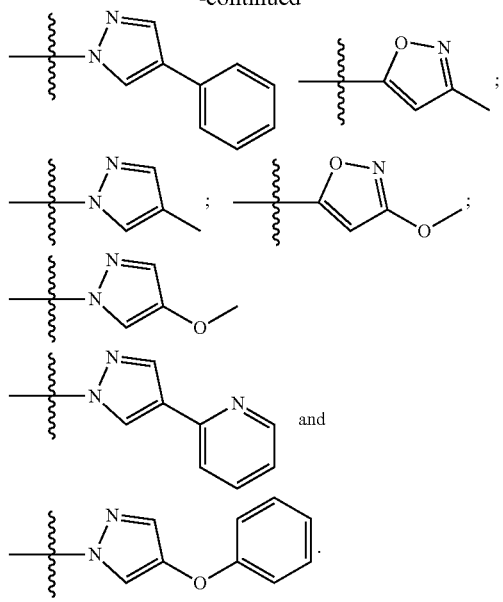

In certain embodiments, ULM (or when present ULM') has the structure:

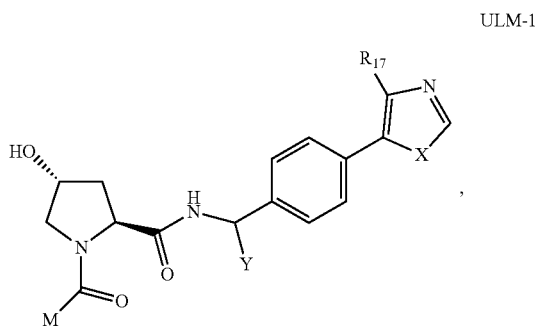

ULM-1 wherein:
at each occurrence X of ULM-1 is independently O or S;
at each occurrence Y of ULM-1 is independently H, methyl or ethyl;
at each occurrence $R_{17}$ of ULM-1 is independently H, methyl, ethyl, hydroxymethyl or cyclopropyl;
at each occurrence M of ULM-1 is independently optionally substituted aryl, optionally substituted heteroaryl, or

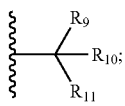

at each occurrence $R_9$ of ULM-1 is H;
at each occurrence $R_{10}$ of ULM-1 is independently H, optionally substituted alkyl, optionally substituted haloalkyl, optionally substituted heteroaryl, optionally substituted aryl, optionally substituted hydroxyalkyl, optionally substituted thioalkyl or cycloalkyl;
at each occurrence $R_{11}$ of ULM-1 is independently optionally substituted heteroaromatic, optionally substituted heterocyclic, optionally substituted aryl or

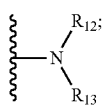

at each occurrence $R^{12}$ of ULM-1 is independently H or optionally substituted alkyl; and at each occurrence $R_{13}$ of ULM-1 is independently H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', have the structure:

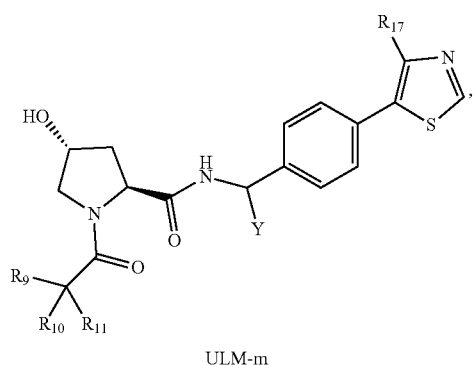

ULM-m wherein:
at each occurrence Y of ULM-m is independently H, methyol or ethyl
at each occurrence $R_9$ of ULM-m is H;
at each occurrence $R_{10}$ of ULM-m is independently isopropyl, tert-butyl, sec-butyl, cyclopentyl, or cyclohexyl;
at each occurrence $R_{11}$ of ULM-m is independently optionally substituted amide, optionally substituted isoindolinone, optionally substituted isooxazole, optionally substituted heterocycles.

In other embodiments, ULM and where present, ULM', have the structure:

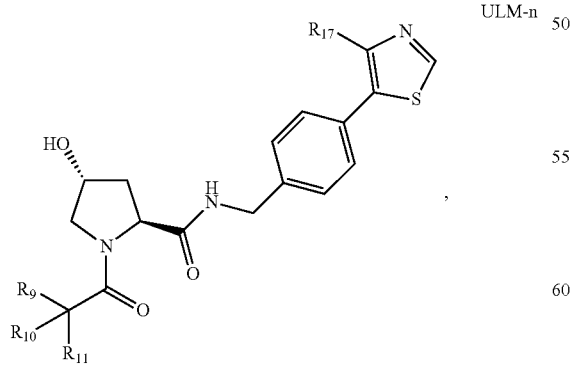

ULM-n wherein:
at each occurrence $R_{17}$ of ULM-n is independently methyl, ethyl, or cyclopropyl; and at each occurrence $R_9$, $R_{10}$, and $R_{11}$ of ULM-n are as defined for ULM-m. In other embodiments, $R_9$ is H; and $R_{10}$ of ULM-n is H, alkyl, or cycloalkyl (preferably, isopropyl, tert-butyl, sec-butyl, cyclopentyl, or cyclohexyl).

In various embodiments, the ULM moiety is selected from the group consisting of:

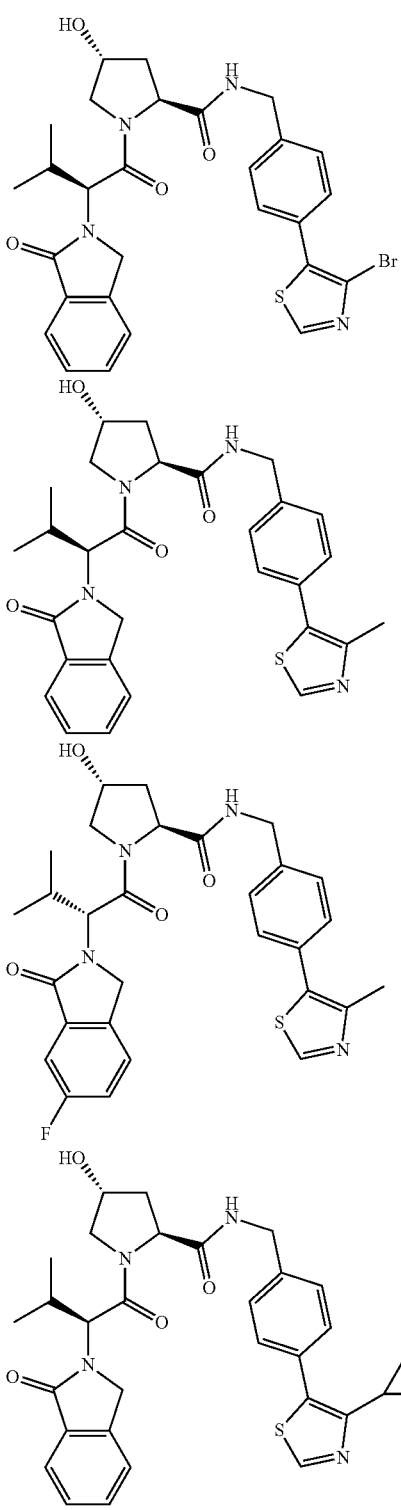

219
-continued
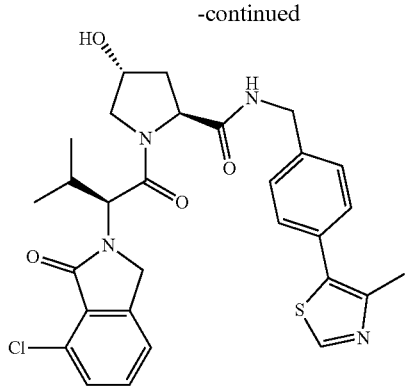
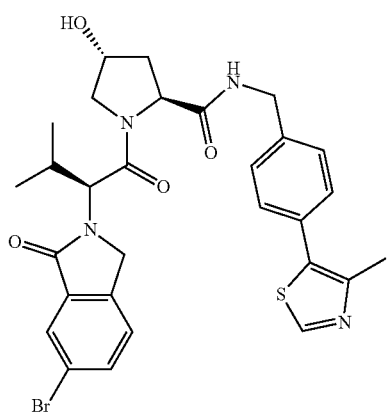
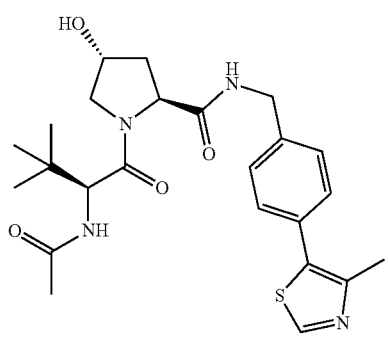
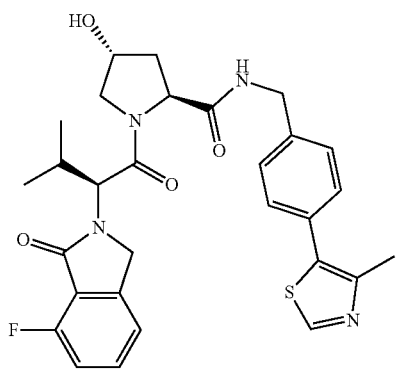
220
-continued
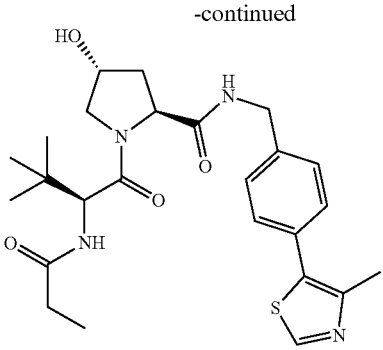
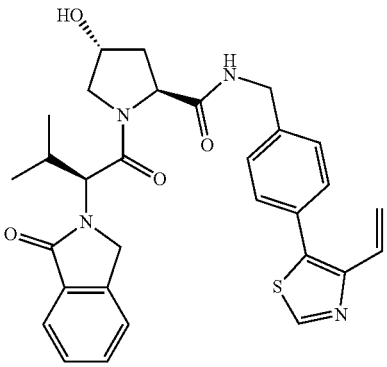
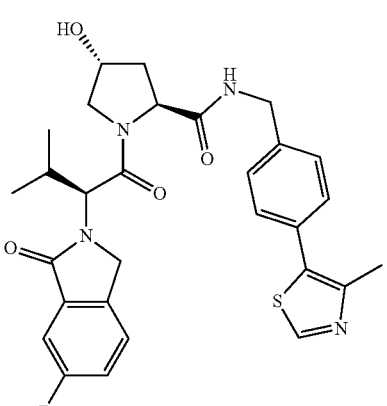
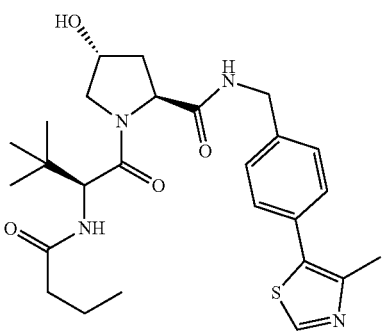

221
-continued
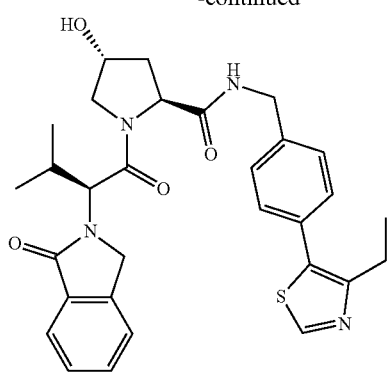
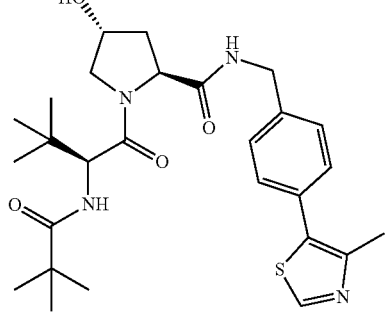
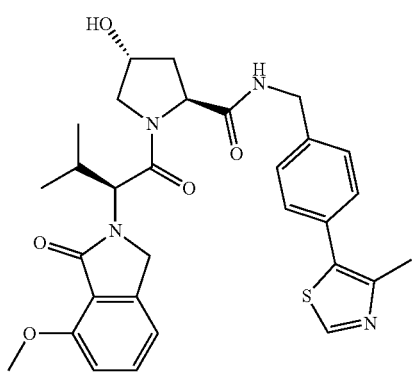
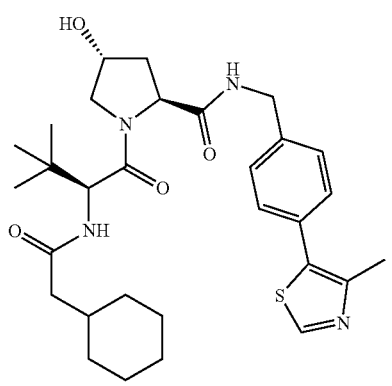
222
-continued
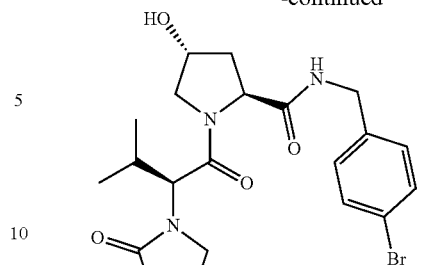
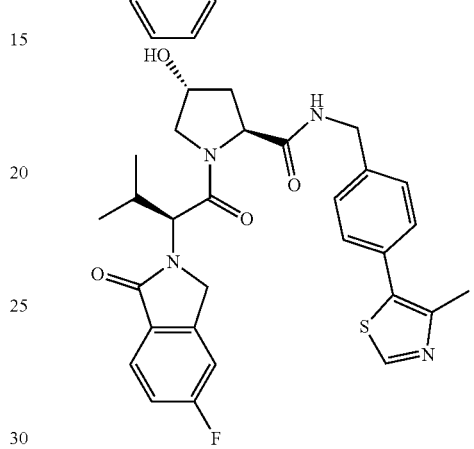
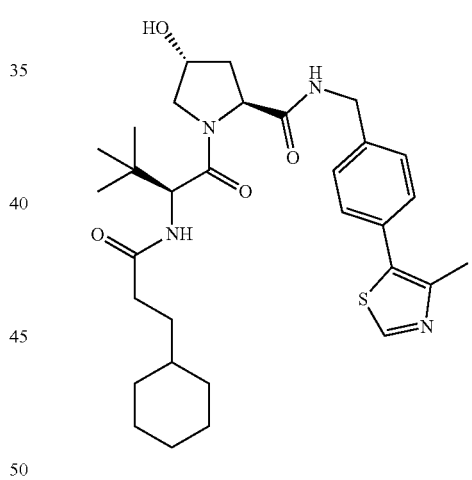
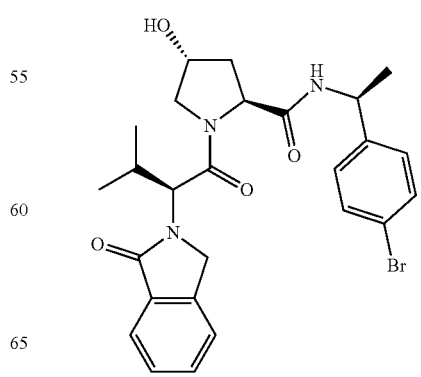

223
-continued
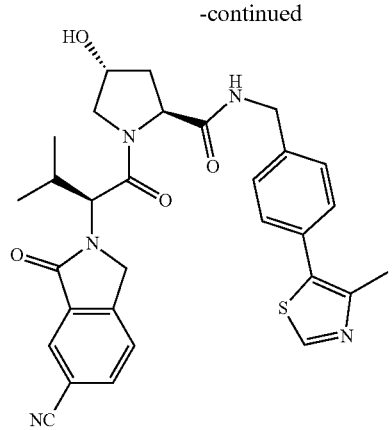
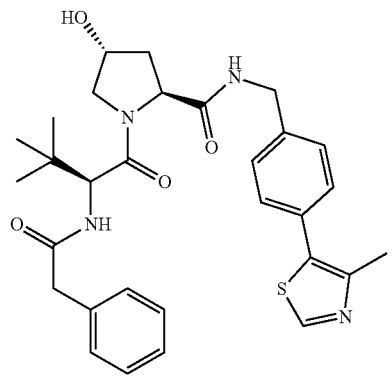
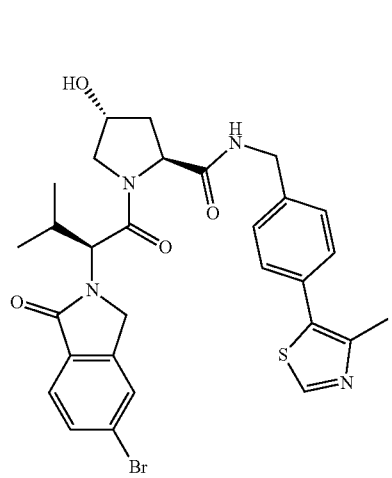
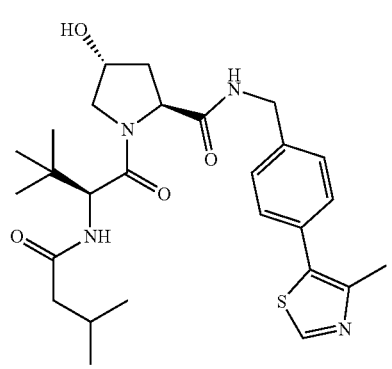
224
-continued
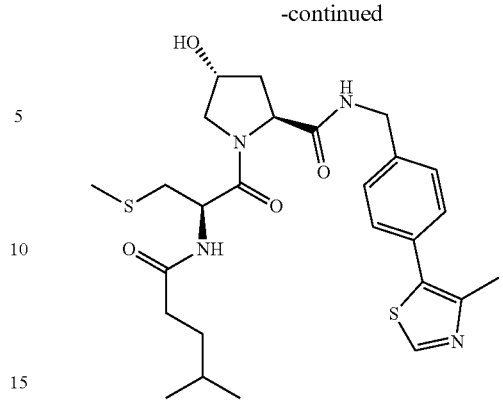
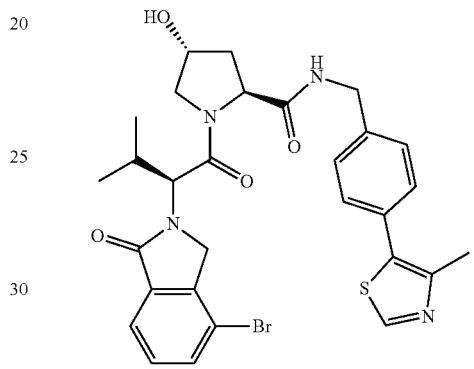
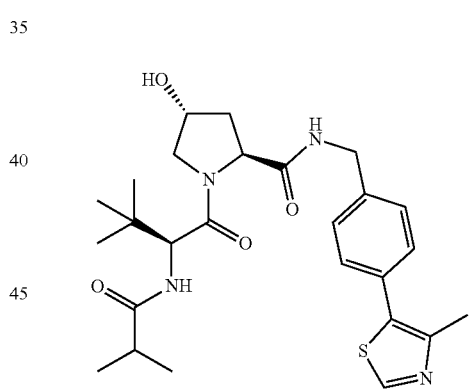
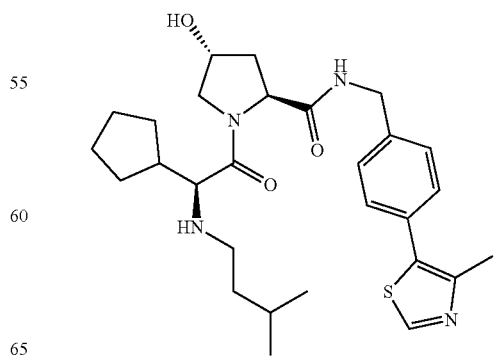

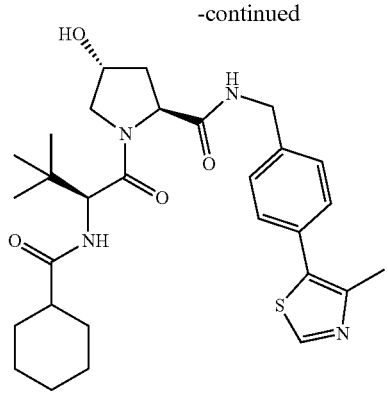
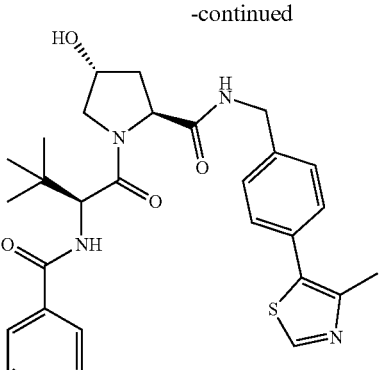
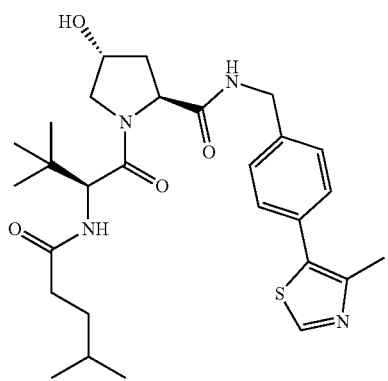
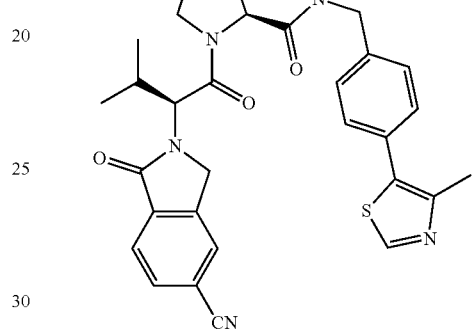
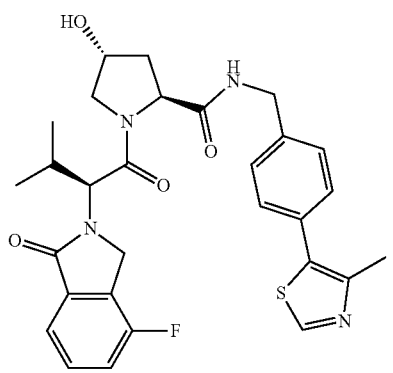
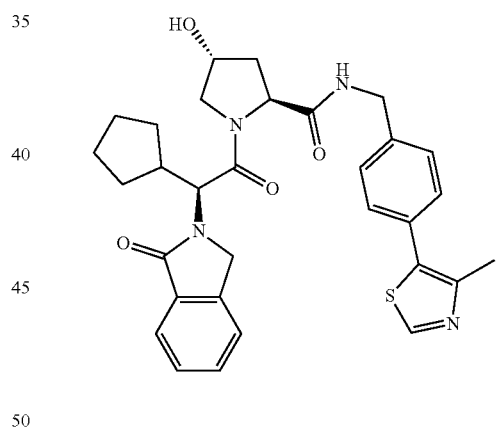
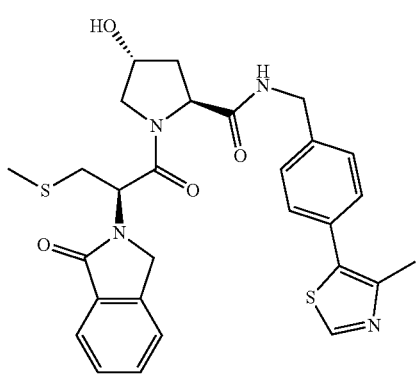
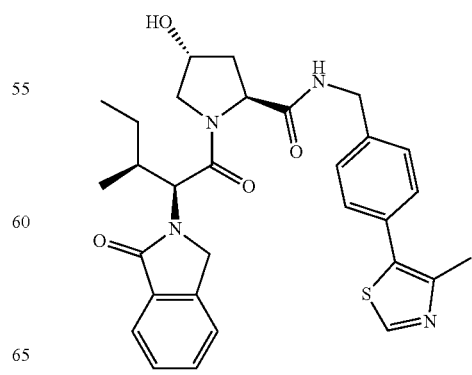

227
-continued
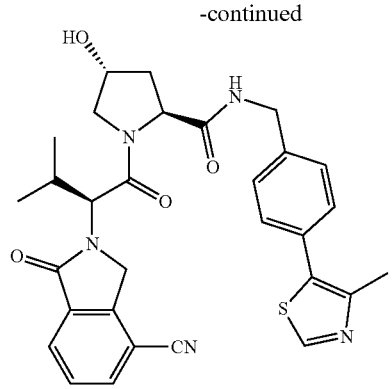
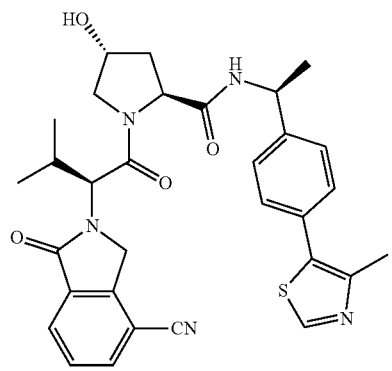
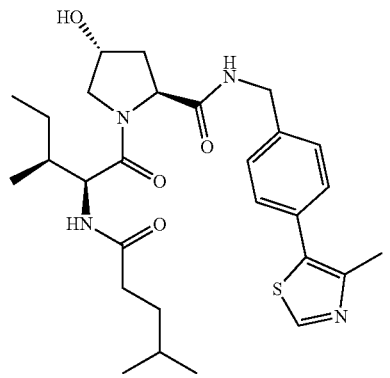
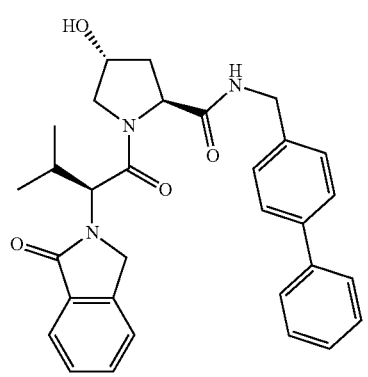
228
-continued
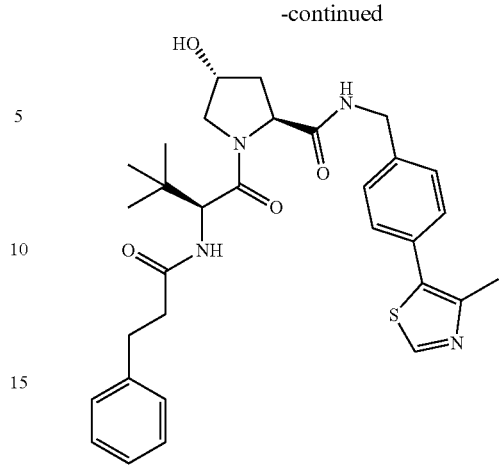
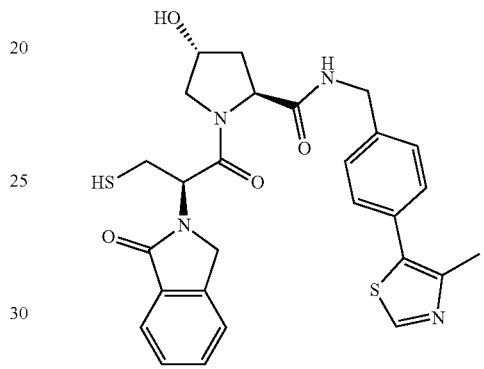
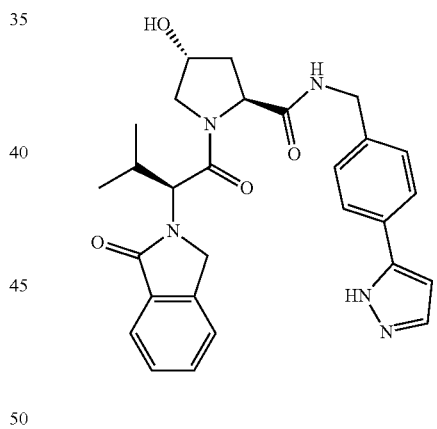
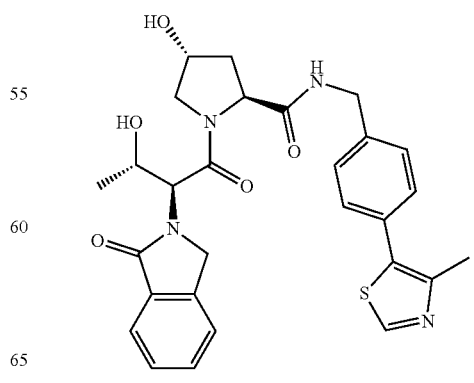

229
-continued
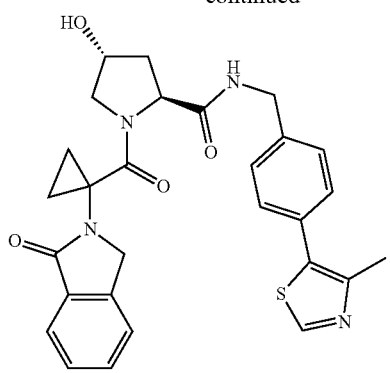
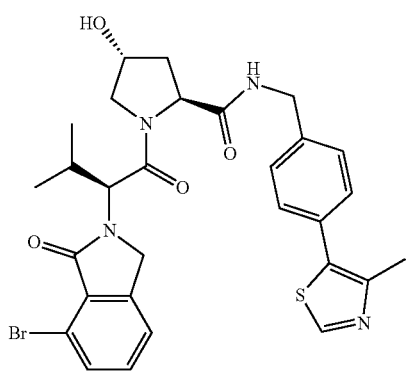
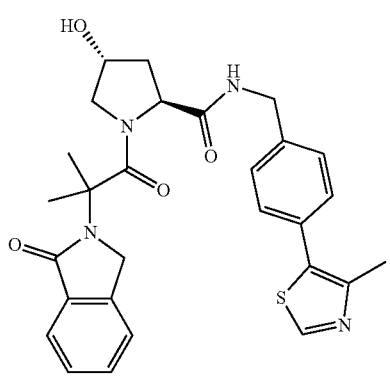
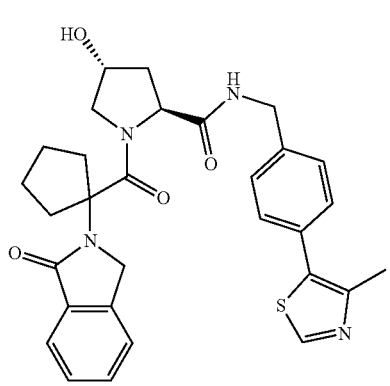
230
-continued
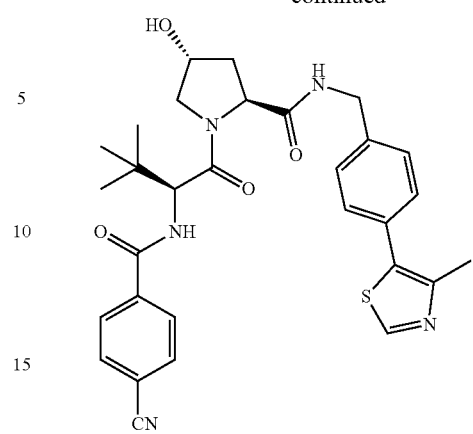
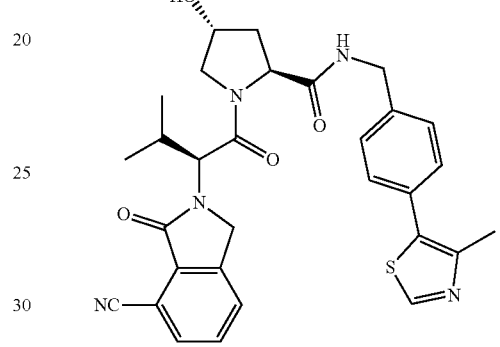
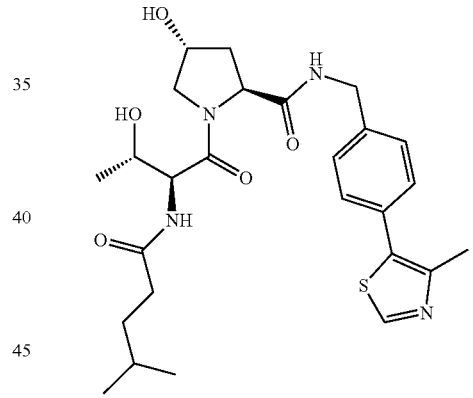
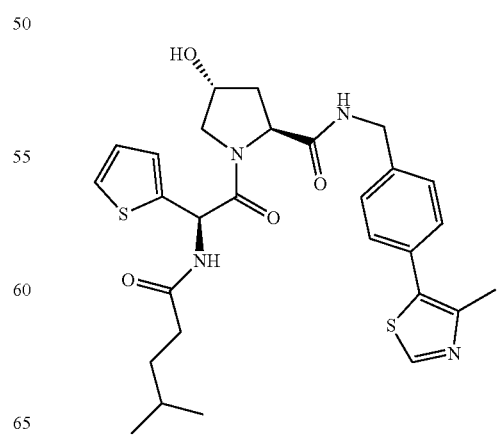

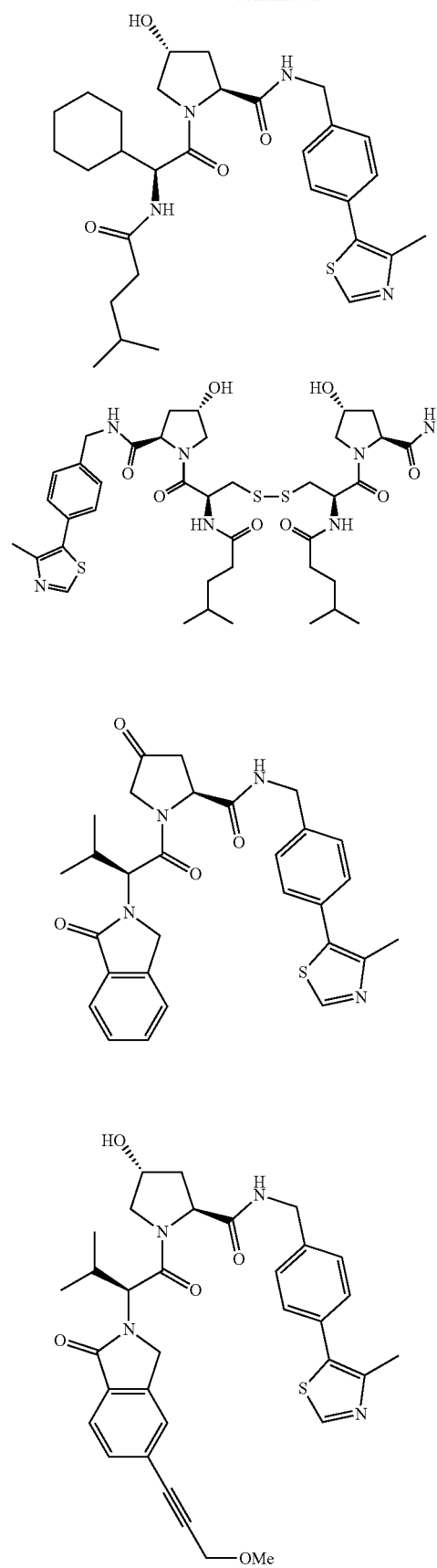
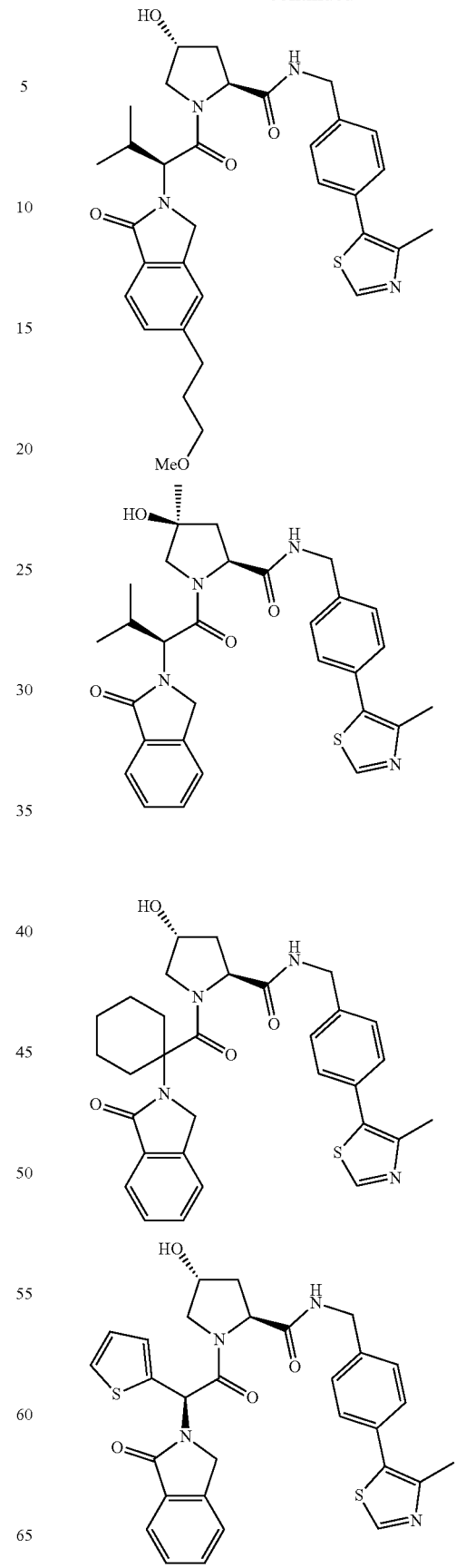

233
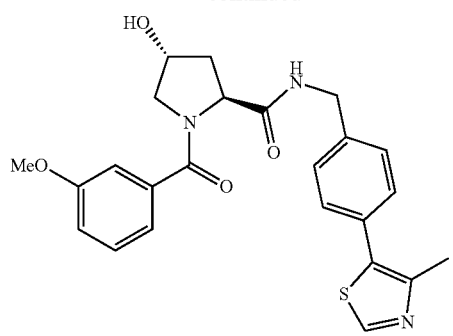
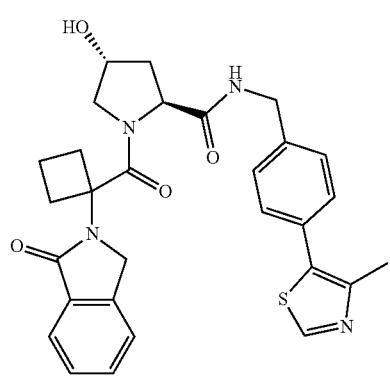
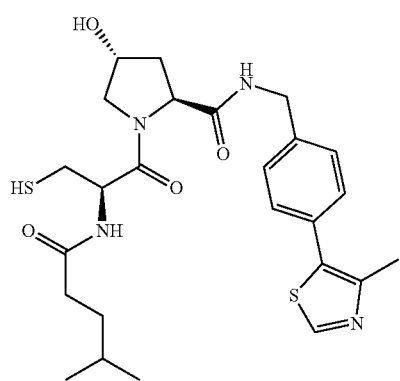
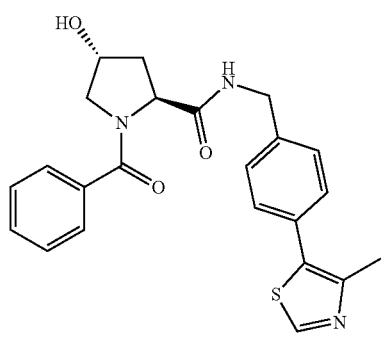
234
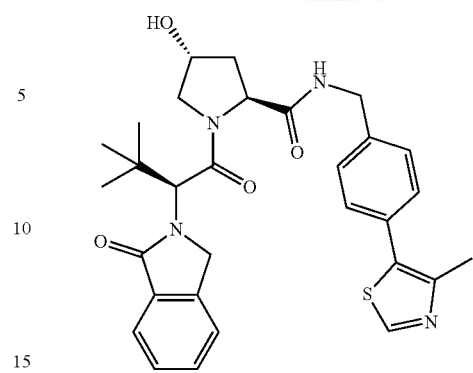
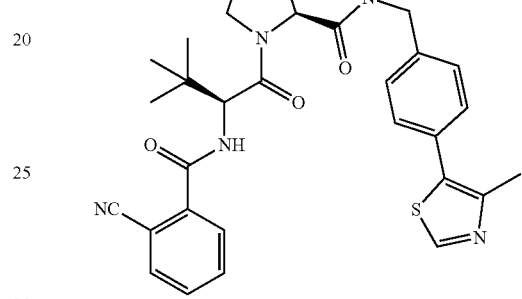
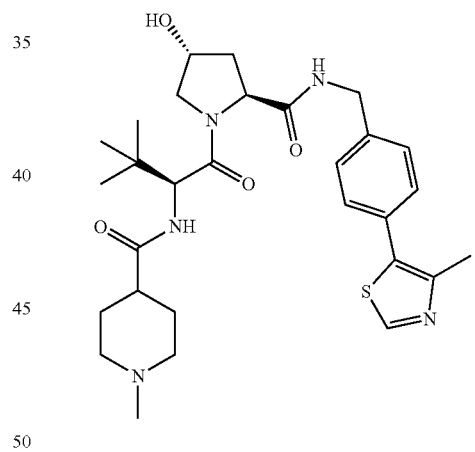
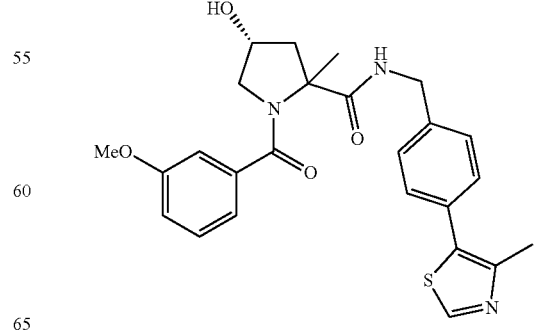

235
-continued
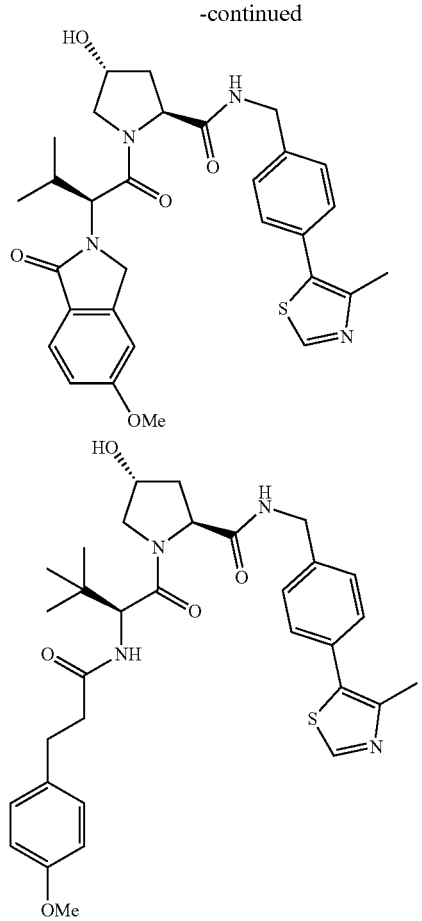
236
-continued
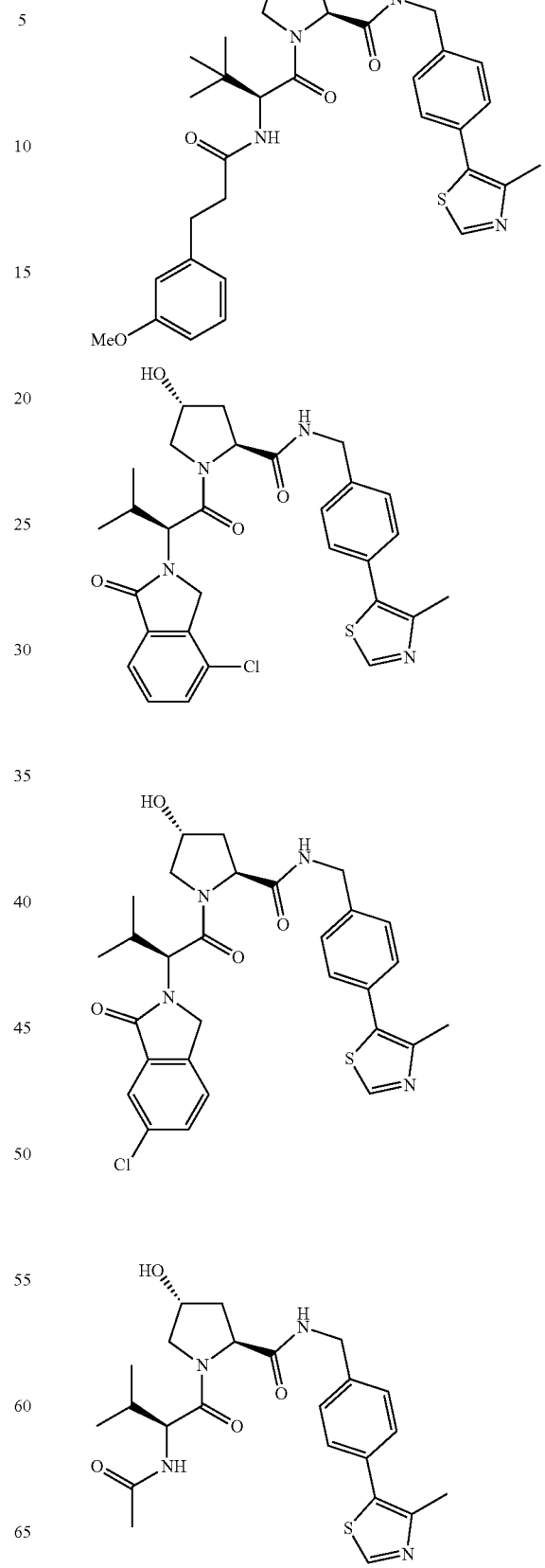

237
-continued
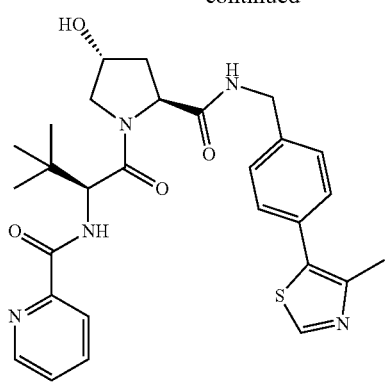
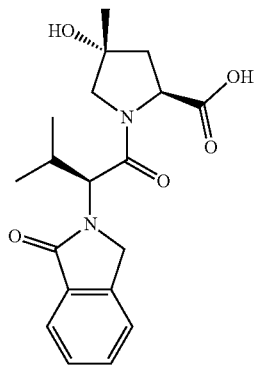
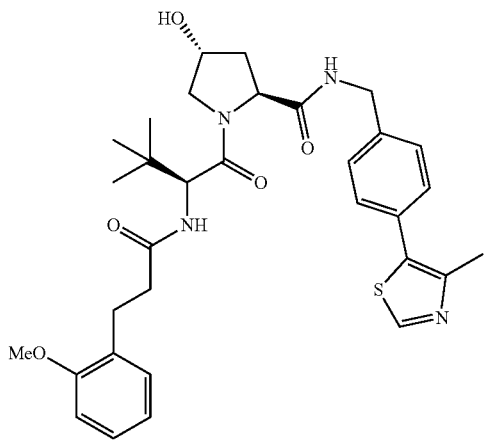
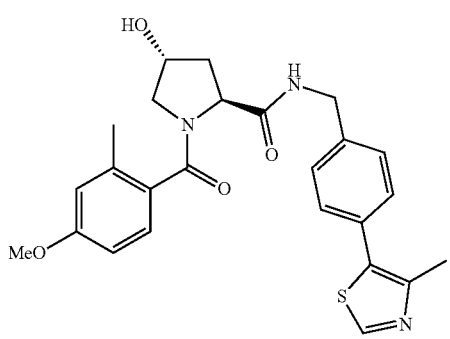
238
-continued
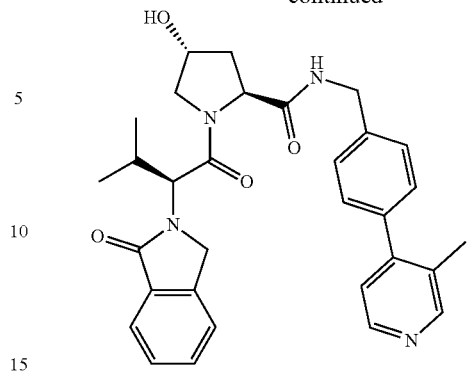
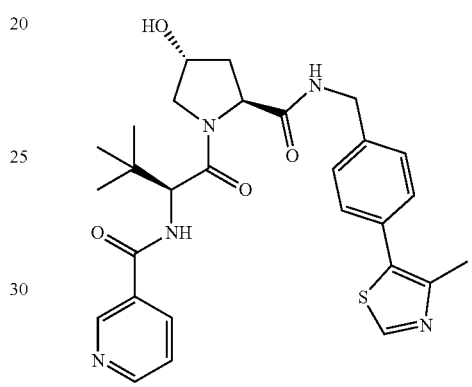
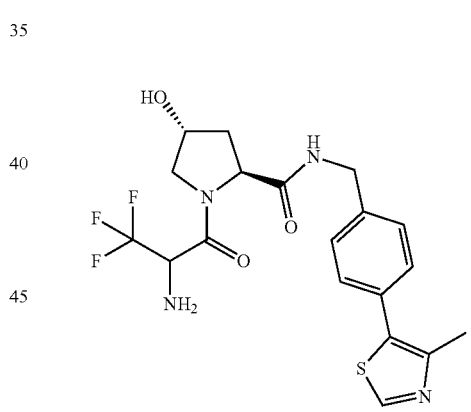
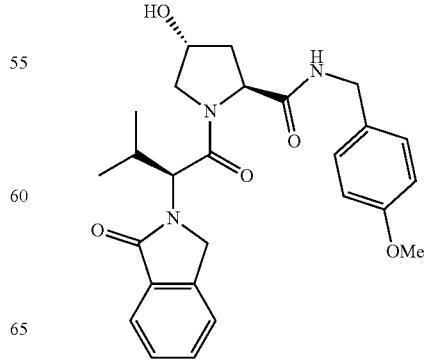

239
-continued
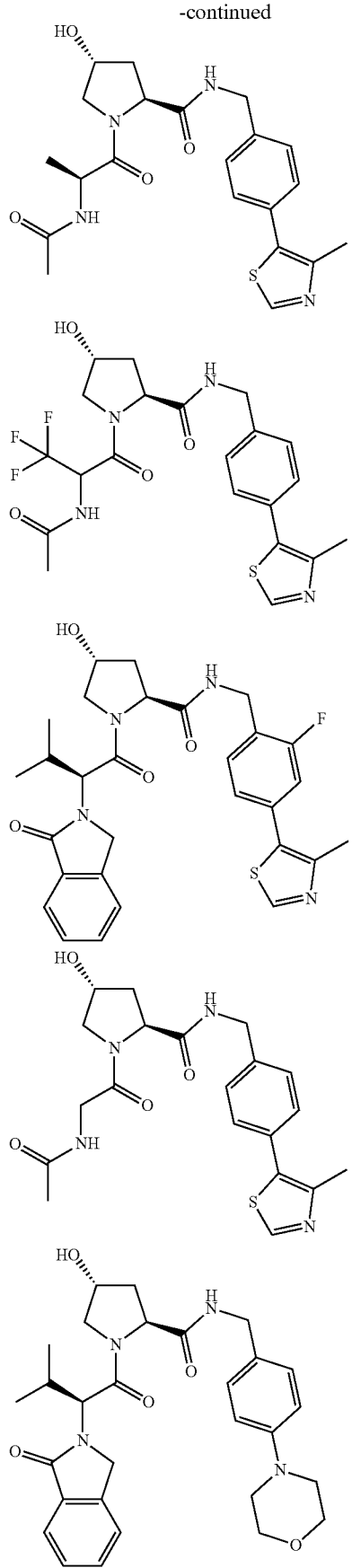
240
-continued
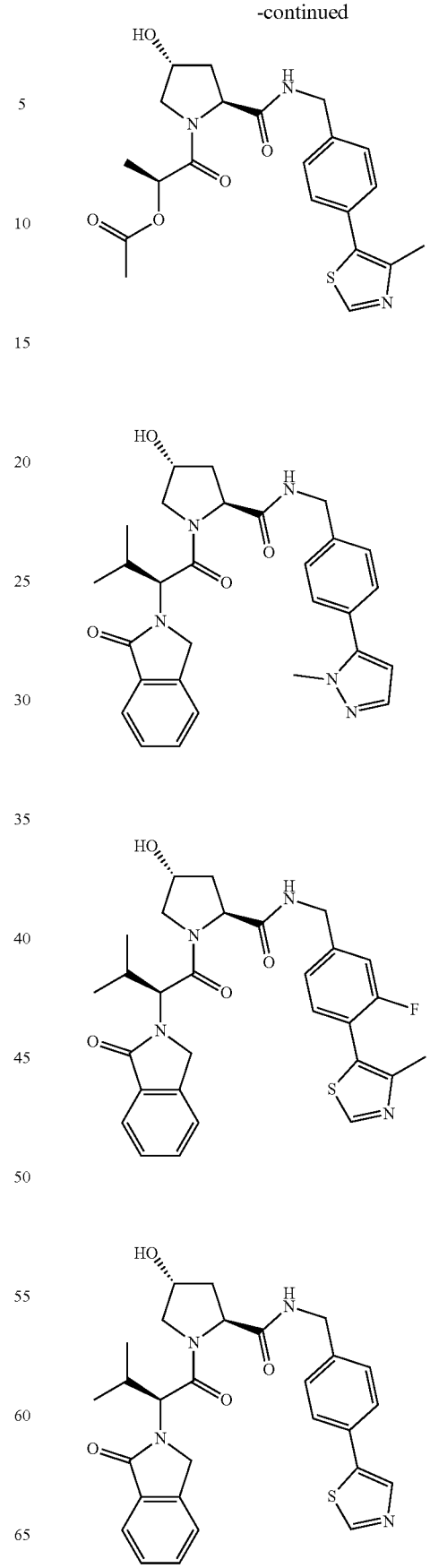

241
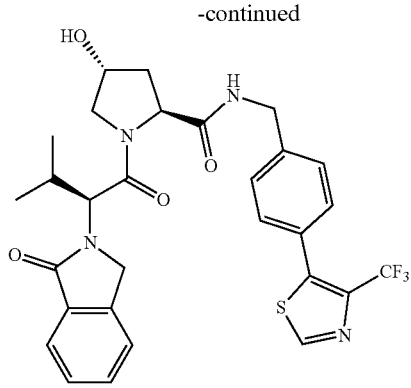
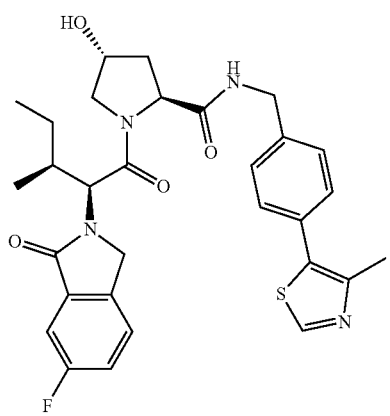
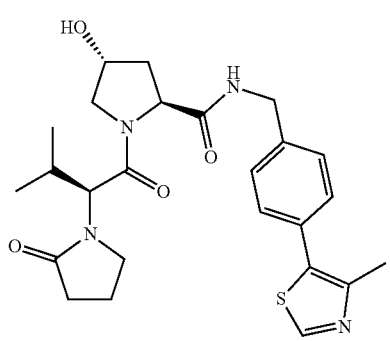
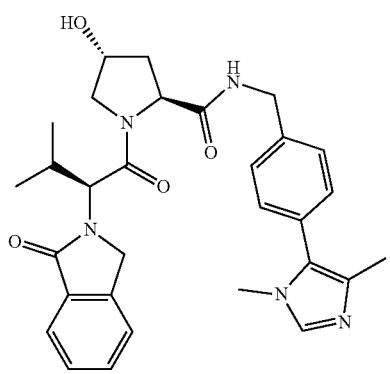
242
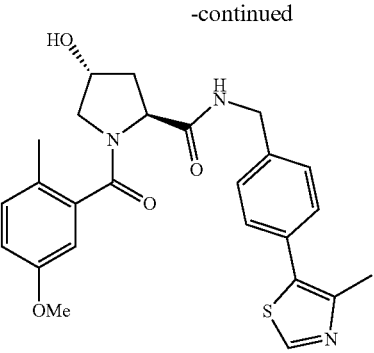
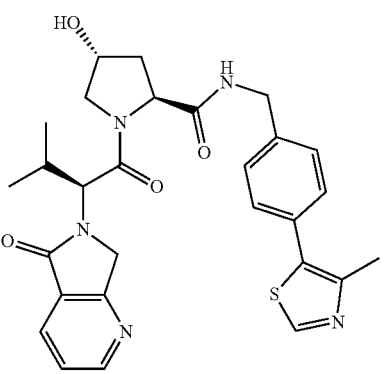
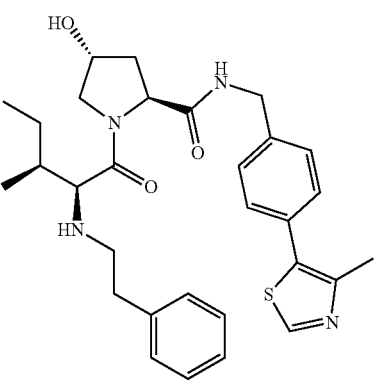
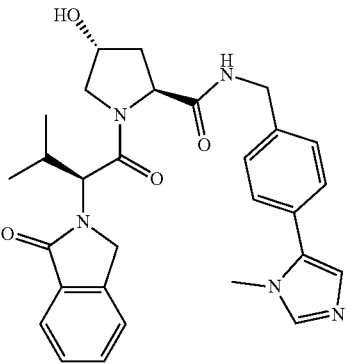

243
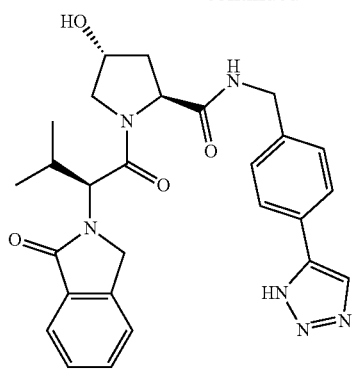
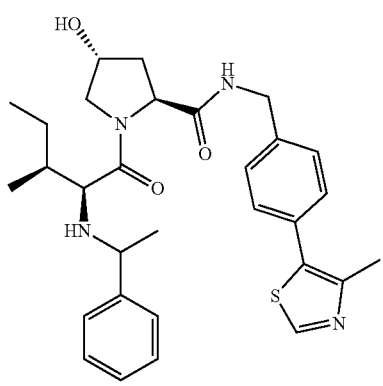
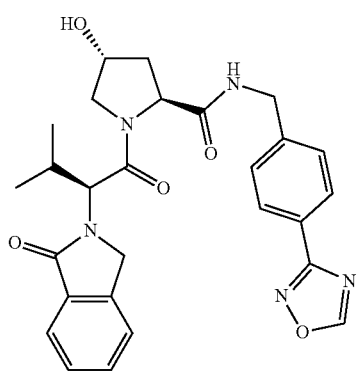
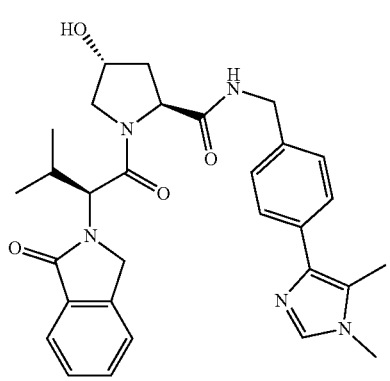
244
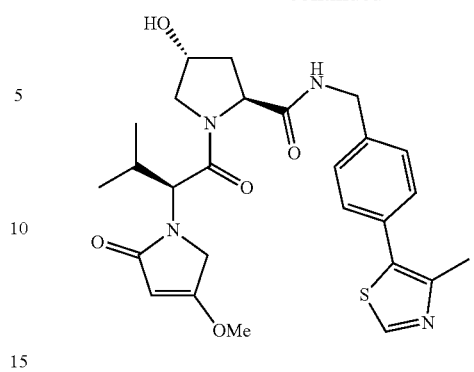
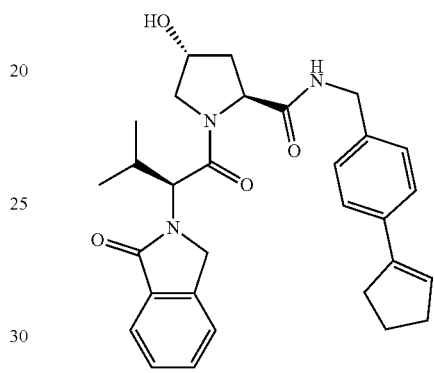
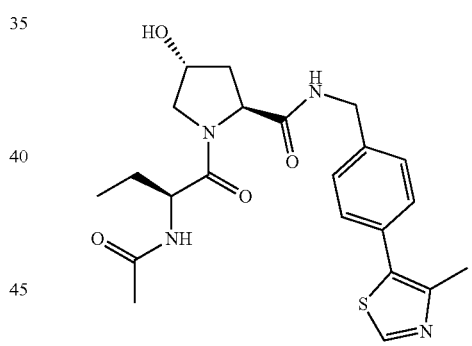
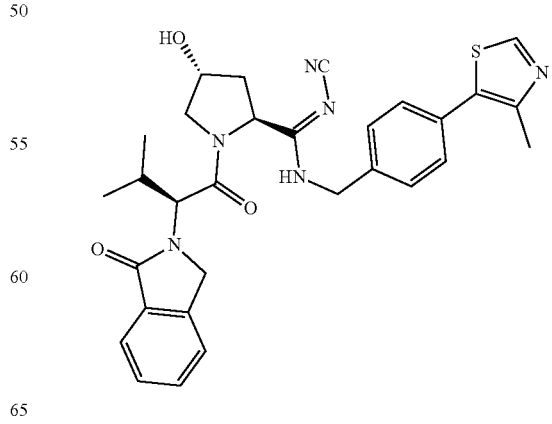

245
-continued
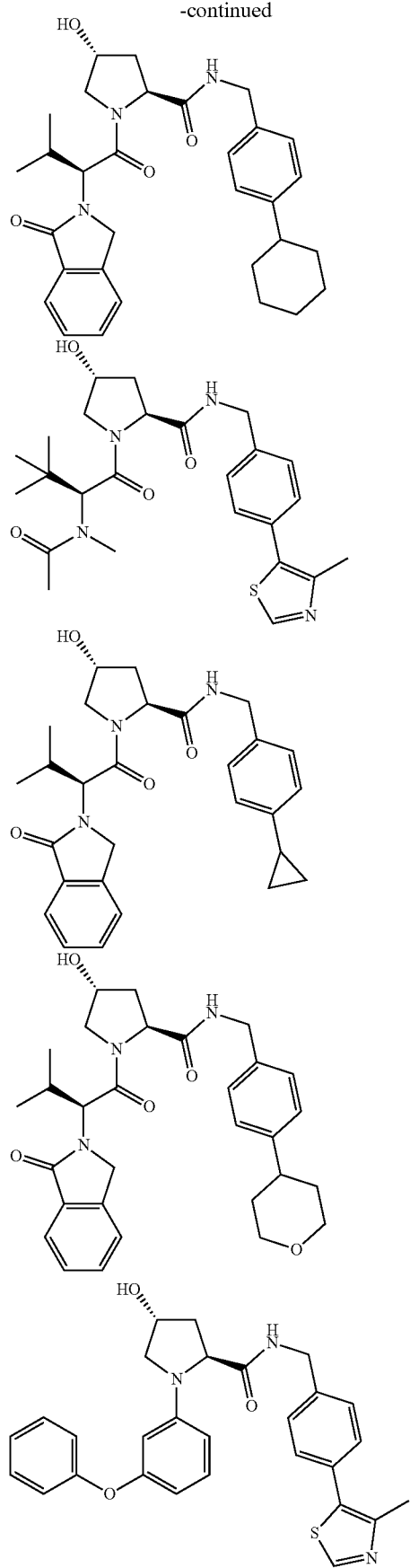
246
-continued
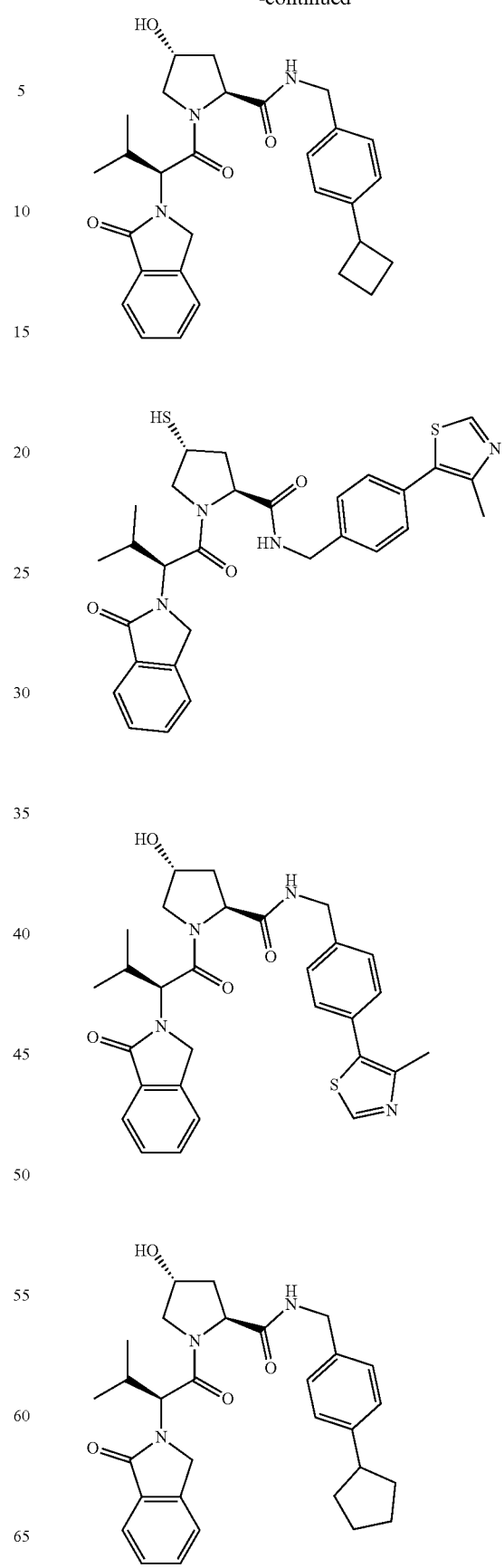

247
-continued
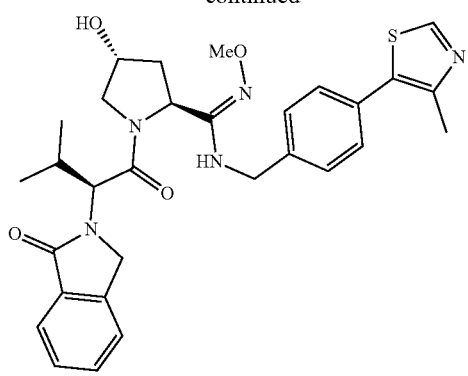
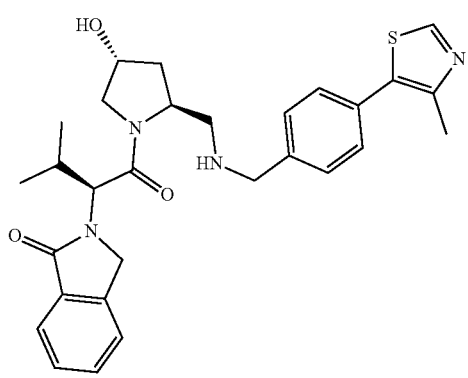
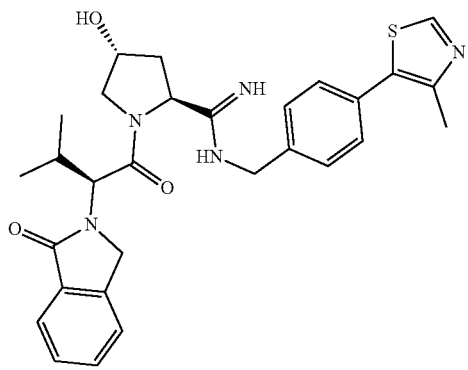
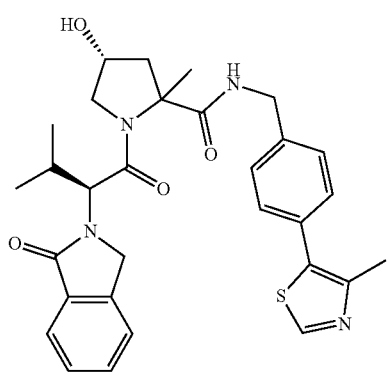
248
-continued
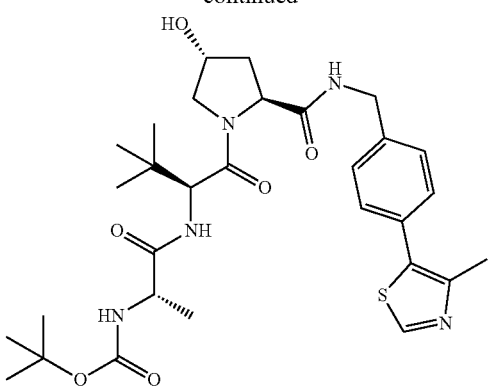
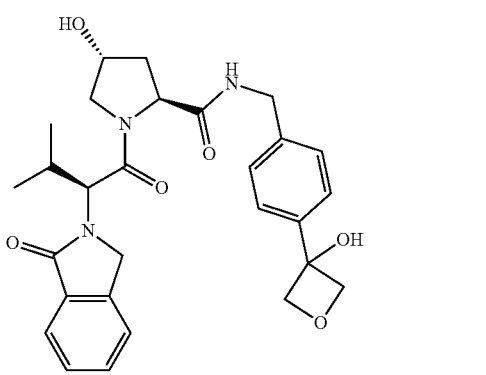
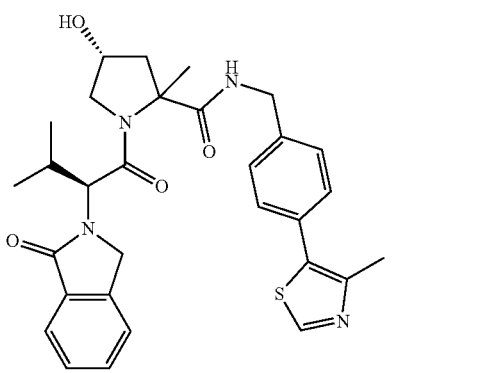
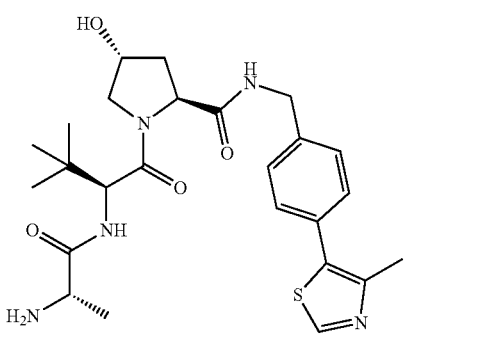

249
-continued
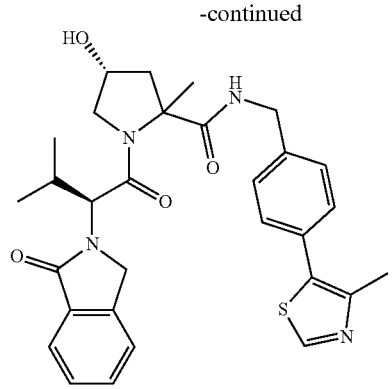
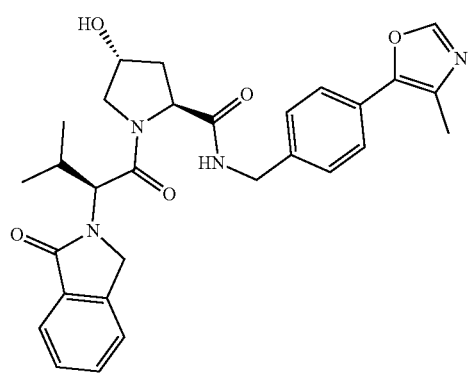
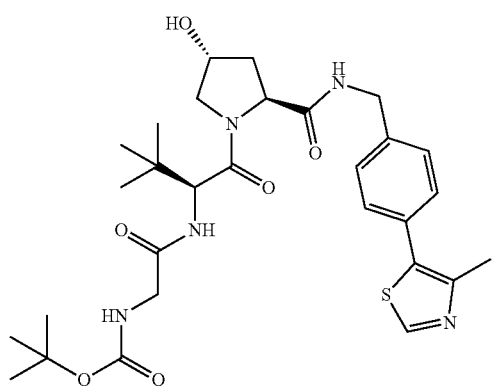
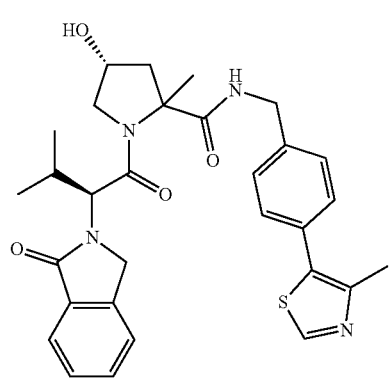
250
-continued
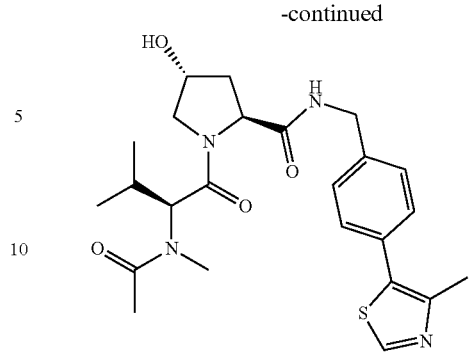
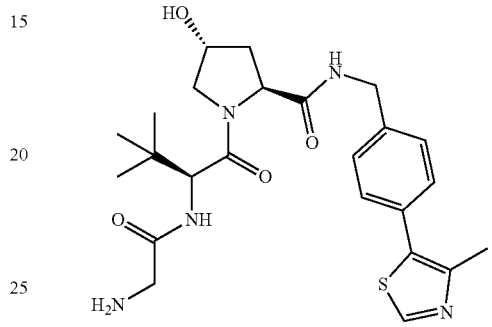
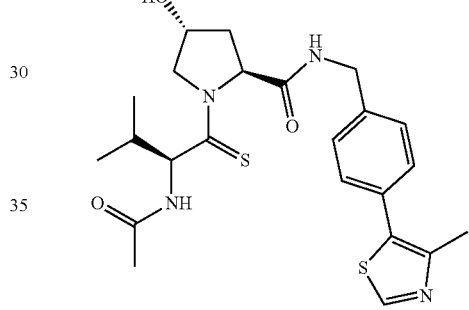
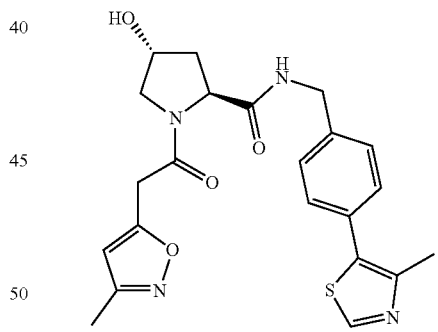
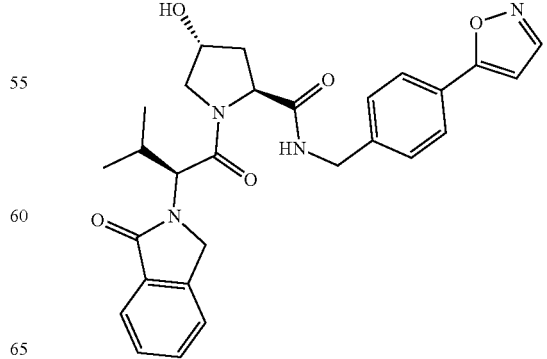

251
-continued
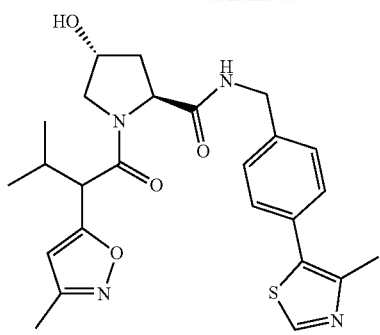
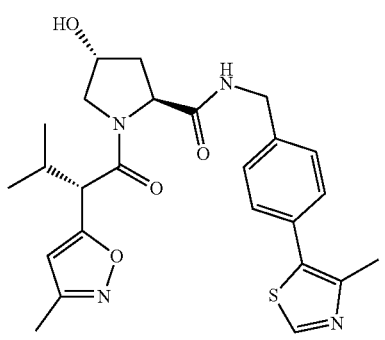
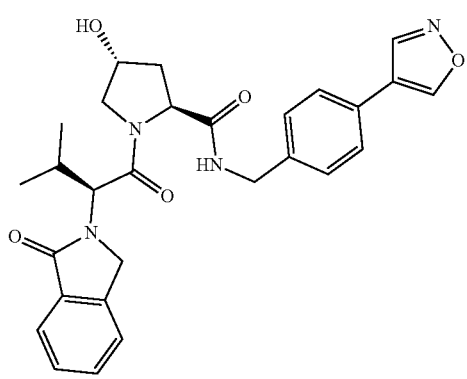
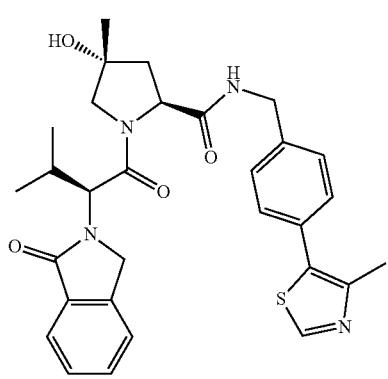
252
-continued
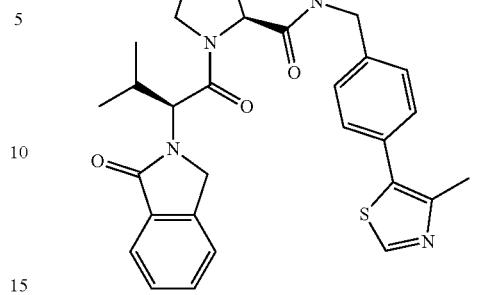
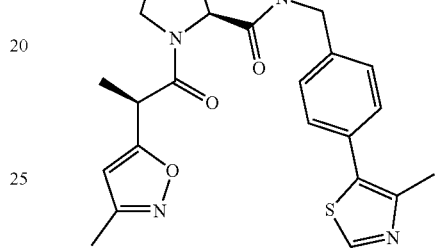
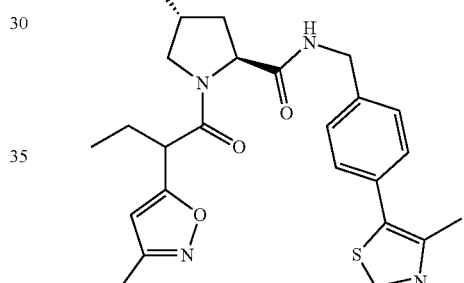
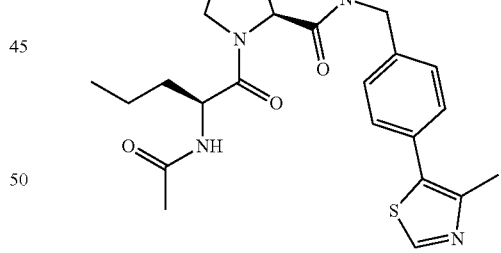
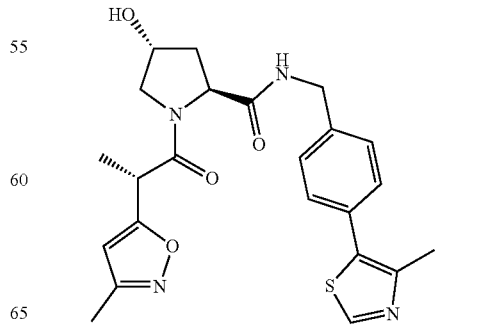

253
-continued
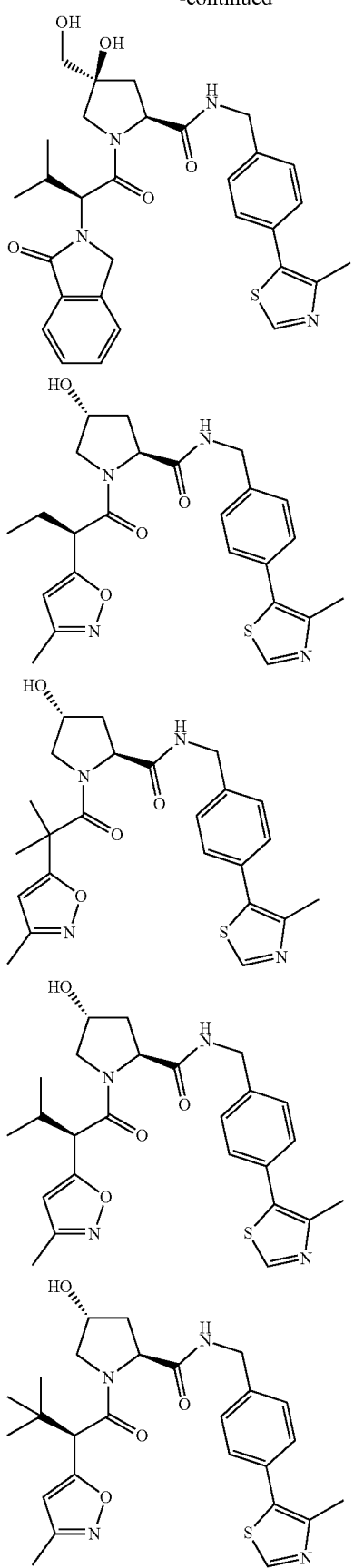
254
-continued
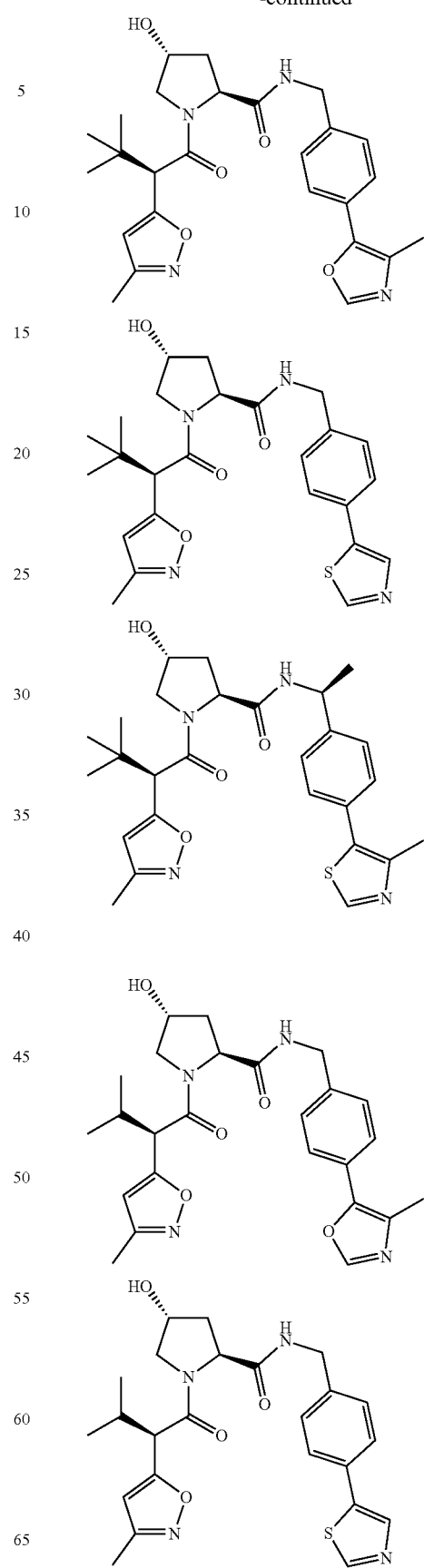

255
-continued
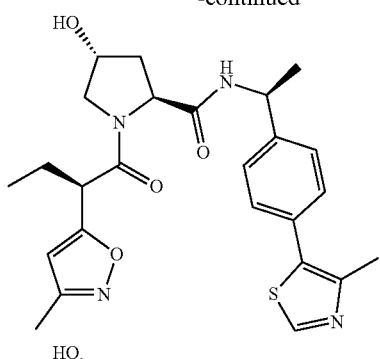
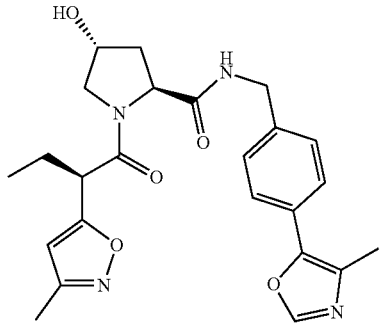
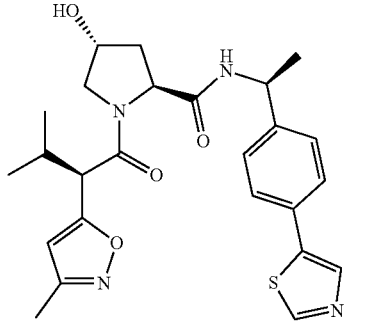
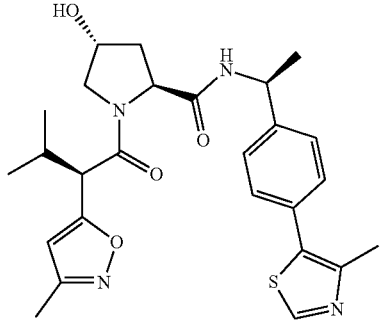
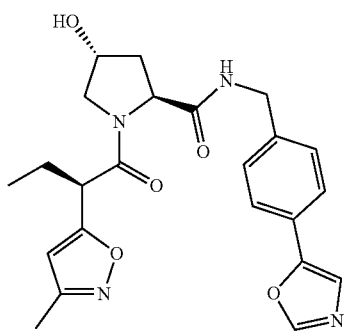
256
-continued
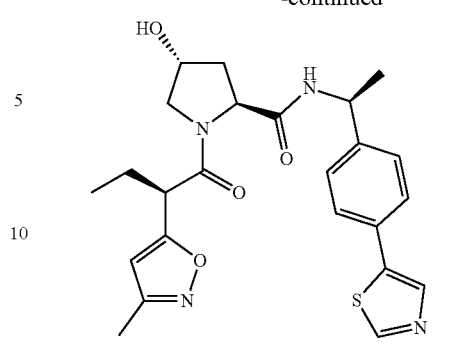
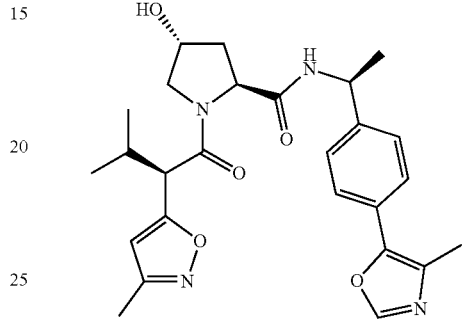
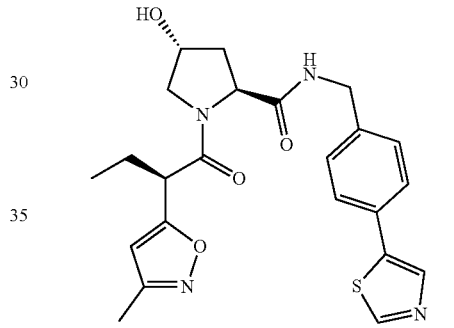
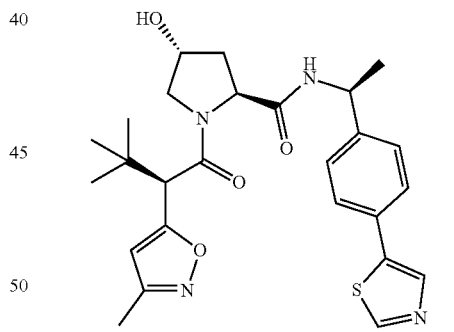
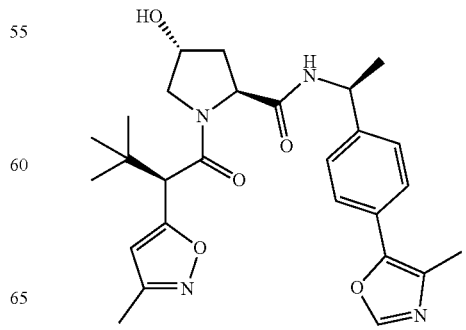

257
-continued
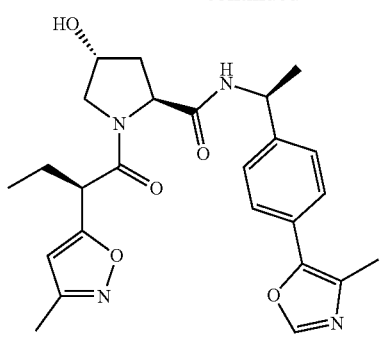
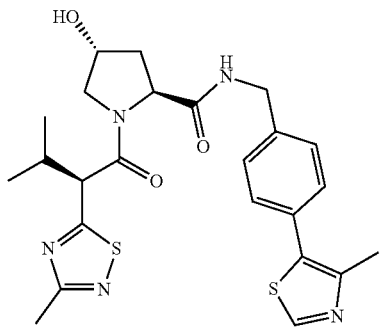
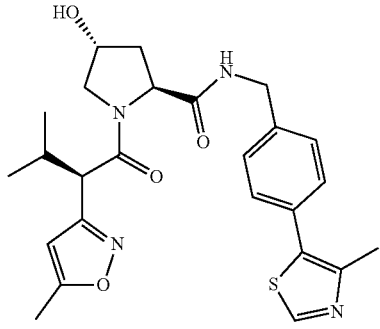
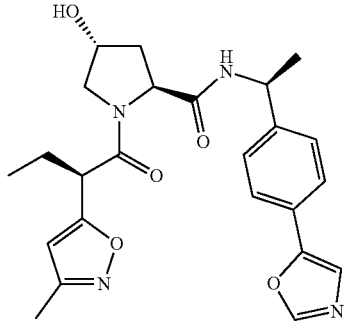
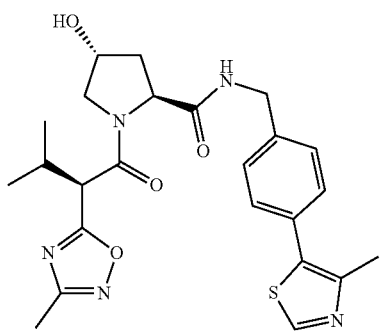
258
-continued
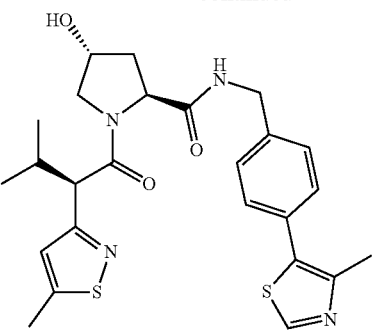
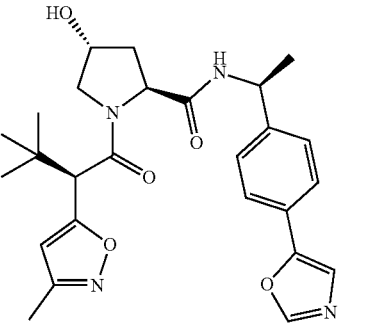
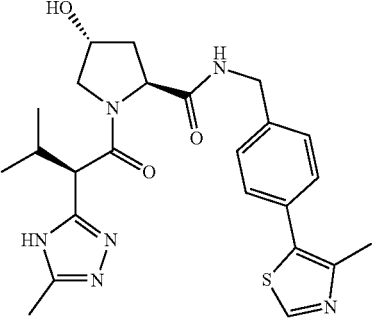
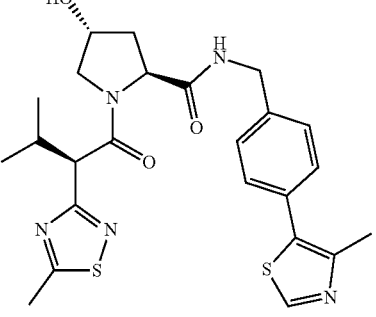
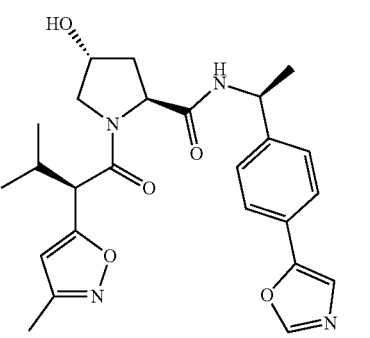

259
-continued
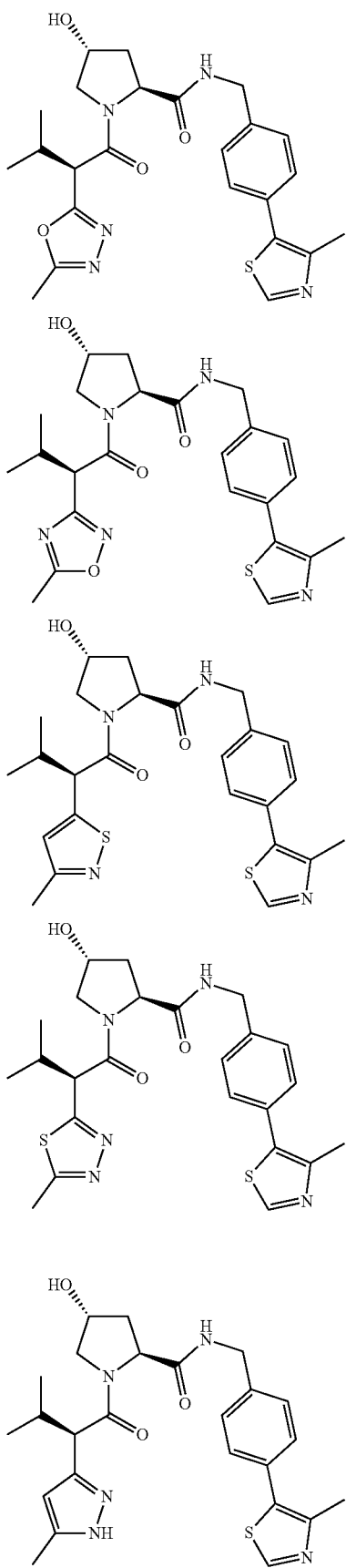
260
-continued
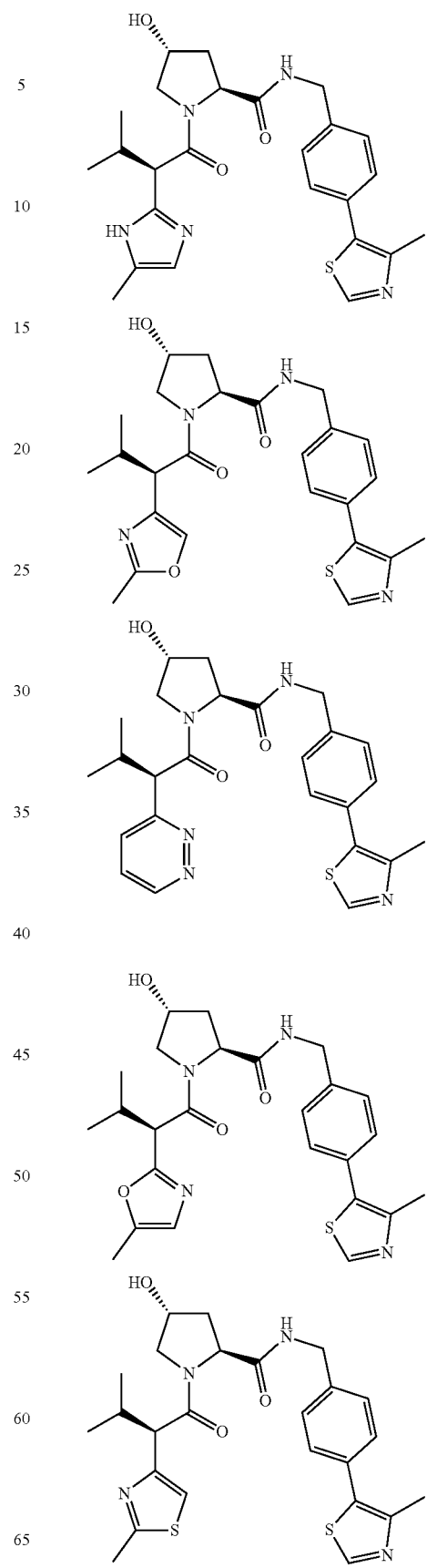

261
-continued
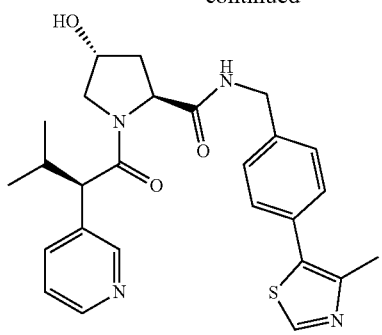
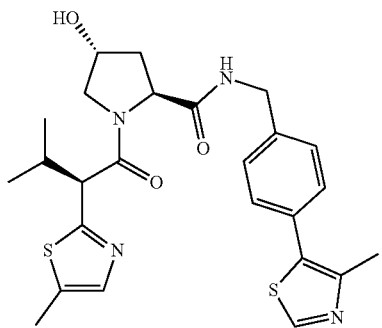
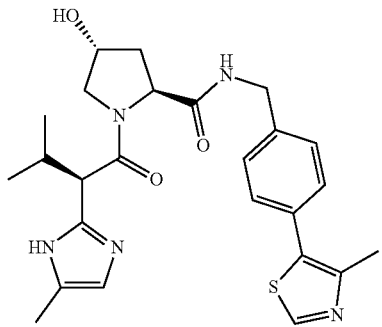
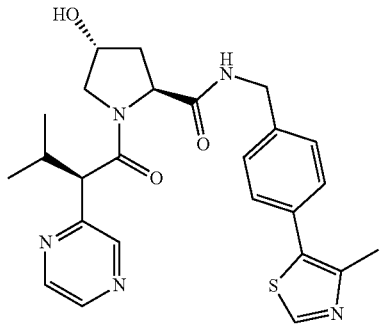
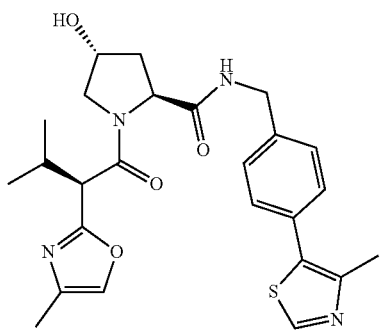
262
-continued
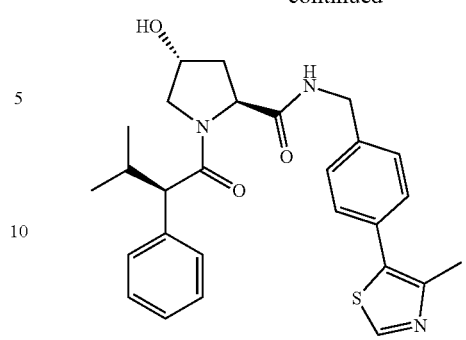
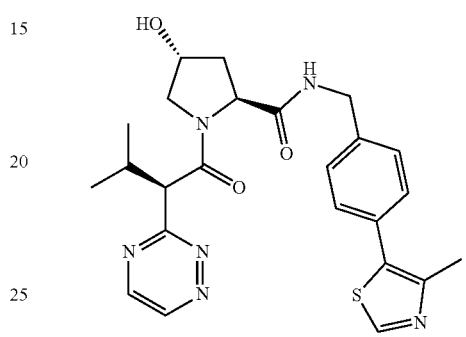
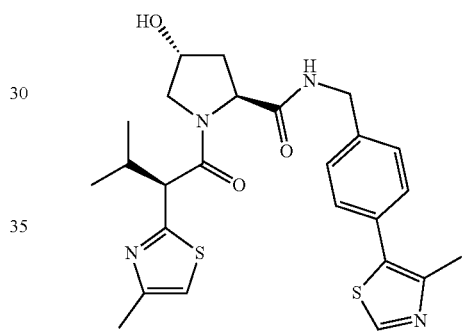
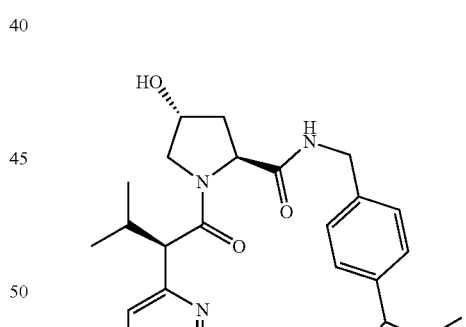
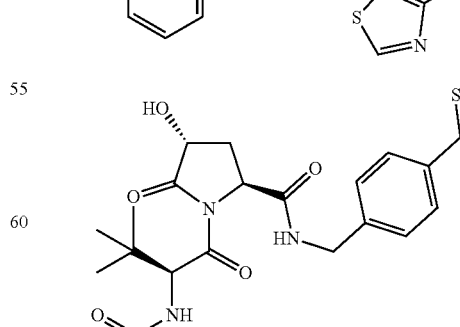

263
-continued
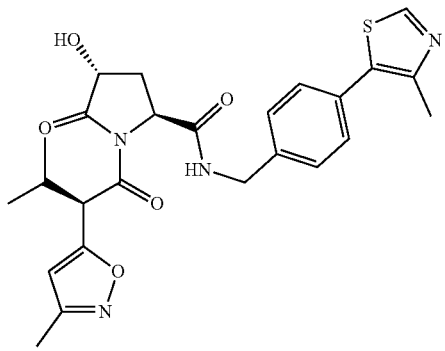
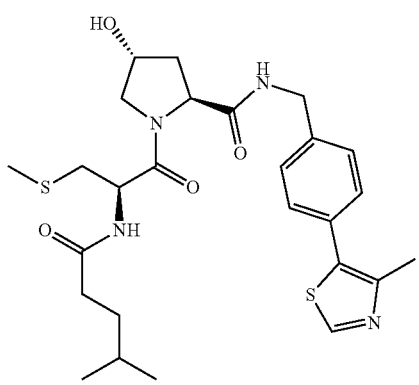
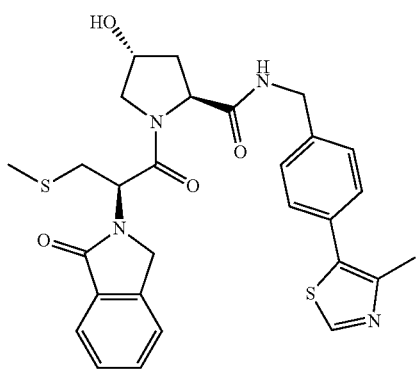
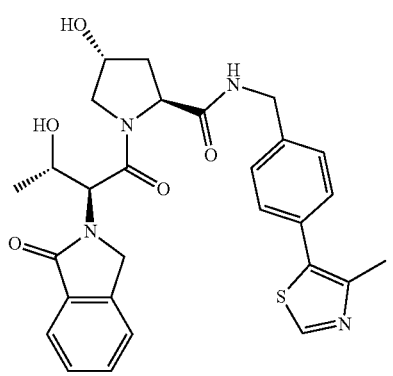
264
-continued
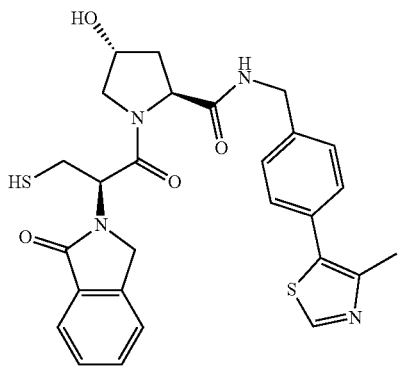
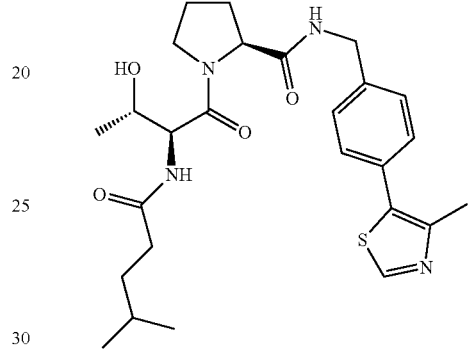
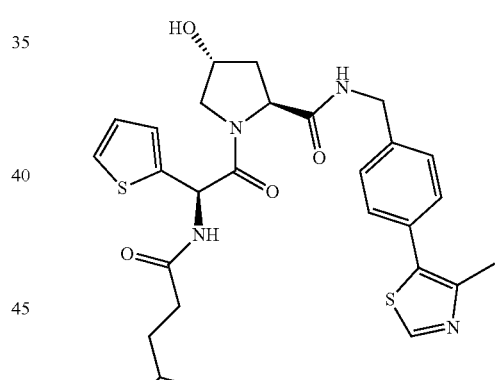
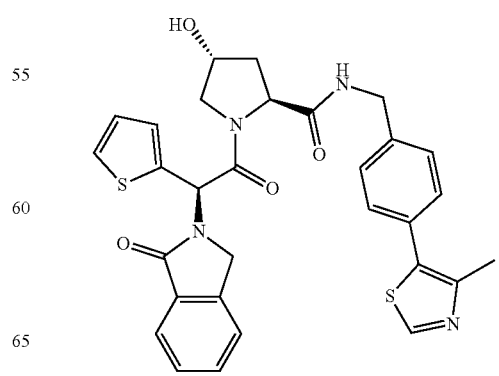

265
-continued
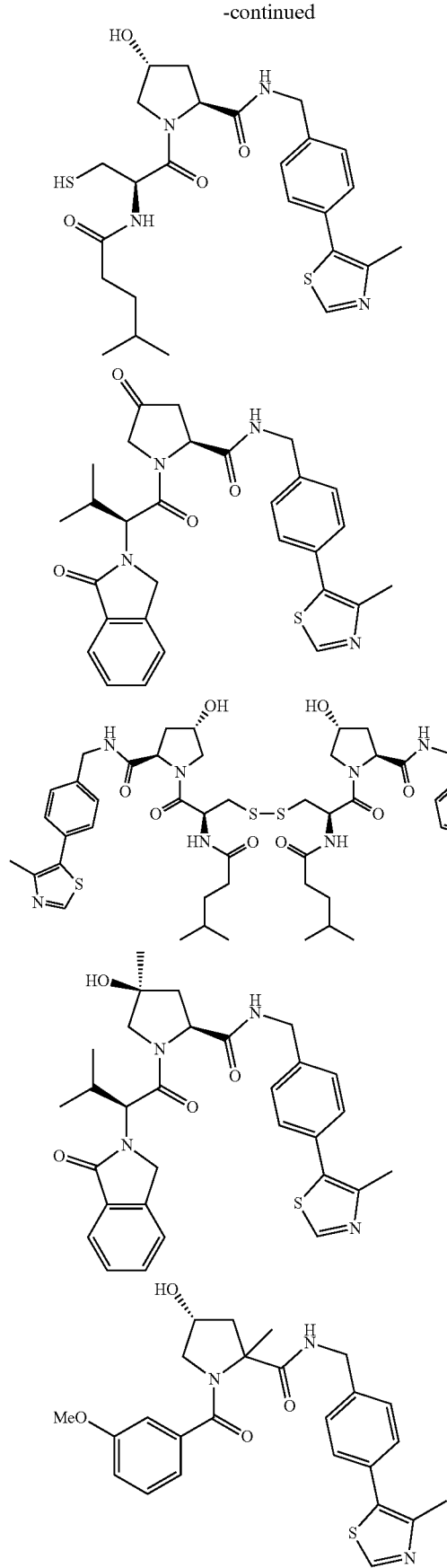
266
-continued
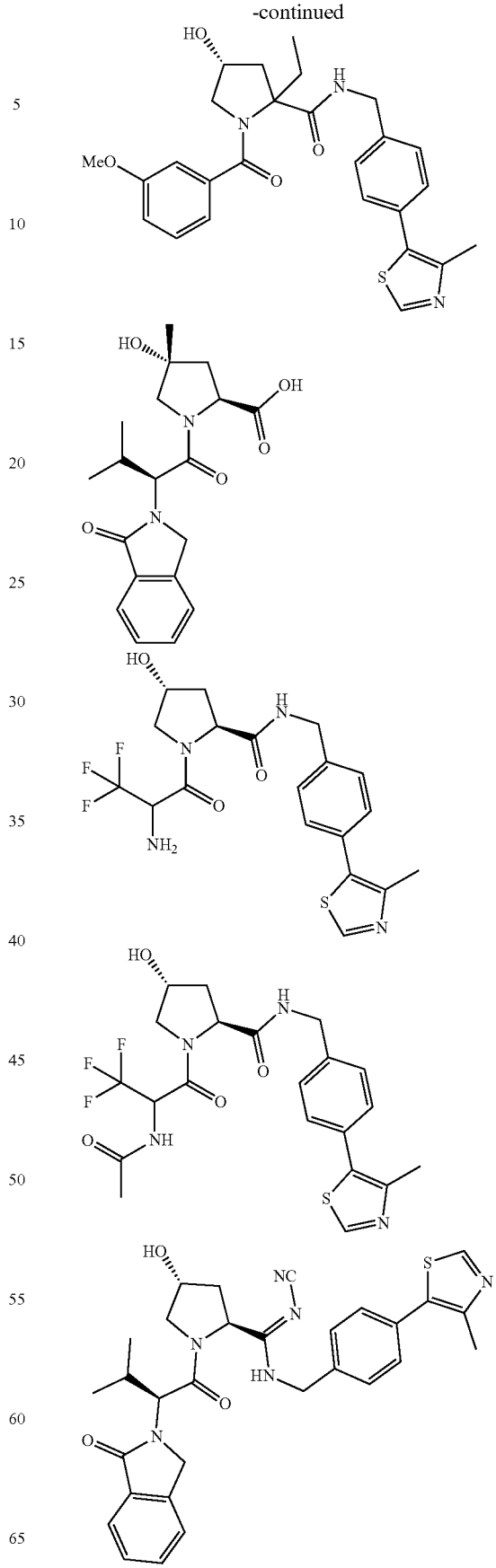

267
-continued
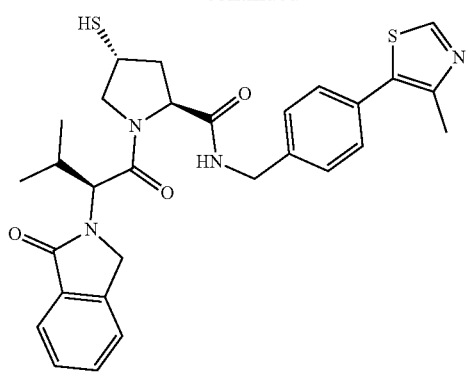
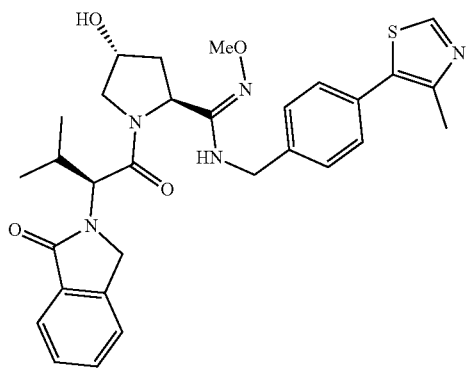
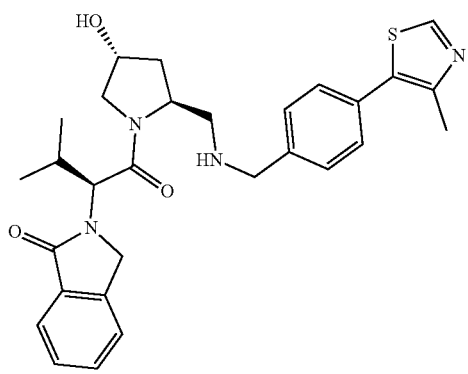
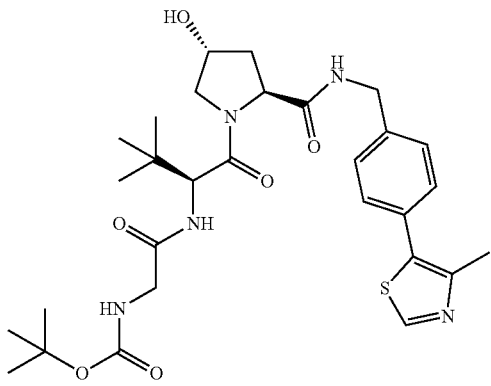
268
-continued
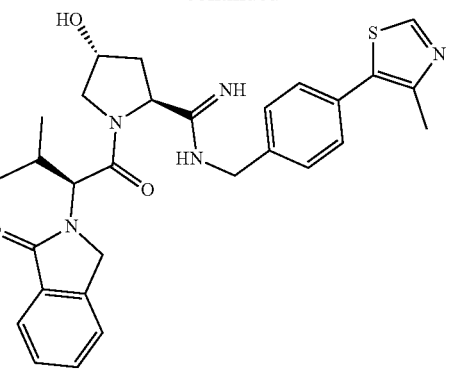
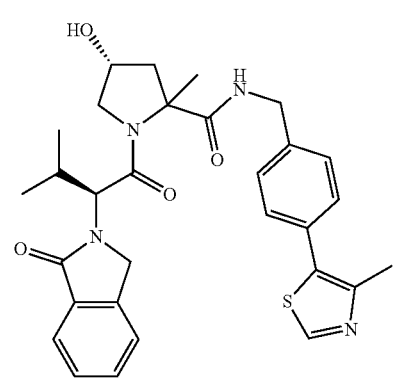
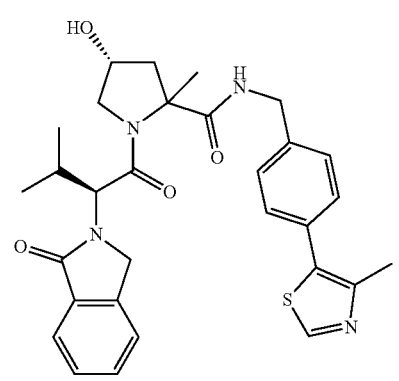
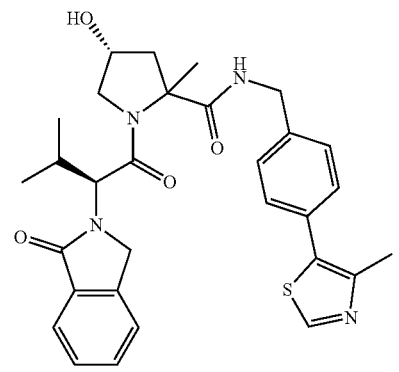

269
-continued
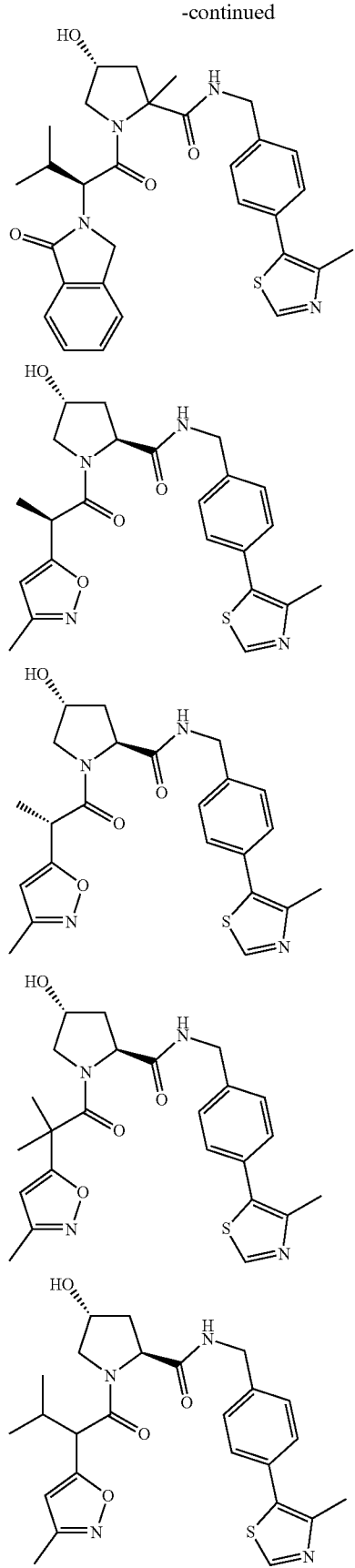
270
-continued
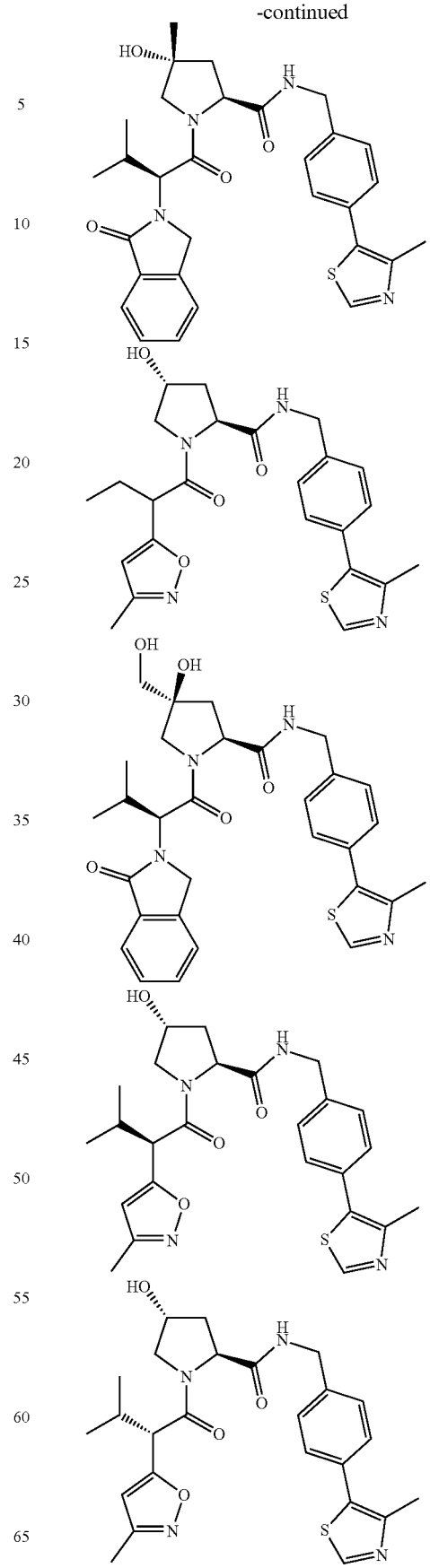

271
-continued
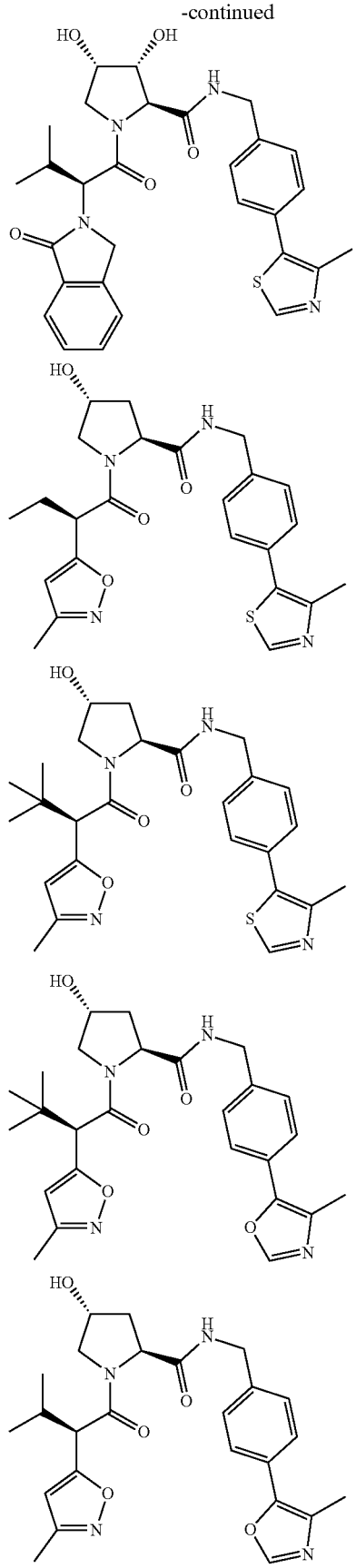
272
-continued
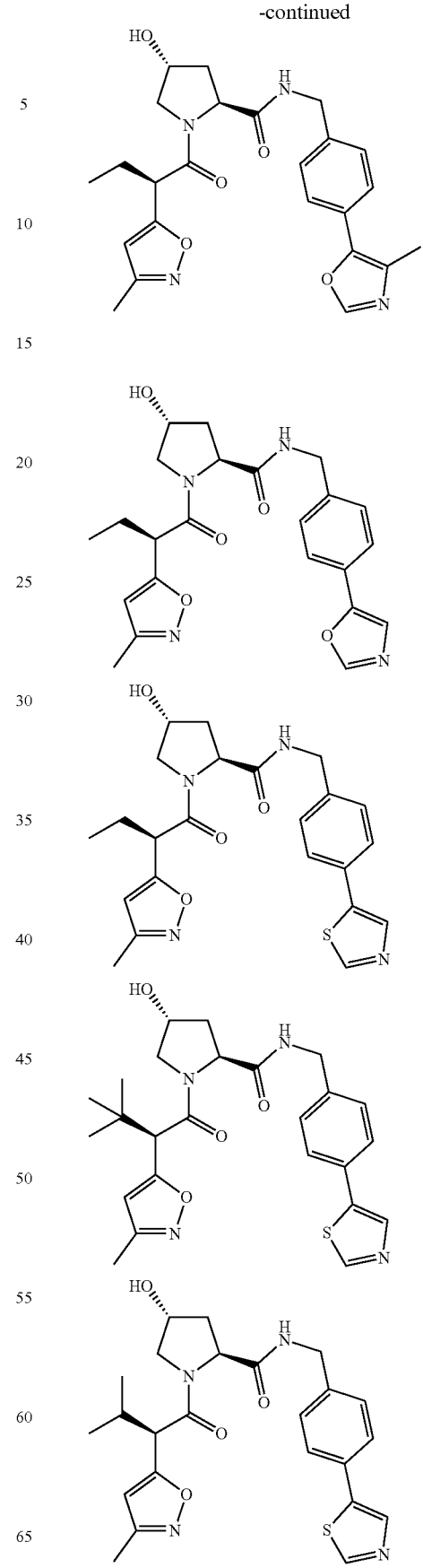

273
-continued
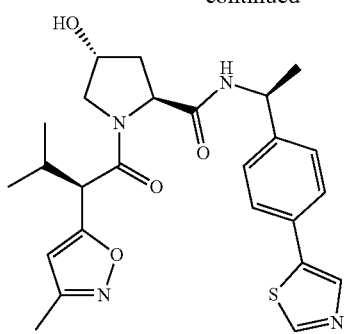
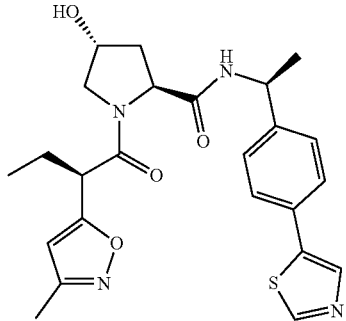
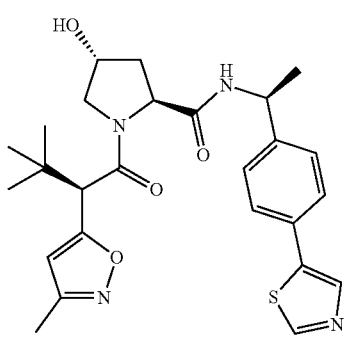
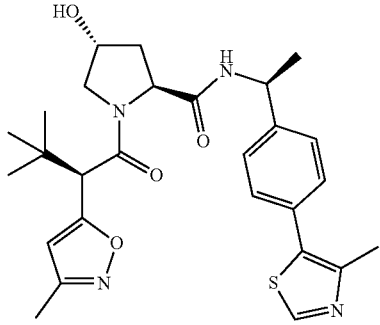
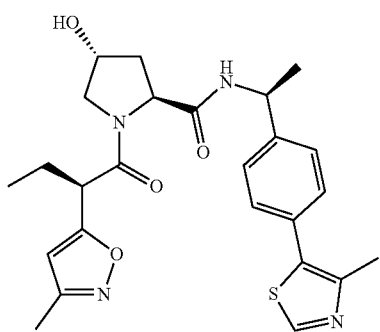
274
-continued
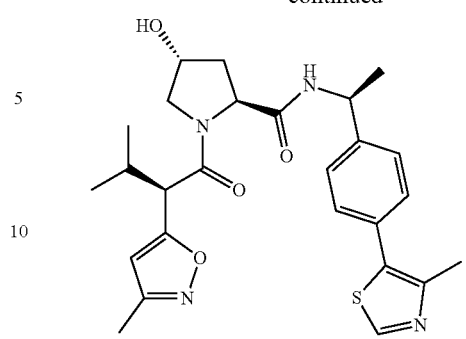
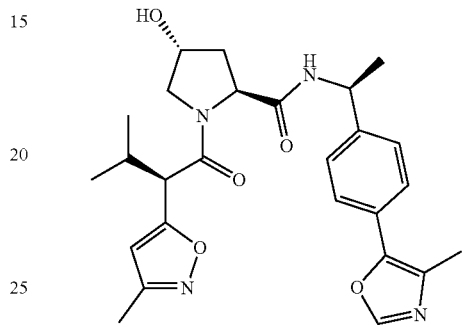
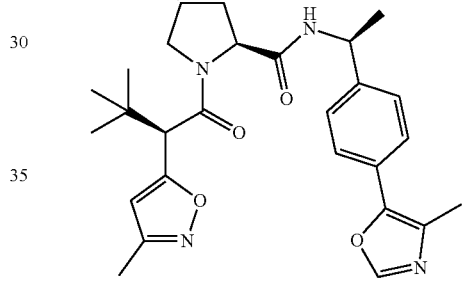
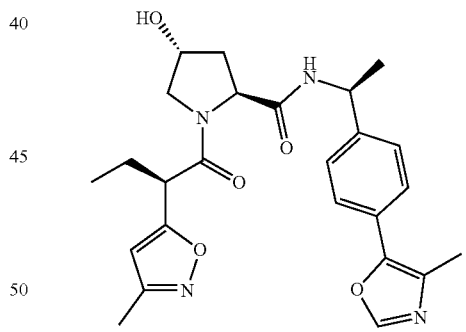
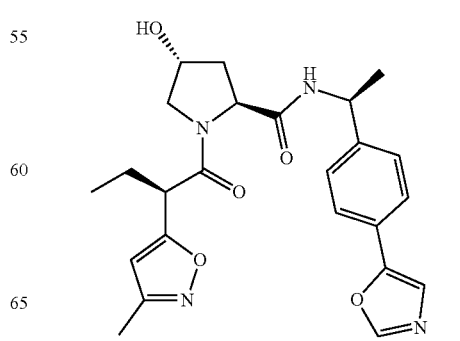

275
-continued
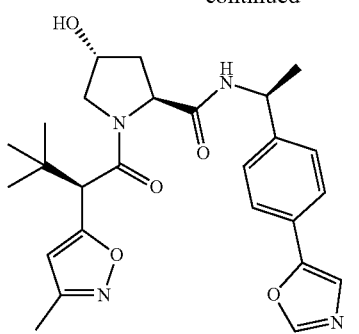
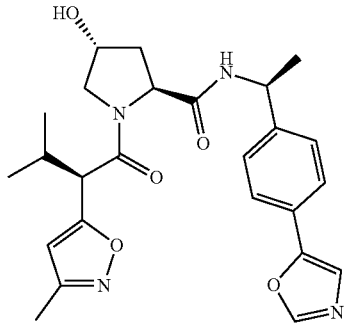
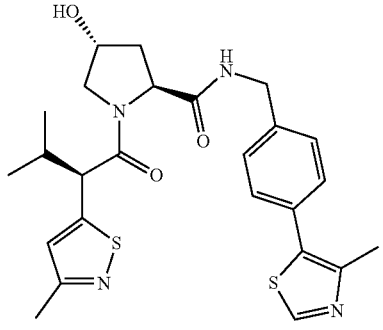
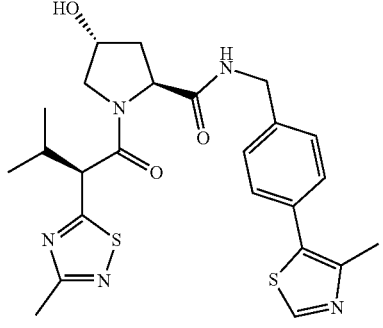
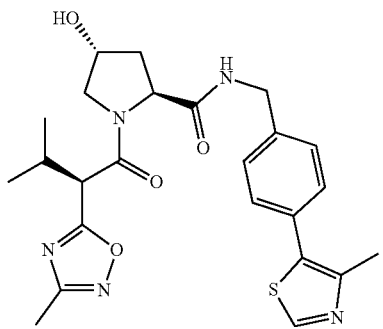
276
-continued
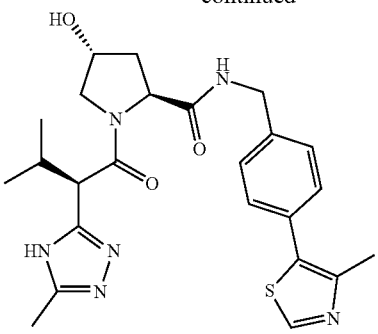
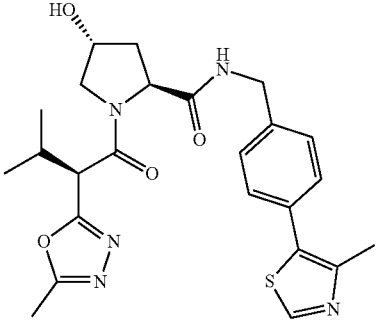
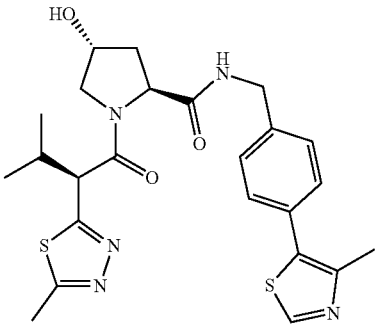
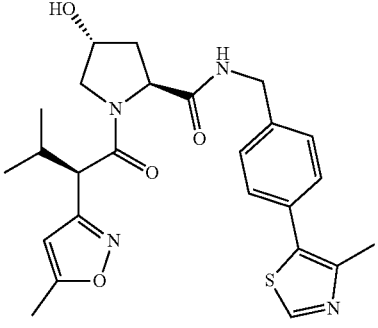
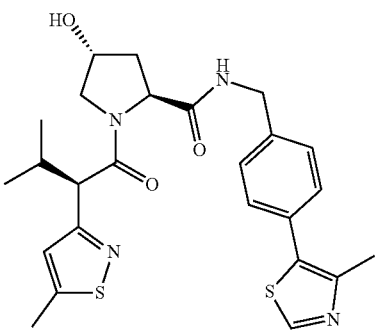

277
-continued
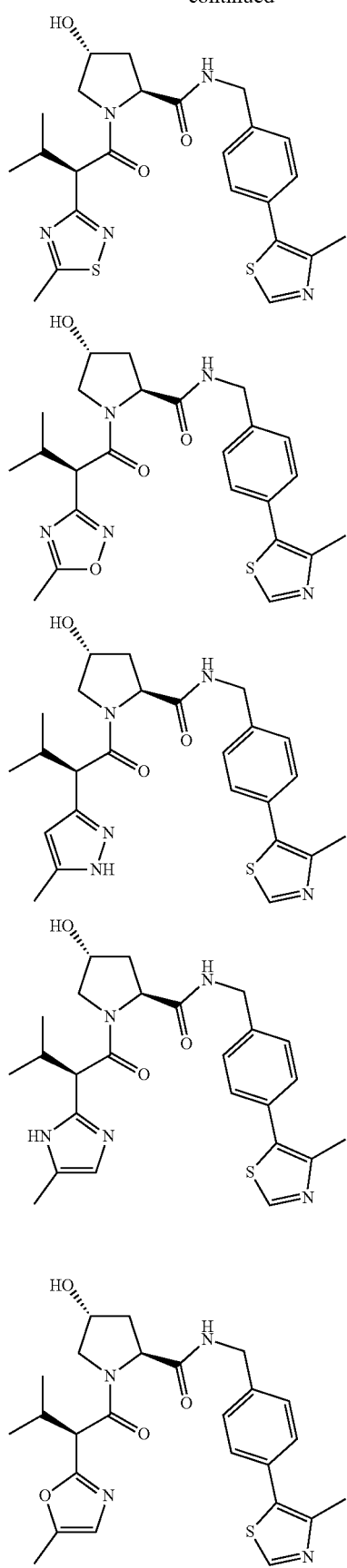
278
-continued
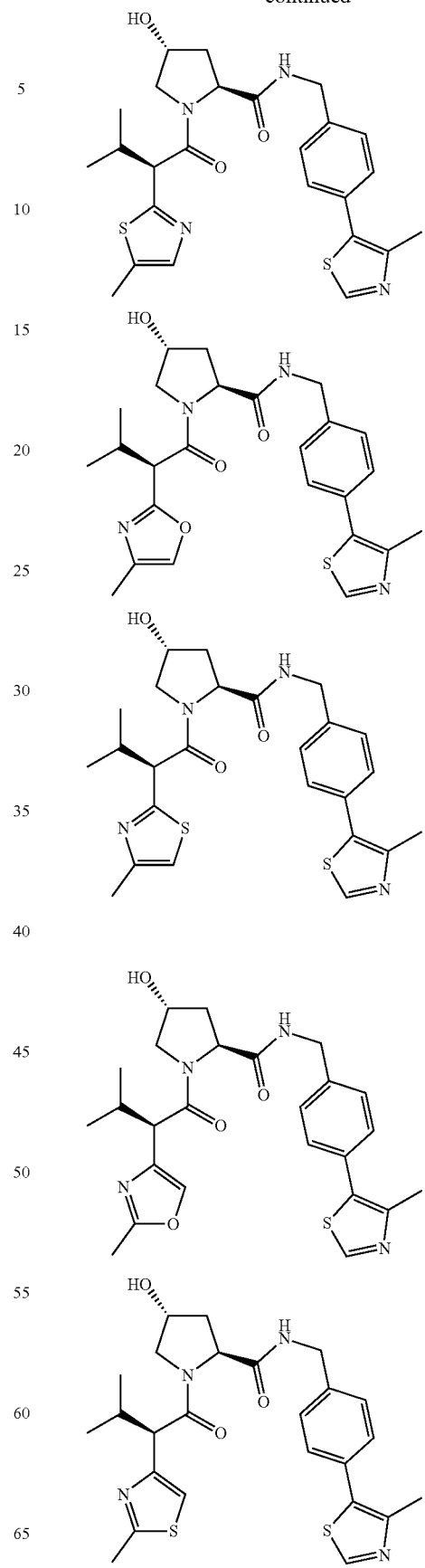

279
-continued
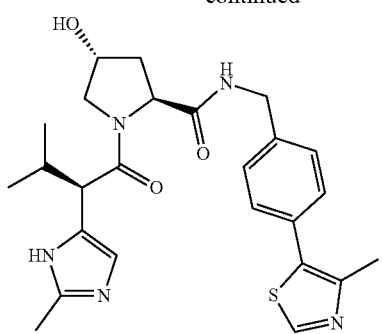
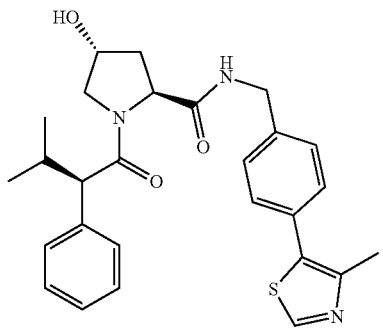
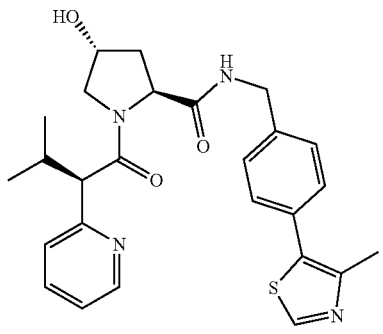
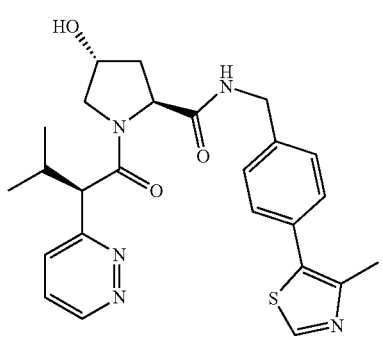
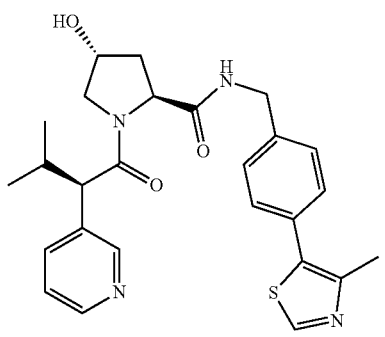
280
-continued
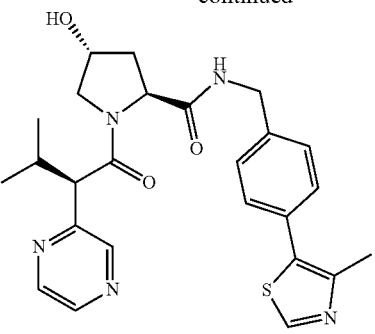
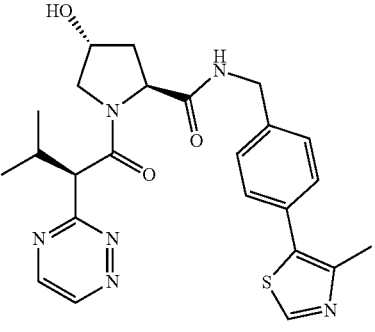
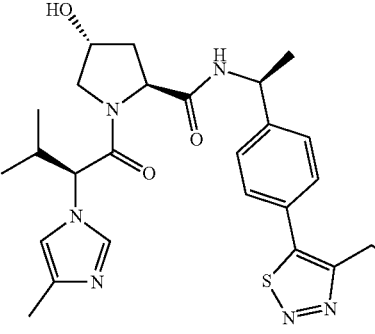
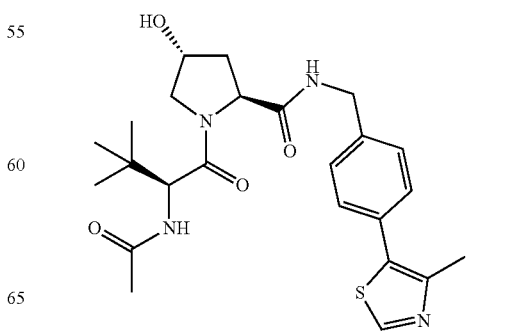

281
-continued
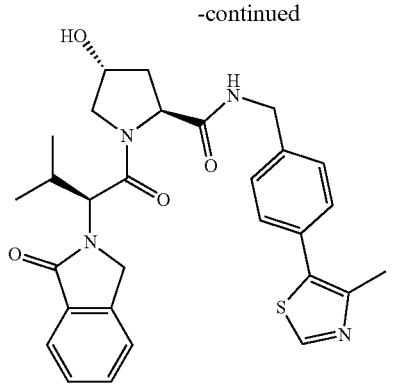
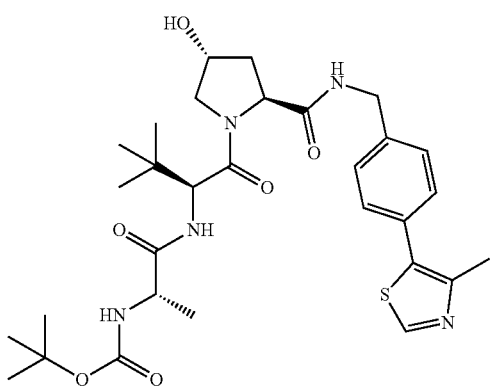
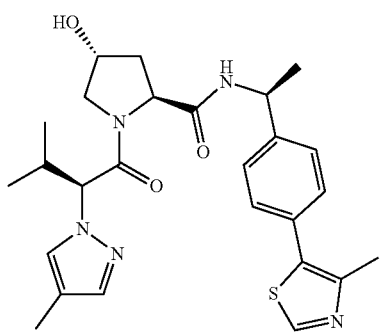
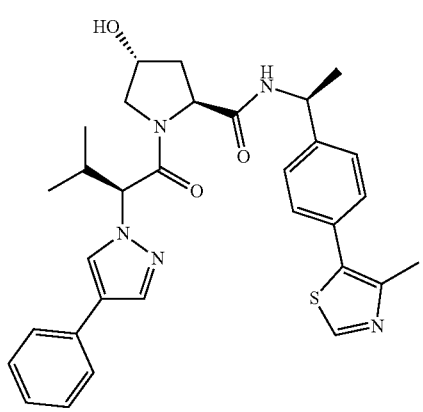
282
-continued
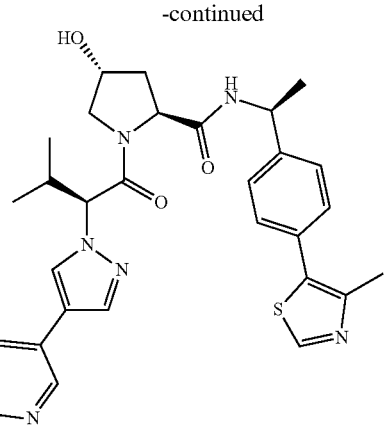
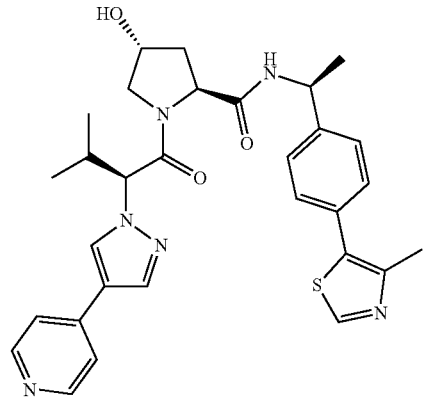
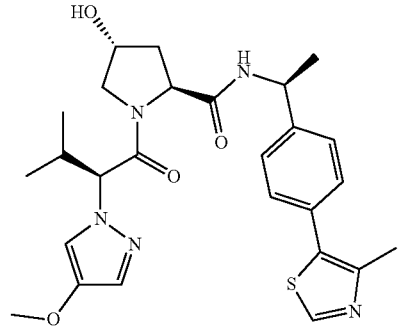
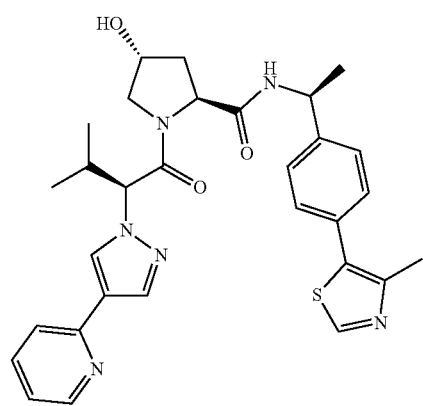

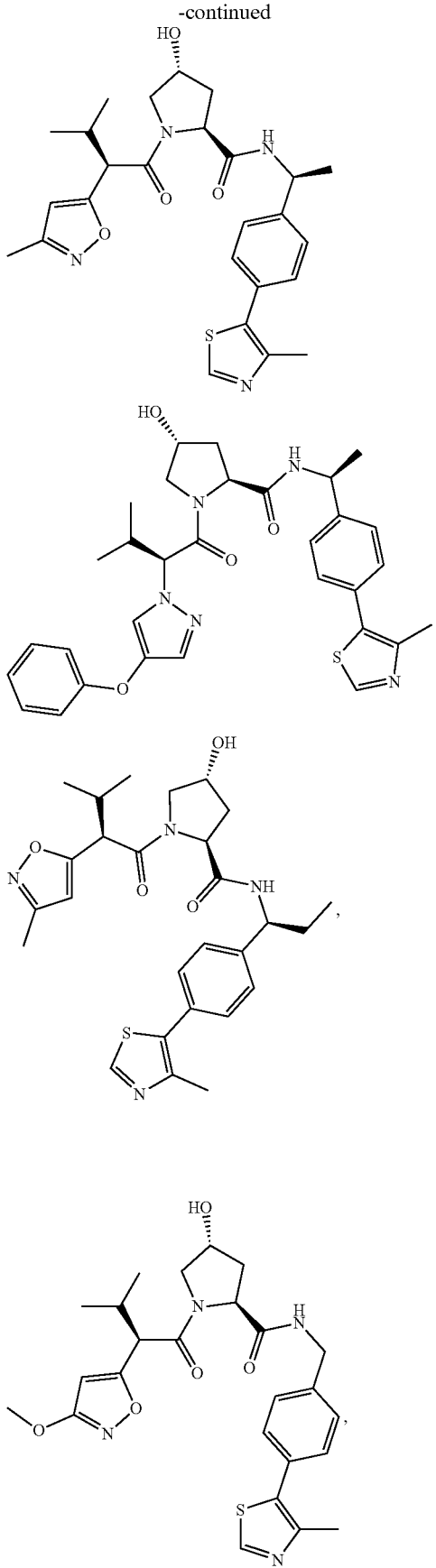

wherein the VLM may be connected to a PTM via a linker, as described herein, at any appropriate location, including, e.g., an aryl, heteroaryl, phenyl, or phenyl of an indole group, optionally via any appropriate functional group, such as an amine, ester, ether, alkyl, or alkoxy.

Linkers (L)

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A_1 \ldots (A^L)_q-$ or $-(A^L)_q-$), wherein $A^L_1$ is a group coupled to PTM, and $(A^L)_q$ is a group coupled to ULM.

In any embodiment or embodiment described herein, the linker group L is a bond or a chemical linker group represented by the formula $-(A^L)_q-$, wherein A is a chemical moiety and q is an integer from 1-100, and wherein L is covalently bound to the PTM and the ULM, and provides for sufficient binding of the PTM to the protein target and the ULM to an E3 ubiquitin ligase to result in target protein ubiquitination.

In certain embodiments, the linker group L is $-(A^L)_q-$, wherein:

$(A^L)_q$ is a group which is connected to at least one of a ULM (such as a CLM or a VLM), PTM moiety, or a combination thereof;

q of the linker is an integer greater than or equal to 1;

at each occurrence $A^L$ is independently selected from the group consisting of, a bond, $CR^{L1}R^{L2}$, O, S, SO, $SO_2$, $NR^u$, $SO_2NR^{L3}$, $SONR^{13}$, $CONR^{13}$, $NR^{L3}CONR^{L4}$, $NR^{L3}SO_2NR^{L4}$, CO, $CR^{L1}=CR^{L2}$, C≡C, $SiR^{L1}R^{L2}$, P(=O)R$^{L1}$, P(=O)OR$^{11}$, NR$^{L3}$C(=NCN)NR$^u$, NR$^{L3}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{5-13}$ spirocycloalkyl optionally substituted with 0-9 R$^{L1}$ and/or R$^{L2}$ groups, C$_{3-11}$heterocyclyl optionally substituted with 0-6 R$^{L1}$ and/or R$^{L2}$ groups, C$_{5-13}$ spiroheterocycloalkyl optionally substituted with 0-8 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and at each occurrence R$^{L1}$, R$^{L2}$, R$^u$, R$^{L4}$ and R$^{L5}$ are, each independently, H, halogen, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(=O)(OC$_{1-8}$alkyl)(C$_{1-8}$alkyl), P(=O)(OC$_{1-8}$alkyl)$_2$, C≡C—C$_{1-8}$alkyl, C=CH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NHSO$_2$NH(C$_{1-8}$alkyl), NH SO$_2$N(C$_{1-8}$alkyl)$_2$, NHSO$_2$NH$_2$.

In certain embodiments, q of the linker is an integer greater than or equal to 0. In certain embodiments, q is an integer greater than or equal to 1.

In certain embodiments, e.g., where q of the linker is greater than 2, (A$^L$)$_q$ is a group which is connected to ULM, and Ai and (A$^L$)$_q$ are connected via structural units of the linker (L).

In certain embodiments, e.g., where q of the linker is 2, (A$^L$)$_q$ is a group which is connected to A$^L_1$ and to a ULM.

In certain embodiments, e.g., where q of the linker is 1, the structure of the linker group L is -A$^L_1$-, and A$^L_1$ is a group which is connected to a ULM moiety and a PTM moiety.

In certain embodiments, the linker (L) comprises a group represented by a general structure selected from the group consisting of: —NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cycloalkyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-ArylO—CH$_2$—, —NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$—, —NR(CH$_2$CH$_2$O)$_n$-(cyclo alkyl)-O-ArylO—CH$_2$—, —NR(CH$_2$CH$_2$O)$_n$-(lower alkyl)-NH-ArylO—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocycle)-CH$_2$—NR(CH$_2$CH$_2$)$_n$-(heterocycle)-(heterocycle)-CH$_2$, —N(R$_1$R$_2$)-(heterocycle)-CH$_2$; wherein at each occurrence n of the linker is independently a whole number from 0 to 10;

R of the linker is H or lower alkyl;

R$_1$ and R$_2$ of the linker optionally form a ring with the connecting N.

In various embodiments, the linker includes a group selected from:

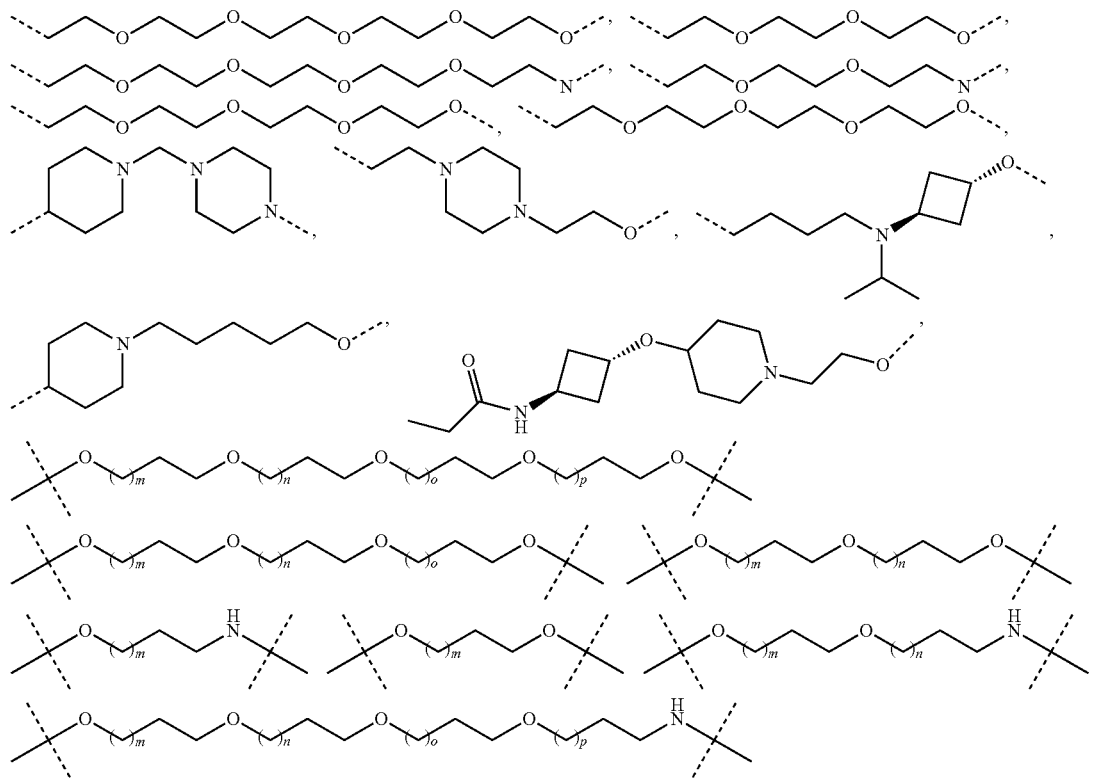

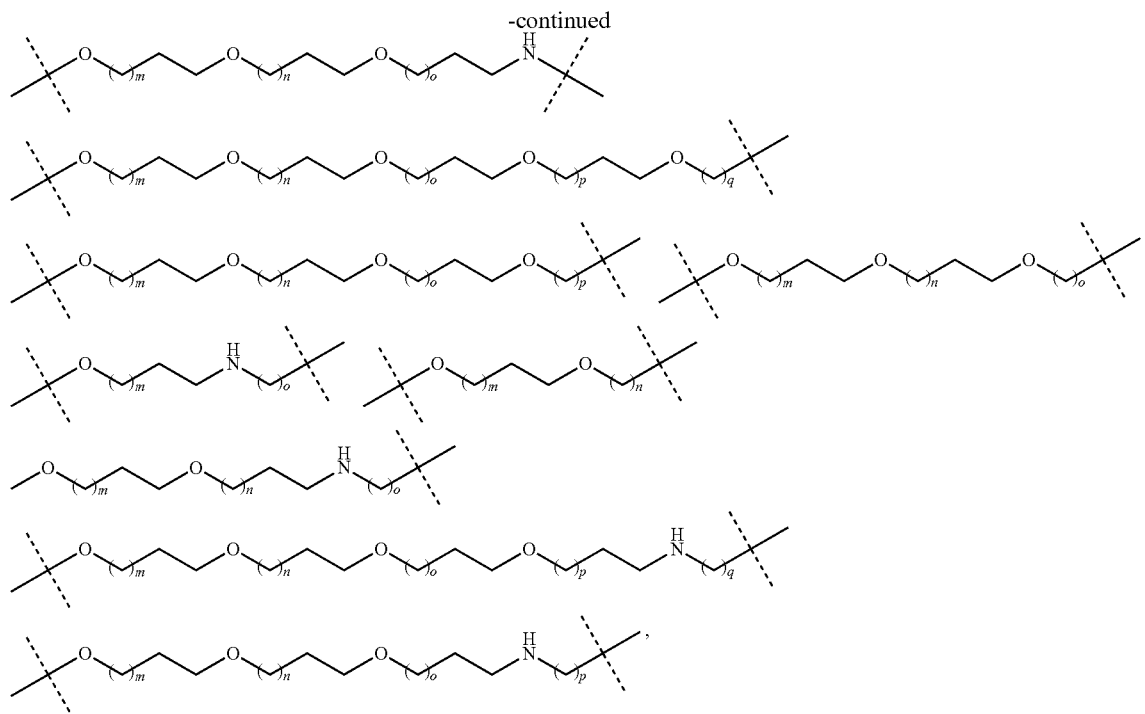

wherein at each occurrence m, n, o, p, and q are independently selected from 0, 1, 2, 3, 4, 5, 6, 7, 8, 9, 10, 11, 12, 13, 14, 15, 16, 17, 18, 19, or 20.

In certain embodiments, the linker (L) comprises a group represented by a general structure selected from the group consisting of: —N(R)—(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—, —O—(CH$_2$)$_m$—O(CH$_2$)$_n$—O(CH$_2$)$_o$—O(CH$_2$)$_p$—O(CH$_2$)$_q$—O(CH$_2$)$_r$OCH$_2$—, —O—(CH$_2$)$_m$—O(CH$_2$)$_n$—O(CH$_2$)$_o$—O(CH$_2$)$_p$—O(CH$_2$)$_q$—O(CH$_2$)$_r$—O—, —N(R)—(CH$_2$)$_m$O(CH$_2$)$_n$—O(CH$_2$)$_o$—O(CH$_2$)$_p$—O(CH$_2$)$_q$—O(CH$_2$)$_r$O—, —(CH$_2$)$_m$—O(CH$_2$)$_n$—O(CH$_2$)$_o$—O(CH$_2$)$_p$—O(CH$_2$)$_q$—O(CH$_2$)$_r$—O—, —(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—,

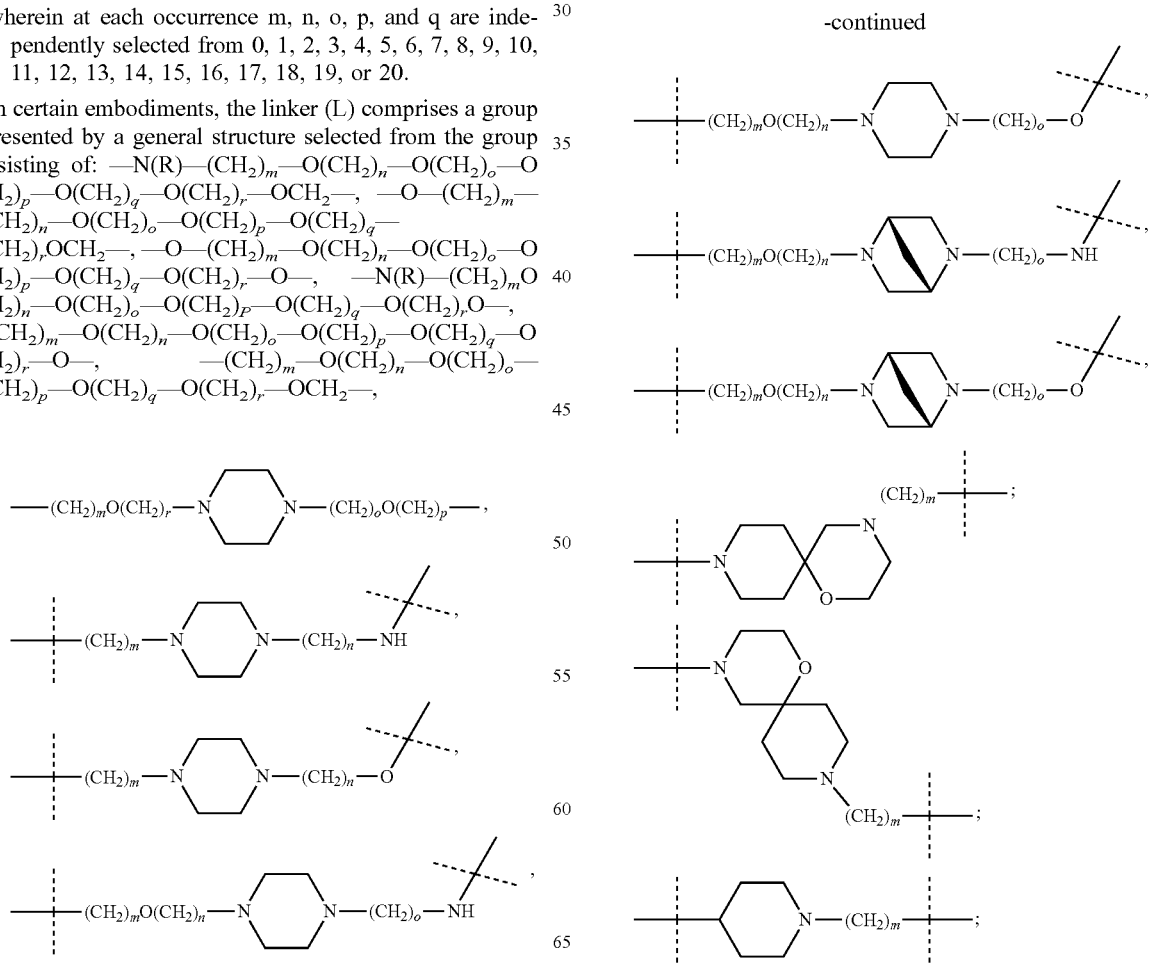

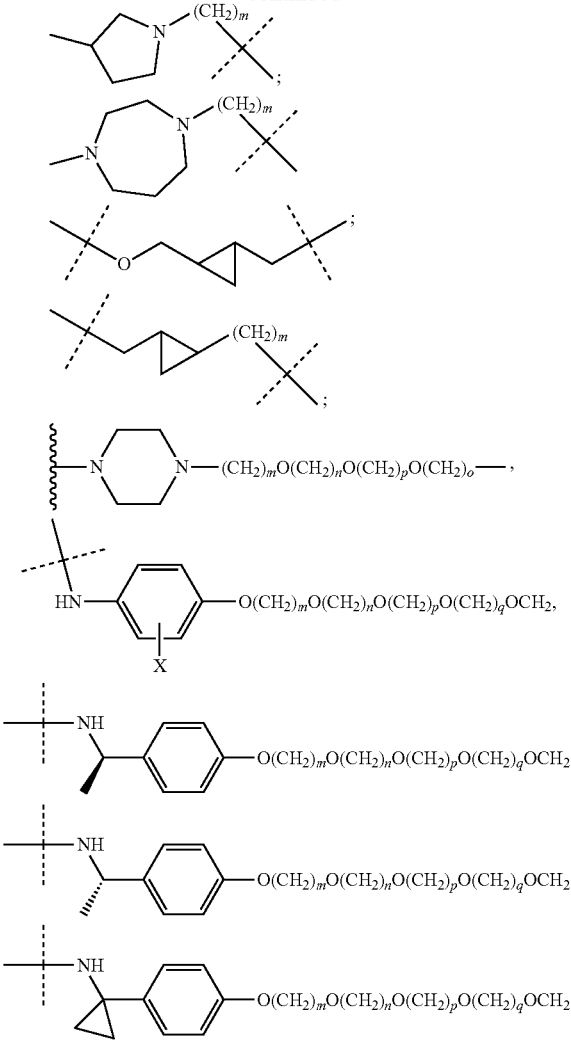

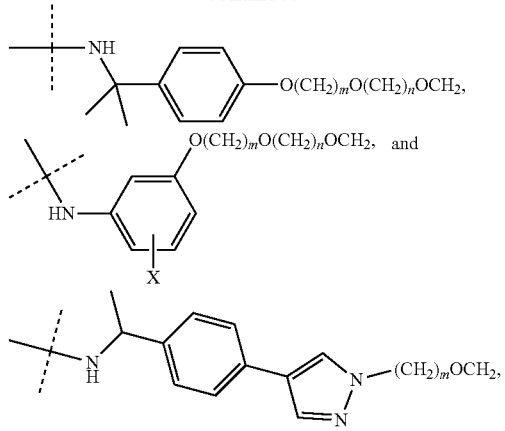

wherein
at each occurrence m, n, o, p, q, and r of the linker are independently 0, 1, 2, 3, 4, 5, 6, 7, 8, 9, 10, 11, 12, 13, 14, 15, 16, 17, 18, 19, 20;
when m, n, o, p, q, and r or zero, there is no N—O or $C_1$-$C_6$ bond;
at each occurrence R of the linker is selected from H, methyl, and ethyl;
at each occurrence X of the linker is selected from H and F.

In various embodiments,

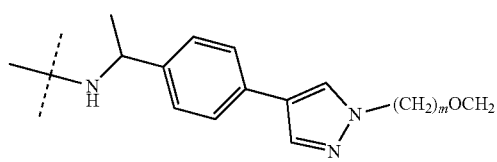

where m of the linker can be 2, 3, 4, 5.

In various embodiments, the linker includes a group selected from:

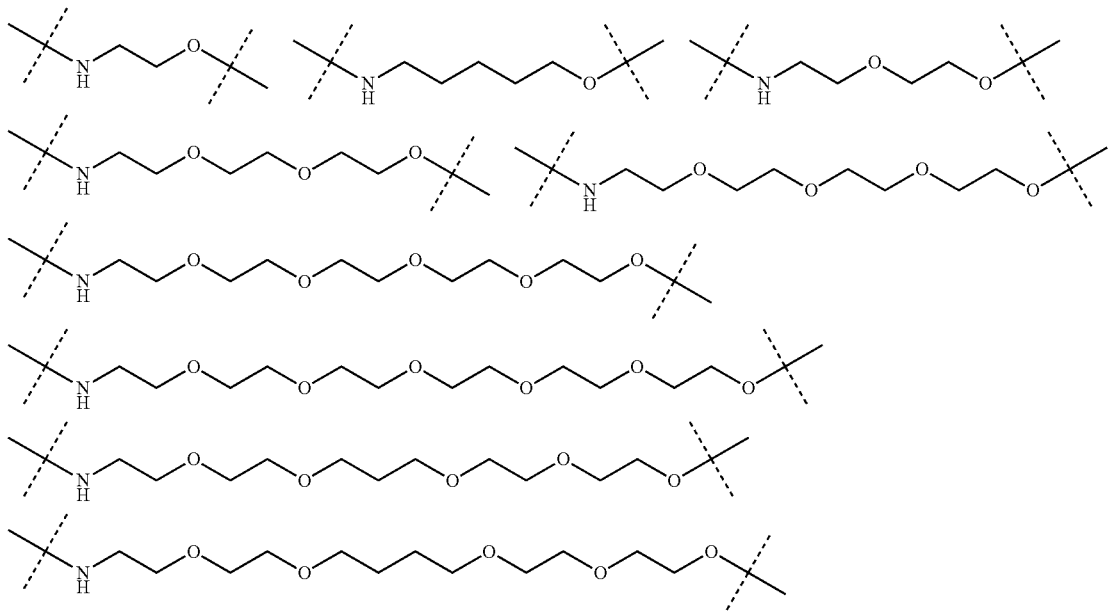

291 292
-continued
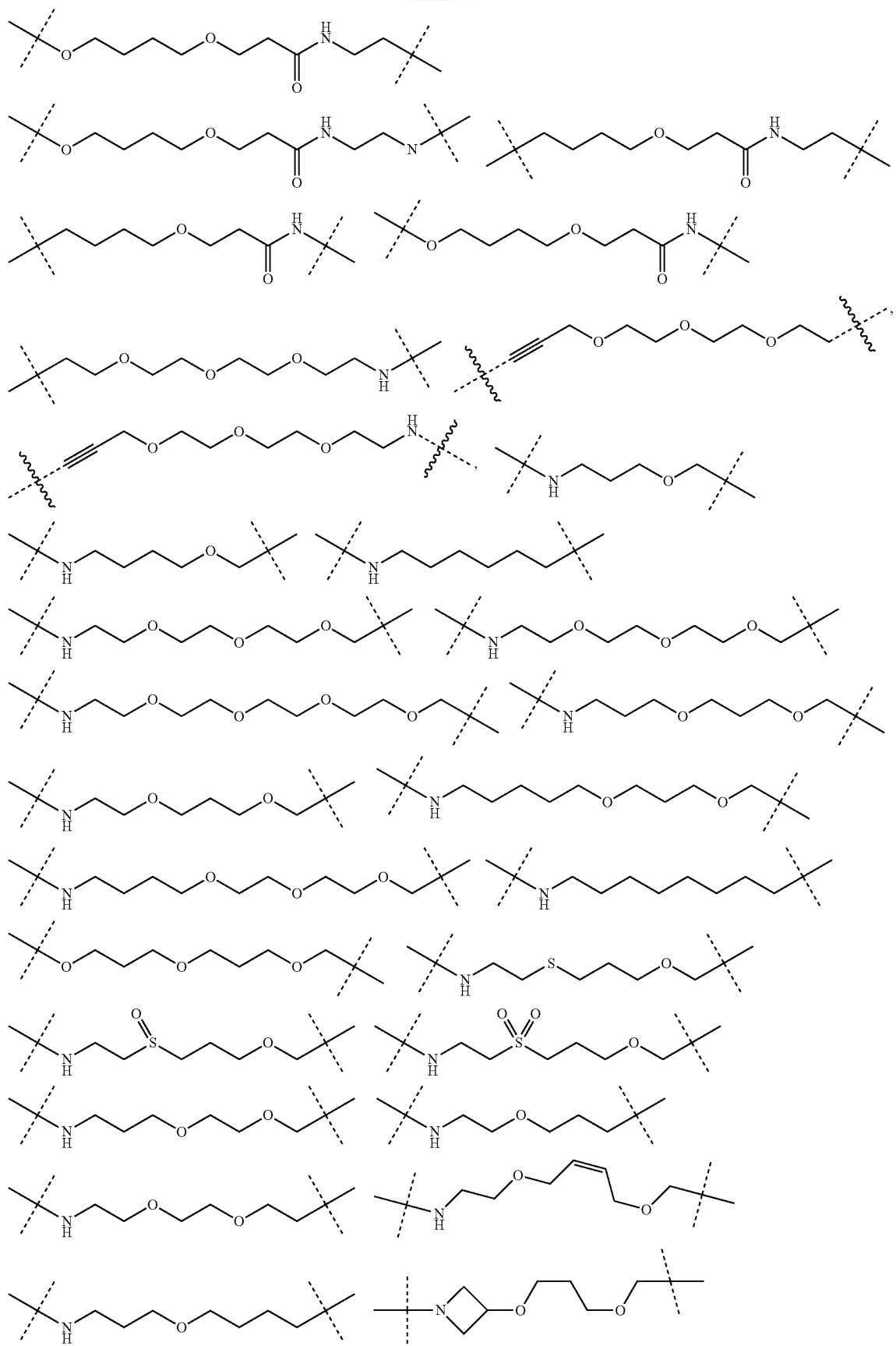

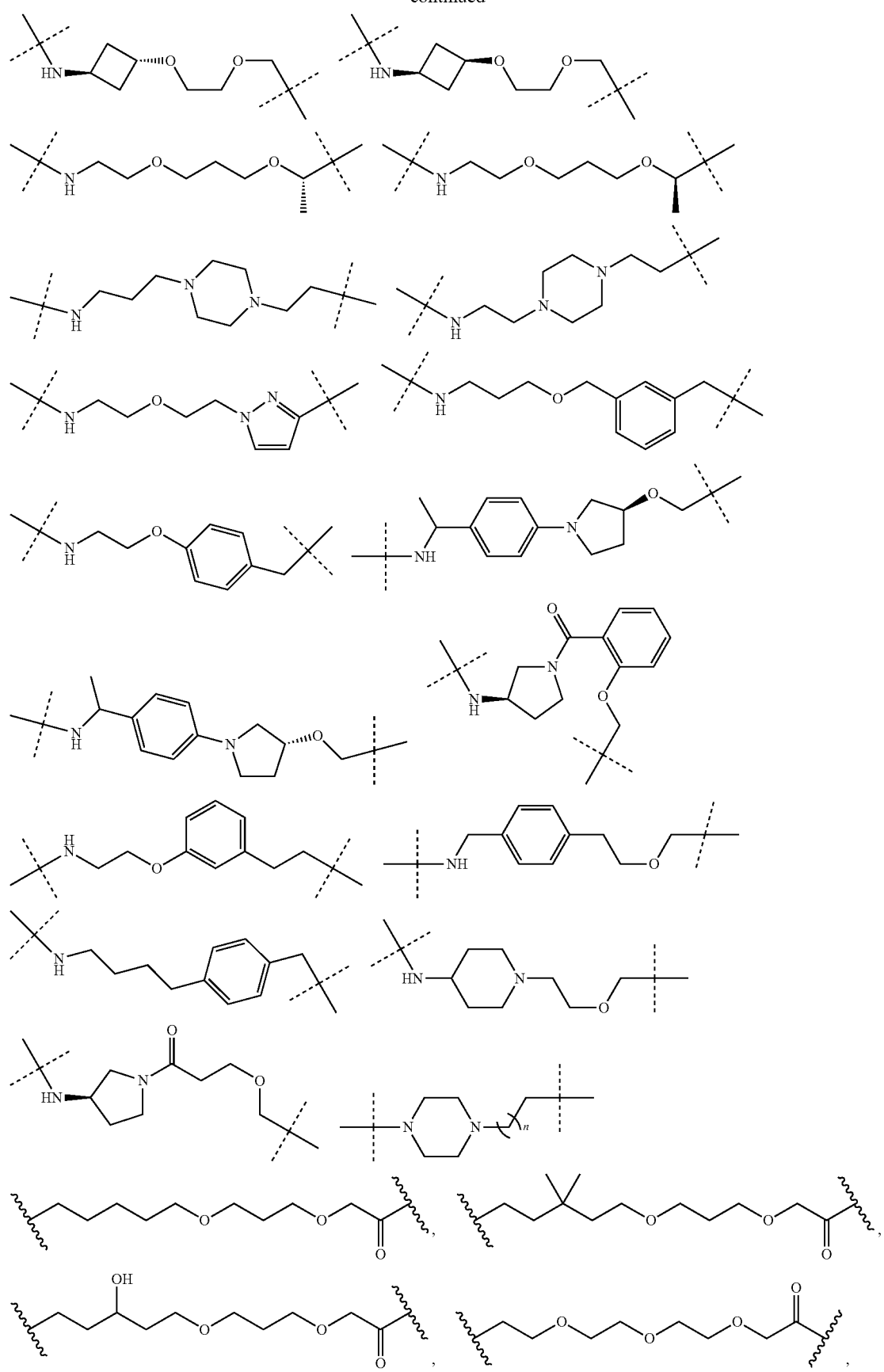

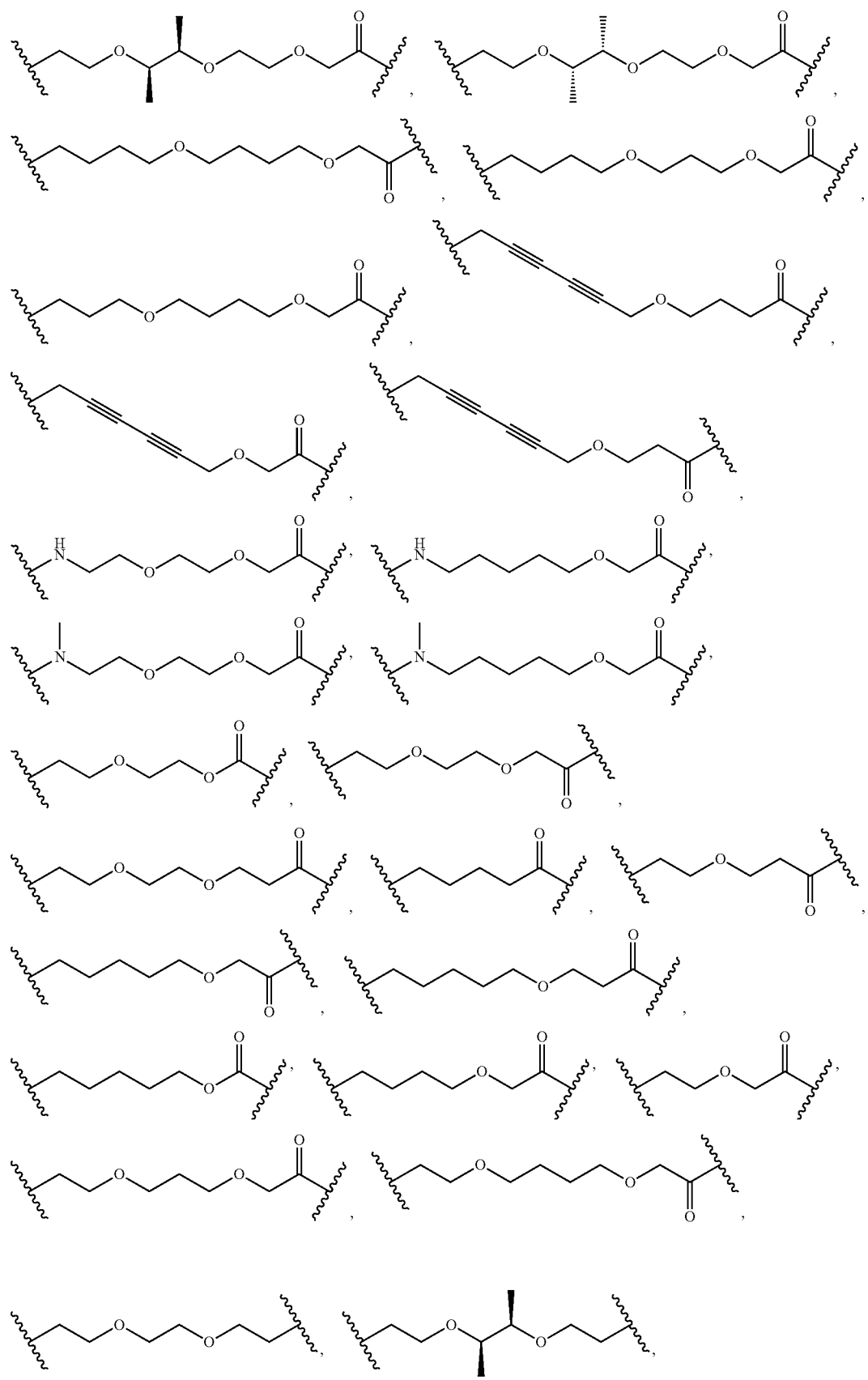

-continued
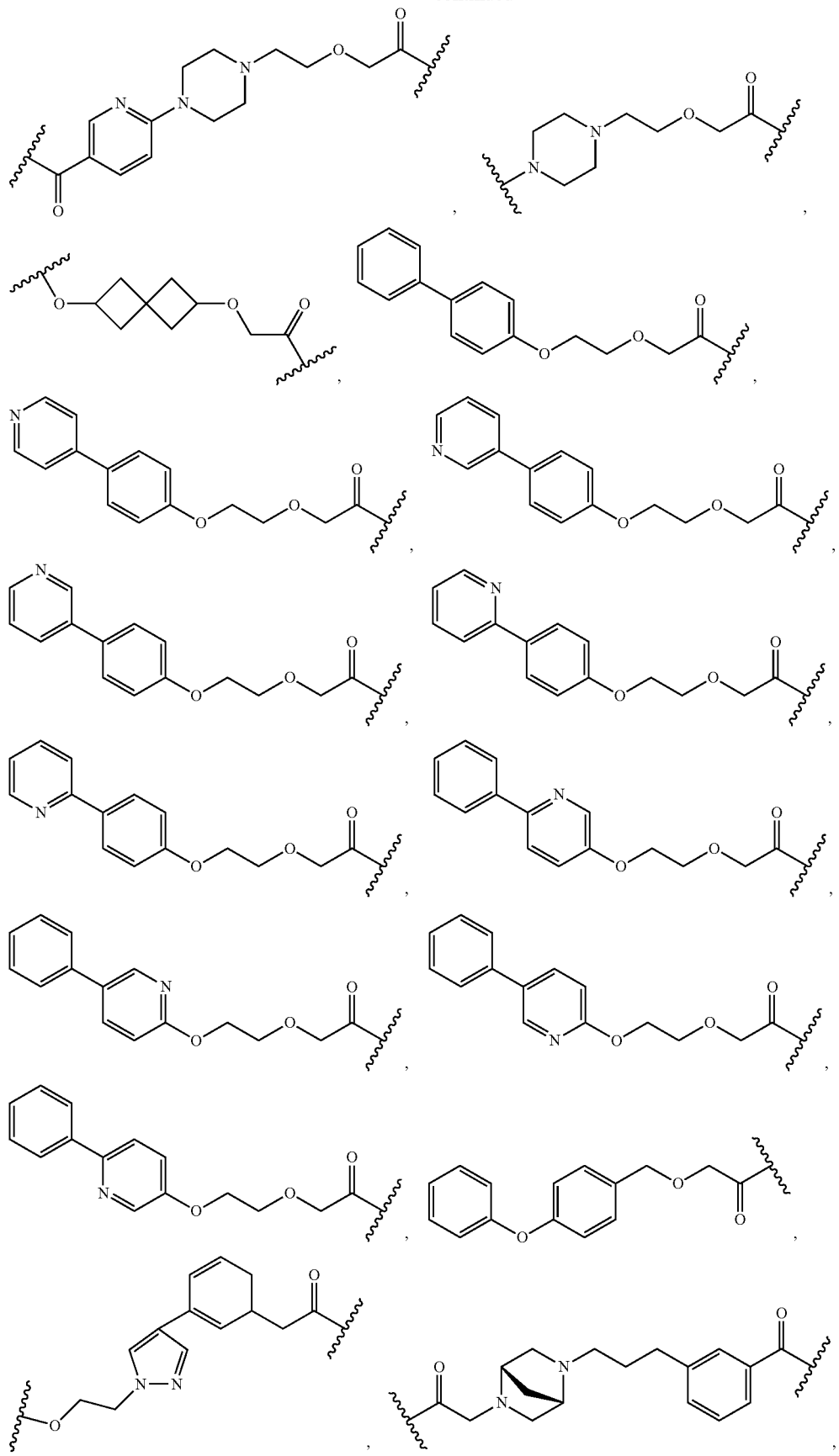

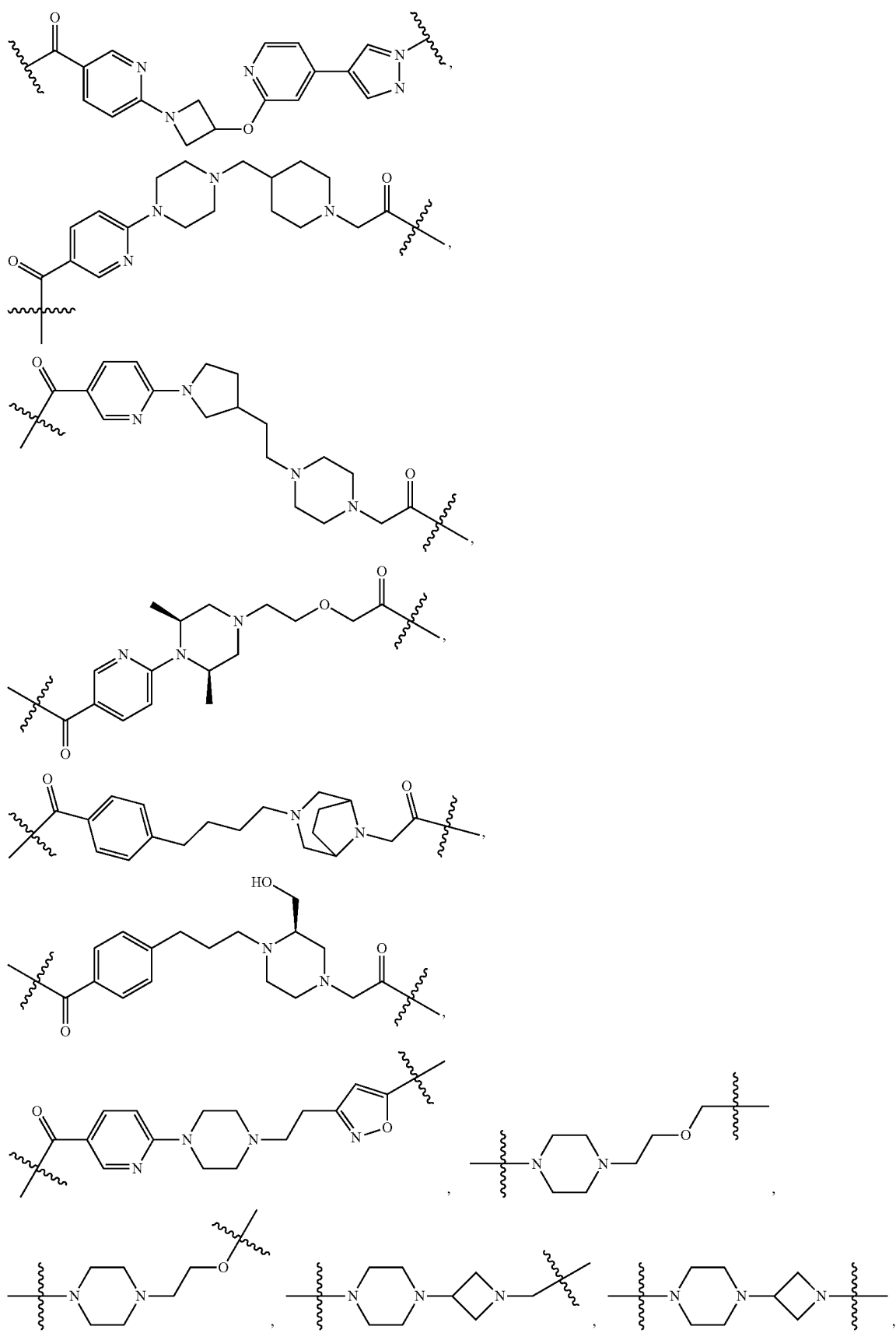

-continued
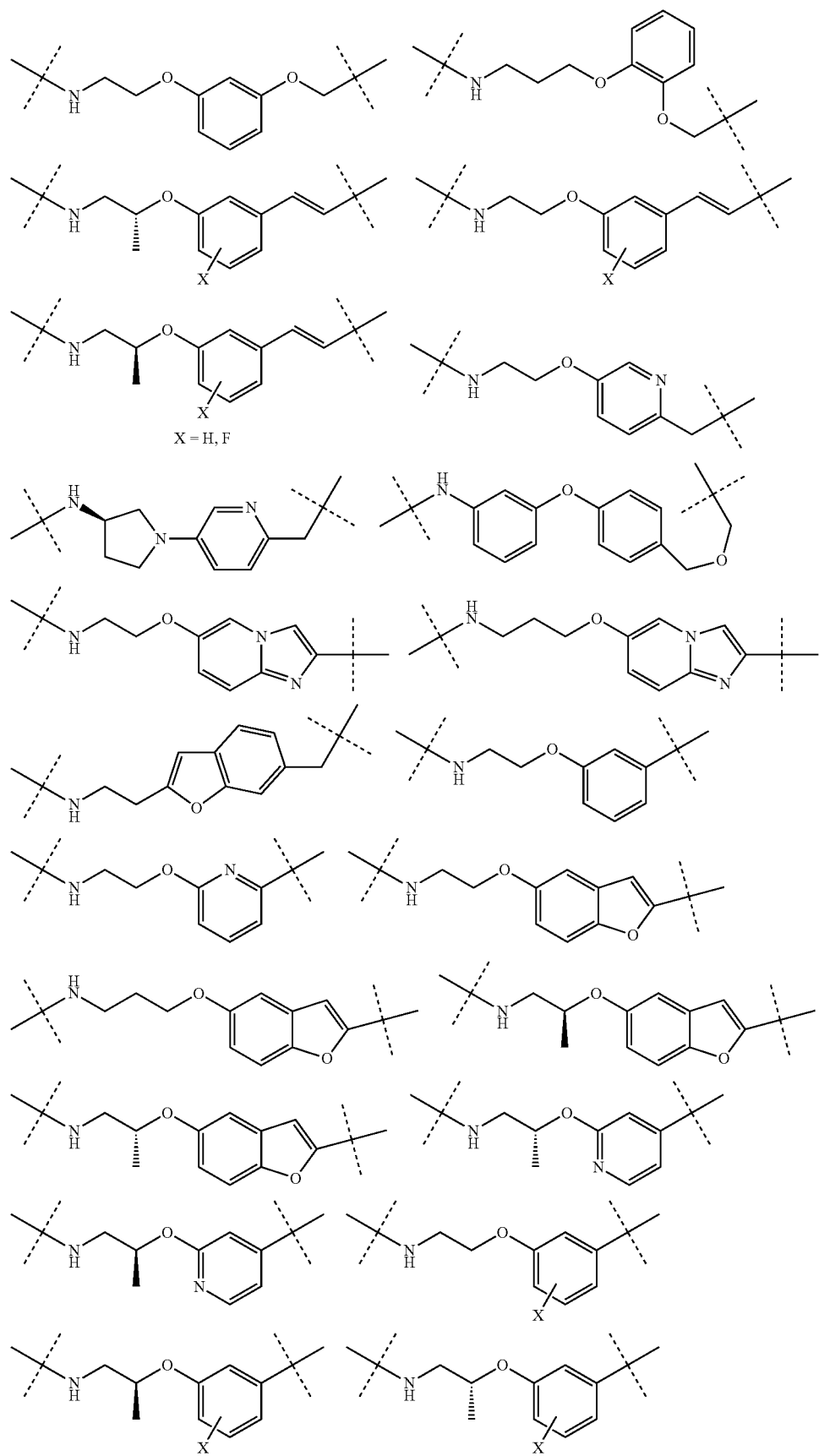

303
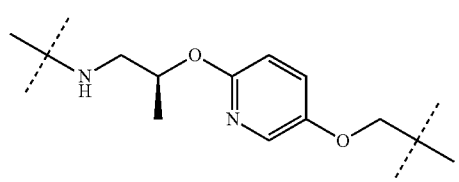
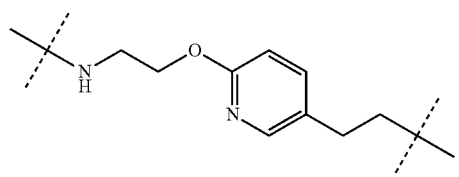
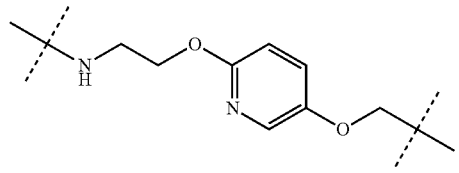
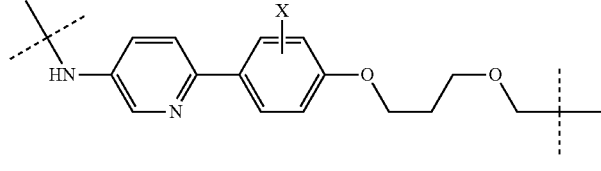
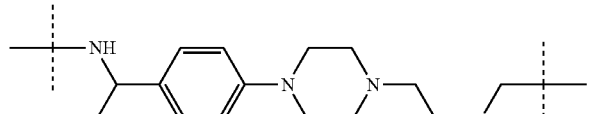
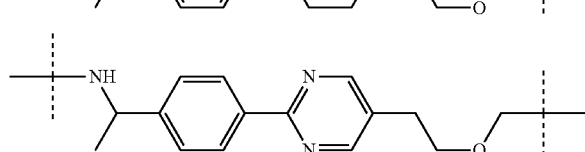
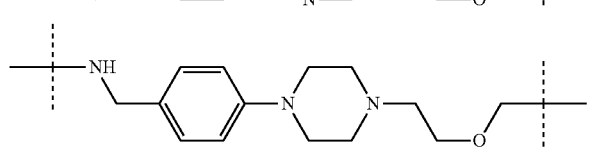
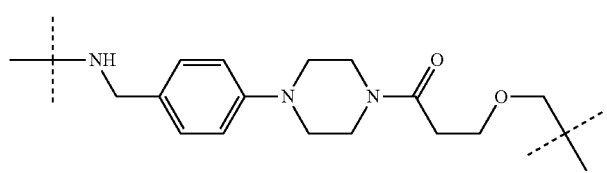
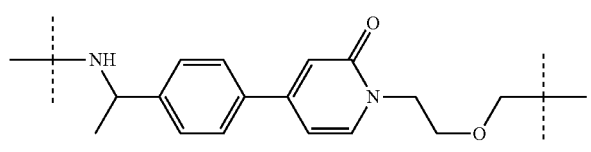
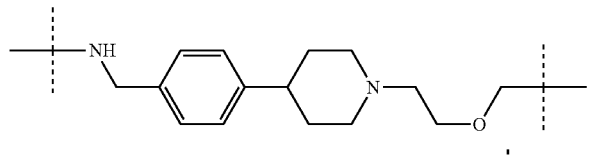
304
-continued
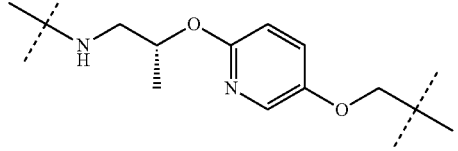
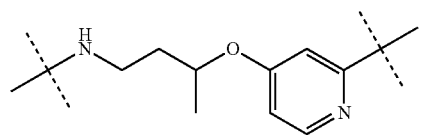
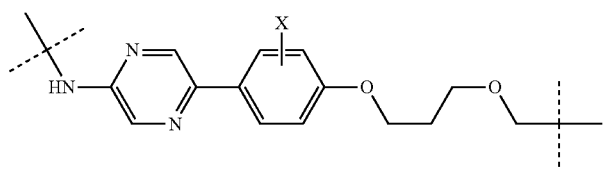
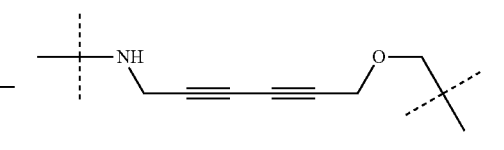
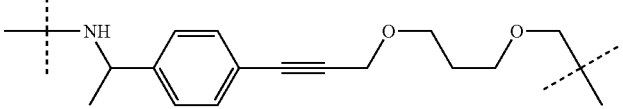

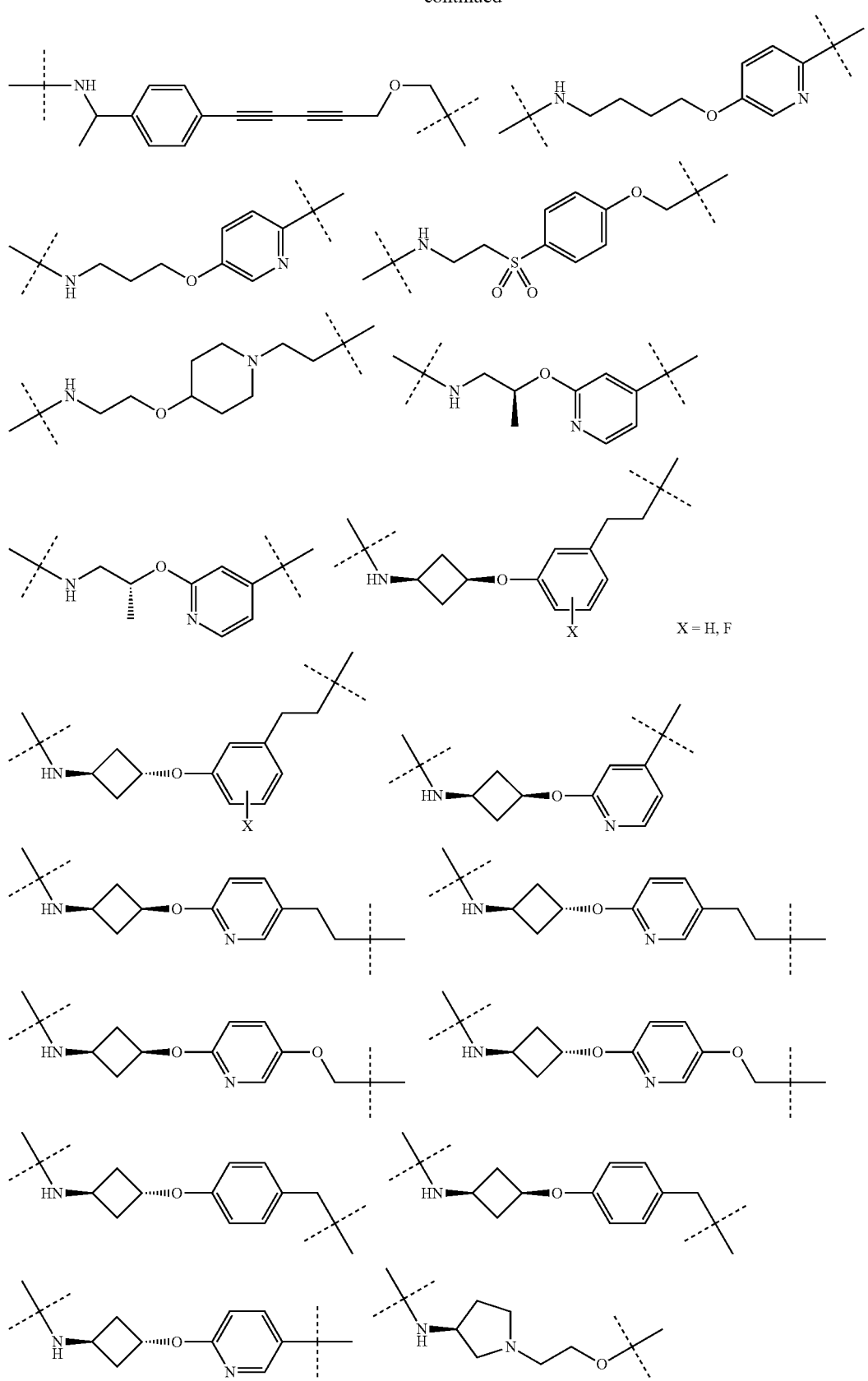

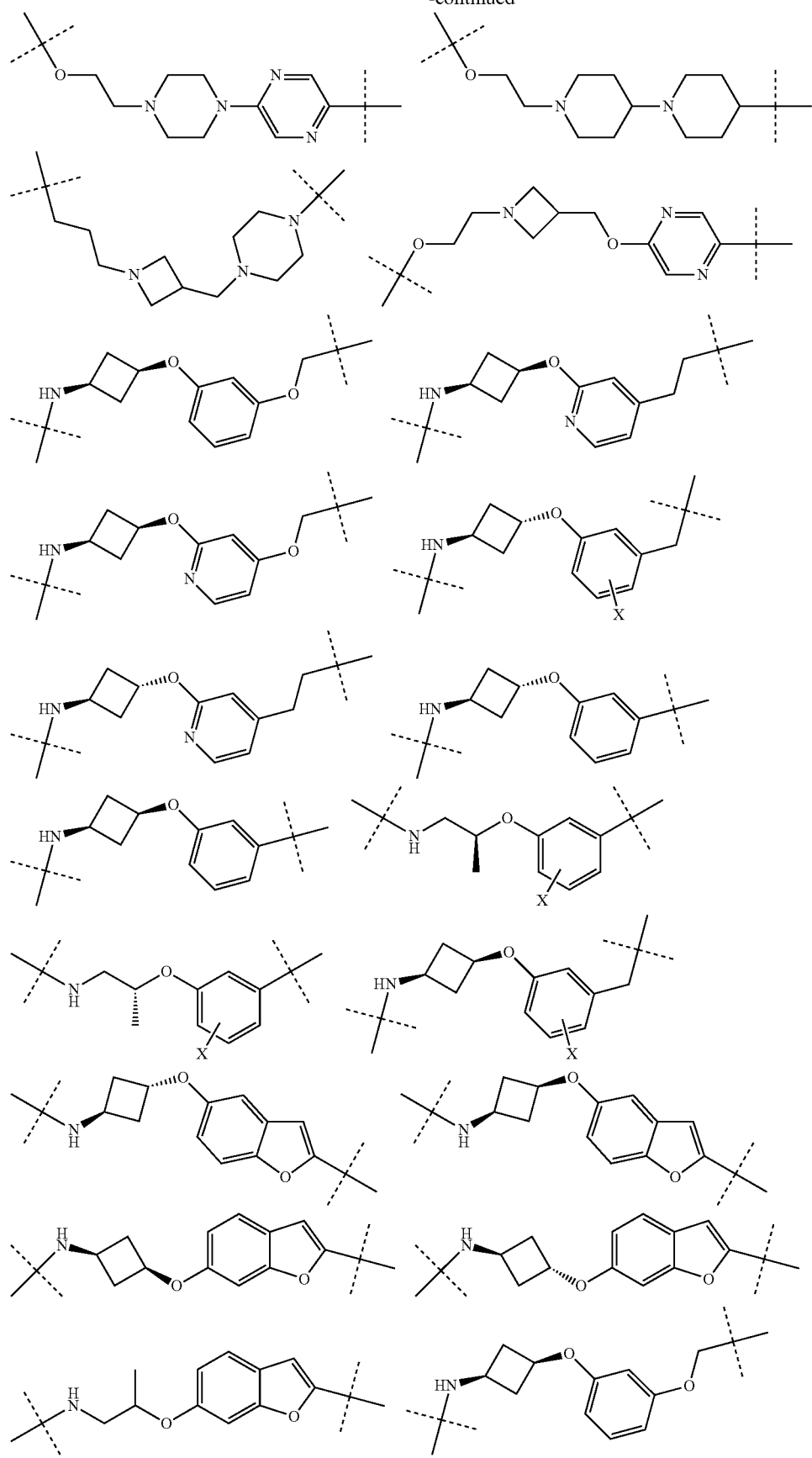

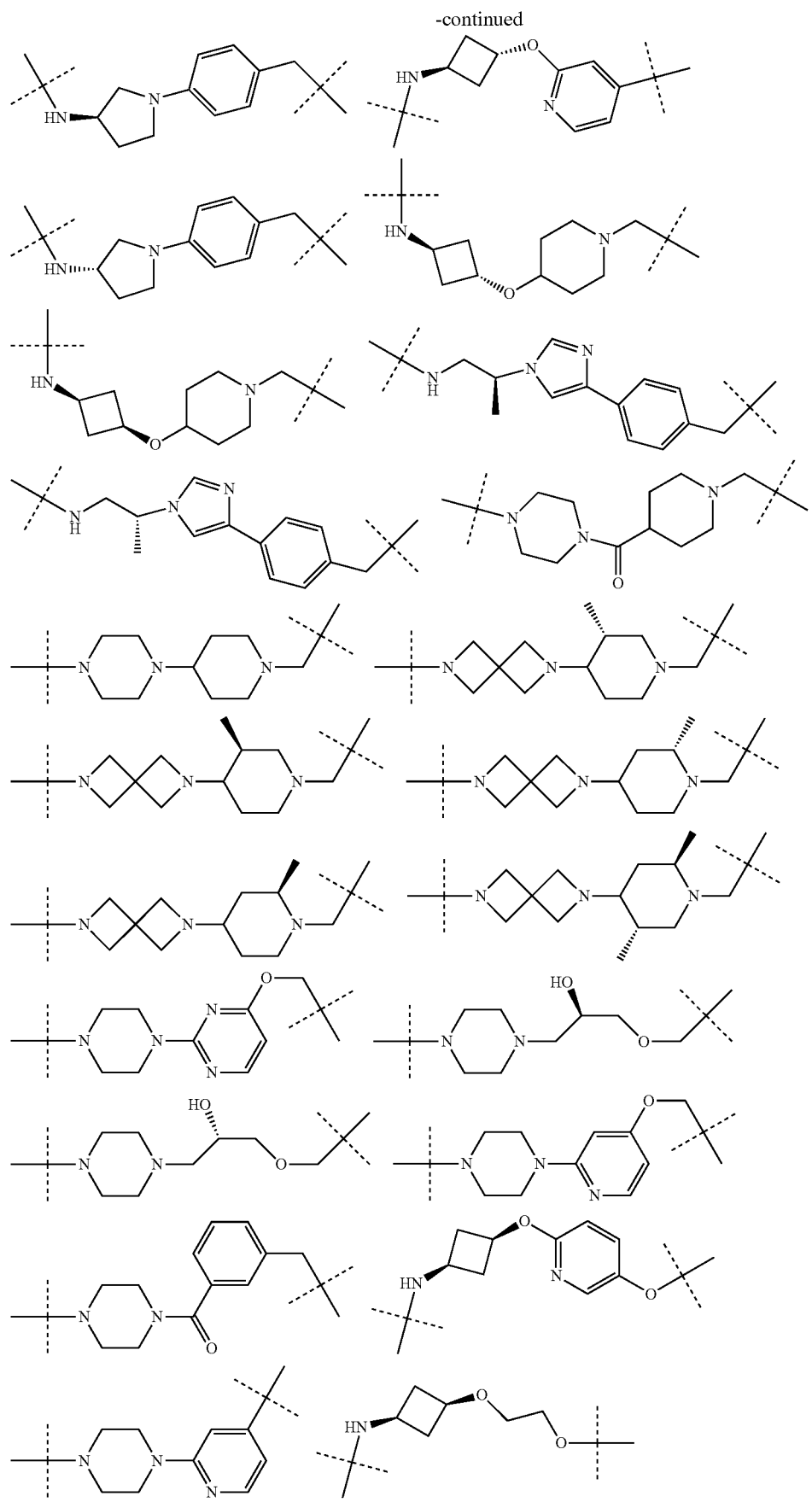

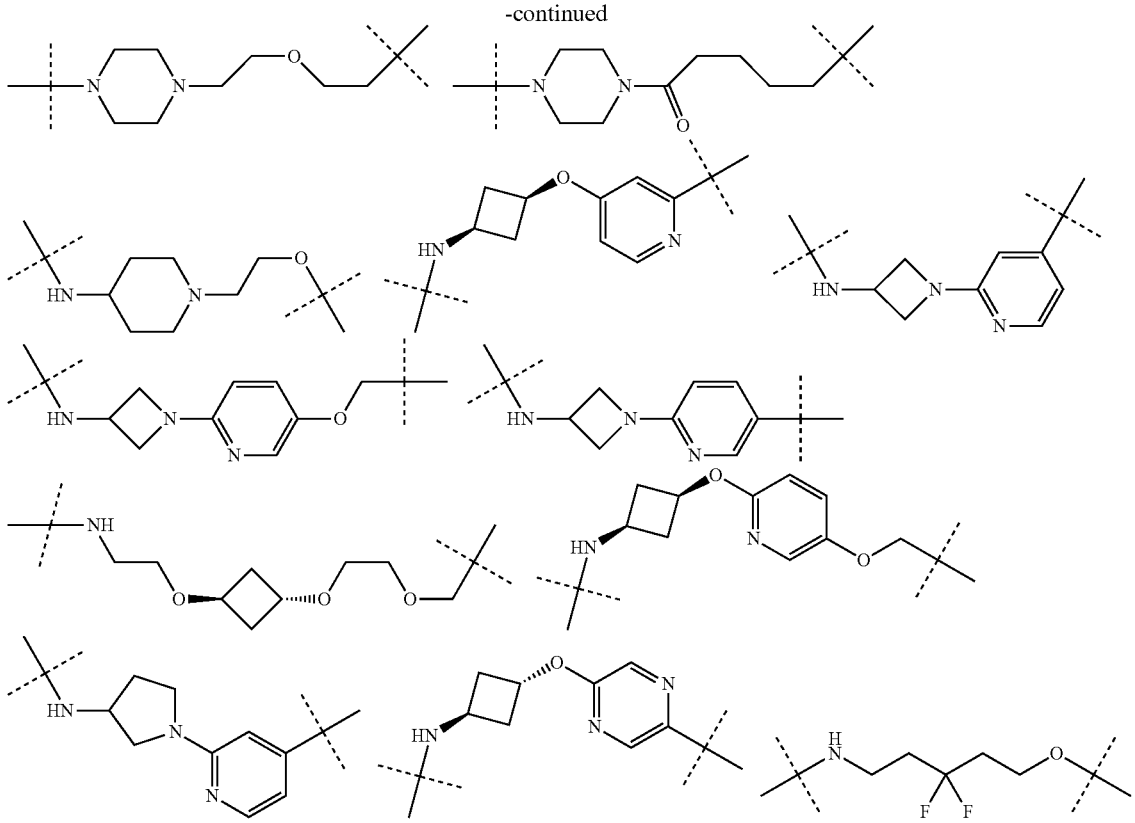

wherein at each occurrence m, n, o, p, q, and r of the linker are independently 0, 1, 2, 3, 4, 5, 6, 7, 8, 9, 10, 11, 12, 13, 14, 15, 16, 17, 18, 19, 20;

wherein when m, n, o, p, q, and r or zero, there is no N—O or O—O bond at each occurrence R of the linker is selected from H, methyl, and ethyl;

at each occurrence X of the linker is selected from H and F.

In various embodiments, the linker is

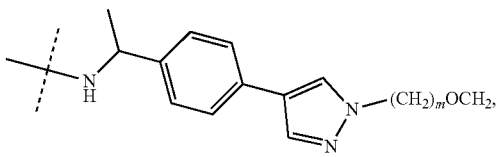

wherein m is 2, 3, 4, or 5.

In various embodiments, the linker (L) is selected from the group consisting of:

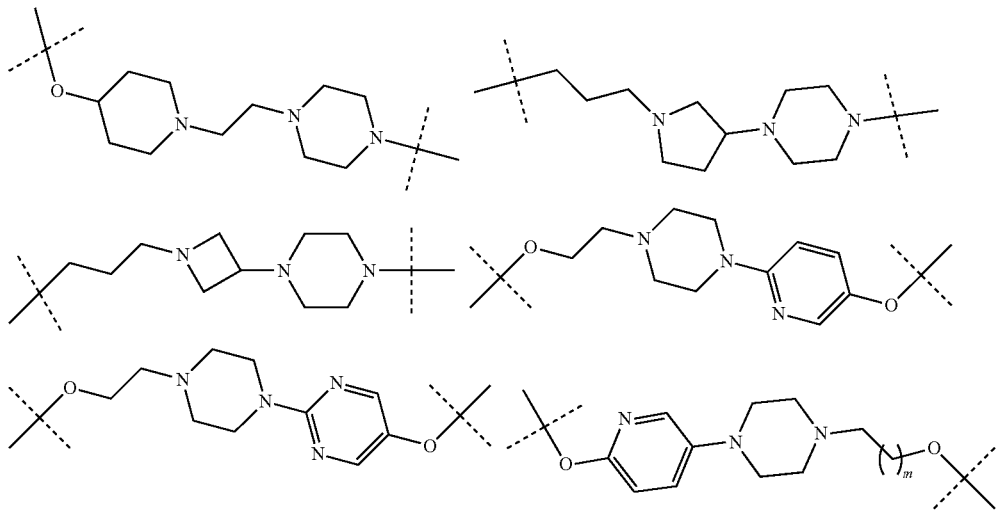

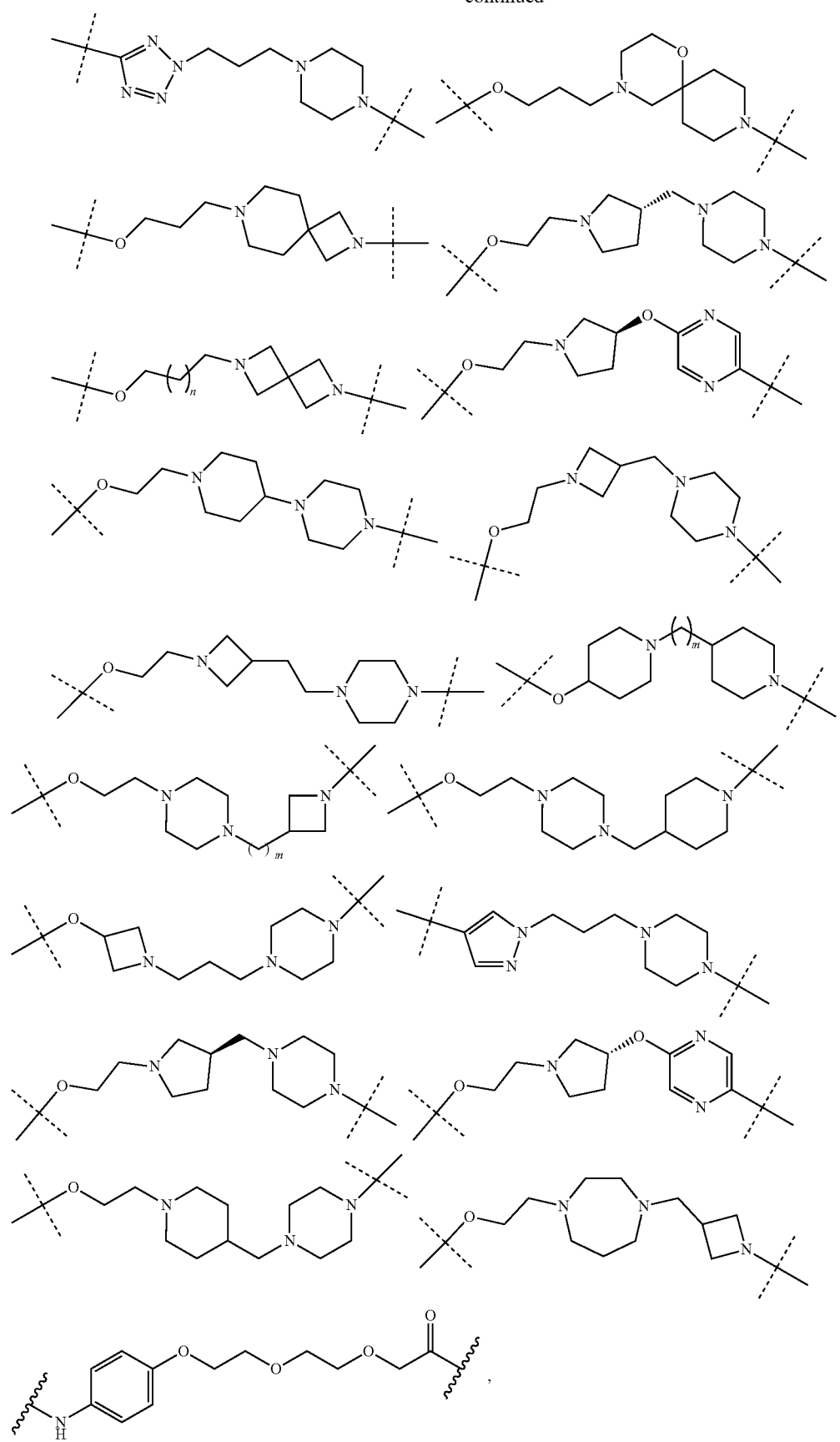

-continued
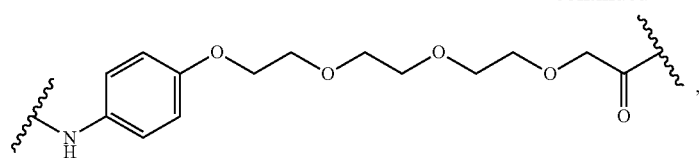
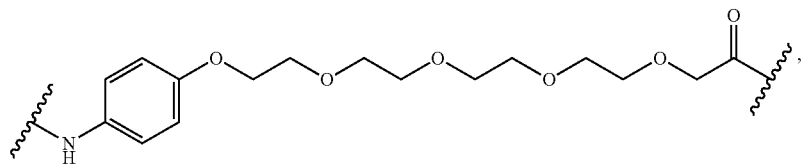
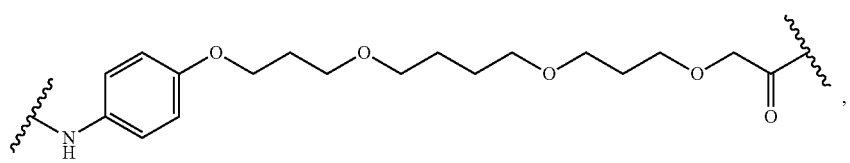
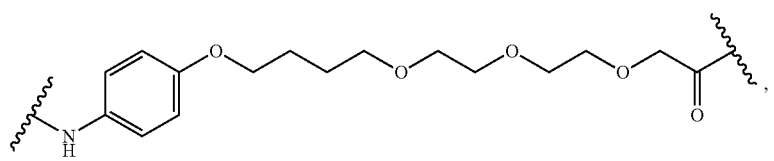
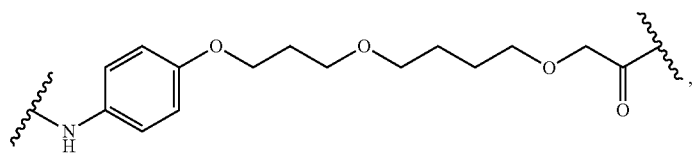
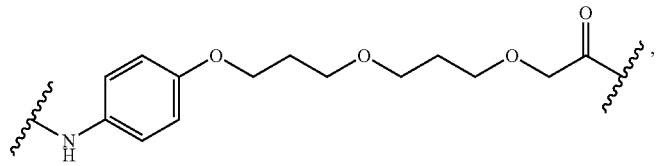
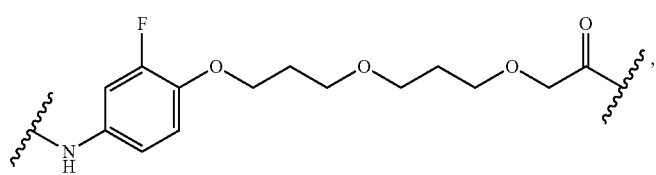
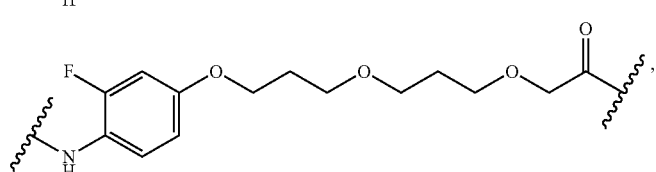
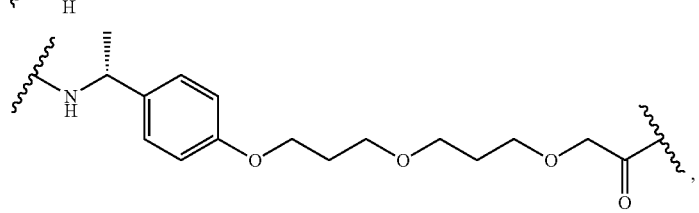
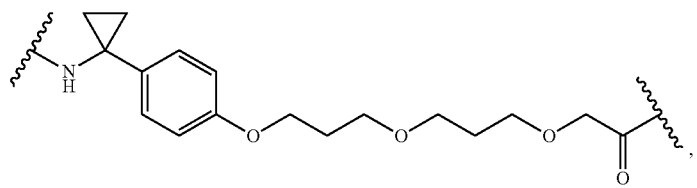

-continued
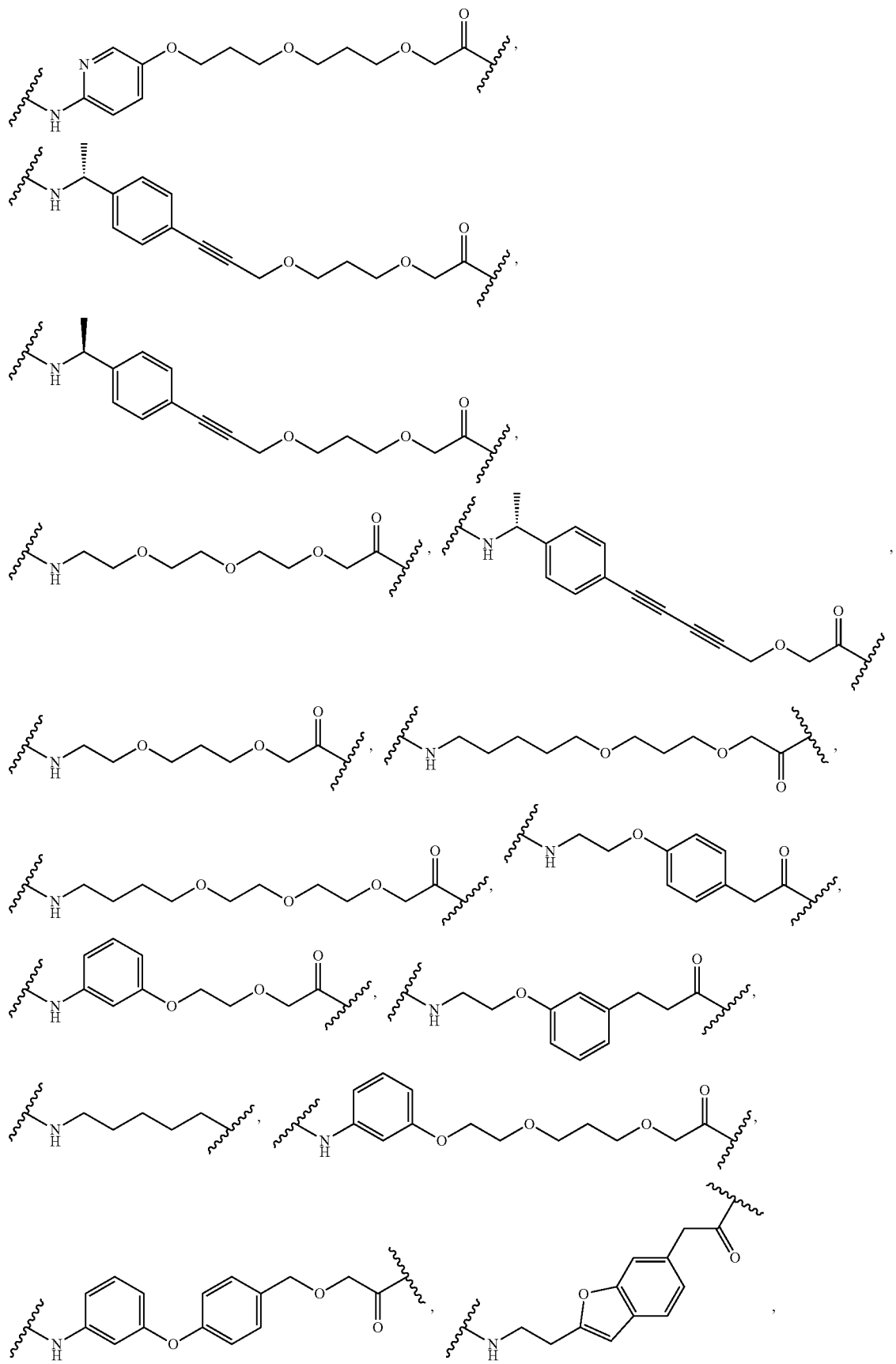

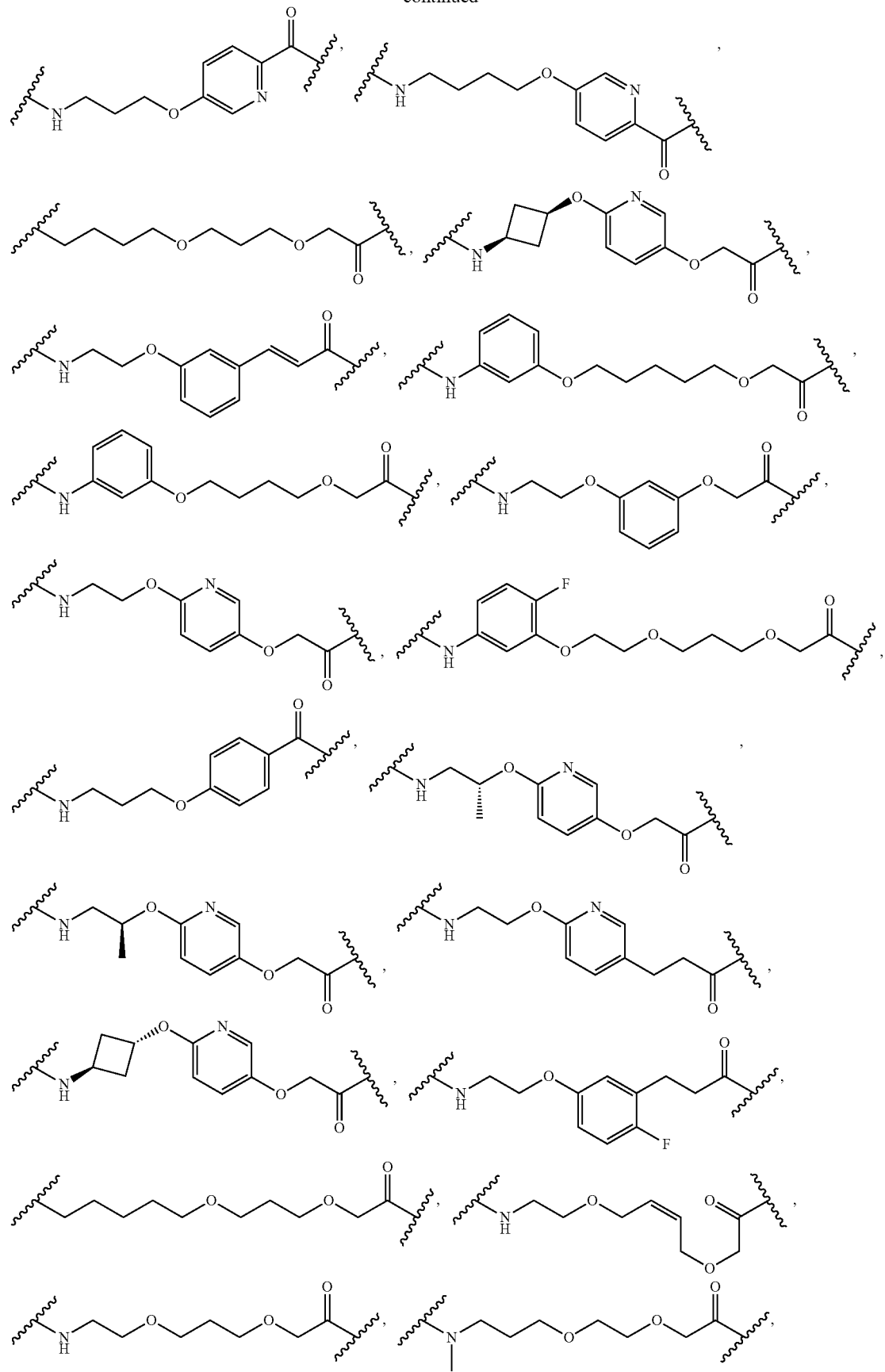

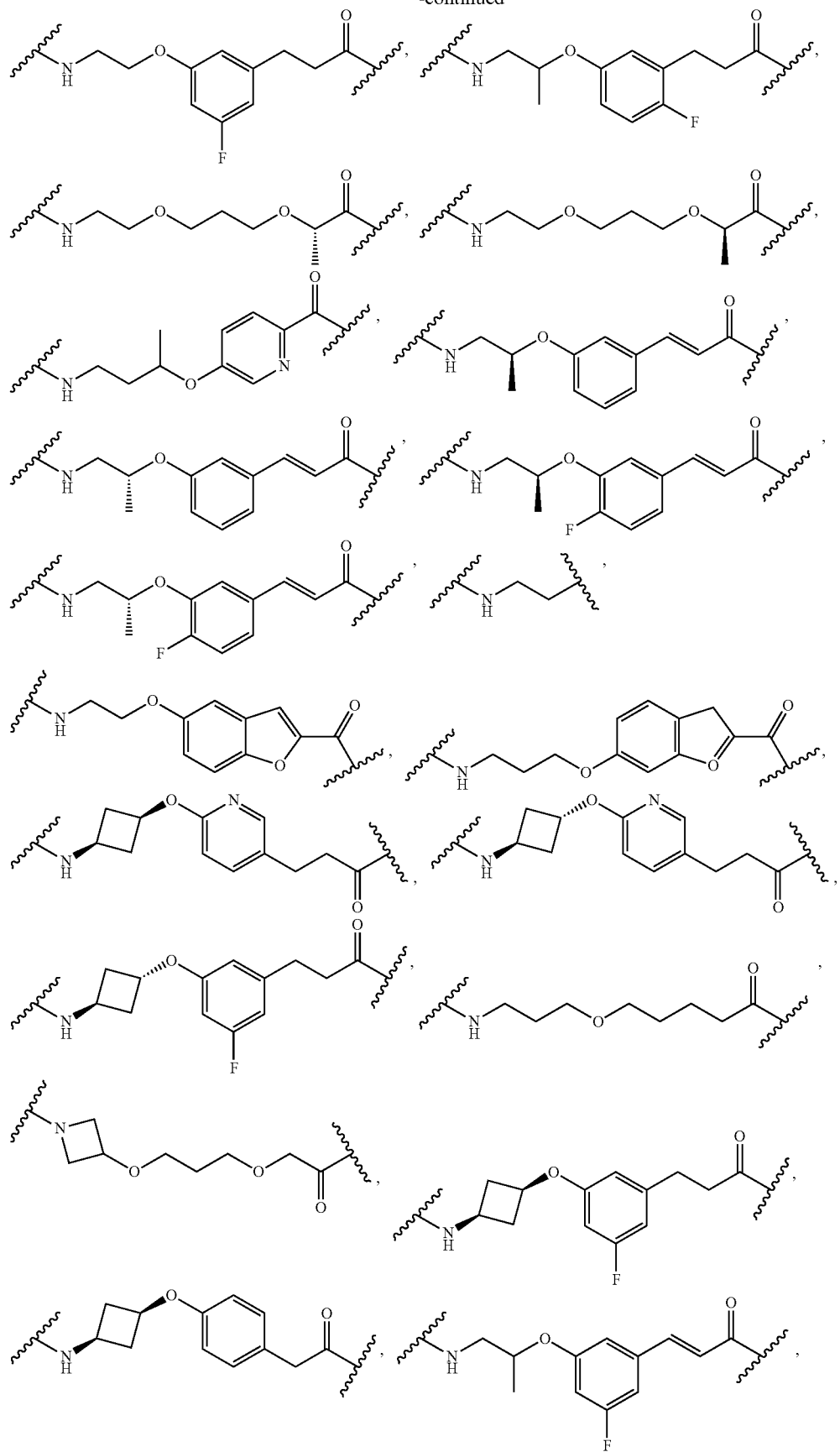

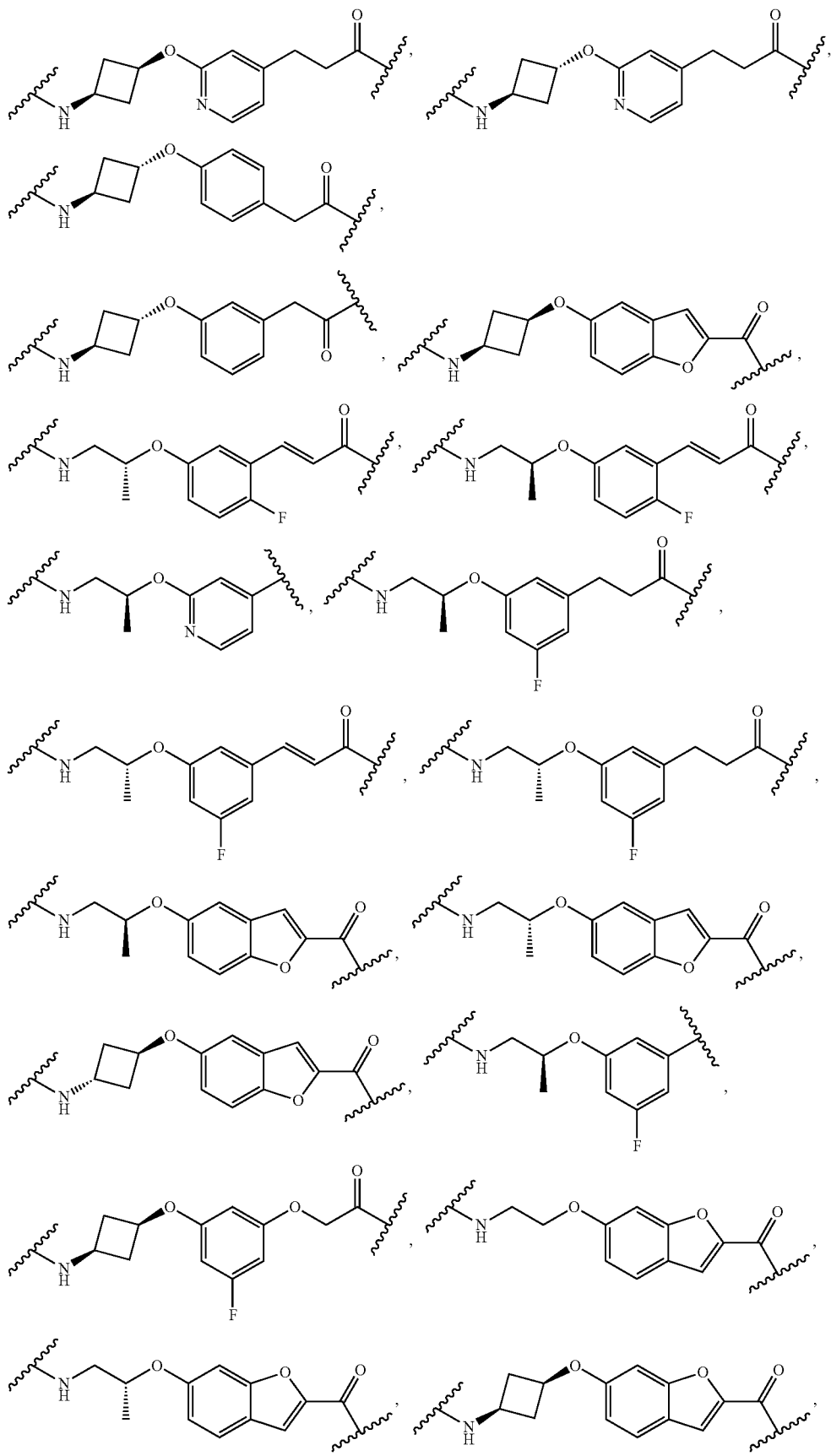
-continued

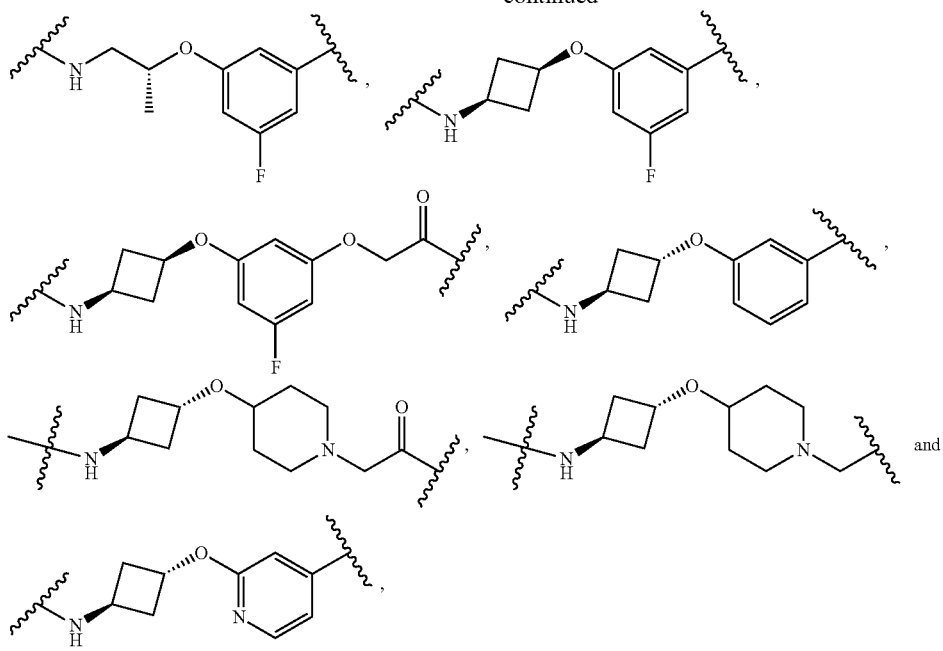
wherein each m and n is independently selected from 0, 1, 2, 3, 4, 5, or 6.
In various embodiments, the linker (L) is selected from the group consisting of:
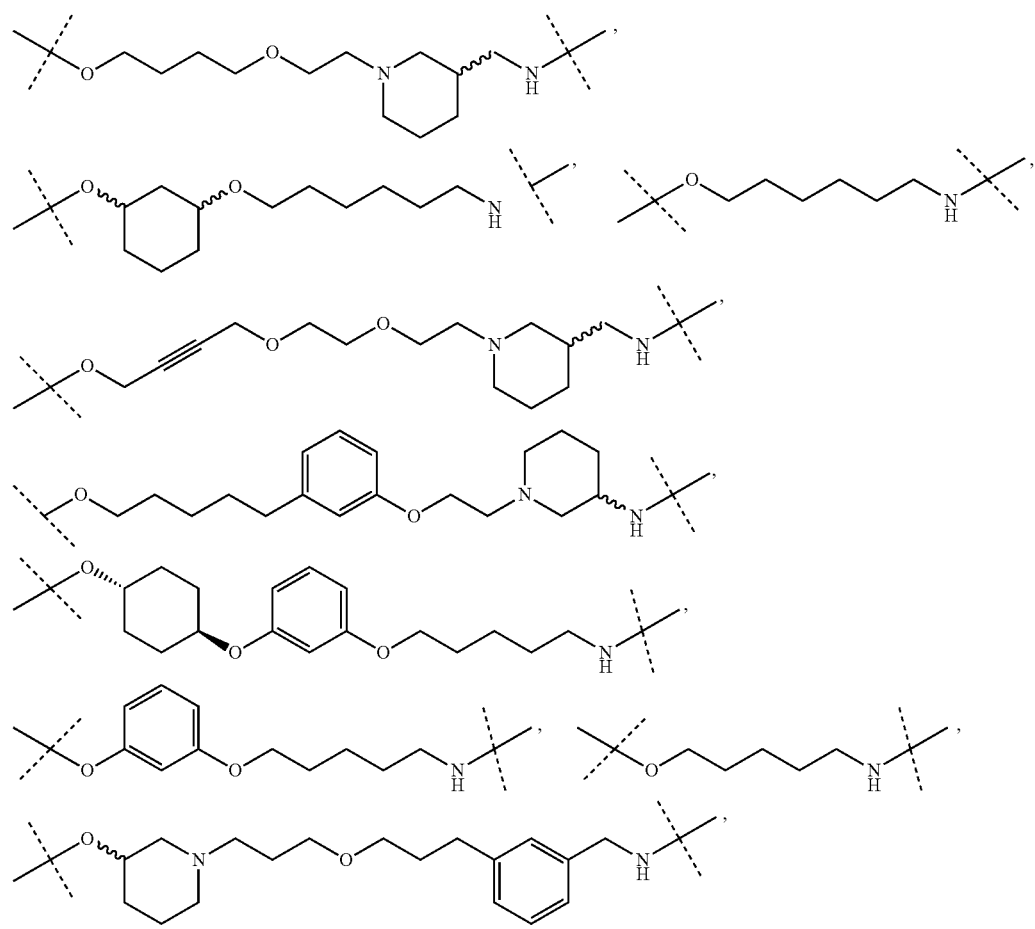

327 328
-continued
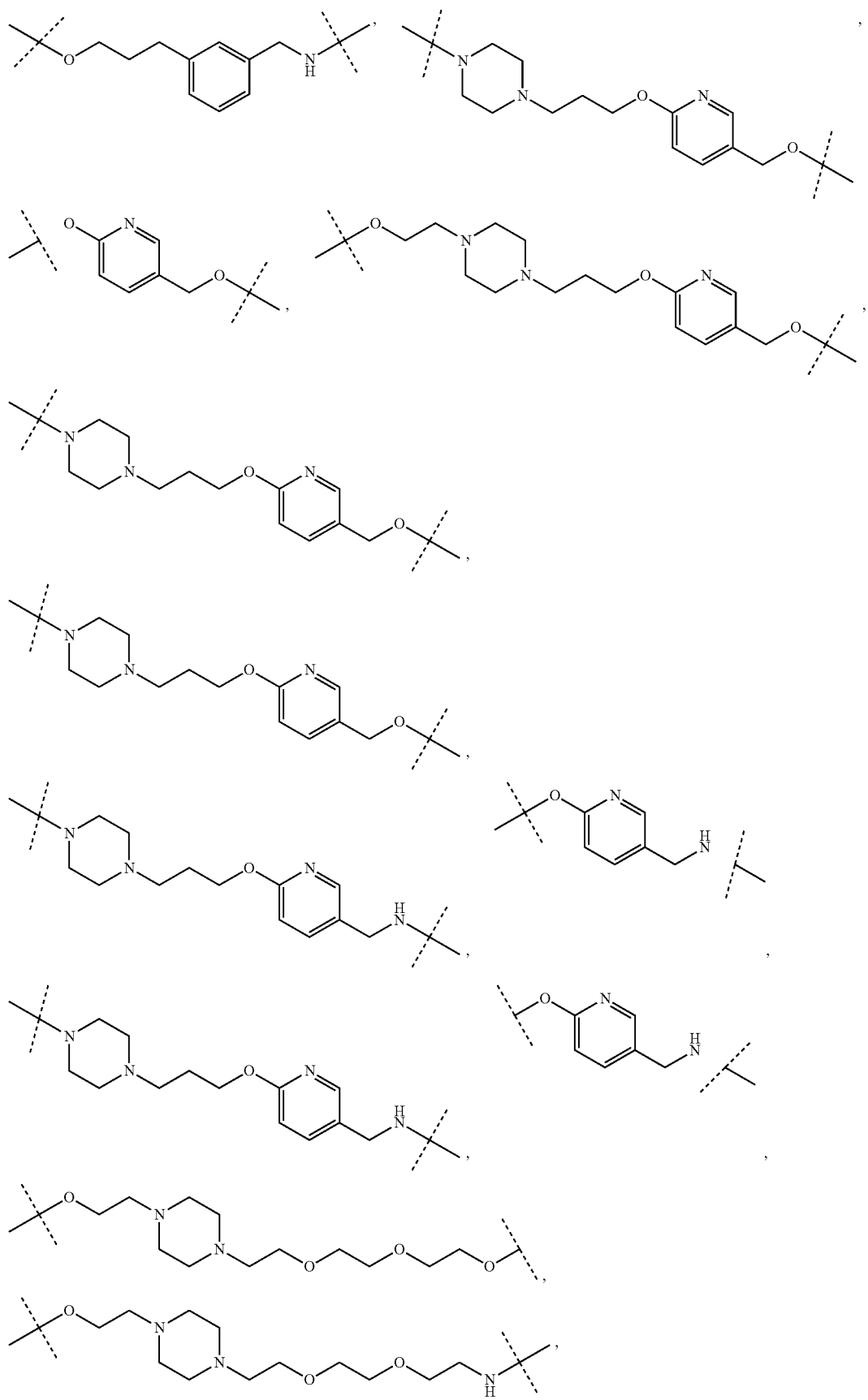

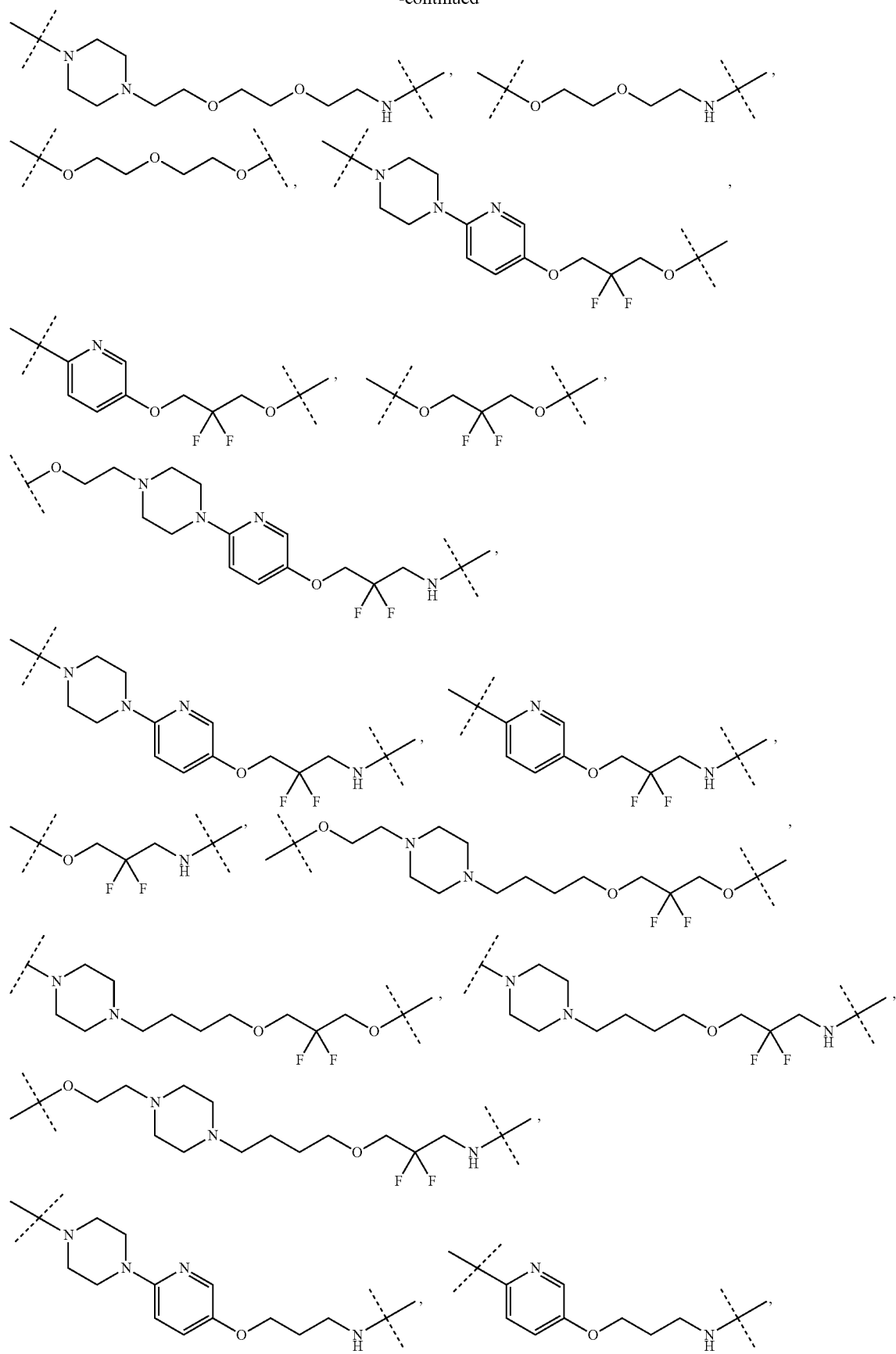

-continued
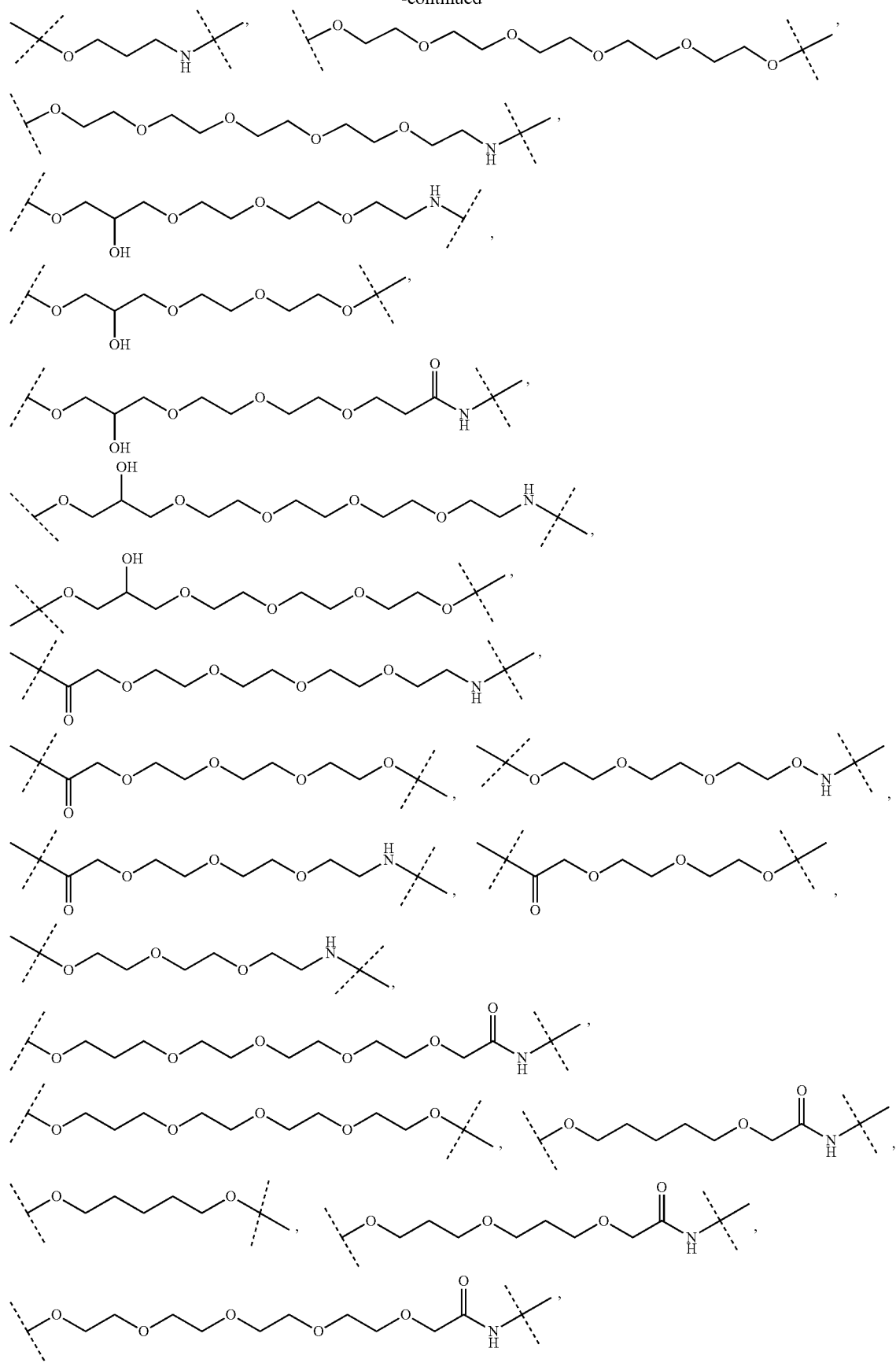

333 334
-continued
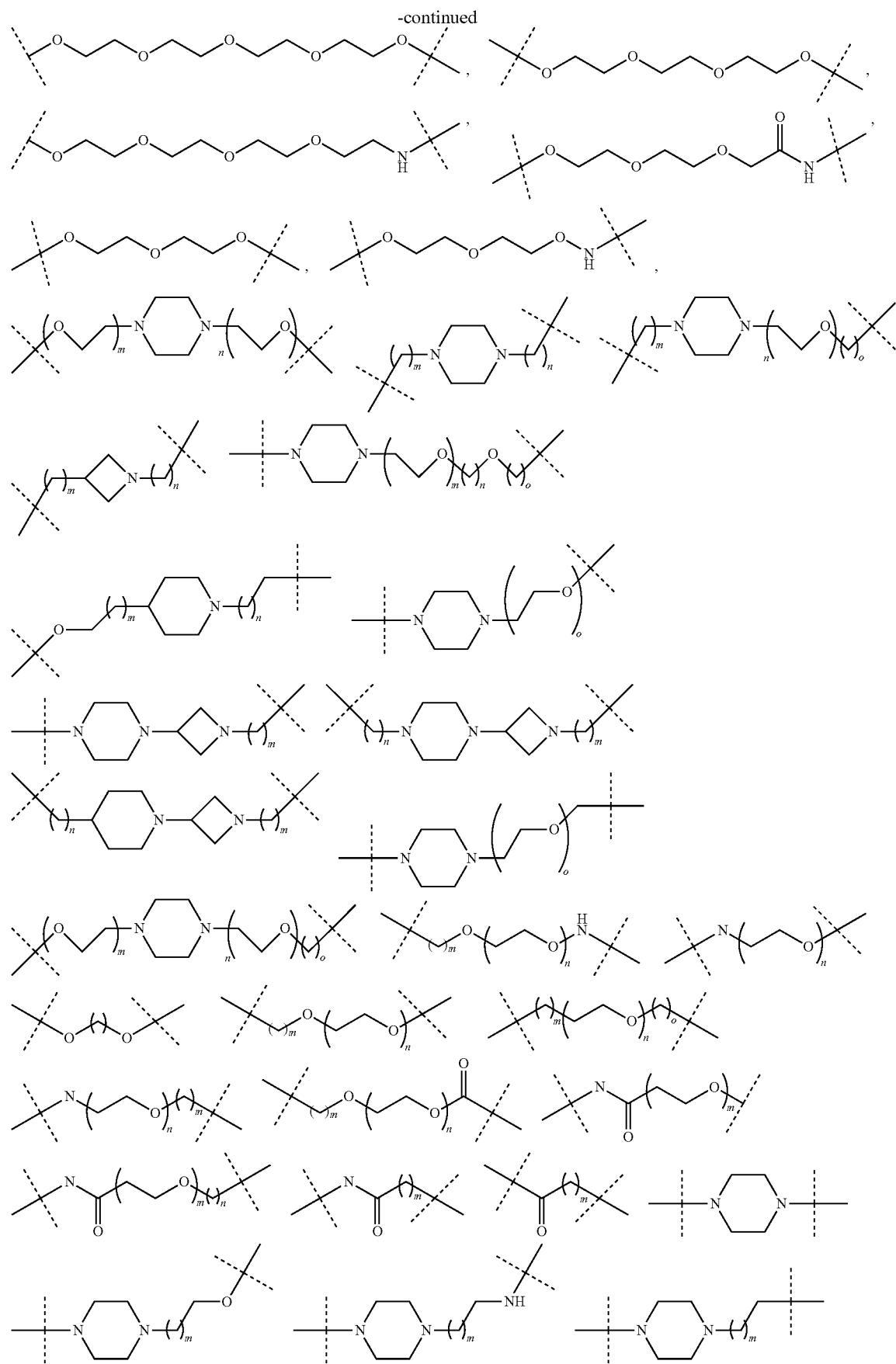

-continued
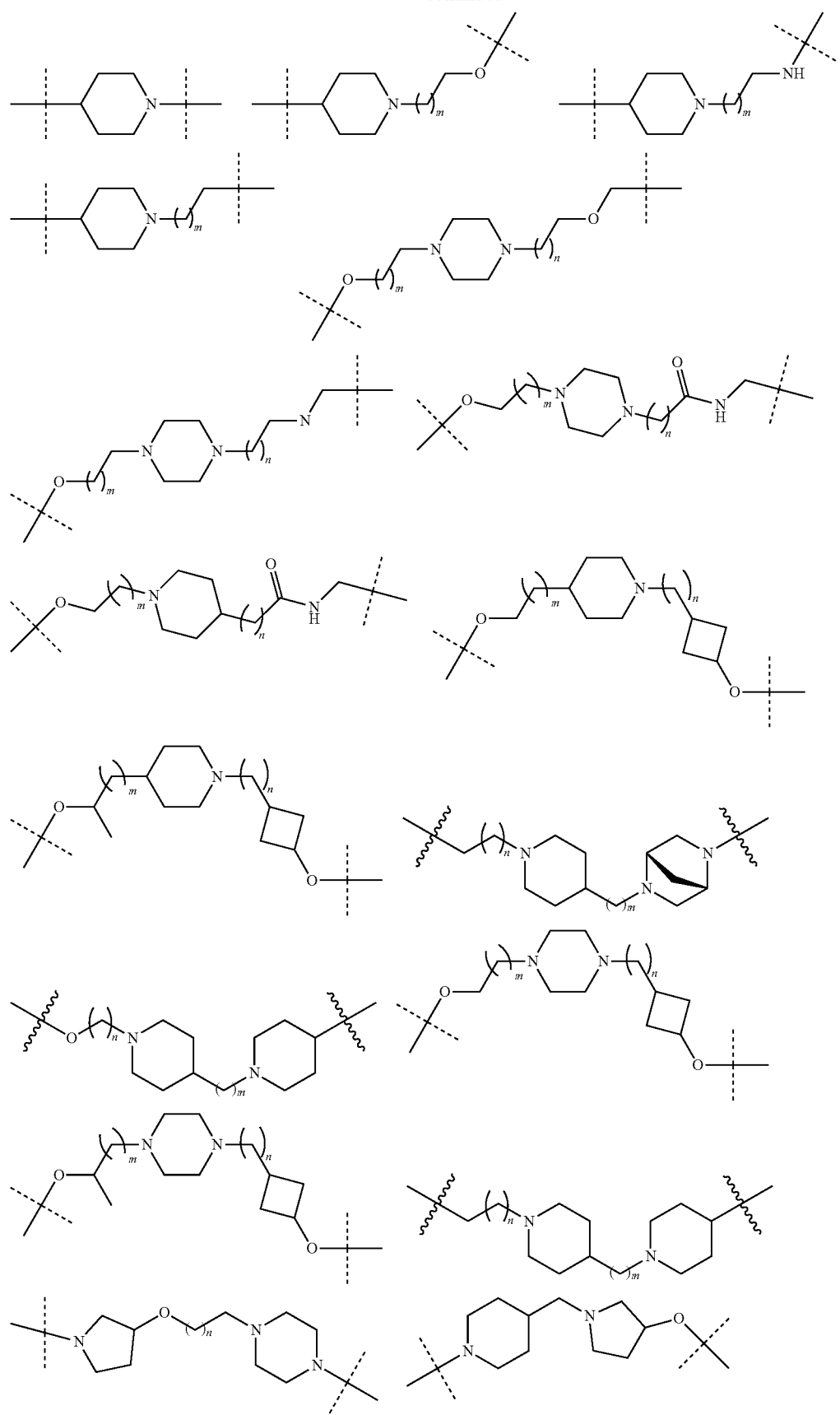

-continued
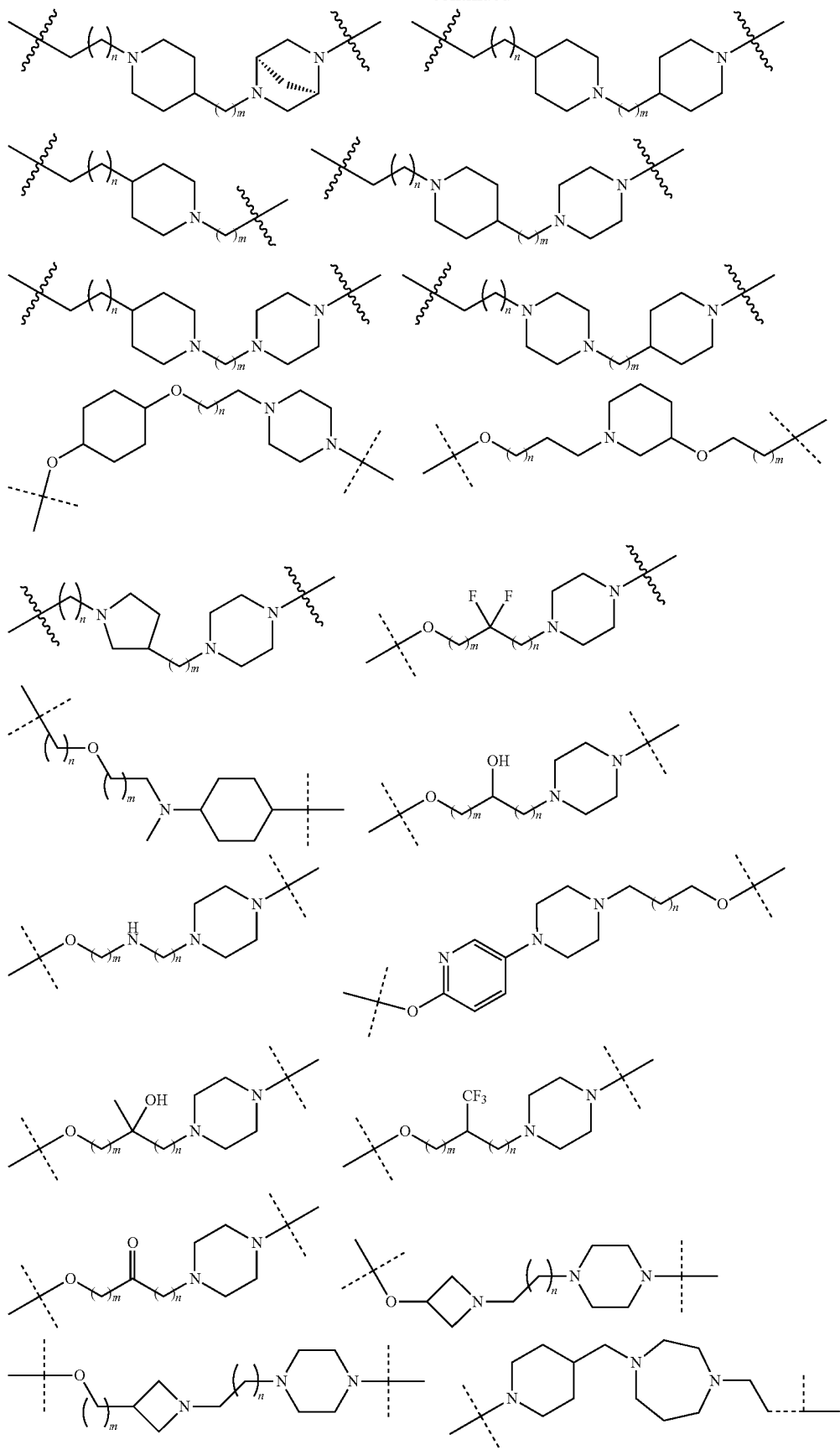

-continued
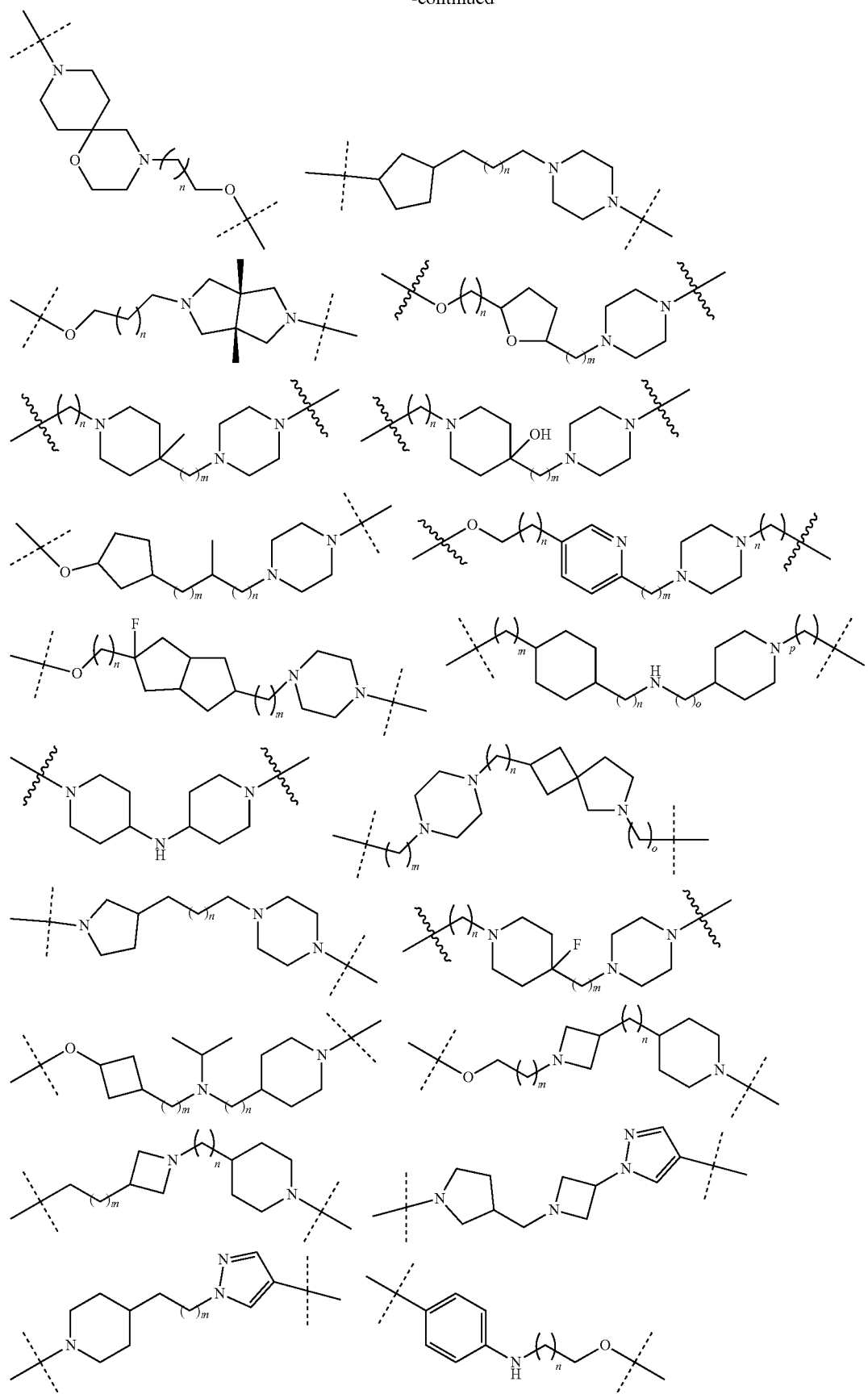

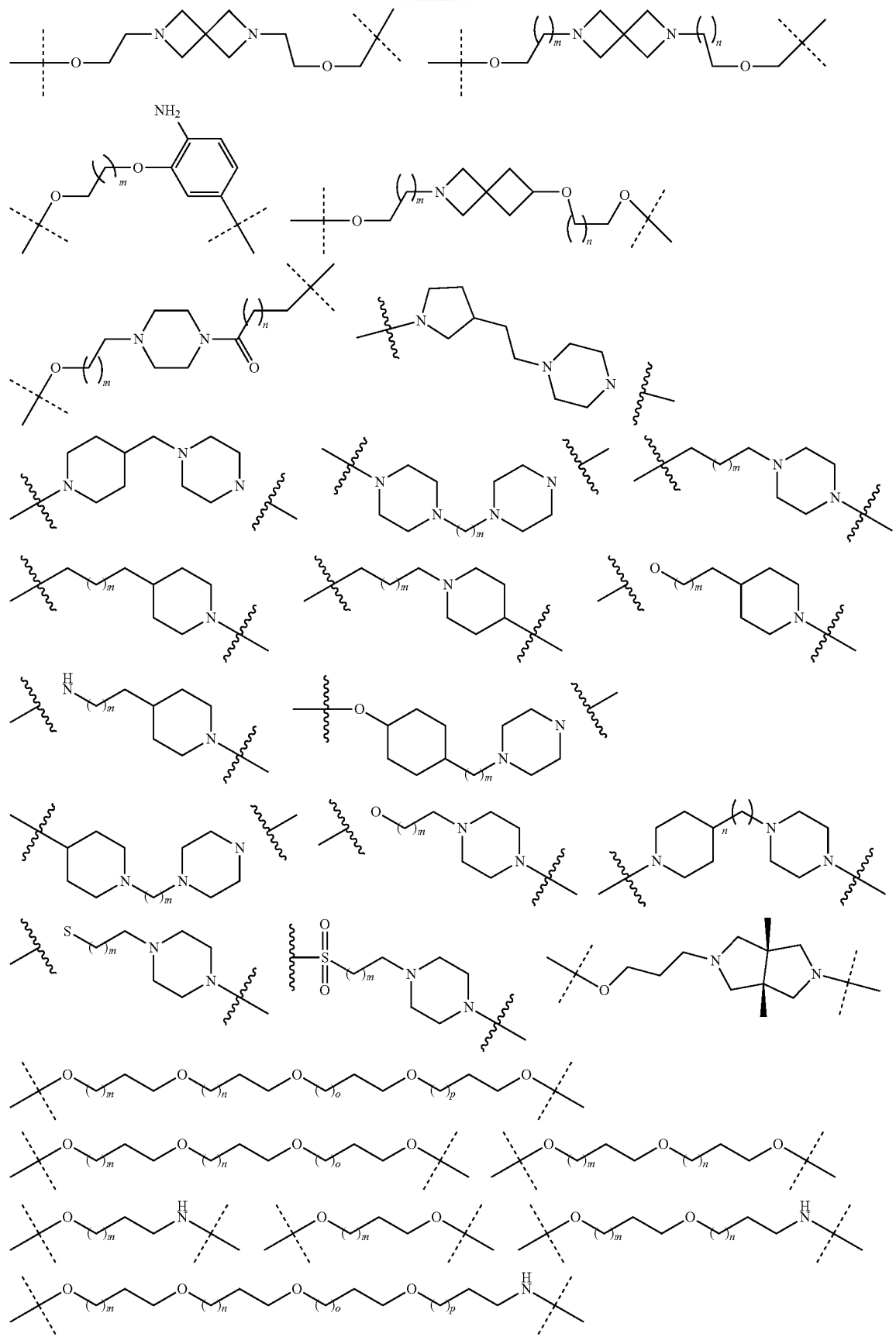

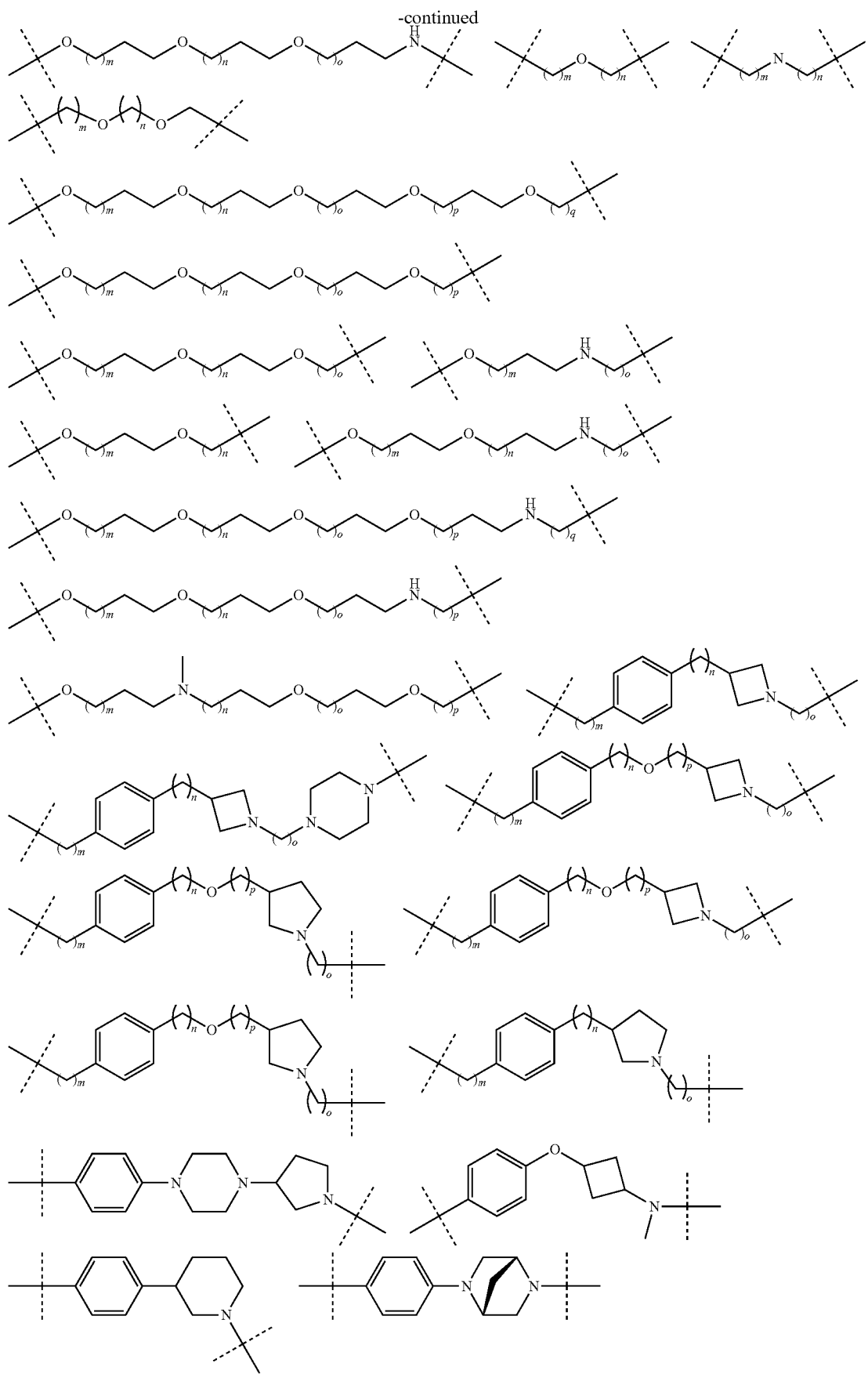

-continued
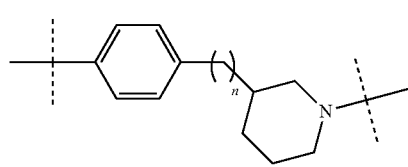
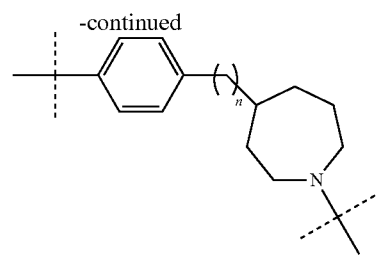
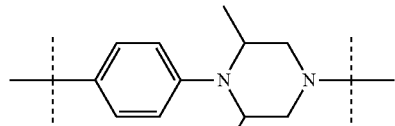
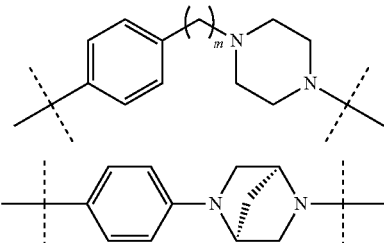
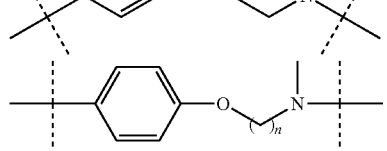
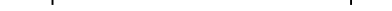
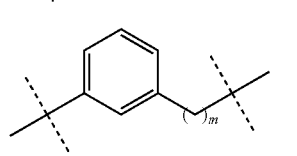
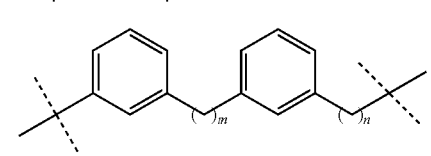
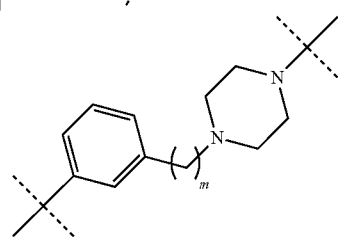
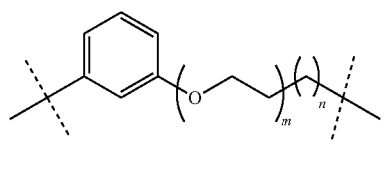
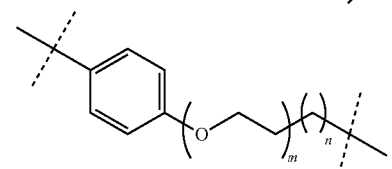
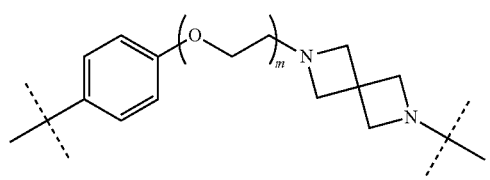
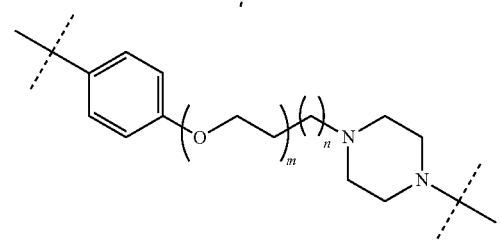
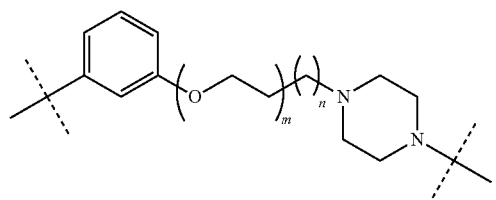
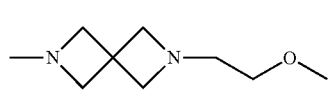
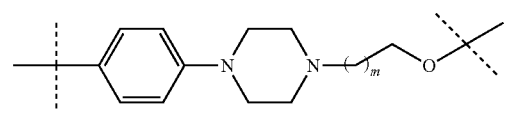

-continued
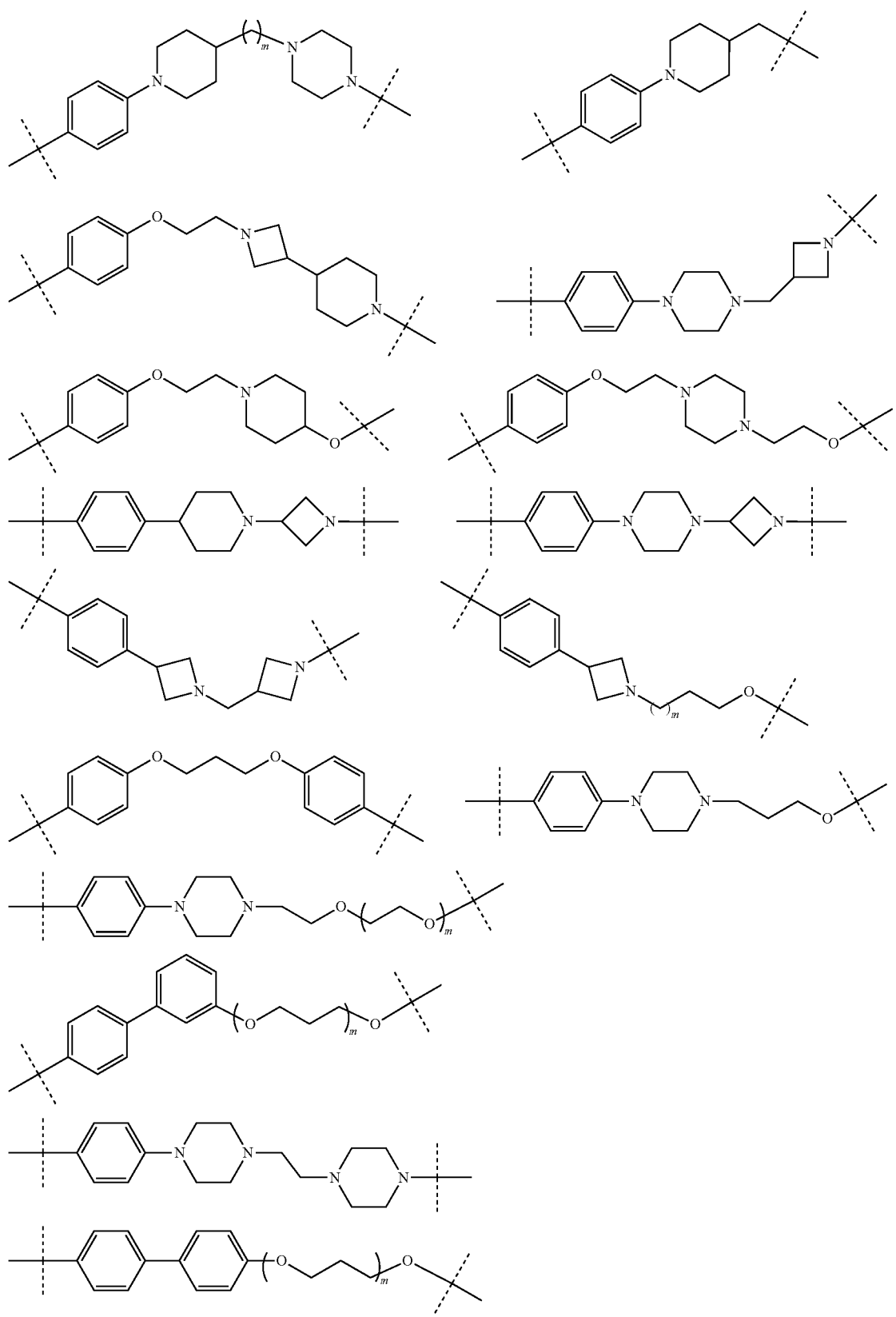

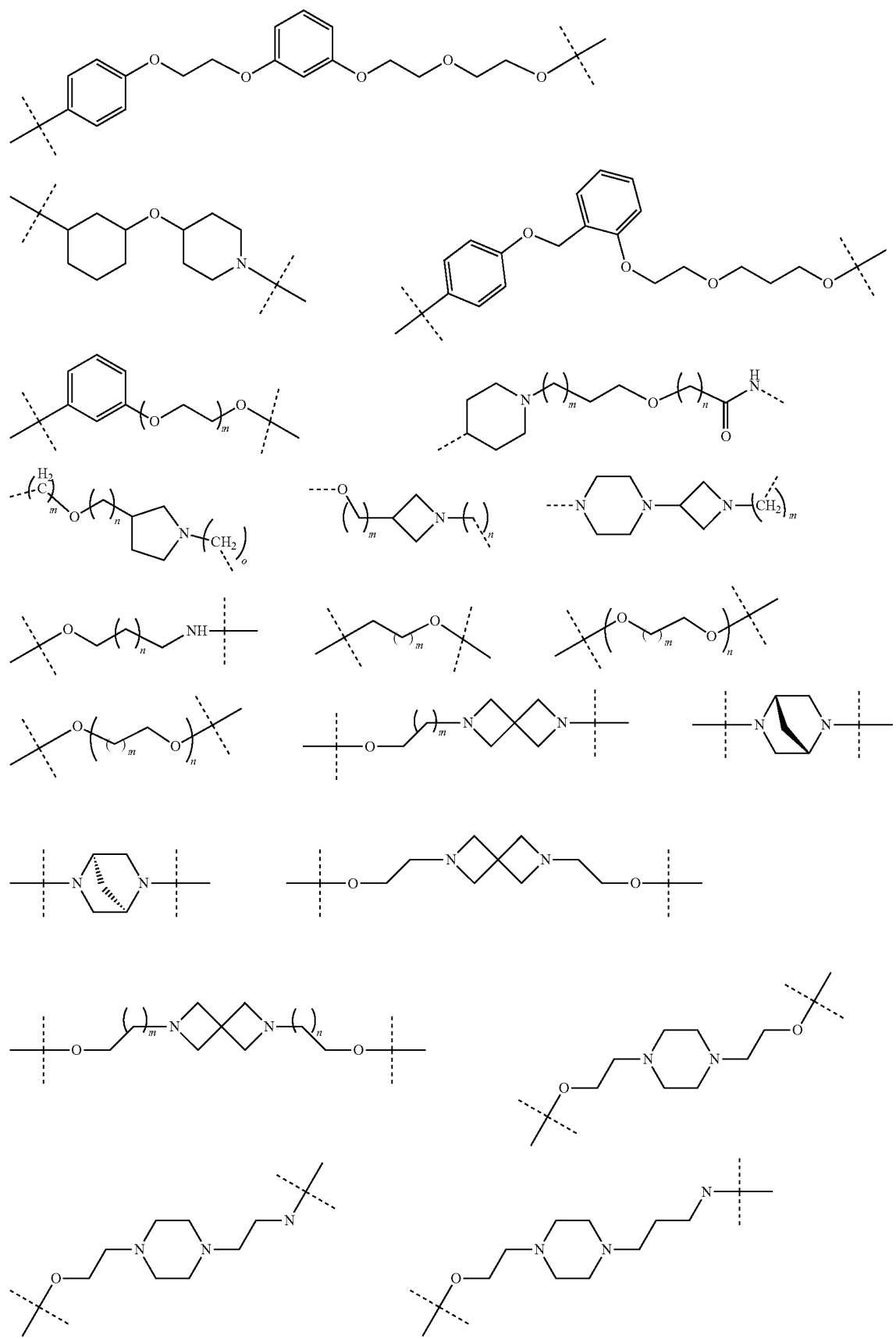

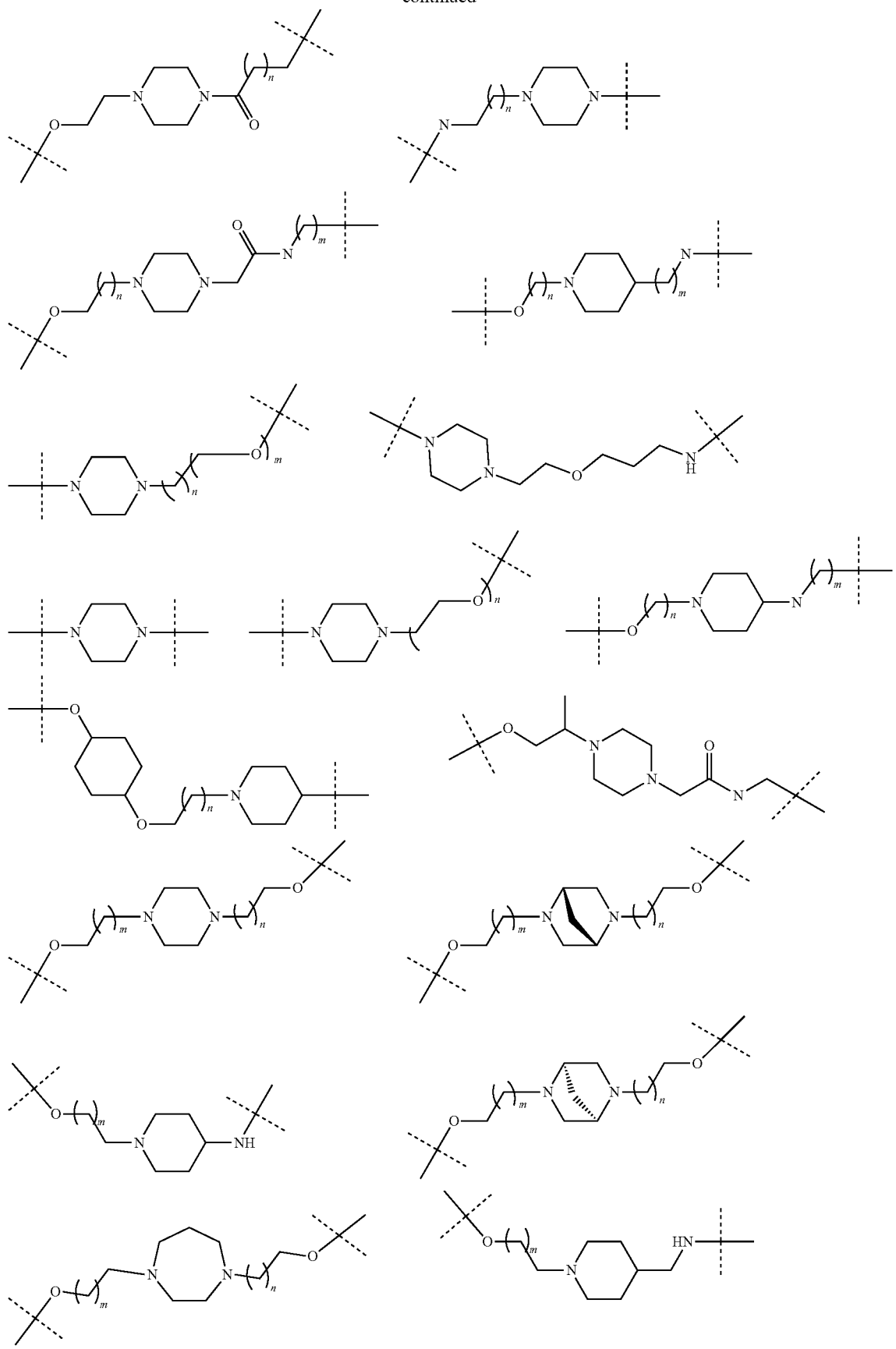

-continued
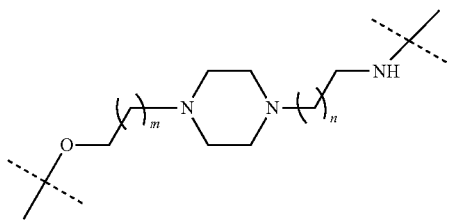
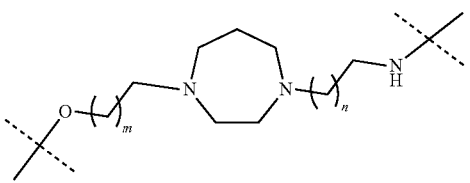
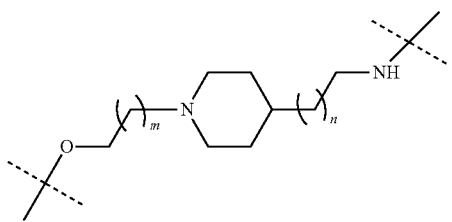
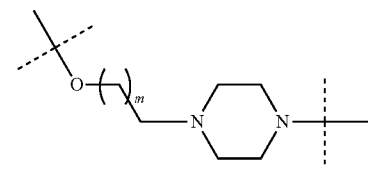
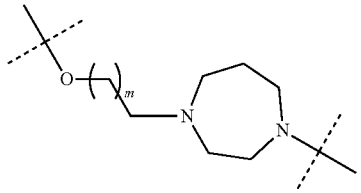
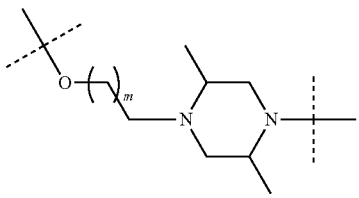
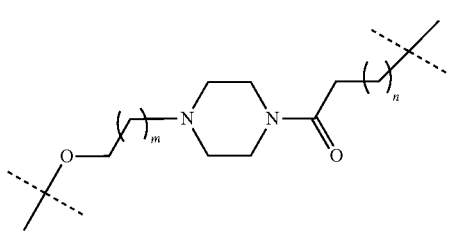
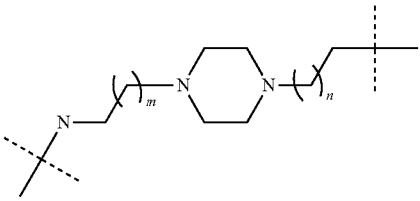
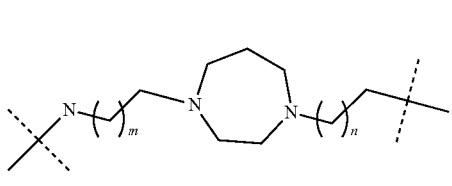
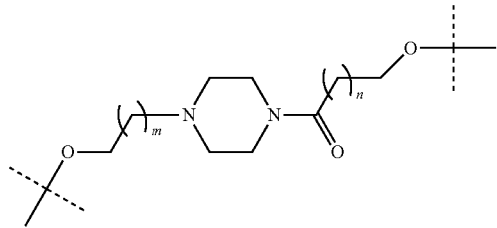
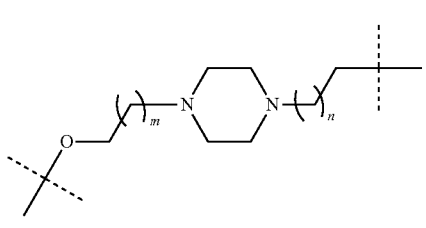
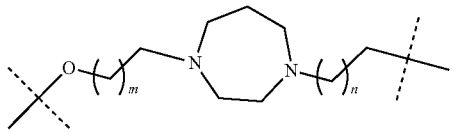
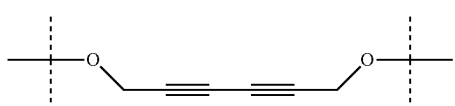
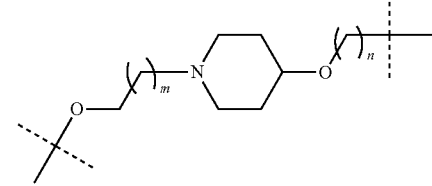

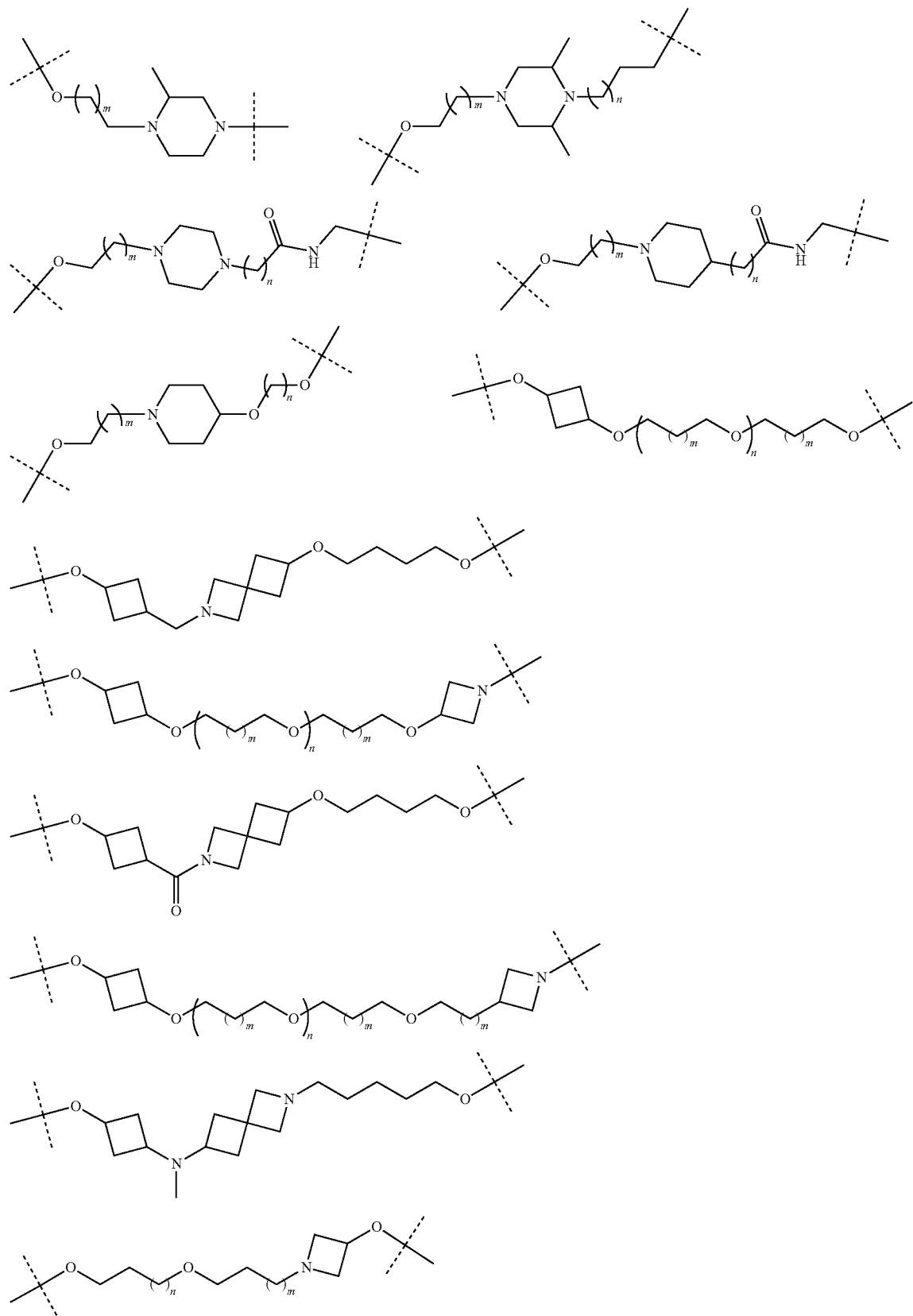

-continued
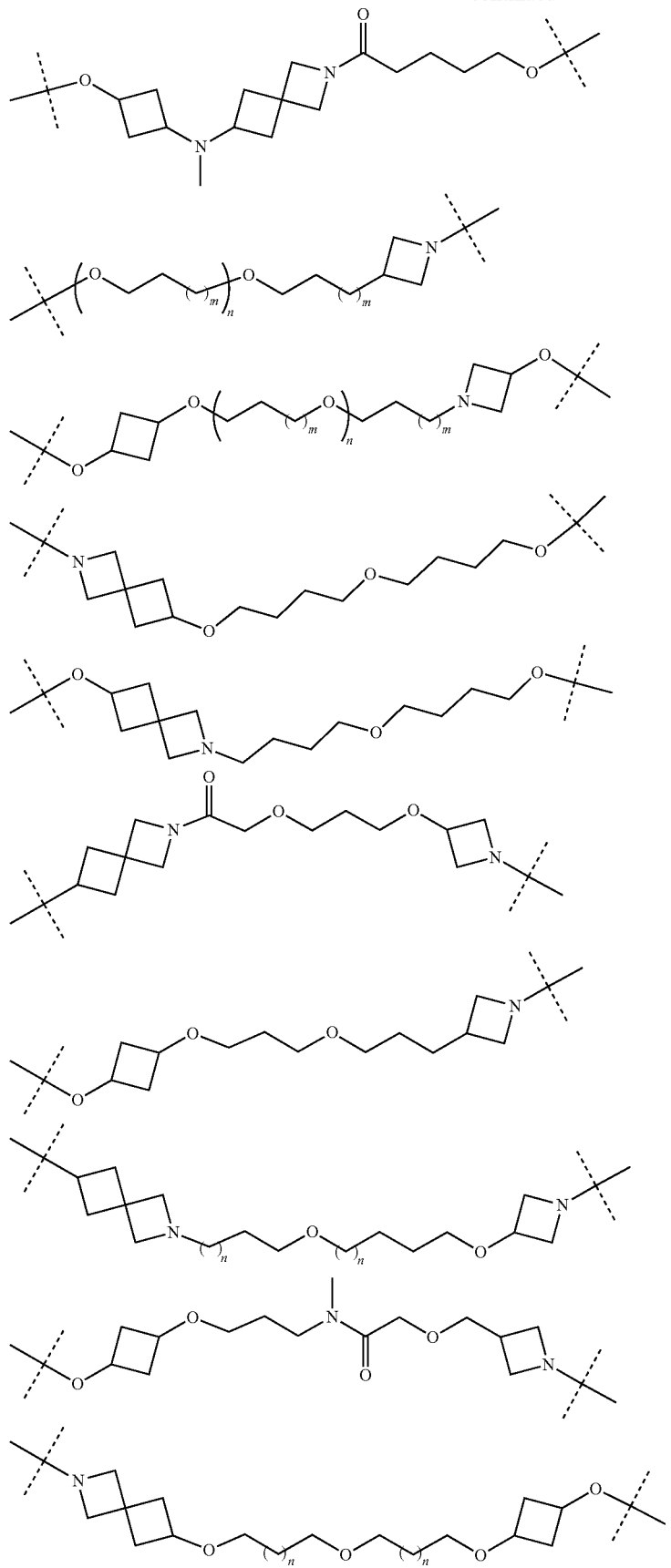

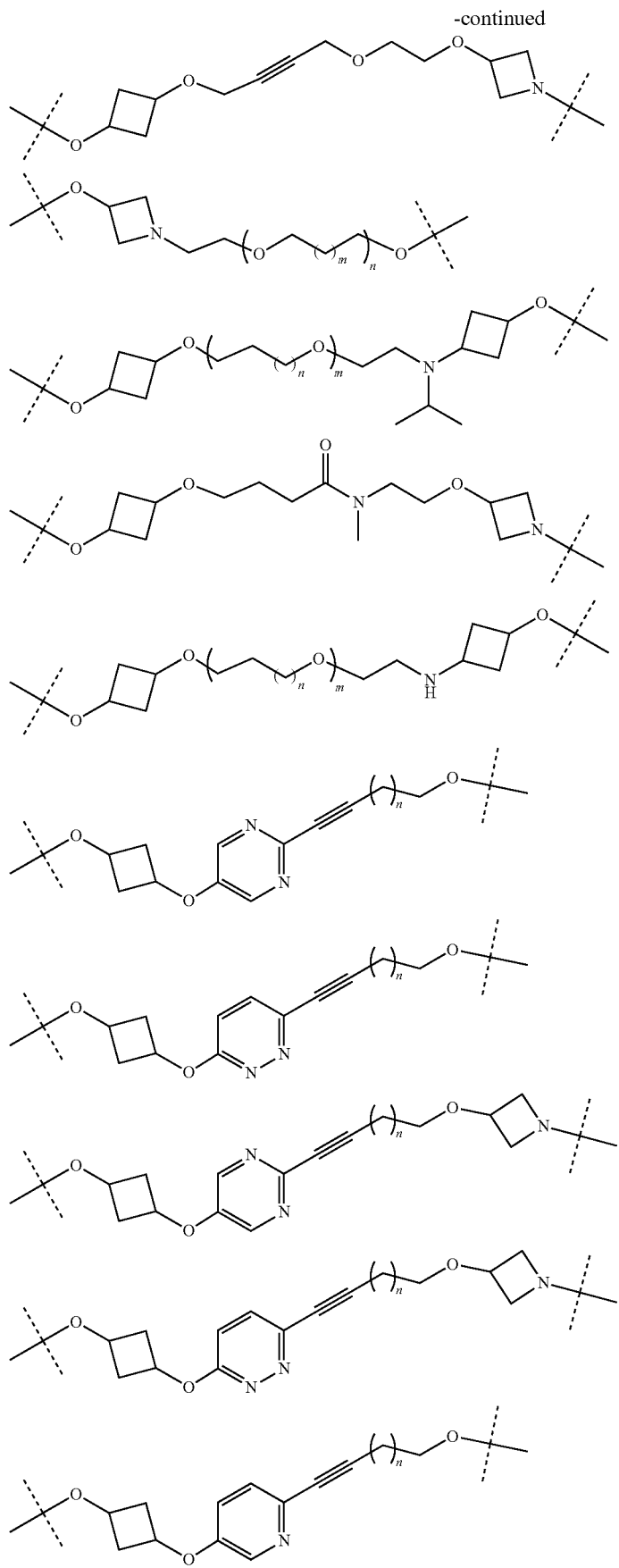

-continued
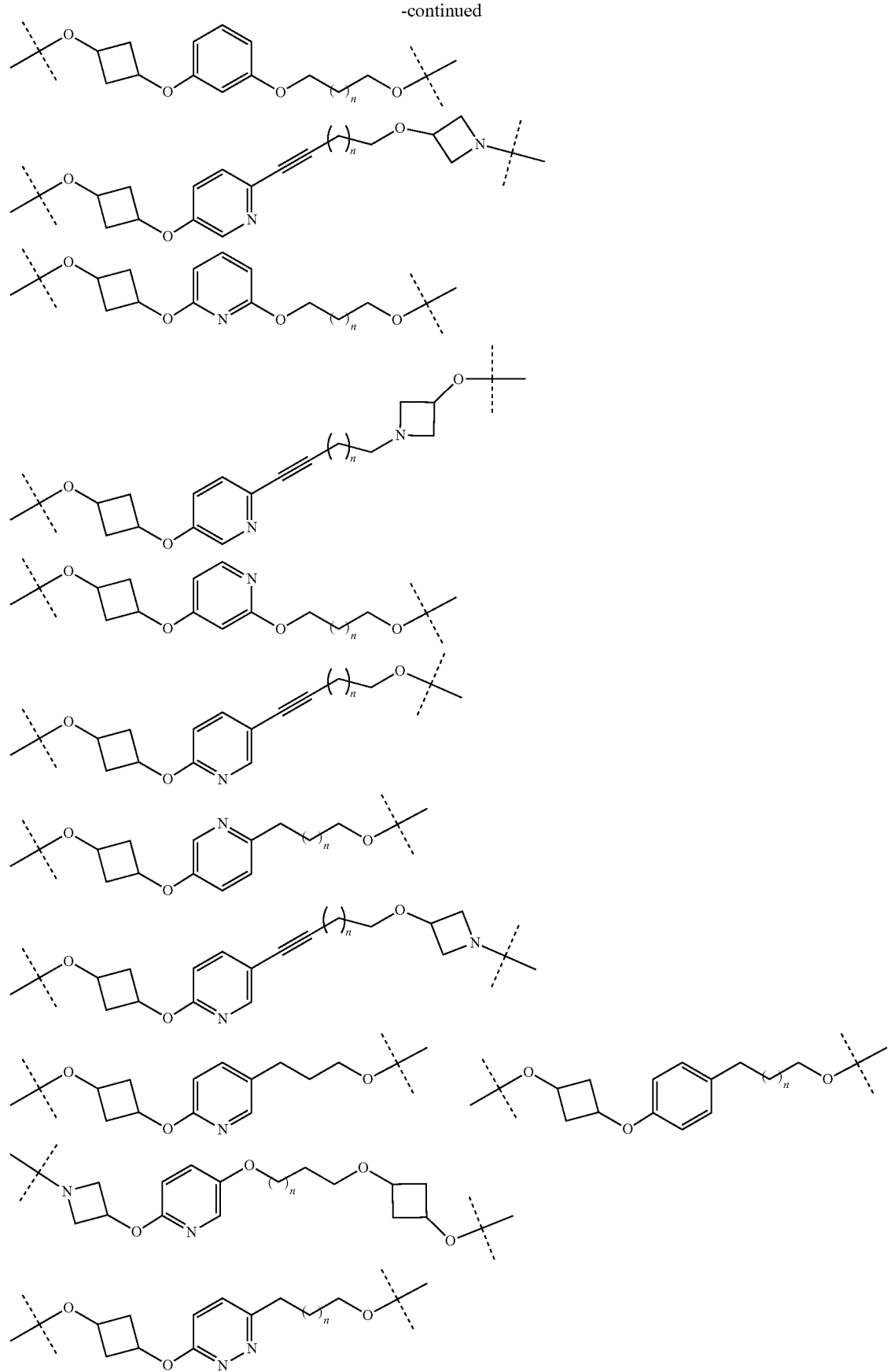

-continued
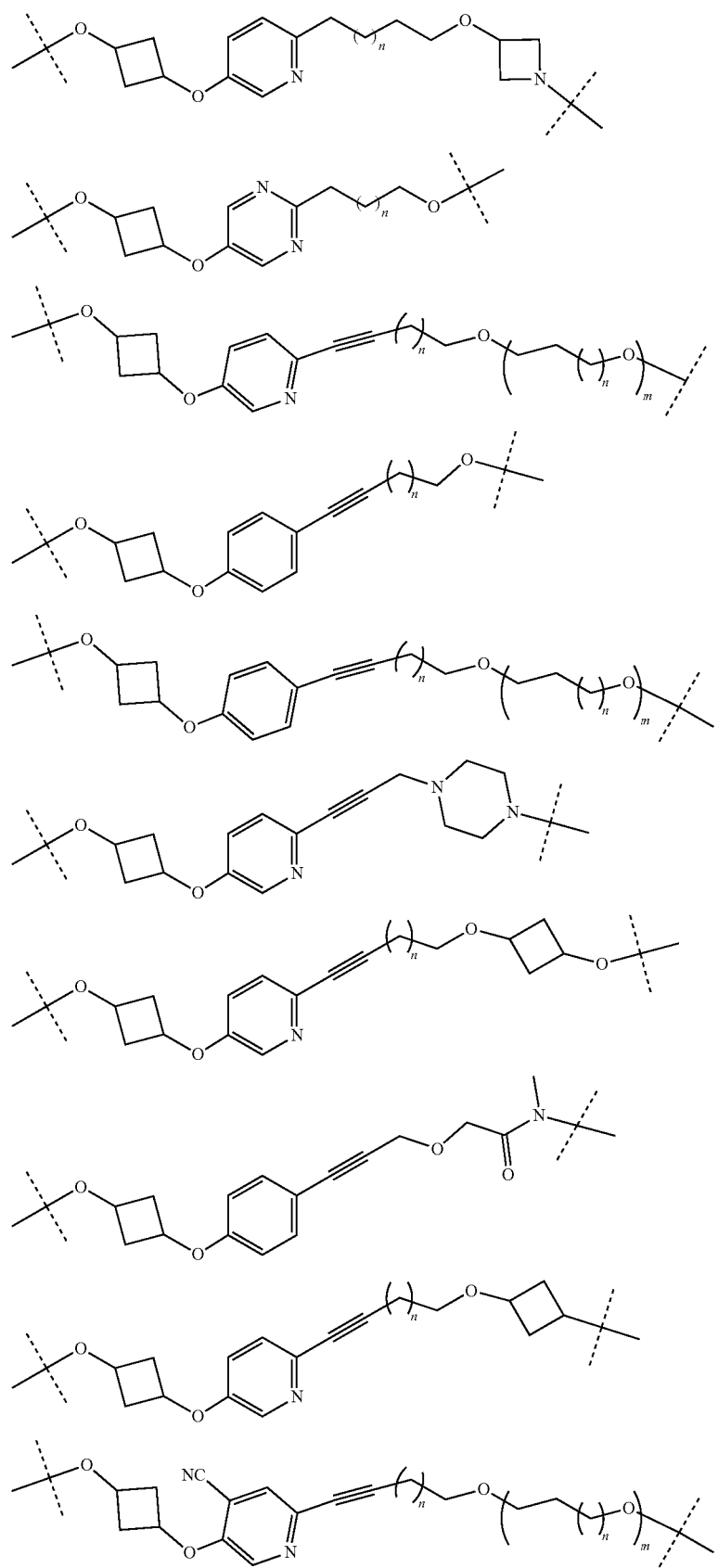

-continued
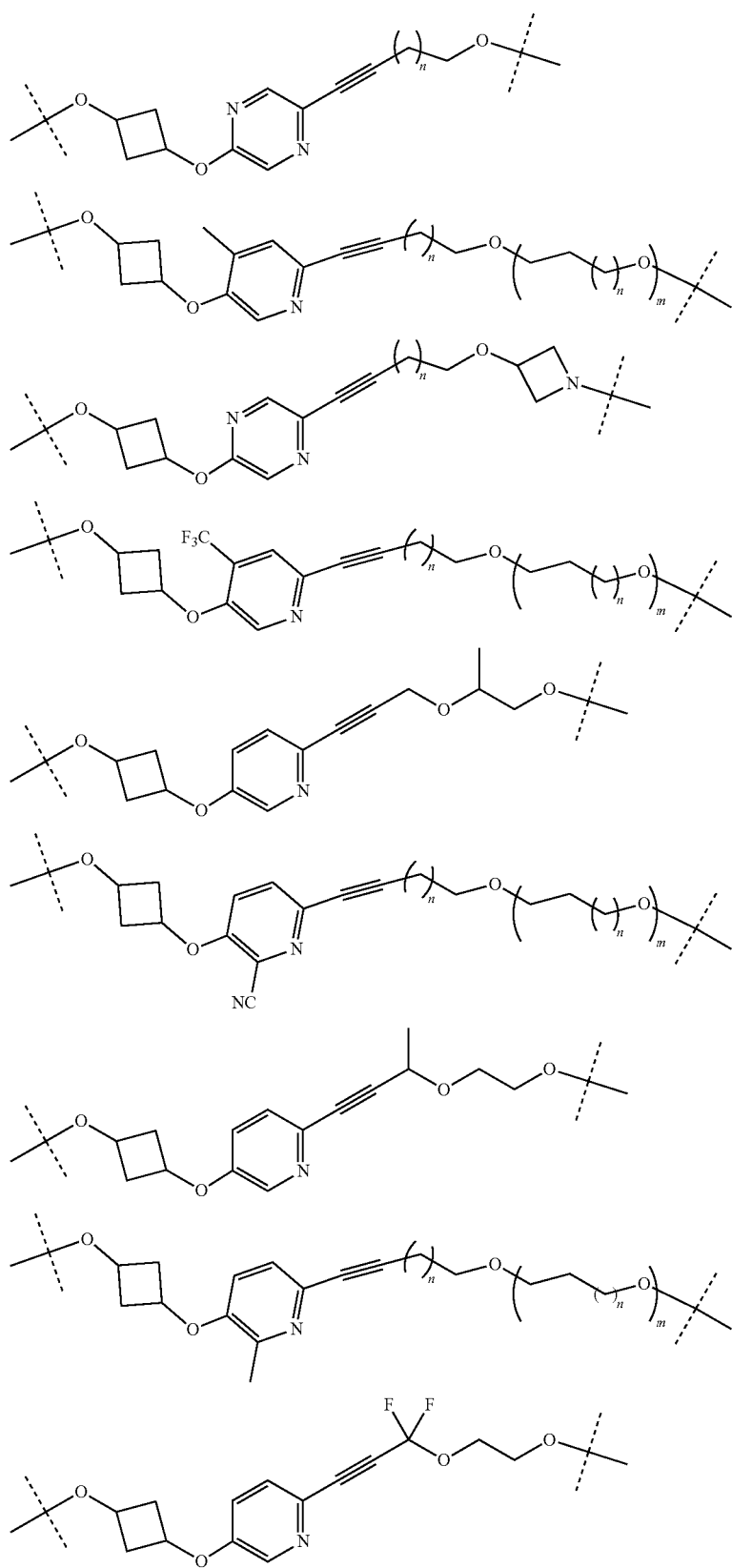

-continued
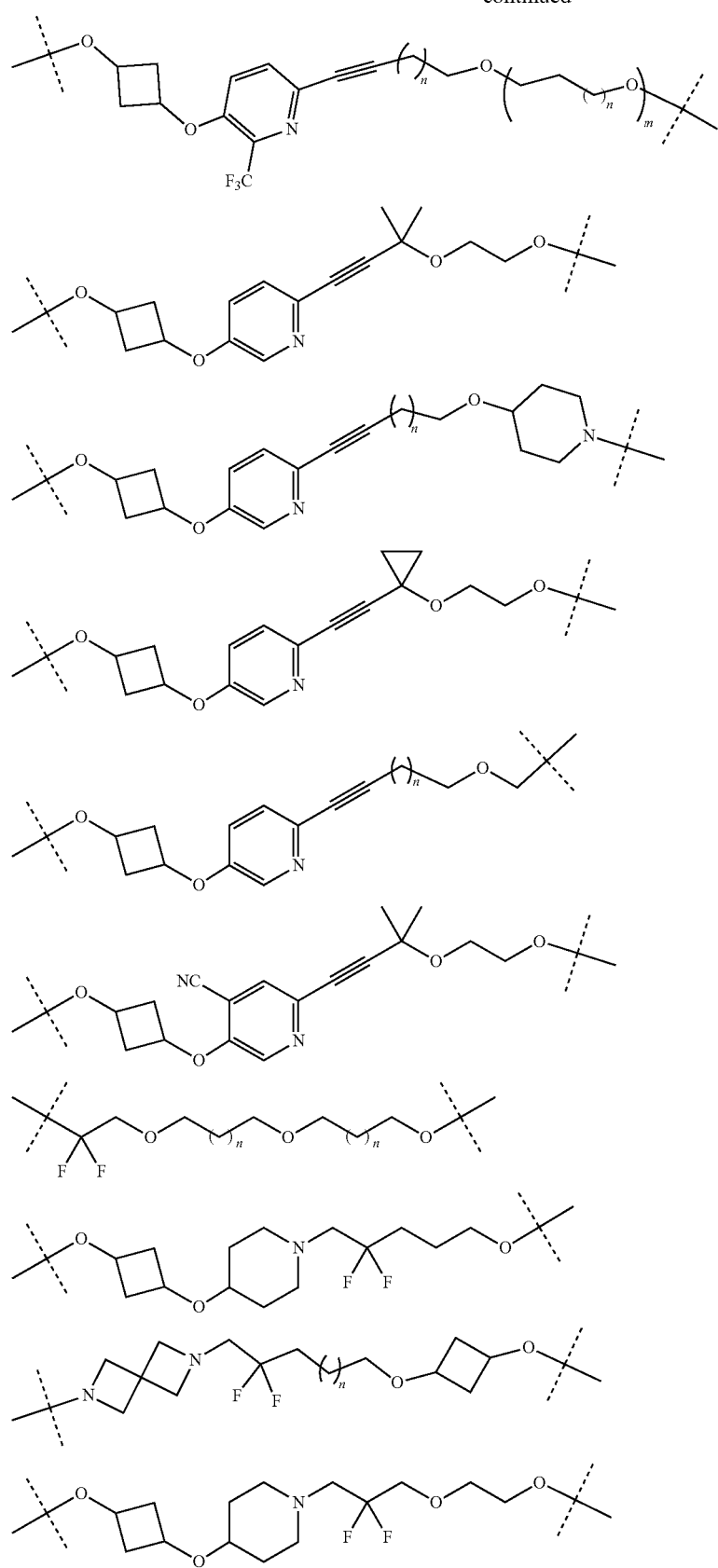

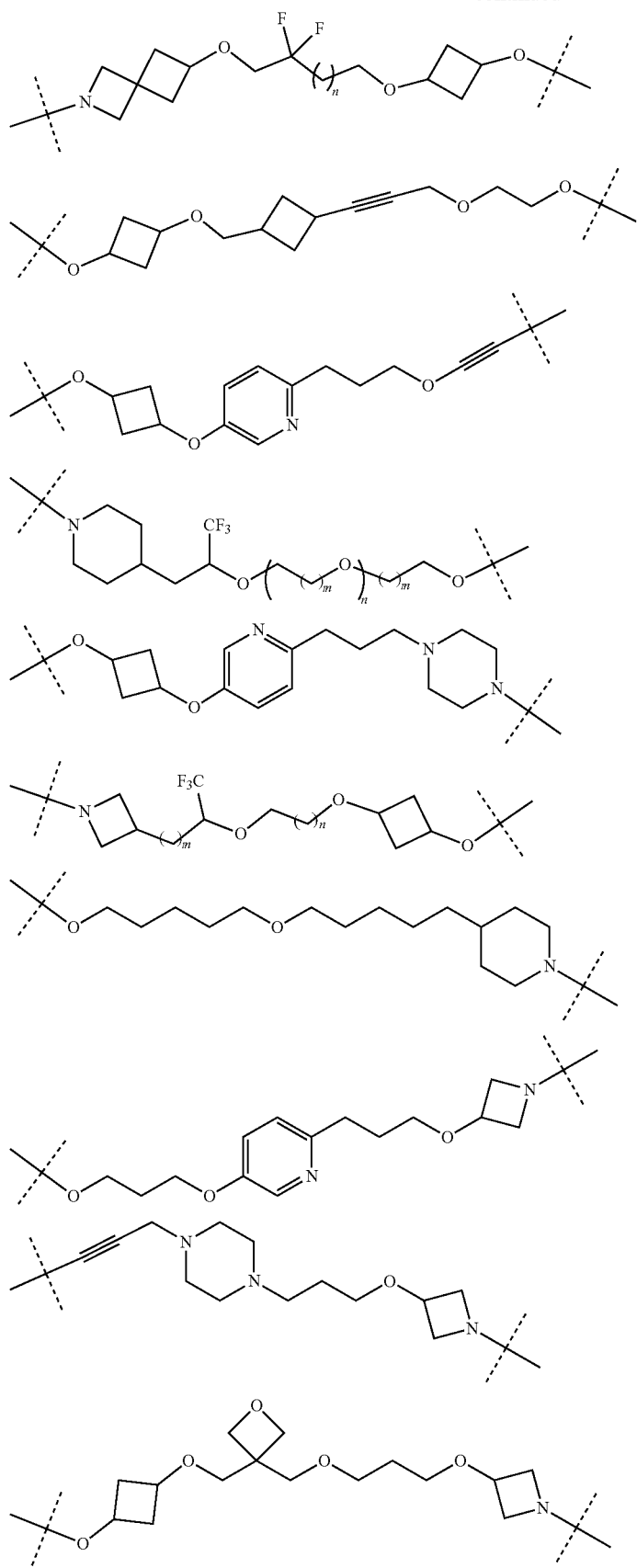

-continued
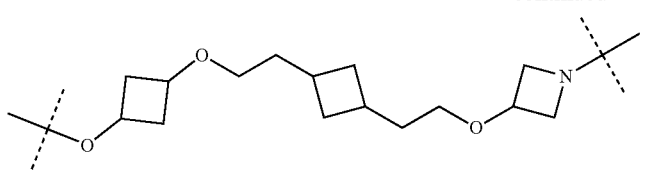
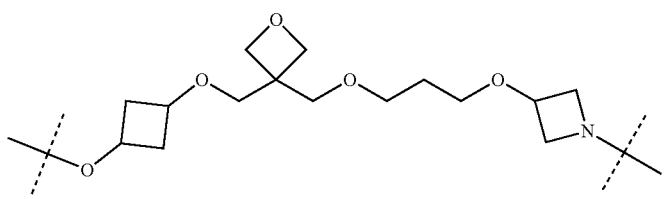
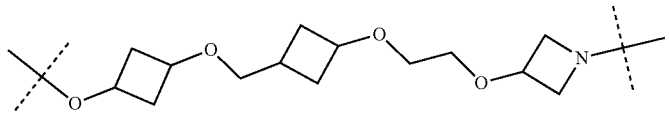
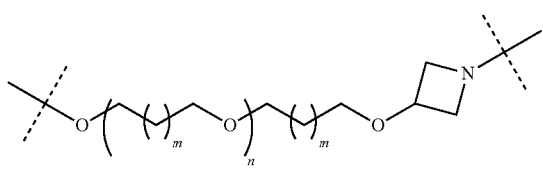
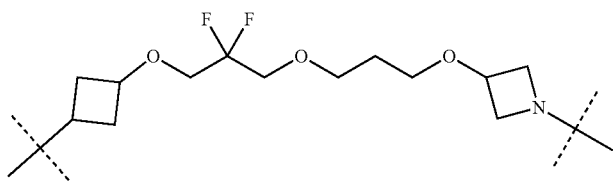
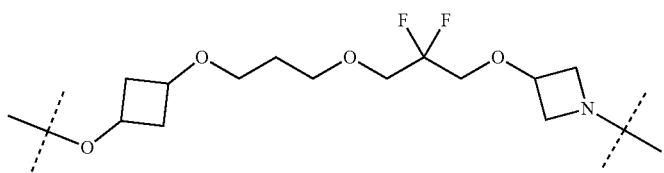
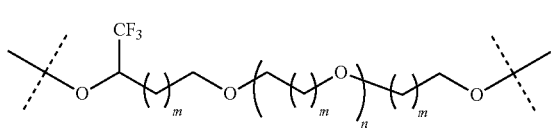
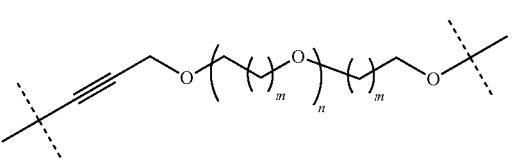
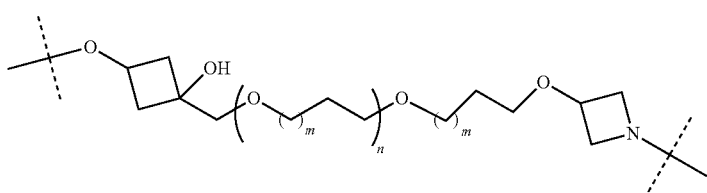
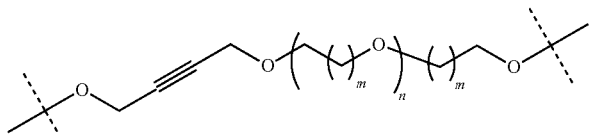
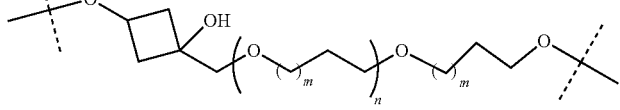

-continued
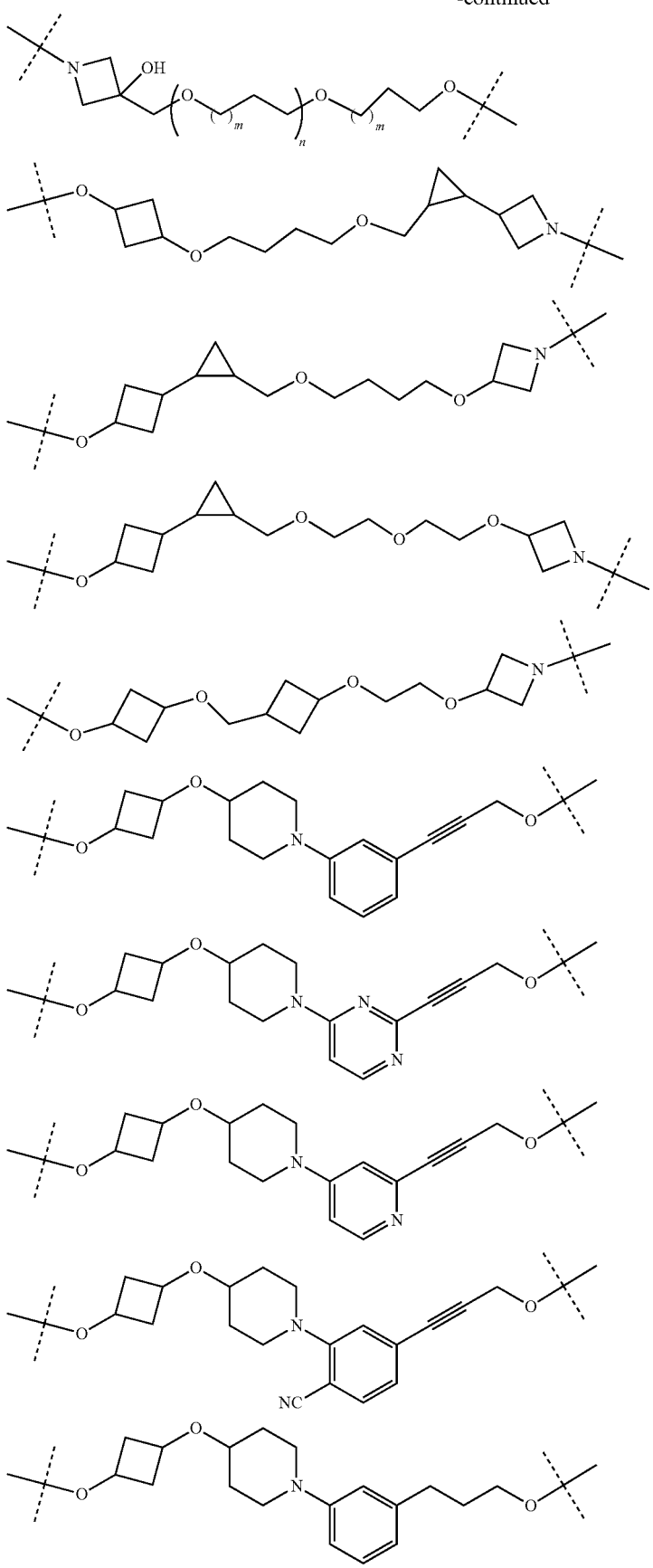

-continued
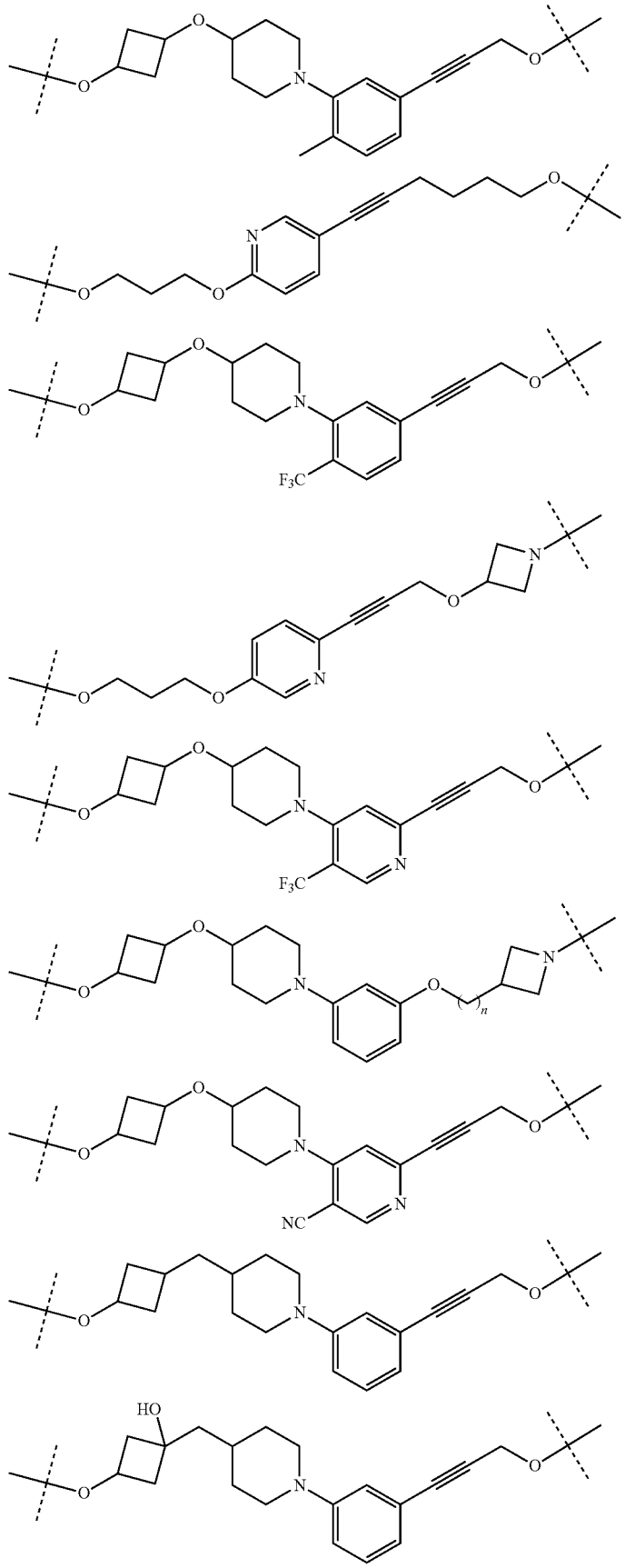

-continued
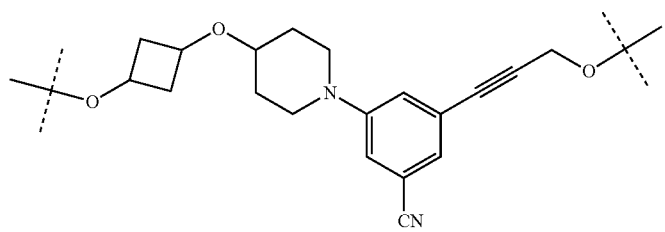
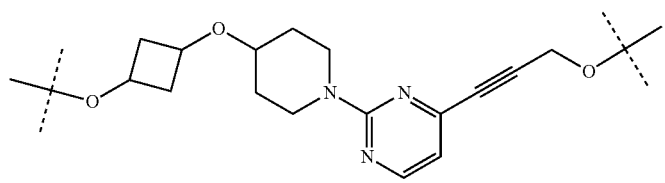
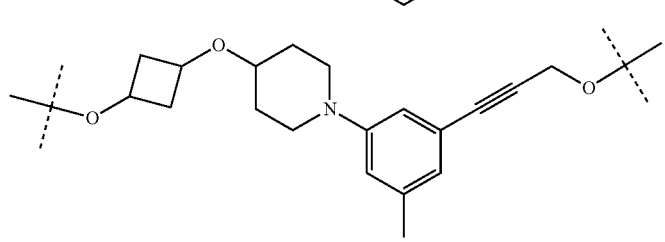
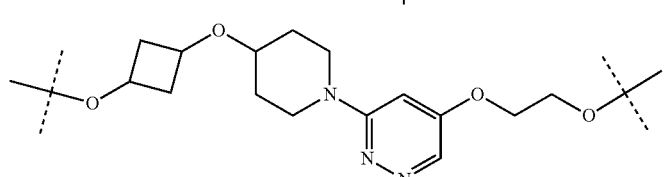
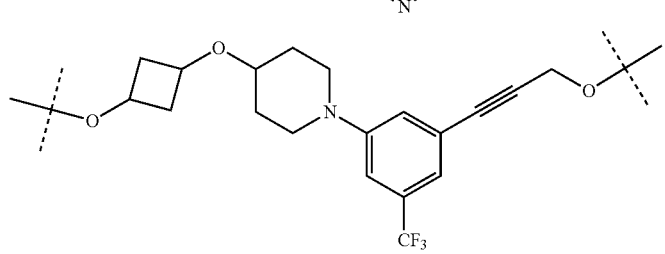
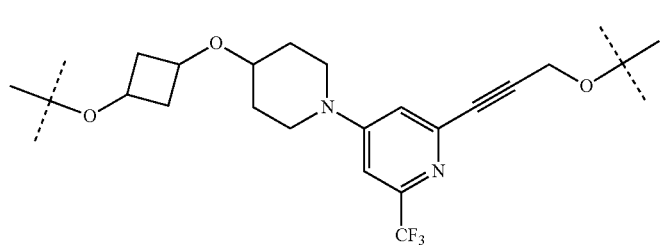
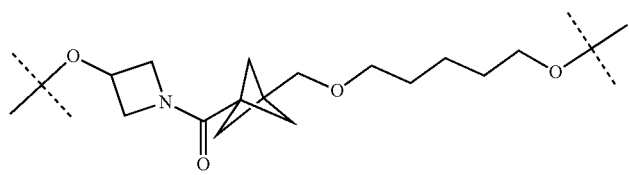

-continued
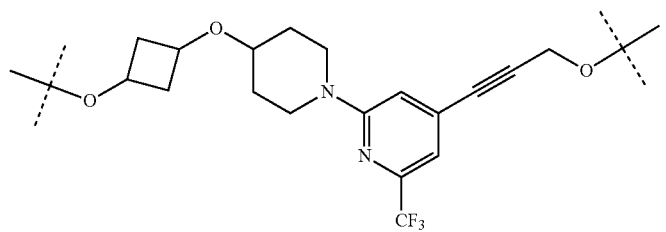
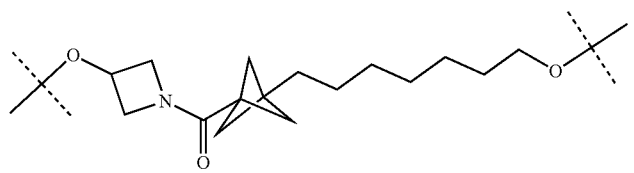
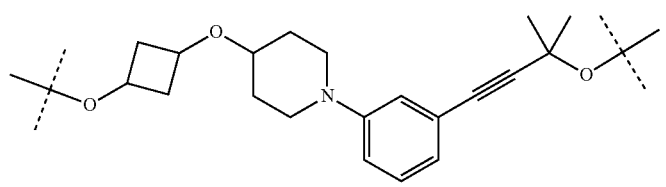
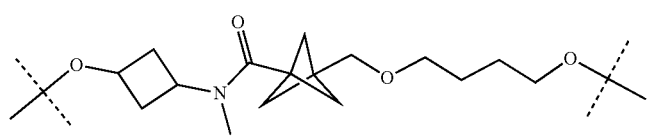
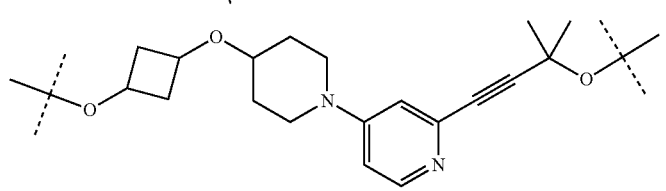
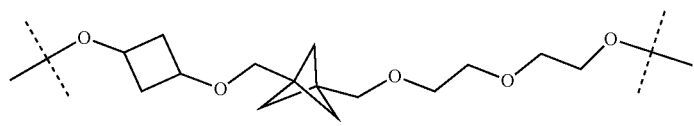
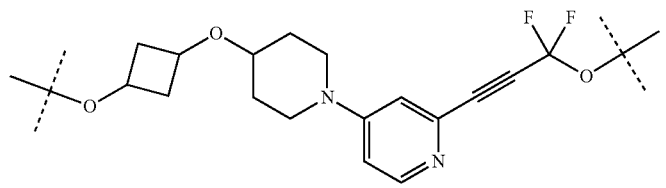
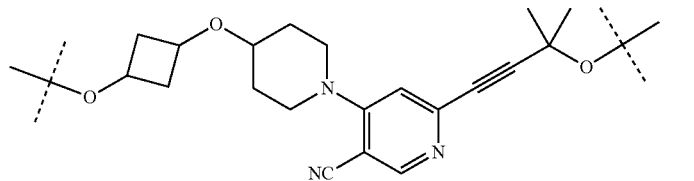
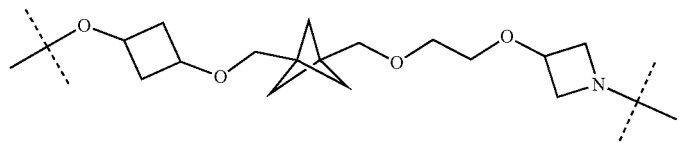

381
-continued
382
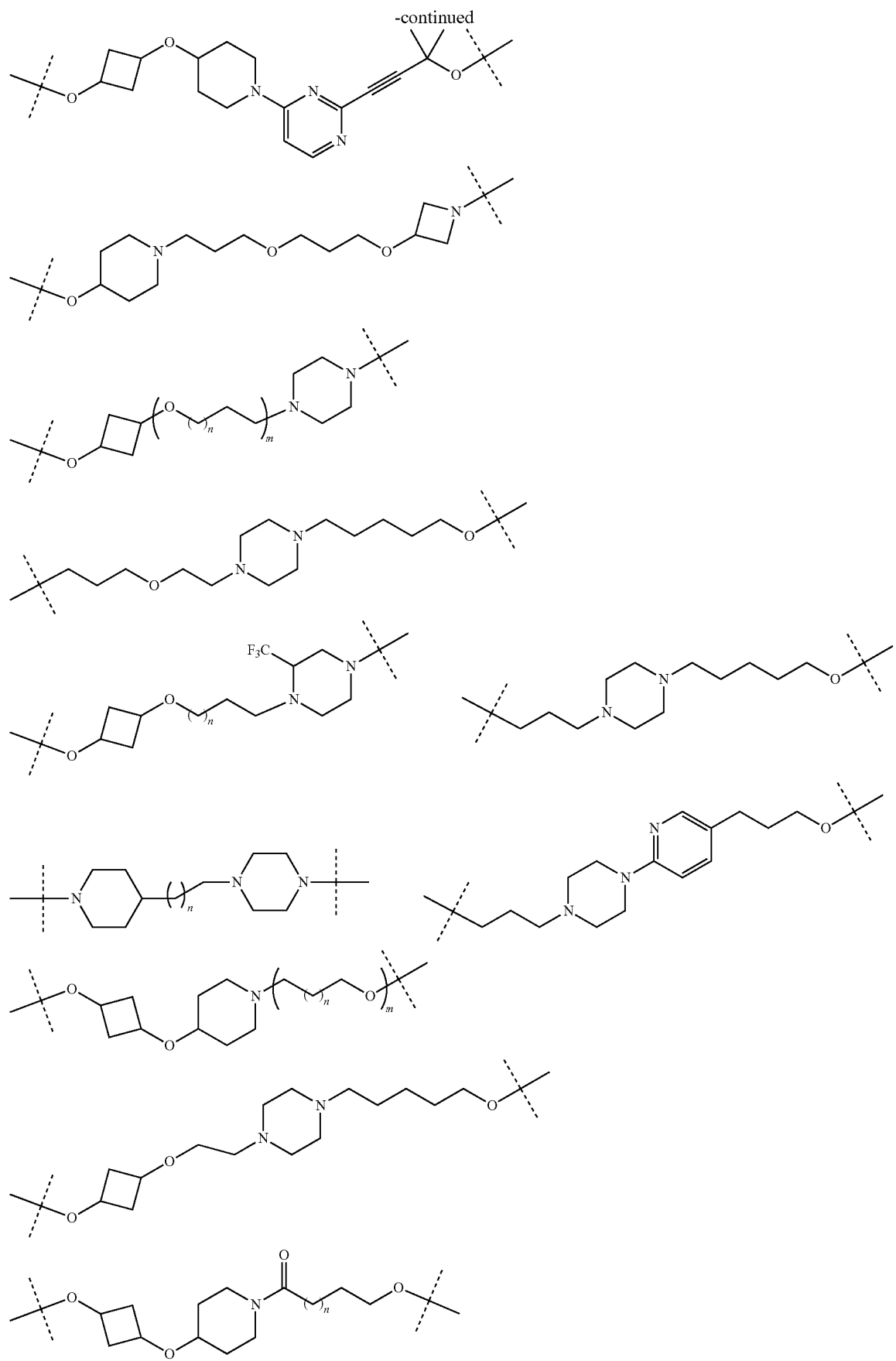

-continued
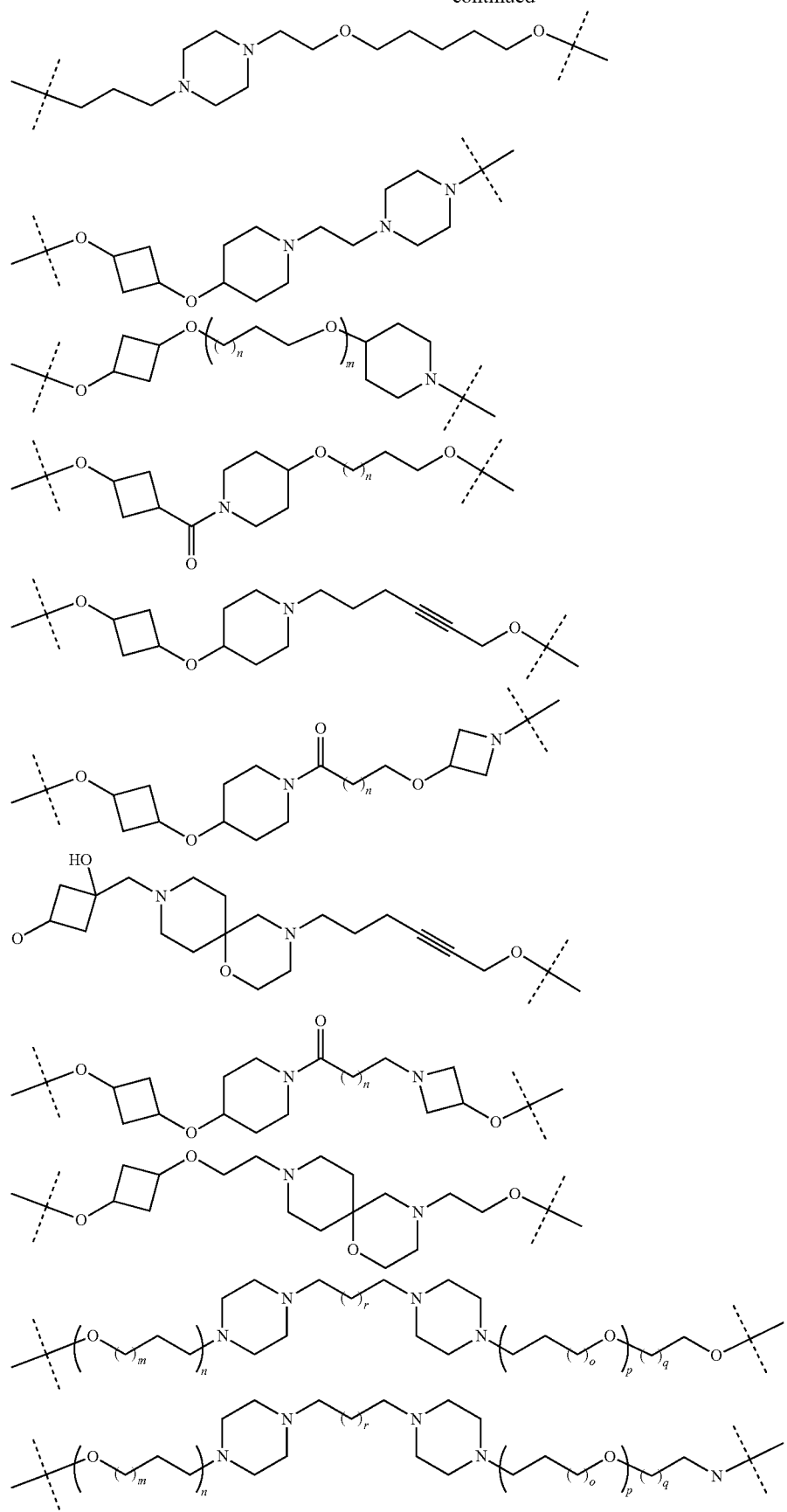

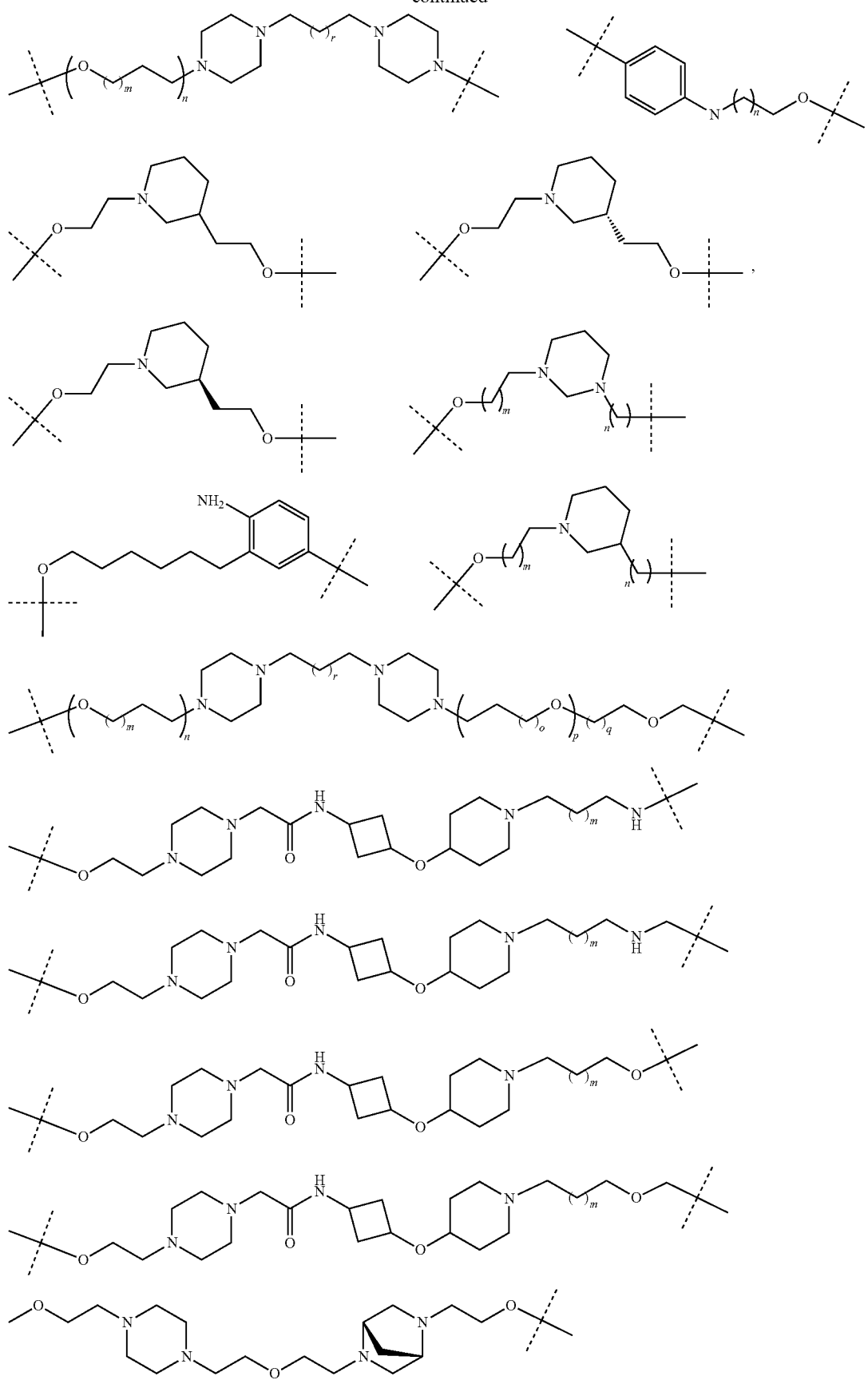

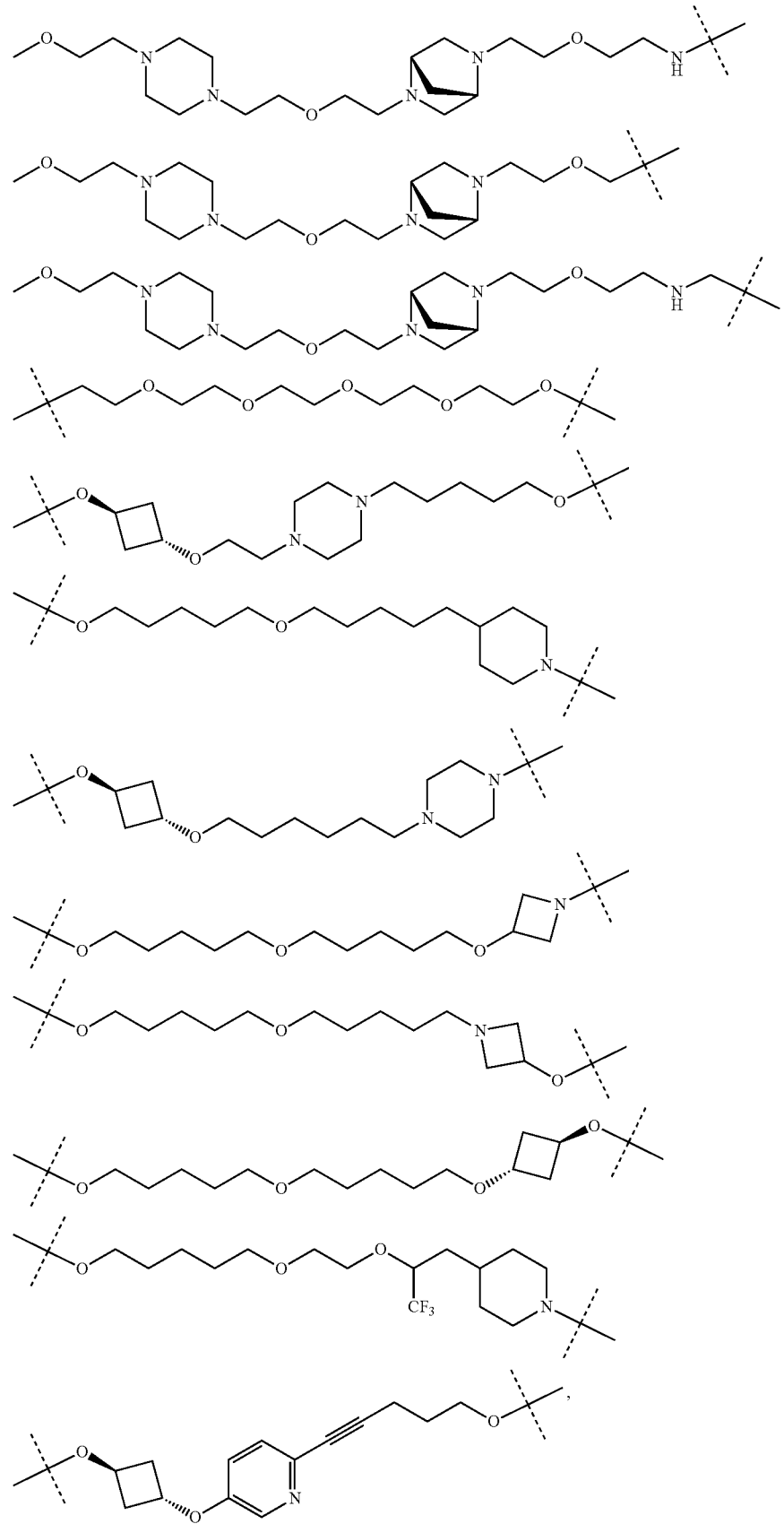

wherein each m, n, o, p, q, and r is independently 0, 1, 2, 3, 4, 5, 6, 7, 8, 9, 10, 11, 12, 13, 14, 15, 16, 17, 18, 19, or 20.
In various embodiments, L is selected from the group consisting of:
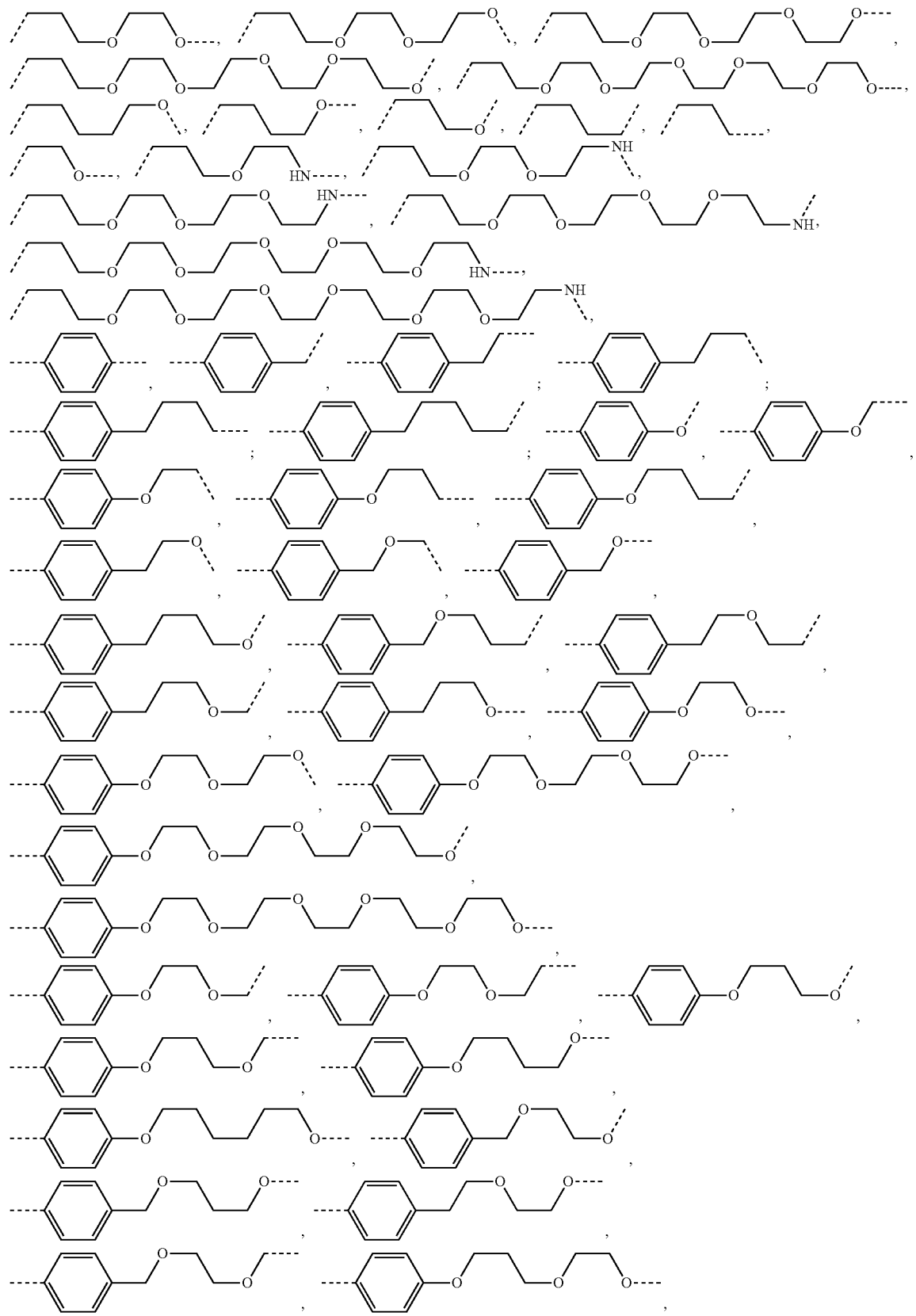

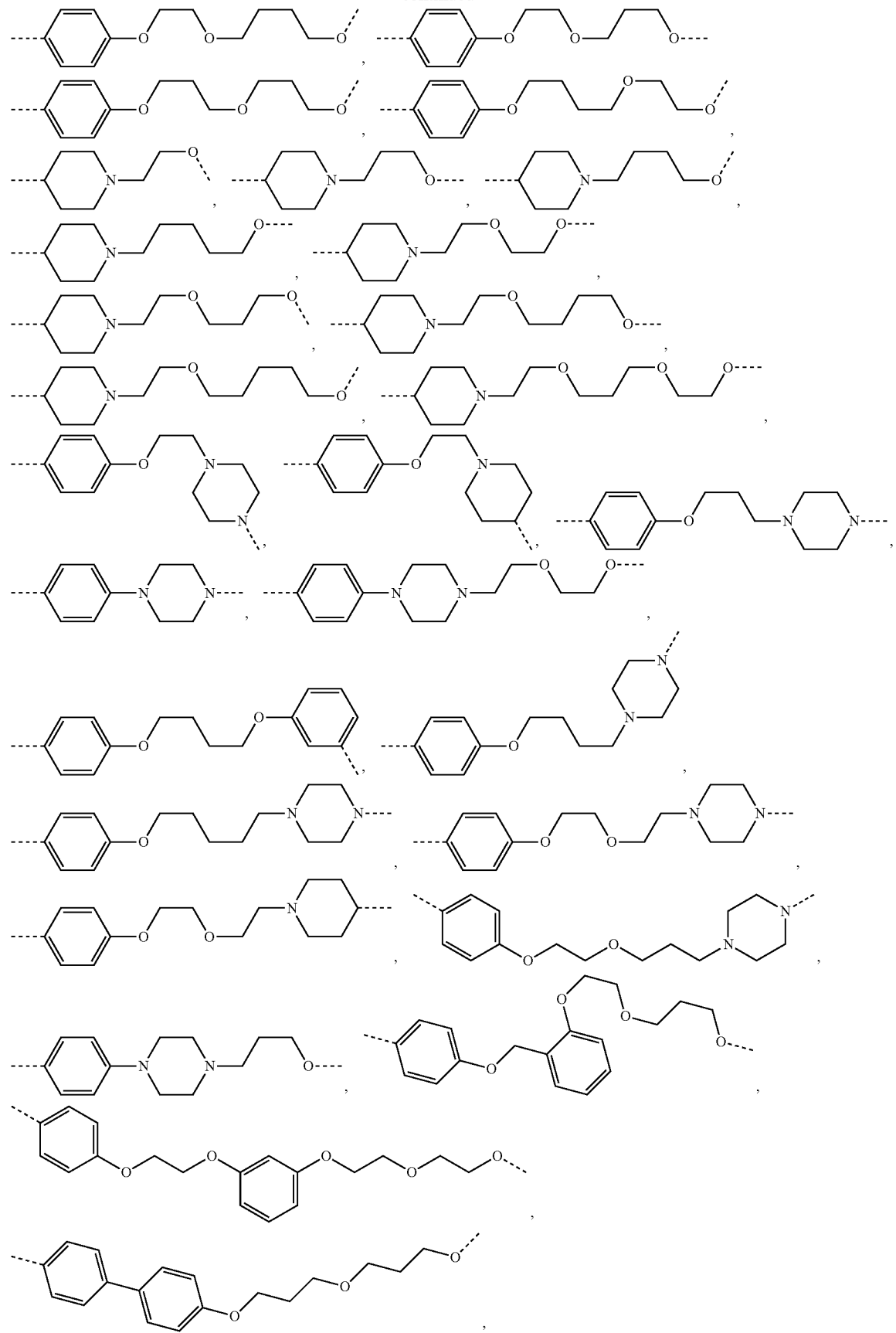

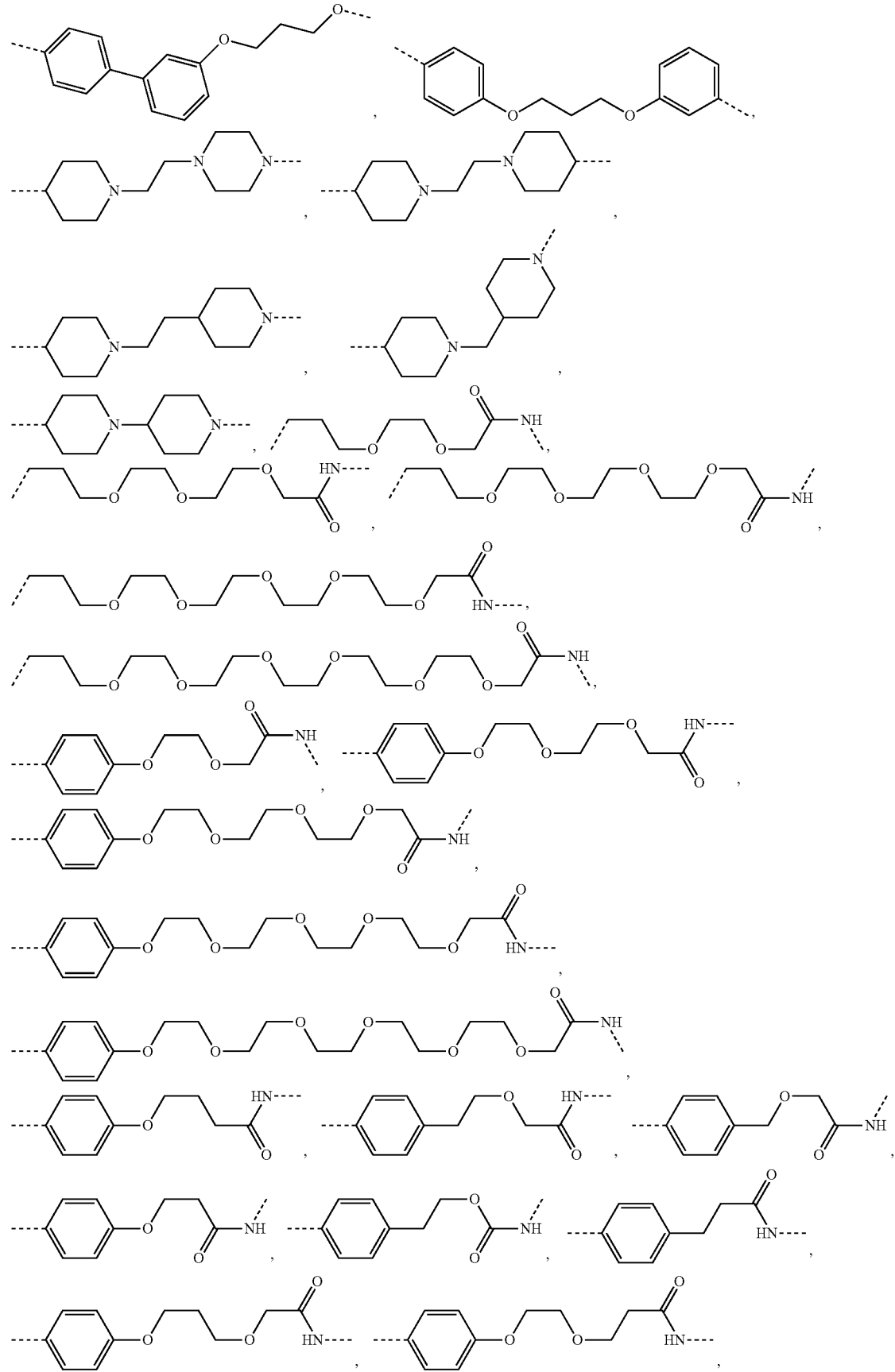

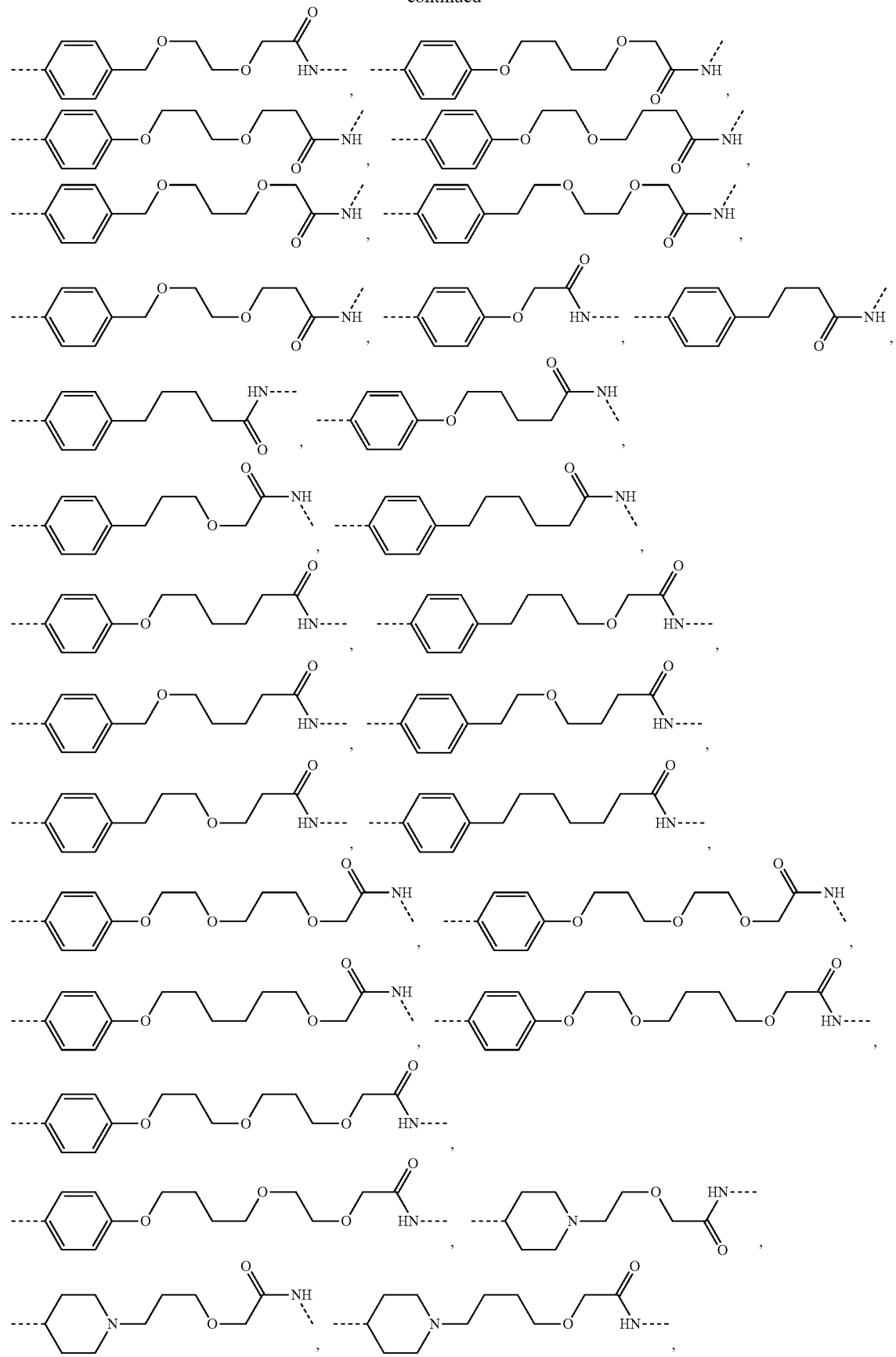

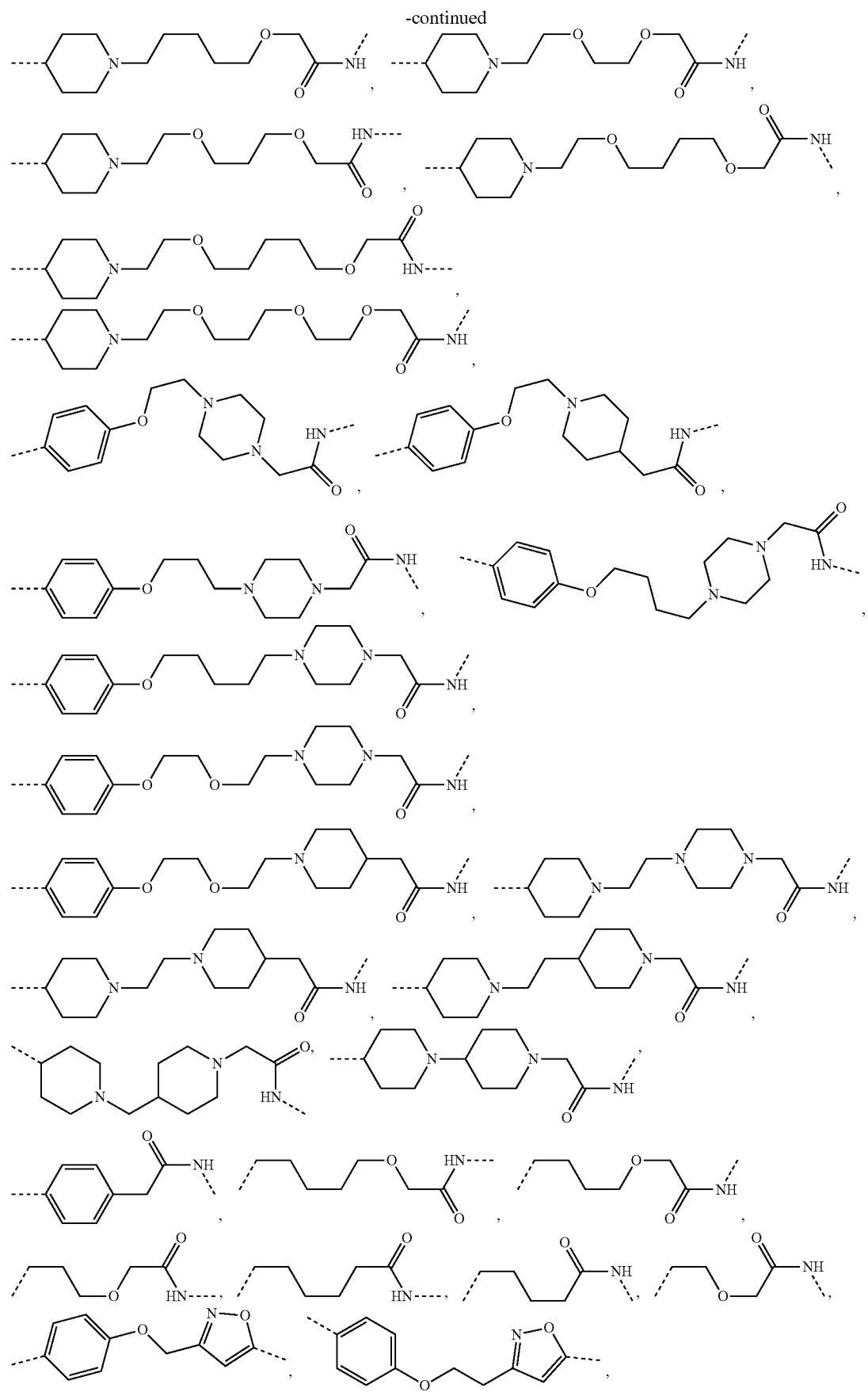
-continued

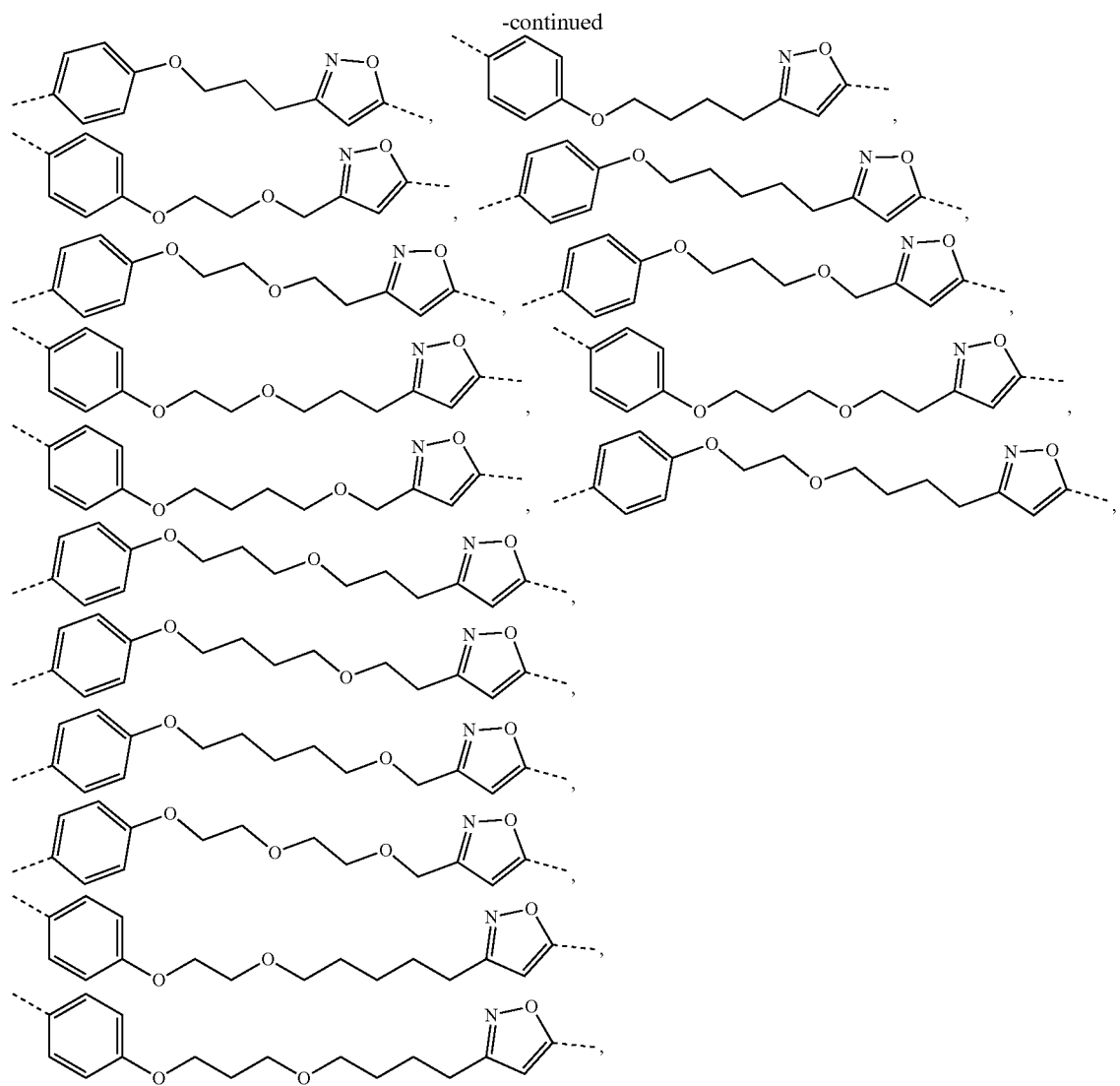
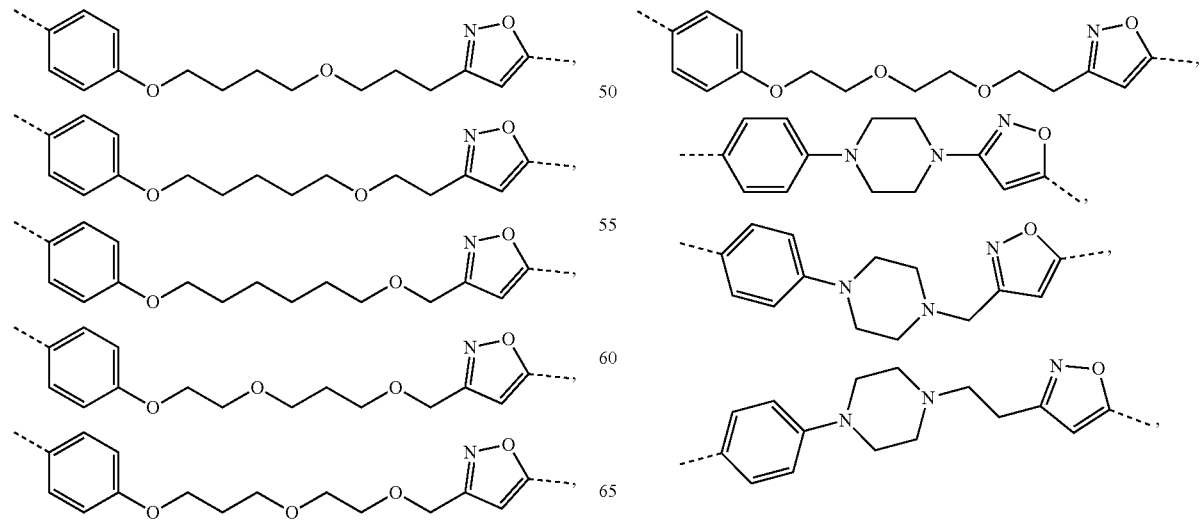

401
-continued
402
-continued
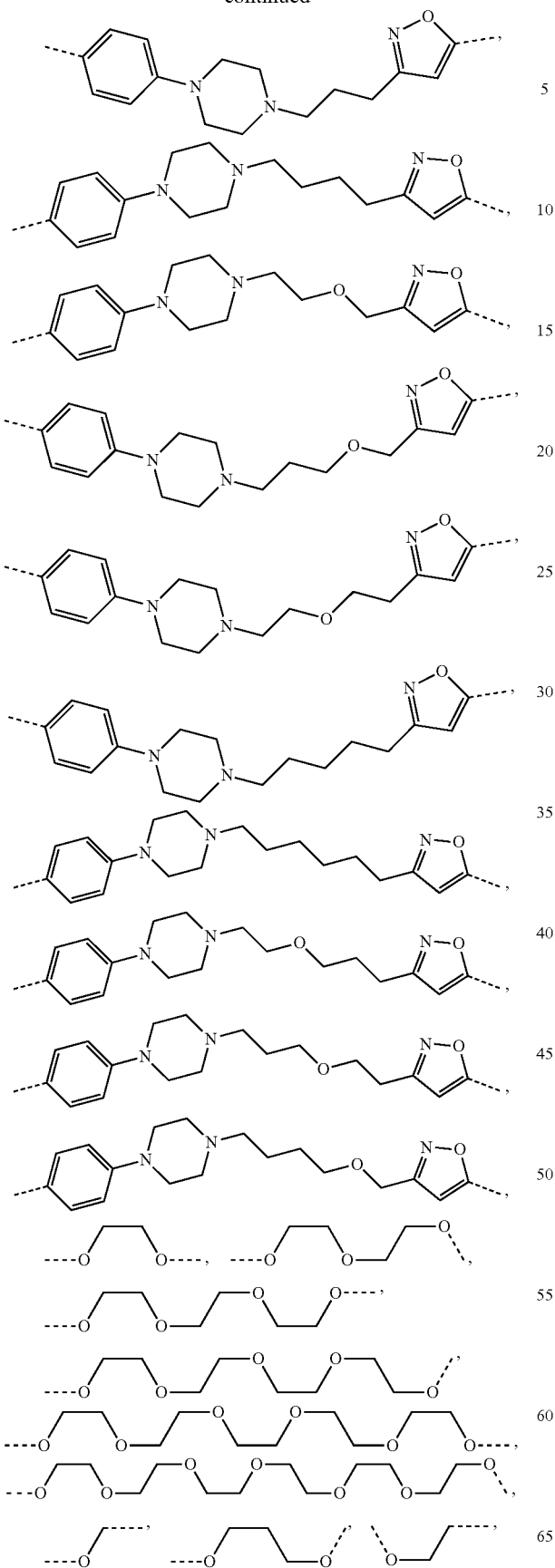
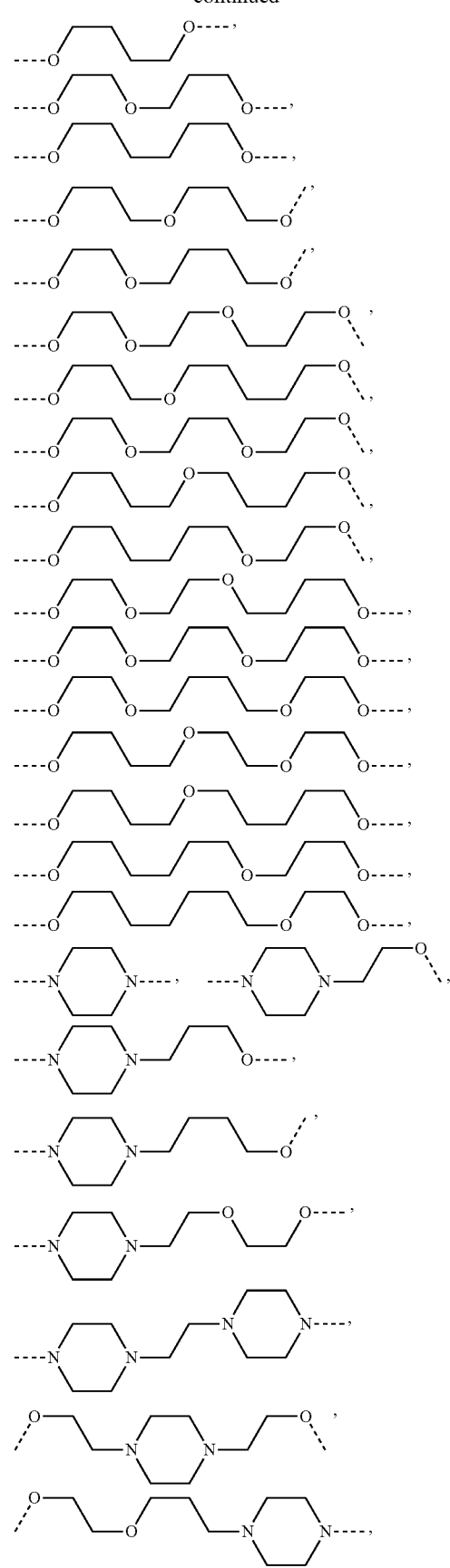

403
-continued
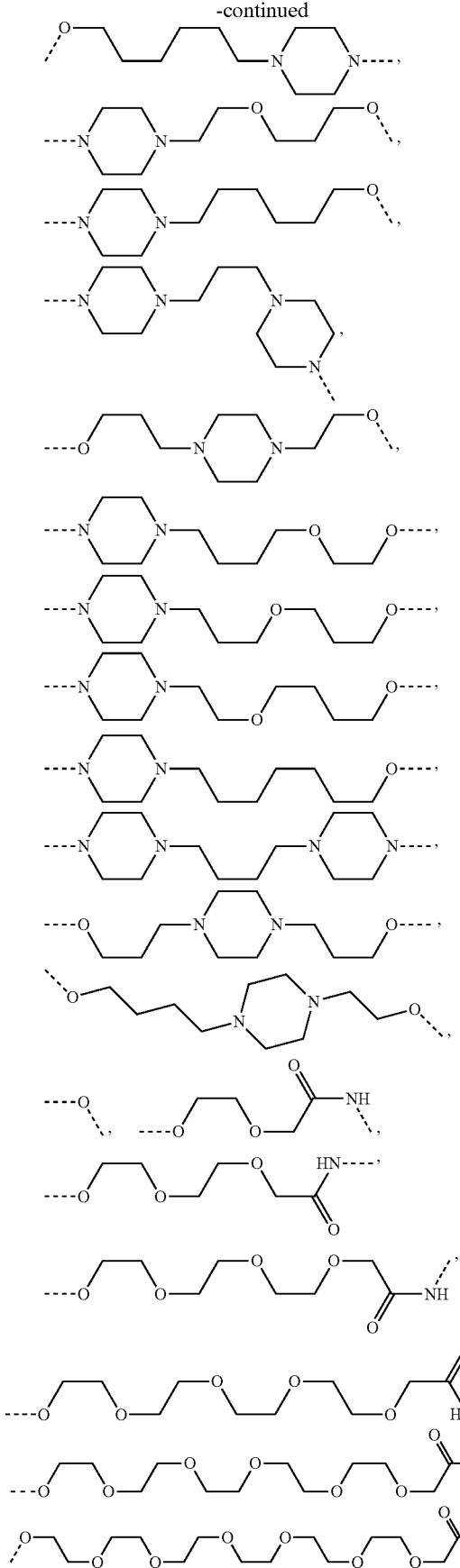
404
-continued
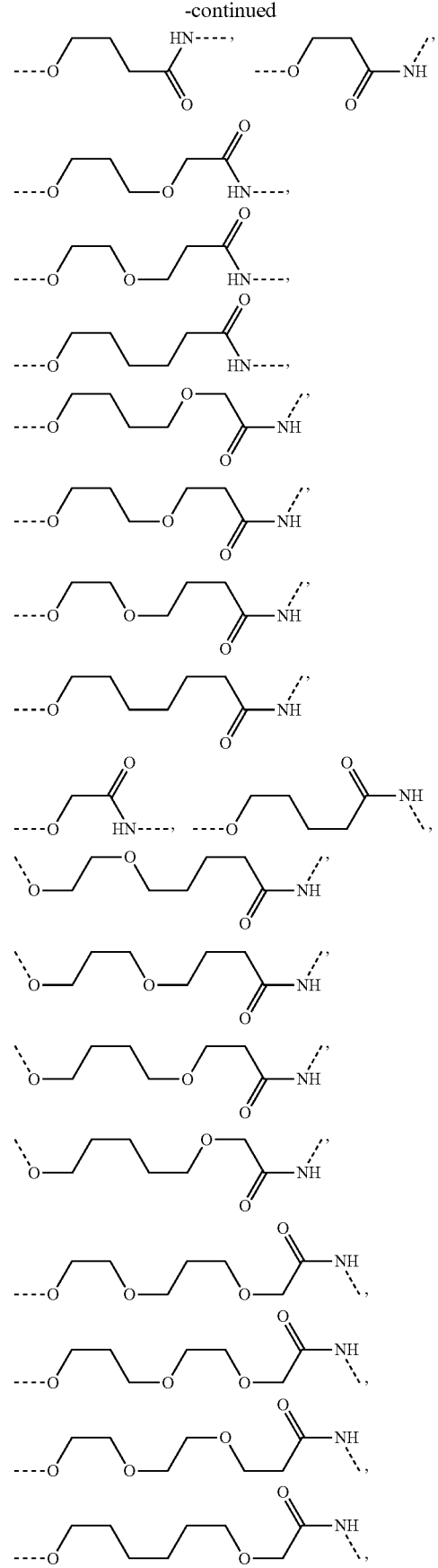

405
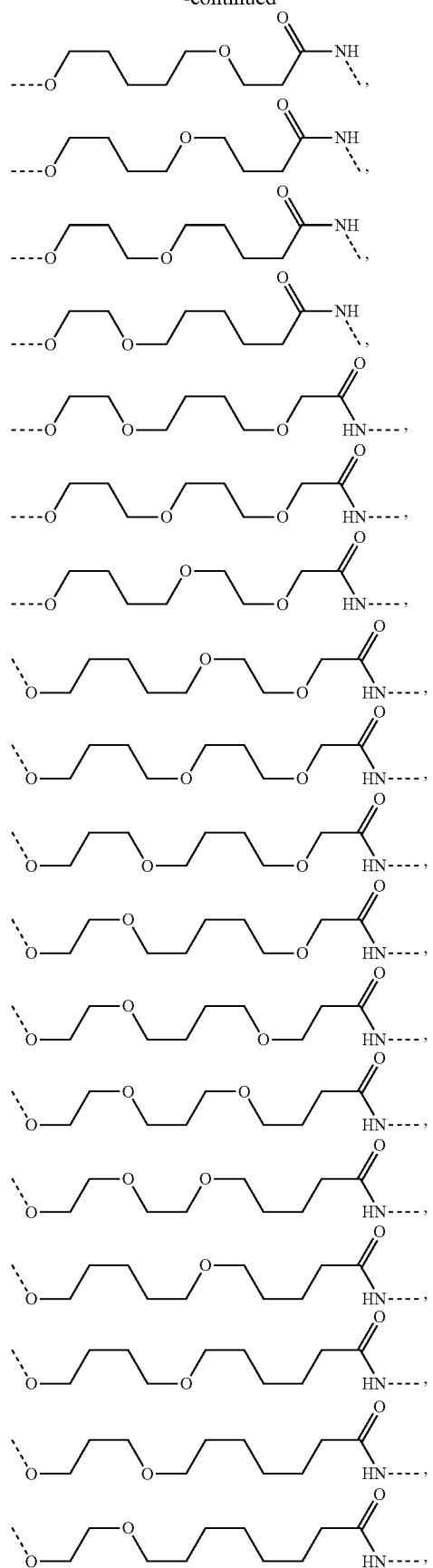
406
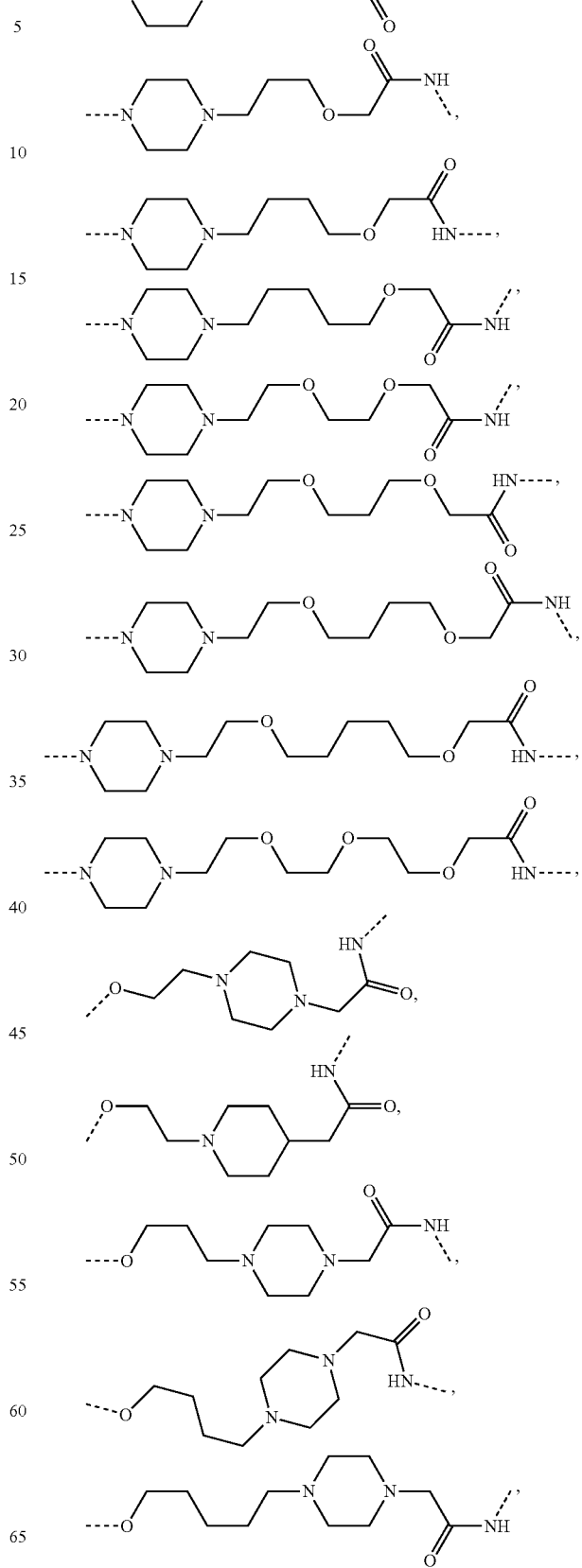

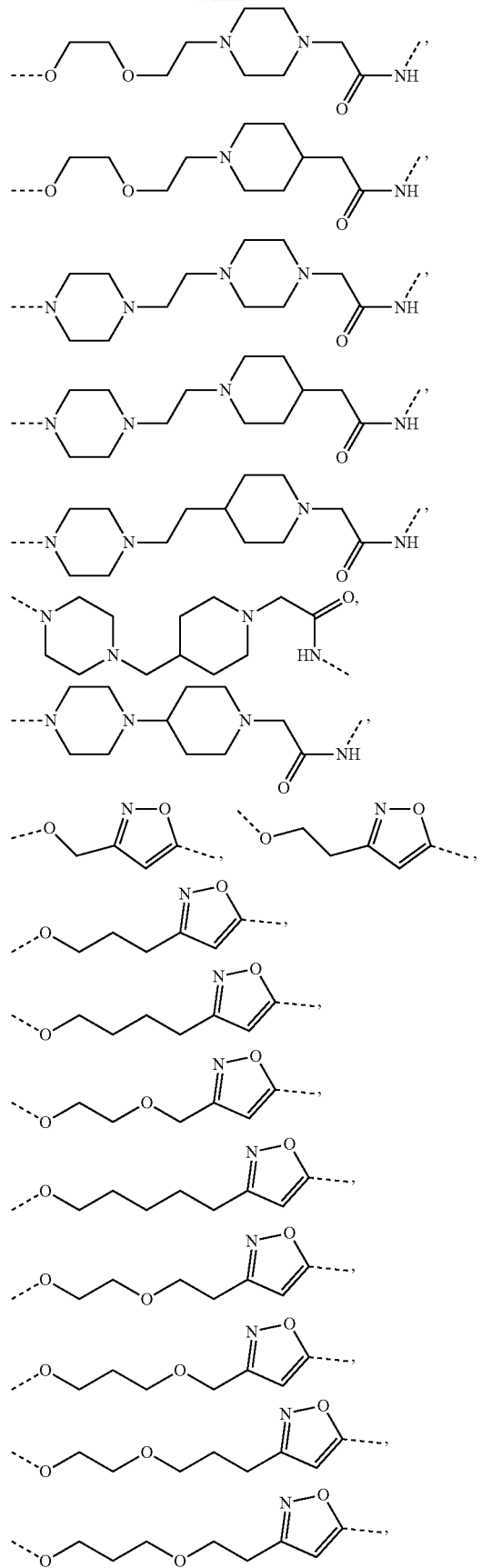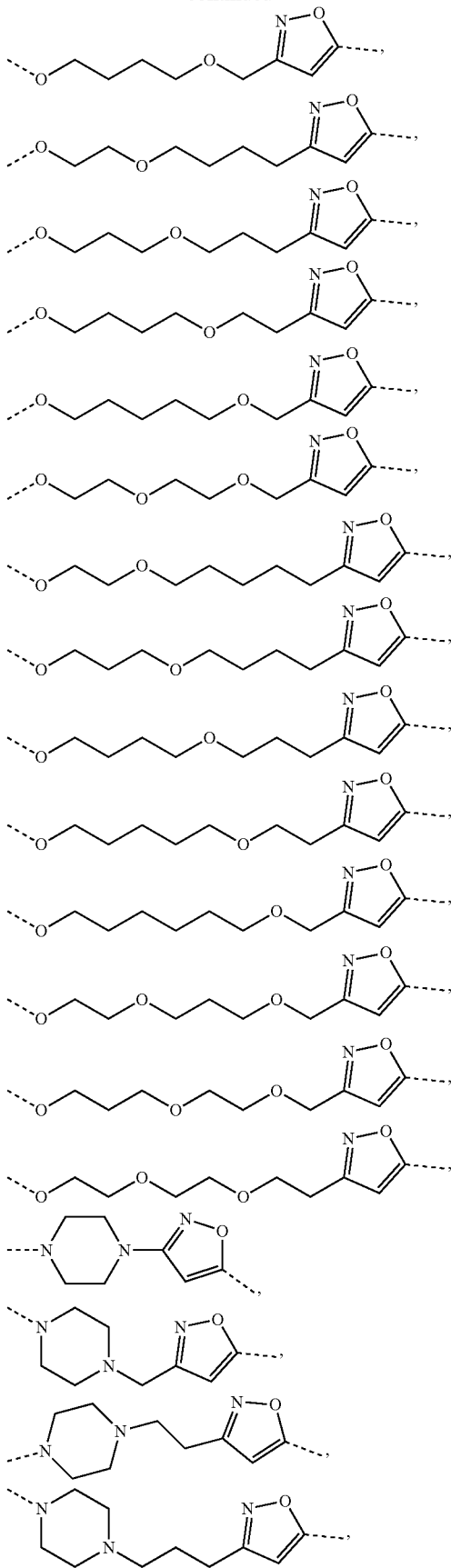

-continued

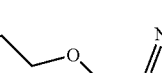

In additional embodiments, the linker (L) includes a structure selected from:

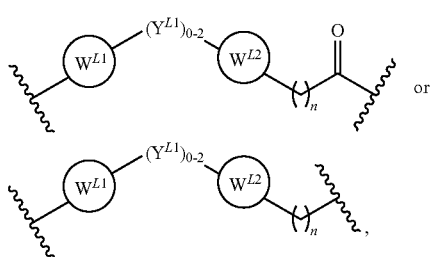

wherein:
at each occurrence $W^{L1}$ and $W^{L2}$ are each independently absent, a 4-8 membered ring with 0-4 heteroatoms, optionally substituted with $R^Q$, each $R^Q$ is independently a H, halogen, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;
at each occurrence $Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);
at each occurrence n is independently 0-10; and
a dashed line indicates the attachment point to the PTM or ULM moieties.

In additional embodiments, the linker (L) includes a structure selected from:

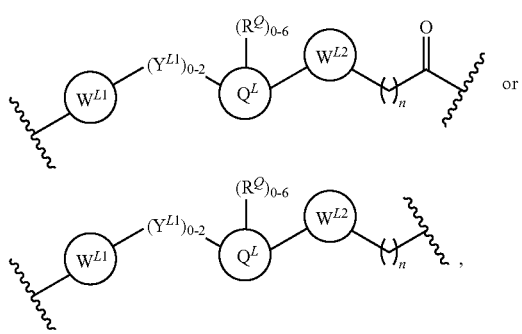

wherein:
at each occurrence $W^{L1}$ and $W^{L2}$ are each independently absent, aryl, heteroaryl, cyclic, heterocyclic, $C_{1-6}$ alkyl and optionally one or more C atoms are replaced with O, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halogen, OH, CN, $CF_3$, hydroxyl, nitro, C=CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;
at each occurrence $Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);
at each occurrence $Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halogen, $C_{1-6}$ alkoxyl), or 2 $R^Q$ groups taken together with the atom they are attached to, form a 3-8 membered ring system containing 0-2 heteroatoms);
at each occurrence $R^{YL1}$, $R^{YL2}$ are each independently H, OH, $C_{1-6}$ alkyl (linear, branched, optionally substituted by 1 or more halogen, $C_{1-6}$ alkoxyl), or $R^1$, $R^2$ together with the atom they are attached to, form a 3-8 membered ring system containing 0-2 heteroatoms);
at each occurrence n is 0-10; and
a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein or polypeptide (e.g., Bruton's tyrosine kinase (BTK) and/or a gain-of-function BTK mutant, including both wild-type and C481S mutant forms, which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

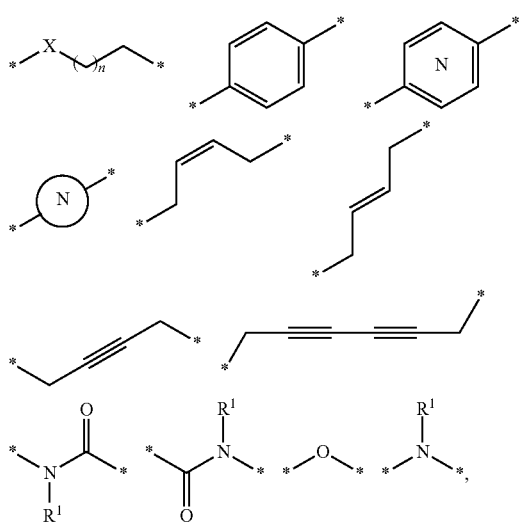

wherein
at each occurrence X is selected from the group consisting of O, N, S, S(=O) and SO$_2$;

n is integer from 1 to 5;
R$^{L1}$ is hydrogen or alkyl,

is a mono- or bicyclic aryl or heteroaryl optionally substituted with 1-3 substituents selected from alkyl, halogen, haloalkyl, hydroxy, alkoxy or cyano;

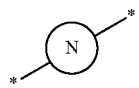

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in non-limiting embodiments of the present dislcosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. In certain non-limiting embodiments, the linker may be linked to an optionally substituted alkyl, alkylene, alkene or alkyne group, an aryl group or a heterocyclic group on the ULM and/or PTM groups.

Protein Targeting Moieties

In various embodiments, the PTM group is a group that binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: Bruton's tyrosine kinase (BTK) inhibitors, KRas inhibitors, Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest, such as Bruton's tyrosine kinase (BTK) and/or mutant BTKs, including gain-of-function BTK mutant(s), including both wild-type and C481S mutant forms. These binding moieties are linked to the ubiquitin ligase binding moiety preferably through a linker in order to present a target protein (to which the protein target moiety is bound), such as BTK and/or gain-of-function BTK mutant(s), in proximity to the ubiquitin ligase for ubiquitination and degradation.

The compounds described herein can be used to treat a number of disease states and/or conditions, including any disease state and/or condition in which proteins are dysregulated and where a patient would benefit from the degradation and/or inhibition of proteins.

In an additional embodiment, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer (including, e.g., pancreatic cancer, colon cancer, lung cancer, non-small cell lung cancer, or a combination thereof). In certain additional embodiments, the disease includes or is pancreatic cancer, colon cancer, colorectal cancer, lung cancer, non-small cell lung cancer, biliary tract malignancies, endometrial cancer, cervical cancer, bladder cancer, liver cancer, myeloid leukemia, breast cancer, or a combination thereof.

In alternative embodiments, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer (including, e.g., pancreatic cancer, colon cancer, colorectal cancer, lung cancer, non-small cell lung cancer, biliary tract malignancies, endometrial cancer, cervical cancer, bladder cancer, liver cancer, myeloid leukemia, breast cancer, or a combination thereof), by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another embodiment, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. For example, in any embodiment or embodiment described herein, the PTM is a small molecule comprising a Bruton's tyrosine kinase (BTK) targeting moiety. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. For example, in any embodiment or embodiment described herein, the PTM is a Bruton's tyrosine kinase (BTK) binding moiety.

These various protein targets, such as Bruton's tyrosine kinase (BTK), may be used in screens that identify compound moieties that bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Bruton's tyrosine kinase (BTK) inhibitors, KRas inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins. Exemplary protein target moieties according to the present disclosure include, Bruton's tyrosine kinase (BTK) inhibitors, KRas inhibitors, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest.

In various embodiments, the PTM is a Bruton's tyrosine kinase (BTK) binding/targeting moiety, e.g., a small molecule comprising a Bruton's tyrosine kinase (BTK) binding/targeting moiety. In any embodiment or embodiment described herein, the PTM binds mutant Bruton's tyrosine kinase (BTK), e.g. gain-of-function mutant BTKs. In a particular embodiment or embodiment described herein, the PTM has a chemical structure represented by:

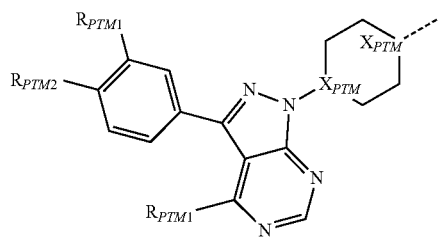

PTM-I wherein:
at each occurrence $X_{PTM}$ is independently N or optionally substituted CH;
at each occurrence $R_{PTM1}$ is independently $NR_{PTM9}R_{PTM10}$, H, optionally substituted C3-C6 cycloalkyl,
optionally substituted $C_3$-$C_6$ heteroalkyl, optionally substituted aryl (e.g., optionally substituted $C_5$-$C_7$ aryl), optionally substituted heteroaryl (e.g., optionally substituted $C_5$-$C_7$ heteroaryl),

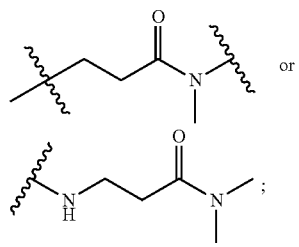

at each occurrence $R_{PTM9}$ and $R_{PTM10}$ are each independently H, —(C=O)—$R_{PTM9}$', optionally substituted $C_1$-$C_6$ alkyl;
at each occurrence $R_{PTM9'}$ is optionally substituted linear or branched alkyl, optionally substituted alkene;
at each occurrence $R_{PTM2}$ is H, —O—$R_{PTM3}$, optionally substituted linear or branched alkyl;
at each occurrence $R_{PTM3}$ is optionally substituted aryl or optionally substituted heteroaryl; and
the ⤴ indicates the site of attachment of at least one of a linker, ULM, ULM', CLM, CLM', VLM, VLM', ILM, ILM', MLM, MLM', or a combination thereof.

In various embodiments, the PTM has the structure:

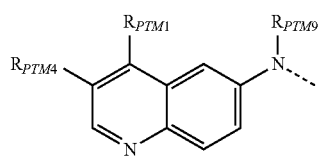

PTM-II wherein:
at each occurrence $R_{PTM1}$ is independently $N_{RPTM9}R_{PTM10}$, H, optionally substituted $C_3$-$C_6$ cycloalkyl, optionally substituted $C_3$-$C_6$ heteroalkyl, optionally substituted aryl (e.g., optionally substituted $C_5$-$C_7$ aryl), optionally substituted heteroaryl (e.g., optionally substituted $C_5$-$C_7$ heteroaryl),

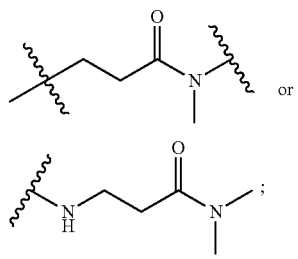

at each occurrence $R_{PTM9}$ and $R_{PTM10}$ is independently H, —(C=O)—$R_{PTM9'}$, optionally substituted $C_1$-$C_6$ alkyl;
at each occurrence $R_{PTM9'}$ is optionally substituted linear or branched alkyl, optionally substituted alkene;
at each occurrence $R_{PTM4}$ is H, —CN, or optionally substituted linear or branched alkyl;
at each occurrence the ⤴ indicates the site of attachment of at least one of a linker, ULM, ULM', CLM, CLM', VLM, VLM', ILM, ILM', MLM, MLM', or a combination thereof as described herein.

In various embodiments, the PTM is selected from:

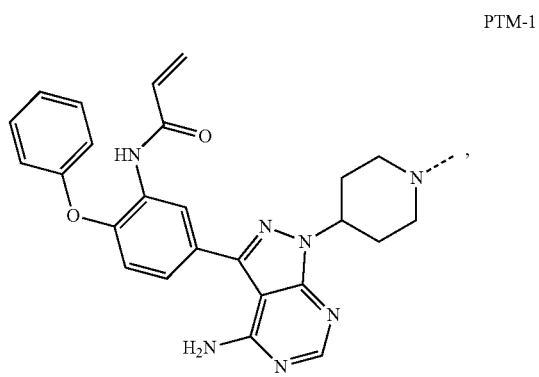

PTM-1

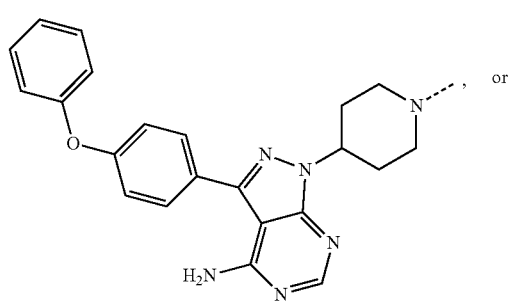

PTM-2

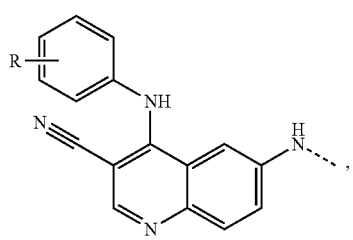

PTM-3 wherein R is an optional substitution.

In various embodiments, the PTM has the structure:

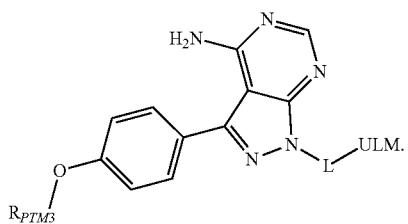

PTM-I-A

In various embodiments, the PTM has the structure:

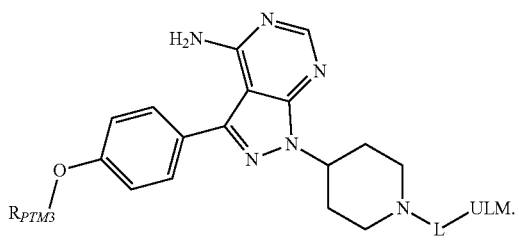

PTM-I-B

In various embodiments, in the compound of formula PTM-I-A or PTM-I-B, $R_{PTM3}$ is phenyl. In various embodiments, L in PTM-I-A or PTM-I-B is selected from the group consisting of L-1, L-2, L-3, L-4, L-5, L-6, L-7, L-8, L-9, L-10, L-11, L-12, L-13, L-14, L-15, L-16, L-17, L-18, L-19, L-20, L-21, and L-22. In various embodiments, in the compound of formula PTM-I-A or PTM-I-B, the ULM is ULM-3. In various embodiments, in the compound of formula PTM-I-A or PTM-I-B, L is L-16.

In various embodiments, the compound or PROTAC of the present disclosure includes a PTM from Table 1 (e.g., PTM-1, PTM-2, PTM-3), a linker from Table 2 (e.g., L-1, L-2, L-3, L-4, L-5, L-6, L-7, L-8, L-9, L-10, L-11, L-12, L-13, L-14, L-15, L-16, L-17, L-18, L-19, L-20, L-21, or L-22), and at least one ULM from Table 3 (e.g., ULM-1, ULM-2, ULM-3, ULM-4, or ULM-5), including salts, prodrugs, polymorphs, analogs, derivatives, and deuterated forms thereof:

TABLE 1

Exemplary PTMs of exemplary PROTACs of the present disclosure

| PTM No. | Chemical Structure |
|---|---|
| PTM-1 | 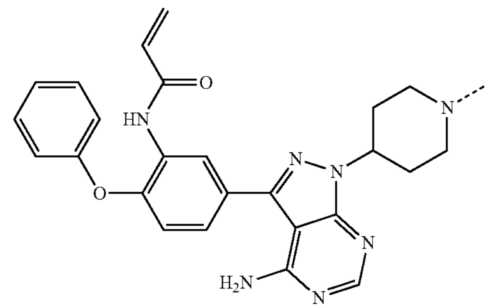 |
| PTM-2 | 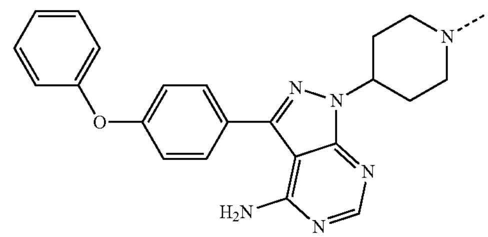 |
| PTM-3 | 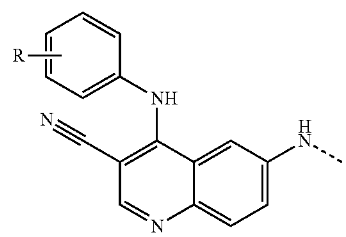 |

TABLE 2

Exemplary linkers of exemplary PROTACs of the present disclosure

| Linker No. | Chemical Structure |
|---|---|
| L-1 | 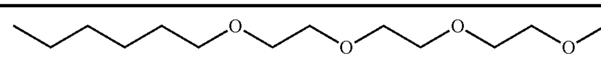 |
| L-2 | 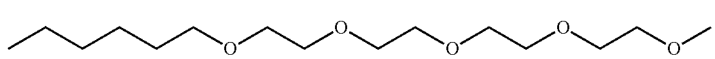 [SMILES: CCCCCCOCCOCCOCCOCCOC] |
| L-3 | 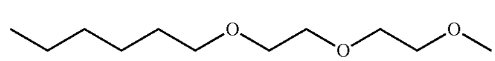 |
| L-4 | 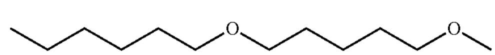 |
| L-5 | 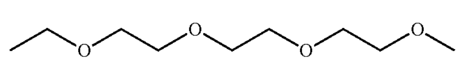 |
| L-6 | 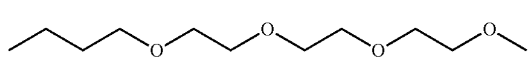 |
| L-7 | 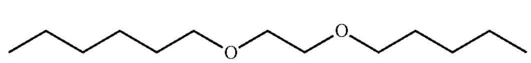 |

TABLE 2-continued
Exemplary linkers of exemplary PROTACs of the present disclosure
| Linker No. | Chemical Structure |
|---|---|
| L-8 | 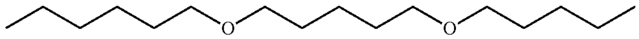 [SMILES: CCCCCCOCCCCCOCCCCC] |
| L-9 | 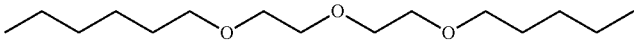 [SMILES: CCCCCCOCCOCCOCCCCC] |
| L-10 | 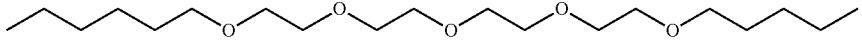 [SMILES: CCCCCCOCCOCCOCCOCCOCCCCC] |
| L-11 | 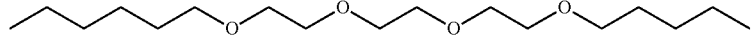 [SMILES: CCCCCCOCCOCCOCCOCCCCC] |
| L-12 | 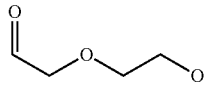 |
| L-13 | 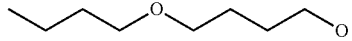 |
| L-14 | 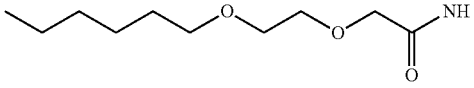 |
| L-15 | 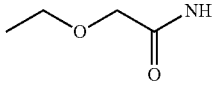 |
| L-16 | 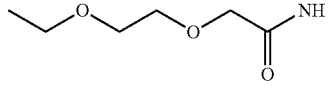 |
| L-17 | 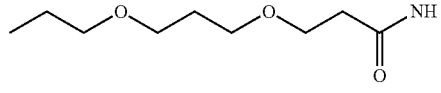 |
| L-18 | 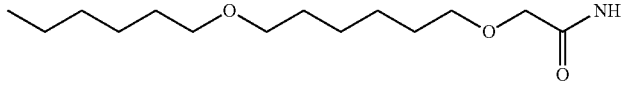 [SMILES: CCCCCCOCCCCCCOCC(N)=O] |
| L-19 | 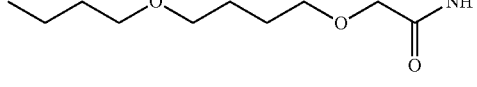 |
| L-20 | 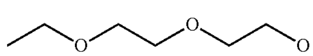 |
| L-21 | 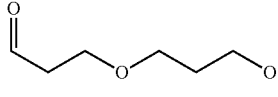 |
| L-22 | 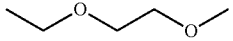 |

TABLE 3
Exemplary ULMs of exemplary PROTACs of the present disclosure
| ULM No. | Chemical Structure |
|---|---|
| ULM-1 | 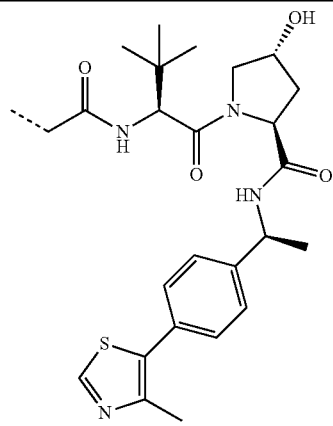 |
| ULM-2 | 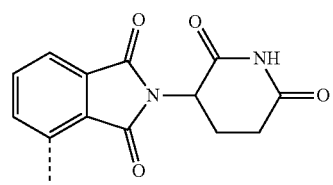 |
| ULM-3 | 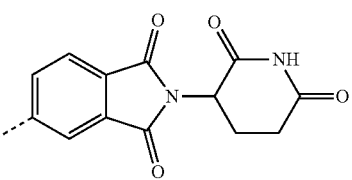 |
TABLE 3-continued
Exemplary ULMs of exemplary PROTACs of the present disclosure
| ULM No. | Chemical Structure |
|---|---|
| ULM-4 | 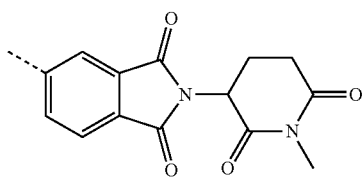 |
| ULM-5 | 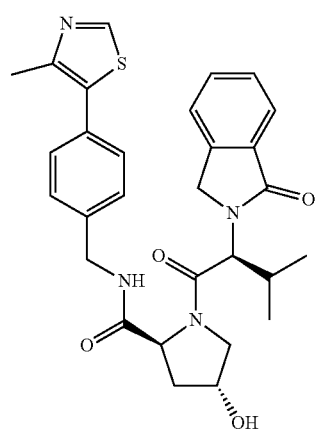 [SMILES: Cc1ncsc1-c1ccc(CNC(=O)[C@@H]2C[C@@H](O)CN2C(=O)[C@H](C(C)C)N2Cc3ccccc3C2=O)cc1] |

TABLE 4

Exemplary PROTACs of the Present Disclosure

| Cmpd No. | Chemical Structure | Cmpd Name | MH+ |
|---|---|---|---|
| 100 | 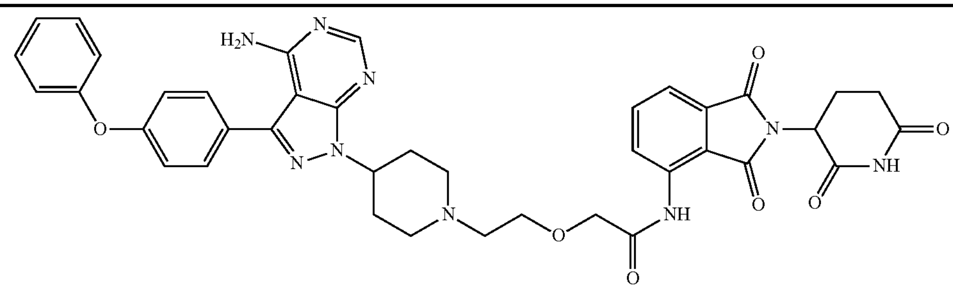 | 2-(2-(4-(4-amino-3-(4-phenoxyphenyl)-1H-pyrazolo[3,4-d]pyrimidin-1-yl)piperidin-1-yl)ethoxy)-N-(2-(2,6-dioxopiperidin-3-yl)-1,3-dioxoisoindolin-4-yl)acetamide | |
| 101 | 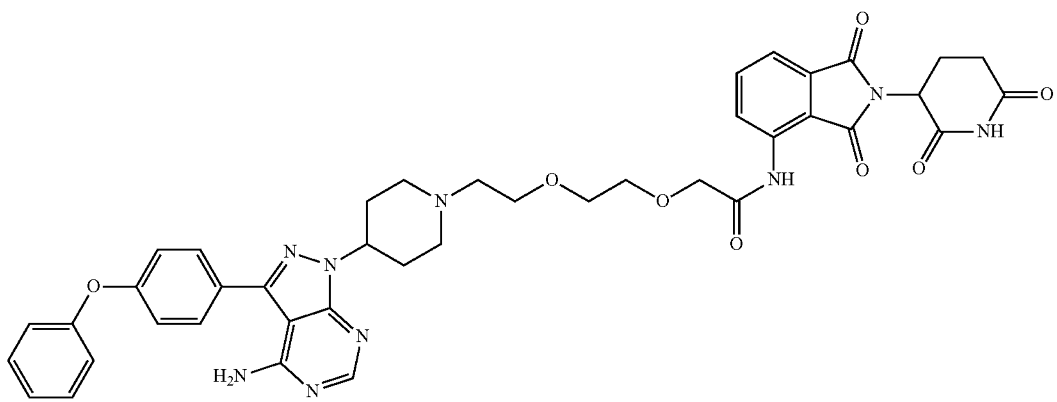 [SMILES: Nc1ncnc2c1c(-c1ccc(Oc3ccccc3)cc1)nn2C1CCN(CCOCCOCC(=O)Nc2cccc3c2C(=O)N(C2CCC(=O)NC2=O)C3=O)CC1] | 2-(2-(2-(4-(4-amino-3-(4-phenoxyphenyl)-1H-pyrazolo[3,4-d]pyrimidin-1-yl)piperidin-1-yl)ethoxy)ethoxy)-N-(2-(2,6-dioxopiperidin-3-yl)-1,3-dioxoisoindolin-4-yl)acetamide | 788.3 |

TABLE 4-continued

Exemplary PROTACs of the Present Disclosure

| Cmpd No. | Chemical Structure | Cmpd Name | MH+ |
|---|---|---|---|
| 102 | 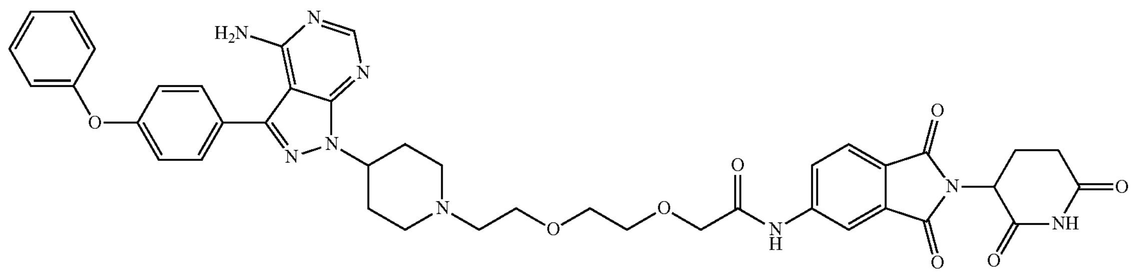 [SMILES: Nc1ncnc2c1c(-c1ccc(Oc3ccccc3)cc1)nn2C1CCN(CCOCCOCC(=O)Nc2ccc3c(c2)C(=O)N(C2CCC(=O)NC2=O)C3=O)CC1] | 2-(2-(2-(4-(4-amino-3-(4-phenoxyphenyl)-1H-pyrazolo[3,4-d]pyrimidin-1-yl)piperidin-1-yl)ethoxy)ethoxy)-N-(2-(2,6-dioxopiperidin-3-yl)-1,3-dioxoisoindolin-5-yl)acetamide | 788.3 |
| 103 | 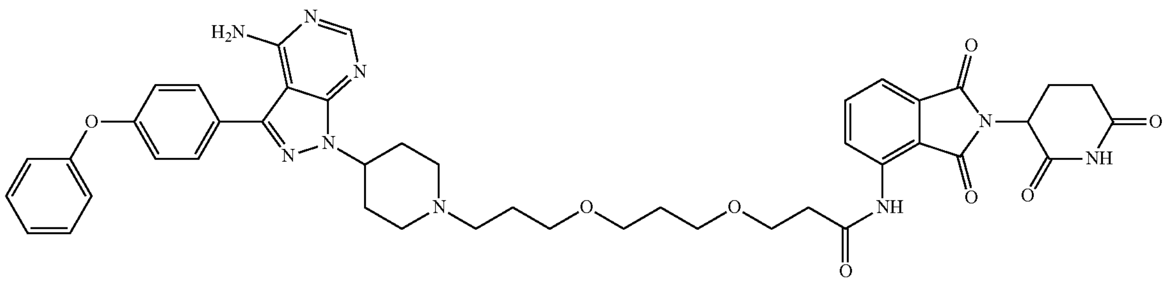 [SMILES: Nc1ncnc2c1c(-c1ccc(Oc3ccccc3)cc1)nn2C1CCN(CCCOCCCOCCC(=O)Nc2cccc3c2C(=O)N(C2CCC(=O)NC2=O)C3=O)CC1] | 3-(3-(4-(4-amino-3-(4-phenoxyphenyl)-1H-pyrazolo[3,4-d]pyrimidin-1-yl)piperidin-1-yl)propoxy)propoxy)-N-(2-(2,6-dioxopiperidin-3-yl)-1,3-dioxoisoindolin-4-yl)propanamide | 830.3 |
| 104 | 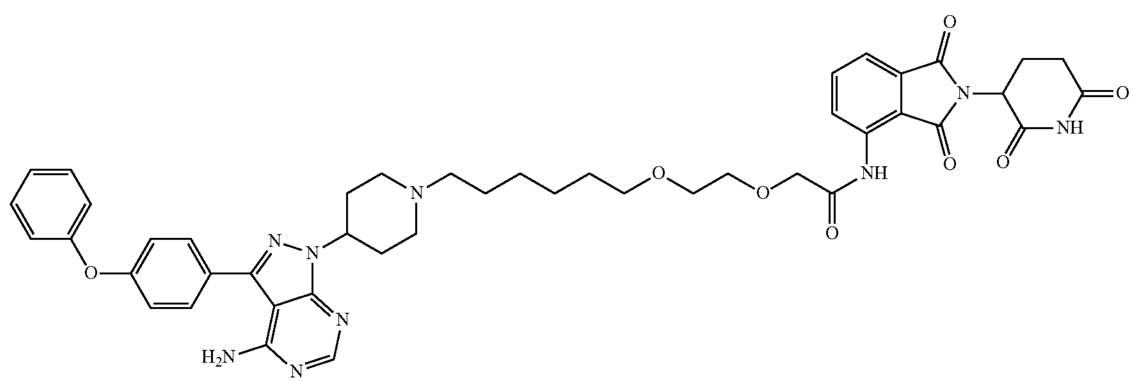 [SMILES: Nc1ncnc2c1c(-c1ccc(Oc3ccccc3)cc1)nn2C1CCN(CCCCCCOCCOCC(=O)Nc2cccc3c2C(=O)N(C2CCC(=O)NC2=O)C3=O)CC1] | 2-(2-(6-(4-(4-amino-3-(4-phenoxyphenyl)-1H-pyrazolo[3,4-d]pyrimidin-1-yl)piperidin-1-yl)hexyloxy)ethoxy)-N-(2-(2,6-dioxopiperidin-3-yl)-1,3-dioxoisoindolin-4-yl)acetamide | 844.5 |

TABLE 4-continued

Exemplary PROTACs of the Present Disclosure

| Cmpd No. | Chemical Structure | Cmpd Name | MH+ |
|---|---|---|---|
| 105 | 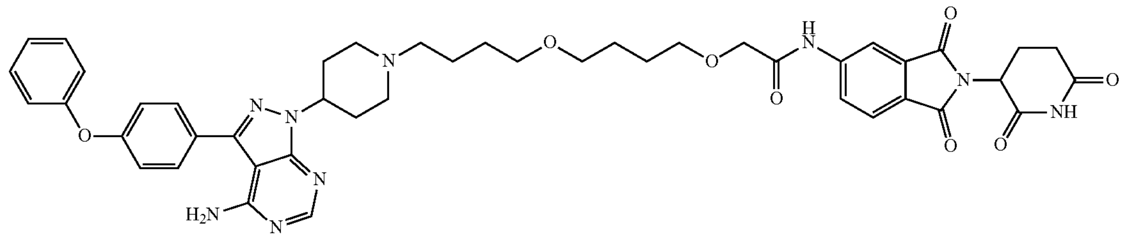 [SMILES: Nc1ncnc2c1c(-c1ccc(Oc3ccccc3)cc1)nn2C1CCN(CCCCOCCCCOCC(=O)Nc2ccc3c(c2)C(=O)N(C2CCC(=O)NC2=O)C3=O)CC1] | 2-(4-(4-(4-amino-3-(4-phenoxyphenyl)-1H-pyrazolo[3,4-d]pyrimidin-1-yl)piperidin-1-yl)butoxy)-N-(2-(2,6-dioxopiperidin-3-yl)-1,3-dioxoisoindolin-5-yl)acetamide | 844.3 |
| 106 | 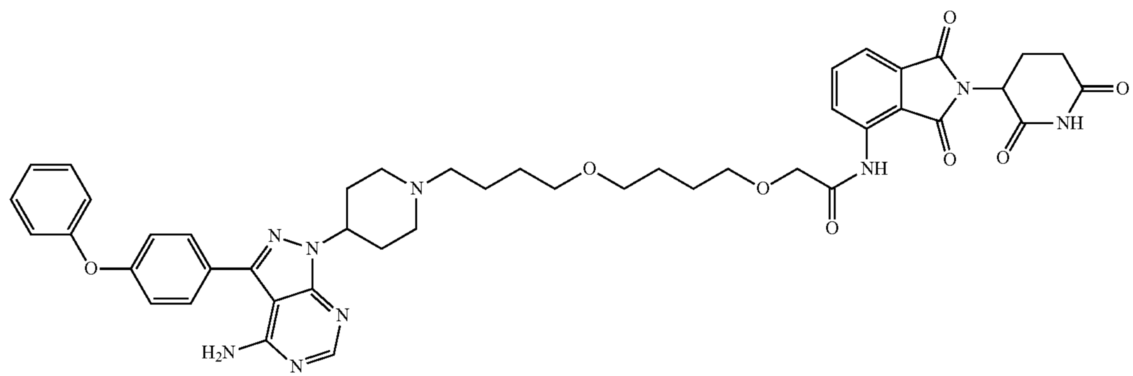 | 2-(4-(4-(4-amino-3-(4-phenoxyphenyl)-1H-pyrazolo[3,4-d]pyrimidin-1-yl)piperidin-1-yl)butoxy)-N-(2-(2,6-dioxopiperidin-3-yl)-1,3-dioxoisoindolin-4-yl)acetamide | 844.5 |
| 107 | 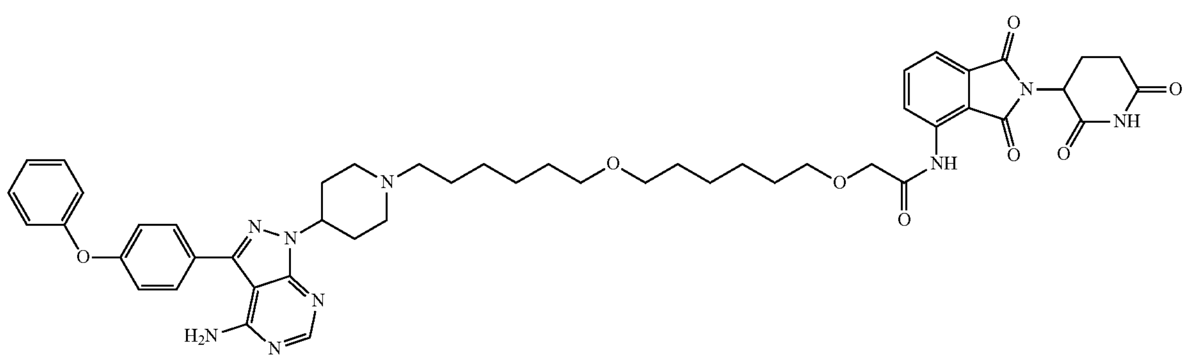 [SMILES: Nc1ncnc2c1c(-c1ccc(Oc3ccccc3)cc1)nn2C1CCN(CCCCCCOCCCCCCOCC(=O)Nc2cccc3c2C(=O)N(C2CCC(=O)NC2=O)C3=O)CC1] | 2-(6-(6-(4-(4-amino-3-(4-phenoxyphenyl)-1H-pyrazolo[3,4-d]pyrimidin-1-yl)piperidin-1-yl)hexyloxy)-N-(2-(2,6-dioxopiperidin-3-yl)-1,3-dioxoisoindolin-4-yl)acetamide | 900.4 |

TABLE 4-continued

Exemplary PROTACs of the Present Disclosure

| Cmpd No. | Chemical Structure | Cmpd Name | MH+ |
|---|---|---|---|
| 108 | 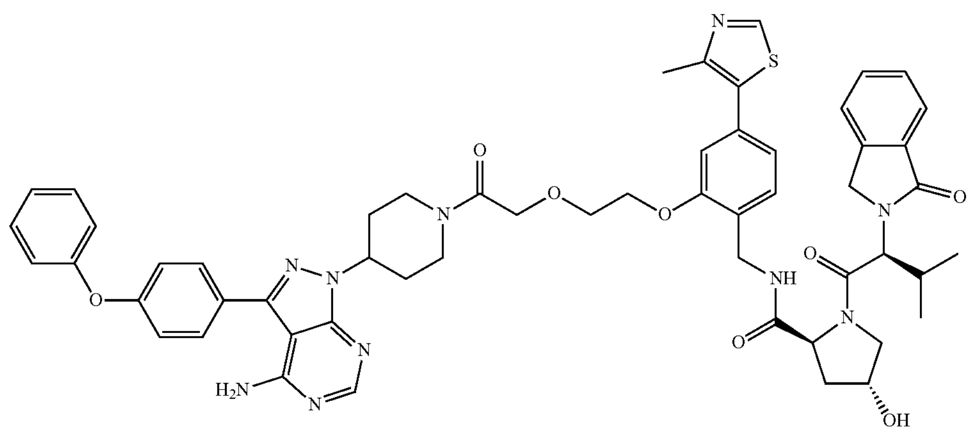 [SMILES: Cc1ncsc1-c1ccc(CNC(=O)[C@@H]2C[C@@H](O)CN2C(=O)[C@H](C(C)C)N2Cc3ccccc3C2=O)c(OCCOCC(=O)N2CCC(n3nc(-c4ccc(Oc5ccccc5)cc4)c4c(N)ncnc43)CC2)c1] | (2S,4R)-N-(2-(2-(4-(4-amino-3-(4-phenoxyphenyl)-1H-pyrazolo[3,4-d]pyrimidin-1-yl)piperidin-1-yl)-2-oxoethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1019.5 |
| 109 | 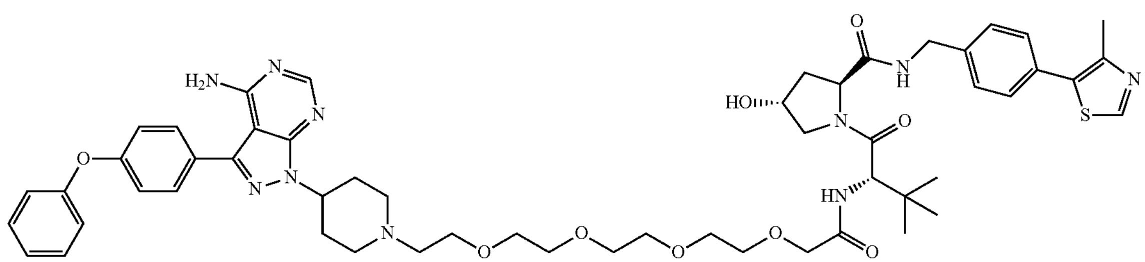 [SMILES: Cc1ncsc1-c1ccc(CNC(=O)[C@@H]2C[C@@H](O)CN2C(=O)[C@@H](NC(=O)COCCOCCOCCOCCN2CCC(n3nc(-c4ccc(Oc5ccccc5)cc4)c4c(N)ncnc43)CC2)C(C)(C)C)cc1] | (2S,4R)-1-((S)-17-(4-(4-amino-3-(4-phenoxyphenyl)-1H-pyrazolo[3,4-d]pyrimidin-1-yl)piperidin-1-yl)-2-tert-butyl-4-oxo-6,9,12,15-tetraoxa-3-azaheptadecane)-4-hydroxy-N-(4-(4-methylthiazol-5-yl)benzyl)pyrrolidine-2-carboxamide | 1033.1 |

TABLE 4-continued

Exemplary PROTACs of the Present Disclosure

| Cmpd No. | Chemical Structure | Cmpd Name | MH+ |
|---|---|---|---|
| 110 | 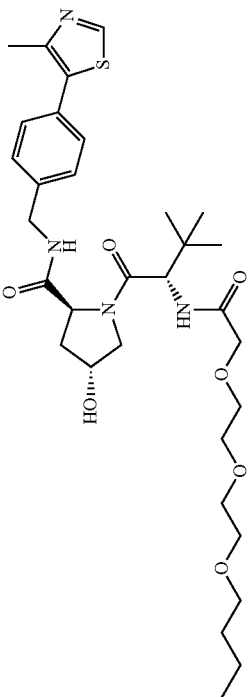 | (2S,4R)-1-((S)-19-(4-(4-amino-3-(4-phenoxyphenyl)-1H-pyrazolo[3,4-d]pyrimidin-1-yl)piperidin-1-yl)-2,2-dimethyl-5-oxo-7,10,13-trioxa-4-azanonadecanecarbonyl)-4-hydroxy-N-(4-(4-methylthiazol-5-yl)benzyl)pyrrolidine-2-carboxamide | 1045.2 |
| 111 | 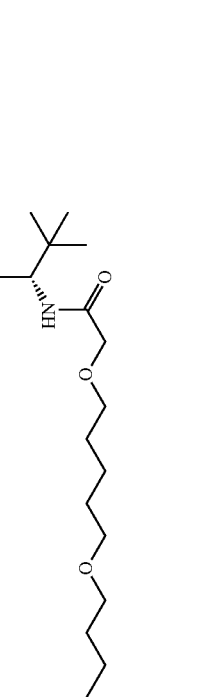 | (2S,4R)-1-((S)-2-(2-(5-(6-(4-(4-amino-3-(4-phenoxyphenyl)-1H-pyrazolo[3,4-d]pyrimidin-1-yl)piperidin-1-yl)hexyloxy)pentyloxy)acetamido)-3,3-dimethylbutanoyl)-4-hydroxy-N-(4-(4-methylthiazol-5-yl)benzyl)pyrrolidine-2-carboxamide | 1043.3 |

TABLE 4-continued

Exemplary PROTACs of the Present Disclosure

| Cmpd No. | Chemical Structure | Cmpd Name | MH+ |
|---|---|---|---|
| 112 | 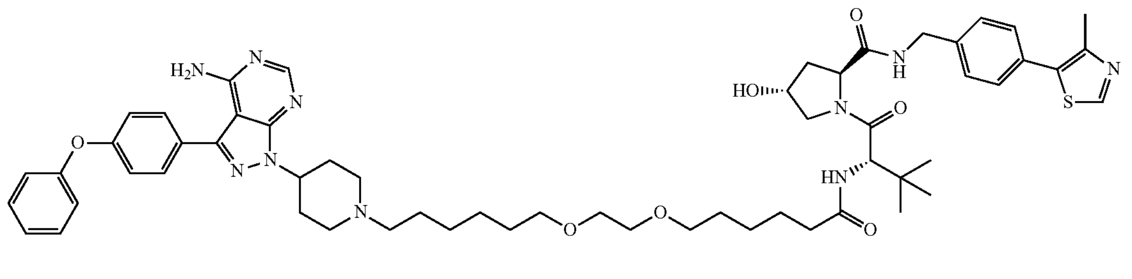 [SMILES: Cc1ncsc1-c1ccc(CNC(=O)[C@@H]2C[C@@H](O)CN2C(=O)[C@@H](NC(=O)CCCCCOCCOCCCCCCN2CCC(n3nc(-c4ccc(Oc5ccccc5)cc4)c4c(N)ncnc43)CC2)C(C)(C)C)cc1] | (2S,4R)-1-((S)-2-(6-(2-(6-(4-amino-3-(4-phenoxyphenyl)-1H-pyrazolo[3,4-d]pyrimidin-1-yl)piperidin-1-yl)hexyloxy)ethoxy)hexanamido)-3,3-dimethylbutanoyl)-4-hydroxy-N-(4-(4-methylthiazol-5-yl)benzyl)pyrrolidine-2-carboxamide | |
| 113 | 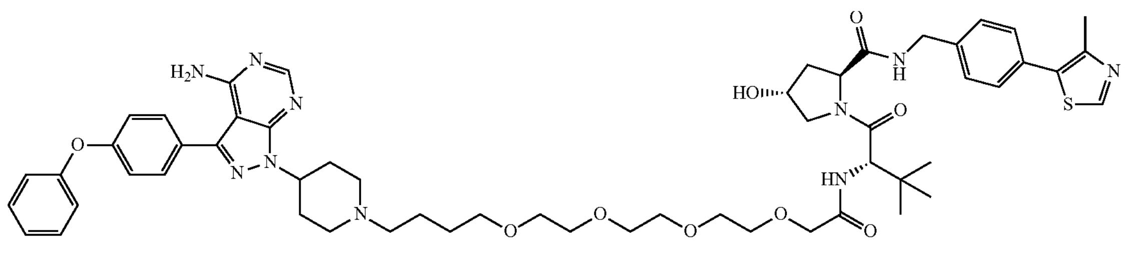 [SMILES: Cc1ncsc1-c1ccc(CNC(=O)[C@@H]2C[C@@H](O)CN2C(=O)[C@@H](NC(=O)COCCOCCOCCOCCCCN2CCC(n3nc(-c4ccc(Oc5ccccc5)cc4)c4c(N)ncnc43)CC2)C(C)(C)C)cc1] | (2S,4R)-1-((S)-19-(4-(4-amino-3-(4-phenoxyphenyl)-1H-pyrazolo[3,4-d]pyrimidin-1-yl)piperidin-1-yl)-2-tert-butyl-4-oxo-6,9,12,15-tetraoxa-3-azanonadecane)-4-hydroxy-N-(4-(4-methylthiazol-5-yl)benzyl)pyrrolidine-2-carboxamide | 1062.3 |
| 114 | 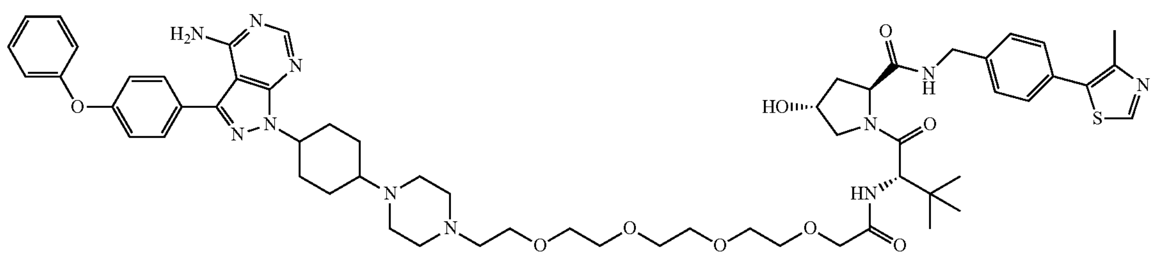 [SMILES: Cc1ncsc1-c1ccc(CNC(=O)[C@@H]2C[C@@H](O)CN2C(=O)[C@@H](NC(=O)COCCOCCOCCOCCN2CCN(C3CCC(n4nc(-c5ccc(Oc6ccccc6)cc5)c5c(N)ncnc54)CC3)CC2)C(C)(C)C)cc1] | (2S,4R)-1-((S)-17-(4-(4-amino-3-(4-phenoxyphenyl)-1H-pyrazolo[3,4-d]pyrimidin-1-yl)cyclohexyl)piperazin-1-yl)-2-tert-butyl-4-oxo-6,9,12,15-tetraoxa-3-azaheptadecane)-4-hydroxy-N-(4-(4-methylthiazol-5-yl)benzyl)pyrrolidine-2-carboxamide | 1016.4 |

TABLE 4-continued

Exemplary PROTACs of the Present Disclosure

| Cmpd No. | Chemical Structure | Cmpd Name | MH+ |
|---|---|---|---|
| 115 | 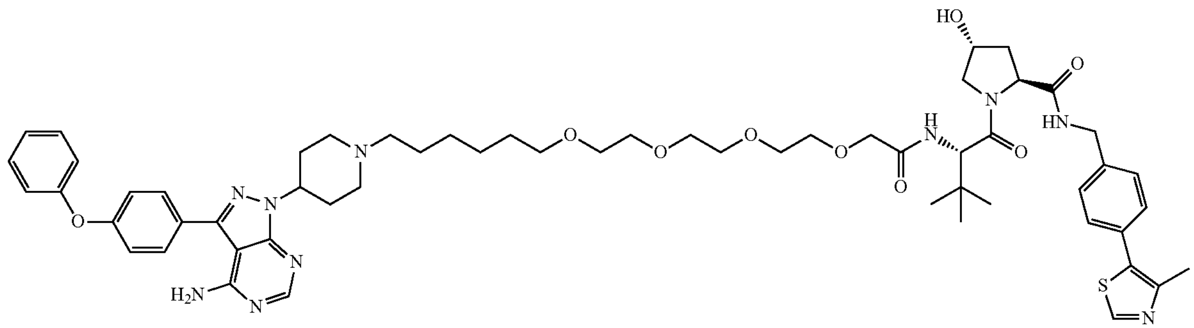 [SMILES: Cc1ncsc1-c1ccc(CNC(=O)[C@@H]2C[C@@H](O)CN2C(=O)[C@@H](NC(=O)COCCOCCOCCOCCCCCCN2CCC(n3nc(-c4ccc(Oc5ccccc5)cc4)c4c(N)ncnc43)CC2)C(C)(C)C)cc1] | (2S,4R)-1-((S)-22-(4-(4-amino-3-(4-phenoxyphenyl)-1H-pyrazolo[3,4-d]pyrimidin-1-yl)piperidin-1-yl)-2,2-dimethyl-5-oxo-7,10,13,16-tetraoxa-4-azadocosanecarbonyl)-4-hydroxy-N-(4-(4-methylthiazol-5-yl)benzyl)pyrrolidine-2-carboxamide | 1089.4 |
| 116 | 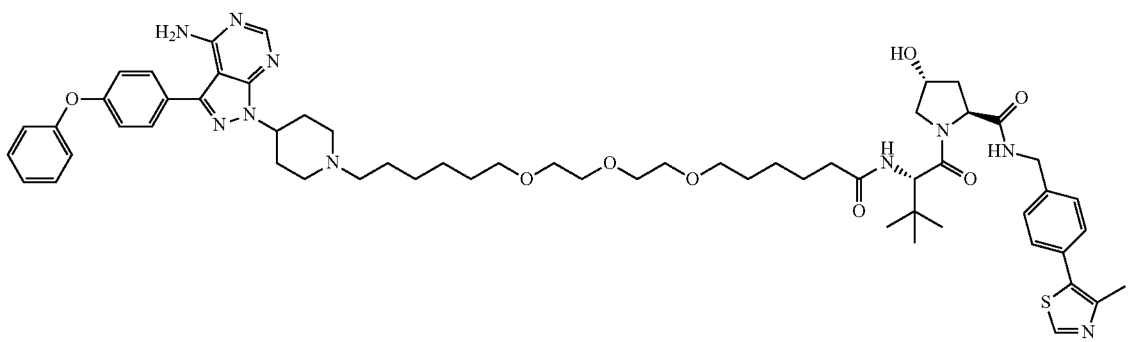 [SMILES: Cc1ncsc1-c1ccc(CNC(=O)[C@@H]2C[C@@H](O)CN2C(=O)[C@@H](NC(=O)CCCCCOCCOCCOCCCCCCN2CCC(n3nc(-c4ccc(Oc5ccccc5)cc4)c4c(N)ncnc43)CC2)C(C)(C)C)cc1] | (2S,4R)-1-((S)-23-(4-(4-amino-3-(4-phenoxyphenyl)-1H-pyrazolo[3,4-d]pyrimidin-1-yl)piperidin-1-yl)-2,2-dimethyl-5-oxo-11,14,17-trioxa-4-azatricosanecarbonyl)-4-hydroxy-N-(4-(4-methylthiazol-5-yl)benzyl)pyrrolidine-2-carboxamide | 1102.1 |

TABLE 4-continued

Exemplary PROTACs of the Present Disclosure

| Cmpd No. | Chemical Structure | Cmpd Name | MH+ |
|---|---|---|---|
| 117 | 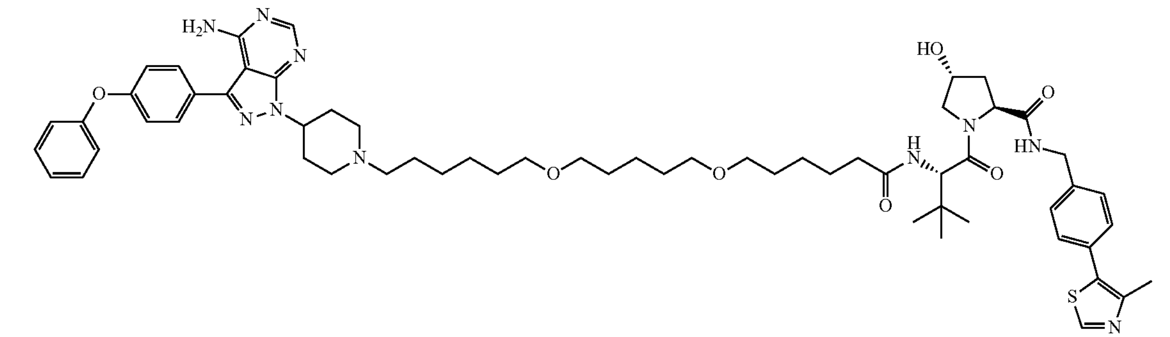 [SMILES: Cc1ncsc1-c1ccc(CNC(=O)[C@@H]2C[C@@H](O)CN2C(=O)[C@@H](NC(=O)CCCCCOCCCCCOCCCCCCN2CCC(n3nc(-c4ccc(Oc5ccccc5)cc4)c4c(N)ncnc43)CC2)C(C)(C)C)cc1] | (2S,4R)-1-((S)-2-(6-(5-(6-(4-(4-amino-3-(4-phenoxyphenyl)-1H-pyrazolo[3,4-d]pyrimidin-1-yl)piperidin-1-yl)hexyloxy)pentyloxy)hexanamido)-3,3-dimethylbutanoyl)-4-hydroxy-N-(4-(4-methylthiazol-5-yl)benzyl)pyrrolidine-2-carboxamide | 1100.2 |
| 118 | 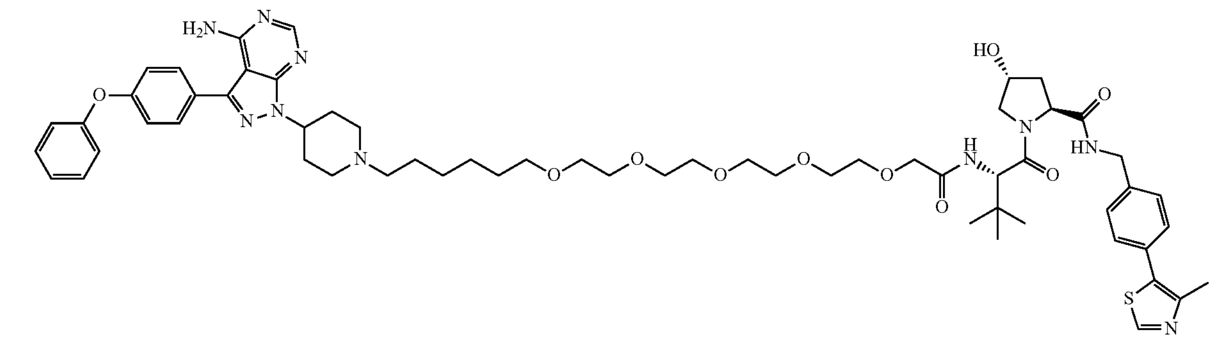 [SMILES: Cc1ncsc1-c1ccc(CNC(=O)[C@@H]2C[C@@H](O)CN2C(=O)[C@@H](NC(=O)COCCOCCOCCOCCOCCCCCCN2CCC(n3nc(-c4ccc(Oc5ccccc5)cc4)c4c(N)ncnc43)CC2)C(C)(C)C)cc1] | (2S,4R)-1-((S)-2-(4-phenoxyphenyl)-1H-pyrazolo[3,4-d]pyrimidin-1-yl)-2,2-dimethyl-5-oxo-7,10,13,16,19-pentaoxa-4-azapentacosanecarbonyl)-4-hydroxy-N-(4-(4-methylthiazol-5-yl)benzyl)pyrrolidine-2-carboxamide | 1133.0 |
| 119 | 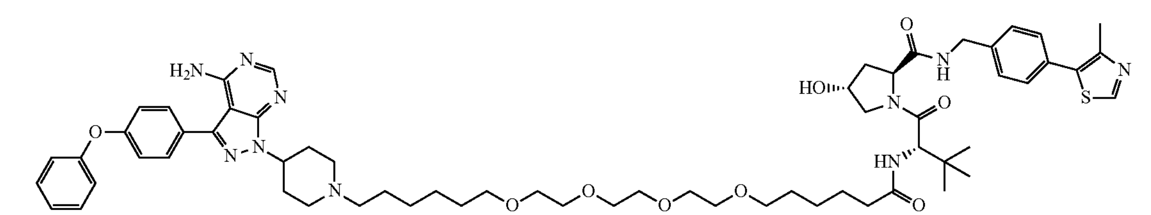 [SMILES: Cc1ncsc1-c1ccc(CNC(=O)[C@@H]2C[C@@H](O)CN2C(=O)[C@@H](NC(=O)CCCCCOCCOCCOCCOCCCCCCN2CCC(n3nc(-c4ccc(Oc5ccccc5)cc4)c4c(N)ncnc43)CC2)C(C)(C)C)cc1] | (2S,4R)-1-((S)-26-(4-(4-amino-3-(4-phenoxyphenyl)-1H-pyrazolo[3,4-d]pyrimidin-1-yl)piperidin-1-yl)-2,2-dimethyl-5-oxo-11,14,17,20-tetraoxa-4-azahexacosanecarbonyl)-4-hydroxy-N-(4-(4-methylthiazol-5-yl)benzyl)pyrrolidine | 1146.3 |

TABLE 4-continued

Exemplary PROTACs of the Present Disclosure

| Cmpd No. | Chemical Structure | Cmpd Name | MH+ |
|---|---|---|---|
| 120 | 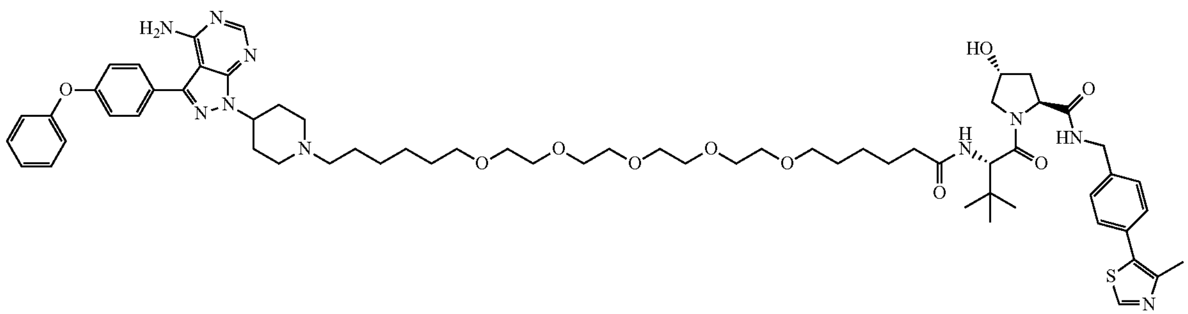 [SMILES: Cc1ncsc1-c1ccc(CNC(=O)[C@@H]2C[C@@H](O)CN2C(=O)[C@@H](NC(=O)CCCCCOCCOCCOCCOCCOCCCCCCN2CCC(n3nc(-c4ccc(Oc5ccccc5)cc4)c4c(N)ncnc43)CC2)C(C)(C)C)cc1] | (2S,4R)-1-((S)-29-(4-(4-amino-3-(4-phenoxyphenyl)-1H-pyrazolo[3,4-d]pyrimidin-1-yl)piperidin-1-yl)-2,2-dimethyl-5-oxo-11,14,17,20,23-pentaoxa-4-azanonacosanecarbonyl)-4-hydroxy-N-(4-(4-methylthiazol-5-yl)benzyl)pyrrolidine-2-carboxamide | 1190.5 |
| 121 | 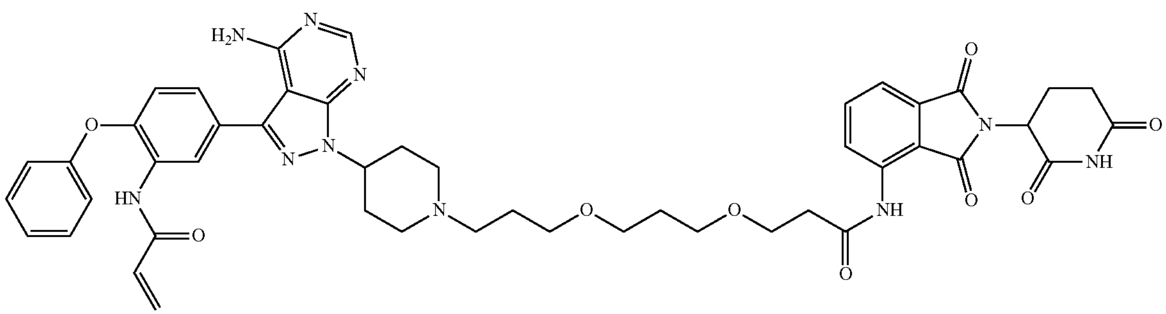 [SMILES: C=CC(=O)Nc1cc(-c2nn(C3CCN(CCCOCCCOCCC(=O)Nc4cccc5c4C(=O)N(C4CCC(=O)NC4=O)C5=O)CC3)c3ncnc(N)c23)ccc1Oc1ccccc1] | N-(5-(4-amino-1-(1-(3-(3-(2-(2,6-dioxopiperidin-3-yl)-1,3-dioxoisoindolin-4-ylamino)-3-oxopropoxy)propoxy)propyl)piperidin-4-yl)-1H-pyrazolo[3,4-d]pyrimidin-3-yl)-2-phenoxyphenyl)acrylamide | 899.4 |

TABLE 4-continued

Exemplary PROTACs of the Present Disclosure

| Cmpd No. | Chemical Structure | Cmpd Name | MH+ |
|---|---|---|---|
| 122 | 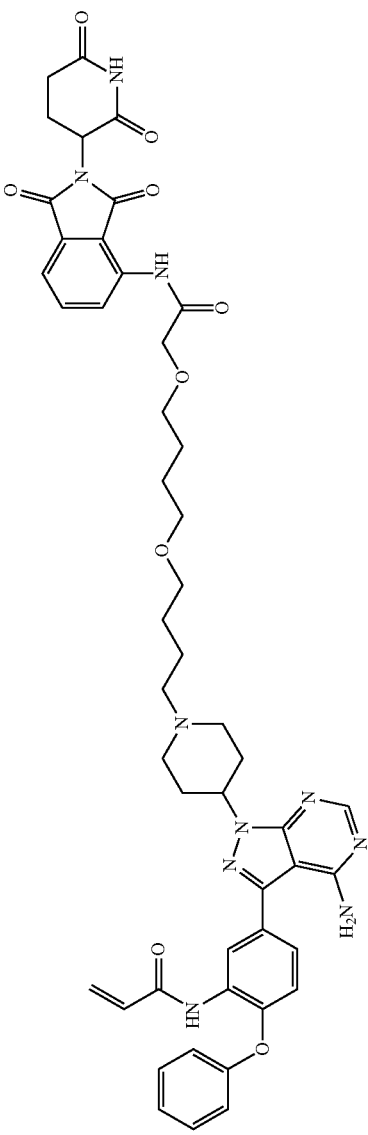 | N-(5-(4-amino-1-(1-(4-(4-(2-(2-(2,6-dioxopiperidin-3-yl)-1,3-dioxoisoindolin-4-ylamino)-2-oxoethoxy)butoxy)butyl)piperidin-4-yl)-1H-pyrazolo[3,4-d]pyrimidin-3-yl)-2-phenoxyphenyl)acrylamide | 913.5 |
| 123 | 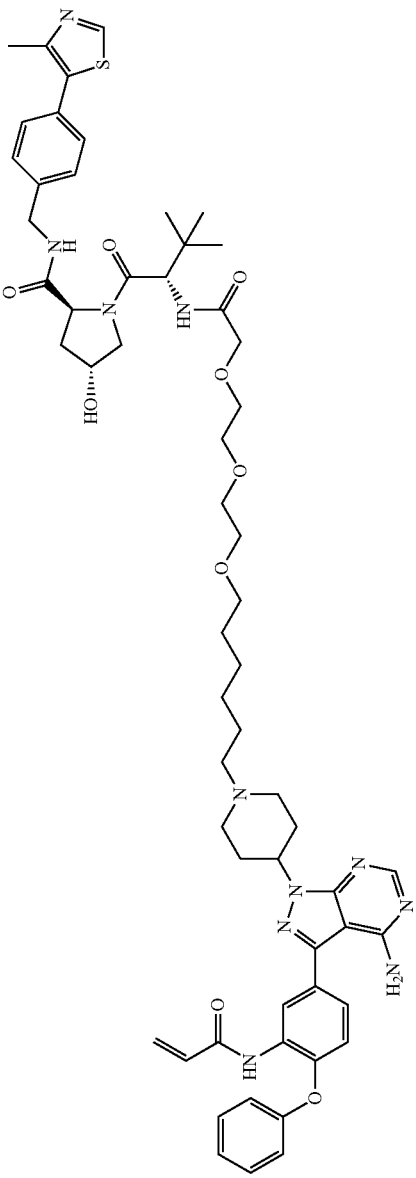 | (2S,4R)-1-((S)-19-(4-(3-acrylamido-4-phenoxyphenyl)-4-amino-1H-pyrazolo[3,4-d]pyrimidin-1-yl)piperidin-1-yl)-2,2-dimethyl-5-oxo-7,10,13-trioxa-4-azanonadecanecarbonyl)-4-hydroxy-N-(4-(4-methylthiazol-5-yl)benzyl)pyrrolidine-2-carboxamide | 1214.3 |

TABLE 4-continued

Exemplary PROTACs of the Present Disclosure

| Cmpd No. | Chemical Structure | Cmpd Name | MH+ |
|---|---|---|---|
| 124 | 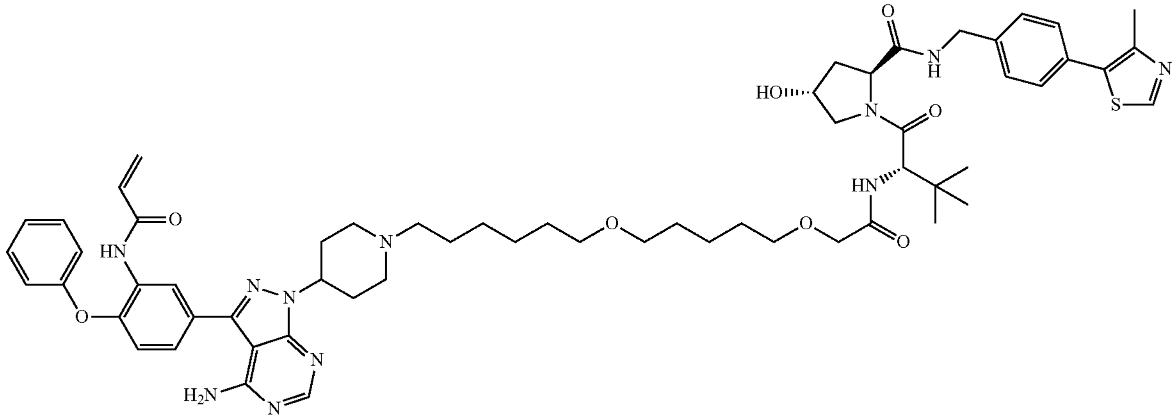 [SMILES: C=CC(=O)Nc1cc(-c2nn(C3CCN(CCCCCCOCCCCCOCC(=O)N[C@H](C(=O)N4C[C@H](O)C[C@H]4C(=O)NCc4ccc(-c5scnc5C)cc4)C(C)(C)C)CC3)c3ncnc(N)c23)ccc1Oc1ccccc1] | (2S,4R)-1-((S)-2-(2-(5-(6-(4-(3-(3-acrylamido-4-phenoxyphenyl)-4-amino-1H-pyrazolo[3,4-d]pyrimidin-1-yl)piperidin-1-yl)hexyloxy)pentyloxy)acetamido)-3,3-dimethylbutanoyl)-4-hydroxy-N-(4-(4-methylthiazol-5-yl)benzyl)pyrrolidine-2-carboxamide | 1112.5 |
| 125 | 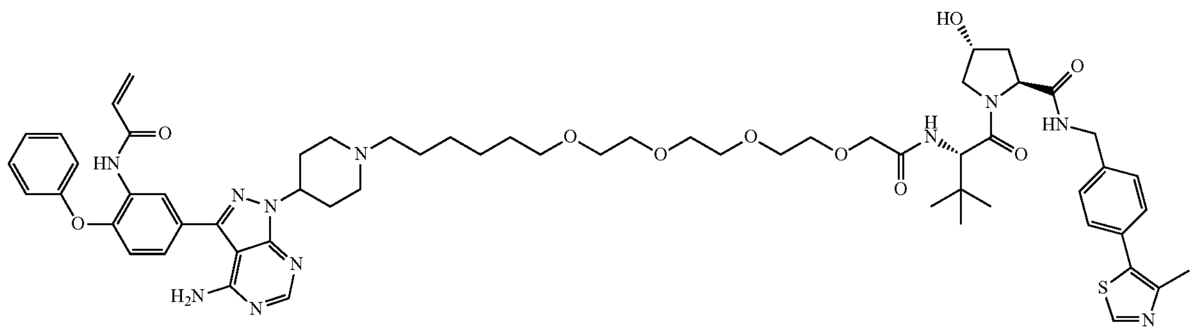 [SMILES: C=CC(=O)Nc1cc(-c2nn(C3CCN(CCCCCCOCCOCCOCCOCC(=O)N[C@H](C(=O)N4C[C@H](O)C[C@H]4C(=O)NCc4ccc(-c5scnc5C)cc4)C(C)(C)C)CC3)c3ncnc(N)c23)ccc1Oc1ccccc1] | (2S,4R)-1-((S)-22-(4-(3-acrylamido-4-phenoxyphenyl)-4-amino-1H-pyrazolo[3,4-d]pyrimidin-1-yl)piperidin-1-yl)-2,2-dimethyl-5-oxo-7,10,13,16-tetraoxa-4-azadocosanecarbonyl)-4-hydroxy-N-(4-(4-methylthiazol-5-yl)benzyl)pyrrolidine-2-carboxamide | 1158.2 |

TABLE 4-continued

Exemplary PROTACs of the Present Disclosure

| Cmpd No. | Chemical Structure | Cmpd Name | MH+ |
|---|---|---|---|
| 126 | 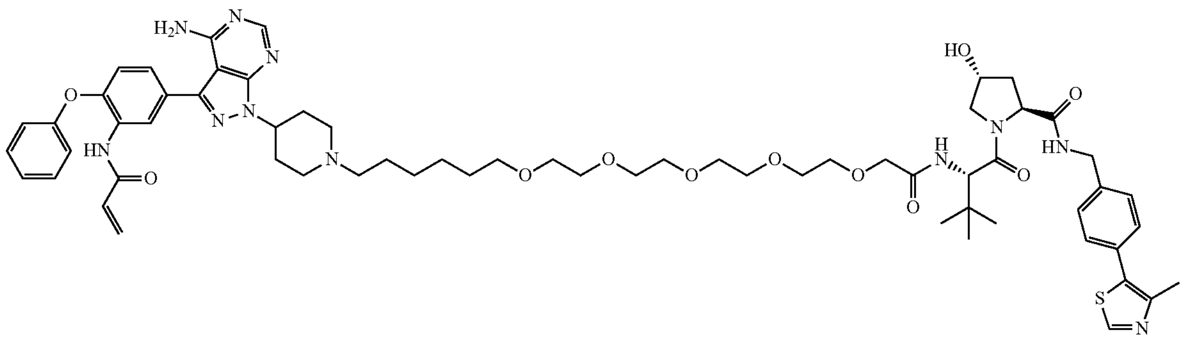 [SMILES: C=CC(=O)Nc1cc(-c2nn(C3CCN(CCCCCCOCCOCCOCCOCCOCC(=O)N[C@H](C(=O)N4C[C@H](O)C[C@H]4C(=O)NCc4ccc(-c5scnc5C)cc4)C(C)(C)C)CC3)c3ncnc(N)c23)ccc1Oc1ccccc1] | (2S,4R)-1-((S)-2-5-(4-(3-acrylamido-4-phenoxyphenyl)-4-amino-1H-pyrazolo[3,4-d]pyrimidin-1-yl)piperidin-1-yl)-2,2-dimethyl-5-oxo-7,10,13,16,19-pentaoxa-4-azapentacosanecarbonyl)-4-hydroxy-N-(4-(4-methylthiazol-5-yl)benzyl)pyrrolidine-2-carboxamide | 1201.3 |
| 127 | 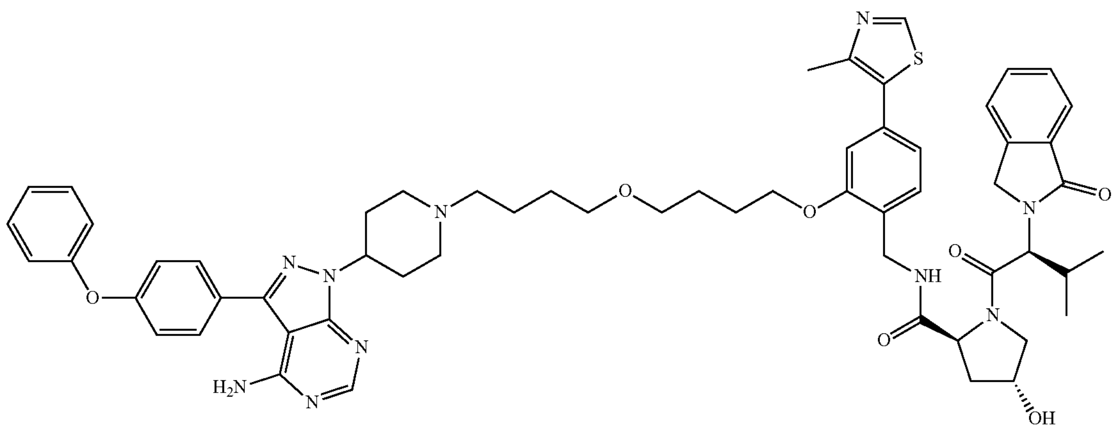 [SMILES: Cc1ncsc1-c1ccc(CNC(=O)[C@@H]2C[C@@H](O)CN2C(=O)[C@H](C(C)C)N2Cc3ccccc3C2=O)c(OCCCCOCCCCN2CCC(n3nc(-c4ccc(Oc5ccccc5)cc4)c4c(N)ncnc43)CC2)c1] | (2S,4R)-N-(2-(4-(4-(4-amino-3-(4-phenoxyphenyl)-1H-pyrazolo[3,4-d]pyrimidin-1-yl)butoxy)butoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1061.5 |

TABLE 4-continued

Exemplary PROTACs of the Present Disclosure

| Cmpd No. | Chemical Structure | Cmpd Name | MH+ |
|---|---|---|---|
| 128 | 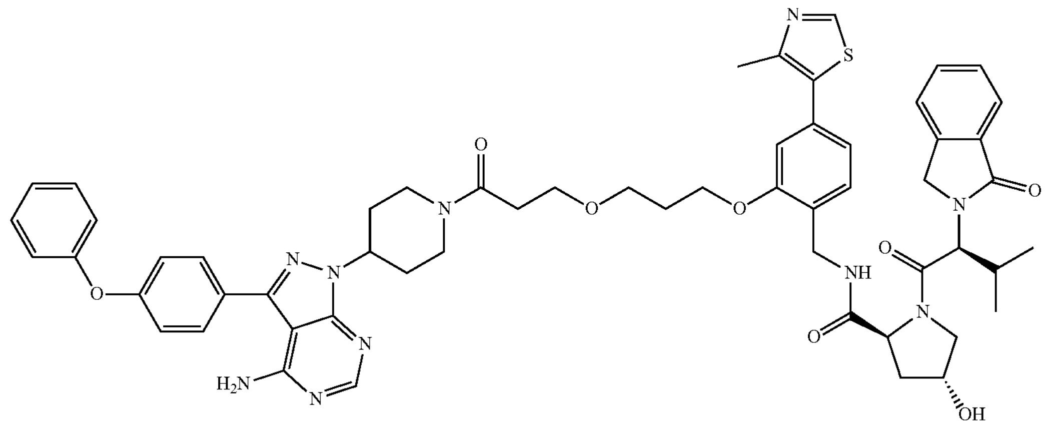 [SMILES: Cc1ncsc1-c1ccc(CNC(=O)[C@@H]2C[C@@H](O)CN2C(=O)[C@H](C(C)C)N2Cc3ccccc3C2=O)c(OCCCOCCC(=O)N2CCC(n3nc(-c4ccc(Oc5ccccc5)cc4)c4c(N)ncnc43)CC2)c1] | (2S,4R)-N-(2-(3-(4-(4-amino-3-(4-phenoxyphenyl)-1H-pyrazolo[3,4-d]pyrimidin-1-yl)piperidin-1-yl)-3-oxopropoxy)propoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1047.5 |
| 129 | 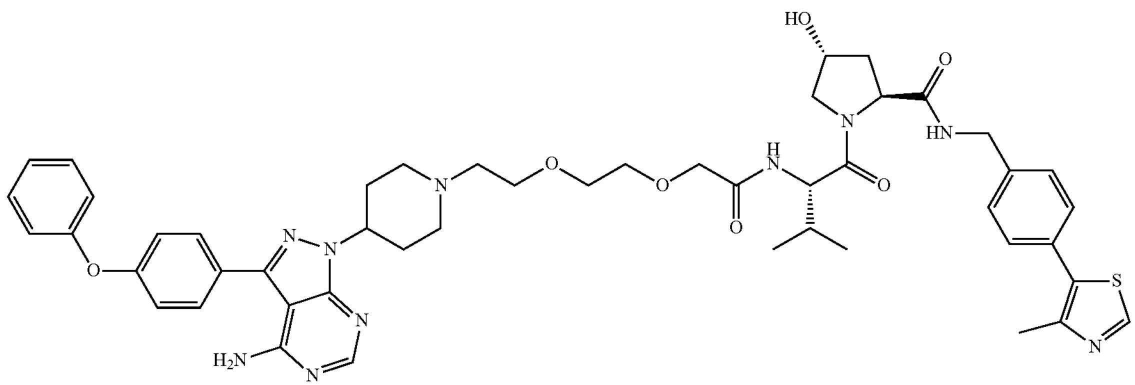 [SMILES: Cc1ncsc1-c1ccc(CNC(=O)[C@@H]2C[C@@H](O)CN2C(=O)[C@@H](NC(=O)COCCOCCN2CCC(n3nc(-c4ccc(Oc5ccccc5)cc4)c4c(N)ncnc43)CC2)C(C)C)cc1] | (2S,4R)-1-((S)-2-(2-(2-(4-(4-amino-3-(4-phenoxyphenyl)-1H-pyrazolo[3,4-d]pyrimidin-1-yl)piperidin-1-yl)ethoxy)ethoxy)acetamido)-3-methylbutanoyl)-4-hydroxy-N-(4-(4-methylthiazol-5-yl)benzyl)pyrrolidine-2-carboxamide | 945.5 |

TABLE 4-continued

Exemplary PROTACs of the Present Disclosure

| Cmpd No. | Chemical Structure | Cmpd Name | MH+ |
|---|---|---|---|
| 130 | 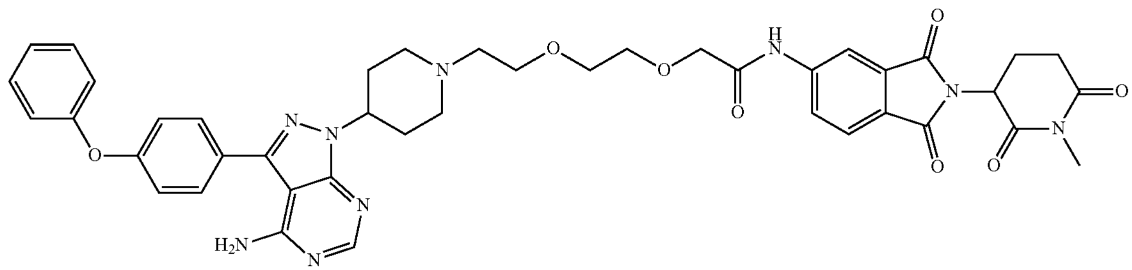 [SMILES: CN1C(=O)CCC(N2C(=O)c3ccc(NC(=O)COCCOCCN4CCC(n5nc(-c6ccc(Oc7ccccc7)cc6)c6c(N)ncnc65)CC4)cc3C2=O)C1=O] | 2-(2-(2-(4-(4-amino-3-(4-phenoxyphenyl)-1H-pyrazolo[3,4-d]pyrimidin-1-yl)piperidin-1-yl)ethoxy)ethoxy)-N-(2-(1-methyl-2,6-dioxopiperidin-3-yl)-1,3-dioxoisoindolin-5-yl)acetamide | 802.3 |
| 131 | 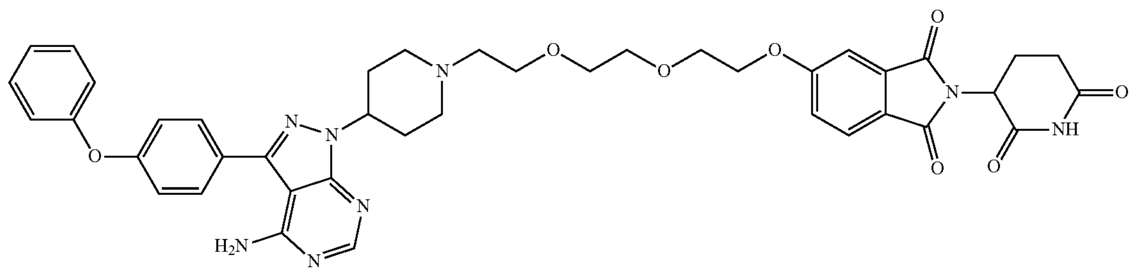 [SMILES: Nc1ncnc2c1c(-c1ccc(Oc3ccccc3)cc1)nn2C1CCN(CCOCCOCCOc2ccc3c(c2)C(=O)N(C2CCC(=O)NC2=O)C3=O)CC1] | 5-(2-(2-(2-(4-(4-amino-3-(4-phenoxyphenyl)-1H-pyrazolo[3,4-d]pyrimidin-1-yl)piperidin-1-yl)ethoxy)ethoxy)ethoxy)-2-(2,6-dioxopiperidin-3-yl)isoindoline-1,3-dione | 775.3 |
| 132 | 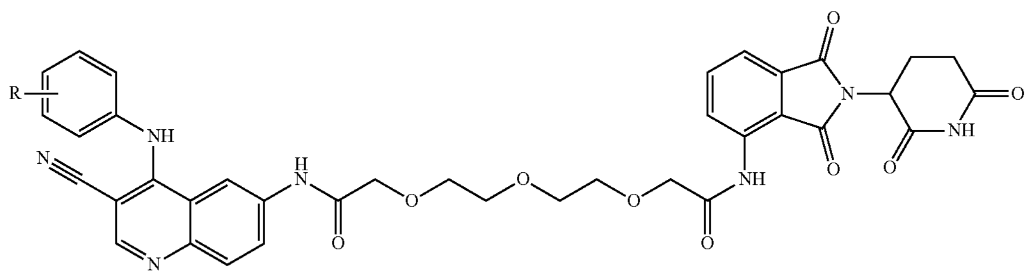 | R is H or a non-H substituent | |

TABLE 4-continued

Exemplary PROTACs of the Present Disclosure

| Cmpd No. | Chemical Structure | Cmpd Name | MH+ |
|---|---|---|---|
| 133 | 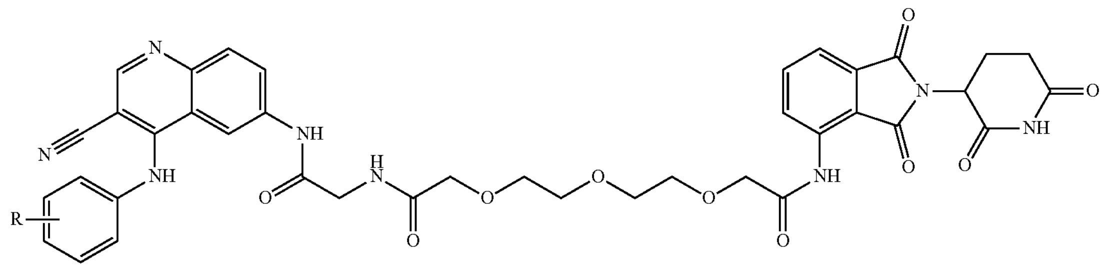 | R is H or a non-H substituent | |
| 134 | 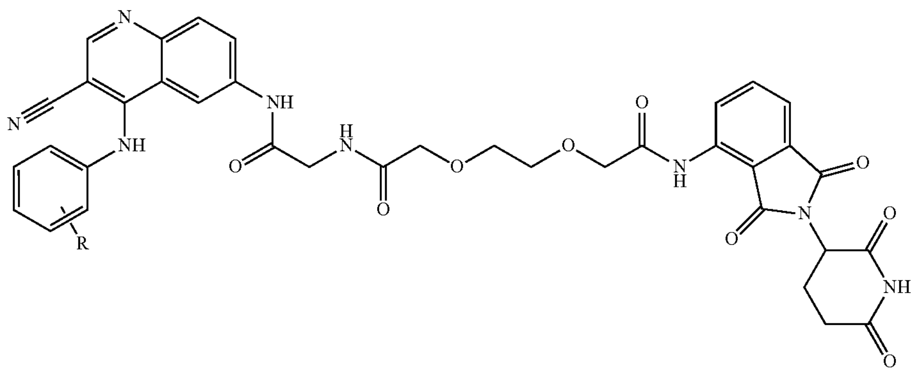 | R is H or a non-H substituent | |
| 135 | 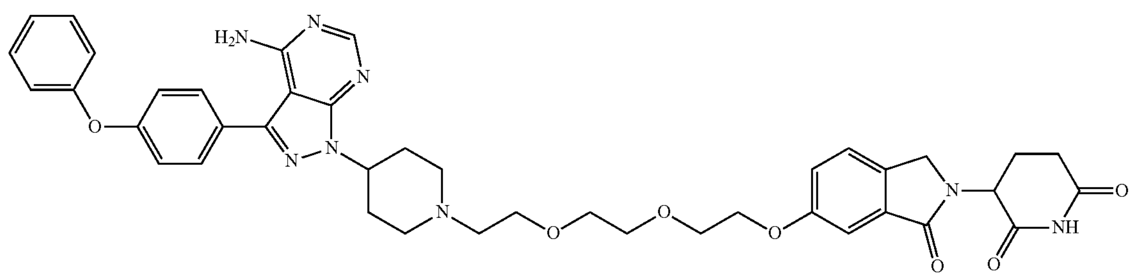 [SMILES: Nc1ncnc2c1c(-c1ccc(Oc3ccccc3)cc1)nn2C1CCN(CCOCCOCCOc2ccc3c(c2)C(=O)N(C2CCC(=O)NC2=O)C3)CC1] | 3-(6-(2-(2-(2-(4-(4-amino-3-(4-phenoxyphenyl)-1H-pyrazolo[3,4-d]pyrimidin-1-yl)piperidin-1-yl)ethoxy)ethoxy)ethoxy)-1-oxoisoindolin-2-yl)piperidine-2,6-dione | 761.4 |

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further embodiment of the present disclosure. In various embodiments, the pharmaceutical composition includes at least one compound with the formula ULM-L-PTM as described herein. In one embodiment, the pharmaceutical composition includes at least one compound from Table 4.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this embodiment are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred embodiments of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, including epidermal growth factor receptor inhibitors, EPO and darbapoietin alfa, among others. In certain preferred embodiments of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional embodiment, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In various embodiments, the therapeutic composition includes at least one compound with the formula ULM-L-PTM as described herein. In one embodiment, the therapeutic composition includes at least one compound from Table 4.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer (e.g., at least one of pancreatic cancer, colon cancer, colorectal cancer, lung cancer, non-small cell lung cancer, biliary tract malignancies, endometrial cancer, cervical cancer, bladder cancer, liver cancer, myeloid leukemia, breast cancer, or combinations thereof), which may be treated using compounds according to the present disclosure are set forth hereinabove.

The description provides therapeutic compositions as described herein for effectuating the degradation of proteins of interest for the treatment or amelioration of a disease, e.g., cancer (such as pancreatic cancer, colon cancer, colorectal cancer, lung cancer, non-small cell lung cancer, biliary tract malignancies, endometrial cancer, cervical cancer, bladder cancer, liver cancer, myeloid leukemia, or breast cancer). In certain additional embodiments, the disease is multiple myeloma. As such, in another embodiment, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another embodiment, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. In any embodiment or embodiment described herein, the disease or disorder is a cancer or neoplasia selected from pancreatic cancer, colon cancer, colorectal cancer, lung cancer, non-small cell lung cancer, biliary tract malignancies, endometrial cancer, cervical cancer, bladder cancer, liver cancer, myeloid leukemia, or breast cancer (e.g., a cancer or neoplasia selected from pancreatic cancer, colon cancer, lung cancer, or non-small cell lung cancer). Malignant neoplasms show partial or complete lack of structural organization and functional coordination with the normal tissue and most invade surrounding tissues, metastasize to several sites, and are likely to recur after attempted removal and to cauSe the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, non-small cell lung cancer, biliary tract malignancies, endometrial cancer, myeloid leukemia, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORCl/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325902, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatinib, canertinib, ABX-EGF antibody, erbitux, EKB-569, PKI-166, GW-572016, lonafarnib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In any embodiment or embodiment described herein, the bioactive agent or additional anti-cancer agent is a chemotherapy or biological therapy that targets epidermal growth factor receptors (e.g., an epidermal growth factor receptor inhibitor, such as at least one of gefitinib, erlotinib, neratinib, lapatinib, cetuximab, vandetanib, necitumamab, osimertinib, or a combination thereof).

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddl (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90252S/T), efavirenz (DMP-266), UC-781 (N-[4-chloro-3-(3-methyl-2-butenyloxy)phenyl]-2-methyl-3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3'3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO—546), DPC 961, E-EBU, E-EBU-dm, E-EPSeU, E-EPU, Foscamet (Foscavir), HEPT (1-[(2-Flydroxyethoxy)methyl]-6-(phenylthio)thymine), FIEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea (PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl(pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

Various embodiments of the present invention can be better understood by reference to the following Examples which are offered by way of illustration. The present invention is not limited to the Examples given herein.

1. Chemistry

Unless otherwise indicated, common reagents or materials were obtained from commercial sources and used without further purification. Tetrahydrofuran (THF), Dimethylformamide (DMF) and Dichloromethane (DCM) were dried by a PureSolv™ solvent drying system. Flash column chromatography was performed using silica gel 60 (230-400 mesh). Analytical thin layer chromatography (TLC) was carried out on Merck silica gel plates with QF-254 indicator and visualized by UV or $KMnO_4$. Flash chromatography was performed using the Biotage Isolera One purification system. $^1H$, $^{13}C$, and $^{19}F$ NMR spectra were recorded on either Agilent DD2 500 (500 MHz $^1H$; 125 MHz $^{13}C$; 471 MHz $^{13}C$) or Agilent DD2 600 (600 MHz $^1H$; 150 MHz $^{13}C$) or Agilent DD2 400 (400 MHz $^1H$; 101 MHz $^{13}C$, 376 MHz $^{19}F$) or Varian 700 (700 MHz $^1H$) spectrometer at RT (RT) unless otherwise indicated. Chemical shifts were reported in ppm relative to the residual DMSO-$d_6$ (δ 2.50 ppm $^1H$; δ 39.52 ppm $^{13}C$). NMR chemical shifts were expressed in ppm relative to internal solvent peaks, and coupling constants were measured in Hz. Mass spectra were obtained using electrospray ionization (ESI) LCQ-Fleet mass spectrometer coupled to an Ultimate 3000 UHPLC (C18 column) and Corona Veo $R_S$. Preparative (prep) HPLC was carried out on 100×21.2 mm 110 A C-18 column using gradient conditions (5-95% B, flow rate=20.0 mL/min, 20 min) monitoring by UV for collection. The eluents used were: solvent A ($H_2O$ with 0.1% trifluoroacetic acid (TFA)) and solvent B ($CH_3CN$ with 0.1% TFA). ENDTAC purity was determined by LC-MS (L=254 nm) using gradient conditions (5-95% $B_1$, flow rate=0.5 mL/min, 6 min). The eluents used here were: solvent Ai ($H_2O$ with 0.1% formic acid) and solvent $B_1$ ($CH_3CN$ with 0.1% formic acid).

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Abbreviations used herein: DIEA or DIPEA: diisopropylethylamine; DMF: N,N-dimethylformamide; DMSO: Dimethyl sulfoxide; EDCI: 1-ethyl-3-(3-dimethylaminopropyl) carbodiimide; HOBt: hydroxybenzotriazole; THF: tetrahydrofuran; DIAD: diisopropyl azodicarboxylate; EtOAc or AcOEt: ethyl acetate; DCM: dichloromethane; MeOH: methanol; TFA: trifluoroacetic acid; TEA: trimethylamine; MeCN: acetonitrile; PyBOP: (Benzotriazol-1-yloxy)tripyrrolidinophosphonium hexafluorophosphate).

Experimental Procedures

Synthesis of Linker and CLM Conjugates

Scheme 1. General synthesis of BTK-targeting PROTACs of varying linker lengths.

Linkers

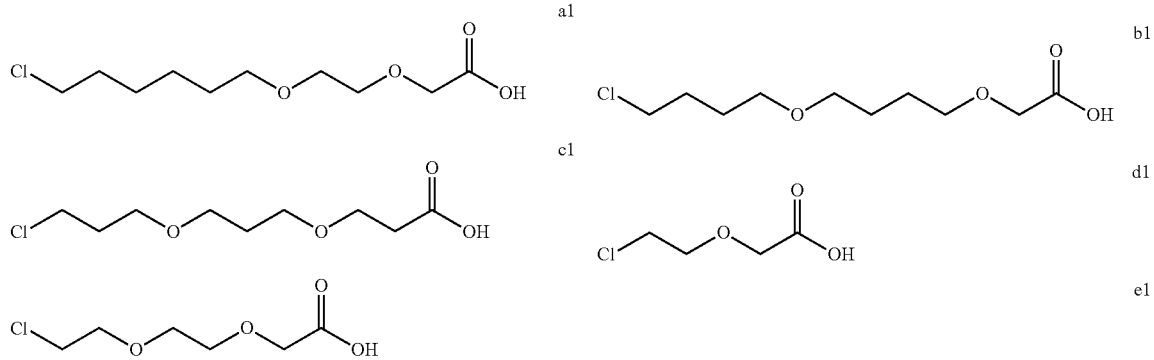

-continued

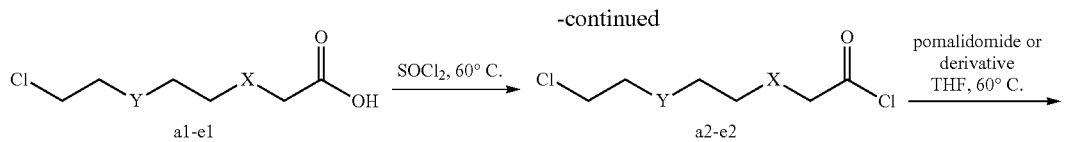

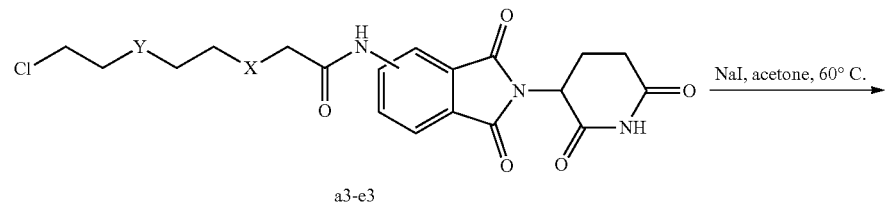

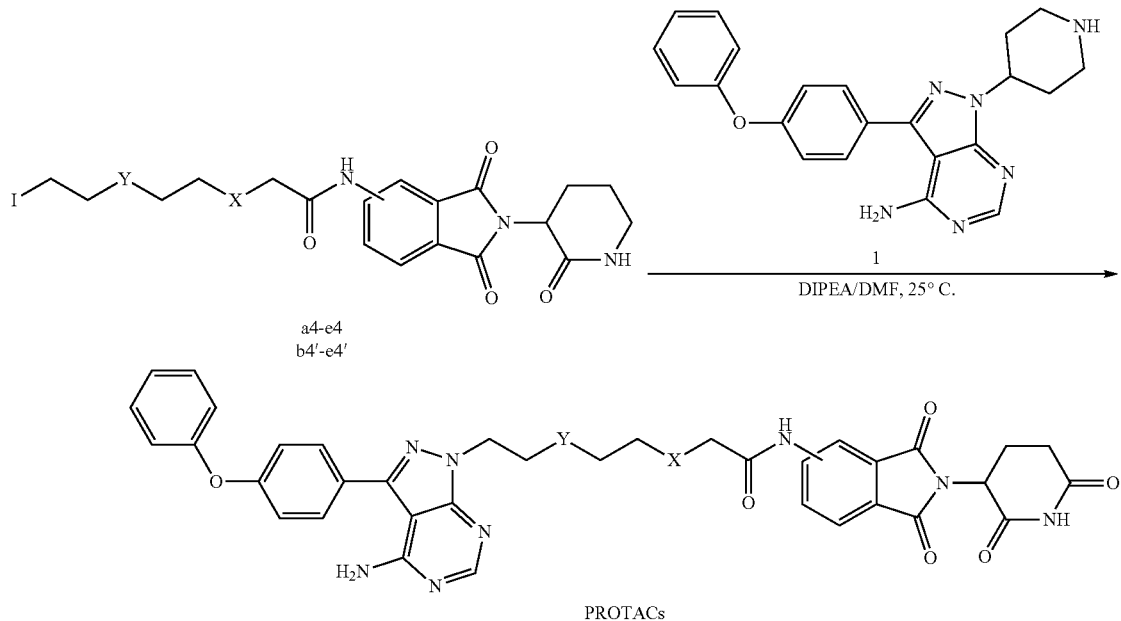

PROTACs

Compounds a1, a2, a3 and a4, linkers b1, c1 were prepared as reported previously and compounds e2, e3 and e4 were prepared according to previously reported procedures. Linkers d2 and e1 were obtained from a commercial source.

Preparation of 2-[4-(4-chlorobutoxy)butoxy]acetyl chloride (compound b2)

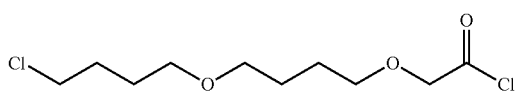 [SMILES: O=C(Cl)COCCCCOCCCCCl]

A solution of 2-[4-(4-chlorobutoxy)butoxy]acetic acid (65 mg, 0.27 mmol) in thionyl chloride was heated at 60° C. for 2 hours. The solvent was evaporated to give 70.02 mg (100%) of 2-[4-(4-chlorobutoxy)butoxy]acetyl chloride as a colorless oil. It was carried to the next step without further purification.

Preparation of 2-[4-(4-chlorobutoxy)butoxy]-N-[2-(2,6-dioxo-3-piperidyl)-1,3-dioxo-isoindolin-4-yl]acetamide (compound b3)

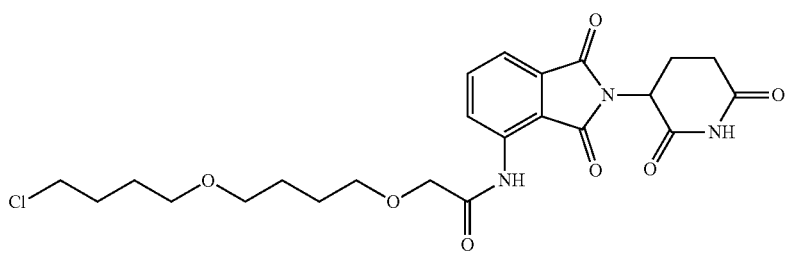 [SMILES: O=C1CCC(N2C(=O)c3cccc(NC(=O)COCCCCOCCCCCl)c3C2=O)C(=O)N1]

(2-[4-(4-chlorobutoxy)butoxy]acetyl chloride (70 mg, 0.27 mmol) was dissolved in THF (2 ml). To this solution was added 4-amino-2-(2,6-dioxo-3-piperidyl)isoindoline-1,3-dione (74.38 mg, 0.27 mmol). The resulting suspension was heated to reflux for 4 hours. The solvent was evaporated in vacuo and the resulting solid was purified by flash chromatography (50/50 to 0/100 hexane/ethyl acetate) to give a light yellow solid 128.1 mg (95.3%) of 2-[4-(4-chlorobutoxy)butoxy]-N-[2-(2,6-dioxo-3-piperidyl)-1,3-dioxo-isoindolin-4-yl]acetamide. $^1$H NMR (500 MHz, Chloroform-d) δ 10.45 (s, 1H), 8.85 (d, J=8.5 Hz, 1H), 8.49 (s, 1H), 7.71 (t, J=7.9 Hz, 1H), 7.56 (d, J=7.3 Hz, 1H), 4.95 (dd, J=12.4, 5.3 Hz, 1H), 4.10 (s, 2H), 3.64 (t, J=6.4 Hz, 2H), 3.55 (t, J=6.7 Hz, 2H), 3.45 (dt, J=10.0, 6.3 Hz, 4H), 2.99-2.69 (m, 3H), 2.15 (ddd, J=12.1, 6.0, 3.3 Hz, 1H), 1.89-1.62 (m, 8H). LC/MS: [M+H]$^+$ for $C_{23}H_{29}ClN_3O_7$ calculated: 494.2; found: 494.1.

Preparation of N-[2-(2,6-dioxo-3-piperidyl)-1,3-dioxo-isoindolin-4-yl]-2-[4-(4-iodobutoxy)butoxy]acetamide (compound b4)

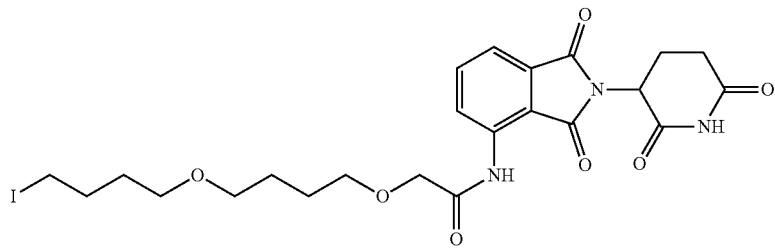 [SMILES: O=C1CCC(N2C(=O)c3cccc(NC(=O)COCCCCOCCCCI)c3C2=O)C(=O)N1]

To a solution of 2-[4-(4-chlorobutoxy)butoxy]-N-[2-(2,6-dioxo-3-piperidyl)-1,3-dioxo-isoindolin-4-yl]acetamide (130 mg, 0.26 mmol) in acetone (10 ml) was added NaI (197.25 mg, 1.32 mmol). The reaction mixture was stirred at refluxed temperature for 24 h, then the solvent was removed under vacuum and the crude product was dissolved in EtOAc (15 mL). An aqueous solution of $Na_2SO_3$ (10%, 10 mL) was added and the organic layer separated, washed with water (10 mL) and dried ($Na_2SO_4$). The solid was filtered off and the volatiles evaporated under vacuum to give 137 mg (88%) of N-[2-(2,6-dioxo-3-piperidyl)-1,3-dioxo-isoindolin-4-yl]-2-[4-(4-iodobutoxy)butoxy]acetamide. It was used in the next step without any further purification.

Preparation of N-[2-(2,6-dioxo-3-piperidyl)-1,3-dioxo-isoindolin-5-yl]-2-[4-(4-iodobutoxy)butoxy]acetamide (compound b4')

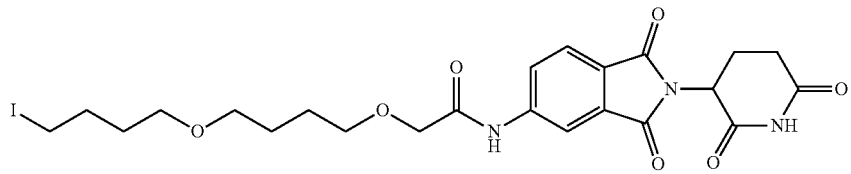 [SMILES: O=C1CCC(N2C(=O)c3ccc(NC(=O)COCCCCOCCCCI)cc3C2=O)C(=O)N1]

Compound b4' was prepared according to the procedure used for the preparation of compound b4. Only filtration in silica gel and evaporation of the solvent was employed to give 28.5 mg (62.6%) of N-[2-(2,6-dioxo-3-piperidyl)-1,3-dioxo-isoindolin-5-yl]-2-[4-(4-iodobutoxy)butoxy]acetamide as a yellow solid. $^1$H NMR (500 MHz, Chloroform-d) δ 8.73 (s, 1H), 8.33 (s, 1H), 8.11 (s, 1H), 7.97 (d, J=7.9 Hz, 1H), 7.81 (d, J=8.1 Hz, 1H), 4.97 (dd, J=12.1, 5.1 Hz, 1H), 4.10 (s, 2H), 3.64 (t, J=6.3 Hz, 2H), 3.46 (dt, J=9.7, 6.2 Hz, 4H), 3.21 (t, J=7.0 Hz, 2H), 2.81 (dq, J=50.5, 17.9, 17.2 Hz, 3H), 2.15 (dd, J=12.9, 4.3 Hz, 1H), 1.90 (p, J=7.1 Hz, 2H), 1.76 (dt, J=13.6, 6.2 Hz, 2H), 1.72-1.64 (m, 4H). LC/MS: [M+H]$^+$ for $C_{23}H_{29}IN_3O_7$ calculated: 586.1; found: 586.2.

Preparation of 3-[3-(3-chloropropoxy)propoxy]propanoyl chloride (compound c2)

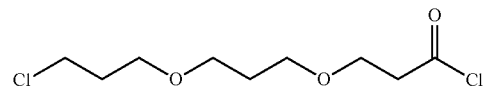 [SMILES: O=C(Cl)CCOCCCOCCCCl]

3-[3-(3-chloropropoxy)propoxy]propanoic acid (88 mg, 0.39 mmol) was heated in $SOCl_2$ at 60° C. for 2h. The solvent was evaporated to give 95 mg (99.8%) of 3-[3-(3-chloropropoxy)propoxy]propanoyl chloride. It was carried to the next step without further purification.

Preparation of 3-(3-(3-chloropropoxy)propoxy)-N-(2-(2,6-dioxopiperidin-3-yl)-1,3-dioxoisoindolin-4-yl)propanamide (compound c3)

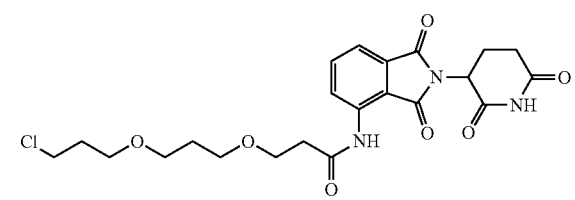

3-[3-(3-chloropropoxy)propoxy]propanoyl chloride (90 mg, 0.37 mmol) was dissolved in THF (2 ml). To this solution was added 4-amino-2-(2,6-dioxo-3-piperidyl)isoindoline-1,3-dione (101 mg, 0.37 mmol). The resulting suspension was heated to reflux for 4 hours. The solvent was evaporated in vacuo and the resulting solid was purified by flash chromatography (50/50 to 0/100 hexane/ethyl acetate)

to give a light yellow solid 157 mg (88.3%) of 3-(3-(3-chloropropoxy)propoxy)-N-(2-(2,6-dioxopiperidin-3-yl)-1,3-dioxoisoindolin-4-yl)propanamide as a yellow solid. $^1$H NMR (500 MHz, Chloroform-7) δ 9.83 (s, 1H), 8.85 (d, J=8.5 Hz, 1H), 8.44 (s, 1H), 7.70 (dd, J=8.5, 7.3 Hz, 1H), 7.54 (d, J=7.3 Hz, 1H), 5.05-4.87 (m, 1H), 3.77 (t, J=5.7 Hz, 2H), 3.60 (td, J=6.5, 4.8 Hz, 4H), 3.50 (dt, J=12.7, 6.1 Hz, 4H), 2.93-2.85 (m, 1H), 2.85-2.69 (m, 4H), 2.16 (ddd, J=8.5, 6.3, 4.3 Hz, 1H), 1.97 (p, J=6.1 Hz, 2H), 1.88 (p, J=6.4 Hz, 2H). LC/MS: [M+H]$^+$ for $C_{22}H_{27}ClN_3O_7$ calculated; 480.1; found: 480.1.

Preparation of N-[2-(2,6-dioxo-3-piperidyl)-1,3-dioxo-isoindolin-4-yl]-2-[4-(4-iodobutoxy)butoxy]acetamide (compound c4)

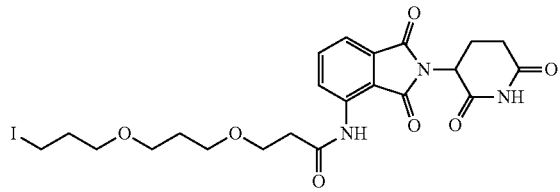 [SMILES: O=C1CCC(N2C(=O)c3cccc(NC(=O)CCOCCCOCCCI)c3C2=O)C(=O)N1]

To a solution of N-(2-(2,6-dioxopiperidin-3-yl)-1,3-dioxoisoindolin-4-yl)-3-(3-(3-iodopropoxy)propoxy)propanamide (150 mg, 0.31 mmol) in acetone (10 ml) was added NaI (234.2 mg, 1.56 mmol). The reaction mixture was stirred at refluxed temperature for 24 h, then the solvent was removed under vacuum and the crude product was dissolved in EtOAc (20 mL). An aqueous solution of Na$_2$SO$_3$ (10%, 15 mL) was added and the organic layer separated, washed with water (15 mL) and dried (Na$_2$SO$_4$). The solid was filtered off and the volatiles evaporated under vacuum to give 172 mg (95%) of N-[2-(2,6-dioxo-3-piperidyl)-1,3-dioxo-isoindolin-4-yl]-2-[4-(4-iodobutoxy)butoxy]acetamide. It was used in the next step without any further purification.

Preparation of 2-(2-chloroethoxy)-N-(2-(2,6-dioxopiperidin-3-yl)-1,3-dioxoisoindolin-4-yl)acetamide (compound d3)

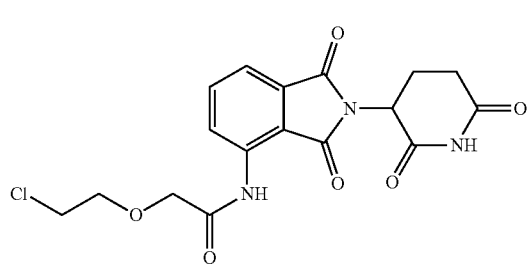 [SMILES: O=C1CCC(N2C(=O)c3cccc(NC(=O)COCCCl)c3C2=O)C(=O)N1]

2-(2-chloroethoxy)acetyl chloride (150 mg, 0.97 mmol) was dissolved in THF (10 ml). To this solution was added 4-amino-2-(2,6-dioxo-3-piperidyl)isoindoline-1,3-dione (230.8 mg, 0.97 mmol). The resulting suspension was heated to reflux for 4 hours. The solvent was evaporated under vacuum and the resulting solid was purified by flash chromatography (50/50 to 0/100 hexane/ethyl acetate) to give a light yellow solid 328.1 mg (86%) of 2-(2-chloroethoxy)-N-(2-(2,6-dioxopiperidin-3-yl)-1,3-dioxoisoindolin-4-yl)acetamide as a yellow solid. It was carried to the next step without any further purification.

Preparation of N-(2-(2,6-dioxopiperidin-3-yl)-1,3-dioxoisoindolin-4-yl)-2-(2-iodoethoxy)acetamide (compound d4)

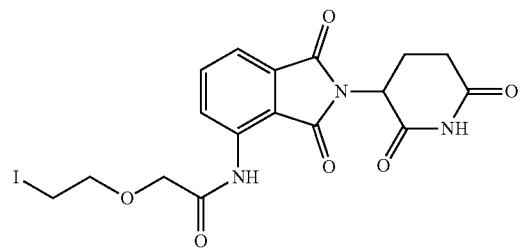 [SMILES: O=C1CCC(N2C(=O)c3cccc(NC(=O)COCCI)c3C2=O)C(=O)N1]

To a solution of 2-(2-chloroethoxy)-N-(2-(2,6-dioxopiperidin-3-yl)-1,3-dioxoisoindolin-4-yl)acetamide (500 mg, 1.27 mmol) in acetone (50 ml) was added NaI (950 mg, 6.1 mmol). The reaction mixture was stirred at refluxed temperature for 24 h, then the solvent was removed under vacuum and the crude product was dissolved in EtOAc (100 mL). An aqueous solution of Na$_2$SO$_3$ (50%, 15 mL) was added and the organic layer separated, washed with water (50 mL) and dried (Na$_2$SO$_4$). The solid was filtered off and the volatiles evaporated under vacuum to give 598 mg (97%) of N-(2-(2,6-dioxopiperidin-3-yl)-1,3-dioxoisoindolin-4-yl)-2-(2-iodoethoxy)acetamide. $^1$H NMR (500 MHz, Acetone-d$_6$) δ 10.46 (s, 1H), 9.92 (s, 1H), 8.84 (dd, J=8.5, 2.0 Hz, 1H), 7.86 (dd, J=8.4, 7.4 Hz, 1H), 7.60 (dd, J=7.3, 0.7 Hz, 1H), 5.17 (dd, J=12.7, 5.5 Hz, 1H), 4.27 (s, 2H), 4.00 (t, J=6.7 Hz, 2H), 3.52 (t, J=6.7 Hz, 2H), 3.07-2.91 (m, 1H), 2.86-2.71 (m, 2H), 2.28 (dtd, J=10.4, 5.4, 2.8 Hz, 1H). LC/MS: [M+H]$^+$ for $C_{17}H_{17}IN_3O_6$ calculated: 486.0; found: 486.2.

Preparation of N-(2-(2,6-dioxopiperidin-3-yl)-1,3-dioxoisoindolin-5-yl)-2-(2-(2-iodoethoxy)ethoxy)acetamide (compound e4')

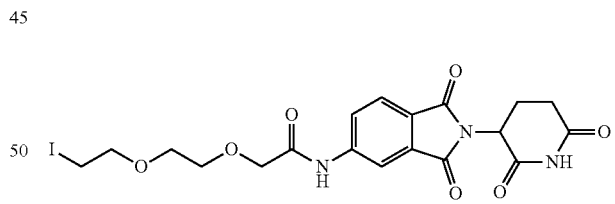

2-(2-(2-chloroethoxy)ethoxy)acetyl chloride (30 mg, 0.14 mmol) was dissolved in THF (2 ml). To this solution was added 4-amino-2-(2,6-dioxo-3-piperidyl)isoindoline-1,3-dione (32.8 mg, 0.12 mmol). The resulting suspension was heated to reflux for 4 hours. The solvent was evaporated under vacuum and the resulting solid dissolved in acetone (5 mL) then NaI (112 mg, 0.74 mmol) was added. The reaction mixture was stirred at refluxed temperature for 4 h, then the solvent was removed under vacuum and the crude product was dissolved in EtOAc (10 mL). An aqueous solution of Na$_2$SO$_3$ (50%, 5 mL) was added, the organic layer was separated, washed with water (10 mL), dried (Na$_2$SO$_4$). The solid was filtered off and the volatiles evaporated under vacuum to give 34.9 mg (44%) of N-(2-(2,6-dioxopiperidin- 3-yl)-1,3-dioxoisoindolin-5-yl)-2-(2-(2-iodoethoxy)ethoxy) acetamide as a yellow solid. $^1$H NMR (500 MHz, Chloroform-d) δ 9.06 (s, 1H), 8.19 (s, 1H), 8.16 (s, 1H), 8.01 (d, J=9.2 Hz, 1H), 7.82 (d, J=8.2 Hz, 1H), 4.97 (dd, J=12.3, 5.3 Hz, 1H), 4.18 (s, 2H), 3.85 (t, J=6.4 Hz, 2H), 3.81 (d, J=4.4 Hz, 2H), 3.75 (d, J=5.1 Hz, 4H), 3.33 (t, J=6.4 Hz, 2H), 2.97-2.69 (m, 3H), 2.17-2.12 (m, 1H). LC/MS: [M+H]$^+$ for $C_{19}H_{21}IN_3O_7$ calculated: 530.0. found: 530.2.

Synthesis of Intermediate 3-(4-phenoxyphenyl)-1-(piperidin-4-yl)-1H-pyrazolo[3,4-d]pyrimidin-4-amine hydrochloride (1)

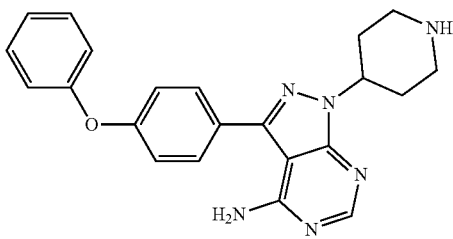

To a solution of triphenylphosphine (864.72 mg, 3.3 mmol) in THF (300 mL) was added DIAD (0.65 ml, 3.3 mmol) at 0° C. The reaction mixture was stirred at this temperature for 0.5 h under argon, then tert-butyl 4-hydroxypiperidine-1-carboxylate (663.53 mg, 3.3 mmol) was added. The reaction mixture was stirred at 0° C. for 0.5 h. After that, 3-(4-phenoxyphenyl)-1H-pyrazolo[3,4-d]pyrimidin-4-amine (500 mg, 1.65 mmol) was added. The reaction mixture was allowed to warm to room temperature with stirring for 4 h. The resulting mixture was then concentrated to afford the crude product, which was purified by flash silica gel column chromatography (SiO$_2$—80 g, hexane: ethyl acetate, gradient 3:7 to 100% in 15 min) to provide the desired Boc-protected compound as an off-white foam (504 mg). $^1$H NMR (400 MHz, DMSO-d6) δ 8.22 (s, 1H), 7.63 (d, J=8.7 Hz, 2H), 7.49-7.33 (m, 2H), 7.27-6.98 (m, 5H), 4.97-4.80 (m, 1H), 4.08 (bs, 2H), 2.97 (bs, 2H), 2.12-1.75 (m, 4H), 1.40 (s, 9H). Then, this foam was dissolved in EtOAc (10 mL) and 4 N HCl in dioxane (5 mL) was added. The reaction mixture was stirred at room temperature for 12 h (overnight). After complete conversion of the starting material, the solid was collected by filtration and washed with (AcOEt, 2 mL×2) to give an off-white solid (1) (560 mg, 80% yield). $^1$H NMR (500 MHz, DMSO-d6) δ 9.35 (bs, 1H), 9.02 (bs, 1H), 8.54 (s, 1H), 7.66 (d, J=8.2 Hz, 2H), 7.45 (t, J=7.5 Hz, 2H), 7.17 (td, J=19.2, 17.4, 7.6 Hz, 5H), 5.12 (t, J=11.1 Hz, 1H), 3.43 (d, J=12.5 Hz, 2H), 3.19 (q, J=11.5 Hz, 2H), 2.39 (q, J=10.9 Hz, 2H), 2.15 (d, J=12.6 Hz, 2H). LC/MS: [M+H]$^+$ for $C_{22}H_{23}N_6O$. calculated 387.1904, found 387.1933.

Synthesis of inactive control Compound 130: 2-(2-(2-(4-(4-amino-3-(4-phenoxyphenyl)-1H-pyrazolol[3,4-d]pyrimidin-1-yl)piperidin-1-yl)ethoxy)ethoxy)-N-(2-(1-methyl-2,6-dioxopiperidin-3-yl)-1,3-dioxoisoindolin-5-yl)acetamide Scheme 2: Synthesis of Compound 130

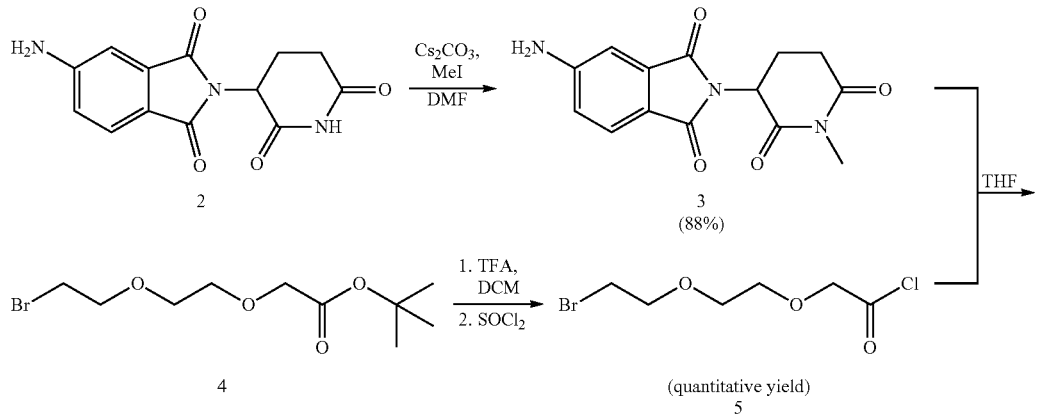

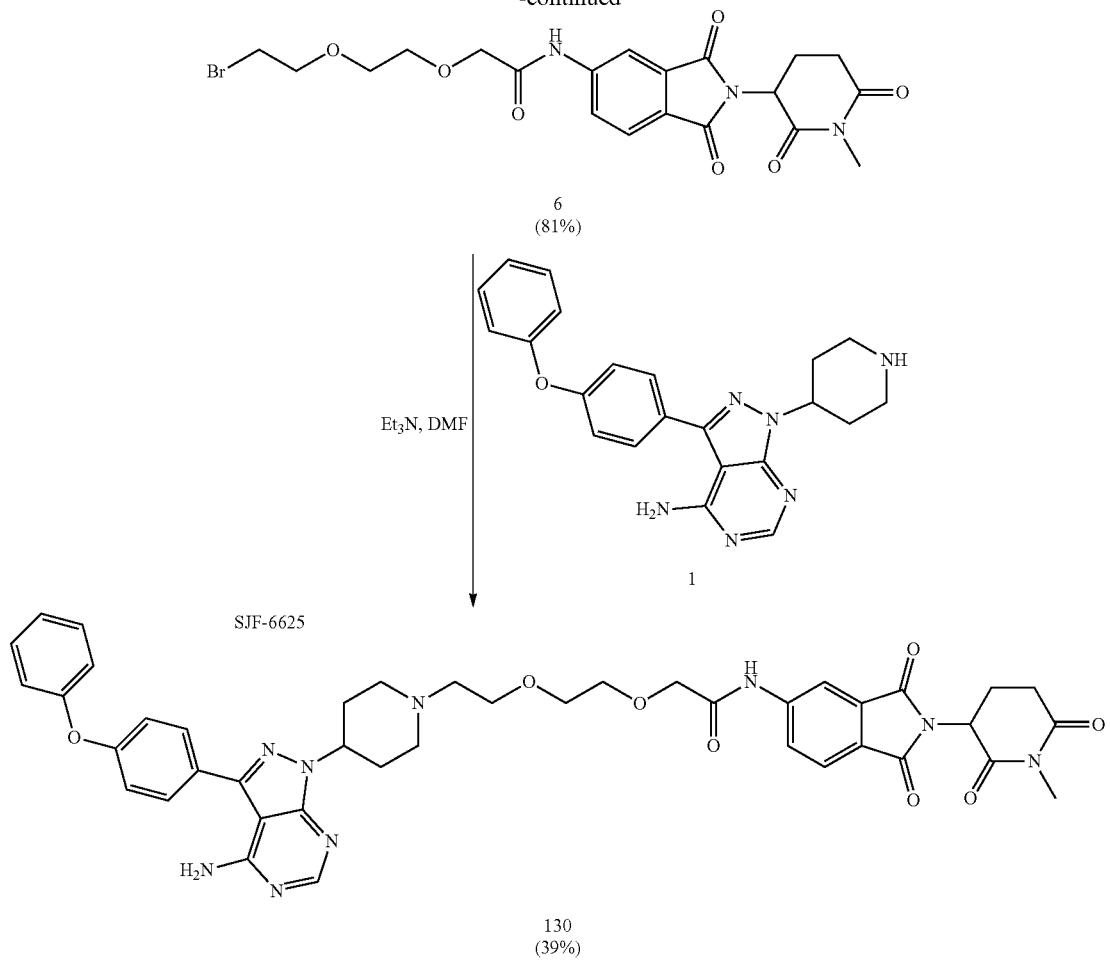

Step A: 5-amino-2-(1-methyl-2,6-dioxopiperidin-3-yl)isoindoline-1,3-dione (3)

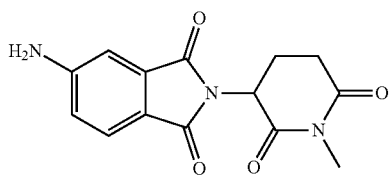

To a solution of 5-amino-2-(2,6-dioxopiperidin-3-yl)isoindoline-1,3-dione (2) (30 mg, 0.11 mmol) in DMF (1 mL) was added Cs$_2$CO$_3$ (35.77 mg, 0.11 mmol) and CH$_3$I (0.01 ml, 0.11 mmol) at room temperature. The reaction mixture was stirred for 2 h at the same temperature, and additional 1 eq of CH$_3$I (0.01 ml, 0.11 mmol) was added. Reaction mixture stirred for an additional 2 h at room temperature. The reaction was diluted with AcOEt (10 mL) and then quenched with aqueous HCl (1 N, 1 mL), the pH was adjusted to 7-8 using an aqueous solution of NaHCO$_3$. Organic phase was separated, washed with brine (5 mL, 5×), dried (Na$_2$SO$_4$), and evaporated under vacuum. Crude product was purified by PTLC (DCM:MeOH:NH$_4$OH, 90:9:1) to give 28 mg of pure product (3) as a yellow solid (88% yield).

$^1$H NMR (500 MHz, DMSO-d6) δ 7.52 (d, J=8.2 Hz, 1H), 6.94 (d, J=2.0 Hz, 1H), 6.83 (dd, J=8.2, 1.5 Hz, 2H), 6.57 (s, 2H), 5.09 (dd, J=13.0, 5.3 Hz, 1H), 3.00 (s, 3H), 2.96-2.85 (m, 1H), 2.78-2.68 (m, 1H), 2.61-2.43 (m, 1H), 2.01 (ddd, J=9.9, 5.5, 2.7 Hz, 1H). $^{13}$CNR (151 MHz, DMSO-d6) δ 172.24, 170.35, 168.08, 167.56, 155.70, 134.63, 125.69, 117.38, 116.56, 107.49, 49.59, 31.57, 27.02, 21.85 LC/MS (ESI); m/z [M+H]$^+$ Calcd. for C$_{14}$H$_{14}$N$_3$O$_4$, 288.0984. Found 288.0987.

Step B: 2-(2-(2-bromoethoxy)ethoxy)-N-(2-(1-methyl-2,6-dioxopiperidin-3-yl)-1,3-dioxoisoindolin-5-yl)acetamide (6)

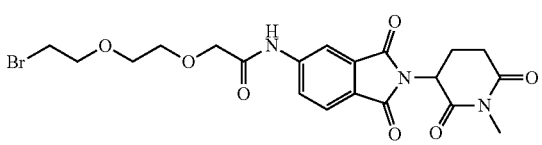

A solution of tert-butyl 2-[2-(2-bromoethoxy)ethoxy]acetate (4) (45 mg, 0.16 mmol) in a mixture of TFA (0.6 ml, 8.08 mmol) and dichloromethane (1.5 ml) was stirred for 1 h. Then the solvent was removed under vacuum and crude product was dried under high vacuum for 2 h. Then the crude product was heated in $SOCl_2$ (1 mL) for 1 h. The solvent was evaporated to dryness to give 38.9 mg (quantitative yield) of 2-[3-(6-chlorohexoxy)propoxy]-acetyl chloride (5) as a colorless oil. Crude product was dissolved in THF (2 mL) and this solution was added into a flask containing 5-amino-2-(1-methyl-2,6-dioxopiperidin-3-yl)isoindoline-1,3-dione (3) (25 mg, 0.09 mmol). The resulting suspension was heated to reflux temperature for 3 hours. The solvent was evaporated in vacuum and the resulting solid was purified by flash chromatography ($SiO_2$—4 g, gradient hexane/ethyl acetate, 1:1 to 100% in 15 min) to give a light yellow product (6) 35 mg (81% yield). $^1H$ NMR (500 MHz, DMSO-d6) δ 10.38 (s, 1H), 8.30 (s, 1H), 8.04 (d, J=8.3 Hz, 2H), 7.89 (d, J=8.2 Hz, 1H), 5.20 (dd, J=13.1, 5.3 Hz, 1H), 4.20 (d, J=1.2 Hz, 2H), 3.77 (td, J=5.7, 1.1 Hz, 2H), 3.73-3.69 (m, 2H), 3.69-3.64 (m, 2H), 3.61 (td, J=5.7, 1.1 Hz, 2H), 3.01 (s, 3H), 3.00-2.89 (m, 1H), 2.80-2.73 (m, 1H), 2.63-2.52 (m, 1H), 2.11-2.02 (m, 1H). $^{13}C$ NMR (151 MHz, DMSO-d6) δ 171.76, 169.66, 169.46, 166.96, 166.73, 144.32, 132.68, 125.29, 124.64, 124.27, 113.58, 70.36, 70.34, 70.28, 69.44, 49.57, 32.27, 31.13, 26.65, 21.24. LC/MS (ESI); m/z $[M+H]^+$ Calcd. for $C_{20}H_{23}BrN_3O_7$, 496.0719. Found 496.0745.

Step C: 2-(2-(2-(4-(4-amino-3-(4-phenoxyphenyl)-1H-pyrazolo[3,4-d]pyrimidin-1-yl)piperidin-1-yl)ethoxy)ethoxy)-N-(2-(1-methyl-2,6-dioxopiperidin-3-yl)-1,3-dioxoisoindolin-5-yl)acetamide
(Compound 130)

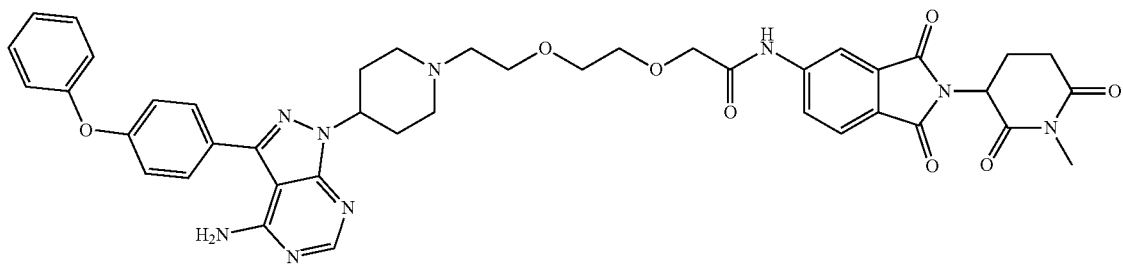

130

To a solution of 3-(4-phenoxyphenyl)-1-(4-piperidyl)pyrazolo[3,4-d]pyrimidin-4-amine (1) (30.7 mg, 0.07 mmol) and TEA (0.1 ml, 0.57 mmol) in DMF (1 ml) was added compound (5) (30 mg, 0.06 mmol) and the resulting solution stirred for 48 h at rt. The reaction mixture was evaporated under vacuum. Crude product was purified by PTLC (DCM: MeOH:$NH_4OH$, 90:9:1) to give 19 mg of pure product (39% yield). $^1H$ NMR (400 MHz, DMSO-d6) δ 10.35 (s, 1H), 8.30 (s, 1H), 8.22 (s, 1H), 8.06 (dd, J=8.3, 1.9 Hz, 1H), 7.88 (d, J=8.2 Hz, 1H), 7.64 (d, J=8.2 Hz, 2H), 7.42 (t, J=7.8 Hz, 2H), 7.15 (dt, J=21.3, 8.0 Hz, 5H), 5.18 (dd, J=13.1, 5.3 Hz, 1H), 4.73-4.54 (m, 1H), 4.19 (s, 2H), 3.82-3.68 (m, 1H), 3.67-3.60 (m, 2H), 3.57 (t, J=5.9 Hz, 2H), 3.00 (s, 3H), 2.99-2.86 (m, 2H), 2.75 (dt, J=17.1, 3.5 Hz, 1H), 2.62-2.46 (m, 4H), 2.26-2.10 (m, 4H), 2.08-1.99 (m, 1H), 1.93-1.79 (m, 2H). $^{13}C$ NMR (126 MHz, DMSO-d6) δ 171.73, 169.61, 169.56, 166.95, 166.71, 158.14, 157.05, 156.29, 155.41, 153.60, 144.34, 142.75, 132.64, 130.12, 130.00, 128.12, 125.28, 124.59, 124.30, 123.79, 118.99, 118.95, 113.65, 97.44, 70.45, 70.33, 69.58, 68.51, 56.99, 53.88, 52.70, 49.57, 31.12, 30.99, 26.62, 21.23. LC/MS (ESI); m/z $[M+H]^+$ Calcd. for $C_{42}H_{44}N_9O_8$, 802.3312. Found 802.3362.

Synthesis of Compound 100: Preparation of 2-(2-(4-(4-amino-3-(4-phenoxyphenyl)-1H-pyrazolo[3,4-d]pyrimidin-1-yl)piperidin-1-yl)ethoxy)-N-(2-(2,6-dioxopiperidin-3-yl)-1,3-dioxoisoindolin-4-yl) acetamide (Compound 100)

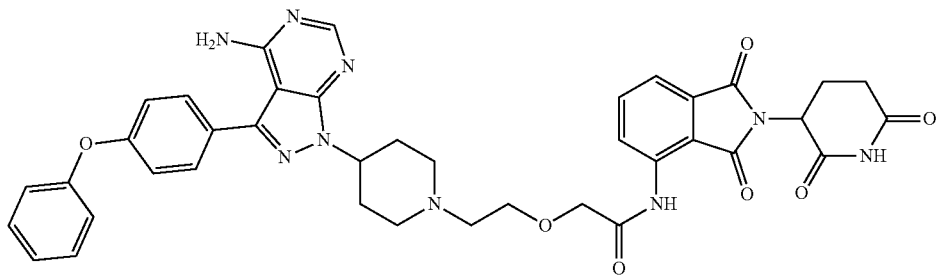 [SMILES: Nc1ncnc2c1c(-c1ccc(Oc3ccccc3)cc1)nn2C1CCN(CCOCC(=O)Nc2cccc3c2C(=O)N(C2CCC(=O)NC2=O)C3=O)CC1]

To a solution of 3-(4-phenoxyphenyl)-1-(4-piperidyl)pyrazolo[3,4-d]pyrimidin-4-amine (15.93 mg, 0.04 mmol) and TEA (21.6 µl, 0.12 mmol) in DMF (1 ml) was added N-[2-(2,6-dioxo-3 piperidyl)-1,3-dioxo-isoindolin-4-yl]-2-(2-iodoethoxy)acetamide (20 mg, 0.04 mmol) and the resulting solution stirred for 16 h at room temperature. The solvent was evaporated and the residue subjected to preparatory TLC purification (MeOH/DCM: 10/90) to give 10.4 mg (33.9%) of 2-[2-[4-[4-amino-3-(4-phenoxyphenyl)pyrazolo[3,4-d]pyrimidin-1-yl]-1-piperidyl]ethoxy]-N-[2-(2,6-dioxo-3-piperidyl)-1,3-dioxo-isoindolin-4-yl]acetamide. $^1$H NMR (500 MHz, Chloroform-d) δ 10.97 (s, 1H), 10.51 (s, 1H), 8.87 (d, J=8.4 Hz, 1H), 8.37 (s, 1H), 7.71 (t, J=7.9 Hz, 1H), 7.61 (d, J=8.2 Hz, 2H), 7.57 (d, J=7.3 Hz, 1H), 7.38 (t, J=7.7 Hz, 2H), 7.19-7.03 (m, 5H), 5.70 (s, 2H), 4.95 (dd, J=12.2, 5.3 Hz, 1H), 4.72 (tt, J=11.6, 4.1 Hz, 1H), 4.22-4.07 (m, 2H), 3.81 (t, J=5.1 Hz, 2H), 3.24 (d, J=11.8 Hz, 1H), 3.12 (d, J=11.3 Hz, 1H), 2.96-2.69 (m, 4H), 2.53-2.22 (m, 4H), 2.21-2.13 (m, 1H), 2.09-1.95 (m, 2H), 1.72 (bs, 1H). $^{13}$C NMR (151 MHz, Chloroform-d) δ 171.87, 169.10, 168.59, 168.34, 166.76, 158.32, 157.89, 156.34, 155.26, 153.39, 143.39, 136.73, 136.23, 131.39, 129.92, 127.94, 125.14, 123.95, 119.50, 119.00, 118.76, 116.16, 98.47, 70.96, 70.69, 60.38, 57.88, 54.68, 54.06, 53.21, 49.31, 31.52, 31.24, 22.93. LC/MS: [M+H]$^+$ for $C_{39}H_{38}N_9O_7$ calculated: 744.3; found: 744.3; [M+MeOH+H]$^+$ for $C_{40}H_{42}N_9O_8$ calculated: 776.3; found: 776.3.

Synthesis of Compound 101: Preparation of 2-[2-[2-[4-[4-amino-3-(4-phenoxyphenyl)pyrazolo[3,4-d]pyrimidin-1-yl]-1-piperidyl]ethoxy]ethoxy]-N-[2-(2,6-dioxo-3-piperidyl)-1,3-dioxo-isoindolin-4-yl] acetamide (Compound 101)

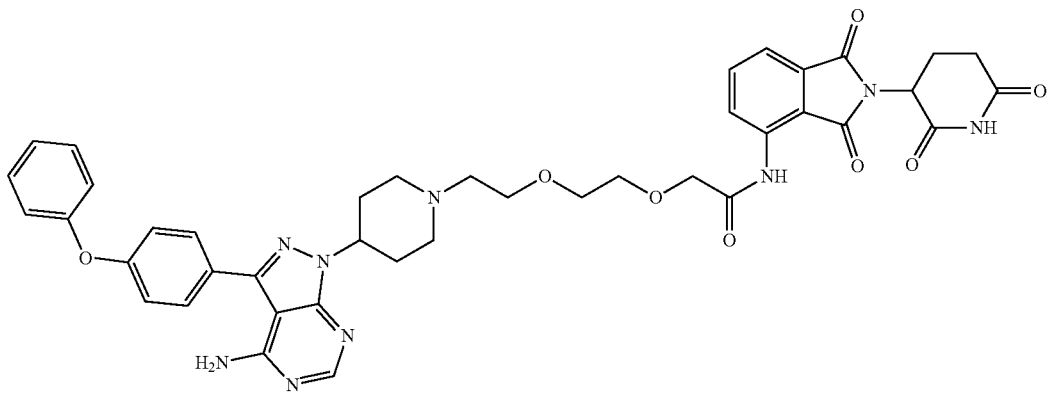 [SMILES: Nc1ncnc2c1c(-c1ccc(Oc3ccccc3)cc1)nn2C1CCN(CCOCCOCC(=O)Nc2cccc3c2C(=O)N(C2CCC(=O)NC2=O)C3=O)CC1]

To a solution of 3-(4-phenoxyphenyl)-1-(4-piperidyl)pyrazolo[3,4-d]pyrimidin-4-amine (7.3 mg, 0.02 mmol) and TEA (0.01 ml, 0.06 mmol) in DMF (1 ml) was added N-[2-(2,6-dioxo-3-piperidyl)-1,3-dioxo-isoindolin-4-yl]-2-[2-(2-iodoethoxy)ethoxy]acetamide (20 mg, 0.04 mmol) and the resulting solution stirred for 16 h at room temperature. The solvent was evaporated and the residue subjected to preparatory TLC purification (ammonia/MeOH/DCM: 1/10/90) to give 16.5 mg (55.4%) of 2-[2-[2-[4-[4-amino-3-(4-phenoxyphenyl)pyrazolo[3,4-d]pyrimidin-1-yl]-1-piperidyl]ethoxy]ethoxy]-N-[2-(2,6-dioxo-3-piperidyl)-1,3-dioxo-isoindolin-4-yl]acetamide. $^1$H NMR (500 MHz, Chloroform-d) δ 11.21 (s, 1H), 10.60 (s, 1H), 8.82 (d, J=8.5 Hz, 1H), 8.36 (d, J=1.6 Hz, 1H), 7.73-7.67 (m, 1H), 7.62 (dd, J=8.6, 1.7 Hz, 2H), 7.56 (dd, J=7.2, 1.6 Hz, 1H), 7.41-7.34 (m, 2H), 7.19-7.09 (m, 3H), 7.10-7.04 (m, 2H), 5.66 (s, 2H), 4.92 (s, 1H), 4.77 (s, 1H), 4.24-4.11 (m, 2H), 3.86-3.63 (m, 6H), 3.19 (s, 2H), 2.90-2.57 (m, 5H), 2.51-2.14 (m, 5H), 2.02 (d, J=16.8 Hz, 2H). $^{13}$C NMR (151 MHz, Chloroform-d) δ 171.85, 169.12, 169.02, 168.60, 166.74, 158.33, 157.76, 156.36, 155.36, 143.31, 136.71, 136.27, 131.41, 129.95, 129.92, 128.01, 124.99, 123.95, 119.48, 119.03, 118.69, 116.10, 98.50, 71.36, 70.77, 70.40, 68.86, 57.03, 54.25, 53.16, 52.75, 49.21, 31.27, 30.84, 23.10. LC/MS: [M+H]$^+$ for $C_{41}H_{42}N_9O_8$ calculated: 788.3; found: 788.3; [M+MeOH+H]$^+$ for $C_{42}H_{46}N_9O_9$ calculated: 820.3; found: 820.3.

Synthesis of Compound 102: Preparation of 2-[2-[2-[4-[4-amino-3-(4-phenoxyphenyl)pyrazolo[3,4-d]pyrimidin-1-yl]-1-piperidyl]ethoxy]ethoxy]-N-[2-(2,6-dioxo-3-piperidyl)-1,3-dioxo-isoindolin-5-yl]acetamide (Compound 102)

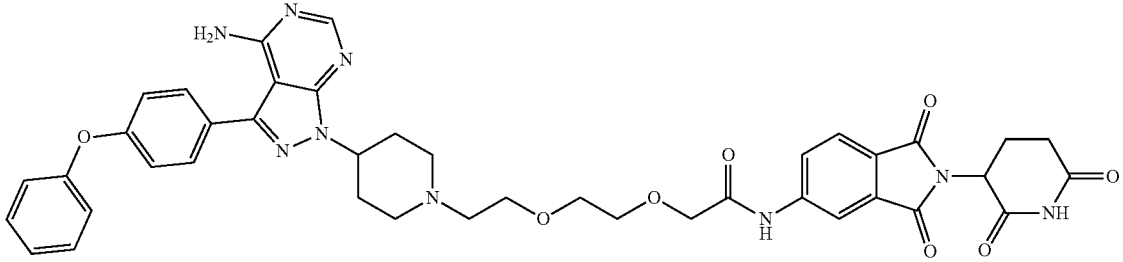 [SMILES: Nc1ncnc2c1c(-c1ccc(Oc3ccccc3)cc1)nn2C1CCN(CCOCCOCC(=O)Nc2ccc3c(c2)C(=O)N(C2CCC(=O)NC2=O)C3=O)CC1]

To a solution of 3-(4-phenoxyphenyl)-1-(4-piperidyl)pyrazolo[3,4-d]pyrimidin-4-amine (12.41 mg, 0.03 mmol) and TEA (0.02 ml, 0.1 mmol) in DMF (1 ml) was added N-[2-(2,6-dioxo-3-piperidyl)-1,3-dioxo-isoindolin-5-yl]-2-[2-(2-iodoethoxy)ethoxy]acetamide (17 mg, 0.03 mmol) and the resulting solution stirred for 16 h at room temperature. The solvent was evaporated and the residue subjected to preparatory TLC purification (ammonia/MeOH/DCM: 1/10/90) to give 13.9 mg (54.9%) of 2-[2-[2-[4-[4-amino-3-(4-phenoxyphenyl)pyrazolo[3,4-d]pyrimidin-1-yl]-1-piperidyl]ethoxy]ethoxy]-N-[2-(2,6-dioxo-3-piperidyl)-1,3-dioxo-isoindolin-5-yl]acetamide. $^1$H NMR (500 MHz, Chloroform-d) δ 10.01 (bs, 1H), 9.38 (s, 1H), 8.40 (s, 1H), 8.21 (d, J=8.1 Hz, 1H), 8.02 (s, 1H), 7.82 (d, J=8.2 Hz, 1H), 7.61 (d, J=8.5 Hz, 2H), 7.37 (t, J=7.9 Hz, 2H), 7.14 (dd, J=19.9, 8.0 Hz, 3H), 7.07 (d, J=7.9 Hz, 2H), 5.70 (bs, 2H), 4.95 (dd, J=12.4, 5.3 Hz, 1H), 4.77 (t, J=10.8 Hz, 1H), 4.23-4.09 (m, 2H), 3.85-3.68 (m, 5H), 3.07 (dd, J=22.1, 8.9 Hz, 2H), 2.92-2.67 (m, 5H), 2.29 (dq, J=22.9, 11.7 Hz, 4H), 2.13 (d, J=10.3 Hz, 1H), 1.99-1.94 (m, 3H). $^{13}$C NMR (126 MHz, Chloroform-d) δ 171.55, 169.04, 168.67, 166.88, 166.82, 158.29, 157.82, 156.41, 155.47, 153.70, 143.38, 143.33, 133.06, 129.91, 128.05, 126.55, 124.97, 124.63, 123.92, 119.46, 119.07, 114.92, 98.49, 71.50, 70.38, 69.89, 69.28, 57.52, 54.32, 53.26, 49.42, 31.48, 31.30, 31.20, 22.71. LC/MS: [M+H]$^+$ for $C_{41}H_{42}N_9O_8$ calculated: 788.3; found: 788.3; [M+MeOH+H]$^+$ for $C_{42}H_{46}N_9O_9$ calculated: 820.3; found: 820.3.

Synthesis of Compound 103: Preparation of 3-(3-(3-(4-(4-amino-3-(4-phenoxyphenyl)-1H-pyrazolo[3,4-d]pyrimidin-1-yl)piperidin-1-yl)propoxy)propoxy)-N-(2-(2,6-dioxopiperidin-3-yl)-1,3-dioxoisoindolin-4-yl)propanamide (Compound 103)

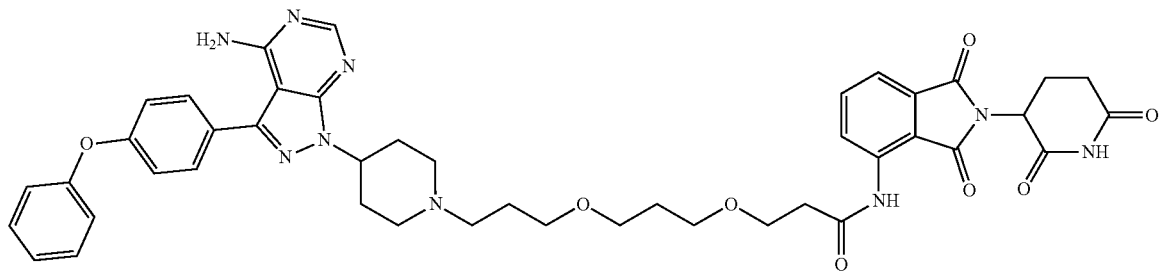 [SMILES: Nc1ncnc2c1c(-c1ccc(Oc3ccccc3)cc1)nn2C1CCN(CCCOCCCOCCC(=O)Nc2cccc3c2C(=O)N(C2CCC(=O)NC2=O)C3=O)CC1]

To a solution of 3-(4-phenoxyphenyl)-1-(4-piperidyl)pyrazolo[3,4-d]pyrimidin-4-amine (13.53 mg, 0.04 mmol)) and TEA (0.02 ml, 0.11 mmol) in DMF (1 ml) was added N-[2-(2,6-dioxo-3-piperidyl)-1,3-dioxo-isoindolin-4-yl]-3-[3-(3-iodopropoxy)propoxy]propanamide (20 mg, 0.04 mmol) and the resulting solution stirred for 16 h at rt. The solvent was evaporated and the residue subjected to preparatory TLC purification (MeOH/DCM: 10/90) to give 16.1 mg (55.4%) of 3-[3-[3-[4-[4-amino-3-(4-phenoxyphenyl)pyrazolo[3,4-d]pyrimidin-1-yl]-1-piperidyl]propoxy]propoxy]-N-[2-(2,6-dioxo-3-piperidyl)-1,3-dioxo-isoindolin-4-yl]propanamide. $^1$H NMR (500 MHz, Chloroform-d) δ 11.01 (bs, 1H), 10.04 (s, 1H), 8.86 (d, J=8.5 Hz, 1H), 8.38 (s, 1H), 7.72-7.61 (m, 3H), 7.59-7.51 (m, 1H), 7.39 (dd, J=8.6, 7.3 Hz, 2H), 7.21-7.05 (m, 5H), 5.54 (bs, 2H), 4.99-4.91 (m, 1H), 4.82-4.71 (m, 1H), 3.82-3.73 (m, 2H), 3.72-3.59 (m, 2H), 3.56-3.39 (m, 4H), 3.17 (bs, 2H), 2.92-1.72 (m, 5H), 2.56 (bs, 1H), 2.48-2.35 (m, 3H), 2.27-2.11 (m, 3H), 1.99 (d, J=14.0 Hz, 2H), 1.94 (dd, J=13.7, 6.9 Hz, 2H), 1.78 (d, J=7.0 Hz, 2H). $^{13}$C NMR (151 MHz, Chloroform-d) δ 171.80, 171.15, 168.76, 168.50, 166.92, 158.32, 157.70, 156.39, 155.44, 153.84, 143.24, 137.53, 136.06, 131.34, 129.97, 129.92, 128.09, 125.73, 123.93, 119.47, 119.08, 118.36, 115.80, 98.57, 68.88, 68.80, 67.58, 65.99, 54.72, 54.54, 53.41, 52.56, 52.16, 49.36, 38.78, 31.67, 30.91, 29.52, 26.83, 22.82. LC/MS: [M+H]+ for $C_{44}H_{48}N_9O_8$ calculated: 830.3626; found: 830.3; [M+MeOH+H]+ for $C_{45}H_{52}N_9O_9$ calculated: 862.4; found: 862.4.

Synthesis of Compound 104: Preparation of 2-[2-[6-[4-[4-amino-3-(4-phenoxyphenyl)pyrazolo[3,4-d]pyrimidin-1-yl]-1-piperidyl]hexoxy]ethoxy]-N-[2-(2,6-dioxo-3-piperidyl)-1,3-dioxo-isoindolin-4-yl]acetamide (Compound 104)

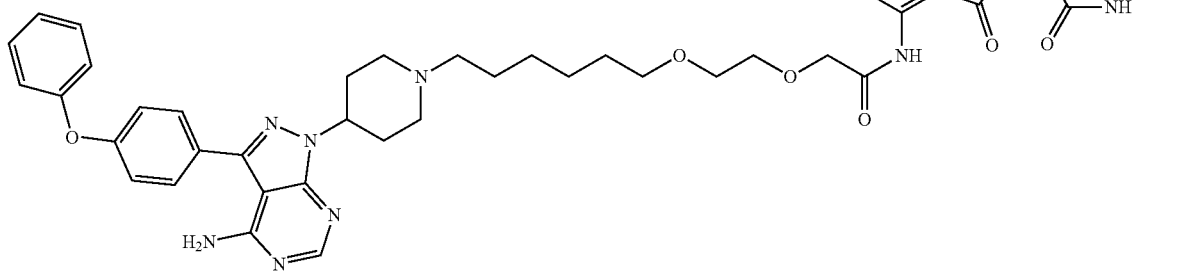

To a solution of 3-(4-phenoxyphenyl)-1-(4-piperidyl)pyrazolo[3,4-d]pyrimidin-4-amine (13.2 mg, 0.03 mmol) and TEA (4.42 mg, 0.03 mmol) in DMF (1 ml) was added N-[2-(2,6-dioxo-3-piperidyl)-1,3-dioxo-isoindolin-4-yl]-2-[2-(6-iodohexoxy)ethoxy]acetamide (20 mg, 0.03 mmol) and the resulting solution stirred for 16 h at room temperature. The solvent was evaporated and the residue subjected to preparatory TLC purification (ammonia/MeOH/DCM: 1/10/60) to give 15.3 mg (53.1%) of 2-[2-[6-[4-[4-amino-3-(4-phenoxyphenyl)pyrazolo[3,4-d]pyrimidin-1-yl]-1-piperidyl]hexoxy]ethoxy]-N-[2-(2,6-dioxo-3-piperidyl)-1,3-dioxo-isoindolin-4-yl]acetamide. 1H NMR (500 MHz, CDCl3) δ 11.19 (bs, 1H), 10.44 (s, 1H), 8.86 (d, J=8.5 Hz, 1H), 8.37 (s, 1H), 7.74-7.68 (m, 1H), 7.67-7.61 (m, 2H), 7.56 (d, J=7.3 Hz, 1H), 7.42-7.34 (m, 2H), 7.19-7.11 (m, 3H), 7.10-7.04 (m, 2H), 5.65 (s, 2H), 4.97 (dd, J=12.7, 5.3 Hz, 1H), 4.76 (s, 1H), 4.25-4.11 (m, 2H), 3.85-3.66 (m, 4H), 3.52 (t, J=6.7 Hz, 2H), 3.17 (bs, 2H), 2.95-2.82 (m, 2H), 2.80-2.69 (m, 1H), 2.42 (d, J=12.7 Hz, 4H), 2.21-2.11 (m, 3H), 2.00 (bs, 2H), 1.66-1.45 (m, 4H), 1.41-1.24 (m, 4H). 13C NMR (151 MHz, CDCl3) δ 171.95, 169.37, 168.78, 168.42, 166.92, 158.30, 157.76, 156.41, 155.36, 153.82, 143.26, 136.67, 136.12, 131.39, 129.97, 129.92, 128.08, 125.29, 123.92, 119.47, 119.10, 118.74, 116.26, 98.55, 71.75, 71.58, 70.99, 69.71, 57.97, 54.63, 52.65, 52.38, 50.81, 49.49, 31.78, 30.87, 29.35, 27.24, 26.60, 25.87, 22.62. LC/MS: [M+H]+ for $C_{45}H_{50}N_9O_8$ calculated: 844.4; found: 844.5.

Synthesis of Compound 105: Preparation of 2-[4-[4-[4-[4-amino-3-(4-phenoxyphenyl)pyrazolo[3,4-d]pyrimidin-1-yl]-1-piperidyl]butoxy]butoxy]-N-[2-(2,6-dioxo-3-piperidyl)-1,3-dioxo-isoindolin-5-yl]acetamide (Compound 105)

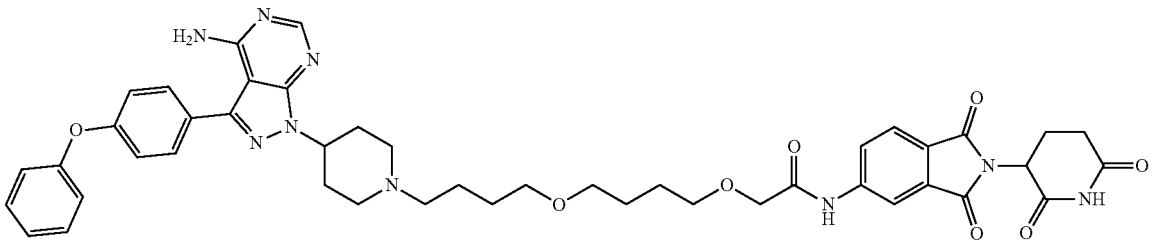 [SMILES: Nc1ncnc2c1c(-c1ccc(Oc3ccccc3)cc1)nn2C1CCN(CCCCOCCCCOCC(=O)Nc2ccc3c(c2)C(=O)N(C2CCC(=O)NC2=O)C3=O)CC1]

To a solution of 3-(4-phenoxyphenyl)-1-(4-piperidyl)pyrazolo[3,4-d]pyrimidin-4-amine (7.9 mg, 0.02 mmol) and TEA (0.02 ml, 0.1 mmol) in DMF (1 ml) was added N-[2-(2,6-dioxo-3-piperidyl)-1,3-dioxo-isoindolin-5-yl]-2-[4-(4-iodobutoxy)butoxy]acetamide (10 mg, 0.02 mmol) and the resulting solution stirred for 16 h at room temperature. The solvent was evaporated and the residue subjected to preparatory TLC purification (ammonia/MeOH/DCM: 1/10/90) to give 6.4 mg (44.4%) of 2-[4-[4-[4-[4-amino-3-(4-phenoxyphenyl)pyrazolo[3,4-d]pyrimidin-1-yl]-1-piperidyl]butoxy]butoxy]-N-[2-(2,6-dioxo-3-piperidyl)-1,3-dioxo-isoindolin-5-yl]acetamide. $^1$H NMR (500 MHz, Chloroform-d) δ 9.28 (s, 1H), 8.74 (s, 1H), 8.39 (s, 1H), 8.11 (s, 1H), 8.01 (d, J=8.2 Hz, 1H), 7.82 (d, J=8.2 Hz, 1H), 7.64 (d, J=8.6 Hz, 2H), 7.38 (t, J=7.9 Hz, 2H), 7.14 (dd, J=19.3, 8.0 Hz, 3H), 7.10-7.02 (m, 2H), 5.64 (s, 2H), 4.96 (dd, J=12.5, 5.3 Hz, 1H), 4.80-4.75 (m, 1H), 4.10 (s, 2H), 3.65 (t, J=6.4 Hz, 2H), 3.52-3.43 (m, 4H), 3.07 (d, J=9.8 Hz, 2H), 2.82 (ddd, J=42.7, 31.7, 15.4 Hz, 3H), 2.42 (d, J=13.2 Hz, 3H), 2.24-2.11 (m, 3H), 2.00 (d, J=11.0 Hz, 2H), 1.83-1.53 (m, 6H). $^{13}$C NMR (126 MHz, Chloroform-d) δ 171.23, 168.32, 166.74, 166.70, 158.30, 157.77, 156.41, 155.43, 153.84, 143.26, 143.06, 133.32, 129.95, 129.91, 128.12, 126.60, 124.98, 124.23, 123.93, 119.59, 119.46, 119.08, 119.03, 114.41, 98.53, 71.97, 71.69, 71.14, 70.84, 70.50, 70.29, 70.12, 62.75, 58.14, 52.83, 49.39, 31.45, 31.36, 27.68, 26.51, 26.39, 23.90, 22.65. LC/MS: [M+H]$^+$ for $C_{45}H_{50}N_9O_8$ calculated: 844.9; found: 844.3.

Synthesis of Compound 106:Preparation of 2-[4-[4-[4-[4-amino-3-(4-phenoxyphenyl)pyrazolo[3,4-d]pyrimidin-1-yl]-1-piperidyl]butoxy]butoxy]-N-[2-(2,6-dioxo-3-piperidyl)-1,3-dioxo-isoindolin-4-yl]acetamide (Compound 106)

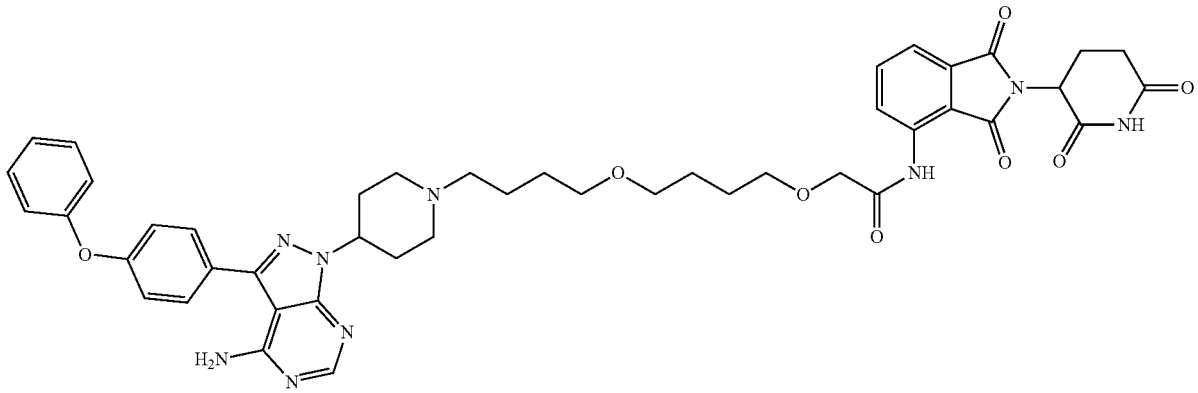 [SMILES: Nc1ncnc2c1c(-c1ccc(Oc3ccccc3)cc1)nn2C1CCN(CCCCOCCCCOCC(=O)Nc2cccc3c2C(=O)N(C2CCC(=O)NC2=O)C3=O)CC1]

To a solution of 3-(4-phenoxyphenyl)-1-(4-piperidyl)pyrazolo[3,4-d]pyrimidin-4-amine (13.2 mg, 0.03 mmol) and TEA (4.42 mg, 0.03 mmol) in DMF (1 ml) was added N-[2-(2,6-dioxo-3-piperidyl)-1,3-dioxo-isoindolin-4-yl]-2-[4-(4-iodobutoxy)butoxy]acetamide (20 mg, 0.03 mmol) and the resulting solution stirred for 16 h at room temperature. The solvent was evaporated and the residue subjected to preparatory TLC purification (ammonia/MeOH/DCM: 1/10/90) to give 17.9 mg (62.1%) of 2-[4-[4-[4-[4-amino-3-(4-phenoxyphenyl)pyrazolo[3,4-d]pyrimidin-1-yl]-1-piperidyl]butoxy]butoxy]-N-[2-(2,6-dioxo-3-piperidyl)-1,3-dioxo-isoindolin-4-yl]acetamide. $^1$H NMR (500 MHZ, Chloroform-d) δ 11.21 (bs, 1H), 10.47 (s, 1H), 8.85 (d, J=8.4 Hz, 1H), 8.37 (s, 1H), 7.69 (t, J=7.8 Hz, 1H), 7.64 (d, J=7.6 Hz, 2H), 7.55 (d, J=1.1 Hz, 1H), 7.38 (t, J=7.4 Hz, 2H), 7.16 (dd, J=12.0, 7.6 Hz, 3H), 7.08 (d, J=8.3 Hz, 2H), 5.65 (s, 2H), 4.95 (d, J=5.4 Hz, 1H), 4.77 (t, J=10.6 Hz, 1H), 4.10 (s, 2H), 3.64 (d, J=5.4 Hz, 2H), 3.45 (d, J=20.4 Hz, 4H), 3.19 (d, J=8.2 Hz, 2H), 2.86 (q, J=14.2, 12.7 Hz, 2H), 2.76 (d, J=15.0 Hz, 1H), 2.53-2.36 (m, 4H), 2.27-2.11 (m, 3H), 2.00 (s, 2H), 1.76 (dd, J=22.0, 4 Hz, 4H), 1.59 (s, 4H). $^{13}$C NMR (151 MHz, CDCl$_3$) δ 171.98, 169.46, 168.79, 168.41, 166.91, 158.29, 157.77, 156.41, 155.37, 153.83, 143.27, 136.68, 136.11, 131.39, 129.96, 129.92, 128.06, 125.16, 123.91, 119.47, 119.10, 118.68, 116.23, 98.55, 72.06, 70.52, 70.50, 70.45, 57.93, 54.61, 52.67, 52.34, 49.46, 31.74, 30.82, 27.80, 26.42, 26.16, 23.59, 22.67. LC/MS: [M+H]$^+$ for C$_{45}$H$_{50}$N$_9$O$_8$ calculated: 844.4; found: 844.5.

Synthesis of Compound 131: 5-(2-(2-(2-(4-(4-amino-3-(4-phenoxyphenyl)-1H-pyrazolo[3,4-d]pyrimidin-1-yl)piperidin-1-yl)ethoxy)ethoxy)ethoxy)-2-(2,6-dioxopiperidin-3-yl)isoindoline-1,3-dione

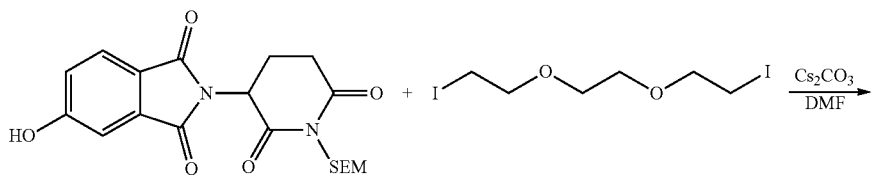

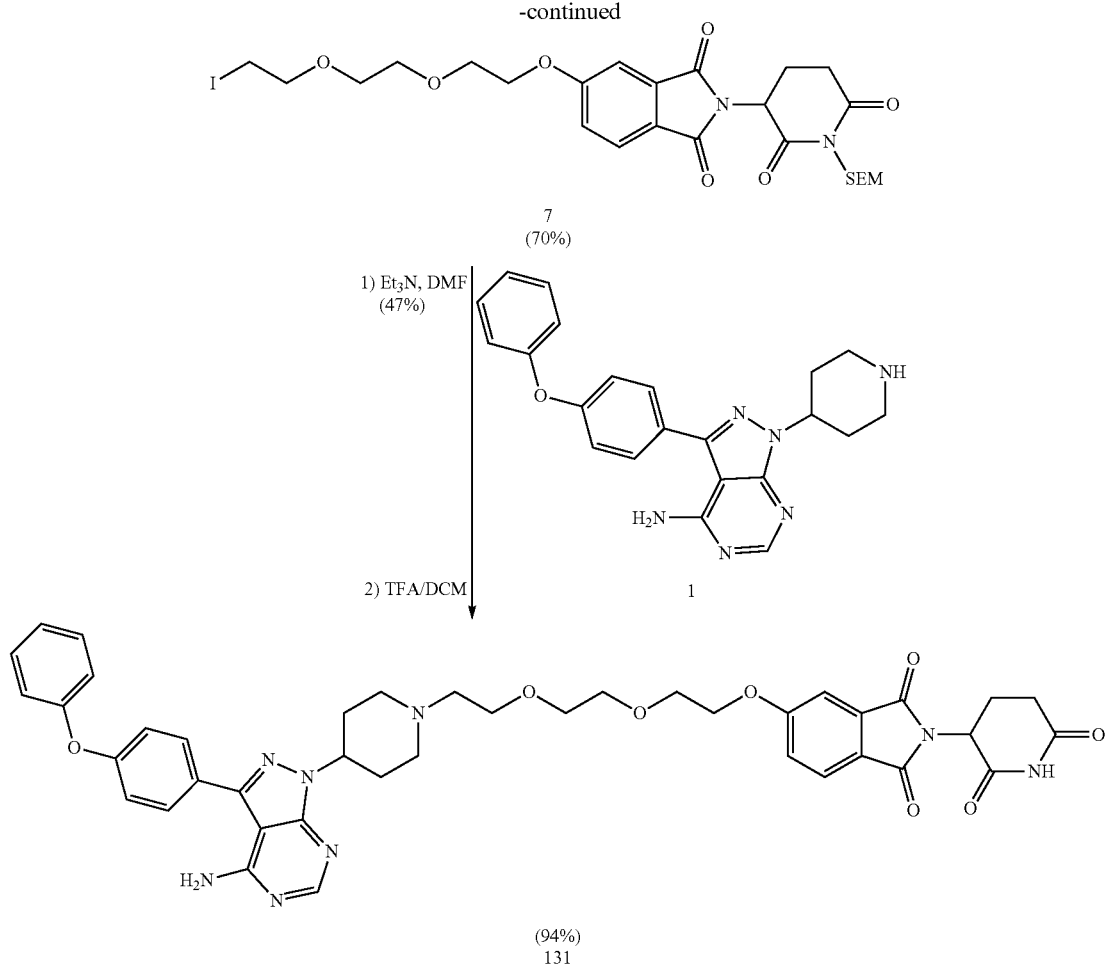

(7)
(70%)

1) Et₃N, DMF
(47%)

2) TFA/DCM

1

(94%)
131

Step A: 2-(2,6-dioxo-1-((2-(trimethylsilyl)ethoxy)methyl)piperidin-3-yl)-5-(2-(2-(2-iodoethoxy)ethoxy)ethoxy)isoindoline-1,3-dione (7)

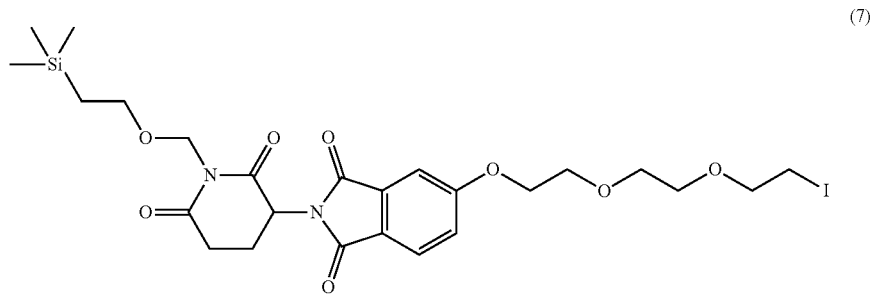 [SMILES: C[Si](C)(C)CCOCN1C(=O)CCC(N2C(=O)c3ccc(OCCOCCOCCI)cc3C2=O)C1=O]

(7)

To a mixture of 2-[2,6-dioxo-1-(2-trimethylsilylethoxymethyl)-3-piperidyl]-5-hydroxy-isoindoline-1,3-dione (64 mg, 0.16 mmol) and 1,2-bis(2-iodoethoxy)ethane (702.45 mg, 1.9 mmol) in DMF (2 mL) was added Cs₂CO₃ (309.31 mg, 0.95 mmol). After stirring at room temperature for 2 hrs, the reaction mixture was diluted with AcOEt (10 mL) and washed with water (5×10 mL), organic phase was dried (Na₂SO₄), and evaporated under vacuum. Crude product was fdtered over a short column of SiO₂ (DCM 100%, then DCM:MeOH:NH₄OH, 92:7:1), then crude product was purified by PTLC (DCM:MeOH:NH₄OH, 92:7:1) to give 71 mg of product (69% yield). ¹H NMR (500 MHz, DMSO-d6) δ 7.83 (d, J=8.3 Hz, 1H), 7.45 (d, J=2.3 Hz, 1H), 7.38 (dd, J=8.4, 2.3 Hz, 1H), 5.25 (dd, J=13.1, 5.3 Hz, 1H), 5.08 (s, 2H), 4.41-4.23 (m, 2H), 3.87-3.76 (m, 2H), 3.66 (t, J=6.4 Hz, 2H), 3.63-3.43 (m, 6H), 3.30 (t, J=6.5 Hz, 2H), 3.03 (ddd, J=18.8, 14.3, 5.3 Hz, 1H), 2.84-2.74 (m, 1H), 2.57 (qd, J=13.4, 4.5 Hz, 1H), 2.16-2.03 (m, 1H), 0.84 (t, J=7.7 Hz, 2H), -0.02 (s, 9H). $^{13}$C NMR (151 MHz, DMSO) δ 171.65, 169.90, 166.80, 166.73, 163.95, 133.90, 125.31, 123.04, 120.94, 108.94, 70.99, 69.95, 69.31, 68.68, 68.44, 68.30, 65.96, 49.54, 31.20, 21.07, 17.43, 5.43, -1.32. LC/MS (ESI); m/z: [M+Na]$^+$ Calcd. for $C_{25}H_{35}IN_2O_8SiNa$, 669.1105. Found 669.1311.

Step B: 5-(2-(2-(2-(4-(4-amino-3-(4-phenoxyphenyl)-1H-pyrazolo[3,4-d]pyrimidin-1-yl)piperidin-1-yl)ethoxy)ethoxy)ethoxy)-2-(2,6-dioxo-1-((2-(trimethylsilyl)ethoxy)methyl)piperidin-3-yl)isoindoline-1,3-dione

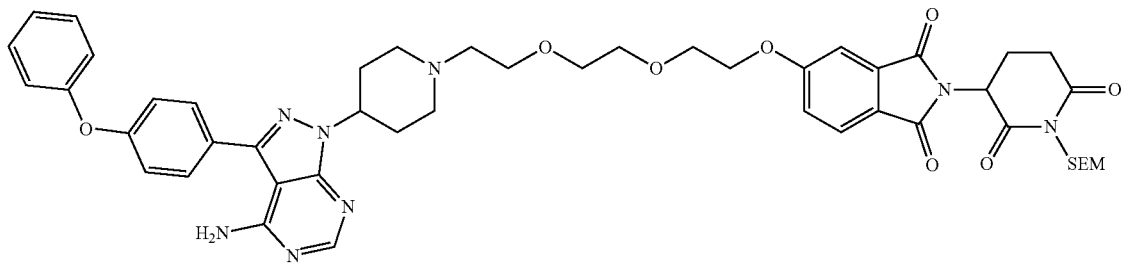 [SMILES: C[Si](C)(C)CCOCN1C(=O)CCC(N2C(=O)c3ccc(OCCOCCOCCN4CCC(n5nc(-c6ccc(Oc7ccccc7)cc6)c6c(N)ncnc65)CC4)cc3C2=O)C1=O]

To a solution of 3-(4-phenoxyphenyl)-1-(4-piperidyl)pyrazolo[3,4-d]pyrimidin-4-amine, hydrochloride (36.63 mg, 0.09 mmol) and TEA (0.1 ml, 0.57 mmol) in DMF (1 ml) was added 2-[2,6-dioxo-1-(2-trimethylsilylethoxymethyl)-3-piperidyl]-5-[2-[2-(2-iodoethoxy) ethoxy]ethoxy]iso-indoline-1,3-dione (56 mg, 0.09 mmol) and the resulting solution stirred for 36 h at rt. The reaction mixture was evaporated under vacuum. Crude product was purified by PTLC (DCM:(60:10:1 DCM/Methanol/NH$_3$), 6:4, and then again DCM:MeOH, 95:5 2×) to give 36.5 mg of pure product (47% yield). $^1$H NMR (400 MHz, DMSO-d6) δ 8.22 (s, 1H), 7.80 (d, J=8.3 Hz, 1H), 7.65 (d, J=8.7 Hz, 2H), 7.50-7.33 (m, 4H), 7.15 (dt, J=22.5, 7.4 Hz, 5H), 5.24 (dd, J=13.1, 5.4 Hz, 1H), 5.06 (s, 2H), 4.68-4.56 (m, 1H), 4.39-4.24 (m, 2H), 3.84-3.76 (m, 2H), 3.65-3.42 (m, 8H), 3.09-2.94 (m, 3H), 2.77 (dd, J=14.1, 3.3 Hz, 1H), 2.64-2.50 (m, 3H), 2.26-2.01 (m, 5H), 1.92-1.80 (m, 2H), 0.82 (t, J=8.6 Hz, 2H), -0.04 (s, 9H). $^{13}$C NMR (151 MHz, DMSO) δ 171.62, 169.87, 166.78, 166.70, 163.96, 158.13, 157.03, 156.28, 155.41, 153.60, 142.75, 133.87, 130.11, 129.99, 128.11, 125.26, 123.78, 123.00, 120.93, 118.98, 118.92, 108.91, 97.43, 69.95, 69.71, 68.65, 68.58, 68.46, 68.29, 65.95, 57.06, 53.89, 52.70, 49.53, 31.19, 31.03, 21.05, 17.41, -1.35. LC/MS (ESI); m/z [M+H]$^+$: Calcd. for $C_{47}H_{57}N_8O_9Si$, 905.4017. Found 905.4290.

Step C: 5-(2-(2-(2-(4-(4-amino-3-(4-phenoxyphenyl)-1H-pyrazolo[3,4-d]pyrimidin-1-yl)piperidin-1-yl)ethoxy)ethoxy)ethoxy)-2-(2,6-dioxopiperidin-3-yl)isoindoline-1,3-dione (compound 131)

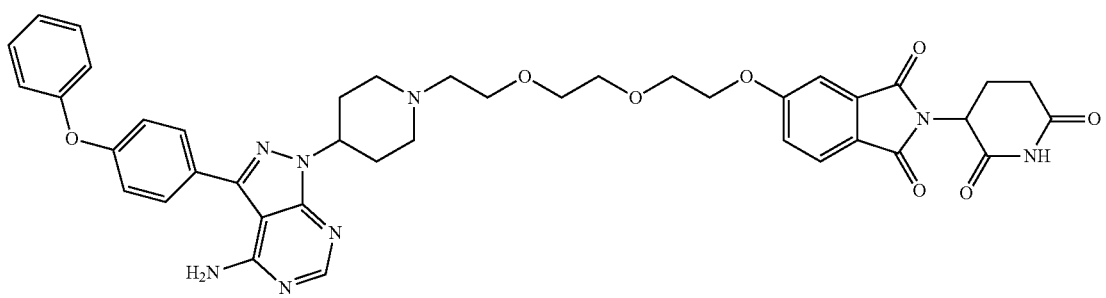

131

A solution of 5-[2-[2-[2-[4-[4-amino-3-(4-phenoxyphenyl)pyrazolo[3,4-d]pyrimidin -1-yl]-1-piperidyl]ethoxy]ethoxy]ethoxy]-2-[2,6-dioxo-1-(2-trimethylsilylethoxymethyl)-3-piperidyl]isoindoline-1,3-dione (30 mg, 0.03 mmol) in a mixture of TFA (1 ml, 13.46 mmol) and Dichloromethane (2 ml) was stirred for 1 h. Then the solvent was removed under vacuum and crude product was dried under high vacuum for 1 h. Crude product was purified by PTLC (DCM:MeOH:NH$_4$OH, 92:7:1) to give 24.2 mg of product (94% yield). $^1$H NMR (400 MHz, DMSO-d6) δ 11.11 (bs, 1H), 8.22 (s, 1H), 7.80 (d, J=8.3 Hz, 1H), 7.65 (d, J=8.4 Hz, 2H), 7.50-7.30 (m, 4H), 7.15 (dt, J=23.0, 7.7 Hz, 5H), 5.10 (dd, J=12.9, 5.3 Hz, 1H), 4.72-4.62 (m, 1H), 4.39-4.23 (m, 2H), 3.86-3.74 (m, 2H), 3.70-3.45 (m, 6H), 3.14-3.00 (m, 1H), 2.93-2.81 (m, 1H), 2.73-2.50 (m, 4H), 2.37-2.14 (m, 4H), 2.07-1.98 (m, 1H), 1.96-1.82 (m, 2H). $^{13}$C NMR (151 MHz, DMSO) δ 172.76, 169.92, 166.84, 166.77, 163.94, 158.15, 157.05, 156.27, 155.43, 153.61, 142.79, 133.89, 130.12, 130.00, 128.10, 125.24, 123.79, 123.03, 120.90, 119.00, 118.93, 108.87, 97.44, 73.80, 69.94, 69.71, 68.66, 68.48, 68.46, 56.99, 53.79, 52.65, 48.96, 30.96, 22.08. LC/MS (ESI); m/z: [M+H]$^+$ Calcd. for C$_{41}$H$_{43}$N$_8$O$_8$, 775.3203. Found 775.3290.

Synthesis of Compound 135: 3-(5-(2-(2-(2-(4-(4-amino-3-(4-phenoxyphenyl)-1H-pyrazolo[3,4-d]pyrimidin-1-yl)piperidin-1-yl)ethoxy)ethoxy)ethoxy)-1-oxoisoindolin-2-yl)piperidine-2,6-dione

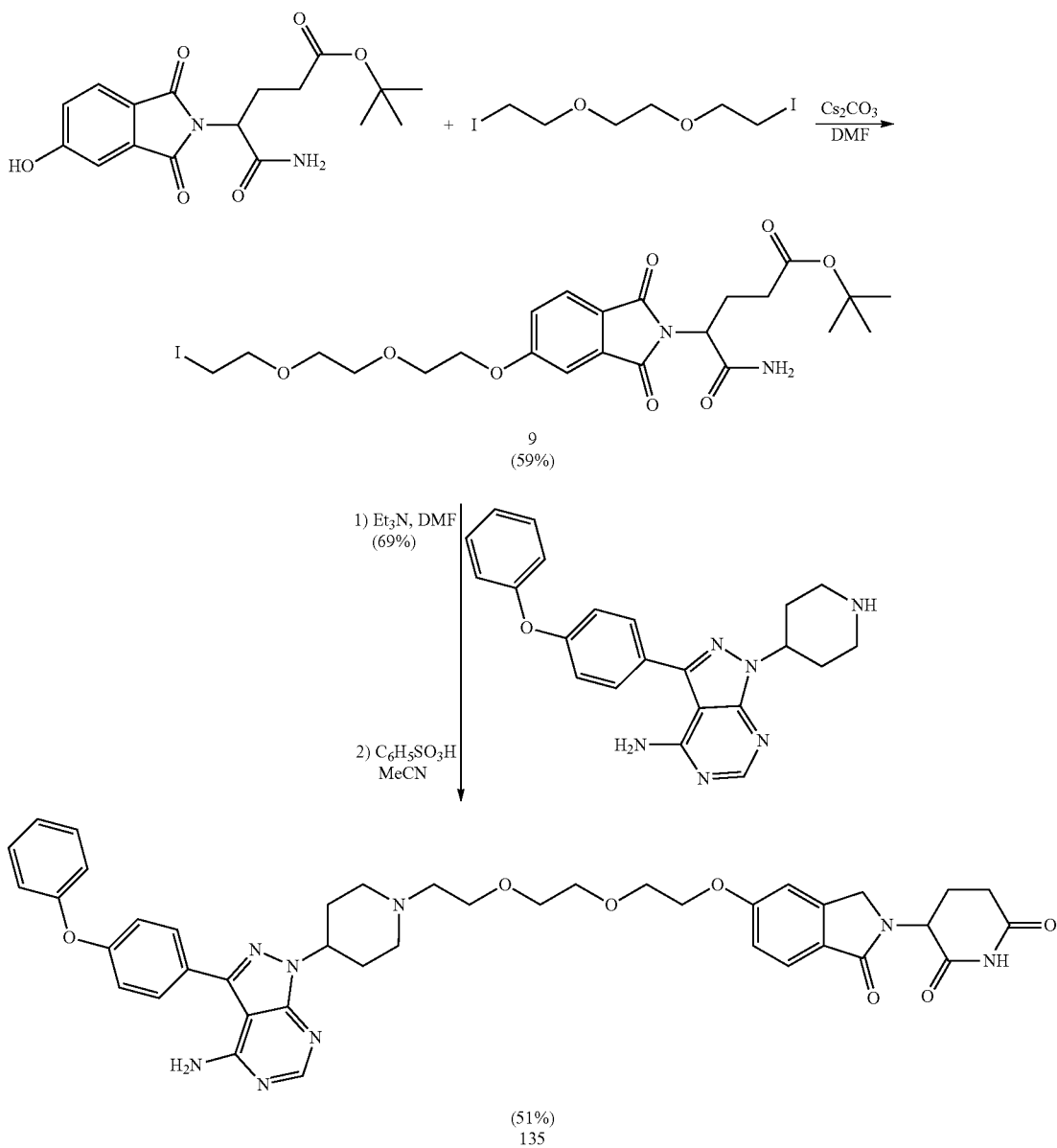

Step A: tert-butyl 5-amino-4-(5-(2-(2-(2-iodoethoxy)ethoxy)ethoxy)-1-oxoisoindolin-2-yl)-5-oxopentanoate (9)

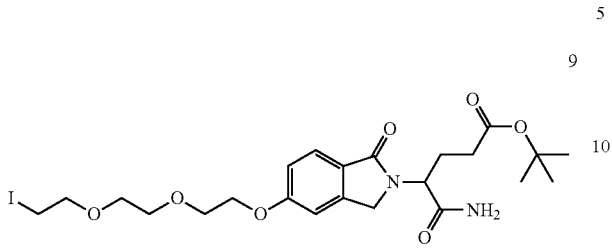

To a mixture of tert-butyl 5-amino-4-(5-hydroxy-1-oxo-isoindolin-2-yl)-5-oxo-pentanoate (50 mg, 0.15 mmol) and 1,2-bis(2-iodoethoxy)ethane (663.88 mg, 1.79 mmol) in DMF (2 mL) was added $Cs_2CO_3$ (243.61 mg, 0.75 mmol). After stirring at room temperature for 2 hrs, the reaction mixture was diluted with AcOEt (10 mL) and washed with water (5×10 mL), organic phase was dried ($Na_2SO_4$), and evaporated under vacuum. Crude product was filtered over a short column of $SiO_2$ (DCM 100%, then DCM:MeOH:$NH_4OH$, 91:8:1) to remove the excess of the bis-iodo reactant, then product was purified again by PTLC (DCM:MeOH:$NH_4OH$, 92:7:1) to give 51 mg of product (59% yield). $^1H$ NMR (500 MHz, Chloroform-d) δ 7.71 (d, J=8.4 Hz, 1H), 7.00 (dd, J=8.4, 2.0 Hz, 1H), 6.95 (d, J=2.1 Hz, 1H), 6.58 (bs, 1H), 5.54 (bs, 1H), 4.86 (dd, J=8.9, 6.2 Hz, 1H), 4.42 (dd, 2H), 4.18 (t, 2H), 3.89 (t, 2H), 3.81-3.61 (m, 6H), 3.25 (t, J=6.8 Hz, 2H), 2.40-2.07 (m, 4H), 1.40 (s, 9H). $^{13}C$ NMR (126 MHz, $CDCl_3$) δ 172.01, 171.93, 169.27, 162.42, 144.08, 125.25, 124.58, 115.72, 108.51, 80.97, 72.12, 70.99, 70.39, 69.75, 68.04, 53.95, 47.16, 32.01, 28.16, 24.31, 2.99. LC/MS (ESI); m/z: $[M+H]^+$ Calcd. for $C_{23}H_{34}IN_2O_7$, 577.1410. Found 577.1578.

Step B: tert-butyl 5-amino-4-(5-(2-(2-(2-(4-(4-amino-3-(4-phenoxyphenyl)-1H-pyrazolo[3,4-d]pyri-midin-1-yl)piperidin-1-yl)ethoxy)ethoxy)ethoxy)-1-oxoisoindolin-2-yl)-5-oxopentanoate

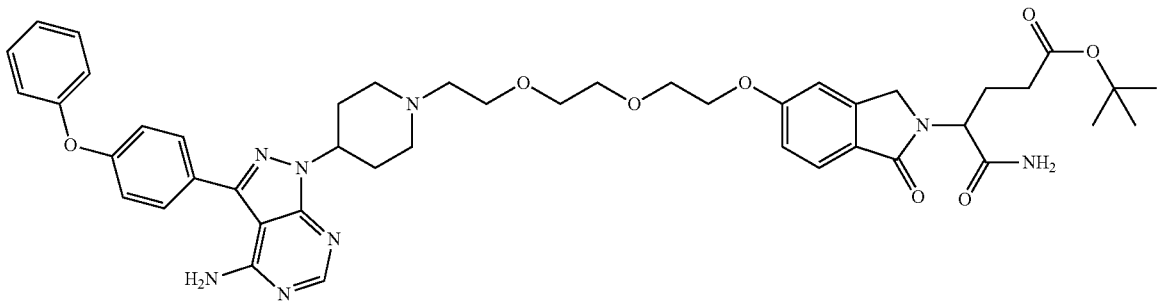 [SMILES: CC(C)(C)OC(=O)CCC(C(N)=O)N1Cc2cc(OCCOCCOCCN3CCC(n4nc(-c5ccc(Oc6ccccc6)cc5)c5c(N)ncnc54)CC3)ccc2C1=O]

To a solution of 3-(4-phenoxyphenyl)-1-(4-piperidyl)pyrazolo[3,4-d]pyrimidin-4-amine; hydrochloride (36.68 mg, 0.09 mmol) and TEA (0.1 ml, 0.57 mmol) in DMF (1 ml) was added tert-butyl 5-amino-4-[5-[2-[2-(2-iodoethoxy)ethoxy]ethoxy]-1-oxo-isoindolin-2-yl]-5-oxo-pentanoate (50 mg, 0.09 mmol) and the resulting solution stirred for 72 h at rt. The reaction mixture was evaporated under vacuum. Crude product was purified by PTLC (DCM:MeOH:$NH_4OH$, 91:8:1) to give 50 mg of pure product (69% yield). $^1H$ NMR (400 MHz, DMSO-d6) δ 8.22 (s, 1H), 7.65 (d, J=7.6 Hz, 2H), 7.60-7.51 (m, 2H), 7.43 (t, J=7.4 Hz, 2H), 7.25-7.07 (m, 7H), 7.02 (d, J=8.4 Hz, 1H), 4.75-4.66 (m, 1H), 4.66-4.60 (m, 1H), 4.54 (d, J=17.5 Hz, 1H), 4.36 (d, J=17.5 Hz, 1H), 4.24-4.12 (m, 2H), 3.83-3.74 (m, 2H), 3.69-3.46 (m, 6H), 3.05-2.96 (m, 2H), 2.57-2.43 (m, 2H), 2.29-2.04 (m, 7H), 2.02-1.80 (m, 3H), 1.31 (s, 9H). $^{13}C$ NMR (151 MHz, DMSO) δ 171.96, 171.36, 167.69, 161.49, 158.15, 157.04, 156.28, 155.42, 153.61, 144.66, 142.77, 130.12, 130.00, 128.11, 124.41, 124.16, 123.78, 118.99, 118.93, 115.16, 108.58, 97.44, 79.73, 69.93, 69.71, 68.79, 68.60, 67.66, 57.06, 53.91, 53.29, 52.71, 46.68, 31.77, 31.04, 27.65, 24.88. LC/MS (ESI); m/z $[M+H]^+$: Calcd. for $C_{45}H_{55}N_8O_8$.

Step C: 3-(5-(2-(2-(2-(4-(4-amino-3-(4-phenoxyphenyl)-1H-pyrazolo[3,4-d]pyrimidin-1-yl)piperidin-1-yl)ethoxy)ethoxy)ethoxy)-1-oxoisoindolin-2-yl)piperidine-2,6-dione (Compound 135)

(135)

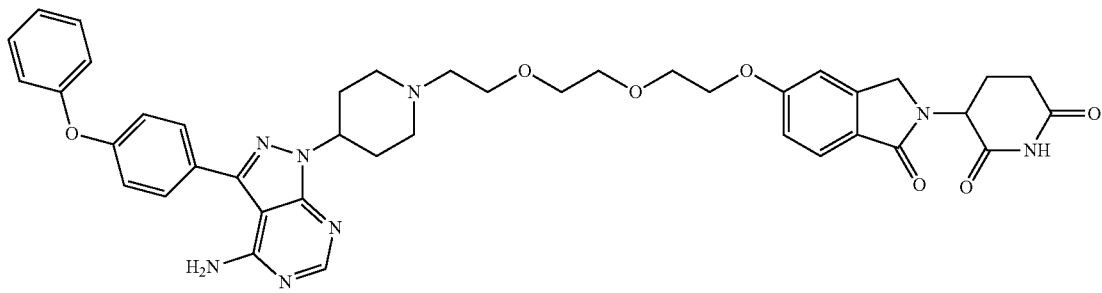

To a solution of tert-butyl 5-amino-4-[5-[2-[2-[2-[4-[4-amino-3-(4-phenoxyphenyl)pyrazolo[3,4-d]pyrimidin-1-yl]-1-piperidyl]ethoxy]ethoxy]ethoxy]-1-oxo-isoindolin-2-yl]-5-oxo-pentanoate (27.0 mg, 0.0323 mmol) in MeCN (15 mL) was added benzenesulfonic acid (10.2 mg, 0.0647 mmol) and the reaction mixture was heated at reflux temperature for 24 h (Dean-Stark distilling trap, with molecular sieves). The reaction mixture was evaporated to dryness under reduced pressure. The crude was purified by PTLC (DCM:MeOH:NH$_4$OH, 91:8:1) to give 13 mg of product (51% yield). $^1$H NMR (400 MHz, DMSO-d6) δ 10.93 (s, 1H), 8.19 (s, 1H), 7.61 (d, J=8.6 Hz, 2H), 7.56 (d, J=8.4 Hz, 1H), 7.39 (t, J=8.0 Hz, 2H), 7.21-7.05 (m, 6H), 7.04-6.97 (m, 1H), 5.02 (dd, J=13.3, 4.9 Hz, 1H), 4.69-4.52 (m, 1H), 4.40-4.07 (m, 4H), 3.84-3.68 (m, 2H), 3.63-3.43 (m, 6H), 3.06-2.92 (m, 2H), 2.92-2.77 (m, 1H), 2.67-2.46 (m, 3H), 2.39-2.23 (m, 1H), 2.25-2.04 (m, 4H), 2.00-1.74 (m, 3H). $^{13}$C NMR (151 MHz, DMSO) δ 172.89, 171.15, 167.89, 161.67, 158.15, 157.05, 156.28, 155.44, 153.62, 144.40, 142.79, 130.13, 130.01, 128.10, 124.31, 124.18, 123.80, 119.00, 118.94, 115.40, 108.63, 97.45, 69.93, 69.72, 68.79, 68.52, 67.72, 57.02, 53.88, 52.67, 51.50, 46.96, 31.25, 30.97, 22.52. LC/MS (ESI); m/z [M+H]$^+$: Calcd. For C$_4$iH$_{45}$N$_8$O$_7$, 761.3411. Found 761.3866.

Synthesis of Compound 129: (2S,4R)-1-((S)-2-(2-(2-(2-(4-(4-amino-3-(4-phenoxyphenyl)-1H-pyrazolo[3,4-d]pyrimidin-1-yl)piperidin-1-yl)ethoxy)acetamido)-3,3-dimethylbutanoyl)-4-hydroxy-N-(4-(4-methylthiazol-5-yl)benzyl)pyrrolidine-2-carboxamide

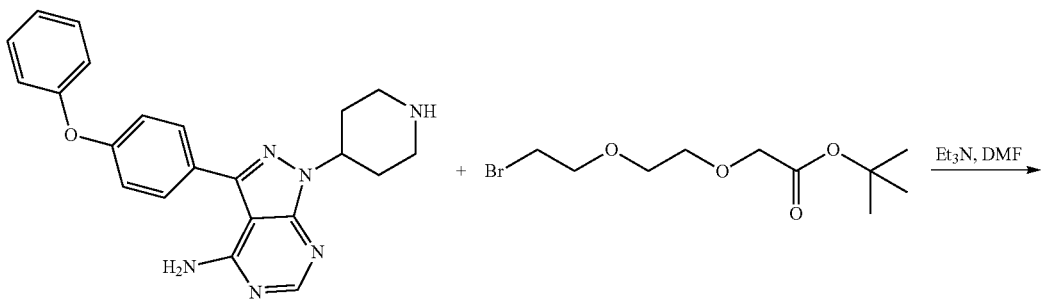

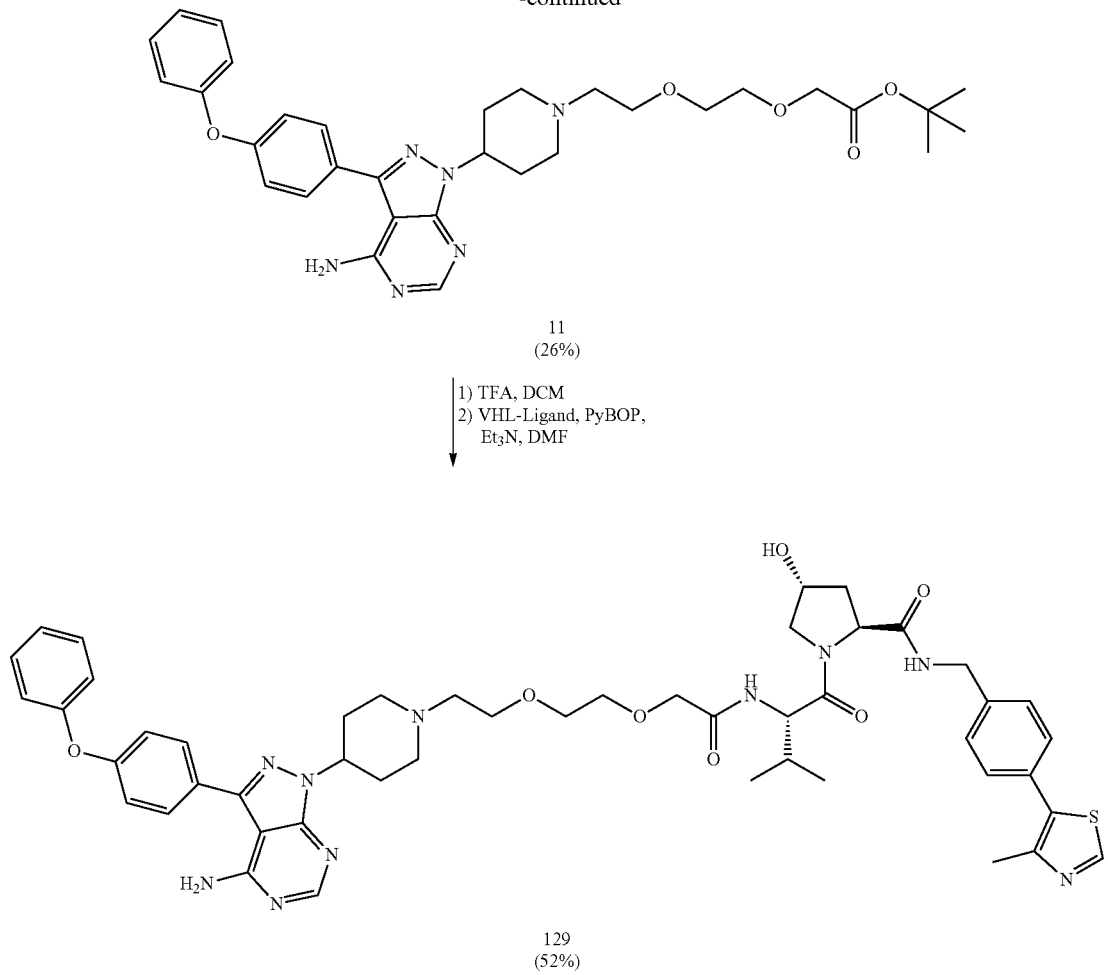

11
(26%)

1) TFA, DCM
2) VHL-Ligand, PyBOP, Et₃N, DMF 129
(52%)

Step A: tert-butyl 2-(2-(2-(4-(4-amino-3-(4-phenoxyphenyl)-1H-pyrazolo[3,4-d]pyrimidin-1-yl)piperidin-1-yl)ethoxy)ethoxy)acetate.

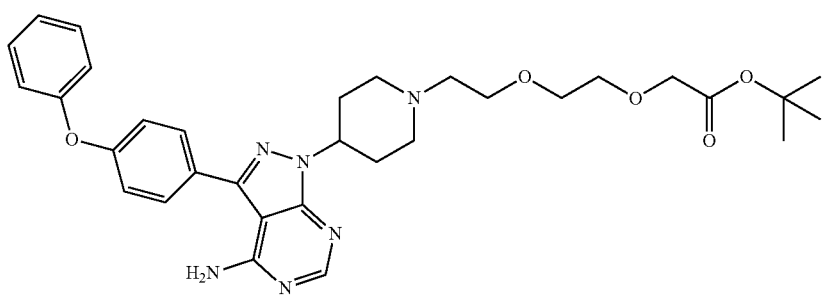 [SMILES: CC(C)(C)OC(=O)COCCOCCN1CCC(n2nc(-c3ccc(Oc4ccccc4)cc3)c3c(N)ncnc32)CC1]

To a solution of 3-(4-phenoxyphenyl)-1-(4-piperidyl)pyrazolo[3,4-d]-pyrimidin-4-amine (7.51 mg, 0.02 mmol) and TEA (0.01 ml, 0.58 mmol) in DMF (1 ml) was added tert-butyl 2-(2-(2-bromoethoxy)ethoxy)acetate (5.5 mg, 0.02 mmol) and the resulting solution stirred for 36 h at room temperature. The reaction mixture was diluted with AcOEt (5 mL) and washed with water/brine (3×5 mL), organic phase was dried (Na₂SO₄), and evaporated under vacuum. Crude product was purified by PTLC (DCM: MeOH:NH₄OH, 91:8:1) to give 3 mg (26%). $^1$H NMR (500 MHz, DMSO-d6) δ 8.24 (s, 1H), 7.66 (d, J=8.3 Hz, 2H), 7.43 (t, J=7.7 Hz, 2H), 7.19 (t, J=7.3 Hz, 1H), 7.14 (dd, J=12.3, 8.5 Hz, 5H), 4.72 (bs, 1H), 4.00 (s, 2H), 3.74-3.44 (m, 6H), 3.14 (bs, 2H), 2.85-2.55 (m, 3H), 2.38-2.14 (m, 3H), 2.02-1.80 (m, 2H), 1.40 (s, 9H). LC/MS (ESI); m/z [M+H]⁺: Calcd. for $C_{32}H_{41}N_6O_5$, 589.3138. Found 589.3347.

Step B: (2S,4R)-1-((S)-2-(2-(2-(2-(4-(4-amino-3-(4-phenoxyphenyl)-1H-pyrazolo[3,4-d]pyrimidin-1-yl)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide (Compound 129)

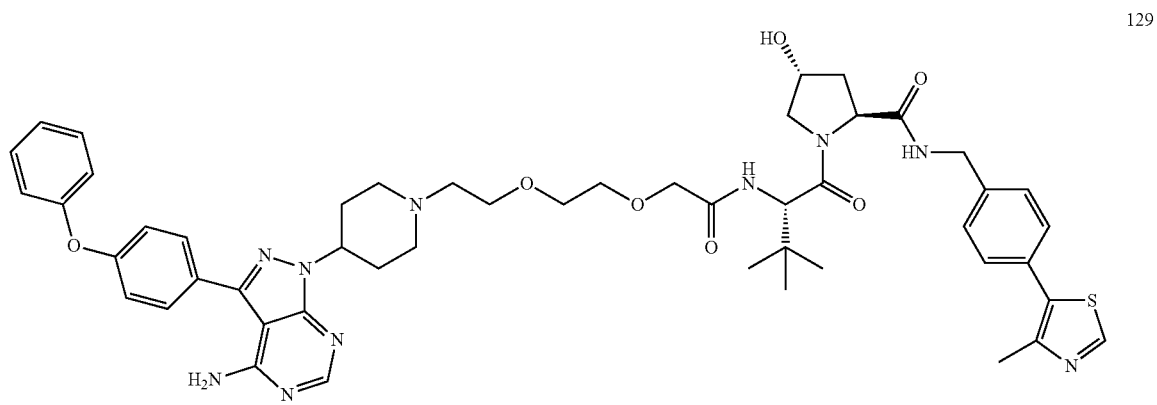 [SMILES: Cc1ncsc1-c1ccc(CNC(=O)[C@@H]2C[C@@H](O)CN2C(=O)[C@@H](NC(=O)COCCOCCN2CCC(n3nc(-c4ccc(Oc5ccccc5)cc4)c4c(N)ncnc43)CC2)C(C)(C)C)cc1]

129

A solution of tert-butyl 2-(2-(2-(4-(4-amino-3-(4-phenoxyphenyl)-1H-pyrazolo[3,4-d]pyrimidin-1-yl)piperidin-1-yl)ethoxy)ethoxy)acetate (3 mg, 0.01 mmol) in a mixture of TFA (1 ml, 13.46 mmol) and dichloromethane (3 ml) was stirred for 2 h. Then the solvent was removed under vacuum and crude product was dried under high vacuum for 2 h. Crude product was used in the next step without any further purification (2.7 mg, quantitative yield). LC/MS (ESI); m/z: [M+H]$^+$ Calcd. for $C_{28}H_{33}N_6O_5$, 533.2512. Found 533.2579.

To a solution of 2-(2-(2-(4-(4-amino-3-(4-phenoxyphenyl)-1H-pyrazolo[3,4-d]-pyrimidin-1-yl)piperidin-1-yl)ethoxy)ethoxy)acetic acid (crude product from previous step) (2.7 mg, 0.01 mmol) and (2S,4R)-1-[(2S)-2-amino-3,3-dimethyl-butanoyl]-4-hydroxy-N-[[4-(4-methylthiazol-5-yl)-phenyl]methyl]pyrrolidine-2-carboxamide; hydrochloride (2.6 mg, 0.006 mmol) in DMF (1 ml) was added TEA (0.1 ml, 0.72 mmol) and PyBOP (2.77 mg, 0.01 mmol) at room temperature. The reaction mixture was stirred for 4 h at the same temperature. The DMF was removed under high vacuum. Crude product was filtered over a silica-carbonate cartridge using a mixture of DCM:MeOH:NH$_4$OH (91:8:1) as a eluent. Filtrate was evaporated under vacuum and crude product was purified by PTLC (DCM: MeOH:NH$_4$OH, 91:8:1) to give 2.5 mg of product (52% yield). $^1$H NMR (600 MHz, DMSO-d6) δ 8.96 (s, 1H), 8.60 (t, J=6.0 Hz, 1H), 8.23 (s, 1H), 7.65 (d, J=8.4 Hz, 2H), 7.48-7.34 (m, 7H), 7.18 (t, J=7.4 Hz, 1H), 7.16-7.07 (m, 4H), 5.16 (d, 1H), 4.63 (bs, 1H), 4.57 (d, J=9.6 Hz, 1H), 4.44 (t, J=8.2 Hz, 1H), 4.40-4.32 (m, 2H), 4.23 (dd, J=15.8, 5.6 Hz, 1H), 3.98 (s, 2H), 3.72-3.50 (m, 8H), 3.01 (bs, 2H), 2.56 (bs, 2H), 2.43 (s, 3H), 2.26-2.11 (m, 4H), 2.10-1.98 (m, 1H), 1.94-1.78 (m, 3H), 0.95 (s, 9H). $^{13}$C NMR (151 MHz, DMSO) δ 171.76, 169.10, 168.57, 158.15, 157.03, 156.29, 155.42, 153.60, 151.42, 147.72, 142.77, 139.42, 131.13, 130.13, 130.01, 129.67, 128.68, 128.11, 127.43, 123.79, 118.99, 118.94, 97.44, 70.51, 69.59, 69.46, 68.88, 58.74, 56.99, 56.58, 55.67, 54.93, 52.72, 52.66, 41.67, 37.90, 35.75, 30.99, 26.19, 15.93. LC/MS (ESI); m/z [M+H]$^+$: Calcd. for $C_{50}H_{61}N_{10}O_7S$, 945.4445. Found 945.4641.

Synthesis of Compound 127: (2S,4R)—N-(2-(4-(4-(4-amino-3-(4-phenoxyphenyl)-1H-pyrazolo[3,4-d]pyrimidin-1-yl)piperidin-1-yl)butoxy)butoxy)-4-(4-methylthiazol-5-yl)benzyl)-4-hydroxy-1-((S)-3-methyl-2-(1-oxoisoindolin-2-yl)butanoyl)pyrrolidine-2-carboxamide

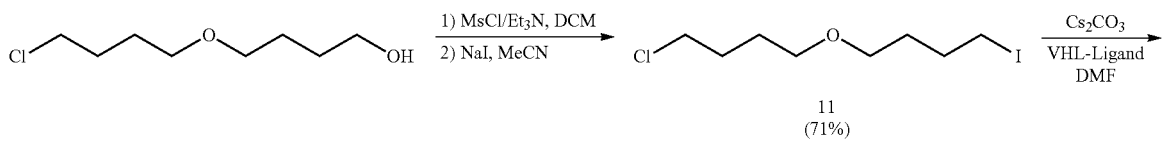

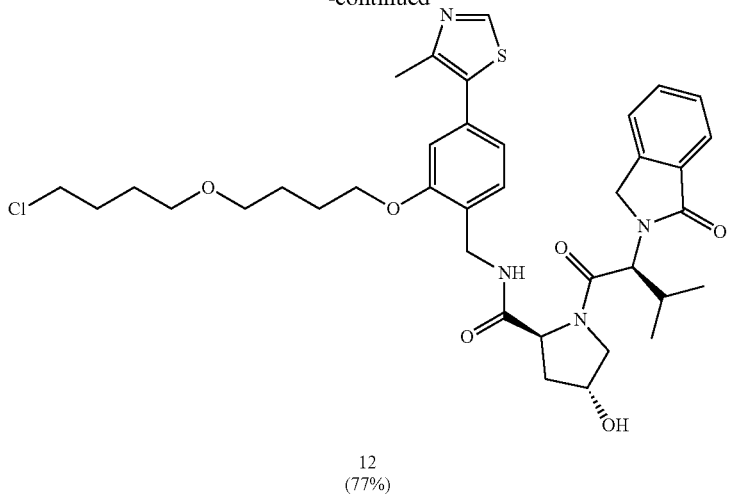

12
(77%)

1) NaI, Acetona
(quantitative yield)
2) 1/Cs₂CO₃, DCM

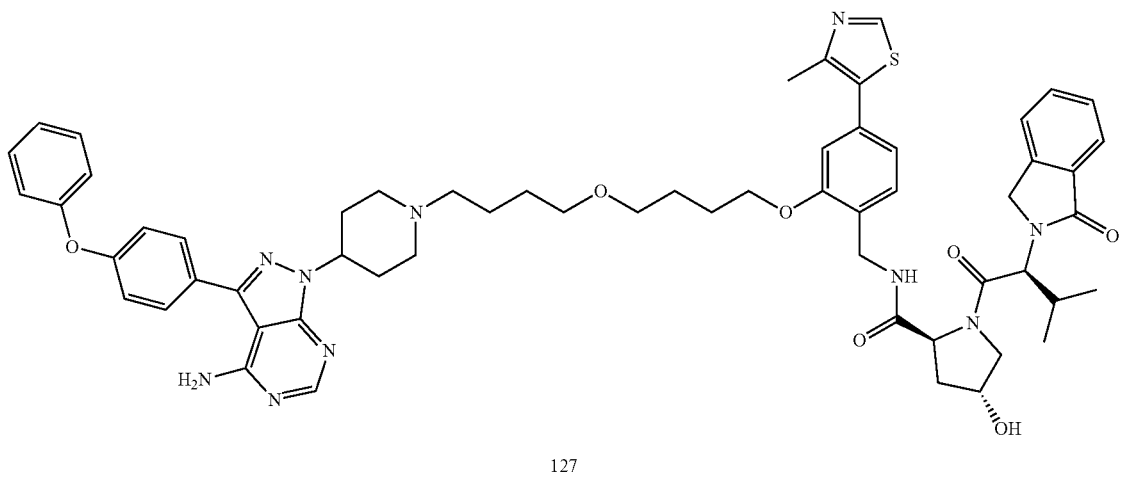

127
(36%)

Step A: chloro-4-(4-iodobutoxy)butane (11)

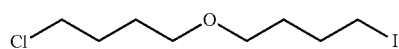

11

To a solution of 4-(4-chlorobutoxy)butan-1-ol (271 mg, 1.5 mmol) in Dichloromethane (5 ml) was added TEA (0.63 ml, 4.5 mmol), then reaction mixture was cooled to 0° C. (water ice/acetone bath) and mesyl chloride (0.14 ml, 1.8 mmol) was added dropwise. The reaction mixture was stirred for 1 h at the same temperature. Reaction mixture was poured into an aqueous solution of NaHCO₃ (20 mL) and product extracted with DCM (20 mL, 2×), the organic extracts were combined, dried (Na₂SO₄), and evaporated under vacuum. The crude product (mesylate) was used in the next step without any further purification (>95% pure by NMR): ¹H NMR (400 MHz, Chloroform-d) δ 4.26 (t, J=6.5 Hz, 2H), 3.57 (t, J=6.6 Hz, 2H), 3.44 (td, J=6.2, 2.0 Hz, 4H), 3.01 (s, 3H), 1.92-1.78 (m, 4H), 1.76-1.62 (m, 4H). Crude mixture from previous step was diluted in Acetonitrile (5 ml) and NaI (247.32 mg, 1.65 mmol) was added, the reaction mixture was stirred at room temperature for 72 h. The reaction was poured into an aqueous solution of Na₂S₂O₃ (10%, 20 mL) and product was extracted with DCM (2×20 mL). Organic extracts were combined, dried (Na₂SO₄), and evaporated under vacuum. Crude product was purified by flash chromatography (SiO₂—40 g, grad. Hexane:AcOEt, 2 to 20% in 10 min), to give 310 mg of product as an oil (71% yield): ¹H NMR (500 MHz, Chloroform-d) δ 3.57 (t, J=6.6 Hz, 2H), 3.43 (td, J=6.3, 2.4 Hz, 4H), 3.22 (t, J=7.0 Hz, 2H), 2.01-1.80 (m, 4H), 1.77-1.61 (m, 4H). ¹³C NMR (151 MHz, CDCl₃) δ 70.13, 69.77, 45.13, 30.74, 30.56, 29.68, 27.22, 7.02. LC/MS (ESI); m/z: [M+H]⁺ Calcd. for C₈H₁₇ClO, 291.001. Found 291.0060.

Step B: (2S,4R)—N-(2-(4-(4-chlorobutoxy)butoxy)-4-(4-methylthiazol-5-yl)benzyl)-4-hydroxy-1-((S)-3-methyl-2-(1-oxoisoindolin-2-yl)butanoyl)pyrrolidine-2-carboxamide (12)

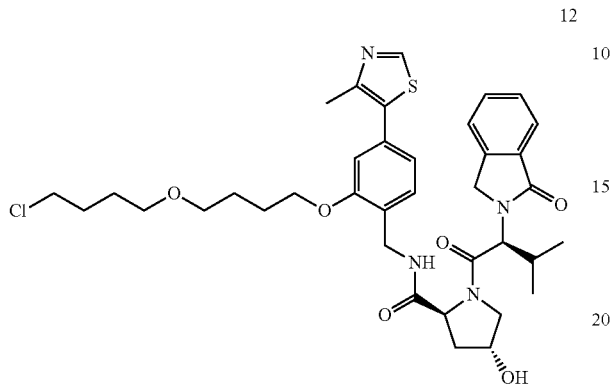

To a mixture of (2S,4R)-4-hydroxy-N-[[2-hydroxy-4-(4-methylthiazol-5-yl)phenyl]methyl]-1-[(2S)-3-methyl-2-(1-oxoisoindolin-2-yl)butanoyl]pyrrolidine-2-carboxamide (83 mg, 0.151 mmol) and 1-chloro-4-(4-iodobutoxy)butane (44 mg, 0.151 mmol) in N,N-Dimethylformamide (1 mL) was added $Cs_2CO_3$ (49.34 mg, 0.151 mmol). After stirring at room temperature for 4 hrs, the reaction mixture was diluted with AcOEt (10 mL) and washed with water (5×10 mL), organic phase was dried ($Na_2SO_4$), and evaporated under vacuum. Crude product was purified by PTLC (DCM: (60:10:1 DCM/Methanol/$NH_3$), 1:1) to give 83 mg of product (77% yield). $^1$H NMR (500 MHz, DMSO-d6) δ 8.99 (s, 1H), 8.36 (t, J=5.7 Hz, 1H), 7.71 (d, J=7.5 Hz, 1H), 7.65-7.57 (m, 2H), 7.50 (t, J=7.7 Hz, 1H), 7.33 (d, J=7.6 Hz, 1H), 7.02-6.96 (m, 2H), 5.08 (d, J=3.9 Hz, 1H), 4.71 (d, J=10.8 Hz, 1H), 4.59-4.18 (m, 6H), 4.07 (t, J=5.0 Hz, 2H), 3.77 (dd, J=10.5, 4.2 Hz, 1H), 3.69 (d, J=10.4 Hz, 1H), 3.63 (t, J=6.6 Hz, 2H), 3.49-3.36 (m, 4H), 2.47 (s, 3H), 2.37-2.29 (m, 1H), 2.07-2.01 (m, 1H), 1.96-1.89 (m, 1H), 1.85-1.56 (m, 8H), 0.96 (d, J=6.4 Hz, 3H), 0.74 (d, J=6.6 Hz, 3H). $^{13}$C NMR (151 MHz, DMSO) δ 171.54, 168.09, 167.48, 155.90, 151.48, 147.89, 142.21, 131.60, 131.37, 131.32, 130.98, 127.92, 127.69, 126.96, 123.63, 123.02, 120.77, 111.69, 69.68, 69.14, 68.62, 67.56, 58.70, 57.79, 55.42, 46.82, 45.36, 38.10, 37.06, 29.18, 28.40, 26.63, 25.90, 25.69, 18.89, 18.64, 16.03. LC/MS (ESI); m/z: [M+H]$^+$ Calcd. for $C_{37}H_{48}ClN_4O_6S$, 711.2983. Found 711.3224.

Step C: (2S,4R)—N-(2-(4-(4-(4-(4-amino-3-(4-phenoxyphenyl)-1H-pyrazolo[3,4-d]pyrimidin-1-yl)piperidin-1-yl)butoxy)butoxy)-4-(4-methylthiazol-5-yl)benzyl)-4-hydroxy-1-((S)-3-methyl-2-(1-oxoisoindolin-2-yl)butanoyl)pyrrolidine-2-carboxamide (Compound 127)

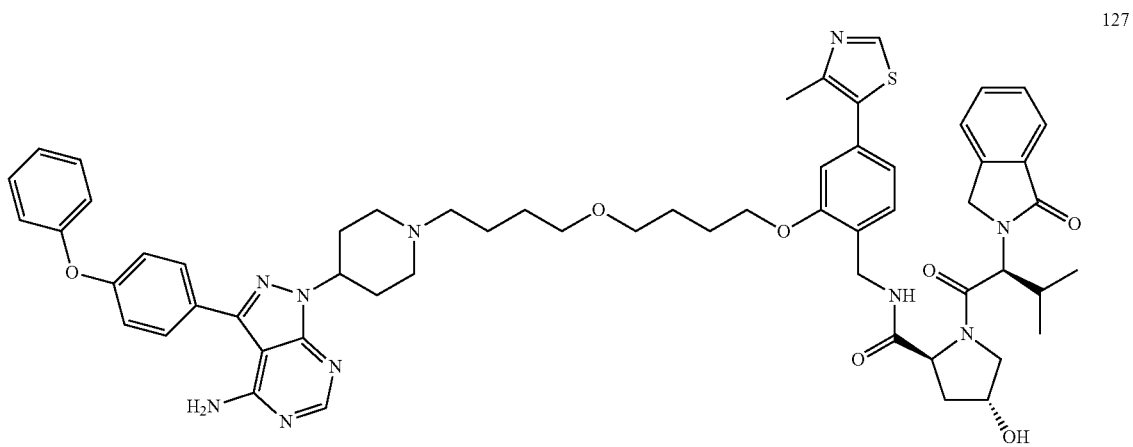 [SMILES: Cc1ncsc1-c1ccc(CNC(=O)[C@@H]2C[C@@H](O)CN2C(=O)[C@H](C(C)C)N2Cc3ccccc3C2=O)c(OCCCCOCCCCN2CCC(n3nc(-c4ccc(Oc5ccccc5)cc4)c4c(N)ncnc43)CC2)c1]

To a solution of (2S,4R)—N-[[2-[4-(4-chlorobutoxy)butoxy]-4-(4-methylthiazol-5-yl)phenyl]methyl]-4-hydroxy-1-[(2S)-3-methyl-2-(1-oxoisoindolin-2-yl)butanoyl]pyrrolidine-2-carboxamide (75 mg, 0.11 mmol) in acetone (10 ml) was added NaI (158.05 mg, 1.05 mmol). The reaction mixture was stirred at reflux temperature for 48 h, then the solvent was removed under vacuum and crude product was dissolved in EtOAc (15 mL) and an aqueous solution of $Na_2SO_3$ (10%, 10 mL), organic layer was separated, washed with water (10 mL), dried ($Na_2SO_4$), and evaporated under vacuum. Crude product was pure by NMR (quantitative yield) no further purification. $^1$H (400 MHz, Chloroform-d) δ 8.68 (s, 1H), 7.78 (d, J=7.6 Hz, 1H), 7.52 (t, J=7.4 Hz, 1H), 7.47-7.37 (m, 2H), 7.34-7.23 (m, 2H), 6.96 (d, J=8.7 Hz, 1H), 6.87 (s, 1H), 4.76 (s, 1H), 4.73 (d, J=6.7 Hz, 1H), 4.64 (t, J=7.8 Hz, 1H), 4.57-4.36 (m, 5H), 4.05 (t, J -6.2 Hz, 2H), 3.65 (dd, J=11.5, 3.5 Hz, 1H), 3.49 (t, J=6.2 Hz, 2H), 3.44 (t, J=6.2 Hz, 2H), 3.19 (t, J=6.9 Hz, 2H), 2.58-2.45 (m, 1H), 2.53 (s, 3H), 2.47-2.27 (m, 2H), 2.12-2.00 (m, 2H), 1.98-1.84 (m, 3H), 1.79 (dt, J=9.4, 6.5 Hz, 2H), 1.71-1.58 (m, 2H), 0.89 (dd, J=6.0 Hz, 6H). $^{13}$C NMR (126 MHz, CDCl$_3$) δ 170.54, 170.47, 169.71, 156.94, 150.41, 148.61, 142.23, 132.35, 131.99, 131.92, 131.73, 129.41, 128.15, 126.47, 123.97, 122.99, 121.65, 112.15, 70.62, 70.13, 69.83, 68.04, 58.81, 58.55, 56.07, 47.59, 39.05, 35.87, 30.75, 30.58, 29.85, 28.89, 26.55, 26.34, 19.23, 16.28, 6.98. LC/MS (ESI); m/z [M+H]$^+$: Calcd. for $C_{37}H_{48}IN_4O_6S$, 803.2339. Found 803.2675.

To a solution of 3-(4-phenoxyphenyl)-1-(4-piperidyl)pyrazolo[3,4-d]pyrimidin-4-amine (4.81 mg, 0.01 mmol) and (2S,4R)-4-hydroxy-N-(2-(4-(4-iodobutoxy)butoxy)-4-(4-methylthiazol-5-yl)benzyl)-1-((S)-3-methyl-2-(1-oxoisoindolin-2-yl)butanoyl)pyrrolidine-2-carboxamide (10 mg, 0.01 mmol) in DMF (1 mL) was added TEA (0.01 ml, 0.04 mmol), the resulting solution stirred for 12 h (overnight) at room temperature. The DMF was evaporated under high vacuum and the crude product was filtered over a silica-carbonate cartridge using DCM:(60:10:1 DCM/Methanol/NH$_3$) (DCM:MeOH:NH$_4$OH, 91:8:1) as a eluent. Filtrate was evaporated and crude was purified by PTLC (DCM:MeOH:NH$_4$OH, 91:8:1) to give 4.8 mg of pure product (36% yield). $^1$H NMR (500 MHz, Chloroform-d) δ 8.66 (s, 1H), 8.34 (s, 1H), 7.75 (d, J=7.6 Hz, 1H), 7.64 (d, J=8.5 Hz, 2H), 7.50 (t, J=7.5 Hz, 1H), 7.44-7.33 (m, 4H), 7.33-7.26 (m, 2H), 7.15 (dd, J=17.5, 8.0 Hz, 3H), 7.08 (d, J=8.4 Hz, 2H), 6.95 (d, J=7.7 Hz, 1H), 6.87 (s, 1H), 5.55 (s, 2H), 4.84-4.68 (m, 3H), 4.62 (t, J=7.8 Hz, 1H), 4.58-4.28 (m, 5H), 4.05 (t, J=6.3 Hz, 2H), 3.67 (dd, J=11.3, 3.5 Hz, 1H), 3.50 (t, J=6.3 Hz, 2H), 3.46-3.38 (m, 2H), 3.15-2.98 (m, 2H), 2.52 (s, 3H), 2.51-2.30 (m, 5H), 2.25-1.88 (m, 8H), 1.85-1.74 (m, 2H), 0.88 (dd, J=18.6, 6.5 Hz, 6H). $^{13}$C NMR (151 MHz, CDCl$_3$) δ 170.62, 170.32, 169.48, 158.50, 157.89, 157.00, 156.50, 155.60, 153.97, 150.39, 148.58, 143.44, 142.19, 132.36, 132.36, 131.97, 131.82, 131.75, 130.08, 129.59, 128.16, 128.07, 126.39, 124.12, 123.89, 122.96, 121.60, 119.65, 119.20, 112.09, 98.71, 70.88, 70.54, 69.92, 68.02, 58.72, 58.71, 58.28, 56.07, 52.91, 47.53, 39.20, 36.21, 31.37, 29.83, 28.97, 27.85, 26.61, 26.31, 23.99, 19.19, 19.13, 16.27. LC/MS (ESI); m/z [M+H]$^+$: Calcd. for $C_{59}H_{69}N_{10}O_7S$, 1061.5071. Found 1061.5353.

Synthesis of Compound 108 (2S,4R)—N-(2-(2-(2-(4-(4-amino-3-(4-phenoxyphenyl)-1H-pyrazolo[3,4-d]pyrimidin-1-yl)piperidin-1-yl)-2-oxoethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide

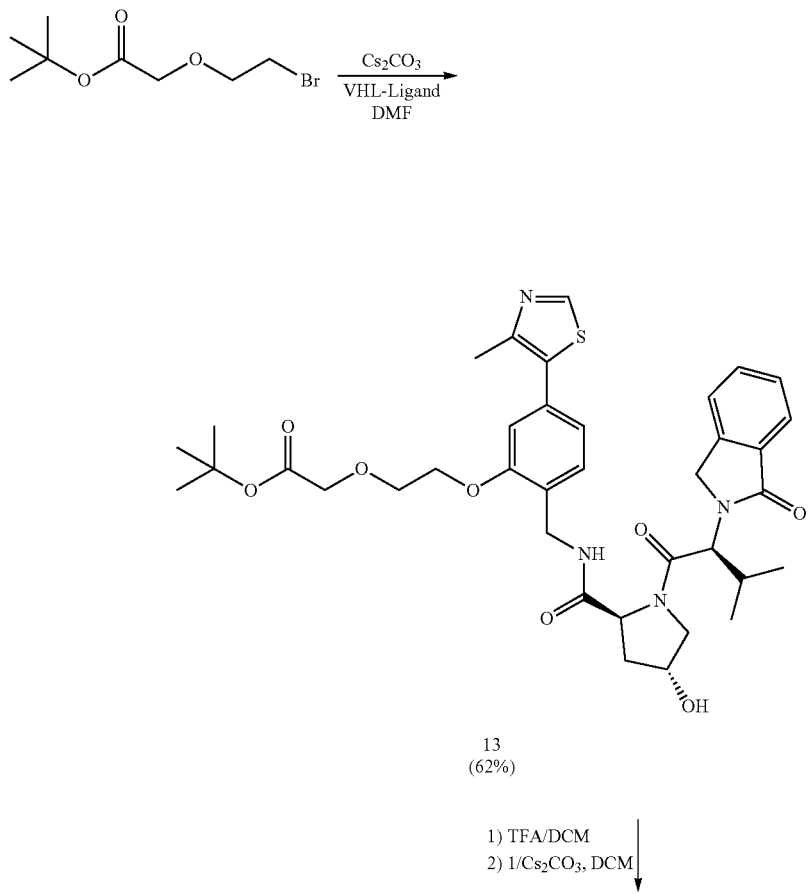

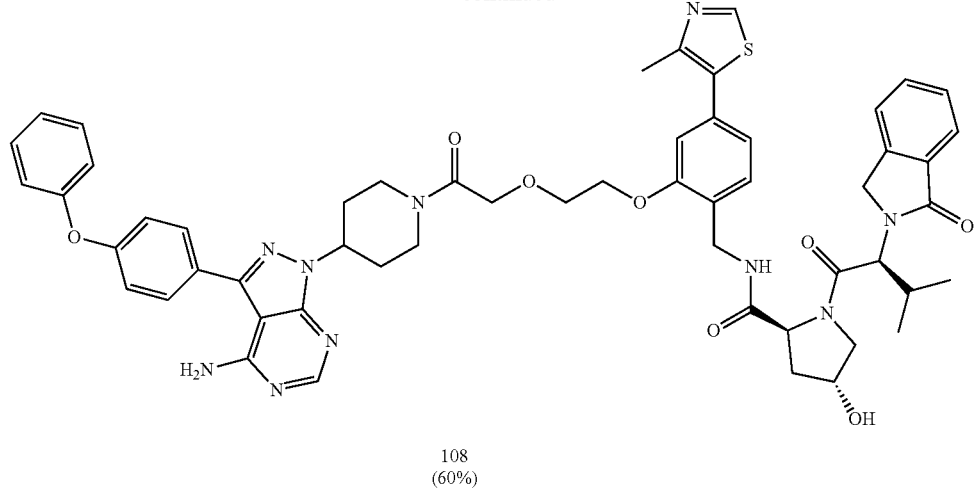

108
(60%)

Step A: tert-butyl 2-[2-[2-[[[(2S,4R)-4-hydroxy-1-[(2S)-3-methyl-2-(1-oxoisoindolin-2-yl)butanoyl]pyrrolidine-2-carbonyl]amino]methyl]-5-(4-methyl-thiazol-5-yl)phenoxy]ethoxy]acetate (13)

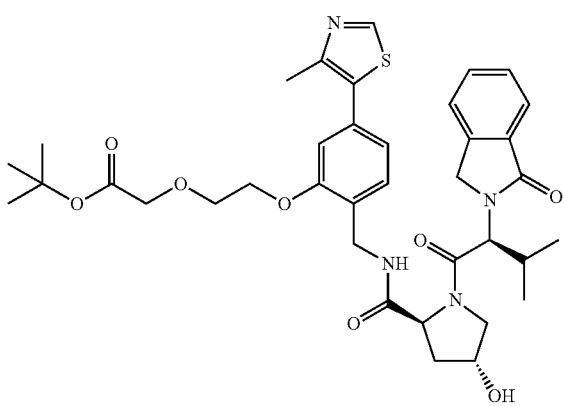

13

To a solution of (2S,4R)-4-hydroxy-N-[[2-hydroxy-4-(4-methylthiazol-5-yl)phenyl]methyl]-1-[(2S)-3-methyl-2-(1-oxoisoindolin-2-yl)butanoyl]pyrrolidine-2-carboxamide (30 mg, 0.05 mmol) and tert-butyl 2-(2-bromoethoxy)acetate (26.15 mg, 0.11 mmol) in DMF (1 mL) was added $Cs_2CO_3$ (71 mg, 0.21 mmol) at room temperature, the reaction mixture was stirred for 12 h (overnight) at the same temperature. Reaction was diluted with AcOEt (10 mL) and washed with water (4×10 mL). Organic extract was dried ($Na_2SO_4$), and concentrated under vacuum. Crude product was purified by PTLC (DCM:MeOH:$NH_4OH$, 91:8:1) to give 24 mg of product (62% yield). $^1$H NMR (400 MHz, DMSO-d6) δ 8.99 (s, 1H), 8.37 (t, J=5.9 Hz, 1H), 7.71 (d, J=7.6 Hz, 1H), 7.67-7.55 (m, 2H), 7.50 (ddd, J=7.5, 5.9, 2.7 Hz, 1H), 7.35 (d, J=7.8 Hz, 1H), 7.14-6.94 (m, 2H), 5.10 (d, J=4.1 Hz, 1H), 4.72 (d, J=10.8 Hz, 1H), 4.56 (d, J=18.1 Hz, 1H), 4.46 (d, J=18.5 Hz, 1H), 4.40 (d, J=8.0 Hz, 1H), 4.38-4.25 (m, 3H), 4.27-4.18 (m, 2H), 4.11 (s, 2H), 3.93-3.83 (m, 2H), 3.79 (dd, J=10.6, 4.3 Hz, 1H), 3.70 (d, J=10.6 Hz, 1H), 2.47 (s, 3H), 2.39-2.27 (m, 1H), 2.10-2.00 (m, 1H), 1.96-1.88 (m, 1H), 1.40 (s, 9H), 0.97 (d, J=6.5 Hz, 3H), 0.74 (d, J=6.6 Hz, 3H). $^{13}$C NMR (151 MHz, DMSO) δ 171.54, 169.43, 168.09, 167.48, 155.81, 151.47, 147.94, 142.20, 131.57, 131.38, 131.25, 131.00, 127.90, 127.75, 127.16, 123.61, 123.02, 121.11, 112.04, 80.75, 69.14, 68.63, 68.31, 67.86, 58.72, 57.79, 55.43, 46.82, 38.10, 37.16, 28.40, 27.74, 18.90, 18.63, 16.03. LC/MS (ESI); m/z: [M+H]$^+$ Calcd. for $C_{37}H_{47}N_4O_8S$, 707.3114. Found 707.3090.

(2S,4R)—N-(2-(2-(2-(4-(4-amino-3-(4-phenoxyphenyl)-1H-pyrazolo[3,4-d]pyrimidin-1-yl)piperidin-1-yl)-2-oxoethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (Compound 108)

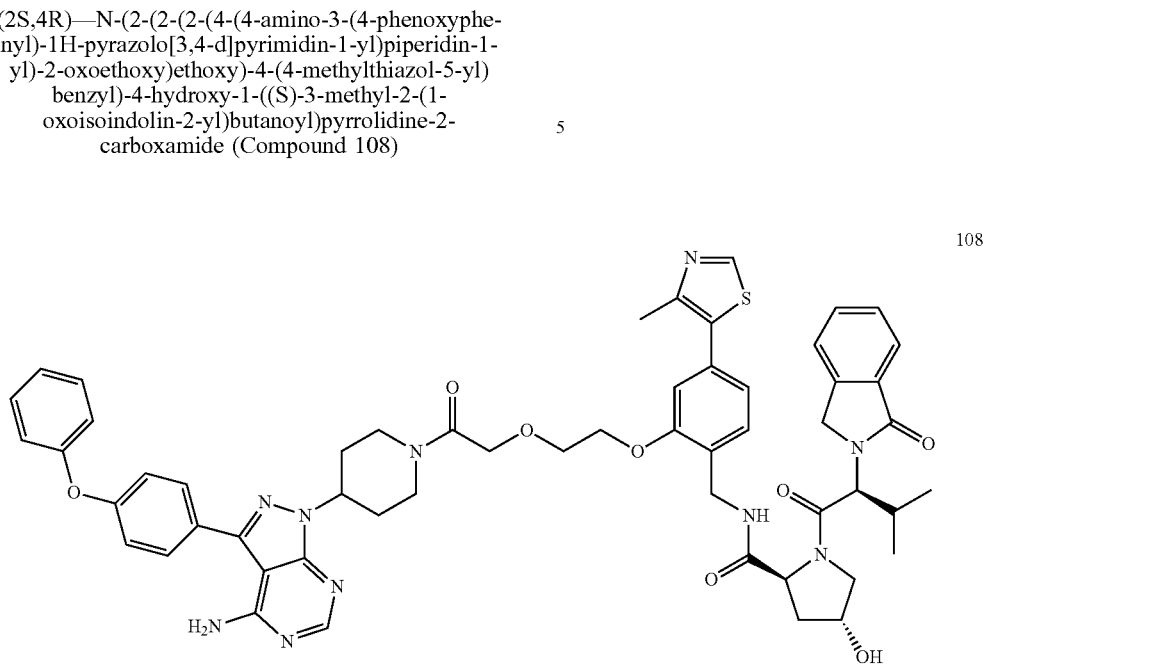

108

A solution of tert-butyl 2-[2-[2-[[[(2S,4R)-4-hydroxy-1-[(2S)-3-methyl-2-(1-oxoisoindolin-2-yl)butanoyl]-pyrrolidine-2-carbonyl]amino]methyl]-5-(4-methylthiazol-5-yl)phenoxy]ethoxy]-acetate (15 mg, 0.02 mmol) in a mixture of TFA (1 ml, 13.46 mmol) and dichloromethane (3 ml) was stirred for 2 h. Then the solvent was removed under vacuum and crude product was dried under high vacuum for 2 h. Crude product was used in the next step without any further purification (13.8 mg, quantitative yield). LC/MS (ESI); m/z: [M+H]$^+$ Calcd. For $C_{33}H_{39}N_4O_8S$, 651.2488. Found 651.2670.

To a solution of 2-(2-(2-(((2S,4R)-4-hydroxy-1-((S)-3-methyl-2-(1-oxoisoindolin-2-yl) -butanoyl)pyrrolidine-2-carboxamido)methyl)-5-(4-methylthiazol-5-yl)phenoxy)ethoxy)acetic acid (13.8 mg, 0.02 mmol) and 3-(4-phenoxyphenyl)-1-(piperidin-4-yl)-1H-pyrazolo[3,4-d]-pyrimidin-4-amine hydrochloride (9.87 mg, 0.02 mmol) in DMF(1 ml) was added TEA (0.1 ml, 0.72 mmol) and PyBOP (11.59 mg, 0.02 mmol) at room temperature. The reaction mixture was stirred for 4 h at the same temperature. The reaction mixture was dissolved in EtOAc (10 mL) and washed with brine/water (3×5 mL). Organic extract was concentrated under vacuum and crude product was purified by PTLC (DCM:MeOH:NH$_4$OH, 91:8:1) to give 13 mg of product (60% yield). $^1$H NMR (500 MHz, DMSO-d6) δ 8.97 (s, 1H), 8.35 (t, J=5.9 Hz, 1H), 8.25 (s, 1H), 7.70 (d, J=7.6 Hz, 1H), 7.64 (d, J=8.1 Hz, 2H), 7.59 (d, J=6.6 Hz, 2H), 7.52-7.45 (m, 1H), 7.46-7.39 (m, 2H), 7.33 (d, J=7.8 Hz, 1H), 7.18 (t, J=7.4 Hz, 1H), 7.11 (t, J=8.2 Hz, 4H), 7.05 (d, J=1.3 Hz, 1H), 7.00 (dd, J=7.8, 1.4 Hz, 1H), 5.07 (d, J=4.1 Hz, 1H), 5.02-4.92 (m, 1H), 4.69 (d, J=10.8 Hz, 1H), 4.61-4.18 (m, 11H), 4.06-3.93 (m, 1H), 3.92-3.82 (m, 2H), 3.80-3.63 (m, 2H), 3.26 (t, J=12.7 Hz, 1H), 2.91-2.79 (m, 1H), 2.46 (s, 3H), 2.34-2.23 (m, 1H), 2.21-2.10 (m, 1H), 2.09-1.81 (m, 5H), 0.93 (d, J=6.5 Hz, 3H), 0.70 (bs, 3H). $^{13}$C NMR (151 MHz, DMSO) δ 171.91, 168.47, 167.87, 167.62, 158.60, 157.48, 156.70, 156.28, 155.94, 154.04, 151.89, 148.35, 143.43, 142.59, 131.98, 131.78, 131.67, 131.43, 130.55, 130.45, 128.42, 128.31, 128.21, 127.56, 124.21, 124.00, 123.42, 121.49, 119.39, 119.36, 112.46, 97.85, 69.96, 69.54, 69.04, 68.13, 59.10, 58.18, 55.86, 53.69, 47.20, 43.71, 38.51, 37.59, 31.80, 31.29, 28.79, 19.25, 19.03, 16.45. LC/MS (ESI); m/z [M+H]$^+$: Calcd. for $C_{55}H_{59}N_{10}O_8S$, 1019.4238. Found 1019.4649.

Synthesis of Compound 128: (2S,4R)—N-(2-(3-(3-(4-(4-amino-3-(4-phenoxyphenyl)-1H-pyrazolo[3,4-d]pyrimidin-1-yl)piperidin-1-yl)-3-oxopropoxy)propoxy)-4-(4-methylthiazol-5-yl)benzyl)-4-hydroxy-1-((S)-3-methyl-2-(1-oxoisoindolin-2-yl)butanoyl)pyrrolidine-2-carboxamide

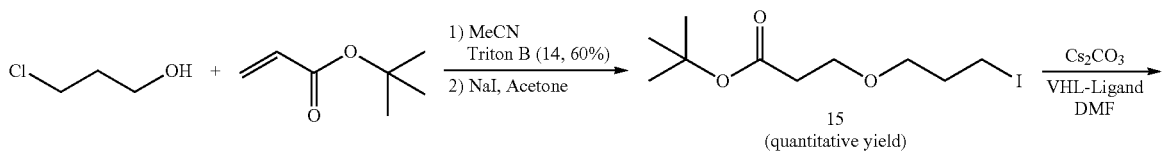

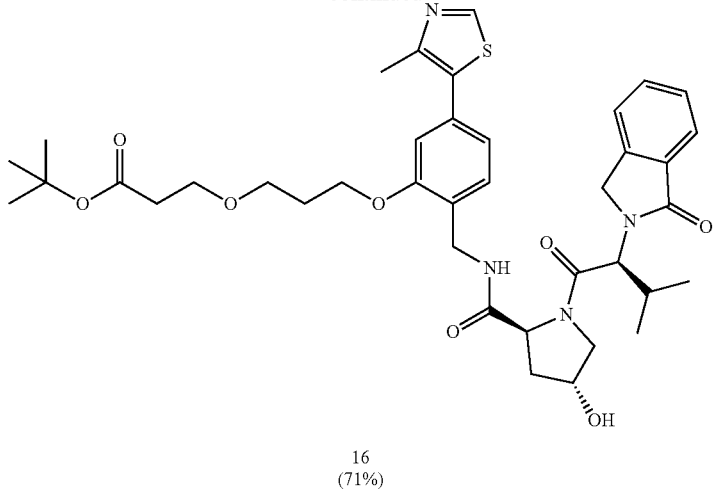

16
(71%)

1) TFA/DCM
2) 1/Cs₂CO₃, DCM

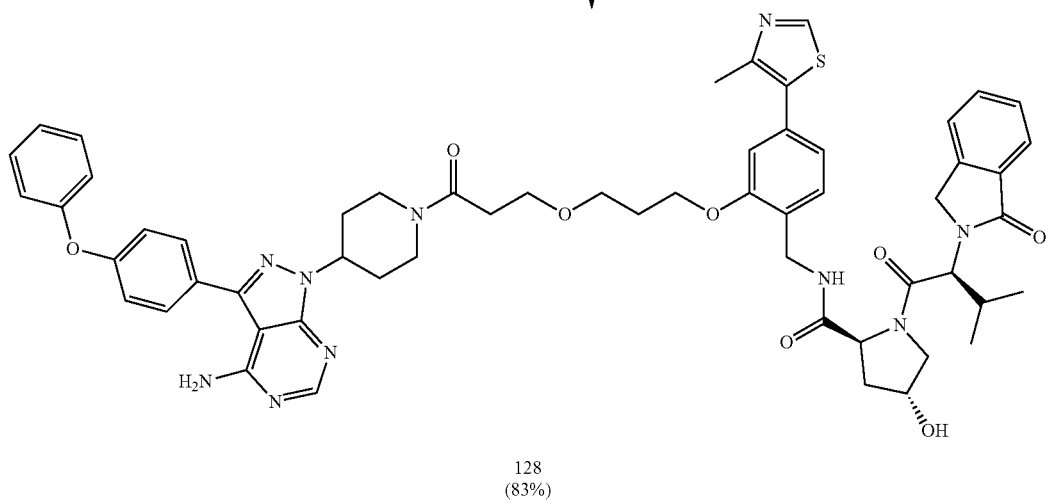

128
(83%)

Step A: tert-Butyl 3-(3-chloropropoxy)propanoate

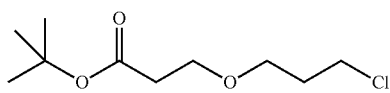

3-chloropropan-1-ol (8.84 ml, 105.78 mmol) in acetonitrile (50 mL) was added tert-butyl prop-2-enoate (15.35 ml, 105.78 mmol) followed by Triton B (1 ml, 2.54 mmol). The mixture was stirred at room temperature for 72 hours. The mixture was concentrated in vacuum and crude product was purified by column chromatography (SiO₂—250 g, gradient Hexane:AcOEt, 95:5 to 9:1 in 15 min) to give 14.2 g of product as an oil (60% yield). ¹H NMR (500 MHz, Chloroform-d) δ 3.66 (t, J=6.4 Hz, 2H), 3.62 (t, J=6.5 Hz, 2H), 3.56 (t, J=5.9 Hz, 2H), 2.51-2.42 (m, 2H), 1.99 (p, J=6.2 Hz, 2H), 1.45 (s, 9H). ¹³C NMR (101 MHz, CDCl₃) δ 171.03, 80.70, 67.32, 66.72, 42.02, 36.46, 32.79, 28.22. LC/MS (ESI); m/z [M+Na]⁺: Calcd. for C₁₀H₁₉ClO₃Na, 245.0920. Found 245.0957.

Step B: tert-Butyl 3-(3-iodopropoxy)propanoate (15)

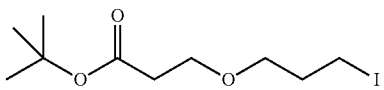

15

To a solution of tert-butyl 3-(3-chloropropoxy)propanoate (1.36 g, 6.11 mmol) in Acetone (100 ml) was added NaI (4.58 g, 30.53 mmol). The reaction mixture was stirred at reflux temperature for 72 h, then the solvent was removed under vacuum and crude product was re-dissolved in EtOAc (100 mL) and washed with water (100 mL), and an aqueous solution of Na₂SO₃ (10%, 50 mL), organic layer was separated, dried (Na₂SO₄), and evaporated under vacuum. Crude product was pure by NMR (>98% purity). It was used in the next step without any further purification. $^1$H NMR (500 MHz, Chloroform-d) δ 3.67 (t, J=6.4 Hz, 2H), 3.49 (t, J=5.8 Hz, 2H), 3.25 (t, J=6.8 Hz, 2H), 2.47 (t, J=6.4 Hz, 2H), 2.04 (p, J=6.3 Hz, 2H), 1.45 (s, 9H). $^{13}$C NMR (151 MHz, CDCl$_3$) δ 171.01, 80.72, 70.26, 66.71, 36.46, 33.52, 28.25, 3.54. LC/MS (ESI); m/z [M+Na]$^+$: Calcd. for C$_{10}$H$_{19}$IO$_3$Na, 337.0276. Found 337.0351.

Step C: tert-butyl 3-(3-(2-(((2S,4R)-4-hydroxy-1-((S)-3-methyl-2-(1-oxoisoindolin-2-yl)butanoyl)pyrrol-idine-2-carboxamido)methyl)-5-(4-methylthiazol-5-yl)phenoxy)propoxy)propanoate (16)

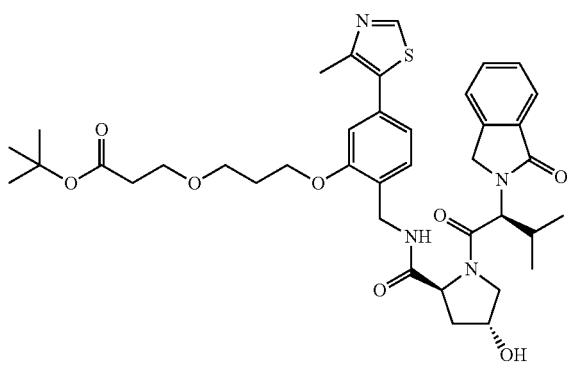

To a solution of (2S,4R)-4-hydroxy-N-[[2-hydroxy-4-(4-methylthiazol-5-yl)phenyl]methyl]-1-[(2S)-3-methyl-2-(1-oxoisoindolin-2-yl)butanoyl]pyrrolidine-2-carboxamide (30 mg, 0.05 mmol) and tert-butyl 2-(2-bromoethoxy)acetate (26.15 mg, 0.11 mmol) in DMF (1 mL) was added Cs$_2$CO$_3$ (71 mg, 0.21 mmol) at room temperature, the reaction mixture was stirred for 12 h (overnight) at the same temperature. Reaction was diluted with AcOEt (10 mL) and washed with water (4×10 mL). Organic extract was dried (Na$_2$SO$_4$), and concentrated under vacuum. Crude product was purified by PTLC (DCM:MeOH:NH$_4$OH, 91:8:1) to give 38 mg of product (71% yield). $^1$H NMR (500 MHz, DMSO-d6) δ 8.98 (s, 1H), 8.36 (t, J=5.8 Hz, 1H), 7.71 (d, J=7.6 Hz, 1H), 7.62 (q, J=7.5, 6.5 Hz, 2H), 7.50 (t, J=6.8 Hz, 1H), 7.35 (d, J=7.7 Hz, 1H), 7.00 (d, J=7.5 Hz, 2H), 5.09 (d, J=4.1 Hz, 1H), 4.72 (d, J=10.8 Hz, 1H), 4.61-4.19 (m, 6H), 4.09 (t, J=6.1 Hz, 2H), 3.78 (dd, J=10.5, 4.3 Hz, 1H), 3.70 (d, J=10.6 Hz, 1H), 3.64-3.49 (m, 4H), 2.47 (s, 3H), 2.42 (t, J=6.0 Hz, 2H), 2.39-2.27 (m, 1H), 2.12-1.87 (m, 4H), 1.34 (s, 9H), 0.97 (d, J=6.5 Hz, 3H), 0.74 (d, J=6.7 Hz, 3H). $^{13}$C NMR (101 MHz, DMSO) δ 171.49, 170.43, 168.09, 167.47, 155.86, 151.42, 147.86, 142.18, 131.56, 131.37, 131.26, 131.00, 127.88, 127.81, 126.99, 123.60, 123.00, 120.83, 111.63, 79.63, 68.61, 66.59, 65.95, 64.71, 58.69, 57.78, 55.40, 46.81, 38.08, 37.05, 35.85, 28.98, 28.38, 27.69, 18.88, 18.61, 15.99. LC/MS (ESI); m/z: [M+H]$^+$ Calcd. for C$_{39}$H$_{51}$N$_4$O$_8$S, 735.3427. Found 735.3720.

Step D: (2S,4R)—N-(2-(3-(3-(4-(4-amino-3-(4-phenoxyphenyl)-1H-pyrazolo[3,4-d]pyrimidin-1-yl)piperidin-1-yl)-3-oxopropoxy)propoxy)-4-(4-methylthiazol-5-yl)benzyl)-4-hydroxy-1-((S)-3-methyl-2-(1-oxoisoindolin-2-yl)butanoyl)pyrrolidine-2-carboxamide (Compound 128)

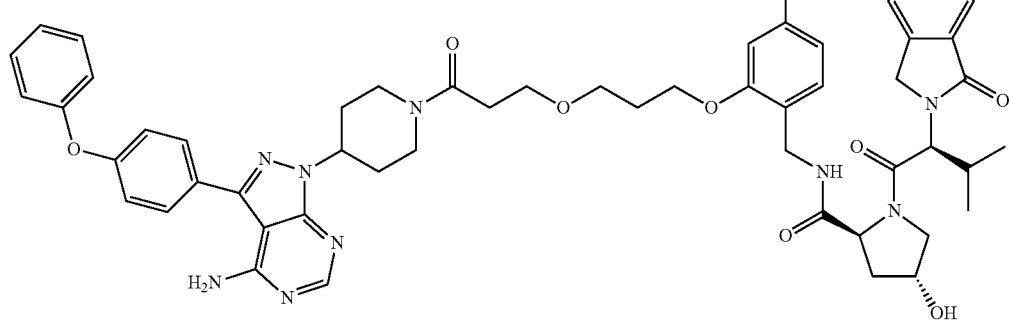

A solution of tert-butyl 3-(3-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)propoxy)-propanoate (19 mg, 0.03 mmol) in a mixture of TFA (0.7 ml, 9.42 mmol) and Dichloromethane (2 ml) was stirred for 2 h. Then the solvent was removed under vacuum and crude product was dried under high vacuum for 1 h. Crude product was used in the next step without any further purification (17.5 mg, quantitative yield). LC/MS (ESI); m/z: [M+H]$^+$ Calcd. for C$_{35}$H$_{43}$N$_4$O$_8$S, 679.2801. Found 679.3105.

To a solution of 3-(3-(2-(((2S,4R)-4-hydroxy-1-((S)-3-methyl-2-(1-oxoisoindolin-2-yl)butanoyl)-pyrrolidine-2-carboxamido)methyl)-5-(4-methylthiazol-5-yl)phenoxy)propoxy)propanoic acid (17.5 mg, 0.03 mmol) and 3-(4-phenoxyphenyl)-1-(piperidin-4-yl)-1H-pyrazolo[3,4-d]pyrimidin-4-amine (10.96 mg, 0.03 mmol) in DMF(1 ml) was added TEA (0.1 ml, 0.72 mmol) and PyBOP (14.76 mg, 0.03 mmol) at room temperature. The reaction mixture was stirred for 4 h at the same temperature. The reaction mixture was dissolved in EtOAc (10 mL) and washed with brine/water (3×5 mL). Organic extract was concentrated under vacuum and crude product was purified by PTLC (DCM: MeOH:NH$_4$OH, 91:8:1) to give 22 mg of product (83% yield). $^1$H NMR (400 MHz, DMSO-d6) δ 8.91 (s, 1H), 8.33 (t, J=5.5 Hz, 1H), 8.22 (s, 1H), 7.68 (d, J=7.5 Hz, 1H), 7.63-7.52 (m, 4H), 7.50-7.43 (m, 1H), 7.43-7.34 (m, 2H), 7.31 (d, J=7.6 Hz, 1H), 7.17-7.11 (m, 1H), 7.07 (dd, J=11.4, 8.4 Hz, 4H), 6.98-6.90 (m, 2H), 5.05 (d, J=3.9 Hz, 1H), 4.98-4.87 (m, 1H), 4.68 (d, J=10.8 Hz, 1H), 4.59-4.16 (m, 7H), 4.06 (t, J=5.6 Hz, 2H), 4.04-3.94 (m, 1H), 3.80-3.60 (m, 4H), 3.57 (t, J=6.0 Hz, 2H), 3.20 (t, J=12.5 Hz, 1H), 2.82-2.53 (m, 3H), 2.40 (s, 3H), 2.33-2.23 (m, 1H), 2.16-1.76 (m, 8H), 0.92 (d, J=6.3 Hz, 3H), 0.69 (d, J=6.3 Hz, 3H). $^{13}$C NMR (151 MHz, DMSO) δ 171.50, 168.79, 168.08, 167.46, 158.17, 157.01, 156.30, 155.88, 155.52, 153.62, 151.37, 147.85, 143.01, 142.19, 131.56, 131.37, 131.26, 130.99, 130.11, 130.00, 128.02, 127.89, 127.79, 127.00, 123.75, 123.60, 123.00, 120.82, 118.96, 118.91, 111.66, 97.42, 68.62, 66.75, 66.69, 64.81, 58.69, 57.78, 55.42, 53.33, 46.81, 44.11, 38.10, 37.06, 32.68, 31.52, 30.90, 29.05, 28.39, 18.87, 18.62, 15.98. LC/MS (ESI); m/z [M+H]$^+$: Calcd. for $C_{57}H_{63}N_{10}O_8S$, 1047.4551. Found 1047.5190.

Summary of NMR Data of Compounds in Table 4

Compound 100

$^1$H NMR (500 MHz, Chloroform-d) δ 10.97 (s, 1H), 10.51 (s, 1H), 8.87 (d, J=8.4 Hz, 1H), 8.37 (s, 1H), 7.71 (t, J=7.9 Hz, 1H), 7.61 (d, J=8.2 Hz, 2H), 7.57 (d, J=7.3 Hz, 1H), 7.38 (t, J=7.7 Hz, 2H), 7.19-7.03 (m, 5H), 5.70 (s, 2H), 4.95 (dd, J=12.2, 5.3 Hz, 1H), 4.72 (tt, J=11.6, 4.1 Hz, 1H), 4.22-4.07 (m, 2H), 3.81 (t, J=5.1 Hz, 2H), 3.24 (d, J=11.8 Hz, 1H), 3.12 (d, J=11.3 Hz, 1H), 2.96-2.69 (m, 4H), 2.53-2.22 (m, 4H), 2.21-2.13 (m, 1H), 2.09-1.95 (m, 2H), 1.72 (bs, 1H). $^{13}$C NMR (151 MHz, CDCl$_3$) δ 171.87, 169.10, 168.59, 168.34, 166.76, 158.32, 157.89, 156.34, 155.26, 153.39, 143.39, 136.73, 136.23, 131.39, 129.92, 127.94, 125.14, 123.95, 119.50, 119.00, 118.76, 116.16, 98.47, 70.96, 70.69, 60.38, 57.88, 54.68, 54.06, 53.21, 49.31, 31.52, 31.24, 22.93.

Compound 101

$^1$H NMR (500 MHz, Chloroform-d) δ 11.21 (s, 1H), 10.60 (s, 1H), 8.82 (d, J=8.5 Hz, 1H), 8.36 (d, J=1.6 Hz, 1H), 7.73-7.67 (m, 1H), 7.62 (dd, J=8.6, 1.7 Hz, 2H), 7.56 (dd, J=12, 1.6 Hz, 1H), 7.41-7.34 (m, 2H), 7.19-7.09 (m, 3H), 7.10-7.04 (m, 2H), 5.66 (s, 2H), 4.92 (s, 1H), 4.77 (s, 1H), 4.24-4.11 (m, 2H), 3.86-3.63 (m, 6H), 3.19 (s, 2H), 2.90-2.57 (m, 5H), 2.51-2.14 (m, 5H), 2.02 (d, J=16.8 Hz, 2H). $^{13}$C NMR (151 MHz, CDCl$_3$) δ 171.85, 169.12, 169.02, 168.60, 166.74, 158.33, 157.76, 156.36, 155.36, 143.31, 136.71, 136.27, 131.41, 129.95, 129.92, 128.01, 124.99, 123.95, 119.48, 119.03, 118.69, 116.10, 98.50, 71.36, 70.77, 70.40, 68.86, 57.03, 54.25, 53.16, 52.75, 49.21, 31.27, 30.84, 23.10.

Compound 102

$^1$H NMR (500 MHz, Chloroform-d) δ 10.01 (bs, 1H), 9.38 (s, 1H), 8.40 (s, 1H), 8.21 (d, J=8.1 Hz, 1H), 8.02 (s, 1H), 7.82 (d, J=8.2 Hz, 1H), 7.61 (d, J=8.5 Hz, 2H), 7.37 (t, J=7.9 Hz, 2H), 7.14 (dd, J=19.9, 8.0 Hz, 3H), 7.07 (d, J=7.9 Hz, 2H), 5.70 (bs, 2H), 4.95 (dd, J=12.4, 5.3 Hz, 1H), 4.77 (t, J=10.8 Hz, 1H), 4.23-4.09 (m, 2H), 3.85-3.68 (m, 5H), 3.07 (dd, J=22.1, 8.9 Hz, 2H), 2.92-2.67 (m, 5H), 2.29 (dq, J=22.9, 11.7 Hz, 4H), 2.13 (d, J=10.3 Hz, 1H), 1.99-1.94 (m, 3H). $^{13}$C NMR (126 MHz, CDCl$_3$) δ 171.55, 169.04, 168.67, 166.88, 166.82, 158.29, 157.82, 156.41, 155.47, 153.70, 143.38, 143.33, 133.06, 129.91, 128.05, 126.55, 124.97, 124.63, 123.92, 119.46, 119.07, 114.92, 98.49, 71.50, 70.38, 69.89, 69.28, 57.52, 54.32, 53.26, 49.42, 31.48, 31.30, 31.20, 22.71.

Compound 103

$^1$H NMR (500 MHz, Chloroform-d) δ 11.01 (bs, 1H), 10.04 (s, 1H), 8.86 (d, J=8.5 Hz, 1H), 8.38 (s, 1H), 7.72-7.61 (m, 3H), 7.59-7.51 (m, 1H), 7.39 (dd, J=8.6, 7.3 Hz, 2H), 7.21-7.05 (m, 5H), 5.54 (bs, 2H), 4.99-4.91 (m, 1H), 4.82-4.71 (m, 1H), 3.82-3.73 (m, 2H), 3.72-3.59 (m, 2H), 3.56-3.39 (m, 4H), 3.17 (bs, 2H), 2.92-1.72 (m, 5H), 2.56 (bs, 1H), 2.48-2.35 (m, 3H), 2.27-2.11 (m, 3H), 1.99 (d, J=14.0 Hz, 2H), 1.94 (dd, J=13.7, 6.9 Hz, 2H), 1.78 (d, J=7.0 Hz, 2H). $^{13}$C NMR (151 MHz, CDCl$_3$) δ 171.80, 171.15, 168.76, 168.50, 166.92, 158.32, 157.70, 156.39, 155.44, 153.84, 143.24, 137.53, 136.06, 131.34, 129.97, 129.92, 128.09, 125.73, 123.93, 119.47, 119.08, 118.36, 115.80, 98.57, 68.88, 68.80, 67.58, 65.99, 54.72, 54.54, 53.41, 52.56, 52.16, 49.36, 38.78, 31.67, 30.91, 29.52, 26.83, 22.82.

Compound 104

$^1$H NMR (500 MHz, Chloroform-d) δ 11.19 (s, 1H), 10.44 (s, 1H), 8.86 (d, J=8.5 Hz, 1H), 8.37 (s, 1H), 7.74-7.68 (m, 1H), 7.67-7.61 (m, 2H), 7.56 (d, J=7.3 Hz, 1H), 7.42-7.34 (m, 2H), 7.19-7.11 (m, 3H), 7.10-7.04 (m, 2H), 5.65 (s, 2H), 4.97 (dd, J=12.7, 5.3 Hz, 1H), 4.76 (s, 1H), 4.25-4.11 (m, 2H), 3.85-3.66 (m, 4H), 3.52 (t, J=6.7 Hz, 2H), 3.17 (s, 2H), 2.95-2.82 (m, 2H), 2.80-2.69 (m, 1H), 2.42 (d, J=12.7 Hz, 4H), 2.21-2.11 (m, 3H), 2.00 (bs, 2H), 1.66-1.45 (m, 4H), 1.41-1.24 (m, 4H). $^{13}$C NMR (151 MHz, CDCl$_3$) δ 71.95, 169.37, 168.78, 168.42, 166.92, 58.30, 157.76, 156.41, 155.56, 153.82, 43.26, 136.67, 136.12, 131.39, 129.97, 129.92, 128.08, 125.29, 123.92, 119.47, 19.10, 118.74, 116.26, 98.55, 71.75, 71.58, 70.99, 69.71, 57.97, 54.63, 52.65, 52.38, 50.81, 49.49, 31.78, 30.87, 29.35, 27.24, 26.60, 25.87, 22.62.

Compound 105

$^1$H NMR (500 MHz, Chloroform-d) δ 9.28 (s, 1H), 8.74 (s, 1H), 8.39 (s, 1H), 8.11 (s, 1H), 8.01 (d, J=8.2 Hz, 1H), 7.82 (d, J=8.2 Hz, 1H), 7.64 (d, J=8.6 Hz, 2H), 7.38 (t, J=7.9 Hz, 2H), 7.14 (dd, J=19.3, 8.0 Hz, 3H), 7.10-7.02 (m, 2H), 5.64 (s, 2H), 4.96 (dd, J=12.5, 5.3 Hz, 1H), 4.80-4.75 (m, 1H), 4.10 (s, 2H), 3.65 (t, J=6.4 Hz, 2H), 3.52-3.43 (m, 4H), 3.07 (d, J=9.8 Hz, 2H), 2.82 (ddd, J=42.7, 31.7, 15.4 Hz, 3H), 2.42 (d, J=13.2 Hz, 3H), 2.24-2.11 (m, 3H), 2.00 (d, J=11.0 Hz, 2H), 1.83-1.53 (m, 6H). $^{13}$C NMR (126 MHz, CDCl$_3$) δ 171.23, 168.32, 166.74, 166.70, 158.30, 157.77, 156.41, 155.43, 153.84, 143.26, 143.06, 133.32, 129.95, 129.91, 128.12, 126.60, 124.98, 124.23, 123.93, 119.59, 119.46, 119.08, 119.03, 114.41, 98.53, 71.97, 71.69, 71.14, 70.84, 70.50, 70.29, 70.12, 62.75, 58.14, 52.83, 49.39, 31.45, 31.36, 27.68, 26.51, 26.39, 23.90, 22.65.

Compound 106

$^1$H NMR (500 MHz, Chloroform-d) δ 11.21 (bs, 1H), 10.47 (s, 1H), 8.85 (d, J=8.4 Hz, 1H), 8.37 (s, 1H), 7.69 (t, J=7.8 Hz, 1H), 7.64 (d, J=7.6 Hz, 2H), 7.55 (d, J=7.1 Hz, 1H), 7.38 (t, J=7.4 Hz, 2H), 7.16 (dd, J=12.0, 7.6 Hz, 3H), 7.08 (d, J=8.3 Hz, 2H), 5.65 (s, 2H), 4.95 (d, J=5.4 Hz, 1H), 4.77 (t, J=10.6 Hz, 1H), 4.10 (s, 2H), 3.64 (d, J=5.4 Hz, 2H), 3.45 (d, J=20.4 Hz, 4H), 3.19 (d, J=8.2 Hz, 2H), 2.86 (q, J=14.2, 12.7 Hz, 2H), 2.76 (d, J=15.0 Hz, 1H), 2.53-2.36 (m, 4H), 2.27-2.11 (m, 3H), 2.00 (s, 2H), 1.76 (dd, J=22.0, 4 Hz, 4H), 1.59 (s, 4H). $^{13}$C NMR (151 MHz, CDCl$_3$) δ 171.98, 169.46, 168.79, 168.41, 166.91, 158.29, 157.77, 156.41, 155.37, 153.83, 143.27, 136.68, 136.11, 131.39, 129.96, 129.92, 128.06, 125.16, 123.91, 119.47, 119.10, 118.68, 116.23, 98.55, 72.06, 70.52, 70.50, 70.45, 57.93

Compound 107

$^1$H NMR (500 MHz, Chloroform-d) δ 10.48 (s, 1H), 8.85 (d, J=8.5 Hz, 1H), 8.40-8.36 (m, 1H), 7.70 (t, J=7.9 Hz, 1H), 7.64 (d, J=8.1 Hz, 2H), 7.55 (d, J=7.3 Hz, 1H), 7.37 (t, J=7.5 Hz, 2H), 7.19-7.10 (m, 3H), 7.10-7.04 (m, 2H), 5.72 (bs, 2H), 4.94 (dd, J=12.4, 5.2 Hz, 1H), 4.76 (bs, 1H), 4.17-4.03 (m, 2H), 3.67-3.54 (m, 2H), 3.42 (q, J=6.9 Hz, 4H), 3.11 (s, 2H), 2.93-2.69 (m, 4H), 2.51-2.32 (m, 4H), 2.27-2.10 (m, 3H), 2.01 (s, 1H), 1.81-1.28 (m, 16H). ¹³C NMR (151 MHz, CDCl₃) δ 171.67, 169.56, 169.49, 168.57, 168.34, 166.77, 162.49, 158.26, 157.79, 156.40, 155.34, 153.85, 143.25, 136.71, 136.16, 131.40, 129.91, 128.11, 125.09, 123.90, 119.44, 119.07, 118.66, 116.13, 98.49, 72.29, 70.96, 70.43, 62.74, 58.25, 54.69, 53.41, 52.73, 49.26, 31.50, 31.16, 29.61, 29.53, 27.34, 26.90, 26.09, 26.02, 25.94, 22.810.

Compound 108

¹H NMR (500 MHz, DMSO-d6) δ 8.97 (s, 1H), 8.35 (t, J=5.9 Hz, 1H), 8.25 (s, 1H), 7.70 (d, J=7.6 Hz, 1H), 7.64 (d, J=8.1 Hz, 2H), 7.59 (d, J=6.6 Hz, 2H), 7.52-7.45 (m, 1H), 7.46-7.39 (m, 2H), 7.33 (d, J=7.8 Hz, 1H), 7.18 (t, J=7.4 Hz, 1H), 7.11 (t, J=8.2 Hz, 4H), 7.05 (d, J=1.3 Hz, 1H), 7.00 (dd, J=7.8, 1.4 Hz, 1H), 5.07 (d, J=4.1 Hz, 1H), 5.02-4.92 (m, 1H), 4.69 (d, J=10.8 Hz, 1H), 4.61-4.18 (m, 11H), 4.06-3.93 (m, 1H), 3.92-3.82 (m, 2H), 3.80-3.63 (m, 2H), 3.26 (t, J=12.7 Hz, 1H), 2.91-2.79 (m, 1H), 2.46 (s, 3H), 2.34-2.23 (m, 1H), 2.21-2.10 (m, 1H), 2.09-1.81 (m, 5H), 0.93 (d, J=6.5 Hz, 3H), 0.70 (bs, 3H). ¹³C NMR (151 MHz, DMSO) δ 171.91, 168.47, 167.87, 167.62, 158.60, 157.48, 156.70, 156.28, 155.94, 154.04, 151.89, 148.35, 143.43, 142.59, 131.98, 131.78, 131.67, 131.43, 130.55, 130.45, 128.42, 128.31, 128.21, 127.56, 124.21, 124.00, 123.42, 121.49, 119.39, 119.36, 112.46, 97.85, 69.96, 69.54, 69.04, 68.13, 59.10, 58.18, 55.86, 53.69, 47.20, 43.71, 38.51, 37.59, 31.80, 31.29, 28.79, 19.25, 19.03, 16.45.

Compound 109

¹H NMR (500 MHz, Methylene Chloride-d) δ 9.31 (s, 1H), 8.68 (s, 1H), 8.10 (d, J=8.5 Hz, 2H), 7.94-7.80 (m, 4H), 7.60 (dd, J=19.4, 8.0 Hz, 2H), 7.53 (d, J=7.9 Hz, 1H), 5.12 (s, 1H), 4.97 (dd, J=25.7, 10.2 Hz, 2H), 4.79 (d, J=15.5 Hz, 1H), 4.54-4.42 (m, 2H), 4.32 (s, 1H), 4.09 (d, J=38.2 Hz, 11H), 3.77 (d, J=19.4 Hz, 8H), 3.72-3.61 (m, 2H), 3.19 (s, 1H), 2.91 (d, J=9.1 Hz, 5H), 2.70-2.63 (m, 1H), 2.46 (d, J=11.7 Hz, 2H), 1.78 (d, J=15.7 Hz, 10H), 1.47 (s, 6H). ¹³C NMR (151 MHz, CDCl₃) δ 176.88, 174.57, 174.14, 162.36, 160.49, 158.99, 157.23, 155.35, 151.53, 148.04, 142.75, 135.90, 133.99, 133.73, 133.58, 131.61, 131.45, 127.56, 123.02, 122.48, 101.76, 74.80, 74.19, 73.92, 73.56, 71.81, 68.72, 63.32, 60.82, 60.64, 58.16, 57.51, 56.49, 46.19, 41.48, 39.61, 34.20, 29.48, 20.30, 18.36, 15.78.

Compound 110

¹H NMR (500 MHz, Chloroform-d) δ 8.66 (s, 1H), 8.33 (s, 1H), 7.63 (d, J=8.5 Hz, 2H), 7.44 (t, J=6.0 Hz, 1H), 7.41-7.28 (m, 5H), 7.21-7.01 (m, 4H), 5.66 (s, 2H), 4.81 (d, J=11.7 Hz, 1H), 4.73 (t, J=8.0 Hz, 1H), 4.61-4.47 (m, 2H), 4.34 (dd, J=15.0, 5.3 Hz, 1H), 4.14-3.95 (m, 3H), 3.73-3.48 (m, 7H), 3.43 (t, J=6.6 Hz, 2H), 3.16 (s, 2H), 2.55-2.30 (m, 8H), 2.08 (s, 3H), 1.63-1.20 (m, 10H), 0.94 (s, 9H). ¹³C NMR (101 MHz, CDCl₃) δ 171.28, 170.78, 170.42, 158.41, 157.76, 156.29, 153.80, 150.28, 148.40, 143.46, 138.11, 131.59, 130.85, 129.95, 129.91, 129.46, 129.37, 128.08, 127.85, 124.01, 119.53, 119.02, 98.53, 77.33, 77.22, 77.01, 76.69, 71.31, 71.11, 70.64, 70.51, 70.37, 70.05, 69.98, 58.48, 58.15, 57.06, 56.73, 53.48, 52.36, 43.20, 35.90, 34.98, 29.49, 27.26, 26.37, 25.98, 16.04.

Compound 111

¹H NMR (500 MHz, Chloroform-d) δ 8.67 (s, 1H), 8.35 (s, 1H), 7.64 (d, J=8.6 Hz, 2H), 7.44 (d, J=5.6 Hz, 1H), 7.41-7.32 (m, 5H), 7.26 (s, 1H), 7.18 (d, J=10.8 Hz, 4H), 7.08 (d, J=7.7 Hz, 2H), 5.60 (s, 2H), 4.84-4.70 (m, 2H), 4.64-4.45 (m, 4H), 4.34 (dd, J=15.0, 5.3 Hz, 1H), 4.16-4.01 (m, 2H), 3.89 (q, J=15.4 Hz, 3H), 3.62 (dd, 11.3, 3.7 Hz, 2H), 3.48 (td, J=6.7, 1.8 Hz, 2H), 3.39 (qd, J=6.4, 5.8, 3.2 Hz, 4H), 2.57-2.44 (m, 7H), 2.12 (ddt, J=12.9, 8.0, 2.0 Hz, 2H), 1.64-1.54 (m, 8H), 1.38 (dqd, J=29.2, 7.6, 6.8, 3.7 Hz, 8H), 0.94 (s, 9H). ¹³C NMR (151 MHz, CDCl₃) δ 171.30, 170.68, 170.39, 158.39, 157.75, 156.32, 155.47, 153.92, 150.26, 148.43, 143.37, 138.07, 131.57, 130.90, 129.91, 129.47, 128.11, 123.99, 119.51, 119.03, 98.55, 71.81, 70.80, 70.59, 70.03, 69.89, 58.45, 56.88, 56.63, 53.42, 43.23, 35.88, 34.95, 29.63, 29.27, 27.30, 26.36, 26.08, 22.71, 16.04.

Compound 113

¹H NMR (500 MHz, Chloroform-d) δ 8.66 (s, 1H), 8.34 (s, 1H), 7.69-7.61 (m, 2H), 7.49 (s, 1H), 7.43-7.32 (m, 5H), 7.30 (m, 1H), 7.15 (dd, J=18.0, 8.0 Hz, 3H), 7.08 (d, J=8.0 Hz, 2H), 5.59 (s, 2H), 4.85-4.68 (m, 2H), 4.54 (td, J=15.3, 7.7 Hz, 3H), 4.34 (dd, J=15.0, 5.3 Hz, 1H), 4.10-3.92 (m, 3H), 3.80-3.51 (m, 12H), 3.46 (s, 2H), 3.21-3.10 (m, 2H), 2.61-2.39 (m, 7H), 2.17-2.01 (m, 3H), 1.72-1.54 (m, 4H), 1.24 (dt, J=10.4, 7.2 Hz, 1H), 0.95 (s, 9H).

Compound 114

¹H NMR (500 MHz, Chloroform-d) δ 8.67 (s, 1H), 8.36 (s, 1H), 7.65 (d, J=8.6 Hz, 2H), 7.52 (s, 1H), 7.42-7.31 (m, 5H), 7.26 (s, 2H), 7.21-7.12 (m, 3H), 7.09 (d, J=8.6 Hz, 2H), 5.53 (s, 2H), 4.93 (s, 1H), 4.75 (d, J=8.0 Hz, 1H), 4.54 (td, J=17.0, 16.0, 7.6 Hz, 3H), 4.40-4.29 (m, 1H), 4.09-3.95 (m, 3H), 3.76-3.55 (m, 14H), 2.85 (d, J=102.2 Hz, 8H), 2.51 (s, 3H), 2.41 (q, J=12.4, 10.9 Hz, 4H), 2.15 (dd, J=13.3, 8.1 Hz, 4H), 1.79 (d, J=57.4 Hz, 4H), 0.95 (s, 9H). ¹³C NMR (151 MHz, CDCl₃) δ 171.18, 170.88, 170.22, 158.40, 157.74, 156.28, 155.48, 153.81, 153.81, 150.25, 148.41, 143.03, 138.20, 131.59, 130.83, 129.96, 129.44, 128.07, 124.03, 119.55, 119.02, 98.41, 77.22, 77.00, 76.88, 76.79, 71.03, 70.55, 70.48, 70.43, 70.27, 70.00, 58.53, 57.14, 56.98, 56.82, 48.61, 43.16, 36.13, 35.15, 27.67, 26.38, 16.05.

Compound 115

¹H NMR (500 MHz, Chloroform-d) δ 8.66 (s, 1H), 8.33 (s, 1H), 7.63 (d, J=8.0 Hz, 2H), 7.48 (s, 1H), 7.35 (h, J=9.4, 8.5 Hz, 6H), 7.15 (dd, J=18.3, 7.7 Hz, 3H), 7.08 (d, J=8.0 Hz, 2H), 5.71 (s, 2H), 4.81 (s, 1H), 4.72 (t, J=7.9 Hz, 1H), 4.52 (d, J=7.8 Hz, 3H), 4.34 (dd, J=14.9, 5.1 Hz, 1H), 4.08-3.93 (m, 3H), 3.75-3.50 (m, 13H), 3.43 (t, J=6.6 Hz, 2H), 3.17 (s, 2H), 3.06 (q, J=7.4 Hz, 1H), 2.49 (d, J=11.4 Hz, 7H), 2.10 (s, 2H), 1.66-1.50 (m, 4H), 1.48-1.28 (m, 8H), 0.95 (s, 9H). ¹³C NMR (151 MHz, CDCl₃) δ 171.21, 170.88, 170.37, 158.41, 157.79, 156.29, 155.31, 153.80, 150.27, 148.39, 143.47, 138.15, 131.60, 130.83, 129.94, 129.91, 129.44, 128.06, 127.85, 124.00, 119.52, 119.03, 98.53, 71.32, 71.12, 70.51, 70.41, 69.99, 58.54, 58.08, 57.03, 56.73, 53.28, 52.45, 43.18, 36.03, 35.10, 29.46, 27.22, 26.37, 25.91, 16.03.

Compound 116

¹H NMR (500 MHz, Chloroform-d) δ 8.66 (s, 1H), 8.35 (s, 1H), 7.63 (d, J=7.0 Hz, 2H), 7.43-7.28 (m, 6H), 7.20-7.10 (m, 3H), 7.07 (d, J=8.0 Hz, 2H), 6.23 (s, 1H), 5.56 (s, 2H), 4.80 (s, 1H), 4.51 (d, J=8.3 Hz, 3H), 4.32 (dd, J=15.3, 5.1 Hz, 1H), 4.09 (d, J=11.3 Hz, 1H), 3.76-3.49 (m, 10H), 3.47-3.38 (m, 4H), 3.24-3.08 (m, 2H), 2.48 (dd, J=18.1, 8.1 Hz, 7H), 2.30-2.09 (m, 6H), 1.56 (dp, J=15.0, 8.0, 7.5 Hz, 9H), 1.33 (q, J=8.1, 7.1 Hz, 7H), 0.92 (s, 9H). ¹³C NMR (151 MHz, CDCl₃) δ 173.65, 171.96, 170.66, 158.39, 157.73, 156.32, 155.50, 153.91, 150.26, 148.44, 143.37, 138.04, 131.54, 130.94, 129.94, 129.49, 128.10, 124.00, 119.52, 119.04, 98.56, 71.30, 71.07, 70.54, 70.01, 69.96, 58.40, 57.45, 56.73, 43.23, 36.30, 35.82, 34.83, 29.47, 29.17, 26.39, 25.91, 25.69, 25.30, 16.04.

Compound 117

¹H NMR (500 MHz, Chloroform-d) δ 8.67 (s, 1H), 8.35 (s, 1H), 7.69-7.59 (m, 2H), 7.36 (dt, J=14.2, 7.9 Hz, 6H), 7.20-7.11 (m, 3H), 7.08 (d, 8.0 Hz, 2H), 6.22 (d, J=8.8 Hz, 1H), 5.64 (s, 2H), 4.81 (s, 1H), 4.72 (t, J=7.9 Hz, 1H), 4.60-4.50 (m, 3H), 4.33 (dd, J=14.9, 5.2 Hz, 1H), 4.12-4.01

(m, 1H), 3.61 (dd, J=11.3, 3.6 Hz, 1H), 3.38 (dt, J=13.3, 6.7 Hz, 7H), 3.16 (s, 2H), 2.62-2.40 (m, 8H), 2.23-2.04 (m, 5H), 1.57 (m, 12H), 1.36 (m, 9H), 0.93 (s, 9H). $^{13}$C NMR (151 MHz, CDCl$_3$) δ 173.61, 171.96, 170.64, 158.37, 157.75, 156.33, 155.38, 153.87, 150.28, 148.44, 143.36, 138.02, 131.54, 130.95, 129.93, 129.91, 129.50, 128.10, 123.98, 119.50, 119.04, 98.53, 77.22, 77.01, 76.88, 76.80, 70.81, 70.78, 70.75, 70.52, 69.95, 56.70, 43.24, 36.36, 35.80, 34.87, 29.65, 29.55, 29.33, 27.29, 26.40, 26.06, 25.83, 25.35, 22.80, 16.04, 16.04.

Compound 118

$^1$H NMR (500 MHz, Chloroform-d) δ 8.67 (s, 1H), 8.35 (s, 1H), 7.63 (d, J=6.8 Hz, 2H), 7.46 (d, J=6.2 Hz, 1H), 7.34 (td, J=23.6, 20.7, 12.0 Hz, 7H), 7.20-7.11 (m, 3H), 7.08 (d, J=7.6 Hz, 2H), 5.57 (s, 2H), 4.73 (t, J=7.4 Hz, 1H), 4.58-4.48 (m, 3H), 4.37-4.31 (m, 1H), 4.09-3.92 (m, 4H), 3.74-3.51 (m, 18H), 3.43 (t, J=5.6 Hz, 2H), 2.51 (s, 7H), 2.15 (d, J=9.2 Hz, 3H), 1.72-1.32 (m, 13H), 0.95 (s, 9H). $^{13}$C NMR (151 MHz, CDCl$_3$) δ 171.28, 170.78, 170.35, 158.48, 157.75, 156.26, 155.52, 150.26, 148.42, 138.15, 131.59, 130.86, 129.95, 129.90, 129.46, 128.10, 124.04, 119.55, 119.02, 98.54, 71.21, 71.13, 70.56, 70.54, 70.36, 70.03, 70.02, 58.44, 57.06, 56.69, 43.19, 35.95, 35.02, 29.41, 26.38, 25.83, 16.05.

Compound 119

$^1$H NMR (500 MHz, Chloroform-d) δ 8.67 (s, 1H), 8.35 (s, 1H), 7.64 (d, J=8.6 Hz, 2H), 7.44-7.29 (m, 6H), 7.15 (dd, J=18.8, 8.0 Hz, 3H), 7.08 (d, J=7.8 Hz, 2H), 6.23 (d, J=8.5 Hz, 1H), 5.61 (s, 2H), 4.79 (s, 1H), 4.73 (q, J=7.9, 7.5 Hz, 1H), 4.60-4.47 (m, 3H), 4.32 (dd, J=14.9, 5.2 Hz, 1H), 4.08 (d, J=11.3 Hz, 1H), 3.74-3.50 (m, 12H), 3.49-3.32 (m, 4H), 3.13 (s, 3H), 2.60-2.30 (m, 8H), 2.26-1.91 (m, 7H), 1.71-1.47 (m, 8H), 1.45-1.19 (m, 7H), 0.92 (s, 9H). $^{13}$C NMR (151 MHz, CDCl$_3$) δ 173.57, 171.98, 170.65, 158.33, 157.75, 156.35, 155.41, 153.86, 150.27, 148.44, 143.29, 138.03, 131.54, 130.95, 129.93, 129.49, 119.49, 119.05, 98.54, 71.35, 71.07, 70.58, 70.53, 70.02, 69.94, 58.42, 57.43, 56.72, 54.56, 52.85, 43.23, 36.32, 35.82, 34.86, 31.20, 29.53, 29.20, 27.32, 26.40, 25.98, 25.71, 25.32, 16.04.

Compound 120

$^1$H NMR (500 MHz, Chloroform-d) δ 8.66 (s, 1H), 8.34 (s, 1H), 7.63 (d, J=8.4 Hz, 2H), 7.44-7.29 (m, 6H), 7.19-7.10 (m, 3H), 7.07 (d, J=8.1 Hz, 2H), 6.25 (s, 1H), 5.59 (s, 2H), 4.72 (t, J=7.9 Hz, 1H), 4.61-4.48 (m, 3H), 4.32 (dd, J=14.9, 5.1 Hz, 1H), 4.08 (d, J=11.3 Hz, 1H), 3.84-3.48 (m, 18H), 3.42 (dt, J=14.3, 6.6 Hz, 4H), 2.51 (d, J=8.2 Hz, 7H), 2.22-2.08 (m, 4H), 1.72-1.51 (m, 8H), 1.46-1.28 (m, 8H), 0.92 (s, 9H). $^{13}$C NMR (151 MHz, CDCl$_3$) δ 173.58, 172.01, 170.64, 158.39, 157.74, 156.31, 155.56, 154.21, 150.26, 148.44, 143.36, 138.04, 131.54, 130.94, 129.94, 129.49, 128.10, 124.00, 119.52, 119.03, 98.53, 71.28, 71.07, 70.52, 70.05, 69.96, 58.39, 57.46, 56.70, 52.83, 43.23, 36.30, 35.82, 34.82, 29.68, 29.48, 29.18, 27.24, 26.41, 25.92, 25.70, 25.31, 16.04.

Compound 121

$^1$H NMR (500 MHz, Chloroform-d) δ 8.84 (d, J=8.4 Hz, 1H), 8.61 (s, 1H), 8.37 (s, 1H), 8.01-7.87 (m, 1H), 7.69 (t, J=8.0 Hz, 1H), 7.53 (d, J=7.3 Hz, 1H), 7.47-7.29 (m, 3H), 7.22 (s, 1H), 7.10 (d, J=8.0 Hz, 2H), 6.98 (d, J=8.4 Hz, 1H), 6.44 (d, J=16.8 Hz, 1H), 6.30 (dd, J=16.9, 10.3 Hz, 1H), 6.06 (s, 2H), 5.81 (d, J=10.3 Hz, 1H), 4.95 (s, 2H), 3.83-3.28 (m, 11H), 2.89-2.63 (m, 6H), 2.19-2.11 (m, 2H), 1.89 (s, 2H), 1.61 (s, 2H), 1.30-1.17 (m, 2H).

Compound 122

$^1$H NMR (500 MHz, Chloroform-d) δ 10.46 (s, 1H), 8.84 (d, J=8.4 Hz, 1H), 8.63 (s, 1H), 8.36 (s, 1H), 7.94 (s, 1H), 7.69 (dd, J=8.5, 7.3 Hz, 1H), 7.53 (d, J=7.3 Hz, 1H), 7.42 (dd, J=8.6, 7.3 Hz, 2H), 7.21 (d, J=7.4 Hz, 1H), 7.15-7.03 (m, 2H), 6.99 (d, J=8.4 Hz, 1H), 6.44 (dd, J=16.9, 1.2 Hz, 1H), 6.30 (dd, J=16.8, 10.2 Hz, 1H), 6.10 (s, 2H), 5.81 (dd, J=10.2, 1.3 Hz, 1H), 4.98 (dd, J=12.4, 5.3 Hz, 1H), 4.80 (s, 1H), 4.10 (s, 2H), 3.63 (dq, J=6.6, 3.6 Hz, 2H), 3.55-3.35 (m, 4H), 3.27 (s, 2H), 2.92-2.71 (m, 3H), 2.48 (s, 3H), 2.14 (dq, J=12.0, 4.2, 3.7 Hz, 1H), 1.70 (d, J=92.6 Hz, 8H). $^{13}$C NMR (151 MHz, CDCl$_3$) δ 171.71, 169.44, 168.51, 168.40, 166.85, 163.88, 157.87, 155.50, 154.09, 147.08, 136.67, 136.11, 131.39, 130.84, 130.19, 128.52, 125.15, 124.56, 121.40, 119.20, 118.66, 118.22, 116.21, 98.47, 72.04, 70.56, 70.43, 57.87, 52.26, 49.41, 31.65, 30.68, 27.74, 26.40, 26.14, 22.69.

Compound 123

$^1$H NMR (500 MHz, Chloroform-d) δ 8.67 (s, 1H), 8.63 (s, 1H), 8.35 (s, 1H), 7.95 (s, 1H), 7.50-7.39 (m, 3H), 7.35 (q, J=8.4 Hz, 5H), 7.24-7.19 (m, 2H), 7.10 (d, J=IN Hz, 2H), 6.98 (d, J=8.5 Hz, 1H), 6.45 (d, J=16.7 Hz, 1H), 6.30 (dd, J=16.9, 10.2 Hz, 1H), 6.05 (s, 2H), 5.82 (d, J=10.7 Hz, 1H), 4.86 (s, 1H), 4.74 (t, J=8.0 Hz, 1H), 4.60-4.49 (m, 3H), 4.35 (dd, J=15.0, 5.4 Hz, 1H), 4.11 (s, 1H), 4.05-3.96 (m, 2H), 3.76-3.55 (m, 10H), 3.45 (t, J=6.5 Hz, 2H), 2.51 (s, 6H), 2.16 (s, 2H), 1.43-1.23 (m, 12H), 0.95 (s, 9H). $^{13}$C NMR (151 MHz, CDCl$_3$) δ 171.36, 170.71, 170.55, 163.93, 157.87, 155.60, 155.52, 150.25, 148.44, 138.09, 131.58, 130.90, 130.79, 130.22, 129.48, 128.79, 128.63, 128.10, 124.72, 121.45, 119.31, 117.99, 98.50, 71.21, 71.08, 70.60, 70.53, 70.35, 70.07, 69.97, 58.44, 57.16, 56.69, 43.23, 35.90, 34.89, 31.91, 29.68, 29.35, 28.10, 26.38, 25.83, 22.68, 16.05, 14.12, 1.01.

Compound 124

$^1$H NMR (500 MHz, Chloroform-d) δ 8.67 (s, 1H), 8.62 (s, 1H), 8.35 (s, 1H), 7.96 (s, 1H), 7.41 (dd, J=29.6, 23.3 Hz, 8H), 7.22 (s, 2H), 7.09 (s, 2H), 6.98 (d, J=8.1 Hz, 1H), 6.45 (d, J=16.9 Hz, 1H), 6.37-6.26 (m, 2H), 6.09 (s, 2H), 5.82 (d, J=10.1 Hz, 1H), 4.84 (s, 1H), 4.73 (t, J=7.3 Hz, 1H), 4.59-4.47 (m, 3H), 4.35 (d, J=17.9 Hz, 1H), 4.09 (d, J=11.0 Hz, 1H), 3.91 (q, J=15.4 Hz, 2H), 3.61 (d, J=10.9 Hz, 1H), 3.49 (d, J=7.0 Hz, 2H), 3.46-3.35 (m, 4H), 3.19 (s, 2H), 2.49 (d, J=20.0 Hz, 7H), 2.10 (d, J=20.1 Hz, 4H), 1.63 (s, 8H), 1.44-1.32 (m, 6H), 0.95 (s, 9H). $^{13}$C NMR (151 MHz, CDCl$_3$) δ 171.31, 170.66, 170.50, 163.92, 157.87, 155.57, 154.12, 150.27, 148.43, 147.17, 143.24, 138.06, 131.57, 130.91, 130.80, 130.20, 129.48, 128.77, 128.59, 128.12, 124.79, 124.66, 121.47, 119.25, 118.05, 98.48, 71.83, 70.76, 70.57, 70.06, 69.87, 58.44, 58.27, 56.92, 56.62, 52.49, 43.24, 35.86, 34.90, 29.60, 29.41, 29.24, 27.20, 26.36, 26.07, 22.74, 16.04.

Compound 125

$^1$H NMR (500 MHz, Chloroform-d) δ 8.67 (s, 1H), 8.63 (s, 1H), 8.35 (s, 1H), 7.95 (s, 1H), 7.54-7.40 (m, 2H), 7.34 (q, J=8.1 Hz, 2H), 7.22 (d, J=1.2 Hz, 1H), 7.17-7.05 (m, 2H), 6.98 (d, J=8.6 Hz, 1H), 6.44 (d, J=16.8 Hz, 1H), 6.34-6.25 (m, 1H), 6.05 (s, 1H), 5.83 (d, J=10.3 Hz, 1H), 4.73-4.64 (m, 1H), 4.62-4.50 (m, 2H), 4.36 (d, J=19.9 Hz, 1H), 4.08 (d, J=8.1 Hz, 1H), 3.99 (d, J=15.6 Hz, 1H), 3.76-3.48 (m, 9H), 3.21-3.13 (m, 1H), 2.48 (d, J=28.1 Hz, 3H), 1.32-1.19 (m, 9H), 0.97 (s, 6H), 0.92-0.80 (m, 7H).

Compound 126

$^1$H NMR (500 MHz, Chloroform-d) δ 8.66 (s, 1H), 8.62 (s, 1H), 8.34 (s, 1H), 7.96 (s, 1H), 7.54-7.38 (m, 3H), 7.33 (s, 3H), 7.25-7.16 (m, 2H), 7.10 (d, J=7.9 Hz, 2H), 6.98 (d, J=8.5 Hz, 1H), 6.45 (d, J=16.9 Hz, 1H), 6.31 (dd, J=16.9, 10.2 Hz, 2H), 6.06 (s, 2H), 5.83 (d, J=10.4 Hz, 1H), 4.71 (t, J=8.1 Hz, 1H), 4.58-4.53 (m, 1H), 4.47 (d, J=12.9 Hz, 1H), 4.38 (d, J=18.0 Hz, 1H), 4.19-3.96 (m, 4H), 3.78-3.52 (m, 14H), 3.50-3.38 (m, 3H), 3.16 (d, J=7.5 Hz, 1H), 2.49 (s, 4H), 1.46 (d, J=6.0 Hz, 4H), 1.26 (s, 9H), 0.99 (s, 6H), 0.93-0.79 (m, 6H).

Compound 127

$^1$H NMR (500 MHz, Chloroform-d) δ 8.66 (s, 1H), 8.34 (s, 1H), 7.75 (d, J=7.6 Hz, 1H), 7.64 (d, J=8.5 Hz, 2H), 7.50 (t, J=7.5 Hz, 1H), 7.44-7.33 (m, 4H), 7.33-7.26 (m, 2H), 7.15 (dd, J=17.5, 8.0 Hz, 3H), 7.08 (d, J=8.4 Hz, 2H), 6.95 (d, J=7.7 Hz, 1H), 6.87 (s, 1H), 5.55 (s, 2H), 4.84-4.68 (m, 3H), 4.62 (t, J=7.8 Hz, 1H), 4.58-4.28 (m, 5H), 4.05 (t, J=6.3 Hz, 2H), 3.67 (dd, J=11.3, 3.5 Hz, 1H), 3.50 (t, J=6.3 Hz, 2H), 3.46-3.38 (m, 2H), 3.15-2.98 (m, 2H), 2.52 (s, 3H), 2.51-2.30 (m, 5H), 2.25-1.88 (m, 8H), 1.85-1.74 (m, 2H), 0.88 (dd, J=18.6, 6.5 Hz, 6H). $^{13}$C NMR (151 MHz, CDCl$_3$) δ 170.62, 170.32, 169.48, 158.50, 157.89, 157.00, 156.50, 155.60, 153.97, 150.39, 148.58, 143.44, 142.19, 132.36, 132.36, 131.97, 131.82, 131.75, 130.08, 129.59, 128.16, 128.07, 126.39, 124.12, 123.89, 122.96, 121.60, 119.65, 119.20, 112.09, 98.71, 70.88, 70.54, 69.92, 68.02, 58.72, 58.71, 58.28, 56.07, 52.91, 47.53, 39.20, 36.21, 31.37, 29.83, 28.97, 27.85, 26.61, 26.31, 23.99, 19.19, 19.13, 16.27.

Compound 128

$^1$H NMR (400 MHz, DMSO-d6) δ 8.91 (s, 1H), 8.33 (t, J=5.5 Hz, 1H), 8.22 (s, 1H), 7.68 (d, J=7.5 Hz, 1H), 7.63-7.52 (m, 4H), 7.50-7.43 (m, 1H), 7.43-7.34 (m, 2H), 7.31 (d, J=7.6 Hz, 1H), 7.17-7.11 (m, 1H), 7.07 (dd, J=11.4, 8.4 Hz, 4H), 6.98-6.90 (m, 2H), 5.05 (d, J=3.9 Hz, 1H), 4.98-4.87 (m, 1H), 4.68 (d, J=10.8 Hz, 1H), 4.59-4.16 (m, 7H), 4.06 (t, J=5.6 Hz, 2H), 4.04-3.94 (m, 1H), 3.80-3.60 (m, 4H), 3.57 (t, J=6.0 Hz, 2H), 3.20 (t, J=12.5 Hz, 1H), 2.82-2.53 (m, 3H), 2.40 (s, 3H), 2.33-2.23 (m, 1H), 2.16-1.76 (m, 8H), 0.92 (d, J=6.3 Hz, 3H), 0.69 (d, J=6.3 Hz, 3H). $^{13}$C NMR (151 MHz, DMSO) δ 171.50, 168.79, 168.08, 167.46, 158.17, 157.01, 156.30, 155.88, 155.52, 153.62, 151.37, 147.85, 143.01, 142.19, 131.56, 131.37, 131.26, 130.99, 130.11, 130.00, 128.02, 127.89, 127.79, 127.00, 123.75, 123.60, 123.00, 120.82, 118.96, 118.91, 111.66, 97.42, 68.62, 66.75, 66.69, 64.81, 58.69, 57.78, 55.42, 53.33, 46.81, 44.11, 38.10, 37.06, 32.68, 31.52, 30.90, 29.05, 28.39, 18.87, 18.62, 15.98.

Compound 129

$^1$H NMR (600 MHz, DMSO-d6) δ 8.96 (s, 1H), 8.60 (t, J=6.0 Hz, 1H), 8.23 (s, 1H), 7.65 (d, J=8.4 Hz, 2H), 7.48-7.34 (m, 7H), 7.18 (t, J=7.4 Hz, 1H), 7.16-7.07 (m, 4H), 5.16 (d, 1H), 4.63 (bs, 1H), 4.57 (d, J=9.6 Hz, 1H), 4.44 (t, J=8.2 Hz, 1H), 4.40-4.32 (m, 2H), 4.23 (dd, J=15.8, 5.6 Hz, 1H), 3.98 (s, 2H), 3.72-3.50 (m, 8H), 3.01 (bs, 2H), 2.56 (bs, 2H), 2.43 (s, 3H), 2.26-2.11 (m, 4H), 2.10-1.98 (m, 1H), 1.94-1.78 (m, 3H), 0.95 (s, 9H). $^{13}$C NMR (151 MHz, DMSO) δ 171.76, 169.10, 168.57, 158.15, 157.03, 156.29, 155.42, 153.60, 151.42, 147.72, 142.77, 139.42, 131.13, 130.13, 130.01, 129.67, 128.68, 128.11, 127.43, 123.79, 118.99, 118.94, 97.44, 70.51, 69.59, 69.46, 68.88, 58.74, 56.99, 56.58, 55.67, 54.93, 52.72, 52.66, 41.67, 37.90, 35.75, 30.99, 26.19, 15.93.

Compound 130

$^1$H NMR (400 MHz, DMSO-d6) δ 10.35 (s, 1H), 8.30 (s, 1H), 8.22 (s, 1H), 8.06 (dd, J=8.3, 1.9 Hz, 1H), 7.88 (d, J=8.2 Hz, 1H), 7.64 (d, J=8.2 Hz, 2H), 7.42 (t, J=7.8 Hz, 2H), 7.15 (dt, J=21.3, 8.0 Hz, 5H), 5.18 (dd, J=13.1, 5.3 Hz, 1H), 4.73-4.54 (m, 1H), 4.19 (s, 2H), 3.82-3.68 (m, 1H), 3.67-3.60 (m, 2H), 3.57 (t, J=5.9 Hz, 2H), 3.00 (s, 3H), 2.99-2.86 (m, 2H), 2.75 (dt, J=17.1, 3.5 Hz, 1H), 2.62-2.46 (m, 4H), 2.26-2.10 (m, 4H), 2.08-1.99 (m, 1H), 1.93-1.79 (m, 2H). $^{13}$C NMR (126 MHz, DMSO) δ 171.73, 169.61, 169.56, 166.95, 166.71, 158.14, 157.05, 156.29, 155.41, 153.60, 144.34, 142.75, 132.64, 130.12, 130.00, 128.12, 125.28, 124.59, 124.30, 123.79, 118.99, 118.95, 113.65, 97.44, 70.45, 70.33, 69.58, 68.51, 56.99, 53.88, 52.70, 49.57, 31.12, 30.99, 26.62, 21.23.

Compound 131

$^1$H NMR (400 MHz, DMSO-d6) δ 11.11 (bs, 1H), 8.22 (s, 1H), 7.80 (d, J=8.3 Hz, 1H), 7.65 (d, J=8.4 Hz, 2H), 7.50-7.30 (m, 4H), 7.15 (dt, J=23.0, 7.7 Hz, 5H), 5.10 (dd, J=12.9, 5.3 Hz, 1H), 4.72-4.62 (m, 1H), 4.39-4.23 (m, 2H), 3.86-3.74 (m, 2H), 3.70-3.45 (m, 6H), 3.14-3.00 (m, 1H), 2.93-2.81 (m, 1H), 2.73-2.50 (m, 4H), 2.37-2.14 (m, 4H), 2.07-1.98 (m, 1H), 1.96-1.82 (m, 2H). $^{13}$C NMR (151 MHz, DMSO) δ 172.76, 169.92, 166.84, 166.77, 163.94, 158.15, 157.05, 156.27, 155.43, 153.61, 142.79, 133.89, 130.12, 130.00, 128.10, 125.24, 123.79, 123.03, 120.90, 119.00, 118.93, 108.87, 97.44, 73.80, 69.94, 69.71, 68.66, 68.48, 68.46, 56.99, 53.79, 52.65, 48.96, 30.96, 22.08.

Compound 135

$^1$H NMR (400 MHz, DMSO-d6) δ 10.93 (s, 1H), 8.19 (s, 1H), 7.61 (d, J=8.6 Hz, 2H), 7.56 (d, J=8.4 Hz, 1H), 7.39 (t, J=8.0 Hz, 2H), 7.21-7.05 (m, 6H), 7.04-6.97 (m, 1H), 5.02 (dd, J=13.3, 4.9 Hz, 1H), 4.69-4.52 (m, 1H), 4.40-4.07 (m, 4H), 3.84-3.68 (m, 2H), 3.63-3.43 (m, 6H), 3.06-2.92 (m, 2H), 2.92-2.77 (m, 1H), 2.67-2.46 (m, 3H), 2.39-2.23 (m, 1H), 2.25-2.04 (m, 4H), 2.00-1.74 (m, 3H). $^{13}$C NMR (151 MHz, DMSO) δ 172.89, 171.15, 167.89, 161.67, 158.15, 157.05, 156.28, 155.44, 153.62, 144.40, 142.79, 130.13, 130.01, 128.10, 124.31, 124.18, 123.80, 119.00, 118.94, 115.40, 108.63, 97.45, 69.93, 69.72, 68.79, 68.52, 67.72, 57.02, 53.88, 52.67, 51.50, 46.96, 31.25, 30.97, 22.52.

2. Biology

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure but should not be seen as limiting the present disclosure in any way.

Assays and Degradation Data i. Culturing of Immortalized Cell Lines and Primary Patient Cells NAMALWA and Jurkat cell lines were purchased from ATCC and cultured according to supplier guidelines at 37° C. 5% CO$_2$ in RPMI 1640 (Gibco) supplemented with 10% fetal bovine serum and 1× penicillin-streptomycin. Wild-type and C481S BTK XLA cell lines were cultured as previously described (39). Written, informed consent was obtained prior to the collection of cells from CLL patients using the IWCLL2008 criteria. Isolation of mononuclear cells from peripheral blood was prepared using density gradient centrifugation. B-cells were then negatively selected (STEMCELL Technologies). Cells were then cultured at 1×10$^7$ cells/mL in RPMI 1640 (Gibco) with supplementation of 10% fetal bovine serum (VWR), 100 μg/mL streptomycin (Gibco), 100 U/mL penicillin-G (Gibco), and 2 mmol/L L-glutamine (Gibco). They were maintained at 37° C. in 5% CO$_2$.

ii. Cell Treatment and Immunoblotting

In various embodiments, treatment with PROTAC was performed in one of two ways: 1) For experiments involving >16 h exposure to compound, a 1000× stock was added to cells followed by gentle agitation; 2) For shorter treatments, a 2× stock was added to an equal volume of cells to ensure uniform drug exposure. For immortalized cell lines, 2×10⁶ cells per treatment condition were collected and washed once with ice cold PBS (IX), followed by lysis in buffer containing 20 mM Tris [pH 8.0], 0.25% sodium deoxycholate, 1% Triton X-100, supplemented with protease (Roche) and phosphatase inhibitors (10 mM NaF, 2 mM $Na_3VO_4$, 10 mM β-glycerophosphate, 10 mM Na-pyrophosphate). Lysates were spun at 15,000×g for 10 min at 4° C. and supernatant was quantified for total protein content using the Pierce BCA Protein Assay (Thermo Fisher Scientific). 30 µg of protein was loaded onto 12% SDS-PAGE gels or 4-15% Mini-PROTEAN TGX precast gradient gels (Bio-Rad), transferred onto nitrocellulose membranes, and probed with the specified primary antibodies overnight with rocking at 4° C. in 1×TBS-T containing 5% non-fat milk.

Either anti-rabbit or anti-mouse HRP-conjugated secondary antibodies (Pierce) were incubated with the membranes for 1 h at room temperature at 1:10,000 dilutions in 5% non-fat milk in IX TBS-T. Imaging was performed using the ECL Prime chemiluminescent western blot detection reagents (Amersham) followed by visualization with the Bio-Rad ChemiDoc imaging instrument. All western blots were subsequently processed and quantified using the accompanying Bio-Rad Image Lab software. Primary antibodies used were: Anti-actin antibody (Cat. #MA 1-744) purchased from ThermoFisher Scientific; anti-BTK (Cat. #8547), anti-pBTK (Y223, Cat. #5082), anti-ITK (Cat. #2380), anti-GAPDH (Cat. #5179), anti-IKZF1 (Cat. #9034), and anti-IKZF3 (Cat. #15103) antibodies purchased from Cell Signaling Technology. All antibodies were used at 1:1,000 dilutions in 5% non-fat milk in 1×TBS-Tween (TBS-T) or Blotto blocker (Thermo Scientific) unless otherwise noted in supplier specifications.

Primary patient cells studied in dose response experiments were treated at densities of 1×10⁷ cells plated for 24 hours per condition. Time course studies were completed by plating cells at 24 hours prior to lysis, with the addition of Compound 102 at 24 hours, 12 hours, 4 hours, 2 hours, and 1 hour before lysis. The baseline and relapse patient sample was collected from ACD cryovials, thawed, and cells were plated with 1 µM Compound 102 at 24 hours before lysis and 1 µM ibrutinib 2 hours before lysis (followed by a 1 hour media washout to simulate in vivo reversible binding). All primary patient samples were stimulated with anti-IgM (Jackson ImmunoResearch) 15 minutes prior to lysis.

Cell lysates were prepared as previously described (40). The cell suspension was kept on ice and agitated every 10 minutes for 30 minutes, followed by centrifugation for 10 minutes at 4° C. The supernatant was then collected and frozen at −80° C. until quantification. Protein quantification was performed for each supernatant using the BCA method (Thermo Scientific). Protein from each sample was added to 2× or 6× Laemmli's Sample buffer as previously described (41). 50 µg of each sample and a protein molecular weight marker were loaded onto 10% polyacrylamide gels and electrophoresed. Transfer of the proteins and blocking of membranes were performed as previously described (40).

Proteins were detected using the antibodies described above: anti-phospho-BTK (Abcam, Cat. #ab68217), anti-BTK (Cell Signaling Technologies, Cat. #8547), anti-GAPDH (Cell Signaling Technologies, Cat. #5179). Antibodies used were diluted 1:1,000 in Blotto blocker (Thermo Scientific) and kept at 4° C. with constant agitation for 12 to 72 hours. The blots were washed with TBS-T (Tris-buffered saline-0.05% Tween) three times for 10 minutes with constant agitation, then incubated with HRP-conjugated anti-rabbit or anti-mouse IgG (Santa Cruz Biotechnologies) diluted 1:5,000 in Blotto for 2 hours at 4° C. with constant agitation. Prior to development, the blots were again washed with TBS-T three times for 10 minutes with constant agitation. Blots were developed using chemiluminescent substrate (WesternBright by Advansta or SuperSignal by ThermoScientific) and X-ray film (GeneMate) was used to perform autoradiography. Quantification was performed on the protein bands using computer densitometry (AlphaView software).

iii. Chemical Reagents and Synthesis of PROTACs

Ibrutinib for cellular and kinase inhibition assays was purchased as a 10 mM stock solution in DMSO from Selleckchem. BTK PROTACs were synthesized as described herein.

The following PROTACs demonstrated target protein degradation when tested under the conditions described above:

TABLE 5

Target protein degradation for Exemplary PROTACs

| Compound No. | Physical Data | Linker Length (atoms) | $DC_{50}$ | Max | $R^2$ of Fit | HER3 Degradation |
|---|---|---|---|---|---|---|
| 100 | Chemical Formula: $C_{39}H_{37}N_9O_7$<br>Molecular Weight: 743.78 | 5 | No Degradation (n = 4) | | | No |
| 101 | Chemical Formula: $C_{41}H_{41}N_9O_8$<br>Molecular Weight: 787.83 | 8 | No Degradation | | | No |
| 102 | Chemical Formula: $C_{41}H_{41}N_9O_8$<br>Molecular Weight: 787.83 | 8 | 9.1 nM | >99% at 250 nM (No hook up to 2.5 µM) | 0.79 | No |
| 103 | Chemical Formula: $C_{44}H_{47}N_9O_8$<br>Molecular Weight: 829.92 | 11 | 68.3 nM | 95% at 1.0 µM | 0.96 | No |
| 104 | Chemical Formula: $C_{45}H_{49}N_9O_8$<br>Molecular Weight: 843.94 | 12 | 80.6 nM | 96% at 1.0 µM | 0.97 | No |
| 105 | Chemical Formula: $C_{45}H_{49}N_9O_8$<br>Molecular Weight: 843.94 | 12 | 11.6 nM | >99% at 250 nM (No hook up to 2.5 µM) | 0.96 | No |

TABLE 5-continued

Target protein degradation for Exemplary PROTACs

| Compound No. | Physical Data | Linker Length (atoms) | $DC_{50}$ | Max | $R^2$ of Fit | HER3 Degradation |
|---|---|---|---|---|---|---|
| 106 | Chemical Formula: $C_{45}H_{49}N_9O_8$<br>Molecular Weight: 843.94 | 12 | 90.1 nM | 93% at 1.0 μM | 0.98 | No |
| 107 | Chemical Formula: $C_{49}H_{57}N_9O_8$<br>Molecular Weight: 900.05 | 16 | 98.5 nM | 98% at 1.0 μM | 0.97 | No |
| 109 | Chemical Formula: $C_{54}H_{68}N_{10}O_9S$<br>Exact Mass: 1032.49<br>tPSA: 226.83<br>CLogP: 5.55705 | 14 | 278.0 nM | 73% at 2.5 μM | 0.94 | No |
| 110 | Chemical Formula: $C_{56}H_{72}N_{10}O_8S$<br>Exact Mass: 1044.53<br>tPSA: 217.6<br>CLogP: 6.92405 | 15 | | No Degradation | | No |
| 111 | Chemical Formula: $C_{57}H_{74}N_{10}O_7S$<br>Molecular Weight: 1043.34<br>tPSA: 208.37<br>CLogP: 7.98025 | 15 | 144.1 nM | 45% at 1.0 μM | 0.88 | No |
| 112 | Chemical Formula: $C_{58}H_{76}N_{10}O_7S$<br>Molecular Weight: 1057.37 | 16 | | No Degradation | | No |
| 113 | Chemical Formula: $C_{56}H_{72}N_{10}O_9S$<br>Molecular Weight: 1061.31<br>tPSA: 226.83<br>CLogP: 5.69044 | 16 | 124.3 nM | 60% at 1.0 μM | 0.66 | No |
| 114 | Chemical Formula: $C_{59}H_{77}N_{11}O_9S$<br>Exact Mass: 1115.56<br>tPSA: 230.07<br>CLogP: 5.35504 | 18* | 248.3 nM | 30% at 1.0 μM | 0.64 | No |
| 115 | Chemical Formula: $C_{58}H_{76}N_{10}O_9S$<br>Exact Mass: 1088.55<br>Melting Point:<br>tPSA: 226.83<br>CLogP: 6.74845 | 18 | 230.8 nM | 32% at 1.0 μM | 0.44 | No |
| 116 | Chemical Formula: $C_{60}H_{80}N_{10}O_8S$<br>Molecular Weight: 1101.42 | 19 | | No Degradation | | No |
| 117 | Chemical Formula: $C_{61}H_{82}N_{10}O_7S$<br>Molecular Weight: 1099.43 | 19 | | No Degradation | | No |
| 118 | Chemical Formula: $C_{60}H_{80}N_{10}O_{10}S$<br>Exact Mass: 1132.58<br>Melting Point:<br>tPSA: 236.06<br>CLogP: 6.57285 | 21 | 230.9 nM | 40% at 1.0 μM | 0.59 | No |
| 119 | Chemical Formula: $C_{62}H_{84}N_{10}O_9S$<br>Molecular Weight: 1145.48 | 22 | | No Degradation | | No |
| 120 | Chemical Formula: $C_{64}H_{88}N_{10}O_{10}S$<br>Molecular Weight: 1189.53 | 25 | | No Degradation | | No |
| 121 | Chemical Formula: $C_{47}H_{50}N_{10}O_9$<br>Molecular Weight: 898.98 | 11 | | No Degradation | | No |
| 122 | Chemical Formula: $C_{48}H_{52}N_{10}O_9$<br>Molecular Weight: 913.01 | 12 | | No Degradation | | No |
| 123 | Chemical Formula: $C_{59}H_{75}N_{11}O_9S$<br>Molecular Weight: 1114.38<br>tPSA: 246.7<br>CLogP: 5.60805 | 15 | | Not Tested | | No |
| 124 | Chemical Formula: $C_{60}H_{77}N_{11}O_8S$<br>Molecular Weight: 1112.41<br>tPSA: 237.47<br>CLogP: 6.66425 | 15 | | Not Tested | | No |
| 125 | Chemical Formula: $C_{61}H_{79}N_{11}O_{10}S$<br>Molecular Weight: 1158.43<br>tPSA: 255.93<br>CLogP: 5.43245 | 18 | | Not Tested | | No |
| 126 | Chemical Formula: $C_{63}H_{83}N_{11}O_{11}S$<br>Molecular Weight: 1202.48<br>tPSA: 265.16<br>CLogP: 5.25685 | 21 | | Not Tested | | No |
| 127 | Chemical Formula: $C_{59}H_{68}N_{10}O_7S$<br>Molecular Weight: 1061.32<br>tPSA: 199.58 | 10 | 162 nM | 50% | | |
| 129 | Chemical Formula: $C_{49}H_{58}N_{10}O_7S$<br>Molecular Weight: 931.13<br>tPSA: 208.37 | 8 | 374.4 nM | 49% at 2.5 μM | 0.76 | |
| 131 | Chemical Formula: $C_{41}H_{42}N_8O_8$<br>Molecular Weight: 774.84<br>Log P: 2.9<br>tPSA: 190.05 | 9 | 13 nM | >99% | | |

TABLE 5-continued

Target protein degradation for Exemplary PROTACs

| Compound No. | Physical Data | Linker Length (atoms) | $DC_{50}$ | Max | $R^2$ of Fit | HER3 Degradation |
|---|---|---|---|---|---|---|
| 135 | Chemical Formula: $C_{41}H_{44}N_8O_7$ Molecular Weight: 760.85 tPSA: 172.98 | 9 | 7 nM | >99% | | |
| | Negative Control: Non-Covalent Ibrutinib Scaffold with Linker | 14 | No Degradation | | | Not Tested |

Results i. Discovery of Potent BTK-Targeting PROTACs

BTK-targeting PROTACs, Compound 104 and Compound 106, possessed 12-atom linkers and showed nearly complete degradation of BTK at 1.0 µM in NAMALWA cells, a Burkitt's lymphoma-derived B-lymphocyte cell line (Table 5). Shortening the linker by a single atom (Compound 103) increased potency, based on the concentration of compound needed to degrade 50% of the total pool of BTK, denoted by DC50 (DC=degradation constant). However, shortening the linker length even further to 8- and 5-atoms (Compound 101 and Compound 100, respectively) resulted in an inability to degrade BTK. Without being bound by theory, these observations are consistent with the expected ternary complex model that plays a role in PROTAC action. In this model, short linkers are expected to be insufficient to bridge BTK and cereblon, and thus cannot induce the complex formation necessary for ubiquitination.

Figure 2A:
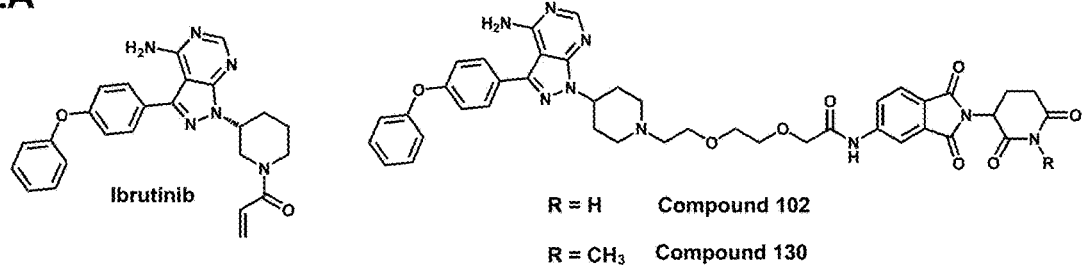
FIG. 2A shows chemical structures of ibrutinib, active PROTAC Compound 102, and inactive control compound, Compound 130.
Figure 6A:
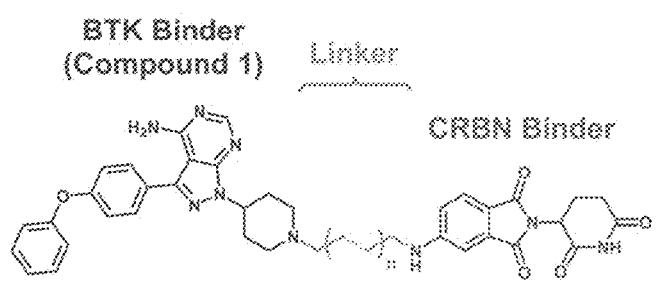
FIG. 6A illustrates a general structure of a BTK PROTAC with a linker connected at the 5-position of the cereblon (CRBN) binding element.
Figure 6B:
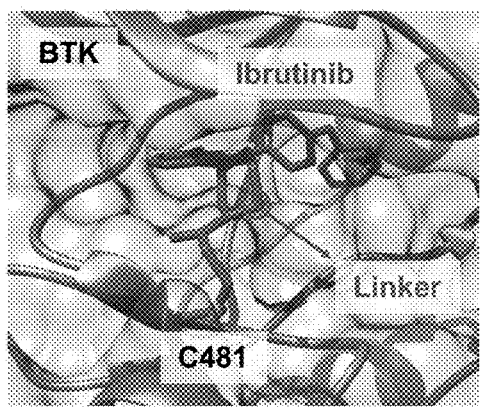
FIG. 6B illustrates molecular modeling based upon the co-crystal structure of BTK and ibrutinib (PDB: 5P9J), and identification of a solvent-exposed linker attachment site (highlighted in red with arrow and circle).
Figure 6C:
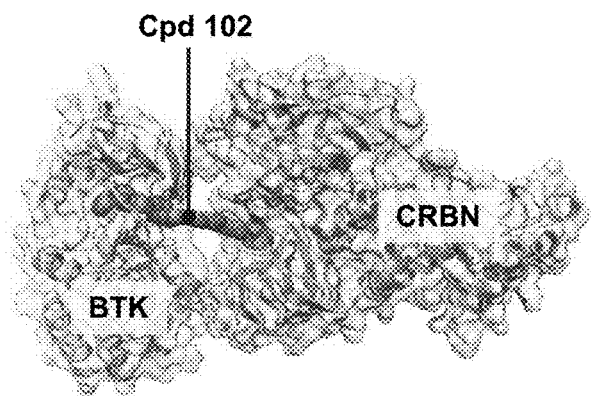
FIG. 6C illustrates molecular modeling of the ternary complex between Compound 102 (green), BTK (purple, left-hand protein), and cereblon (CRBN) (gray, right-hand protein) by docking the respective binding elements into the corresponding pockets of the proteins.
Figure 6D:
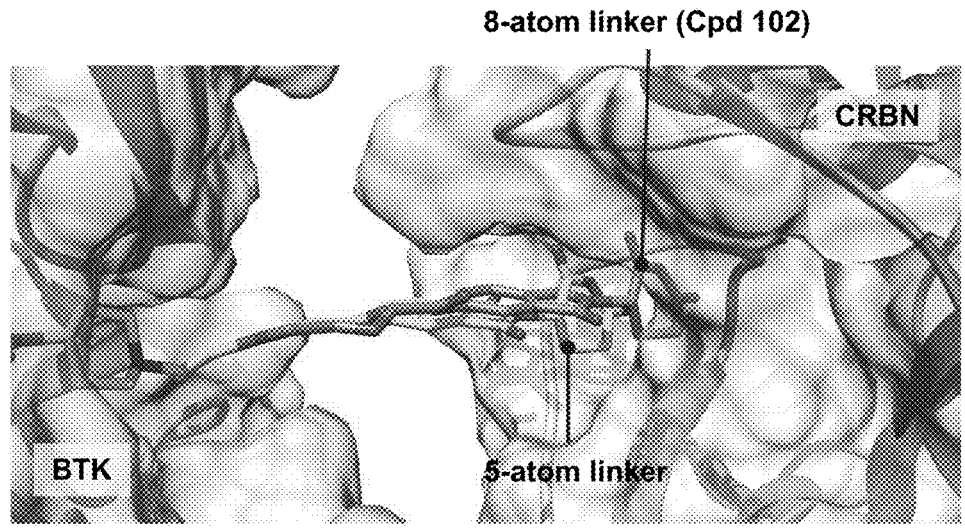
FIG. 6D illustrates that shortening the linker of Compound 102 (green) to 5 atoms (yellow) results in an inability to bridge the binding pockets of BTK (purple, left-hand protein) and cereblon (CRBN) (gray, right-hand protein) without inducing clashes and may explain the poor degradation observed experimentally with shorter linkers.
Figure 7A:
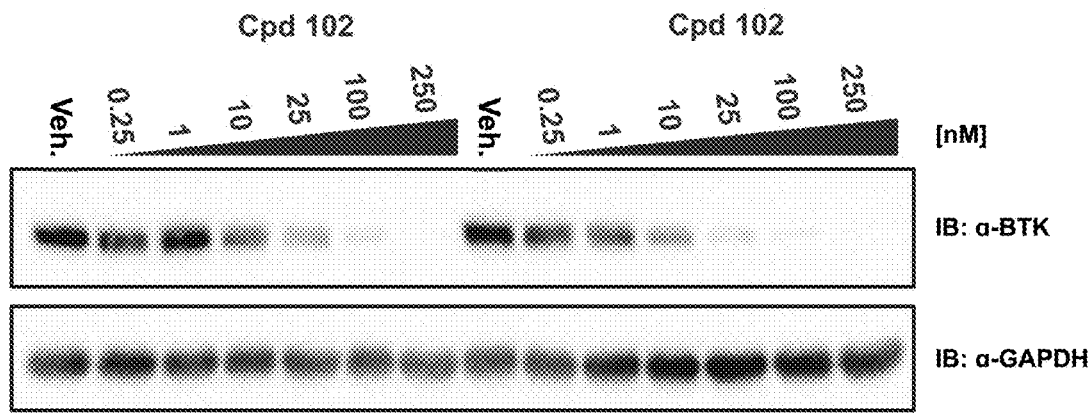
FIGS. 7A and 7B illustrate experiments where NAMALWA cells were subjected to increasing concentrations of Compound 102 for 24 h without observation of a "hook-effect".
Figure 7B:
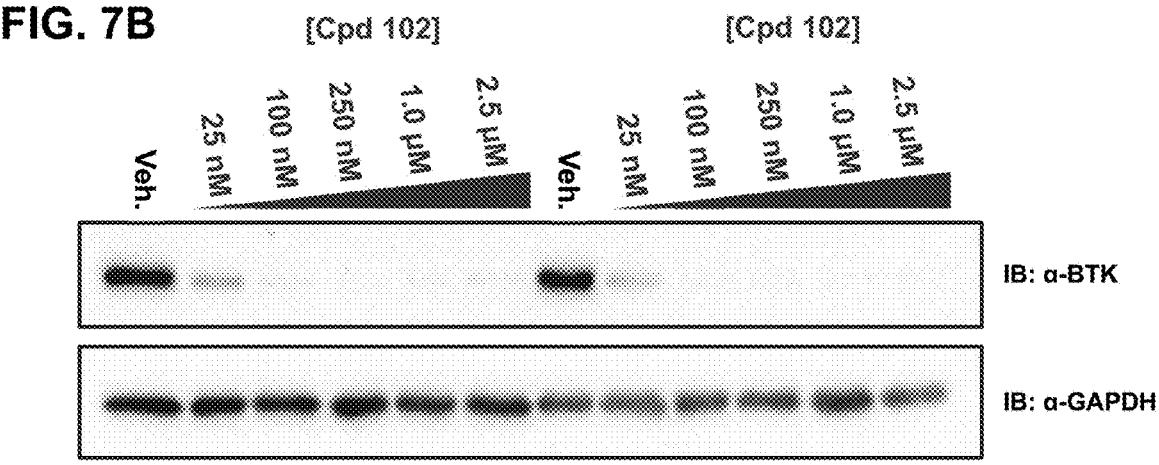
Figure 7C:
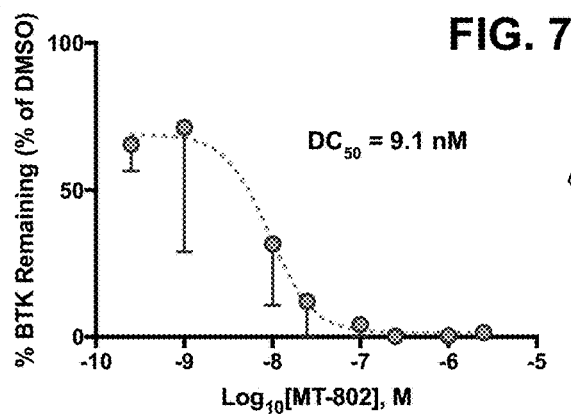
FIG. 7C illustrates a plot of the concentration required to deplete half of the total pool of BTK, which was 9.1 nM with full degradation observed after 100 nM. No "hook-effect" (increase in target protein levels at high [PROTAC] due to saturation of unproductive binary complexes) was observed at concentrations of up to 2.5 µM Compound 102.
Figure 7D:
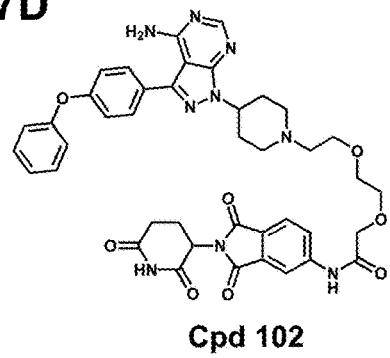
FIG. 7D is the structure of Compound 102.

Compound 102 was eventually identified as being particularly potent, having an 8-atom linker at the 5-position on the phthalimide ring (FIG. 2A). Interestingly, an increase in potency was also observed when the 12-atom linker was placed at the 5-position (Compound 105), indicating that this vector may be generally more favorable for inducing a cereblon-BTK ternary complex. Docking of Compound 102 into the crystal structures of BTK and cereblon showed that the 8-atom linker was the minimal length needed to bridge the two binding sites (FIG. 6C) and shorter linkers would be unable to bridge the gap without inducing clashes, which is consistent with experimental observations (FIG. 6D).

ii. Compound 102 is a Potent and Rapid Degrader of BTK

Figure 2B:
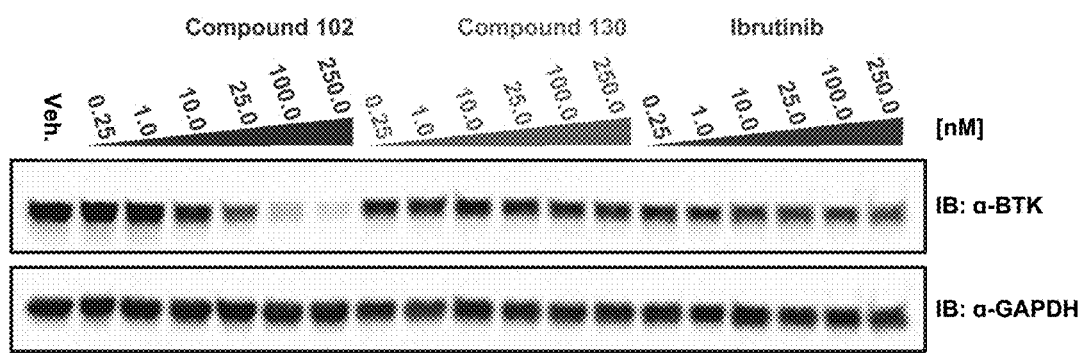
FIG. 2B illustrates BTK levels in response to dose escalations of Compound 102, Compound 130, and ibrutinib in NAMALWA cell line after 24 h treatment.

In initial characterization experiments, it was shown that Compound 102 degrades BTK with a $DC_{50}$ of 9.1 nM with complete degradation being observed at 250 nM. Since PROTACs work via a ternary complex driven mechanism, a common observation for many PROTACs is the "hook-effect", whereby the binary species (BTK:PROTAC and PROTAC:cereblon) predominate over the active ternary complex at sufficiently high concentrations, thereby resulting in reduced degradation. However, no significant increases in BTK levels (i.e. a "hook") were observed in cells treated with up to 2.5 µM Compound 102 (FIG. 7). PROTACs inducing ternary complexes with significant positive cooperativity would be expected to have a width expansion of their maximal effect, diminishing the effects of the unproductive binary complexes over a wider concentration window (44). The lack of an observable hook-effect suggests that Compound 102 induces a high affinity ternary complex with significant positive cooperativity. Compound 130, an inactive version of Compound 102 that is incapable of binding to cereblon due to methylation on the glutarimide ring of pomalidomide was also synthesized (FIG. 2A). As expected, neither ibrutinib nor Compound 130 were able to induce degradation of BTK (FIG. 2B), demonstrating that binding to cereblon is required for Compound 102's mechanism of action.

Figure 2C:
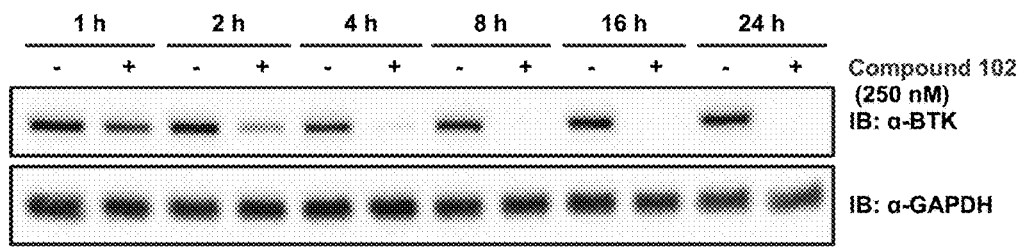
FIG. 2C illustrates the time course of BTK degradation with 250 nM Compound 102 in NAMALWA cells. Each time point was matched with a DMSO (vehicle) treated condition.
Figure 2D:
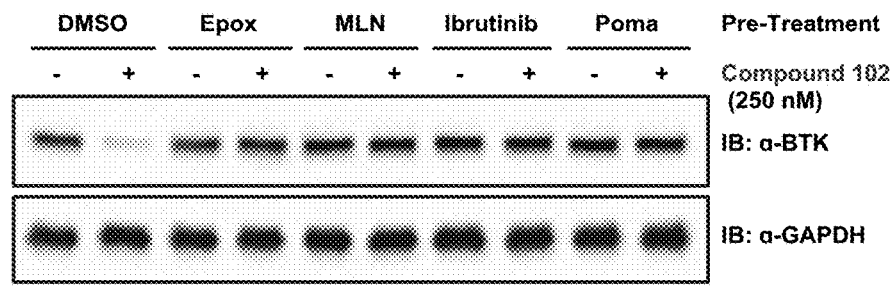
FIG. 2D shows NAMALWA cells that were pre-treated with DMSO, epoxomicin (1 µM), MLN-4924 (1 µM), ibrutinib (25 µM), and pomalidomide (25 µM) for 2.5 h before treatment with DMSO (vehicle) or 250 nM Compound 102 for 4 h.
Figure 8A:
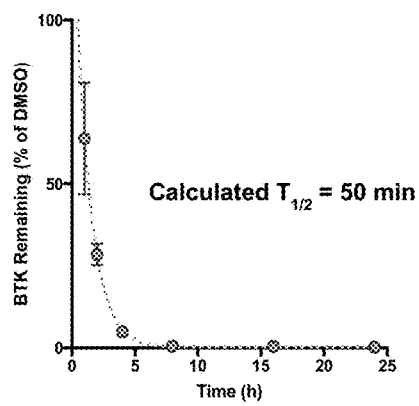
FIG. 8A illustrates the corresponding quantification of the immunoblotting in FIG. 1C. Half-life was calculated from an exponential fit.
Figure 8B:
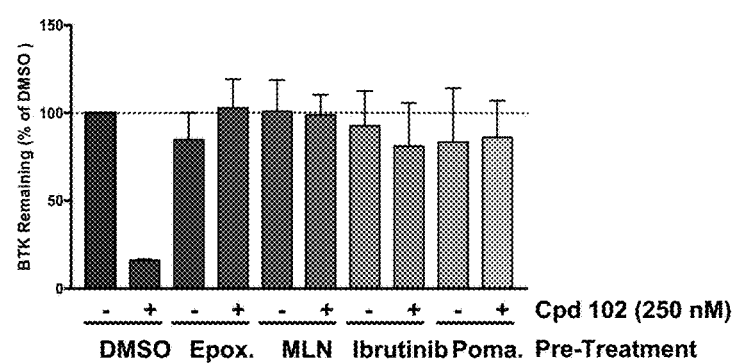
FIG. 8B illustrates the corresponding quantification of the immunoblotting in FIG. 1D. Pre-treatment with 1 µM epoxomicin and MLN-4924 results in rescue of BTK levels due to inhibition of proteasome function and neddylation, respectively. Pre-treatment with 25-fold molar excess of ibrutinib and pomalidomide similarly rescues BTK levels in the presence of a 4 h treatment with 250 nM Compound 102.

Compound 102 also fully degrades BTK as early as 4 hours with half of the total BTK at the matched vehicle-treated time point degraded after approximately 50 minutes (FIGS. 2C & 8A). Pre-treatment with epoxomicin, a proteasome inhibitor, followed by treatment with Compound 102 did not result in BTK degradation, indicating that proteasome function is required for BTK knockdown. The same was observed after treatment with MLN-4924, an inhibitor of NEDD8-activating enzyme which neddylates and activates many cullin-RING ligases, including the cullin-4 based cereblon complex. The necessity for direct binding to both BTK and cereblon was shown by pre-treating with excess ibrutinib and pomalidomide, both of which rescued BTK levels in response to Compound 102 (FIGS. 2D & 8B). These assays demonstrate definitively that Compound 102 directly engages BTK and cereblon to engender knockdown in a proteasome-dependent manner.

iii. Enhanced Kinase Selectivity by Compound 102 Over Ibrutinib

Figure 9A:
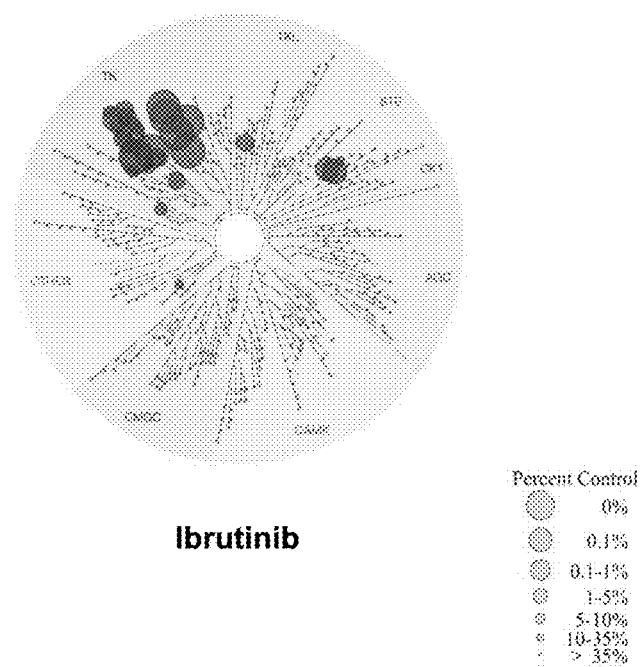
FIG. 9A illustrates a TREEspot™ diagram for kinome inhibition after treatment with 1 µM ibrutinib. BTK is highlighted with a blue circle.
Figure 9B:
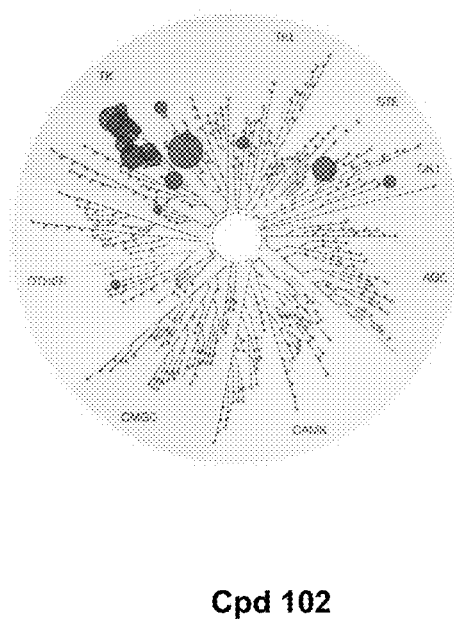
FIG. 9B illustrates a TREEspot™ diagram for kinome inhibition after treatment with 1 µM Compound 102. BTK is highlighted with a blue circle.
Figure 9C:
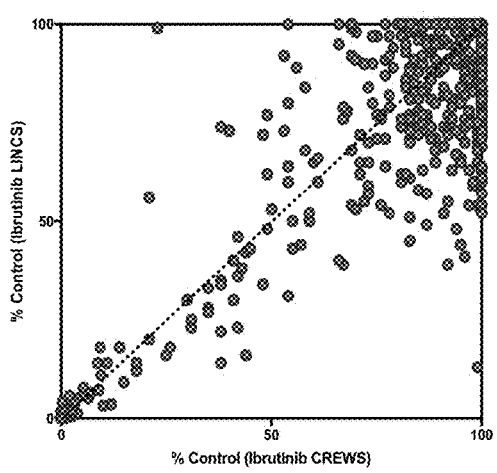
FIG. 9C illustrates a plot of the ibrutinib KINOMEscan™ dataset versus a previously reported dataset for ibrutinib from the Library of Integrated Network-based Cellular Signatures (LINCS) database.
Figure 10:
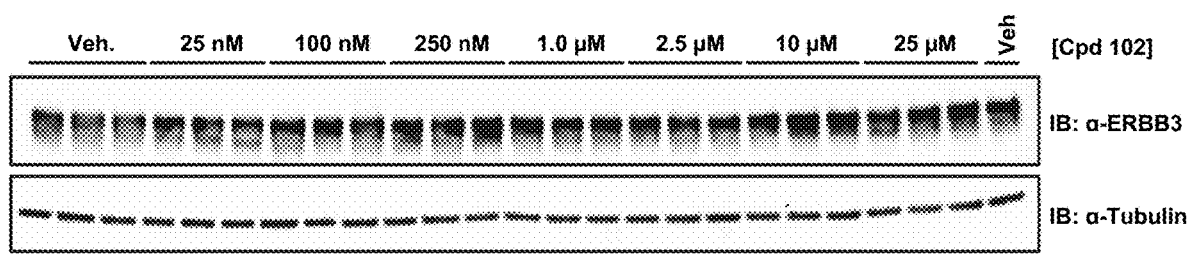
FIG. 10 illustrates a Western blot of Compound 102-related degradation of ERBB3. Compound 102 fully displaced the competitive probe bound to ERBB3 in the KfNOMEscan™ dataset, but this did not lead to ERBB3 degradation when tested in OVCAR8 cells.
Figure 13A:
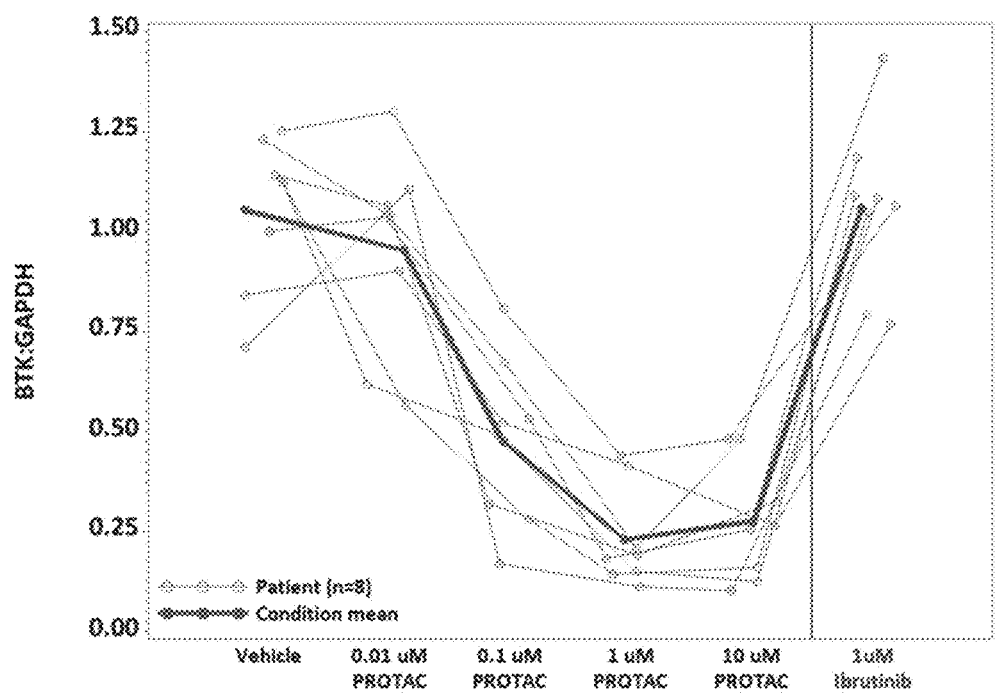
FIG. 13A illustrates individual responses to various doses of PROTAC over 24 hours.
Figure 13B:
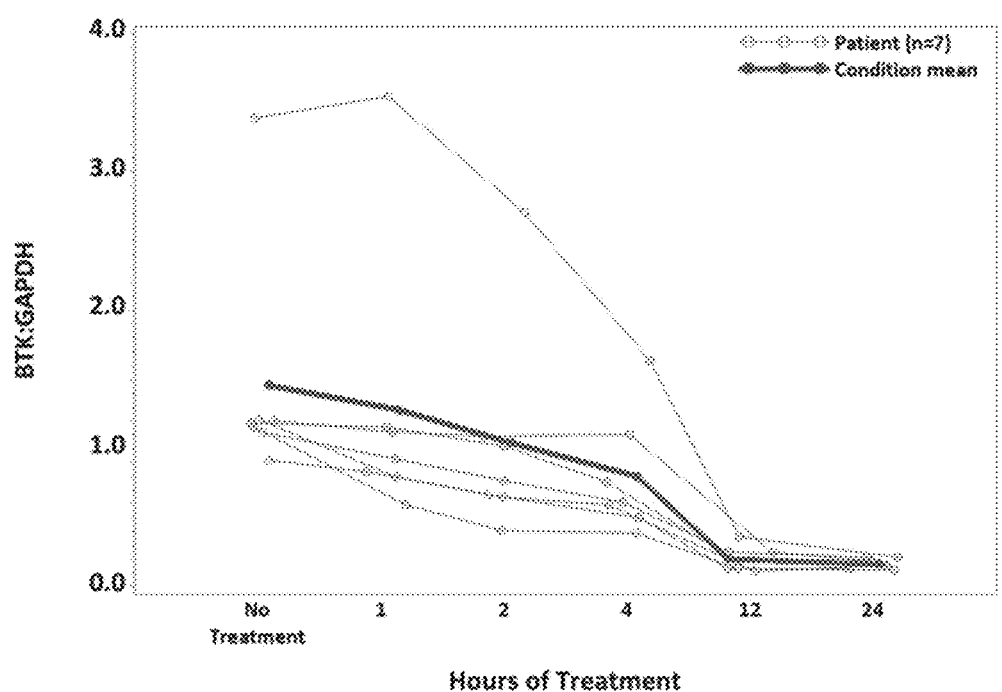
FIG. 13B illustrates individual responses to various times of treatment with 1 μM PROTAC treatment. An outlier is seen with overexpressed BTK, as is expected in CLL patients.

In general, it has been shown that the potency of in vitro kinase inhibition decreases when the linker and E3-targeting moiety are added to the parent warhead. It is known that ibrutinib shows off-target inhibition of other kinases, particularly those with cysteines homologous to C481 in BTK. Since Compound 102 lacks the acrylamide moiety that binds C481, it was reasoned that the PROTAC of the invention may bind fewer off-target kinases than ibrutinib. If confirmed, this finding would be relevant to efforts to develop more specific BTK inhibitors that are free of the negative side-effects of ibrutinib, which include adverse cardiac, gastrointestinal, and skin events (47, 48). To address this, KINOMEscan™, the high-throughput, competition-based binding assay service provided by DiscoverX, was utilized. This assay reports potency of inhibition as a "percentage of control", where lower values represent higher levels of kinase inhibition. Using this assay, ibrutinib and Compound 102 were screened in parallel at 1.0 µM against a panel of 450 human kinases (FIGS. 9A & B). Previously assembled datasets on ibrutinib's kinome-wide inhibition showed reasonable correlation ($R^2$=0.71) (FIG. 9C). BTK was among the most potently inhibited kinases by both compounds (0.0 and 0.25% of control for ibrutinib and Compound 102, respectively). Other kinases in the Tec family that were potently inhibited by both ibrutinib and Compound 102 were TEC (1.9 and 3.6% of control, respectively) and BLK (0.1 and 0.35% of control, respectively) (FIG. 3A). Of note, Compound 102 fully displaced the competitive probe bound to ERBB3 in the KINOMEscan™ dataset, but this did not lead to ERBB3 degradation when tested in OVCAR8 cells (FIG. 10). This example underscores the previous observation that potency of target engagement does not always correlate with degradation and that other factors such as ternary complex affinity and lysine accessibility may also be relevant.

To identify those kinases where there exists a differential in the level of inhibition by Compound 102 and ibrutinib, a Bland-Altman difference analysis was performed (FIG. 3B). Using this approach several kinases in the TK and STE groups that were significantly inhibited by ibrutinib (% of control <10%) but poorly inhibited by Compound 102 (% of control >80%) were identified. The three kinases for which the greatest differential was observed were ITK, MKK7, and JAK3, all of which are known off-target kinases inhibited by ibrutinib. Testing was performed to understand the ability for Compound 102 to show reduced inhibition of these kinases by structurally aligning the primary sequences of the strongly-inhibited (% of control <10%) and weakly-inhibited (% of control >80%) kinase domains (FIG. 3C). In line with previous reports, the dataset shows that ibrutinib strongly inhibited those kinases bearing a cysteine homologous to C481. All kinases that were inhibited potently by PROTAC and ibrutinib showed complete conservation of the gatekeeper threonine (position 474 in BTK).

Figure 3E:
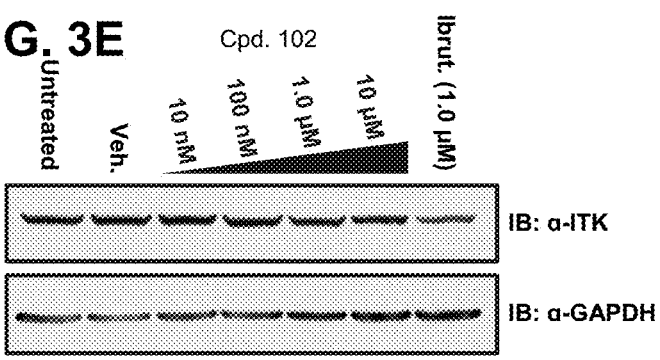
FIG. 3E illustrates ITK levels after Jurkat cells (Acute T-cell leukemia) were treated with increasing concentrations of Compound 102.
Figure 3F:
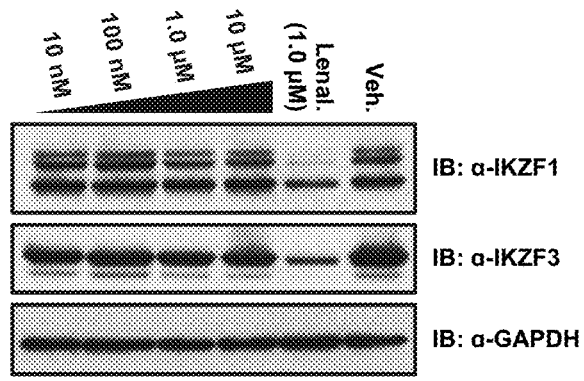
FIG. 3F depicts primary cells from CLL patients that were treated with 1.0 µM lenalidomide and increasing concentrations of Compound 102 and levels of IKZF1 and IKZF3 transcription factors were assessed by immunoblotting.

However, it was observed that ITK, JAK3, and MKK7 had a bulky residue (either methionine or phenylalanine) at this gatekeeper site. Structural docking experiments showed that replacement of the threonine with these bulky residues induced significant clashes with the ibrutinib scaffold (FIG. 3D). Without being bound by theory, it is believed that ibrutinib's covalent nature can overcome the energy penalty associated with binding these more crowded kinase pockets. Thus, it is believed that the PROTAC of the invention, which only reversibly binds BTK, shows enhanced specificity due to decreased tolerance for the sub-optimal binding pockets of these off-target kinases. To that end, upon treating Jurkat cells, a T-lymphocyte cell line, with increasing concentrations of Compound 102, no significant degradation of ITK was observed, likely due to poor ability to bind this kinase (FIG. 3E). As the PROTAC of the invention is based upon the pomalidomide ligand for cereblon, the degradation of IKZF1 and IKZF3, transcription factors known to be degraded by free pomalidomide, were also tested. No degradation of either protein was observed when tested in B-lymphocytes derived from CLL patients (FIG. 3F). Altogether, these findings demonstrated that reversible degraders based on the ibrutinib scaffold can show enhanced specificity for BTK inhibition, which can reduce adverse side-effects from off-target inhibition.

iv. Compound 102 Degrades Wild-type and C481S Mutated BTK

While no significant degradation of ERBB3 was observed, which possesses a serine at the position homologous to cysteine 481, Compound 102 retained binding affinity to kinases with this substitution. This suggested that Compound 102 would retain interaction with the C481S mutant of BTK, which has been reported in CLL patients exhibiting relapse to ibrutinib therapy. Relapse is proposed to occur due to loss of the covalent acceptor site, which makes the kinase sensitive only to the reversible inhibition provided by ibrutinib. It was believed that the loss of the covalent acceptor position would be inconsequential for PROTAC activity due to the need for only transient association to induce ubiquitination and knockdown. The C481S resistant context, therefore, would serve as a prime example where the event-driven paradigm of PROTACs can evade a resistance mechanism arising in response to the occupancy-paradigm of inhibition.

Figure 4A:
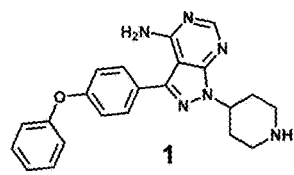
FIG. 4A illustrates IC50 values for ibrutinib, SJF-4676, and Compound 102 were calculated from 10-point dose response curves in duplicate in the presence of 10 µM ATP.

When screened for binding affinity, the PROTAC and its parent warhead, compound 1, showed retained inhibition potency against C481S mutant BTK (FIG. 4A). Interestingly, the in vitro kinase inhibition assay showed that ibrutinib could still potently inhibit C481S mutant kinase, which is consistent with previous reports. However, ibrutinib does show a rightward shift in inhibition potency when the mutation is introduced, unlike Compound 102 and SJF-4676, which highlights the importance of C481 for ibrutinib potency (FIG. 11). In the in vitro setting, ibrutinib shows a nearly 10-fold greater inhibition of the mutant kinase than PROTAC, which may be due to an interaction between the backbone amine and carbonyl oxygen of the acrylamide group that is preserved even when serine is substituted (FIG. 12). While these in vitro assays do show ibrutinib can retain binding and inhibition of C481S BTK, they do not fully recapitulate a cellular context, where ibrutinib is known to be ineffective at inhibiting mutant BTK signaling. In particular, ibrutinib's short half-life makes it challenging to reach sufficient inhibitory concentrations in the C481S mutational context. Therefore, PROTAC and ibrutinib's performance in the available cellular systems recapitulating C481S signaling was assessed.

Figure 4B:
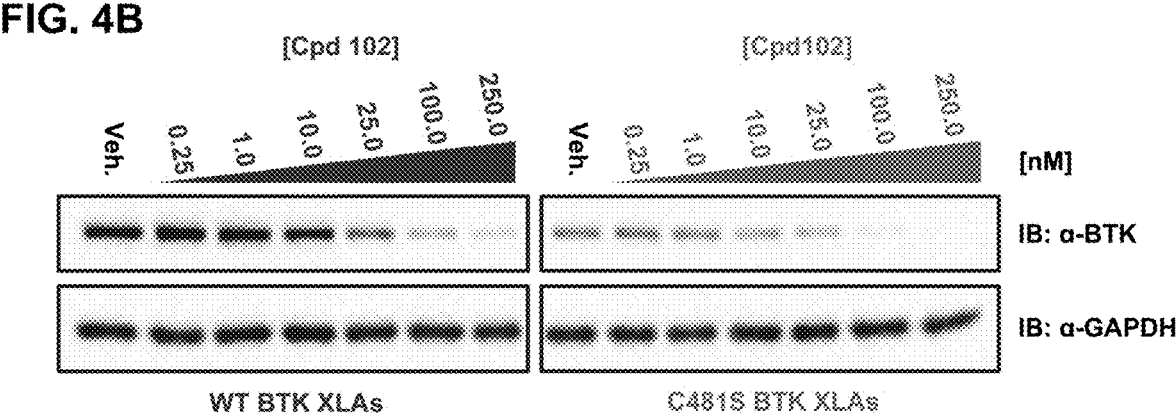
FIG. 4B illustrates an experiment where wild-type and C481S BTK expressing XLA cells were treated with increasing concentrations of Compound 102 and levels of BTK were quantified by immunoblot.
Figure 4B:
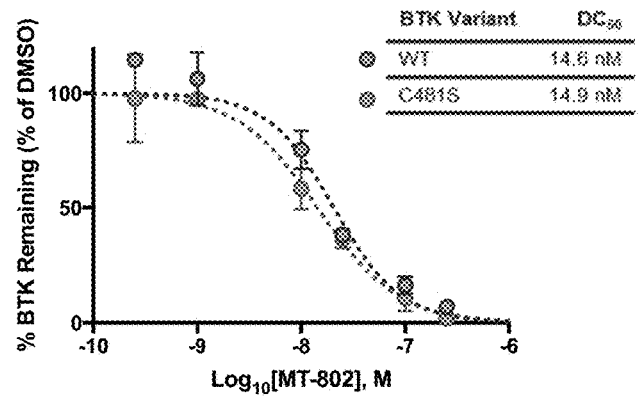
Figure 4C:
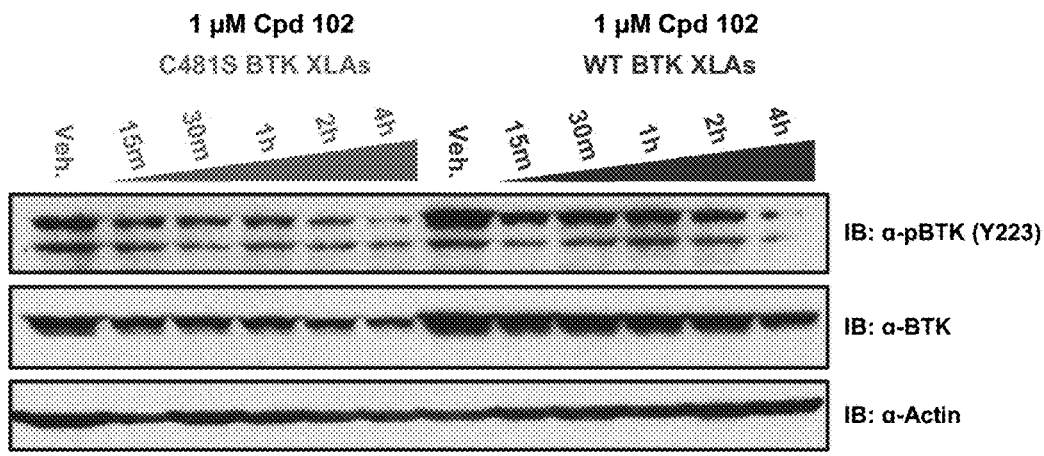
FIG. 4C illustrates an experiment where wild-type and C481S XLA cells were treated with 1 µM Compound 102 for indicated times and levels of BTK and pBTK (Y223) were quantified by immunoblot.

A previously reported human B-lymphocyte cell line derived from a patient with X-linked agammaglobulinemia (XLA), a primary immunodeficiency caused by inability to produce functional BTK was utilized. In the presence of a BTK null background, the cells were transduced to express either wild-type or C481S BTK. Compound 102 showed equivalent potency of degradation based on $DC_{50}$ and $D_{max}$, the maximal percentage of protein that can be degraded by the PROTAC (FIG. 4B). Time course experiments also showed that wild-type and C481S BTK are degraded with similar kinetics (FIG. 4C). While the XLA lines also showed that the PROTAC could reduce the autophosphorylated form of BTK (a marker of active, signaling-competent kinase) concomitant with degradation of the total protein, patient CLL B-cells with a constitutively active BCR pathway reliant on BTK are the ultimate translational tool in studying the ability of this molecule to degrade BTK. In an effort to demonstrate the potential clinical applicability of this approach, isolated primary cells from patients presenting with CLL before and after relapse were utilized.

v. Compound 102 Outperforms Ibrutinib in C481S Primary CLL Patient Samples

Figure 5A:
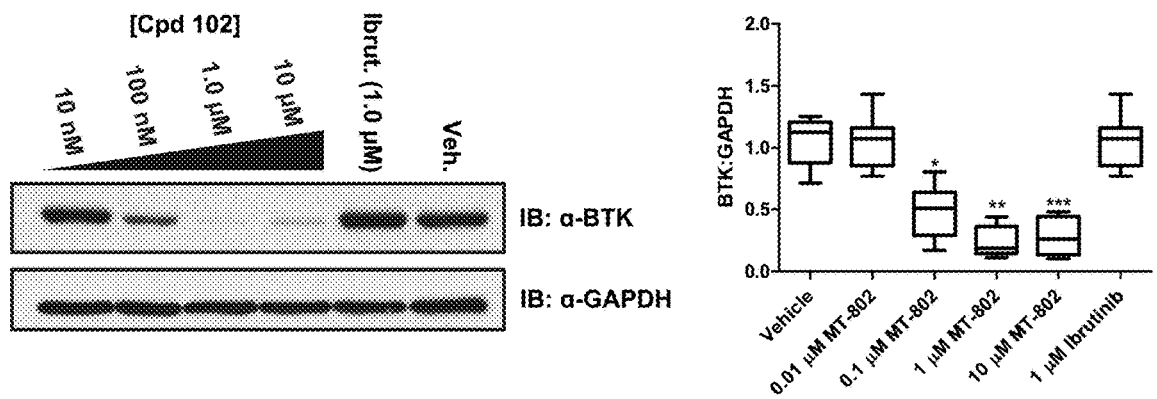
FIG. 5A illustrates an experiment where primary cells from patients presenting with CLL were treated with increasing concentrations of Compound 102 and levels of BTK were assessed by immunoblot (left panel). Results from dose responses in eight independent patients were quantified (right panel). (* correlates to a p-value <0.001 compared to vehicle treatment).
Figure 5B:
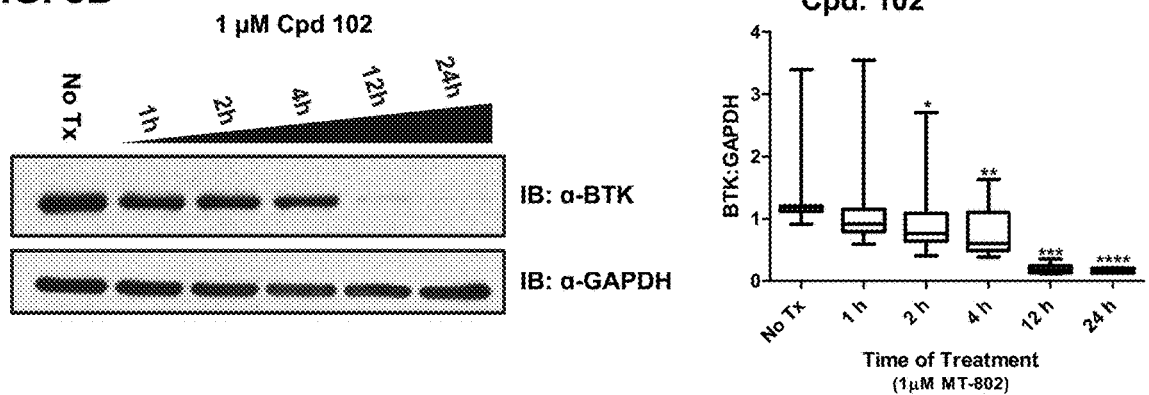
FIG. 5B illustrates an experiment where primary CLL patient lymphocytes were treated with 1 µM Compound 102 for indicated times and levels of BTK were quantified by immunoblot (left panel). Time courses in seven independent patients were quantified (right panel). (* and ** correlates to a p-value of 0.008 and <0.001 compared to no treatment, respectively).

In order to compare the PROTAC to other BTK-targeting moieties, a range of doses and exposure times of patient cells to Compound 102 was assessed. Treatment-naïve B-lymphocytes were isolated from the blood of patients presenting with CLL as previously described. Consistent with experiments with immortalized cell lines, it was observed that potent knockdown of BTK in the B-lymphocytes of all patients tested (FIG. 12). In order to examine the trends of BTK degradation over multiple doses and time points, a mixed effects model was applied to the log-transformed data to estimate differences relative to vehicle or no treatment. P-values for comparisons have been adjusted using the Dunnett-Hsu method (for comparisons against vehicle control). The dose response study shows statistically significant degradation at just 0.1 μM PROTAC (FIG. 5A). Time course experiments showed that maximal degradation was observed between 4 and 12h, and statistically significant degradation at just 2 hours of treatment (FIG. 5B). These experiments confirm the ability of the PROTAC to work in isolated patient B-cells with overexpression of BTK.

Figure 5C:
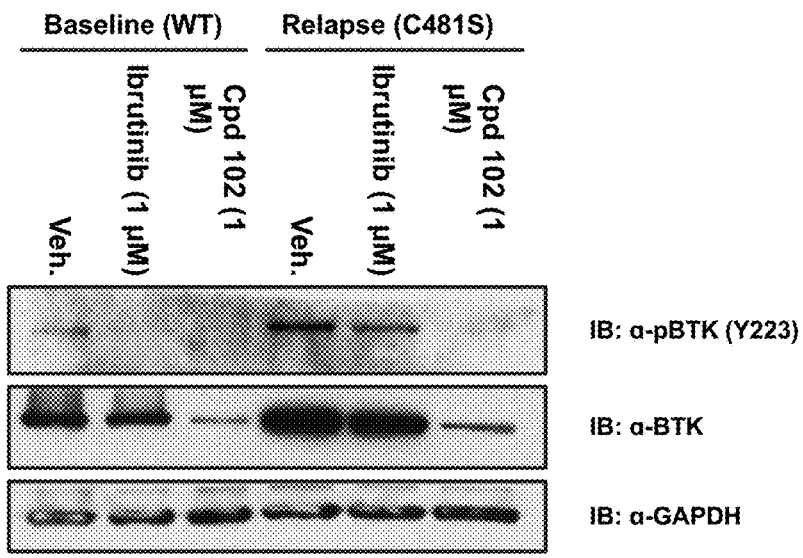
FIG. 5C illustrates an experiment where primary cells from a CLL patient before and after relapse to ibrutinib were treated with indicated concentrations of ibrutinib and Compound 102 followed by detection of pBTK and total BTK.

Next, CLL cells from patients before and after ibrutinib relapse were isolated. The C481S mutation in BTK was determined to be the cause of drug failure, confirmed by deep sequencing. Compound 102 was able to degrade both the wild-type baseline and C481S BTK relapse primary patient sample. Ibrutinib and PROTAC both showed efficacy in abrogating BTK signaling at baseline. However, after relapse, only Compound 102 retained its ability to reduce the pool of active, Y223 phosphorylated BTK (FIG. 5C). This indicates that what was previously ineffective, reversible binding to C481S BTK is sufficient to induce knockdown when ibrutinib's scaffold is incorporated into the PROTAC Compound 102. Thus, the same chemotype can have very different functional consequences when it is incorporated into molecules that follow event-driven pharmacology, such as the compounds described herein, as opposed to an occupancy-driven pharmacology of traditional inhibitors. These findings suggest that C481S resistance in CLL will not be sufficient to induce cell survival and proliferation in cells treated with BTK PROTAC as described herein.

What is claimed is:

1. A compound, or a pharmaceutically acceptable salt, enantiomer, stereoisomer, solvate, polymorph, or prodrug thereof, having the structure:

ULM-L-PTM, wherein:
the ULM is an E3 ubiquitin ligase binding moiety that binds an E3 ubiquitin ligase;
the PTM is a Bruton's Tyrosine Kinase (BTK) targeting moiety having the structure:

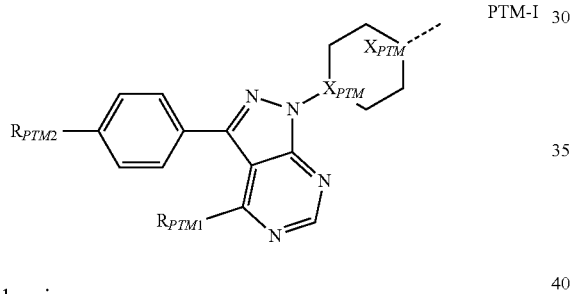

PTM-I wherein:
at each occurrence $X_{PTM}$ is independently N or optionally substituted CH;
$R_{PTM1}$ is independently $NR_{PTMP9}P_{TM10}$, H, optionally substituted $C_3$-$C_6$ cycloalkyl, optionally substituted $C_3$-$C_6$ heteroalkyl, optionally substituted aryl, optionally substituted heteroaryl,

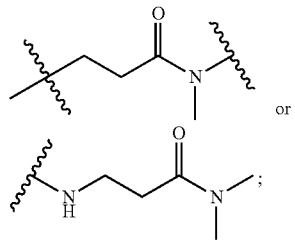

$R_{PTM9}$ and $R_{PTM10}$ are each independently H, —(C═O)—$R_{PTM9}$', or optionally substituted $C_1$-$C_6$ alkyl;
$R_{PTM9}$' is optionally substituted linear or branched alkyl, or optionally substituted alkene;
at each occurrence $R_{PTM2}$ is independently H, —O—$R_{PTM3}$, optionally substituted linear or branched alkyl;

at each occurrence $R_{PTM3}$ is independently an optionally substituted aryl or optionally substituted heteroaryl; and the ⁓ indicates a site of attachment of at least one of a linker, ULM, ULM' or a combination thereof; and the L is a bond or a linker connecting the ULM and the PTM.

2. The compound of claim 1, wherein the ULM is selected from the group consisting of an IAP E3 ubiquitin ligase binding moiety (ILM), a cereblon E3 ubiquitin ligase binding moiety (CLM), a Von Hippel-Lindau E3 ubiquitin ligase binding moiety (VLM), a mouse double minute 2 homologue (MDM2) E3 ubiquitin ligase binding moiety (MLM), and combinations thereof.

3. The compound of claim 1, wherein the PTM has the structure:

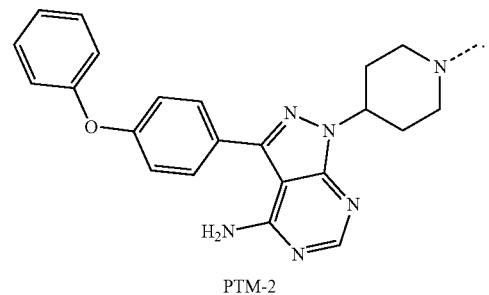

PTM-2

4. The compound of claim 1, wherein the ULM is a Von Hippel-Lindau (VHL) ligase-binding moiety (VLM) with the structure:

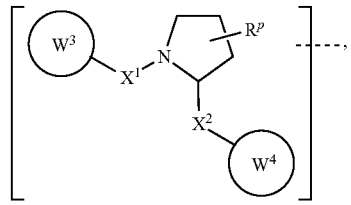

wherein:
at each occurrence $X^1$, $X^2$ are each independently selected from the group consisting of a bond, O, $NR^{Y3}$, $CR^{Y3}R^{Y4}$, C═O, C═S, SO, and $SO_2$;
$R^{Y3}$, $R^{Y4}$ are each independently selected from the group consisting of H, linear or branched $C_{1-6}$ alkyl optionally substituted by 1 or more halogen, and C$_{1-6}$ alkoxyl optionally substituted by 0-3 R$^P$ groups;

at each occurrence R$^P$ is 0, 1, 2, or 3 groups independently selected from the group consisting of H, halogen, —OH, C$_{1-3}$ alkyl, and C=O;

at each occurrence W$^3$ is independently selected from the group of an optionally substituted T, an optionally substituted -T-N(R$^{1a}$R$^{1b}$)X$^3$, an optionally substituted -T-N(R$^{1a}$R$^{1b}$), an optionally substituted -T-Aryl, an optionally substituted -T-Heteroaryl, an optionally substituted -T-Heterocycle, an optionally substituted —NR$^1$-T-Aryl, an optionally substituted —NR$^1$-T-Heteroaryl or an optionally substituted —NR$^1$-T-Heterocycle;

at each occurrence X$^3$ is C(=O), R$^1$, R$^{1a}$, or R$^{1b}$;

each of R$^1$, R$^{1a}$, R$^{1b}$ is independently selected from the group consisting of H, linear or branched C$_1$-C$_6$ alkyl group optionally substituted by 1 or more halogen or —OH groups, R$^{Y3}$C(=O), R$^{Y3}$C=S, R$^{Y3}$SO, R$^{Y3}$SO$_2$, N(R$^{Y3}$R$^{Y4}$)C(=O), N(R$^{Y3}$R$^{Y4}$)C(=S), N(R$^{Y3}$R$^{Y4}$)SO, and N(R$^{Y3}$R$^{Y4}$)SO$_2$;

T is selected from the group of an optionally substituted alkyl, —(CH$_2$)$_n$— group, wherein:

each one of the methylene groups in T is optionally substituted with one or two substituents selected from the group of halogen, methyl, optionally substituted alkoxy, a linear or branched C$_1$-C$_6$ alkyl group optionally substituted by 1 or more halogen, C(=O)NR$^1$R$^{1a}$, NR$_1$R$^{1a}$ in which R$^1$ and R$^{1a}$ are optionally joined to form substituted heterocycle, —OH, or an optionally substituted amino acid; and at each occurrence n is independently a whole number from 0 to 6, at each occurrence W$^4$ is independently

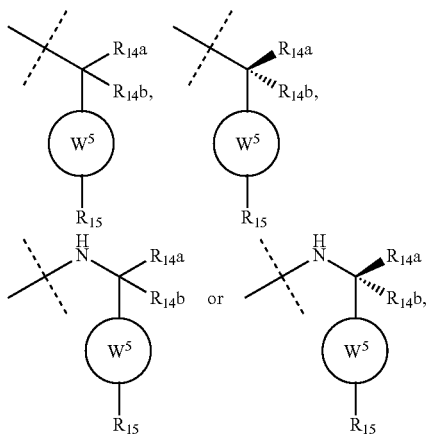

at each occurrence R$_{14a}$, R$_{14b}$, are each independently selected from the group consisting of H, haloalkyl, and optionally substituted alkyl;

at each occurrence W$^5$ is independently selected from the group consisting of a phenyl and a 5-10 membered heteroaryl, at each occurrence R$_{15}$ is independently selected from the group consisting of H, halogen, CN, OH, NO$_2$, NR$_{14a}$R$_{14b}$, OR$_{14a}$, C(=O)NR$_{14a}$R$_{14b}$, NR$_{14a}$C(=O)R$_{14b}$, SO$_2$NR$_{14a}$R$_{14b}$, NR$_{14a}$SO$_2$R$_{14b}$, optionally substituted alkyl, optionally substituted haloalkyl, optionally substituted haloalkoxy, optionally substituted aryl, optionally substituted heteroaryl, optionally substituted cycloalkyl, and optionally substituted cycloheteroalkyl; and wherein the dashed line indicates the site of attachment of at least one PTM, another ULM (ULM') or a chemical linker moiety coupling at least one PTM or a ULM' or both to ULM.

5. The compound of claim 1, wherein the ULM is a Von Hippel-Lindau (VHL) ligase-binding moiety (VLM) with a structure represented by:

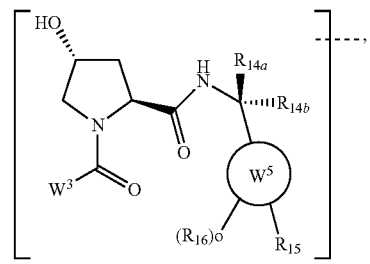

wherein:

at each occurrence W$^3$ is selected from the group consisting of an optionally substituted aryl, optionally substituted heteroaryl, and

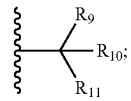

at each occurrence R$_9$ and R$_{10}$ are independently hydrogen, optionally substituted alkyl, optionally substituted cycloalkyl, optionally substituted hydroxyalkyl, optionally substituted heteroaryl, or haloalkyl, or R$_9$, R$_{10}$, and the carbon atom to which they are attached form an optionally substituted cycloalkyl;

at each occurrence R$_{11}$ is independently selected from the group consisting of an optionally substituted heterocyclic, optionally substituted alkoxy, optionally substituted heteroaryl, optionally substituted aryl,

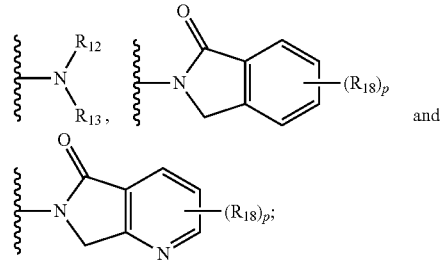

at each occurrence R$_{12}$ is independently selected from the group of H or optionally substituted alkyl;

at each occurrence R$_{13}$ is independently selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

at each occurrence R$_{14a}$, R$_{14b}$, are each independently selected from the group of H, haloalkyl, or optionally substituted alkyl;

at each occurrence $W^5$ is selected from the group of a phenyl or a 5-10 membered heteroaryl, at each occurrence $R_{15}$ is independently selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

at each occurrence $R_{16}$ is independently selected from the group of halogen, optionally substituted alkyl, optionally substituted haloalkyl, hydroxy, or optionally substituted haloalkoxy;

at each occurrence o is independently 0, 1, 2, 3, or 4;

at each occurrence $R_{18}$ is independently selected from the group of halogen, optionally substituted alkoxy, cyano, optionally substituted alkyl, haloalkyl, haloalkoxy or a linker; and at each occurrence p is independently 0, 1, 2, 3, or 4, and wherein the dashed line indicates the site of attachment of at least one PTM, another ULM (ULM') or a chemical linker moiety coupling at least one PTM or a ULM' or both to ULM.

6. The compound of claim 1, wherein the ULM has a chemical structure selected from the group consisting of:

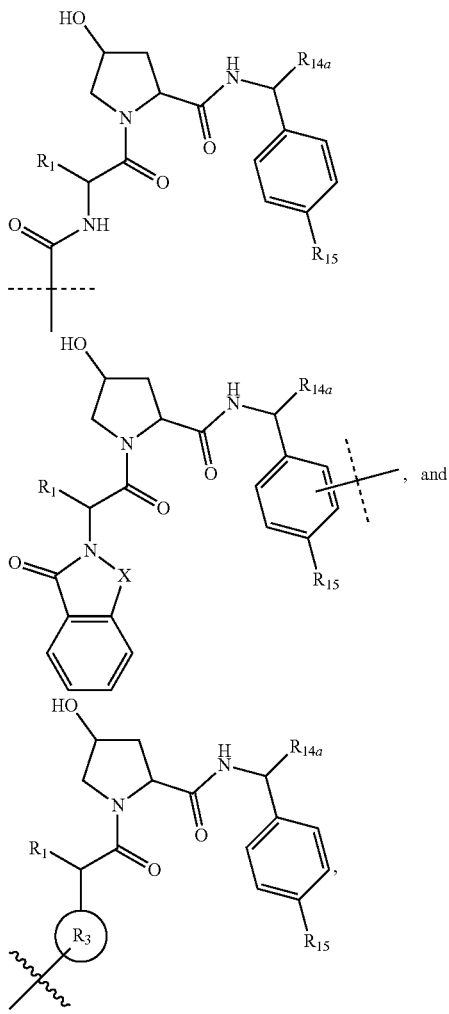

, and wherein:
at each occurrence $R_1$ is independently H, ethyl, isopropyl, tert-butyl, sec-butyl, cyclopropyl, cyclobutyl, cyclopentyl, or cyclohexyl, optionally substituted alkyl, optionally substituted hydroxyalkyl, optionally substituted heteroaryl, or haloalkyl;

at each occurrence $R_{14a}$ is independently H, haloalkyl, optionally substituted alkyl, methyl, fluoromethyl, hydroxymethyl, ethyl, isopropyl, or cyclopropyl;

at each occurrence $R_{15}$ is independently selected from the group consisting of H, halogen, CN, OH, $NO_2$, optionally substituted heteroaryl, optionally substituted aryl, optionally substituted alkyl, optionally substituted haloalkyl, optionally substituted haloalkoxy, optionally substituted cycloalkyl, and optionally substituted cycloheteroalkyl;

X is C or C(=O)

at each occurrence $R_3$ is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to the ULM.

7. The compound of claim 1, wherein the ULM comprises a group according to the chemical structure:

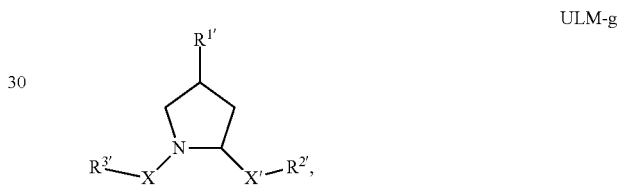

ULM-g wherein:
at each occurrence $R^1$ is independently an optionally substituted $C_1$-$C_6$ alkyl group, an optionally substituted —$(CH_2)_n$OH, an optionally substituted —$(CH_2)_n$SH, an optionally substituted $(CH_2)_n$—O—($C_1$-$C_6$)alkyl group, an optionally substituted $(CH_2)_n$—WCOCW—($C_0$-$C_6$)alkyl group containing an epoxide moiety WCOCW, wherein each W is independently H or a $C_1$-$C_3$ alkyl group, an optionally substituted —$(CH_2)_n$COOH, an optionally substituted —$(CH_2)_n$C(=O)—($C_1$-$C_6$ alkyl), an optionally substituted —$(CH_2)_n$NHC(=O)—$R_1$, an optionally substituted —$(CH_2)_n$C(=O)—$NR_1R_2$, an optionally substituted —$(CH_2)_n$OC(=O)—$NR_1R_2$, —$(CH_2O)_n$H, an optionally substituted —$(CH_2)_n$OC(=O)—($C_1$-$C_6$ alkyl), an optionally substituted —$(CH_2)_n$C(=O)—O—($C_1$-$C_6$ alkyl), an optionally substituted —$(CH_2O)_n$COOH, an optionally substituted —$(OCH_2)_n$O—($C_1$-$C_6$ alkyl), an optionally substituted —$(CH_2O)_n$C(=O)—($C_1$-$C_6$ alkyl), an optionally substituted —$(OCH_2)_n$NHC(=O)—$R_1$, an optionally substituted —$(CH_2O)_n$C(=O)—$NR_1R_2$, —$(CH_2CH_2O)_n$H, an optionally substituted —$(CH_2CH_2O)_n$COOH, an optionally substituted —$(OCH_2CH_2)_n$O—($C_1$-$C_6$ alkyl), an optionally substituted —$(CH_2CH_2O)_n$C(=O)—($C_1$-$C_6$ alkyl), an optionally substituted —$(OCH_2CH_2)_n$NHC(=O)—$R_1$, an optionally substituted —$(CH_2CH_2O)_n$C(=O)—$NR_1R_2$, an optionally substituted —$SO_2R_S$, an optionally substituted $S(=O)R_S$, $NO_2$, CN or halogen;

at each occurrence $R_1$ and $R_2$ are each independently H or a $C_1$-$C_6$ alkyl group which may be optionally substituted with one or two hydroxyl groups or up to three halogen groups;

at each occurrence $R_S$ is a $C_1$-$C_6$ alkyl group, an optionally substituted aryl, heteroaryl or heterocycle group or a —$(CH_2)_m NR_1 R_2$ group;

X and X' are each independently C=O, C=S, —S(=O), S(=O)$_2$;

at each occurrence $R^2$ is independently an optionally substituted —$(CH_2)_n$—$(C=O)_u(NR_1)_v(SO_2)_w$alkyl group, an optionally substituted —$(CH_2)_n$—$(C=O)_u(NR_1)_v(SO_2)_w NR_1 NR_{2N}$ group, an optionally substituted —$(CH_2)_n$—$(C=O)_u(NR_1)_v(SO_2)_w$-Aryl, an optionally substituted —$(CH_2)_n$—$(C=O)_u(NR_1)_v(SO_2)_w$-Heteroaryl, an optionally substituted —$(CH_2)_n$—$(C=O)_v NR_1(SO_2)_w$-Heterocycle, an optionally substituted —$NR^1$—$(CH_2)_n$—$C(=O)_u(NR_1)_v(SO_2)_w$-alkyl, an optionally substituted —$NR^1$—$(CH_2)_n$—$C(=O)_u(NR_1)_v(SO_2)_w$—$NR_{1N}R_{2N}$, an optionally substituted —$NR^1$—$(CH_2)_n$—$C(=O)_u(NR_1)_v(SO_2)_w$—$NR_1C(=O)R_{1N}$, an optionally substituted —$NR^1$—$(CH_2)_n$—$(C=O)_u(NR_1)_v(SO_2)_w$-Aryl, an optionally substituted —$NR^1$—$(CH_2)_n$—$(C=O)_u(NR_1)_v(SO_2)_w$-Heteroaryl or an optionally substituted —$NR^1$—$(CH_2)_n$—$(C=O)_v NR_1(SO_2)_w$-Heterocycle, an optionally substituted —$X^{R2'}$-alkyl group; an optionally substituted —$X^{R2'}$— Aryl group; an optionally substituted —$X^{R2'}$— Heteroaryl group; an optionally substituted —$X^{R2'}$— Heterocycle group;

at each occurrence $R^{3'}$ is independently an optionally substituted alkyl, an optionally substituted —$(CH_2)_n$—$(O)_u(NR_1)_v(SO_2)_w$-alkyl, an optionally substituted —$(CH_2)_n$—$C(=O)_u(NR_1)_v(SO_2)_w$—$NR_1 NR_{2N}$, an optionally substituted —$(CH_2)_n$—$C(=O)_u(NR_1)_v(SO_2)_w$—$NR_1 C(=O)R_{1N}$, an optionally substituted —$(CH_2)_n$—$C(=O)_u(NR_1)_v(SO_2)_w$—$C(=O)NR_1 R_2$, an optionally substituted —$(CH_2)_n$—$C(=O)_u(NR_1)_v(SO_2)_w$-Aryl, an optionally substituted —$(CH_2)_n$—$C(=O)_u(NR_1)_v(SO_2)_w$-Heteroaryl, an optionally substituted —$(CH_2)_n$—$C(=O)_u(NR_1)_v(SO_2)_w$-Heterocycle, an optionally substituted —$NR^1$—$(CH_2)_n$—$C(=O)_u(NR_1)_v(SO_2)_w$-alkyl, an optionally substituted —$NR^1$—$(CH_2)_n$—$C(=O)_u(NR_1)_v(SO_2)_w$—$NR_{1N}R_{2N}$, an optionally substituted —$NR^1$—$(CH_2)_n$—$C(=O)_u(NR_1)_v(SO_2)_w$—$NR_1C(=O)R_{1N}$, an optionally substituted —$NR^1$—$(CH_2)_n$—$C(=O)_u(NR_1)_v(SO_2)_w$-Aryl, an optionally substituted —$NR^1$—$(CH_2)_n$—$C(=O)_u(NR_1)_v(SO_2)_w$-Heteroaryl, an optionally substituted —$NR^1$—$(CH_2)_n$—$C(=O)_u(NR_1)_v(SO_2)_w$-Heterocycle, an optionally substituted —O—$(CH_2)_n$—$(C=O)_u(NR_1)_v(SO_2)_w$-alkyl, an optionally substituted —O—$(CH_2)_n$—$(C=O)_u(NR_1)_v(SO_2)_w$—$NR_1 NR_{2N}$, an optionally substituted —O—$(CH_2)_n$—$(C=O)_u(NR_1)_v(SO_2)_w$—$NR_1C(=O)R_{1N}$, an optionally substituted —O—$(CH_2)_n$—$(C=O)_u(NR_1)_v$ $(SO_2)_w$-Aryl, an optionally substituted —O—$(CH_2)_n$—$(C=O)_u(NR_1)_v(SO_2)_w$-Heteroaryl or an optionally substituted —O—$(CH_2)_n$—$(C=O)_u(NR_1)_v(SO_2)_w$-Heterocycle; —$(CH_2)_n$—$(V)_{n'}$—$(CH_2)_n$—$(V)_{n'}$-alkyl group, an optionally substituted —$(CH_2)_n$—$(V)_{n'}$—$(CH_2)_n$—$(V)_{n'}$-Aryl group, an optionally substituted —$(CH_2)_n$—$(V)_{n'}$—$(CH_2)_n$—$(V)_{n'}$-Heteroaryl group, an optionally substituted —$(CH_2)_n$—$(V)_{n'}$—$(CH_2)_n$—$(V)_{n'}$-Heterocycle group, an optionally substituted —$(CH_2)_n$—$N(R_{1'})(C=O)_{m'}$—$(V)_{n'}$-alkyl group, an optionally substituted —$(CH_2)_n$—$N(R_{1'})(C=O)_{m'}$—$(V)_{n'}$-Aryl group, an optionally substituted —$(CH_2)_n$—$N(R_{1'})(C=O)_{m'}$—$(V)_{n'}$-Heteroaryl group, an optionally substituted —$(CH_2)_n$—$N(R_{1'})(C=O)_{m'}$—$(V)_{n'}$-Heterocycle group, an optionally substituted —$X^{R3'}$— alkyl group; an optionally substituted —$X^{R3'}$— Aryl group; an optionally substituted —$X^{R3'}$— Heteroaryl group; an optionally substituted —$X^{R3'}$— Heterocycle group;

at each occurrence $R_{1N}$ and $R_{2N}$ are each independently H, $C_1$-$C_6$ alkyl which is optionally substituted with one or two hydroxyl groups and up to three halogen groups or an optionally substituted —$(CH_2)_n$-Aryl, —$(CH_2)_n$—Heteroaryl or —$(CH_2)_n$—Heterocycle group;

at each occurrence V is O, S or MU;

at each occurrence $R^1$ and $R_{1'}$ are each independently H or a $C_1$-$C_3$ alkyl group;

at each occurrence $X^{R2'}$ and $X^{R3'}$ are each independently an optionally substituted —$CH_2)_n$—, —$CH_2)_n$—CH $(X_v)$=CH$(X_v)$— (cis or trans), —$CH_2)_n$—CH≡CH—, —$(CH_2CH_2O)_n$— or a $C_3$-$C_6$ cycloalkyl group, wherein at each occurrence $X_v$ is independently H, a halogen, or an optionally substituted $C_1$-$C_3$ alkyl group;

at each occurrence m is independently 0, 1, 2, 3, 4, 5, 6;

at each occurrence m' is independently 0 or 1;

at each occurrence n is independently 0, 1, 2, 3, 4, 5, 6;

at each occurrence n' is independently 0 or 1;

at each occurrence u of is independently 0 or 1;

at each occurrence v is independently 0 or 1;

at each occurrence w is independently 0 or 1; and at each occurrence $R^{1'}$, $R^{2'}$, $R^{3'}$, X and X' is independently optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group.

8. The compound of claim 1, wherein the ULM is a cereblon E3 ligase-binding moiety (CLM) selected from the group consisting of a thalidomide, lenalidomide, and pomalidomide.

9. The compound of claim 2, wherein the CLM has a structure selected from:

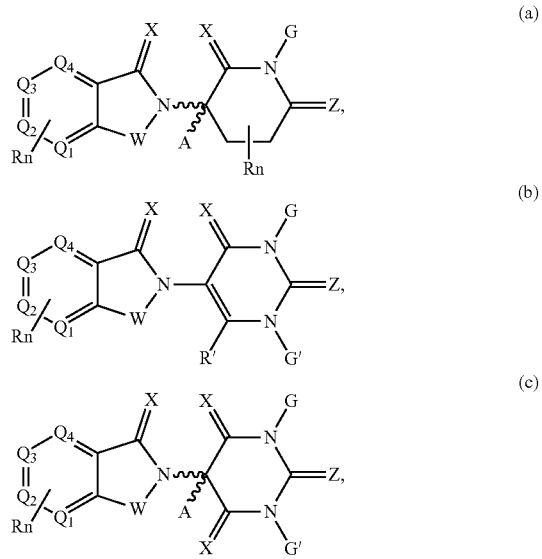

-continued

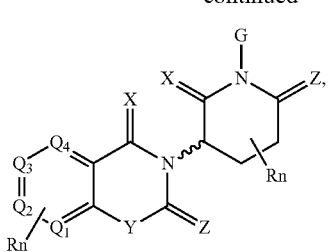
(d)

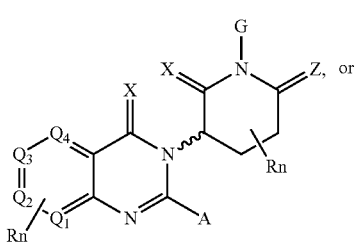
(e)

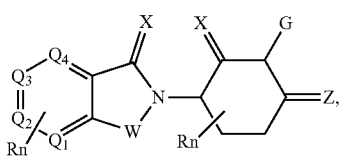
(f)

wherein:
at each occurrence W is selected from the group consisting of $CH_2$, CHR, C(=O), $SO_2$, NH, and N-alkyl;
at each occurrence X is independently selected from the group consisting of O, S, and $H_2$;
at each occurrence Y is selected from the group consisting of $CH_2$, —C=CR', NH, N-alkyl, N-aryl, N-hetaryl, N-cycloalkyl, N-heterocyclyl, O, and S;
at each occurrence Z is selected from the group consisting of O, S, and $H_2$;
at each occurrence G and G' are independently selected from the group consisting of H, optionally substituted linear or branched alkyl, OH, R'OCOOR, R'OCONRR", $CH_2$-heterocyclyl optionally substituted with R', and benzyl optionally substituted with R';
at each occurrence $Q_1$, $Q_2$, $Q_3$, and $Q_4$ represent a carbon atom substituted with a group independently selected from R', N, or N-oxide;
at each occurrence A is independently selected from the group H, optionally substituted linear or branched alkyl, cycloalkyl, Cl, or F;
at each occurrence R is selected from the group consisting of —CONR'R", —OR', —NR'R", —SR', —$SO_2$R', —$SO_2$NR'R", —CR'R"—, —CR'NR'R"—, (—CR'O)$_n$R", -aryl, -hetaryl, optionally substituted linear or branched alkyl, -cycloalkyl, -heterocyclyl, —P(=O)(OR')R", —P(=O)R'R", —OP(=O)(OR')R", —OP(=O)R'R", —Cl, —F, —Br, —I, —$CF_3$, —CN, -$MCSO_2MCR$", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —C=CR', —S(C=O)(C=N—R')R", —$SF_5$ and —$OCF_3$;
at each occurrence R' and R" are independently selected from the group consisting of a bond, H, alkyl, cycloalkyl, aryl, heteroaryl, heterocyclic, —C(=O)R, and heterocyclyl, each of which is optionally substituted;

at each occurrence ~~~ represents a bond that may be stereospecific ((R) or (S)) or non-stereospecific; and
at each occurrence $R_n$ is from 1 to 4 groups selected from H, OH, $C_1$-$C_6$ alkyl, $C_1$-$C_6$ alkoxy, -alkyl-aryl, amine, amide, or carboxy,
wherein at each occurrence n is independently an integer from 1-10, and wherein when n is 1, $R_n$ is modified to be covalently joined to the linker group (L), and
when n is 2, 3, or 4, then one $R_n$ is modified to be covalently joined to the linker group (L), and any other $R_n$ is optionally modified to be covalently joined to a PTM, a CLM, a second CLM having the same chemical structure as the CLM, a CLM', a second linker, or any combination thereof.

10. The compound of claim 2, wherein the CLM has a structure selected from:

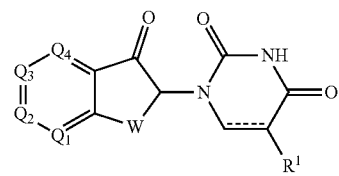
(h)

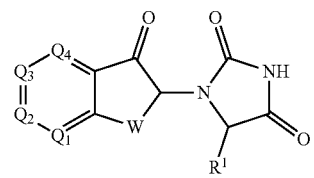
(i)

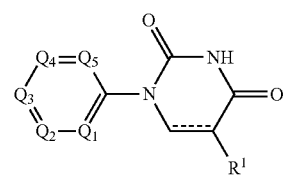
(j)

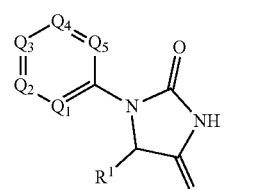
(k)

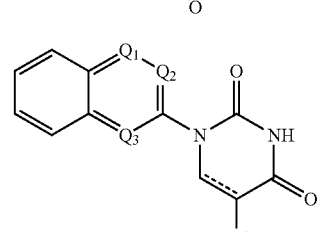
(l)

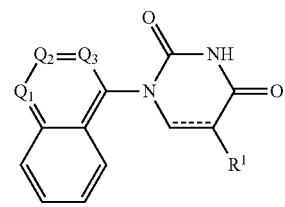
(m)

-continued
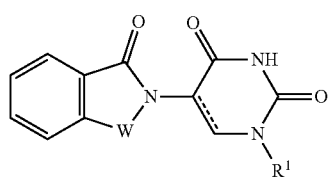
(n)
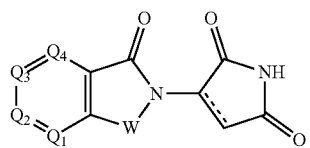
(o)
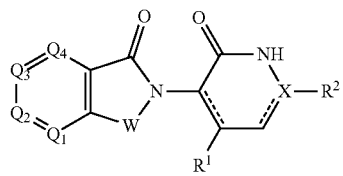
(p)
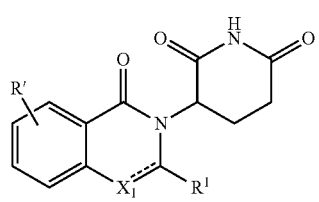
(q)
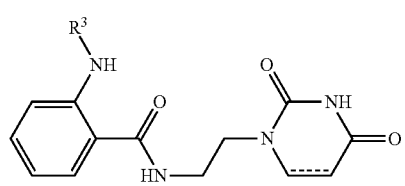
(r)
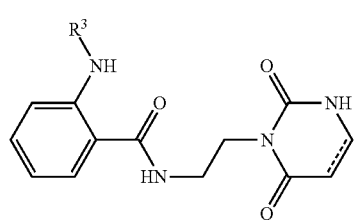
(s)
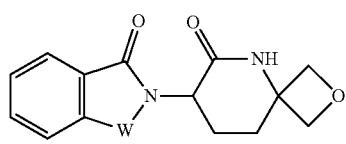
(t)
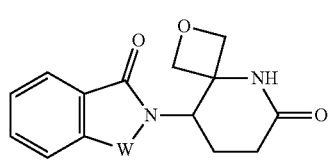
(u)
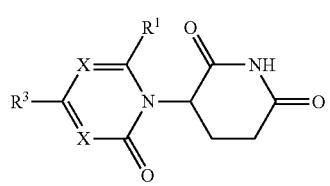
(v)
-continued
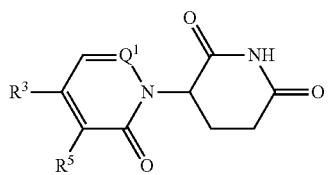
(w)
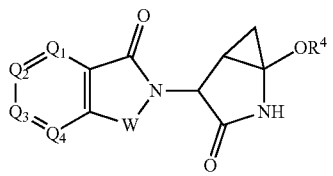
(x)
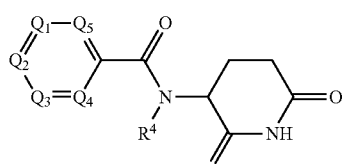
(y)
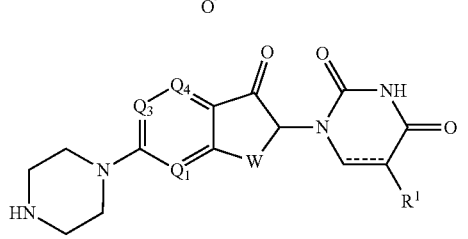
(z)
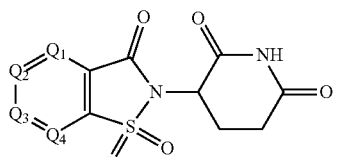
(aa)
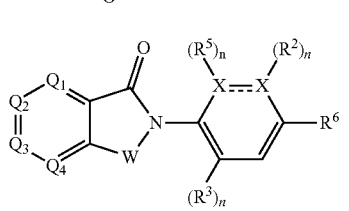
(ab)
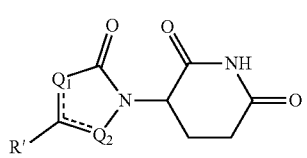
(ac)
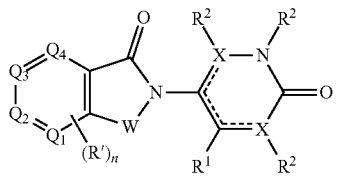
(ad)
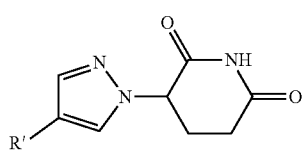
(ae)

547
-continued

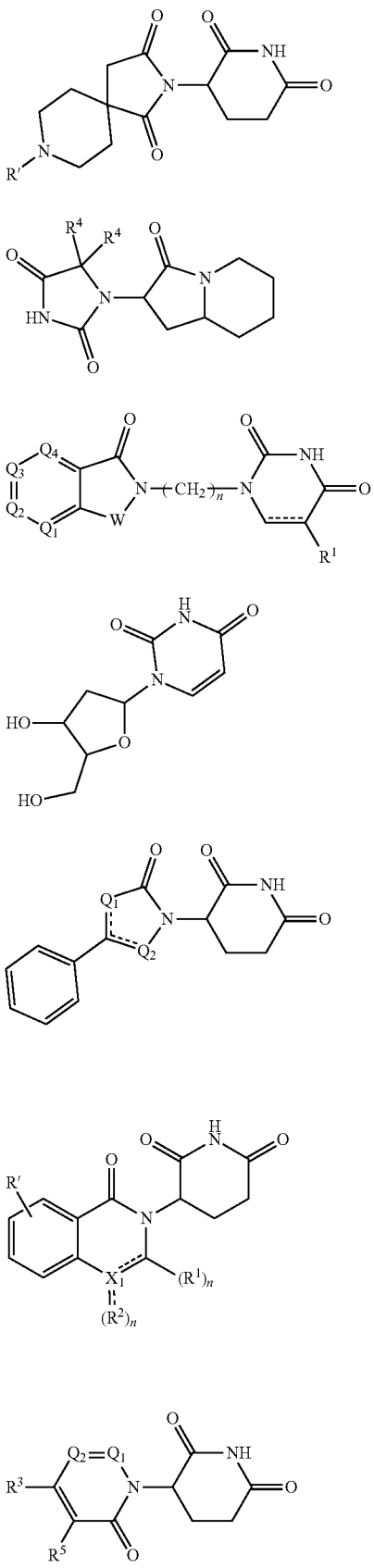

548
-continued (af)
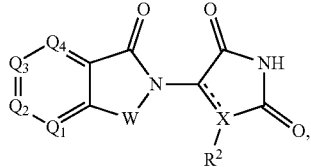

(am)

wherein:
at each occurrence W is independently selected from $CH_2$, CHR, C=O, $SO_2$, NH, and N-alkyl;
at each occurrence $Q_1$, $Q_2$, $Q_3$, $Q_4$, $Q_5$ are each independently C or N substituted with a group independently selected from R', N or N-oxide;
at each occurrence $R^1$ is independently selected from absent, H, OH, CN, $C_1$-$C_3$ alkyl, C=O;
at each occurrence $R^2$ is independently selected from the group absent, H, OH, CN, $C_1$-$C_3$ alkyl, $CHF_2$, $CF_3$, CHO, C(=O)$NH_2$;
at each occurrence $R^3$ is independently selected from H, alkyl, alkoxy, substituted alkoxy;
at each occurrence $R^4$ is independently selected from H, alkyl, substituted alkyl;
at each occurrence $R^5$ and $R^6$ are each independently H, halogen, C(=O)R', CN, OH, $CF_3$;
at each occurrence X is independently C, CH, C=O, or N;
at each occurrence $X_1$ is independently C=O, N, CH, or $CH_2$;
at each occurrence R' is independently selected from H, halogen, amine, alkyl, substituted alkyl, alkoxy, substituted alkoxy, $NR^2R^3$, C(=O)$OR^2$, or optionally substituted phenyl;
at each occurrence n is independently 0-4;
at each occurrence ⫽ is a single or double bond; and
the CLM is covalently joined to a PTM, a chemical linker group (L), a ULM, CLM, CLM', or combinations thereof.

11. The compound of claim 1, wherein the ULM is an MDM2 binding moiety (MLM) selected from the group consisting of a substituted imidazoline, a substituted spiroindolinone, a substituted pyrrolidine, a substituted piperidinone, a substituted morpholinone, a substituted pyrrolopyrimidine, a substituted imidazolopyridine, a substituted thiazoloimidazoline, a substituted pyrrolopyrrolidinone, and a substituted isoquinolinone.

12. The compound of claim 1, wherein the ULM is a IAP E3 ubiquitin ligase binding moiety (ILM) comprising alanine (A), valine (V), proline (P), or isoleucine (I), combinations thereof, or their unnatural mimetics.

13. The compound of claim 1, wherein the ULM is a IAP E3 ubiquitin ligase binding moiety (ILM) comprising an AVPI tetrapeptide fragment or derivative thereof.

14. The compound of claim 1, wherein the linker (L) comprises a chemical structural unit represented by the formula:

$$-(A^L)_q-,$$

wherein:
-$(A^L)_q$- is a group which is connected to at least one of ULM, PTM, or both;
q is an integer greater than or equal to 1;
each $A^L$ is independently selected from the group consisting of, a bond, $CR^{L1}R^{L2}$, O, S, S(=O), $SO_2$, $NR^{L3}$, $SO_2NR^{L3}$, $SONR^{L3}$, $CONR^{L3}$, $NR^{L3}CONR^{L4}$, NR$^{L3}$SO$_2$NR$^{L4}$, C(=O), CR$^{L1}$=CR$^{L2}$, C=C, SiR$^{L1}$R$^{L2}$, P(=O)R$^{L1}$, P(=O)OR$^{11}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 R$^{L1}$ or R$^{L2}$ groups, C$_{3-11}$heterocyclyl optionally substituted with 0-6 R$^{L1}$ or R$^{L2}$ groups, aryl optionally substituted with 0-6 R$^{L1}$ or R$^{L2}$ groups, heteroaryl optionally substituted with 0-6 R$^{L1}$ or R$^{L2}$ groups, where R$^{L1}$ or R$^{L2}$, each independently are optionally linked to other groups to form cycloalkyl or heterocyclyl moiety, optionally substituted with 0-4 R$^{L5}$ groups; and R$^{L1}$, R$^{L2}$, R$^{L3}$, R$^{L4}$ and R$^{L5}$ are, each independently, H, halogen, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(=O)(OC$_{1-8}$alkyl)(C$_{1-8}$alkyl), P(=O)(OC$_{1-8}$alkyl)$_2$, C≡C—C$_{1-8}$alkyl, C=CH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$ alkyl), NHCON(C$_{1-8}$alkyl)$_2$, NHCONH$_2$, N(C$_{1-8}$alkyl) SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

15. The compound of claim 1, wherein the linker (L) is selected from the group consisting of:

—N(R)—(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—, —O—(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—, —O—(CH$_2$)$_m$—O(CH$_2$)$_n$—O(CH$_2$)$_o$—O(CH$_2$)$_p$—O(CH$_2$)$_q$—O(CH$_2$)$_r$—O—, —N(R)—(CH$_2$)$_m$—O(CH$_2$)$_n$—O(CH$_2$)$_o$—O(CH$_2$)$_p$—O(CH$_2$)$_q$—O(CH$_2$)$_r$—O—, —(CH$_2$)$_m$—O(CH$_2$)$_n$—O(CH$_2$)$_o$—O(CH$_2$)$_p$—O(CH$_2$)$_q$—O(CH$_2$)$_r$—O—, —(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—,

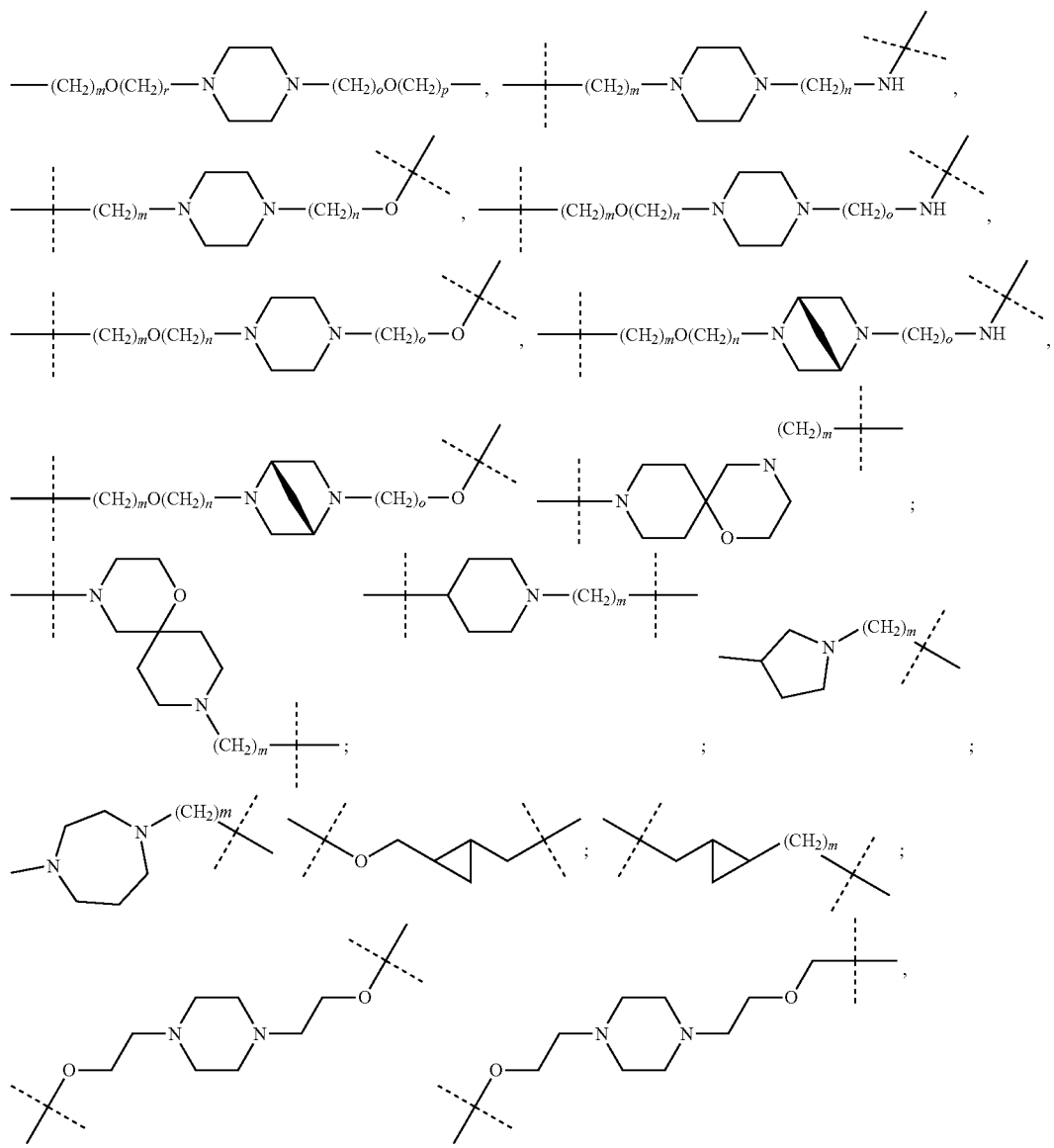

-continued
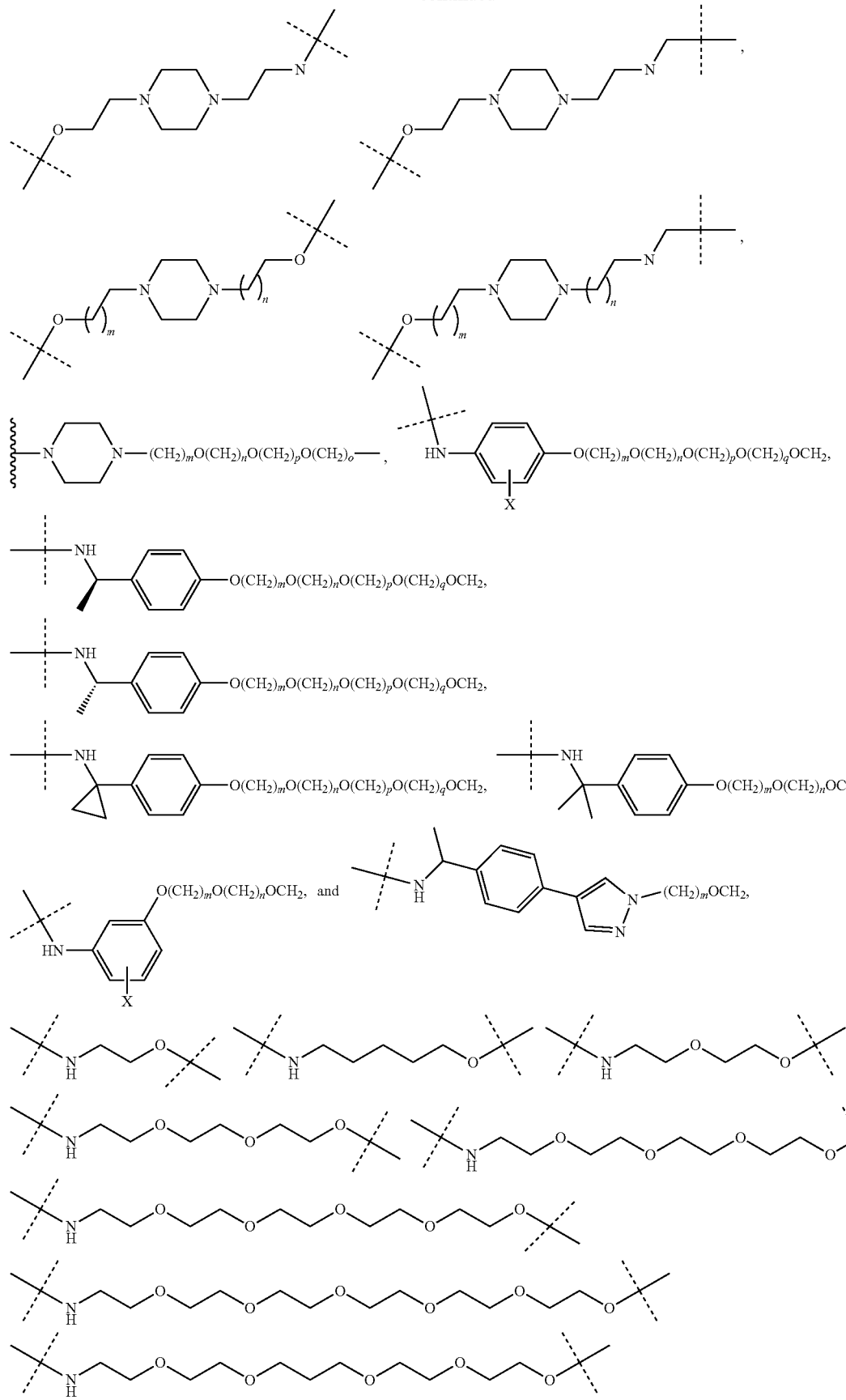

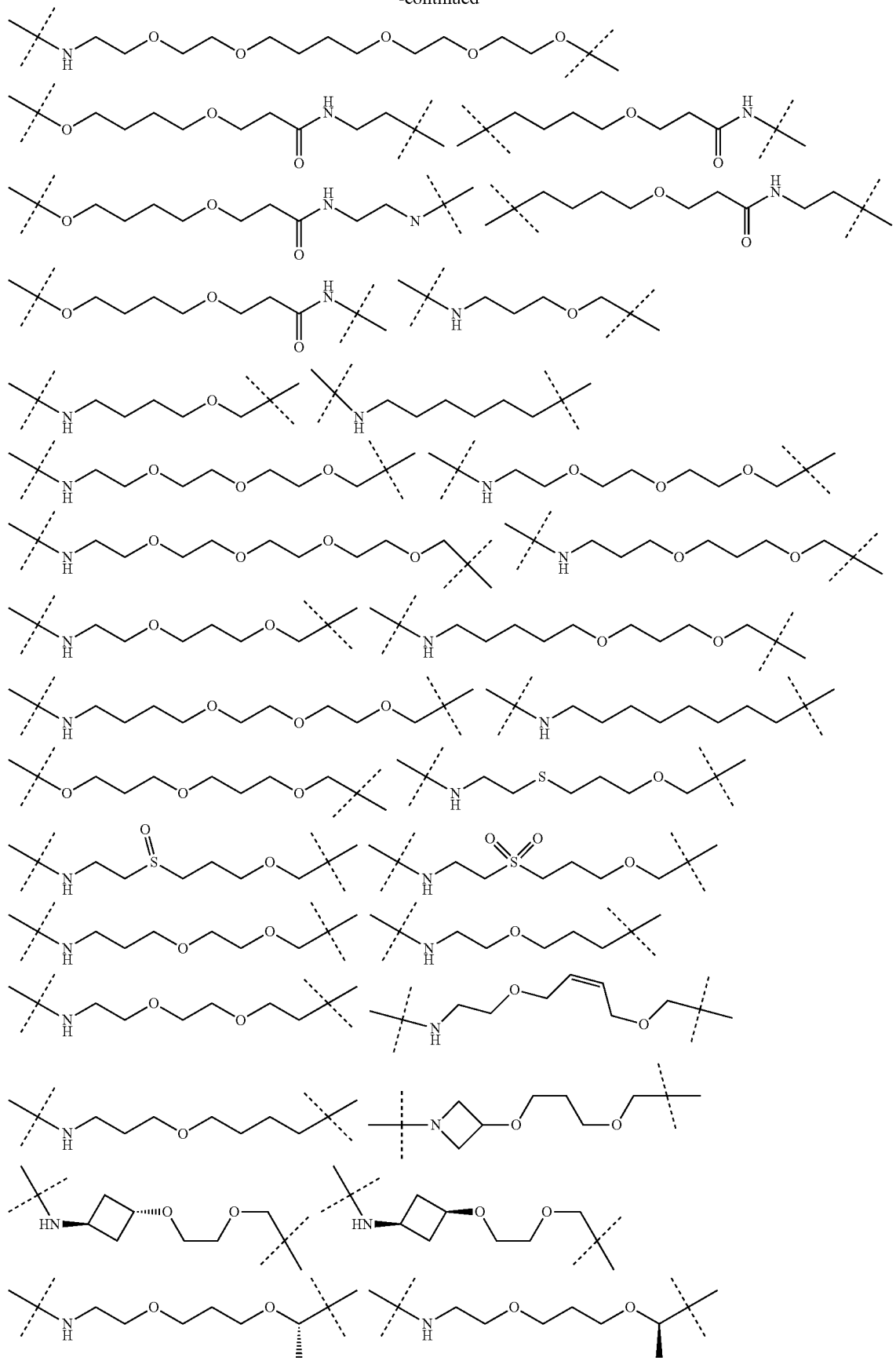

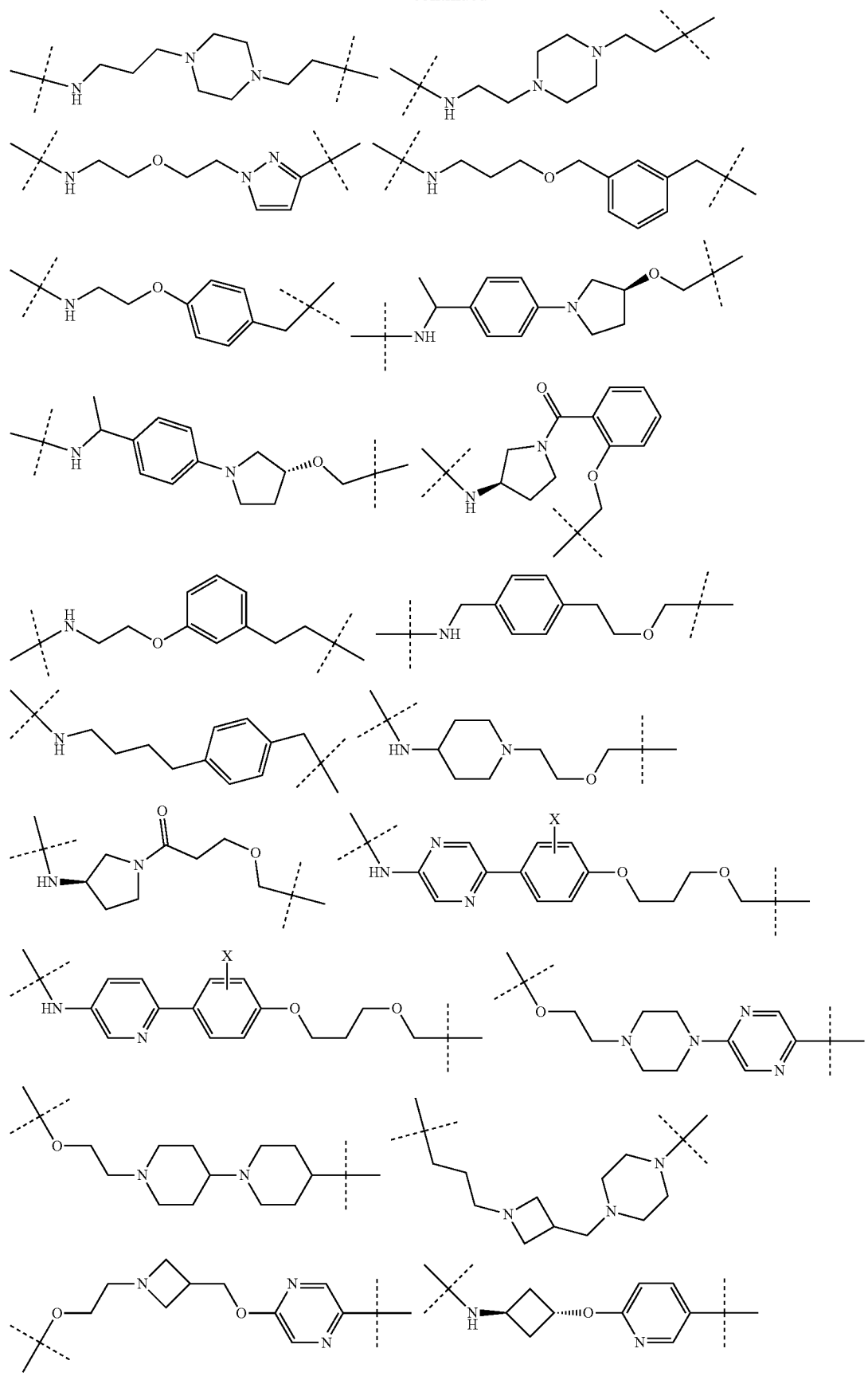

-continued
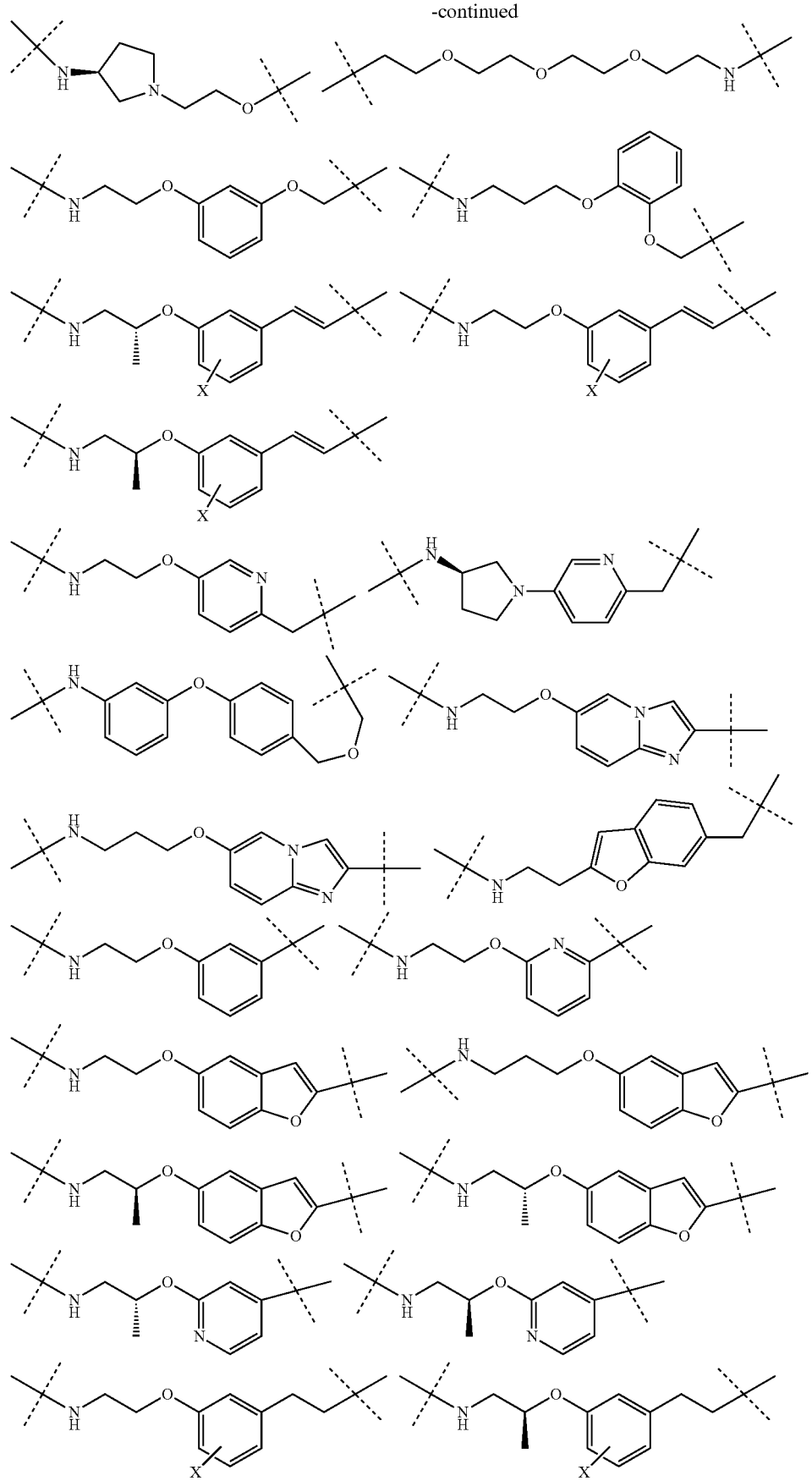

-continued
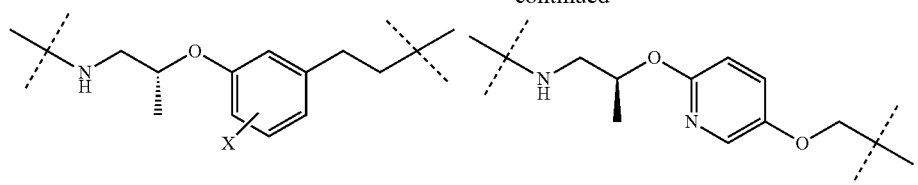
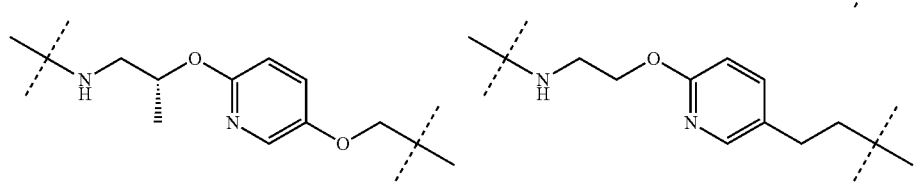
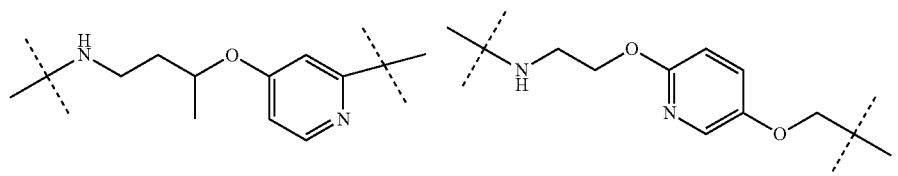
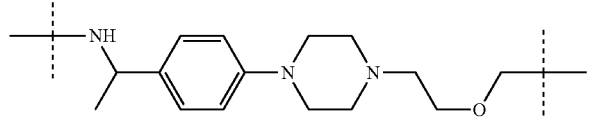
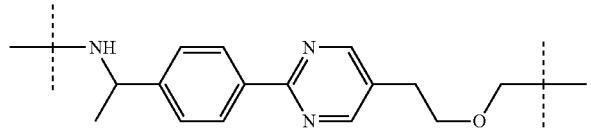
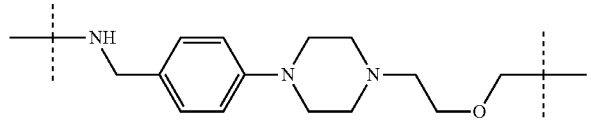
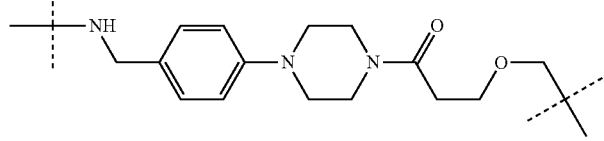
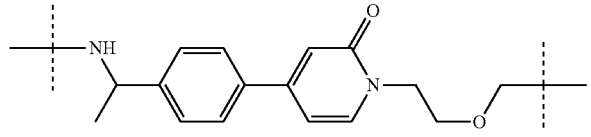
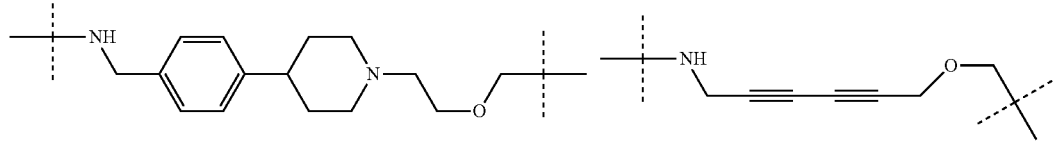
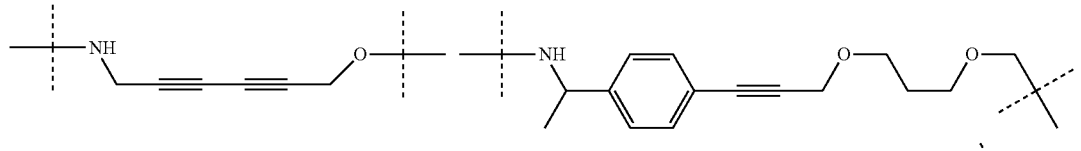
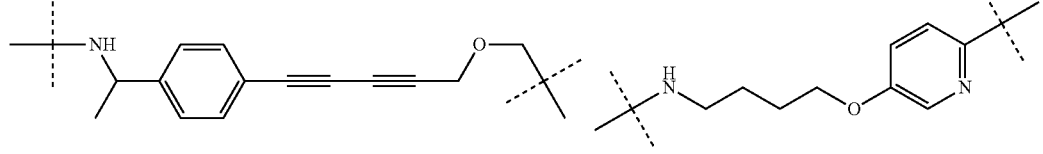

-continued
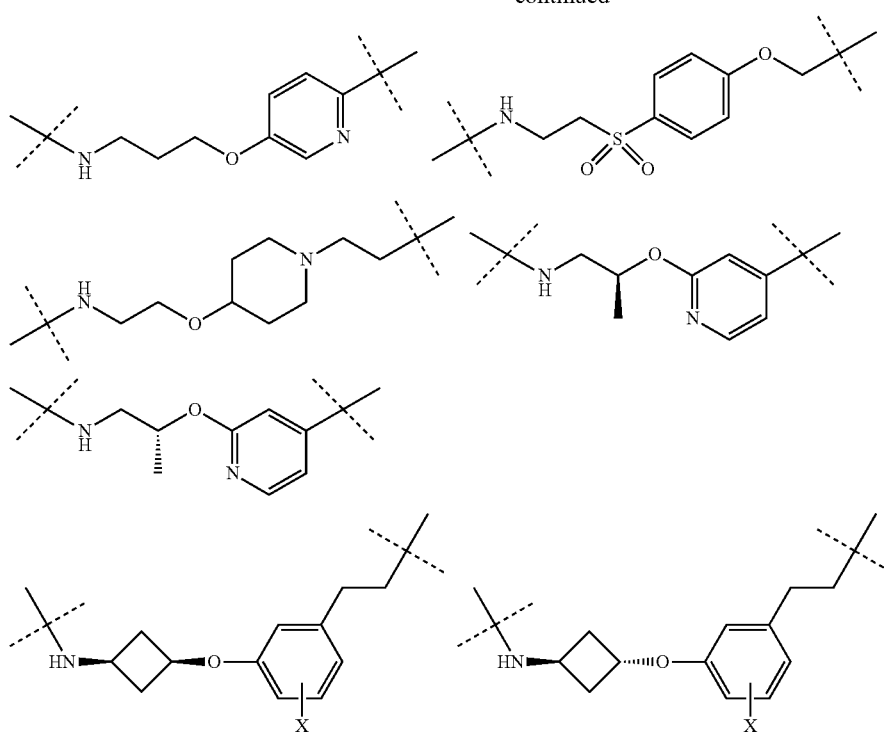
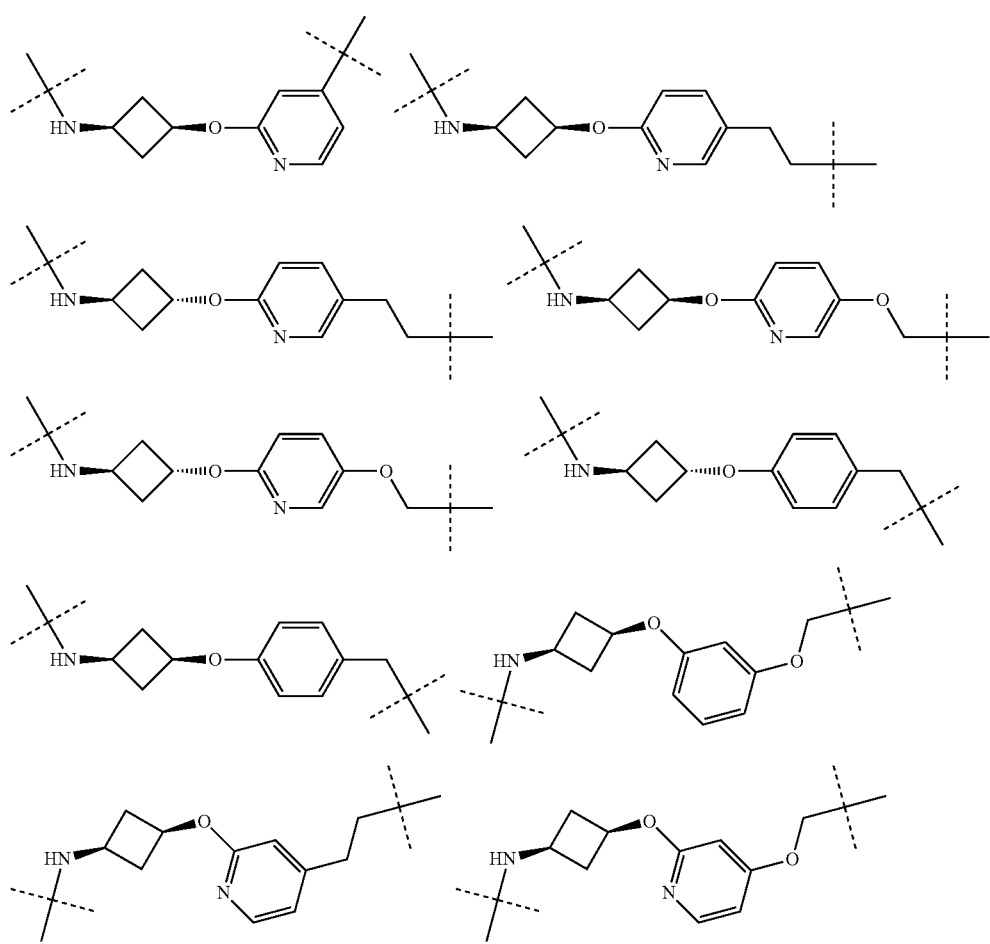
X = H, F

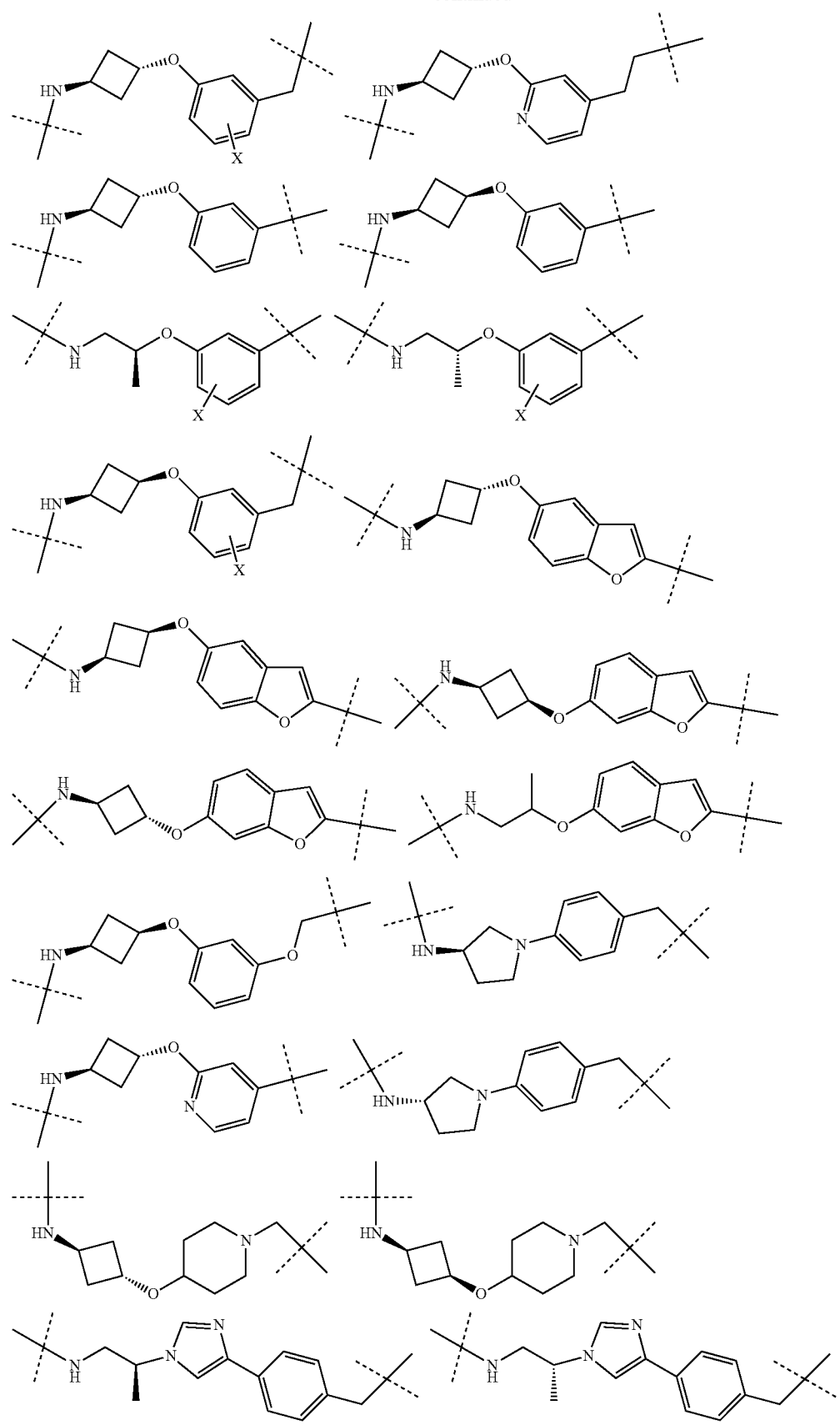

-continued
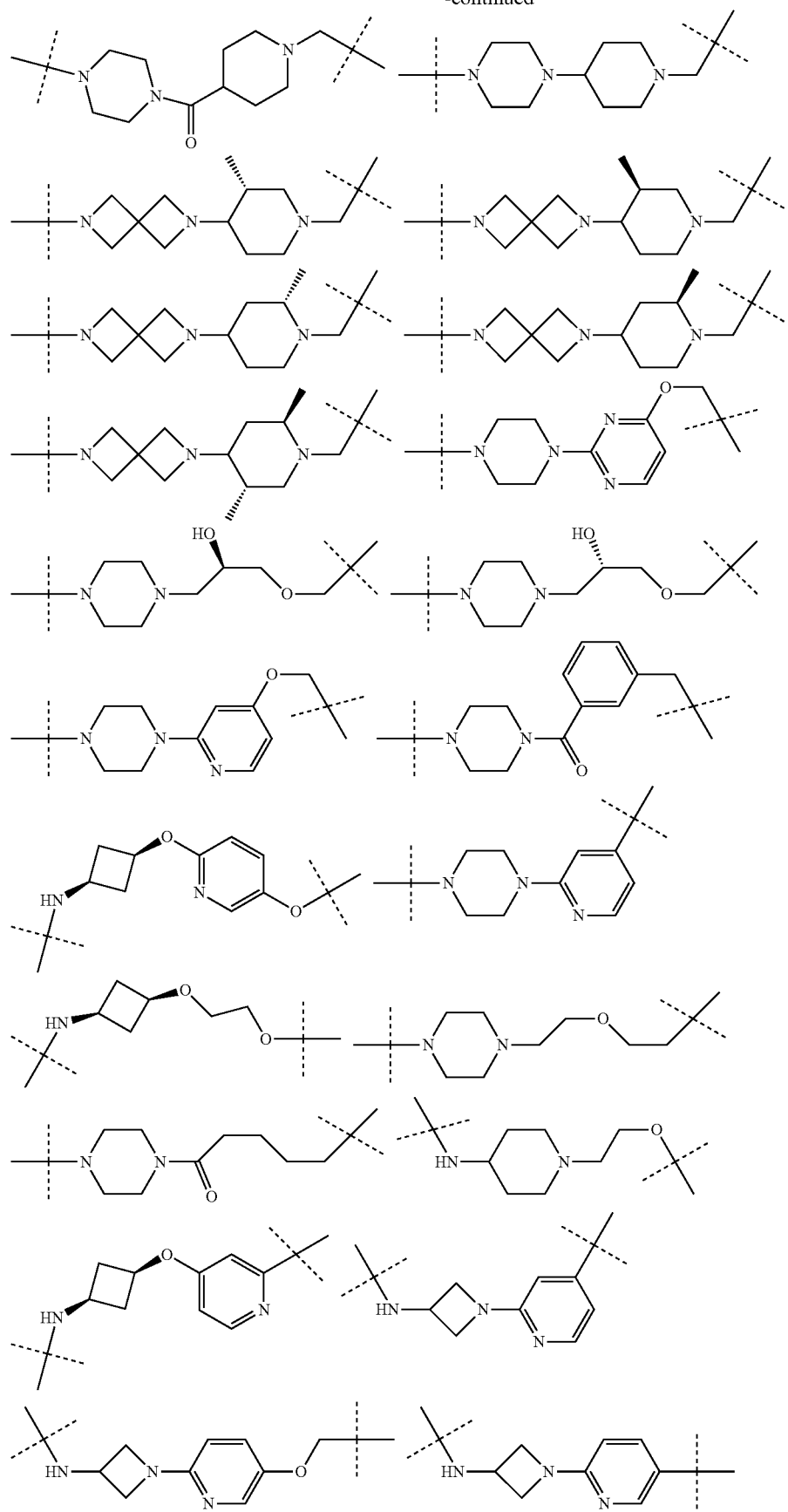

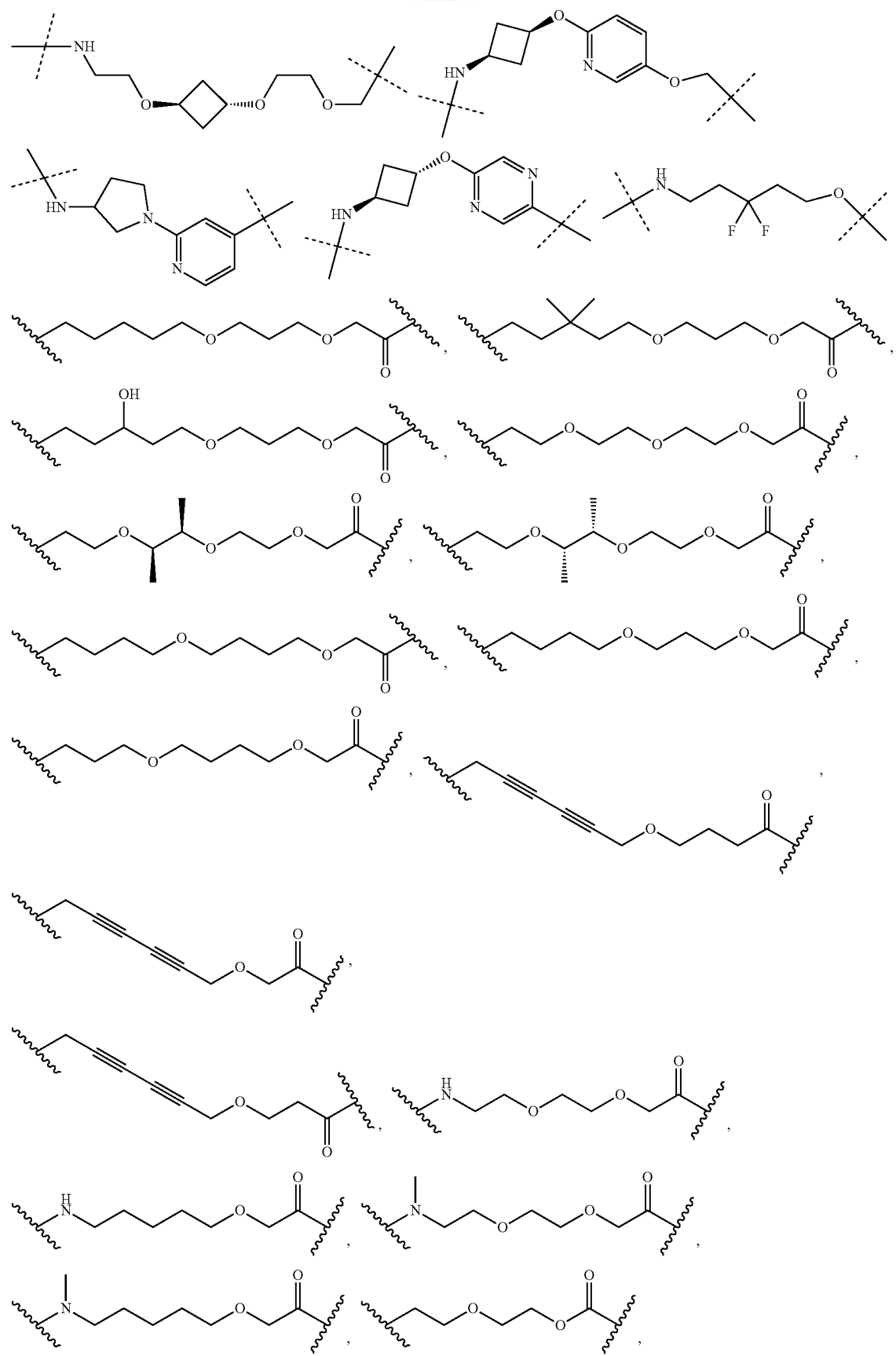

-continued
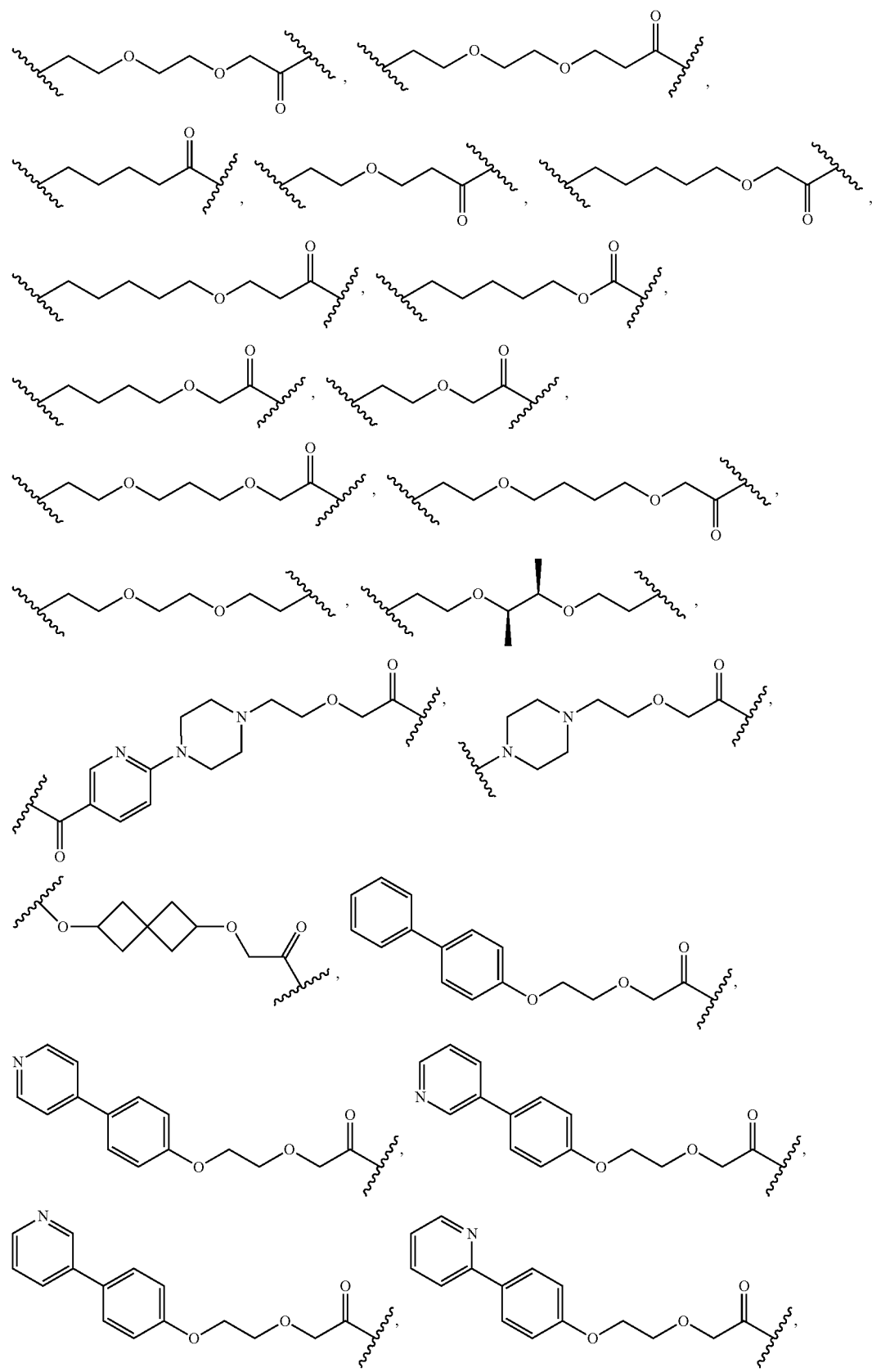

-continued
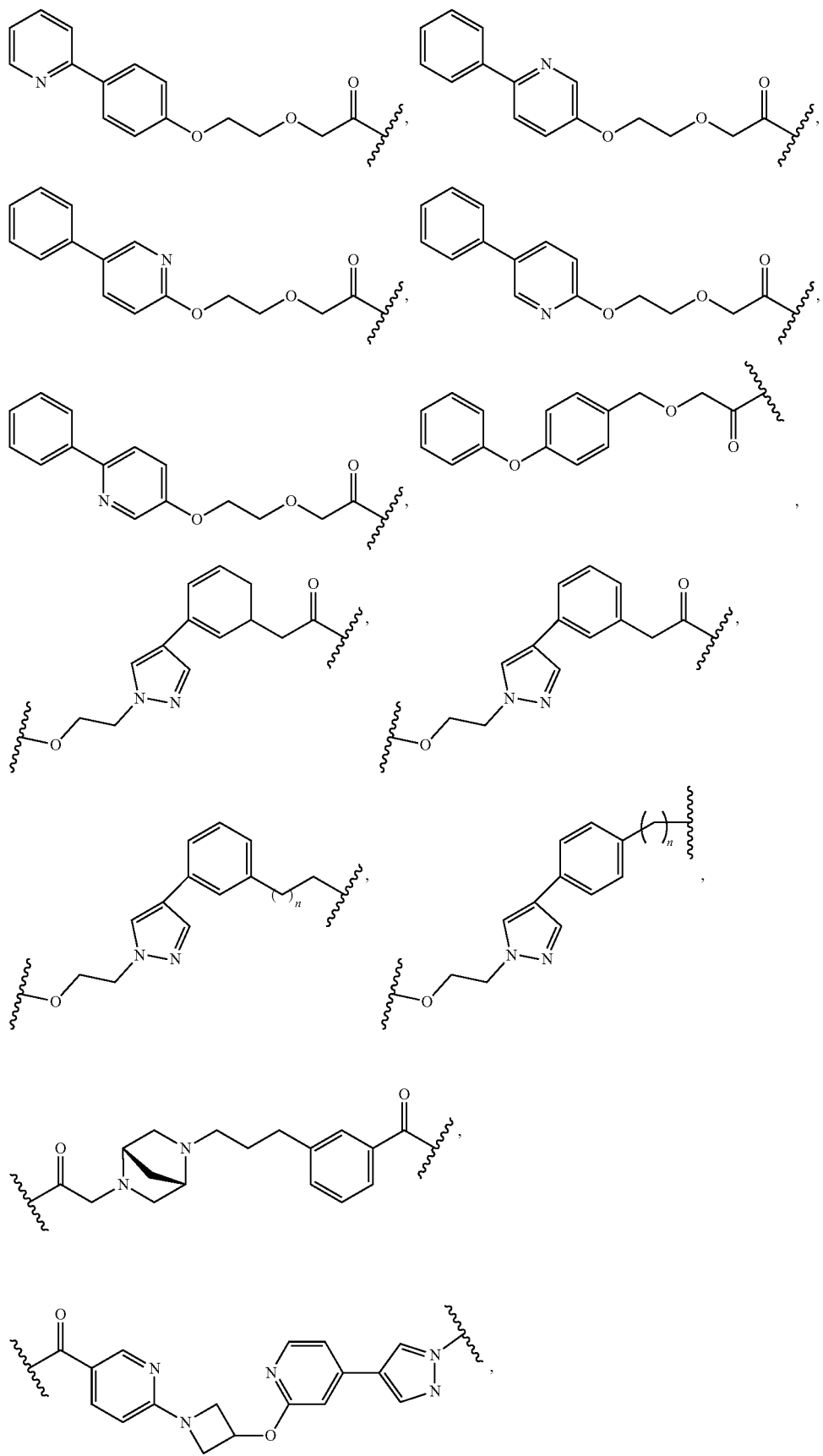

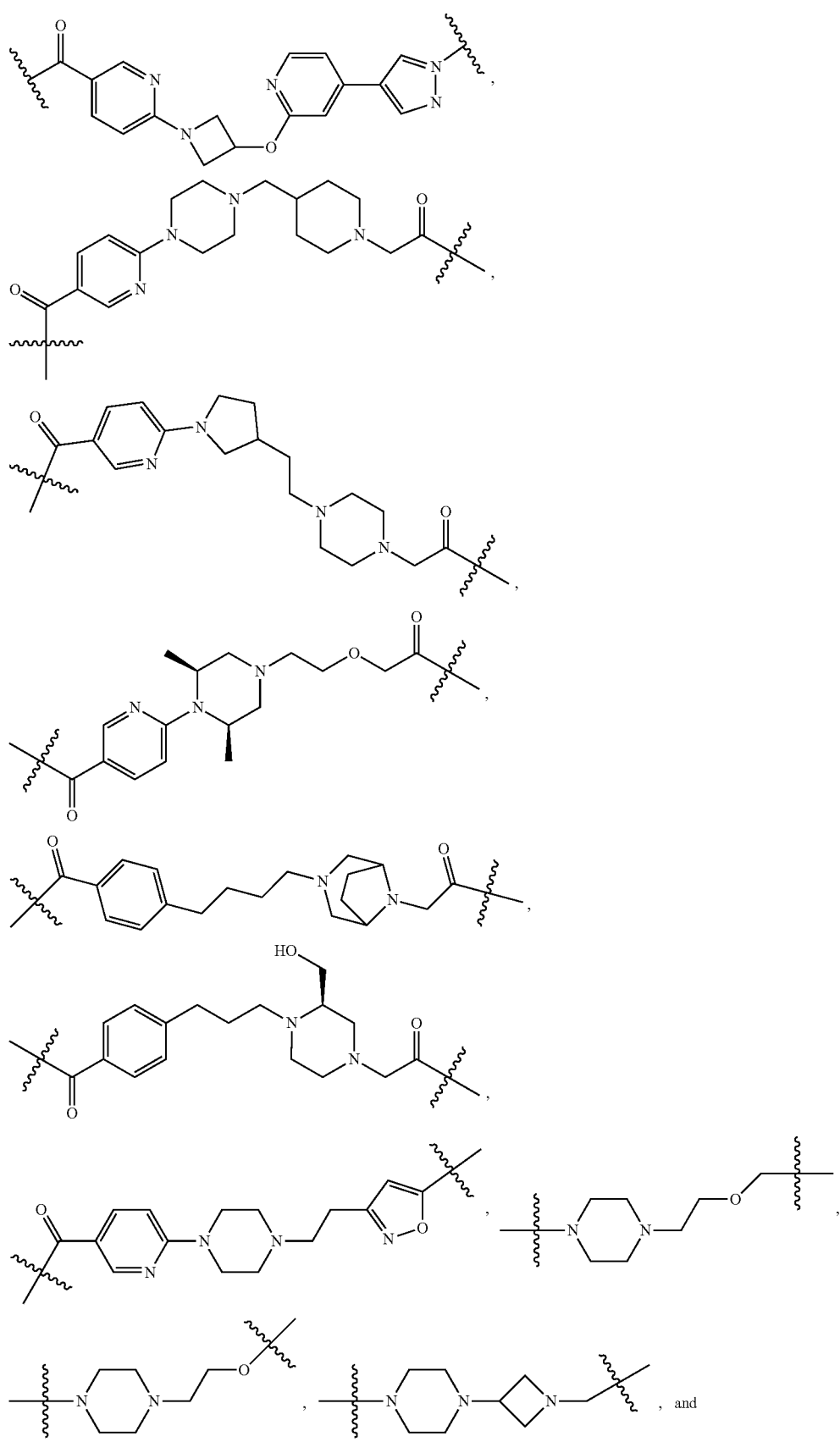

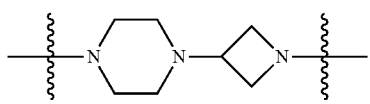
-continued
wherein each m, n, o, p, q, and r, is independently 0, 1, 2, 3, 4, 5, 6, 7, 8, 9, 10, 11, 12, 13, 14, 15, 16, 17, 18, 19, or 20, with the proviso that when m, n, o, p, q, or r is zero, there is no N-0 or $C_1$-$C_6$ bond, at each occurrence R is independently selected from the group consisting of H, methyl, and ethyl, and at each occurrence X is H or F.
16. The compound of claim 1, wherein the linker (L) is selected from the group consisting of:
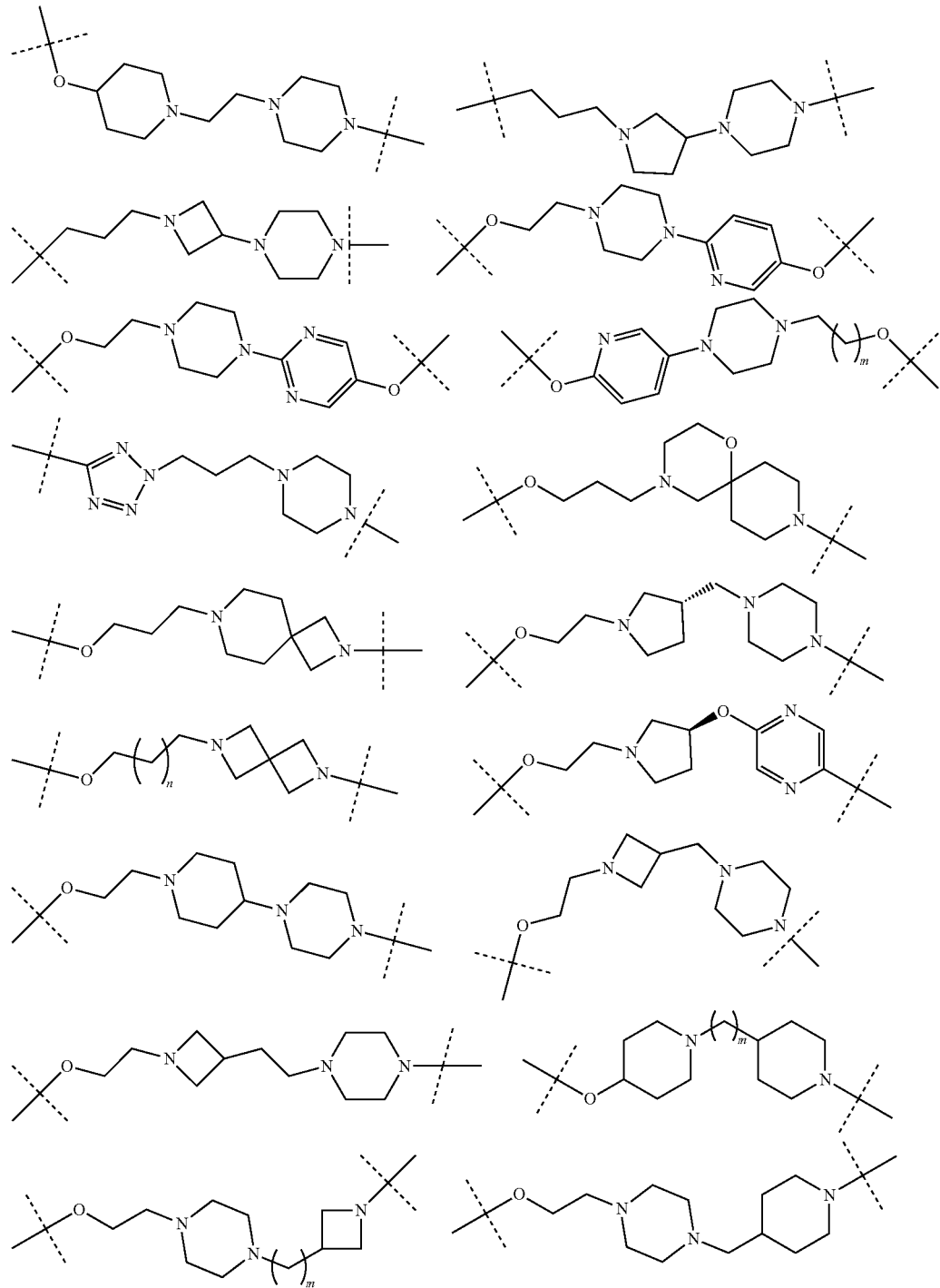

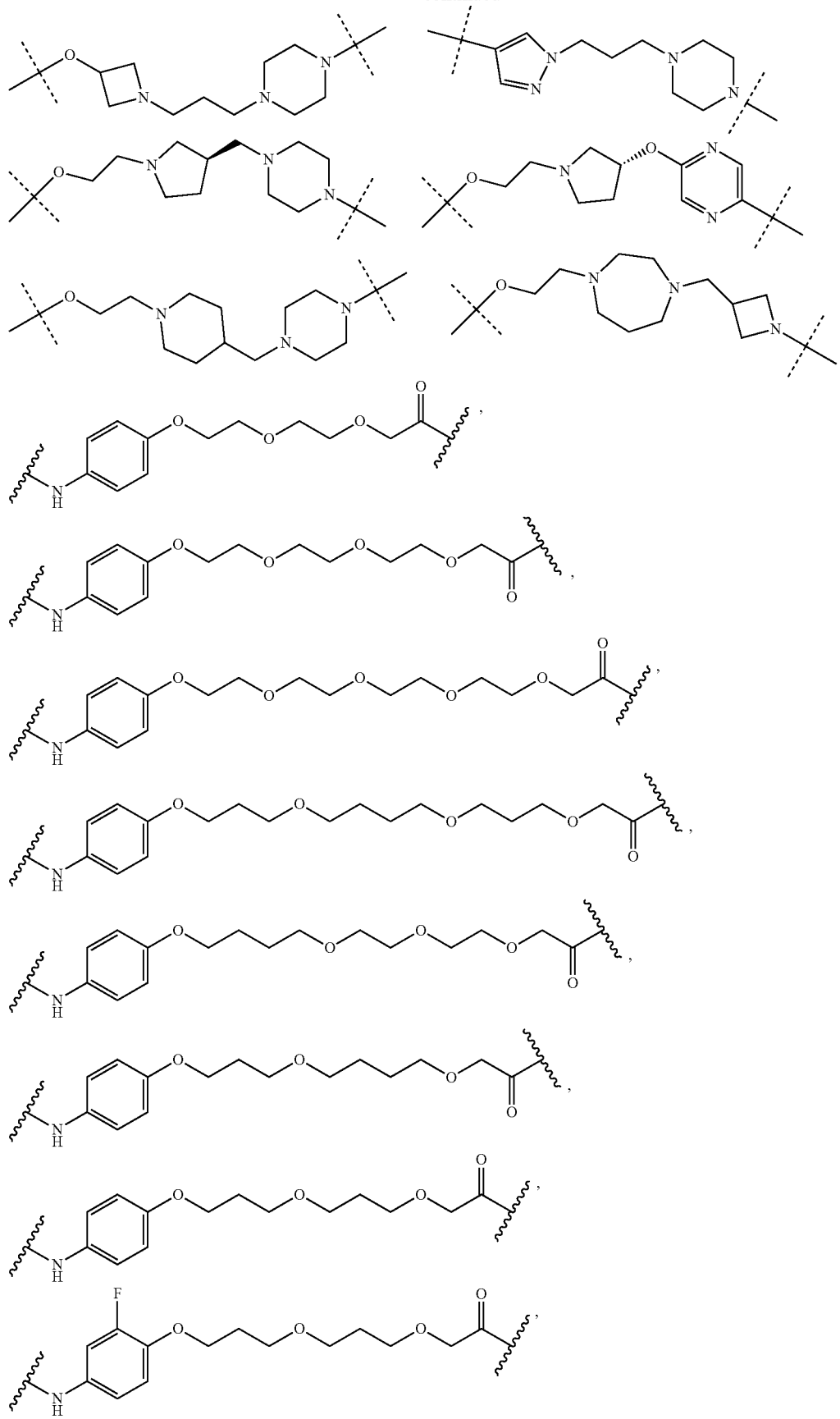

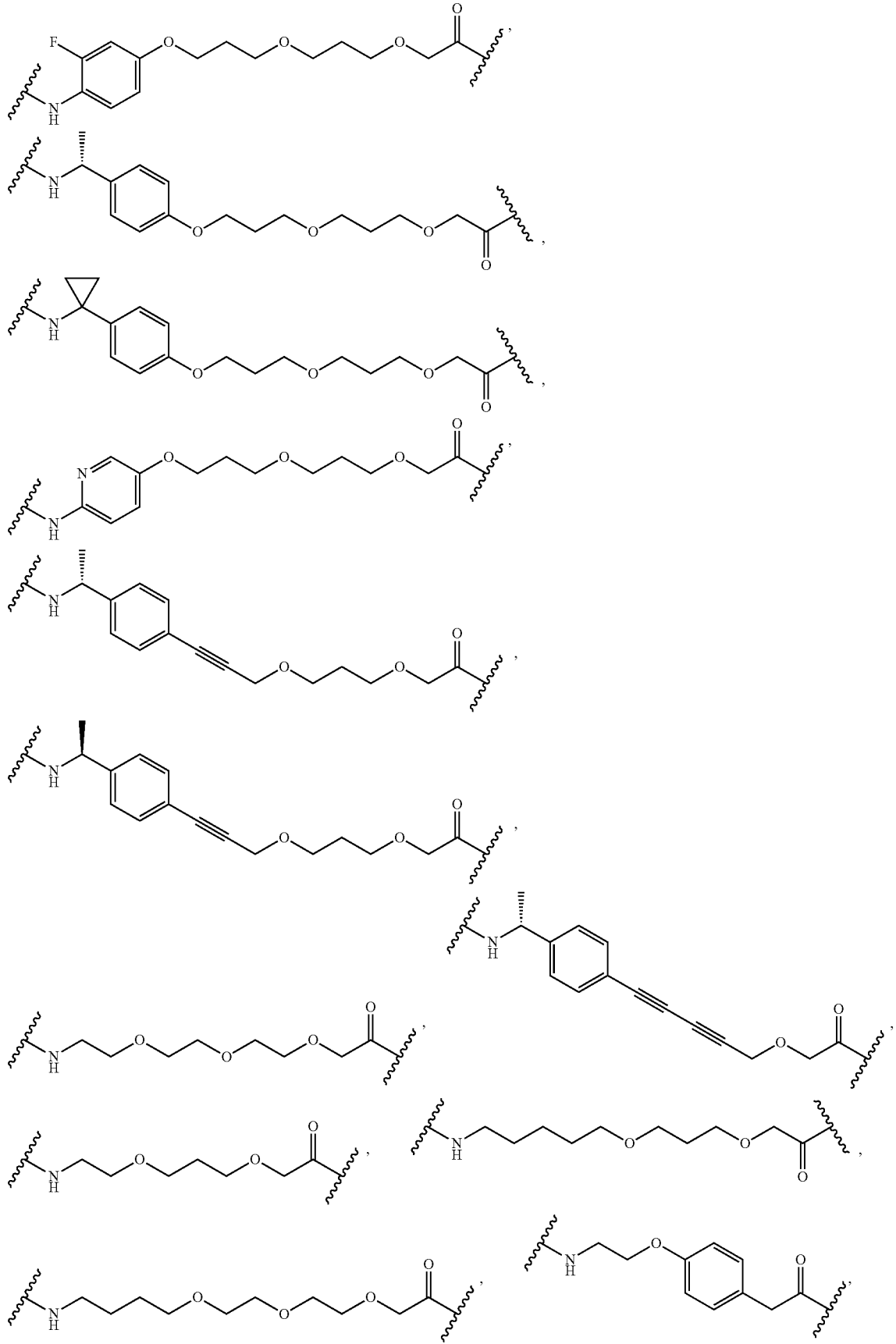

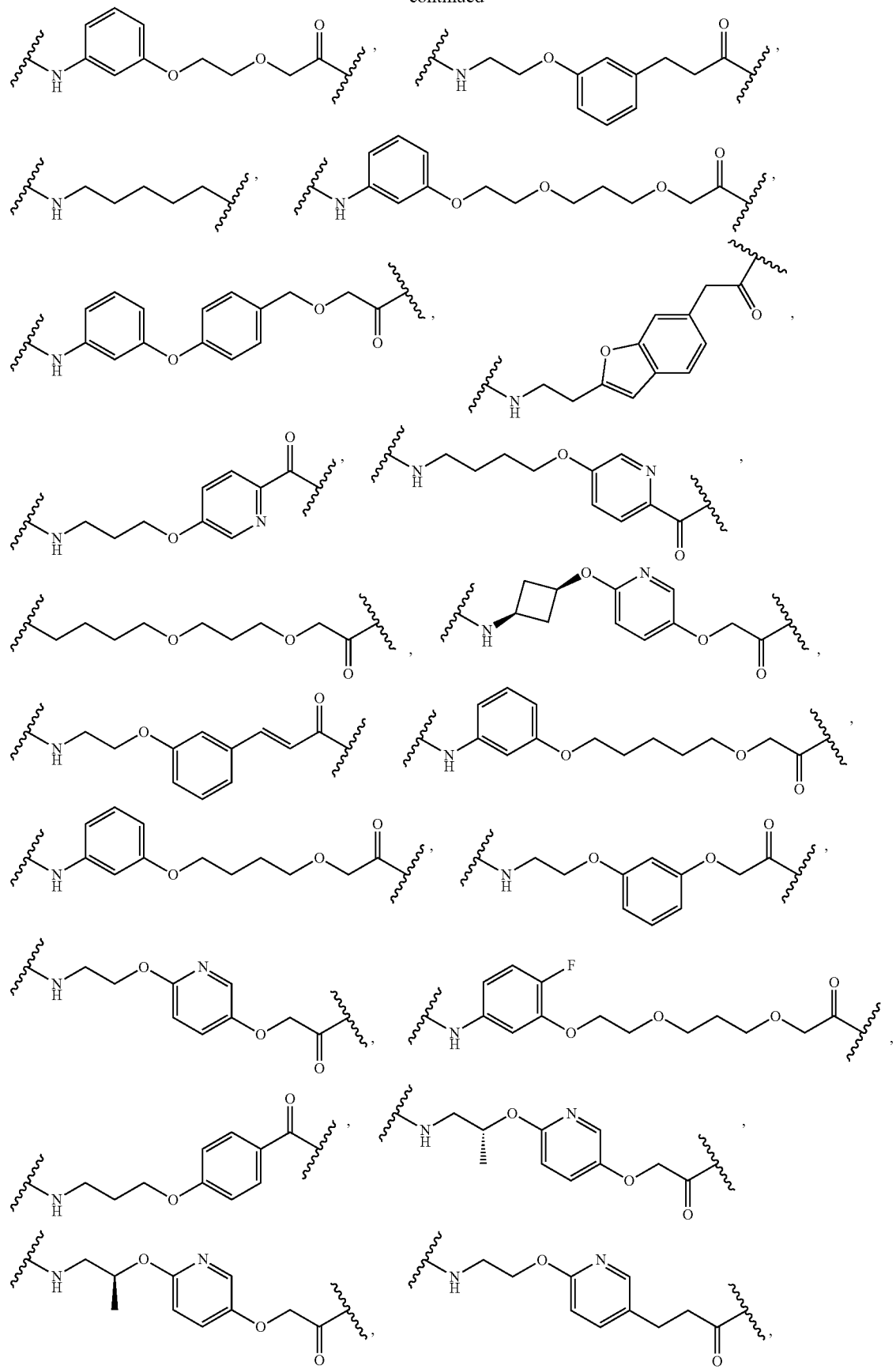

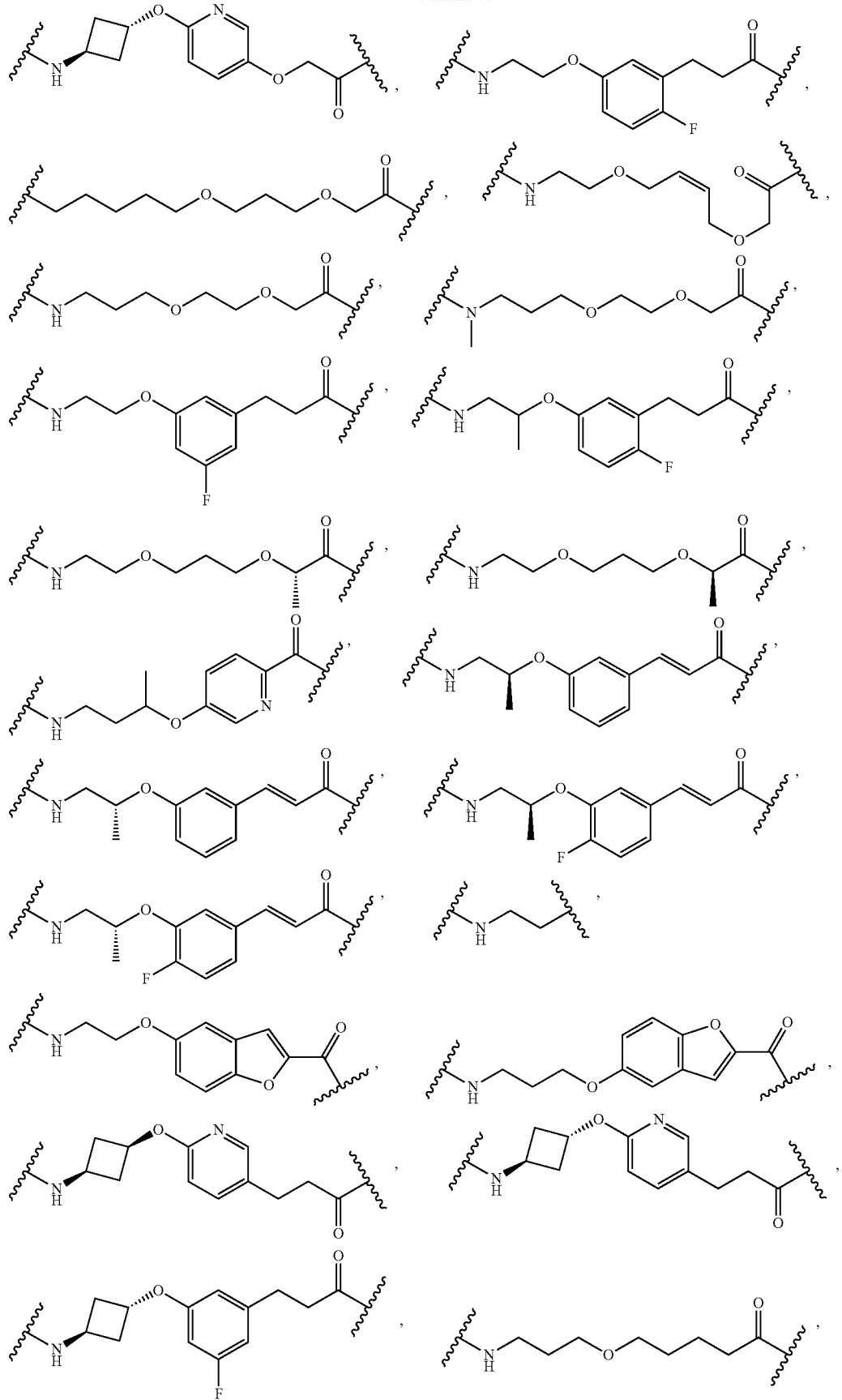

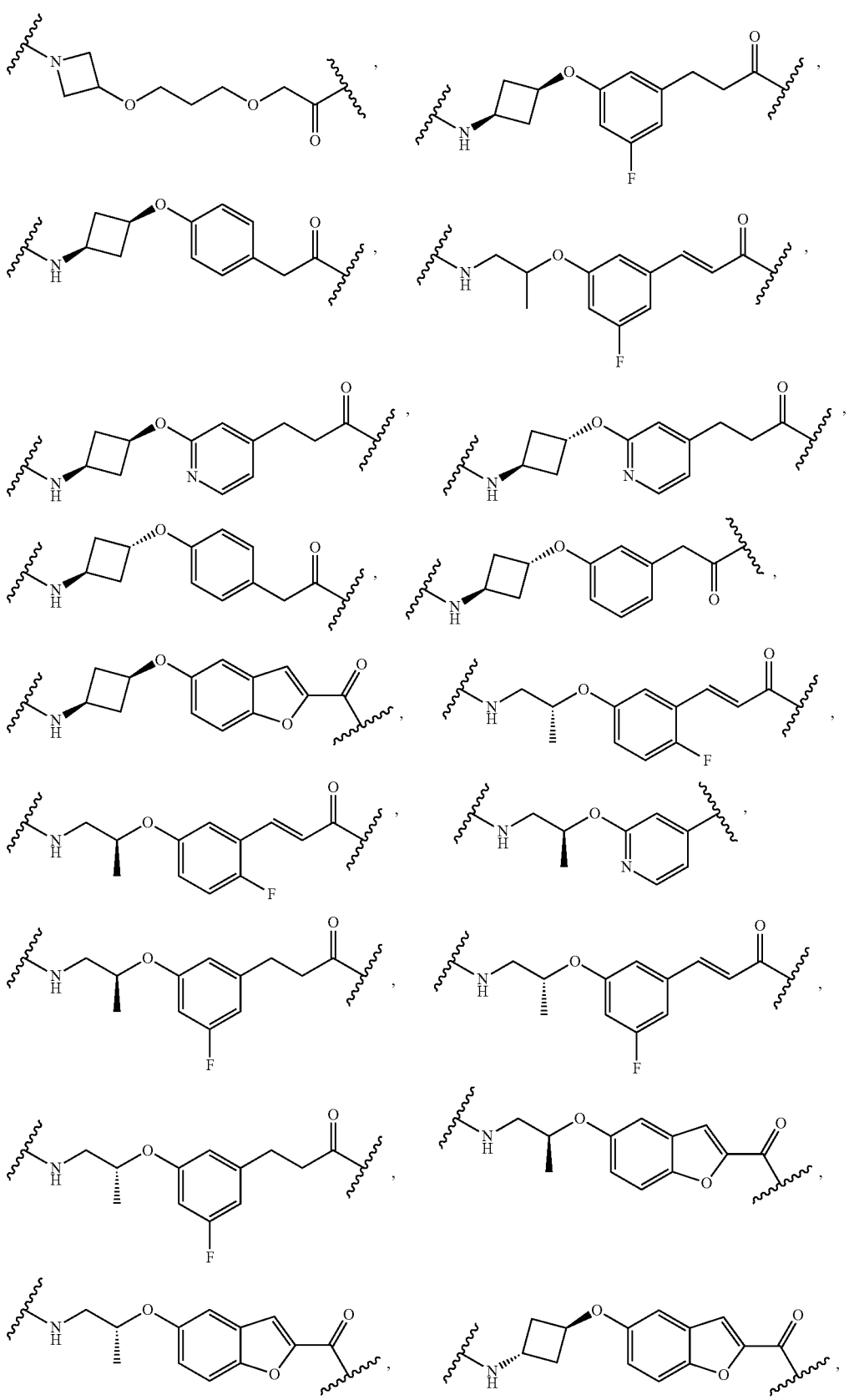

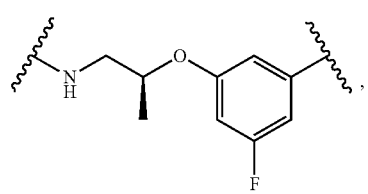
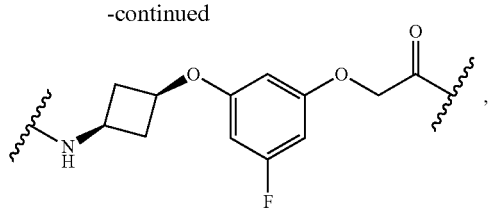
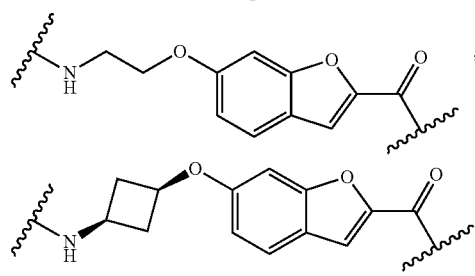
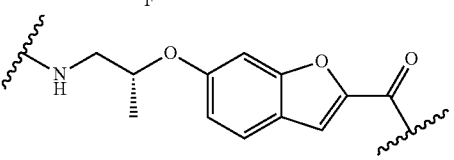
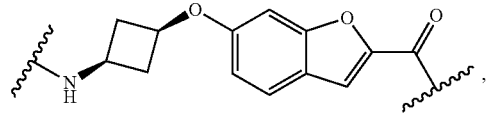
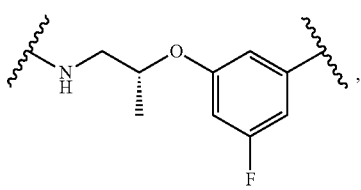
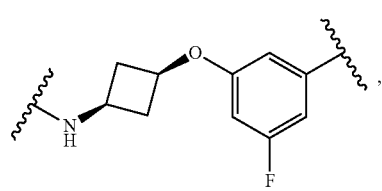
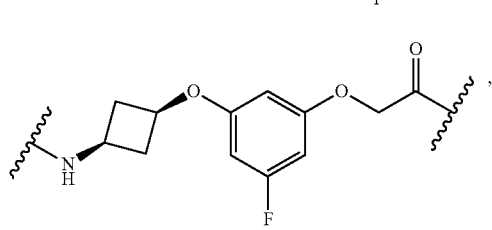
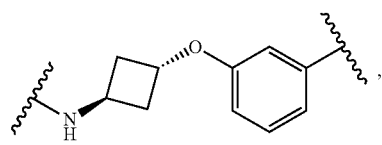
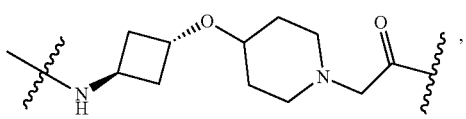
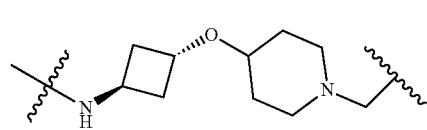
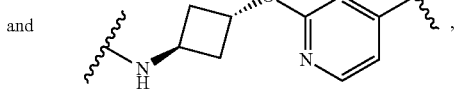
wherein at each occurrence m and n is independently selected from 0, 1, 2, 3, 4, 5, or 6.
17. The compound of claim 1, wherein the linker (L) is selected from the group consisting of:
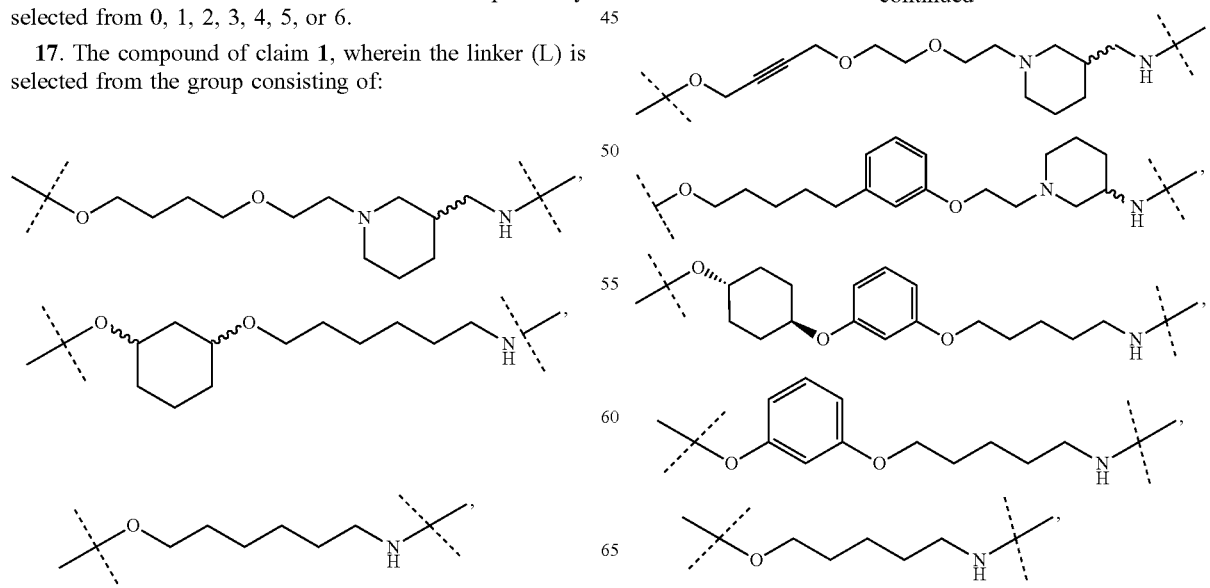

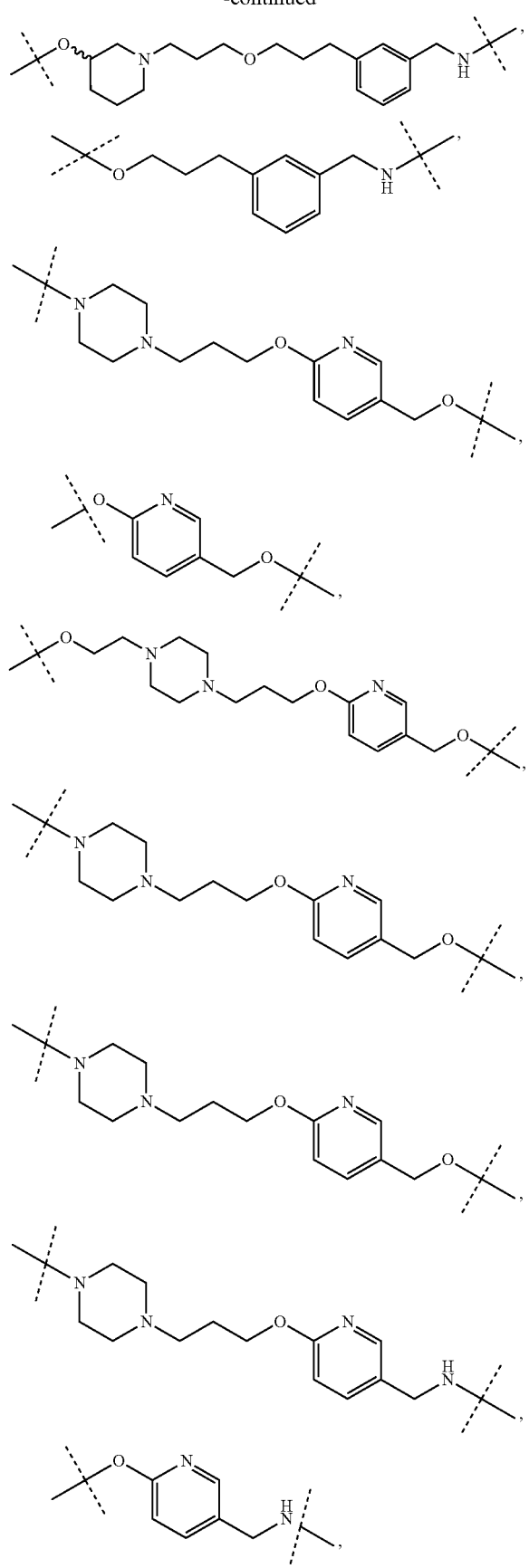
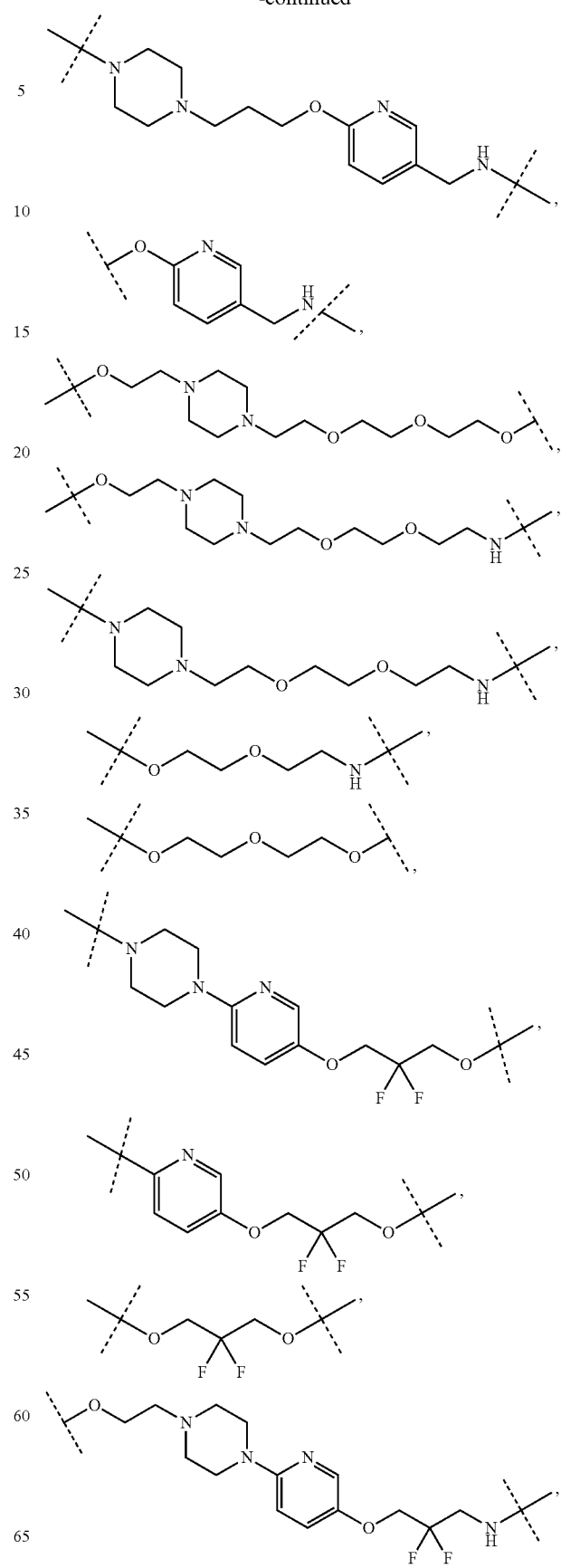

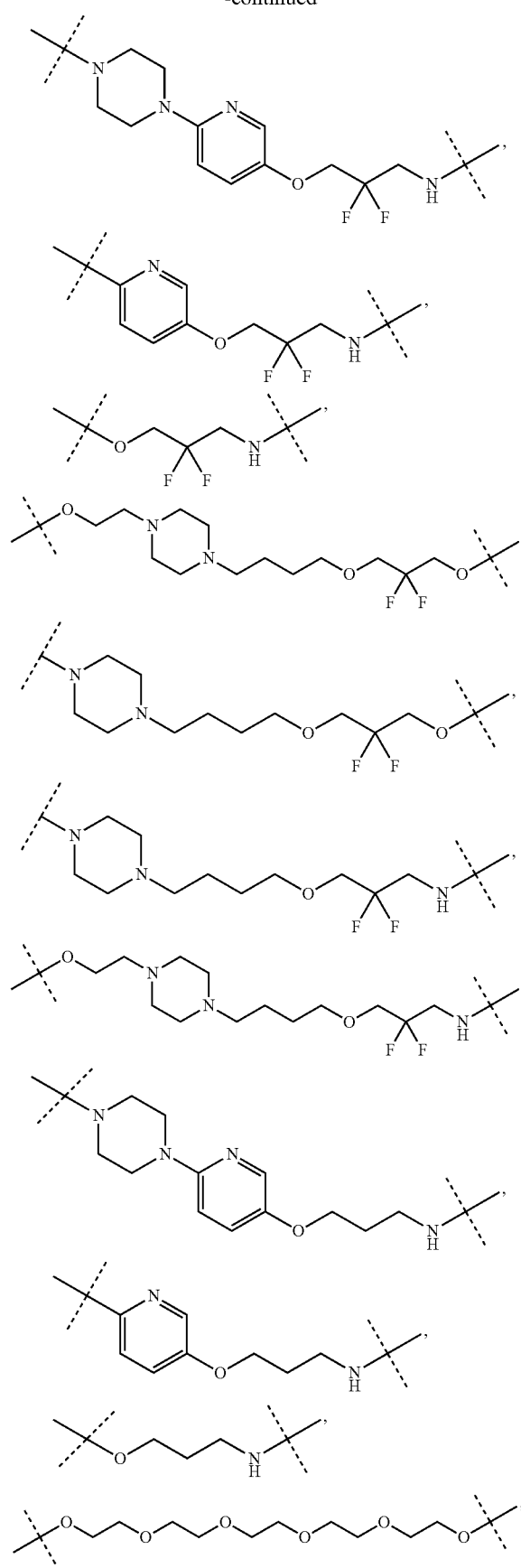
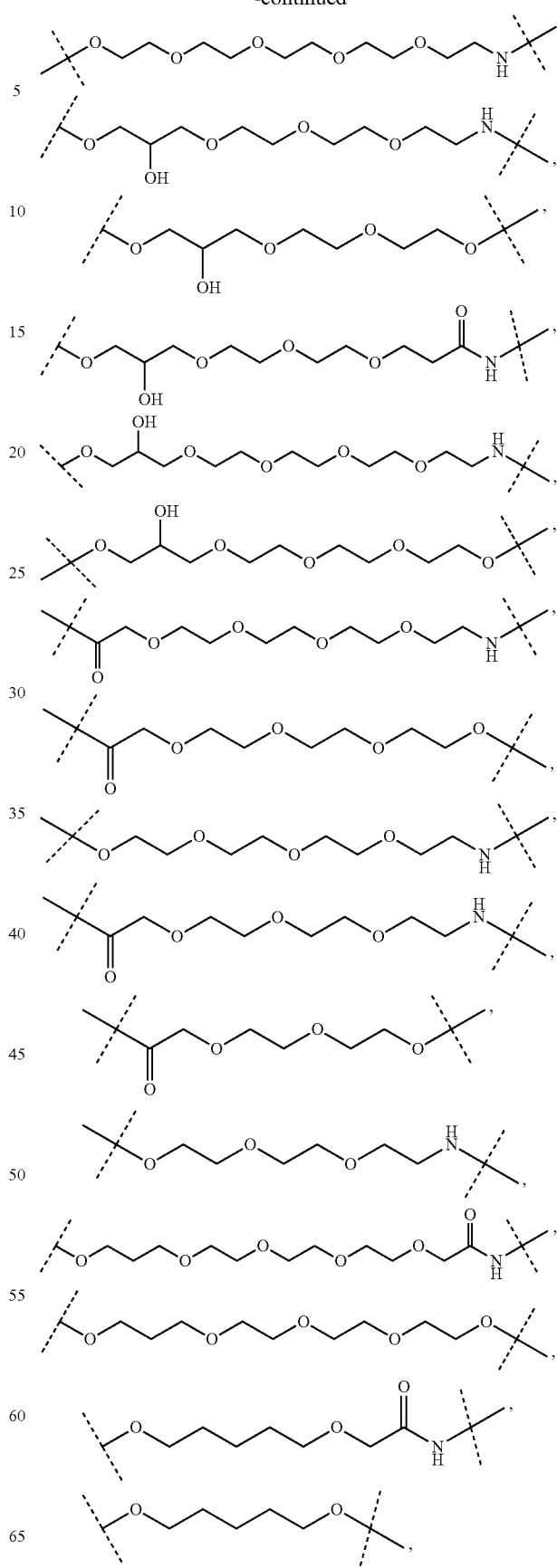

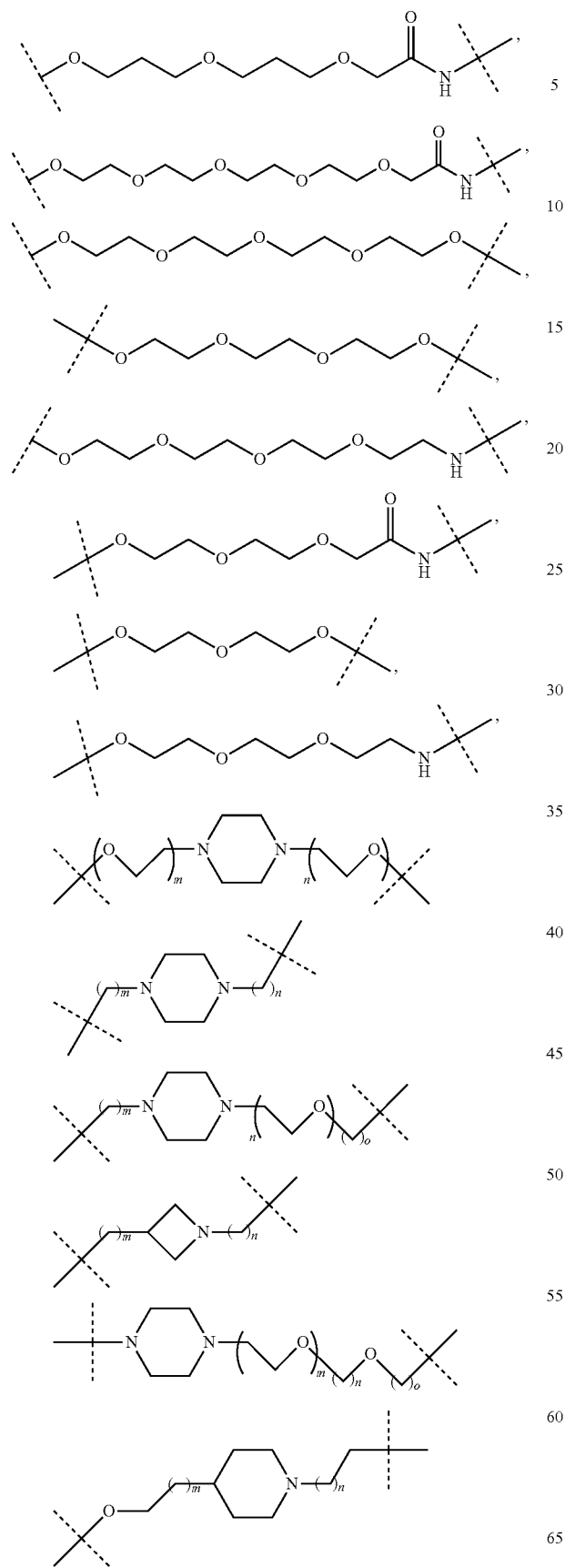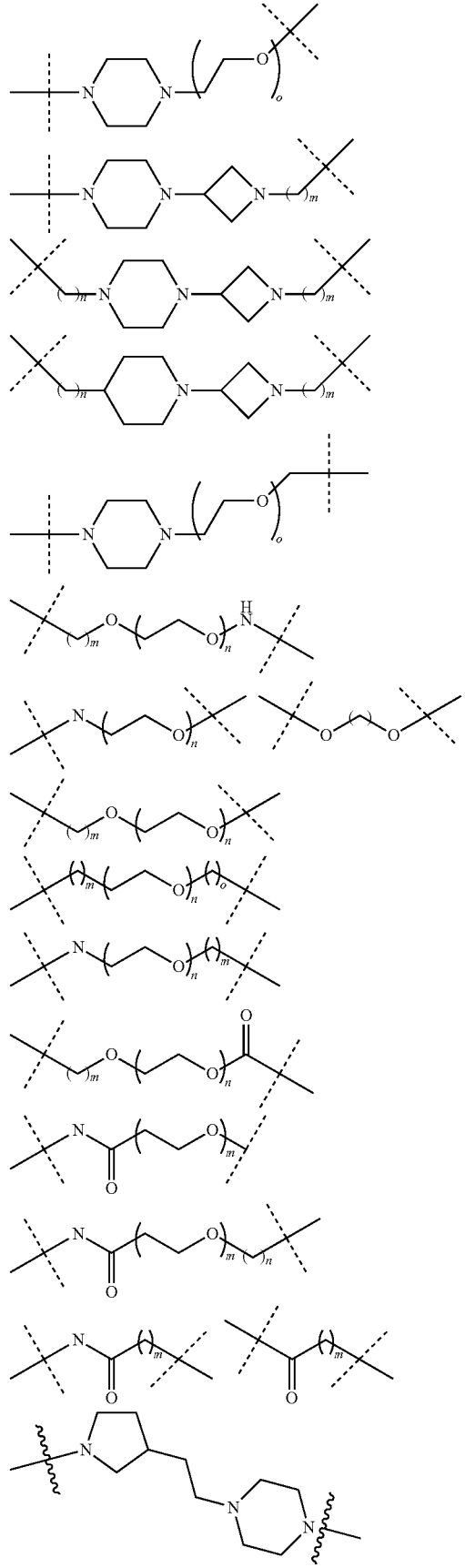

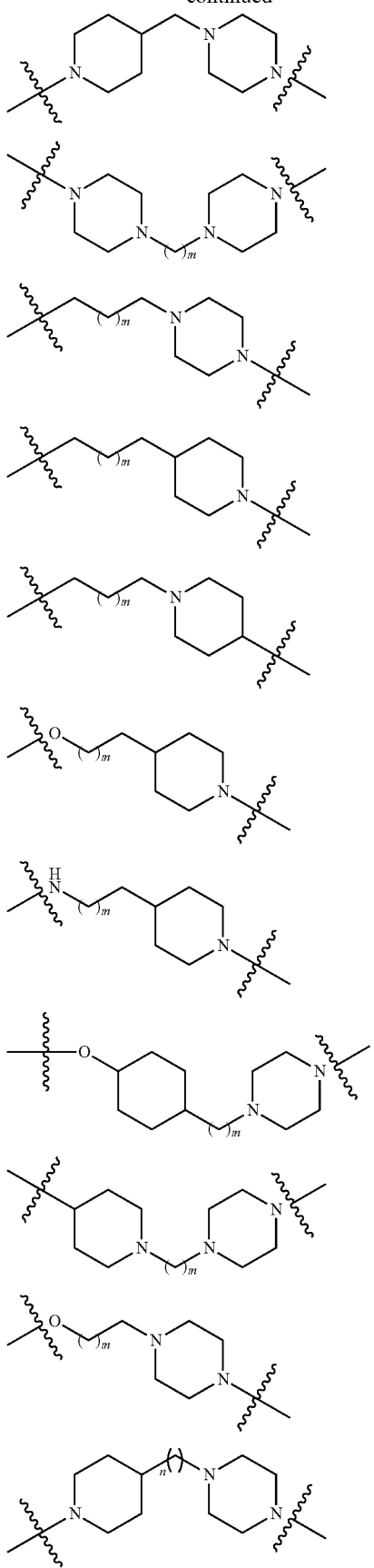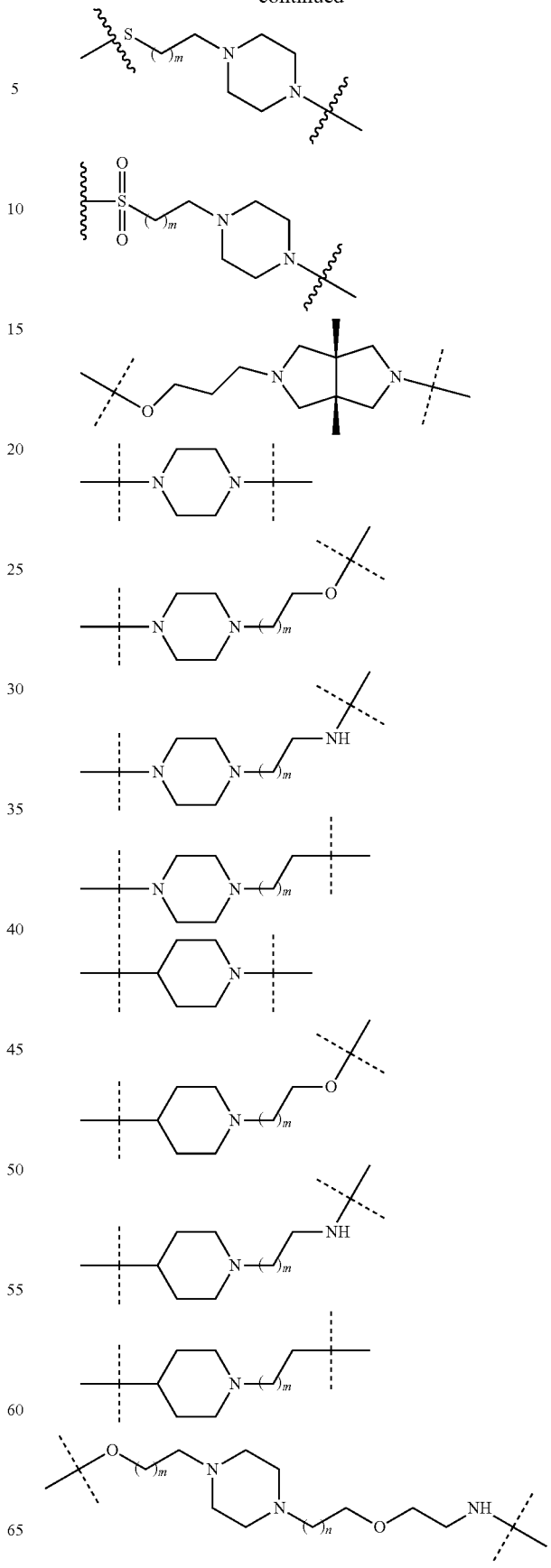

597
-continued
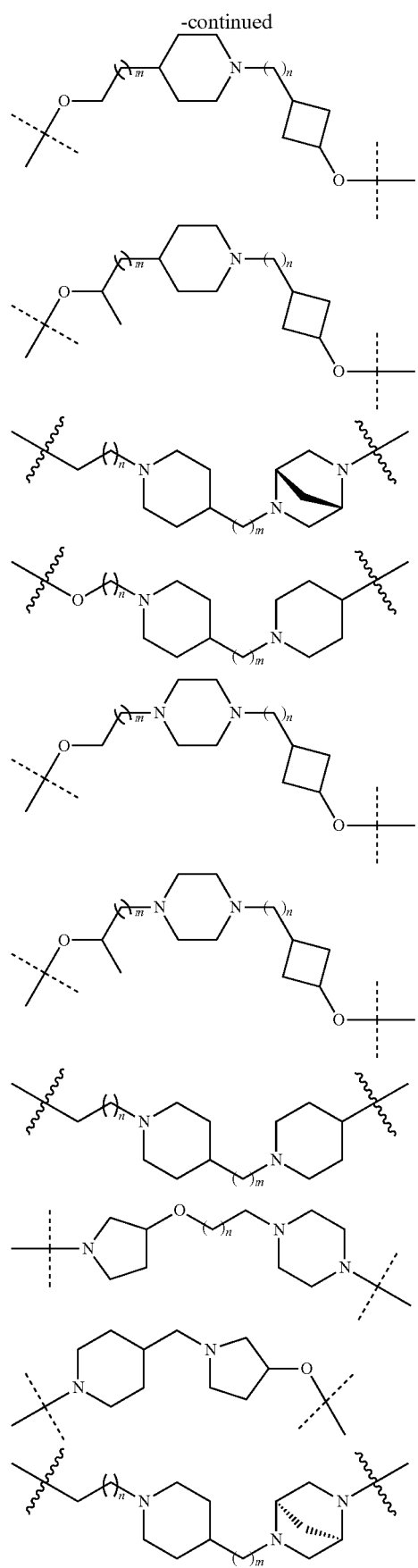
598
-continued
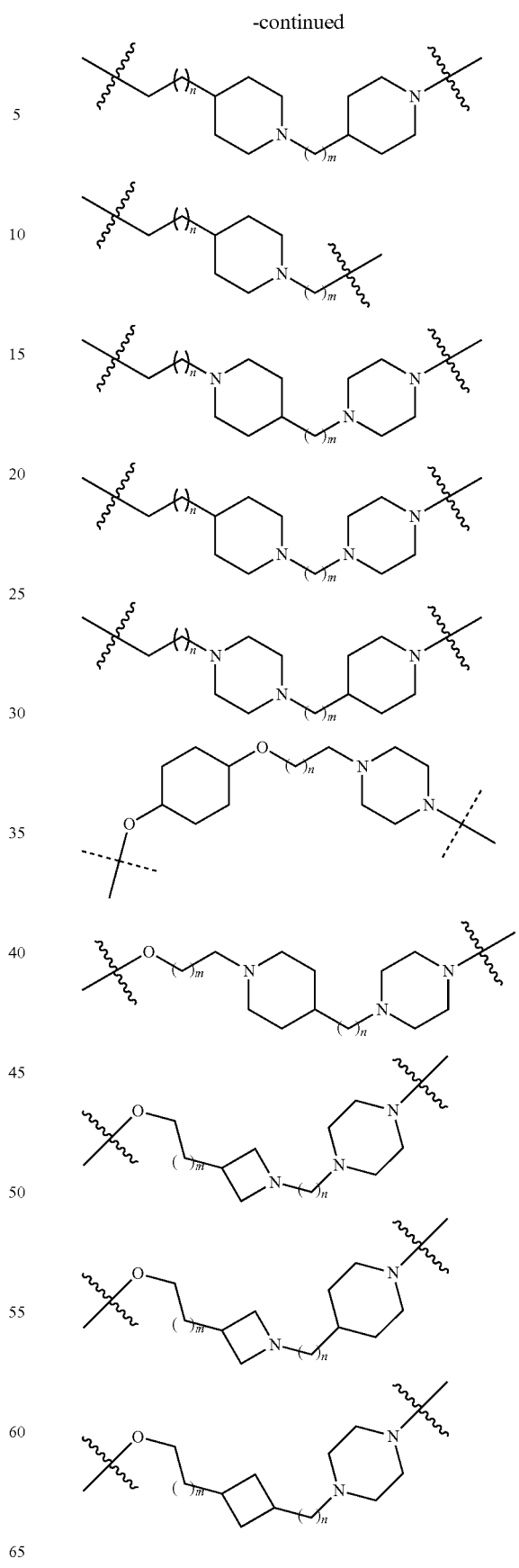

599
-continued
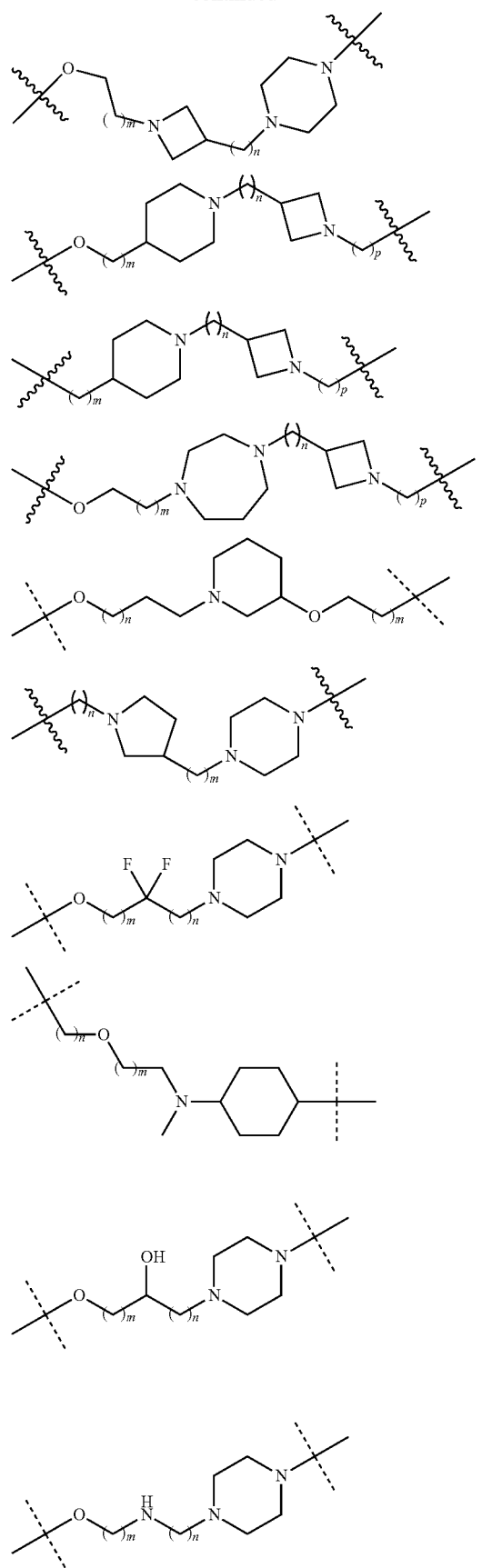
600
-continued
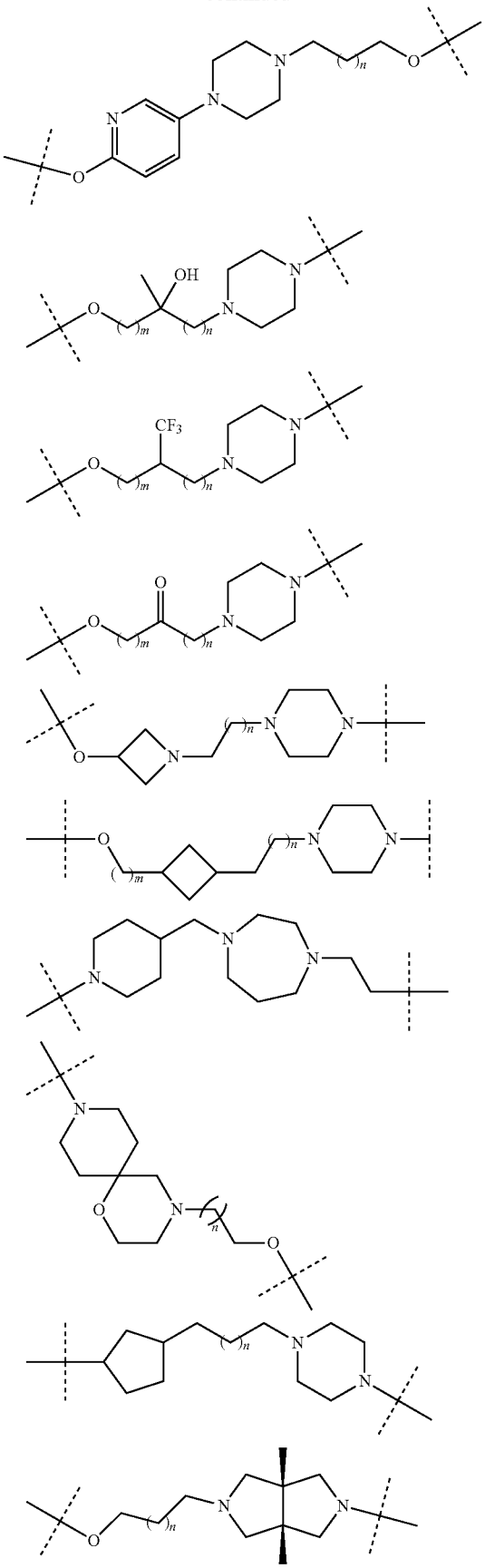

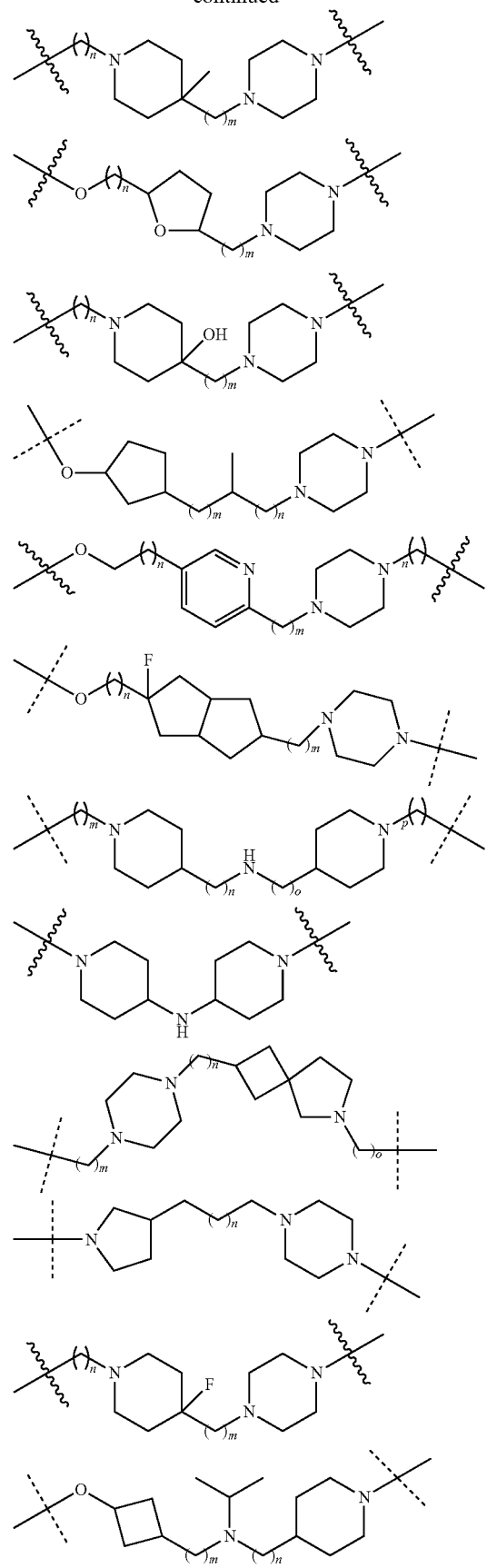
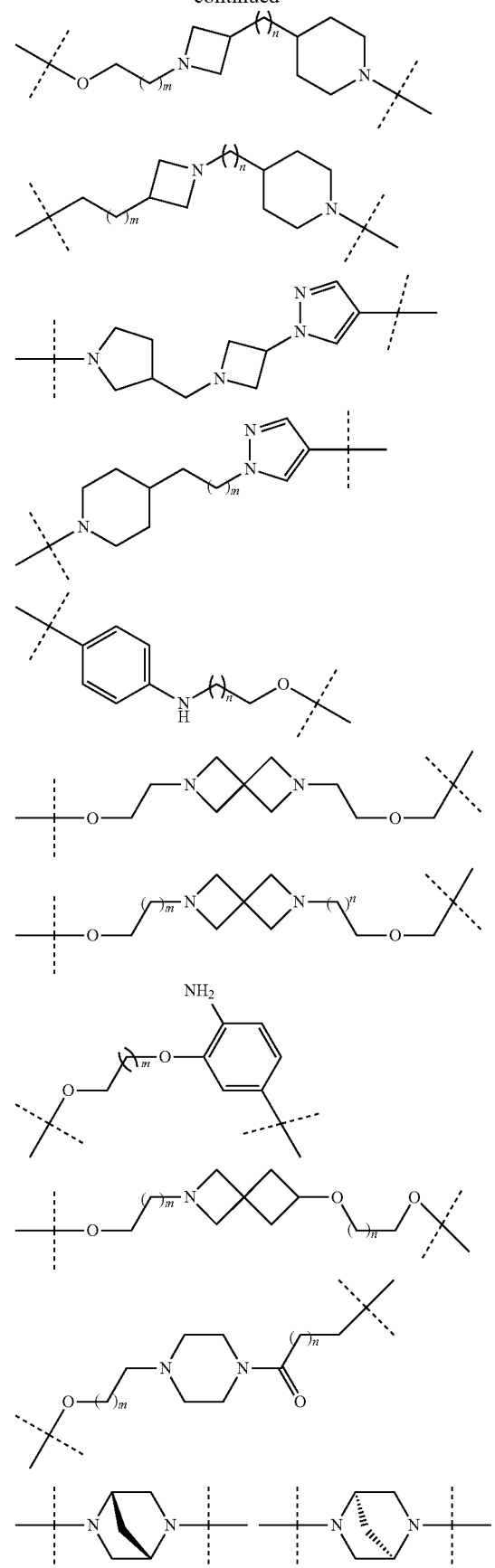

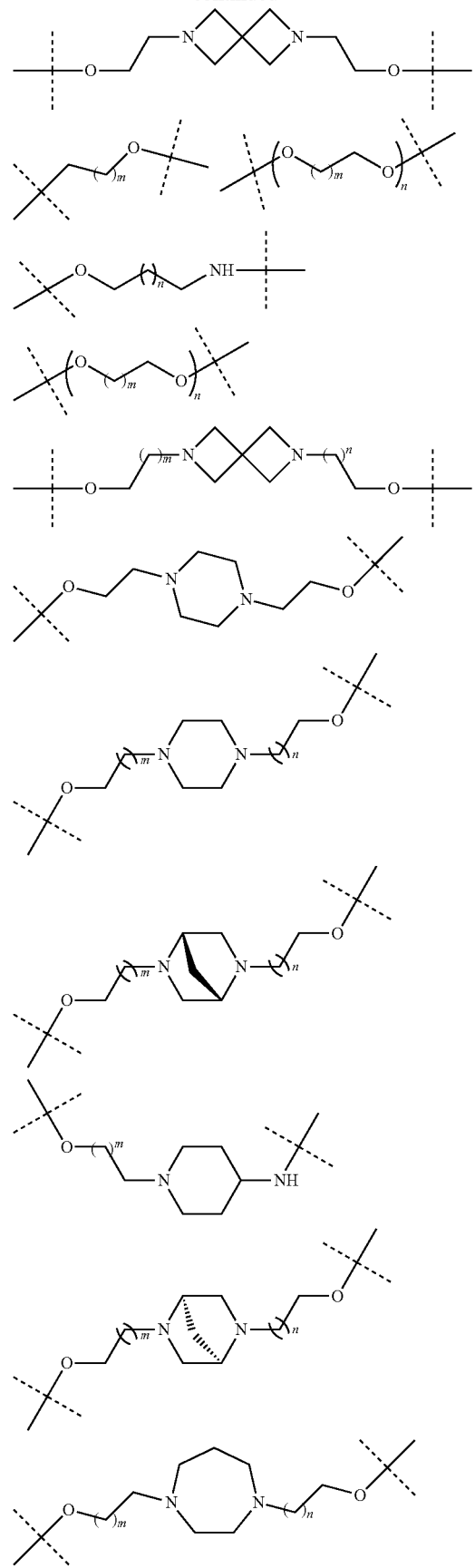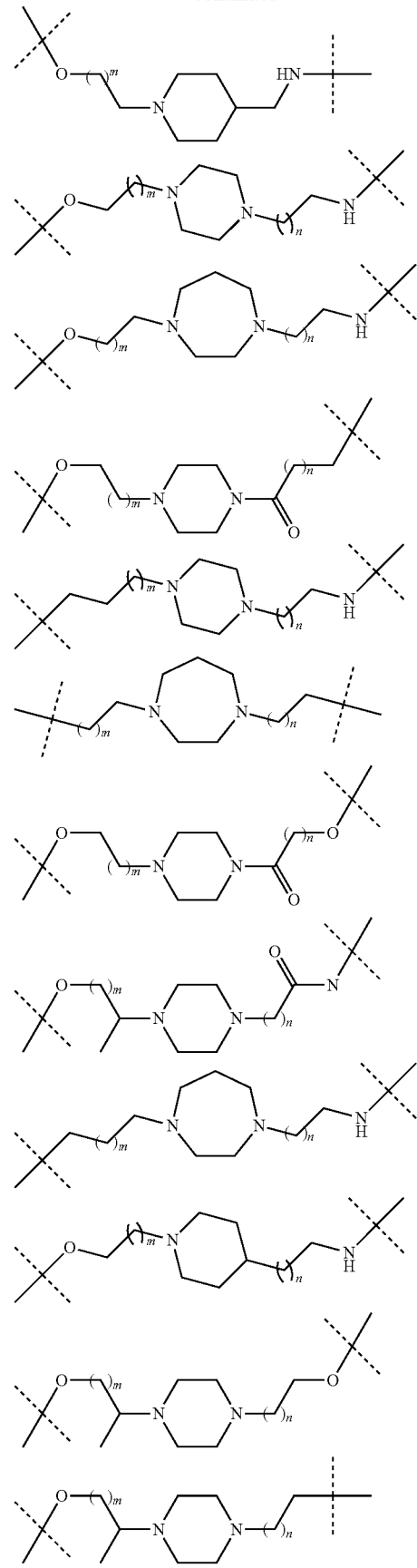

605
-continued
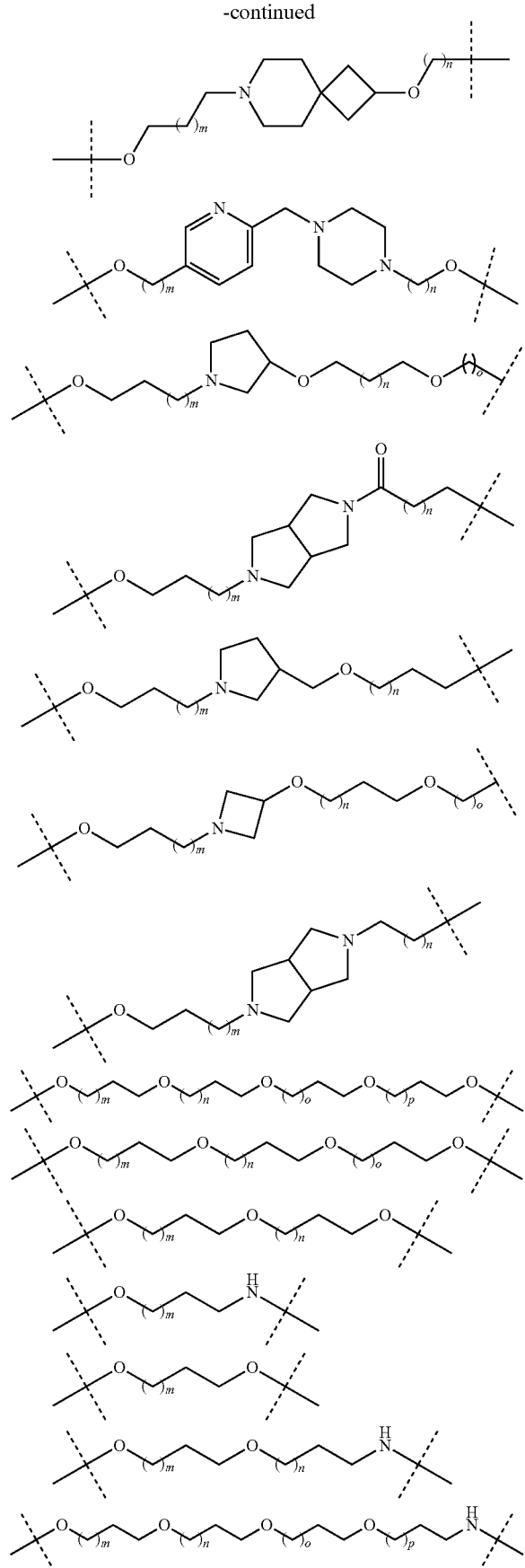
606
-continued
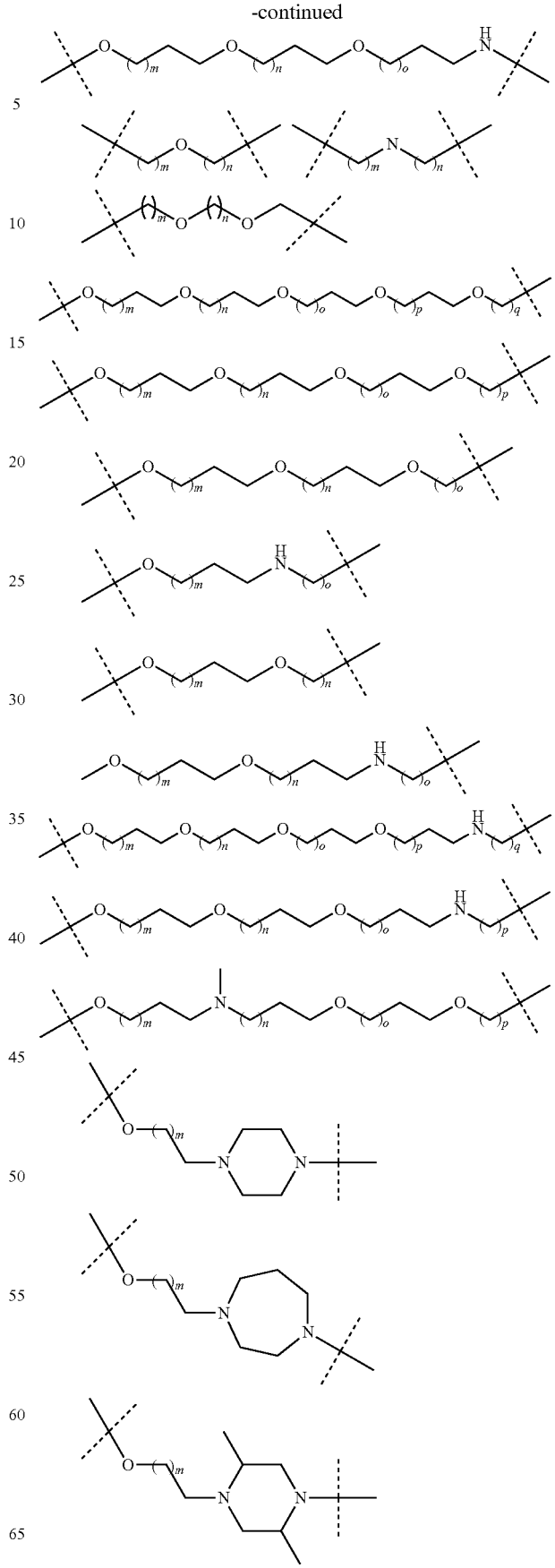

607
-continued
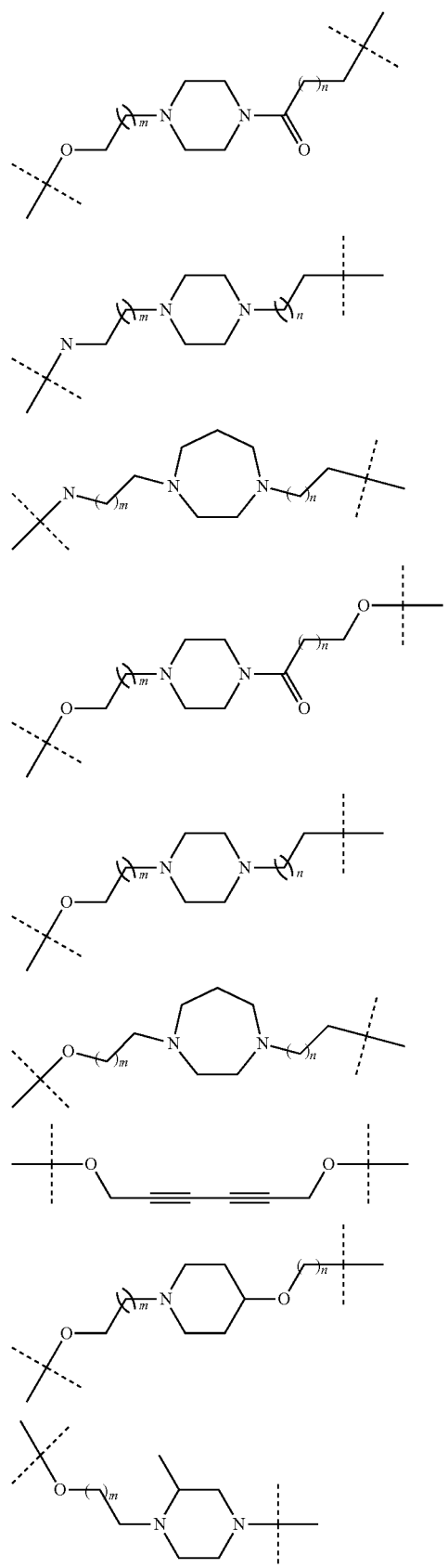
608
-continued
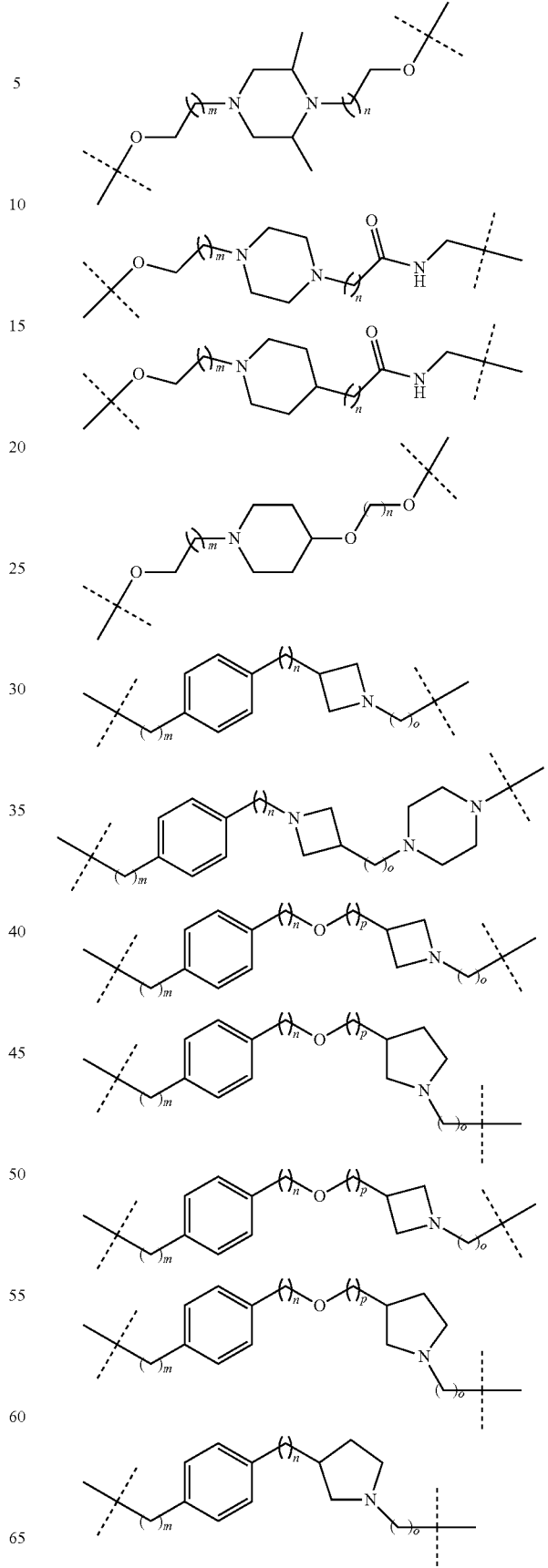

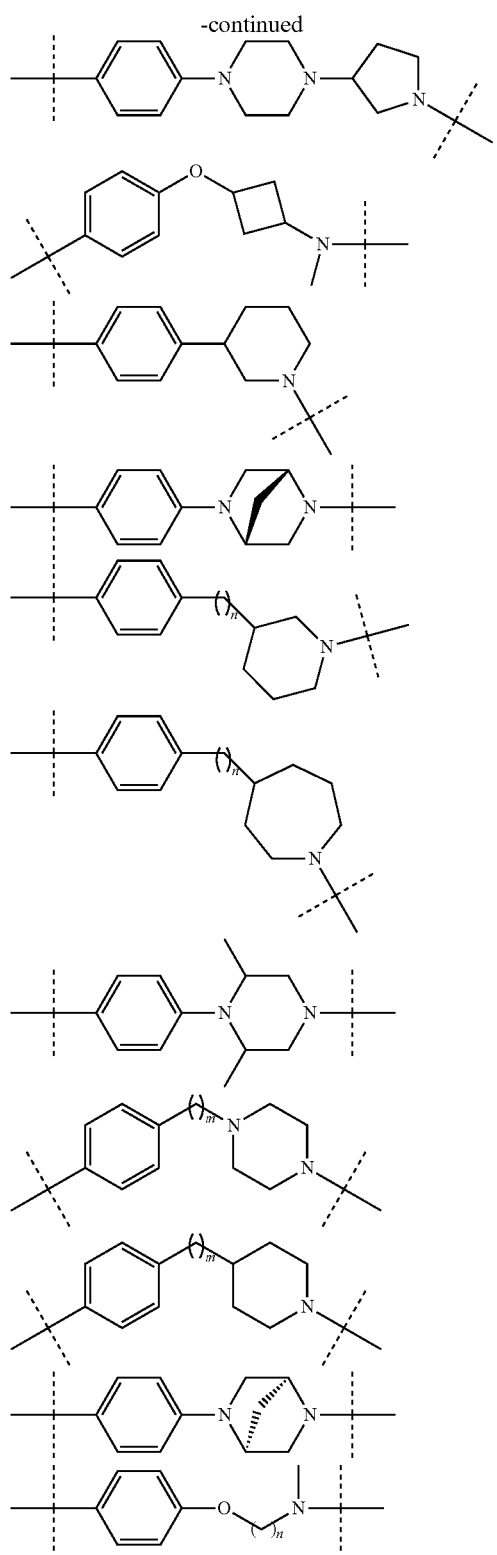
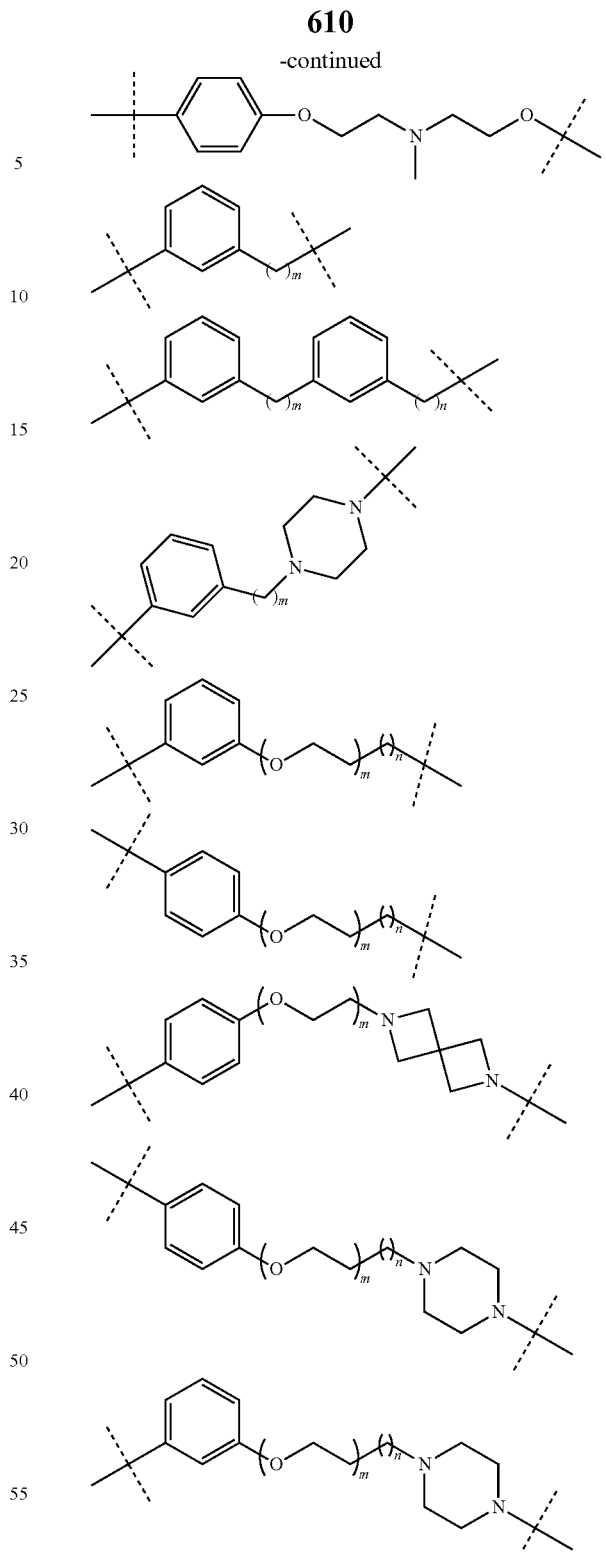
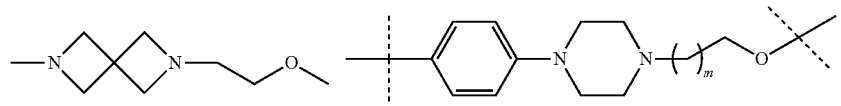

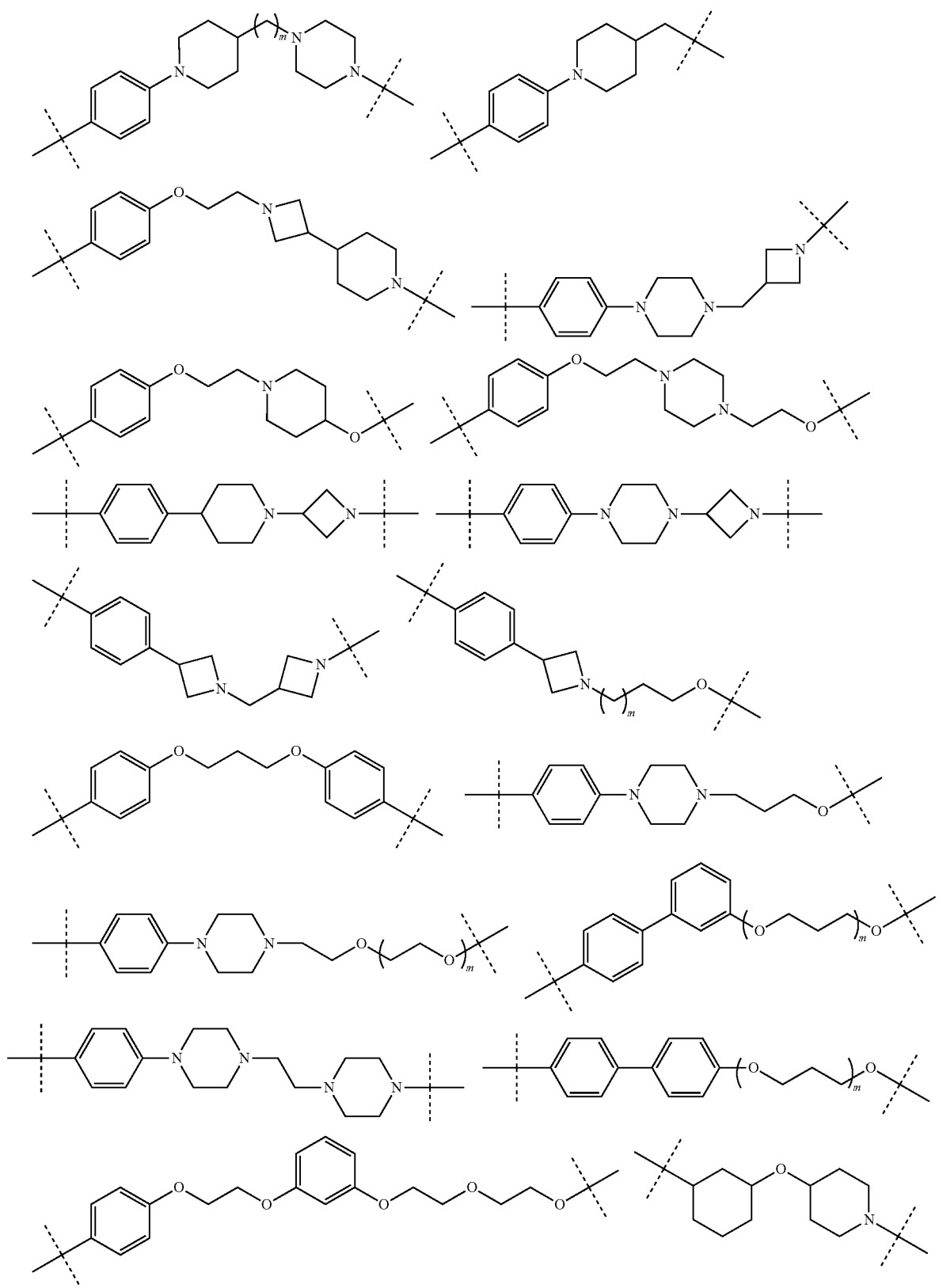

613 614
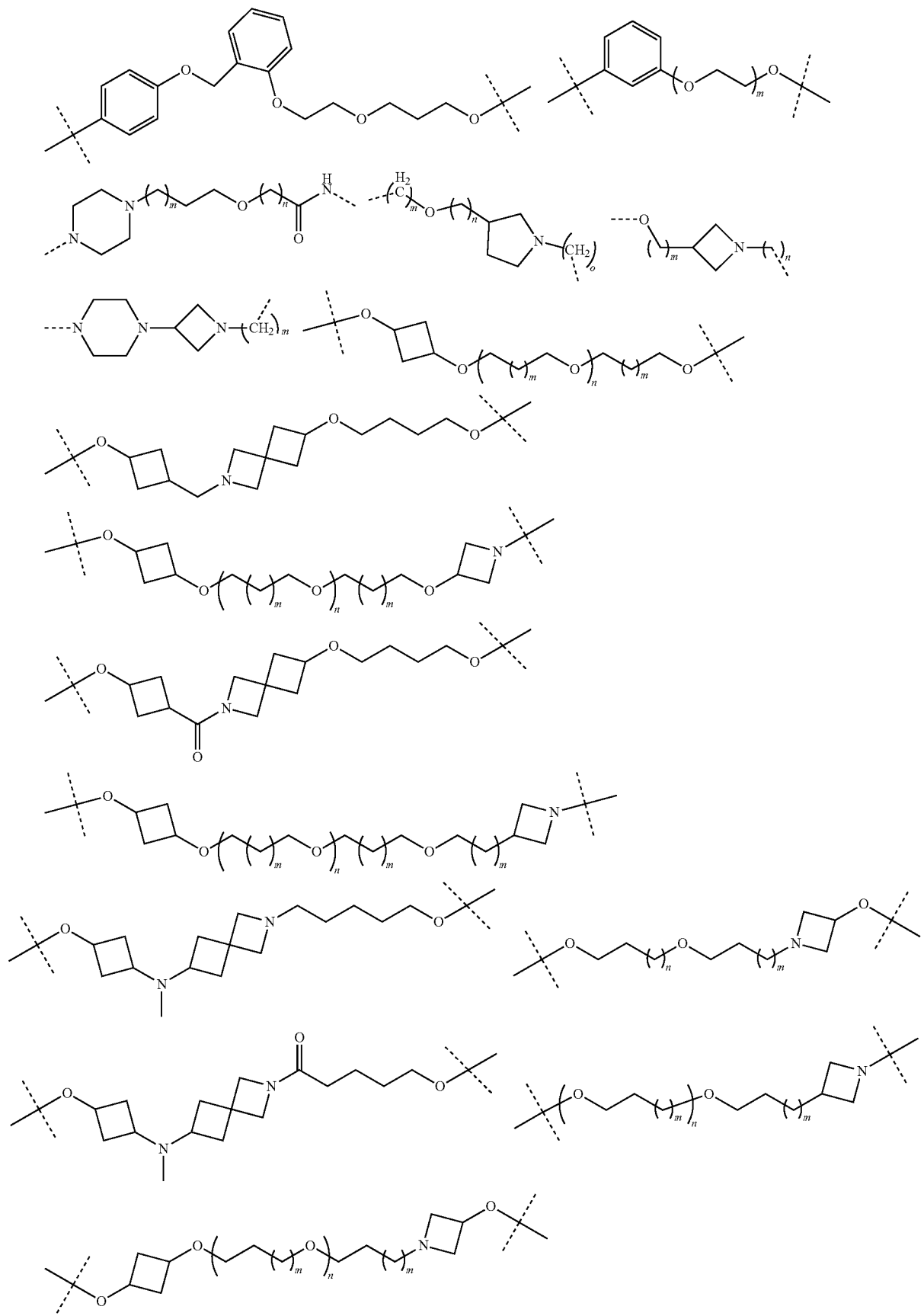

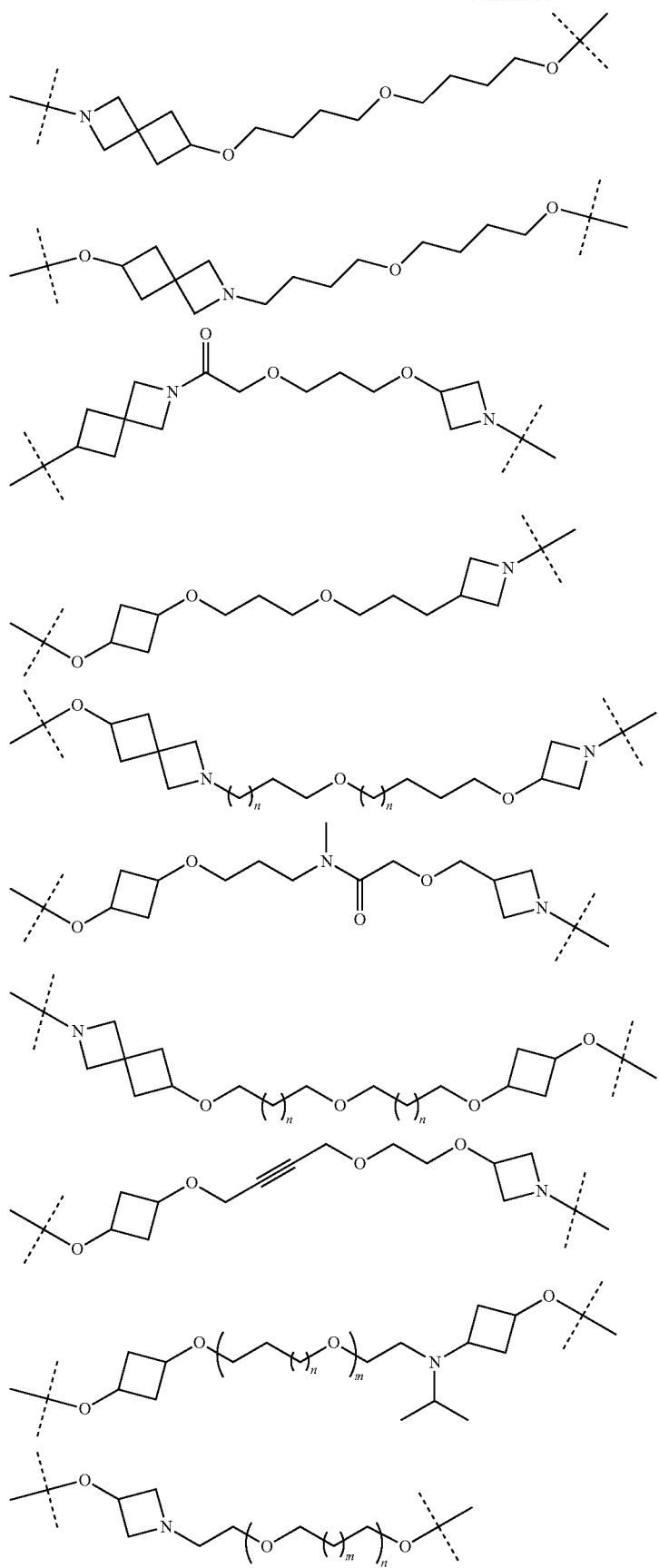

-continued
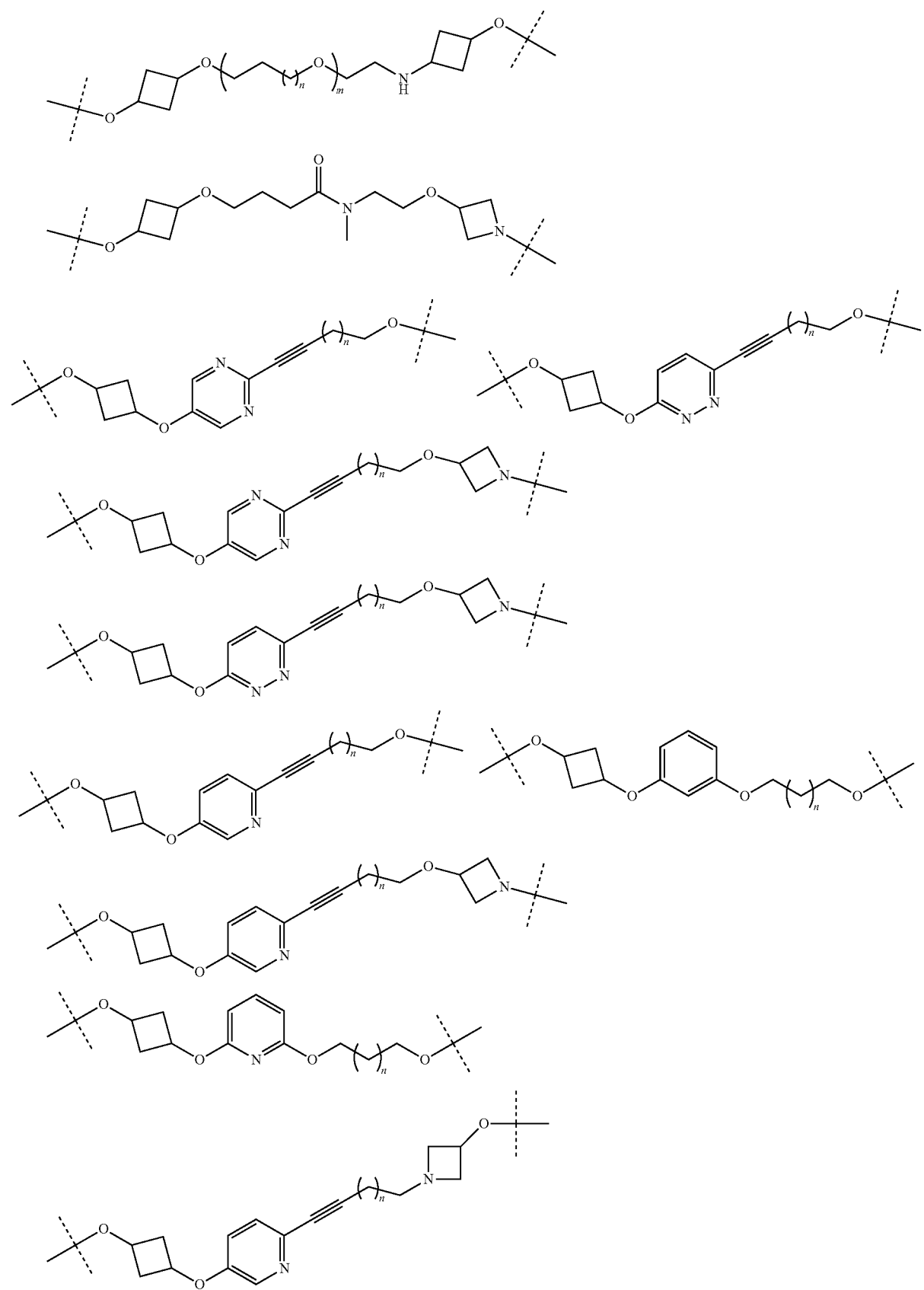

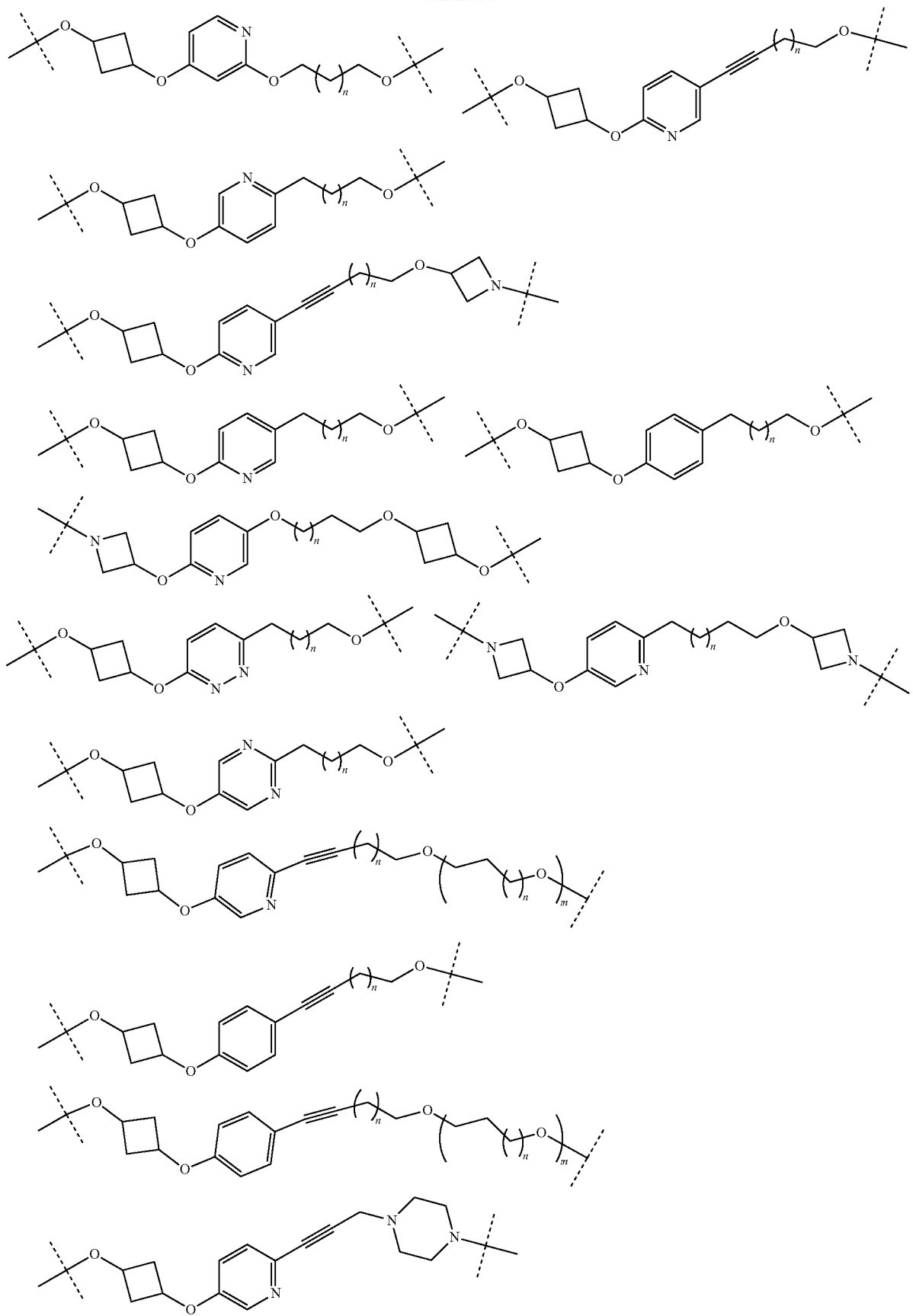

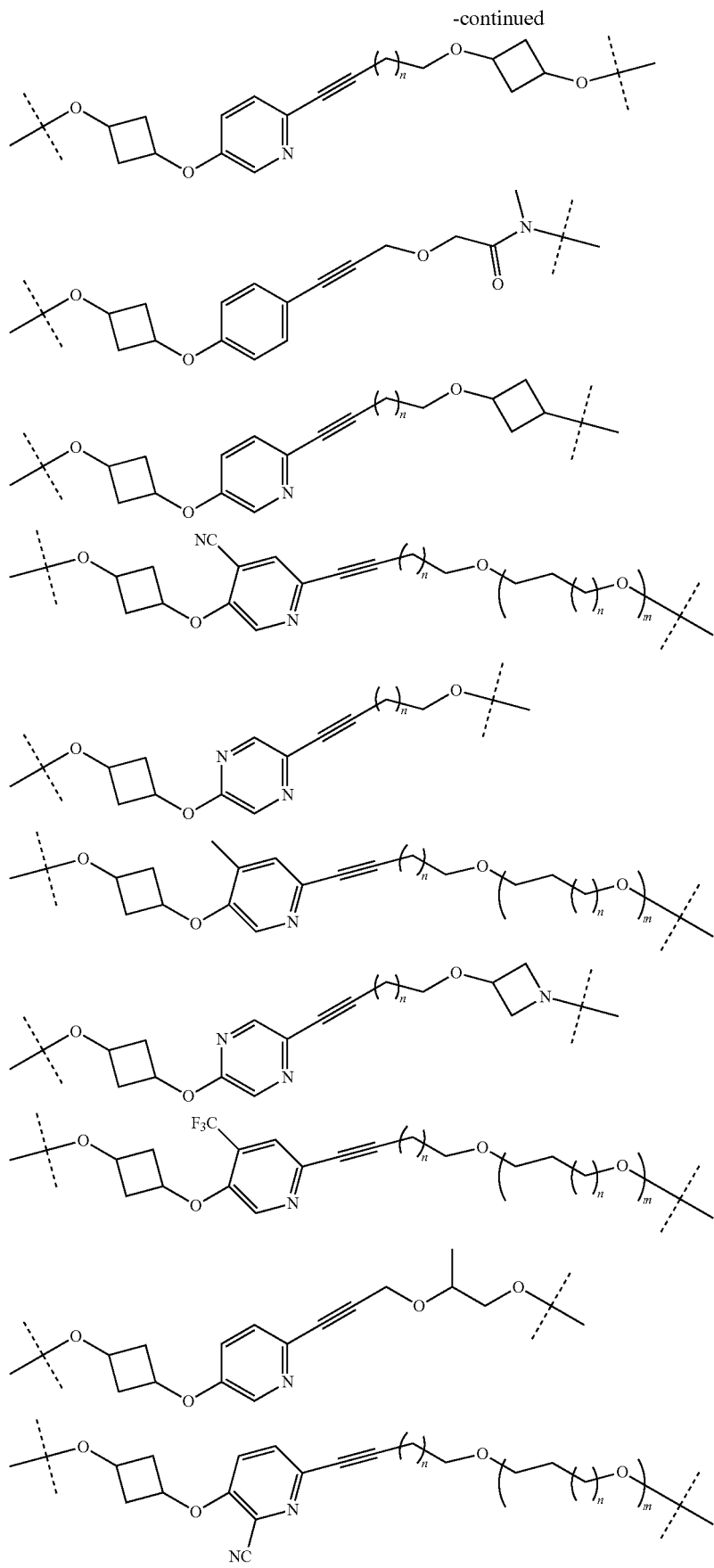

-continued
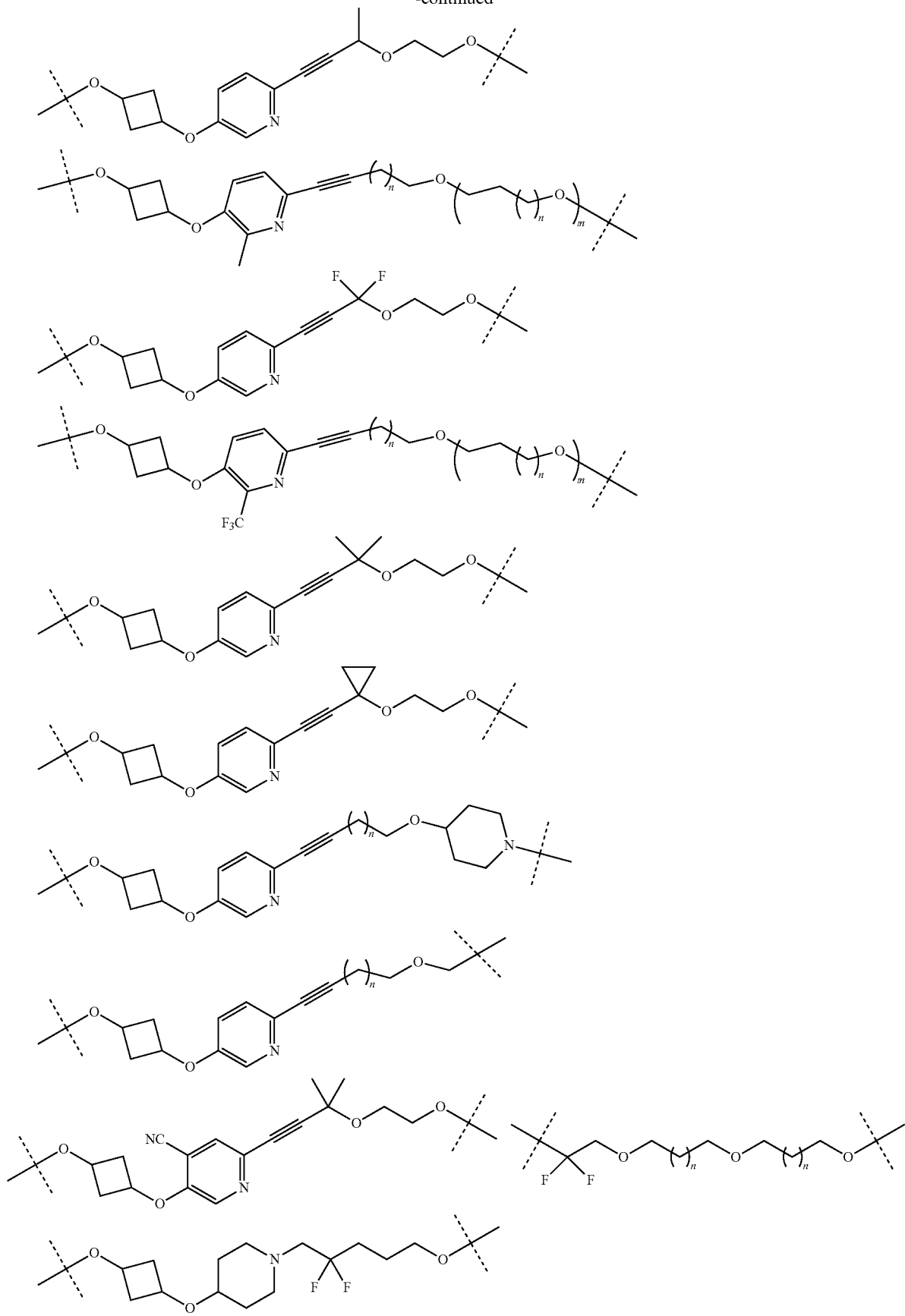

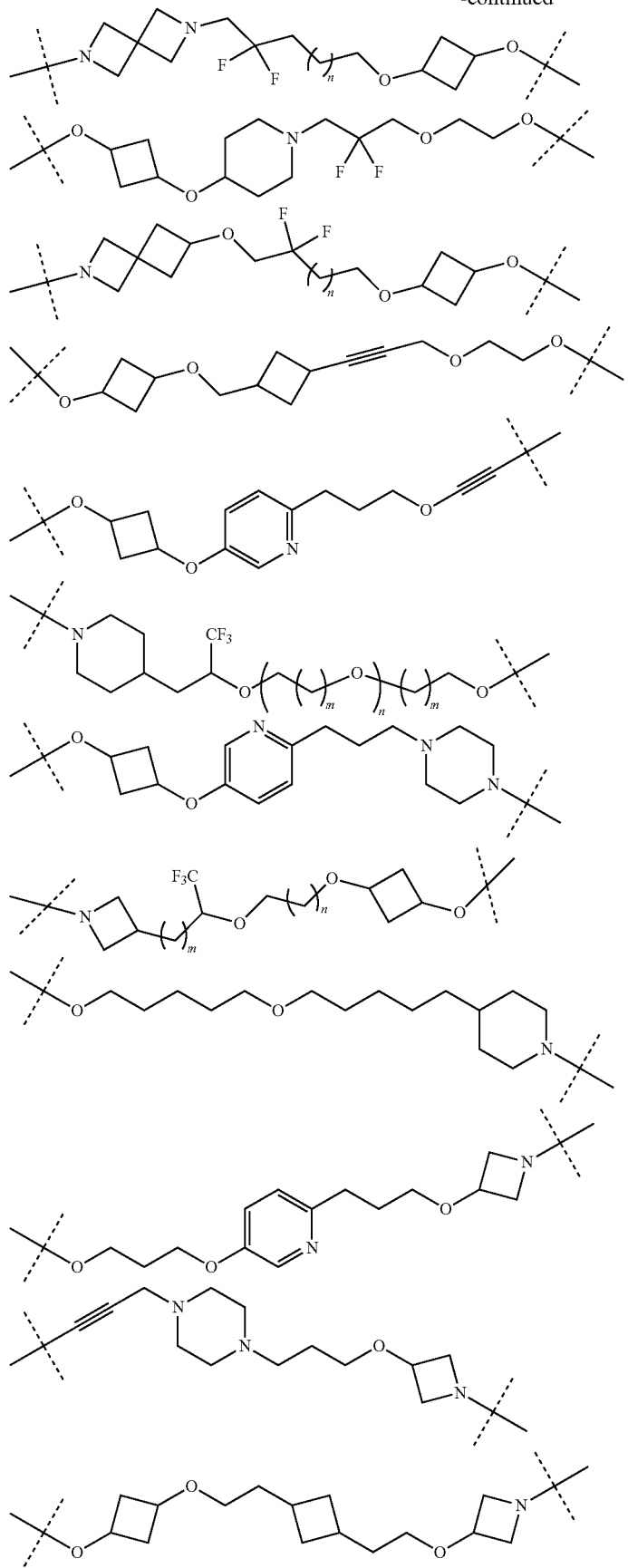

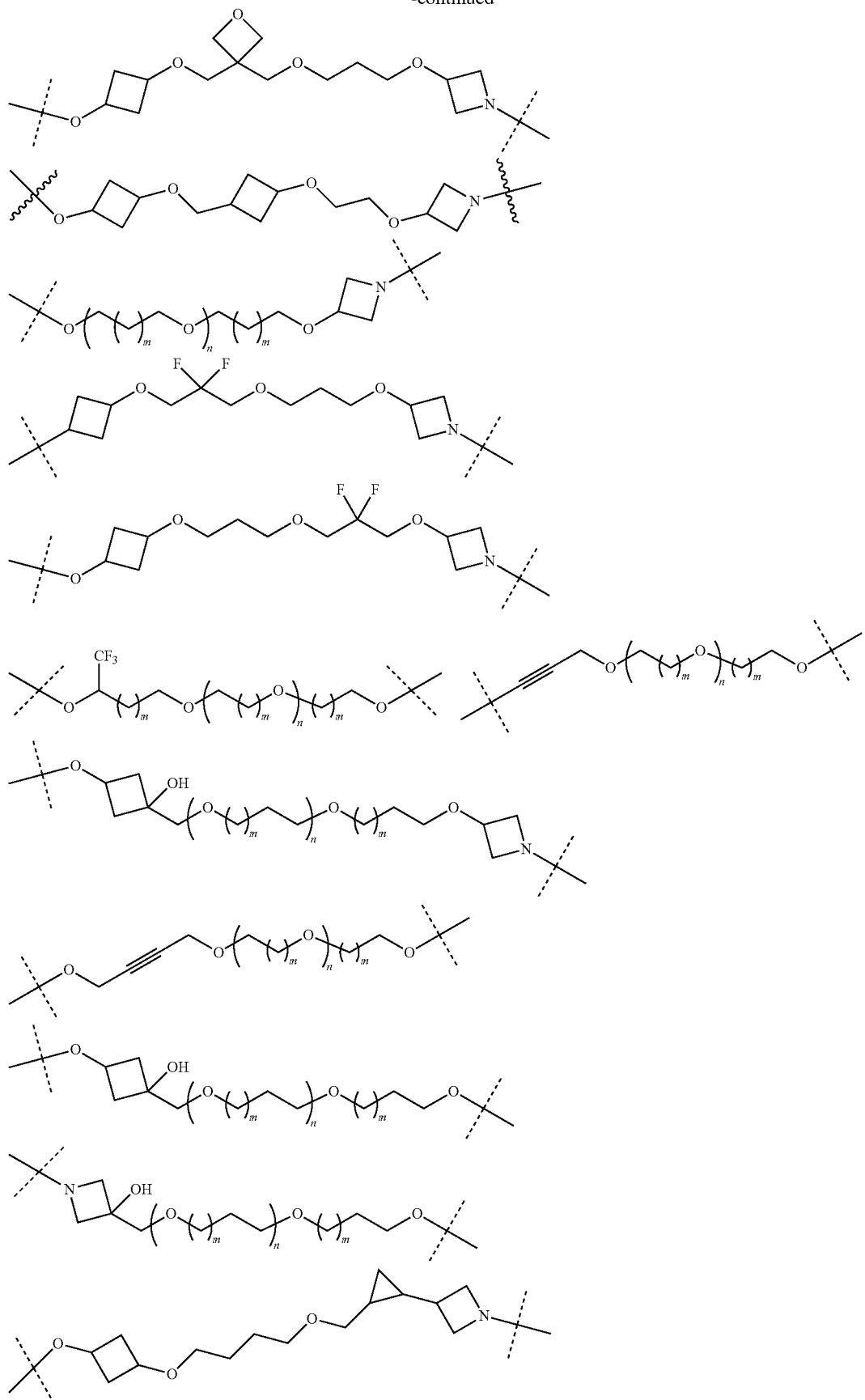

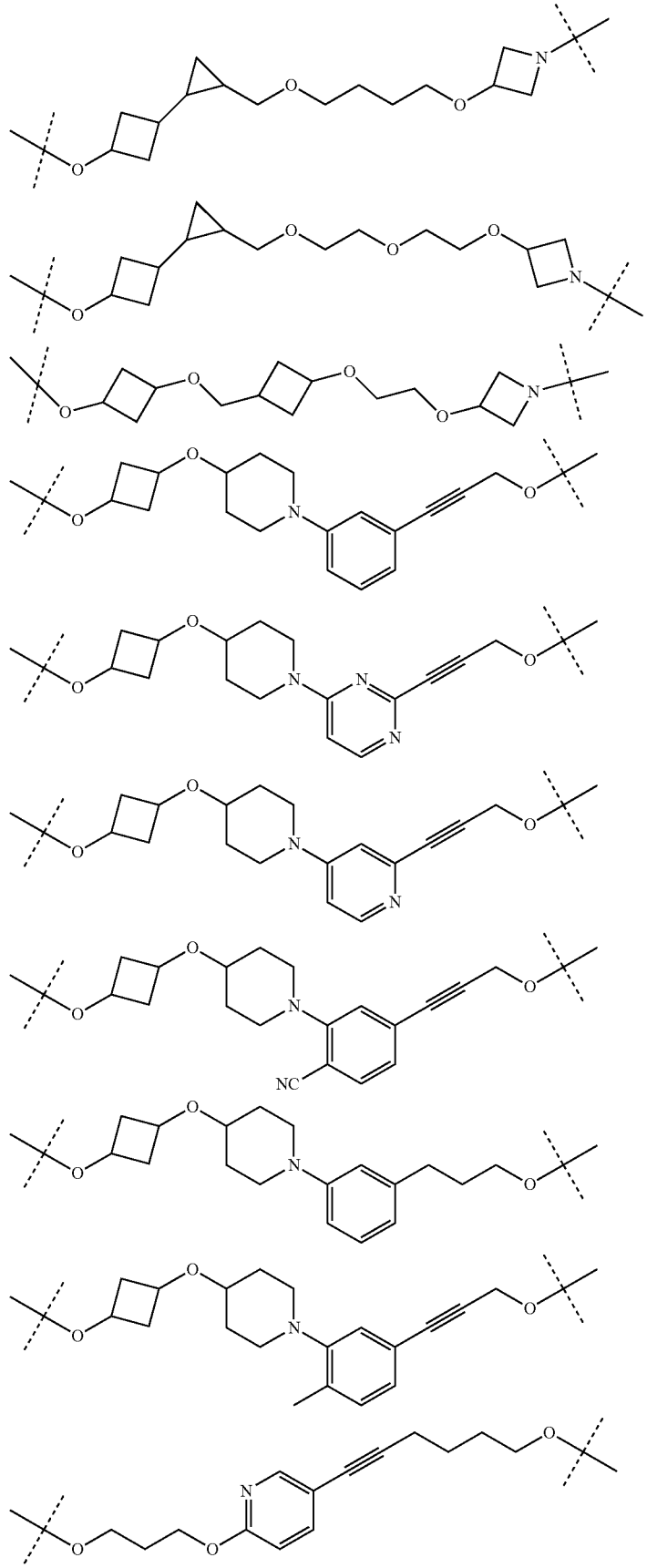

631 632 -continued
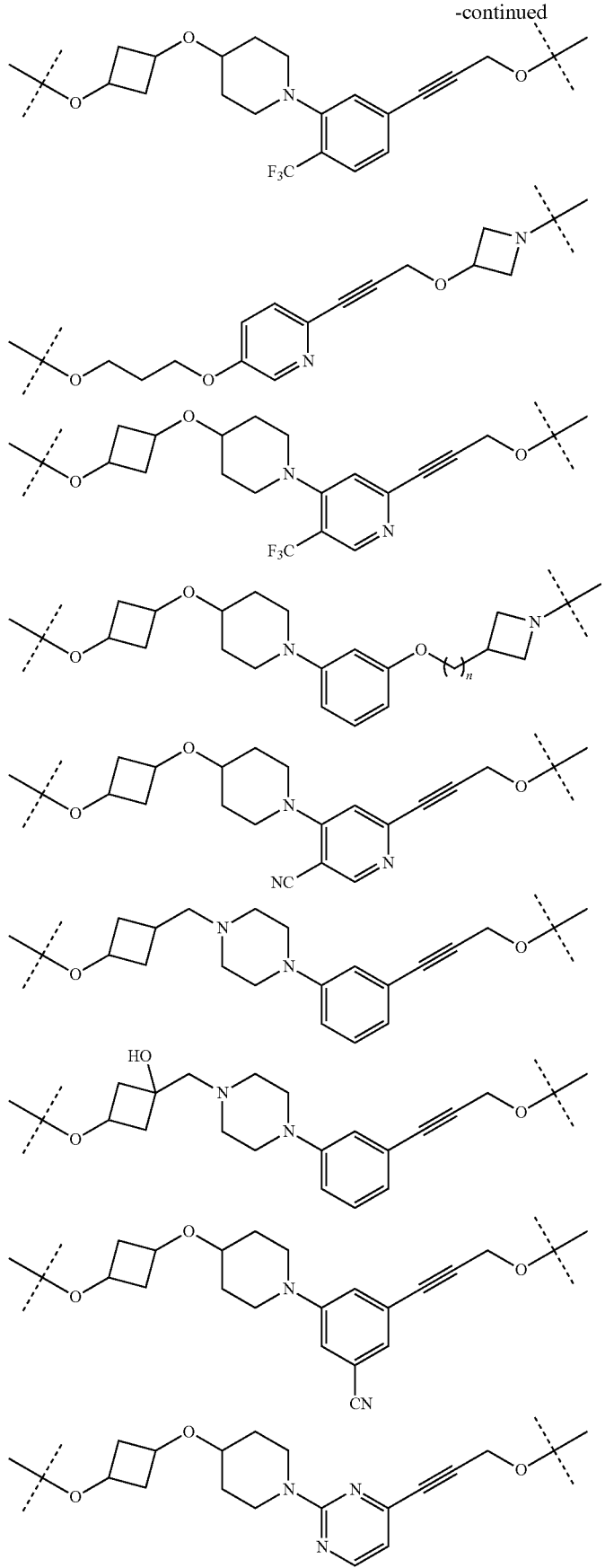

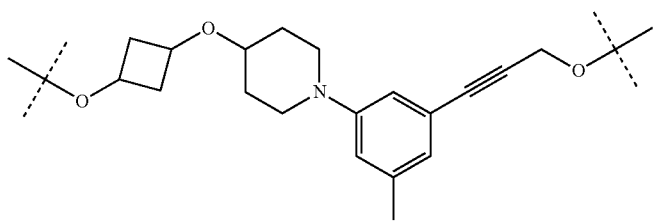
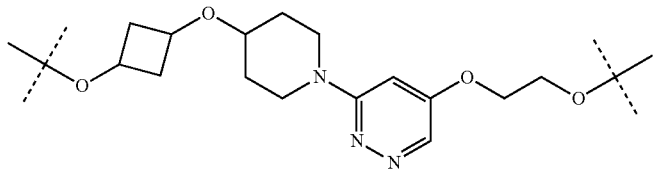
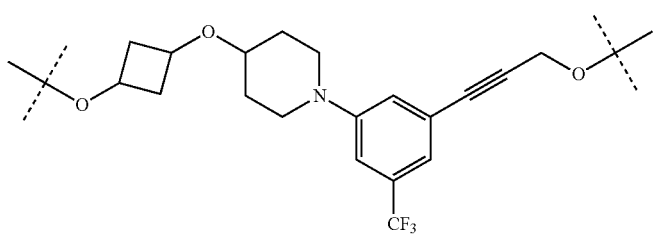
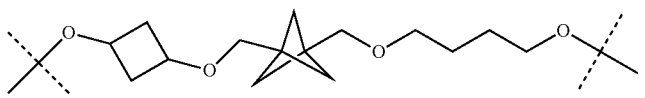
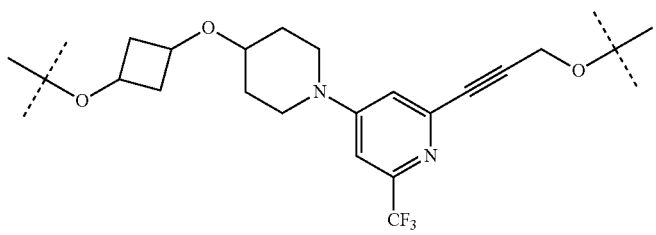
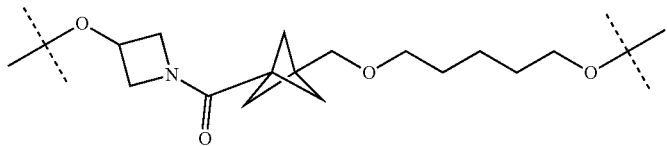
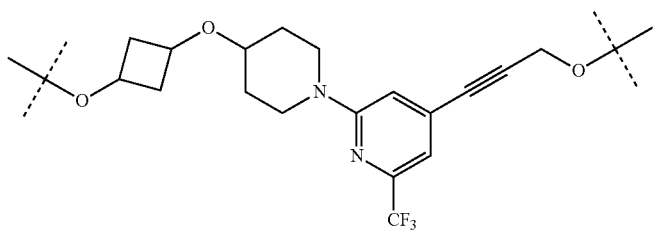
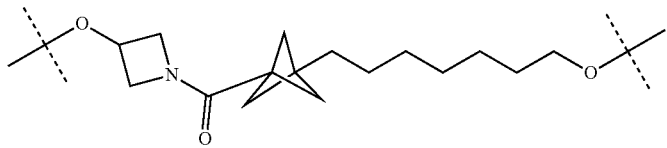
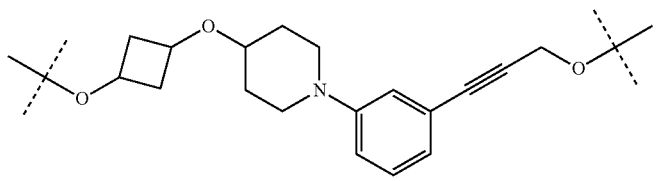

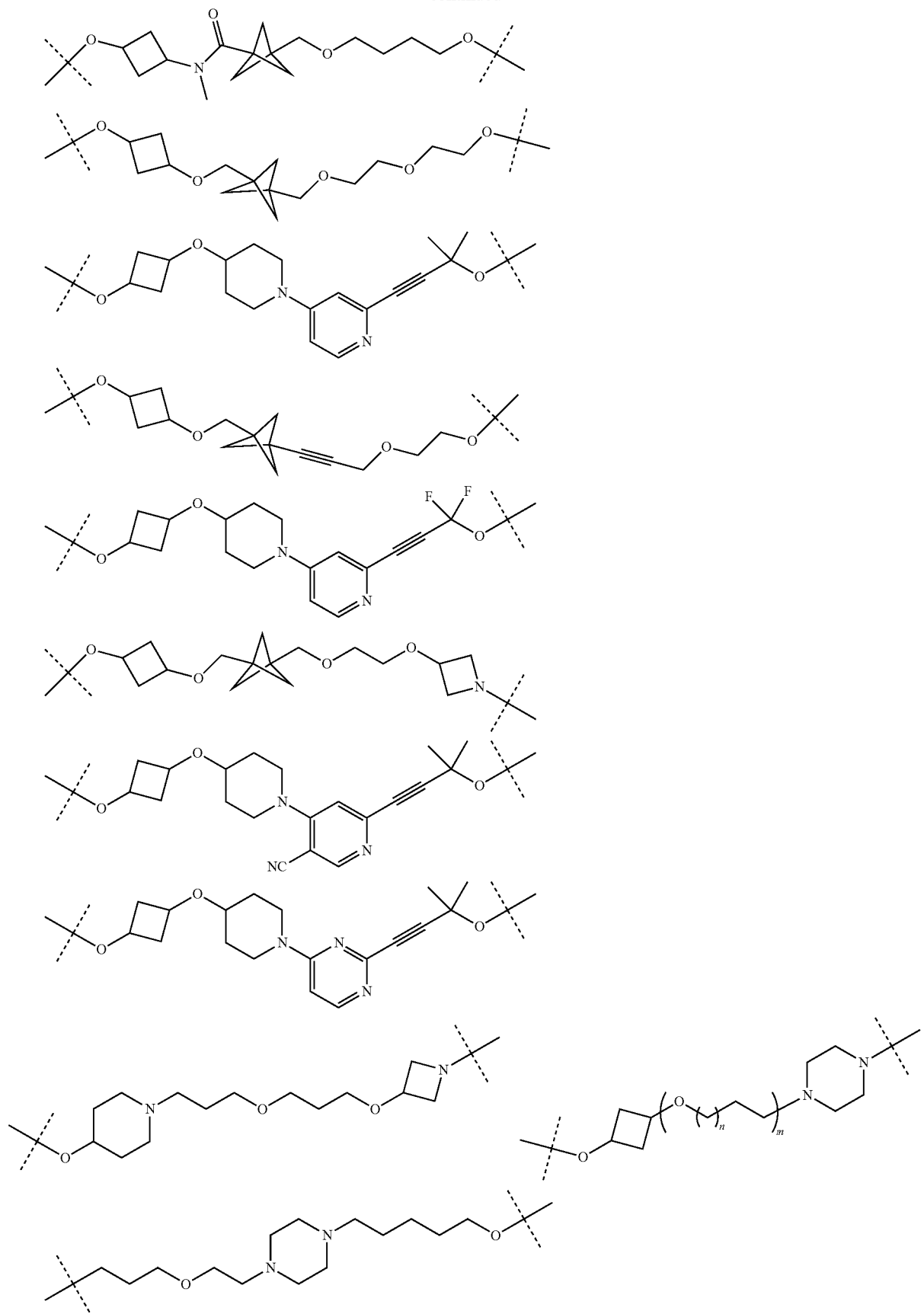

-continued
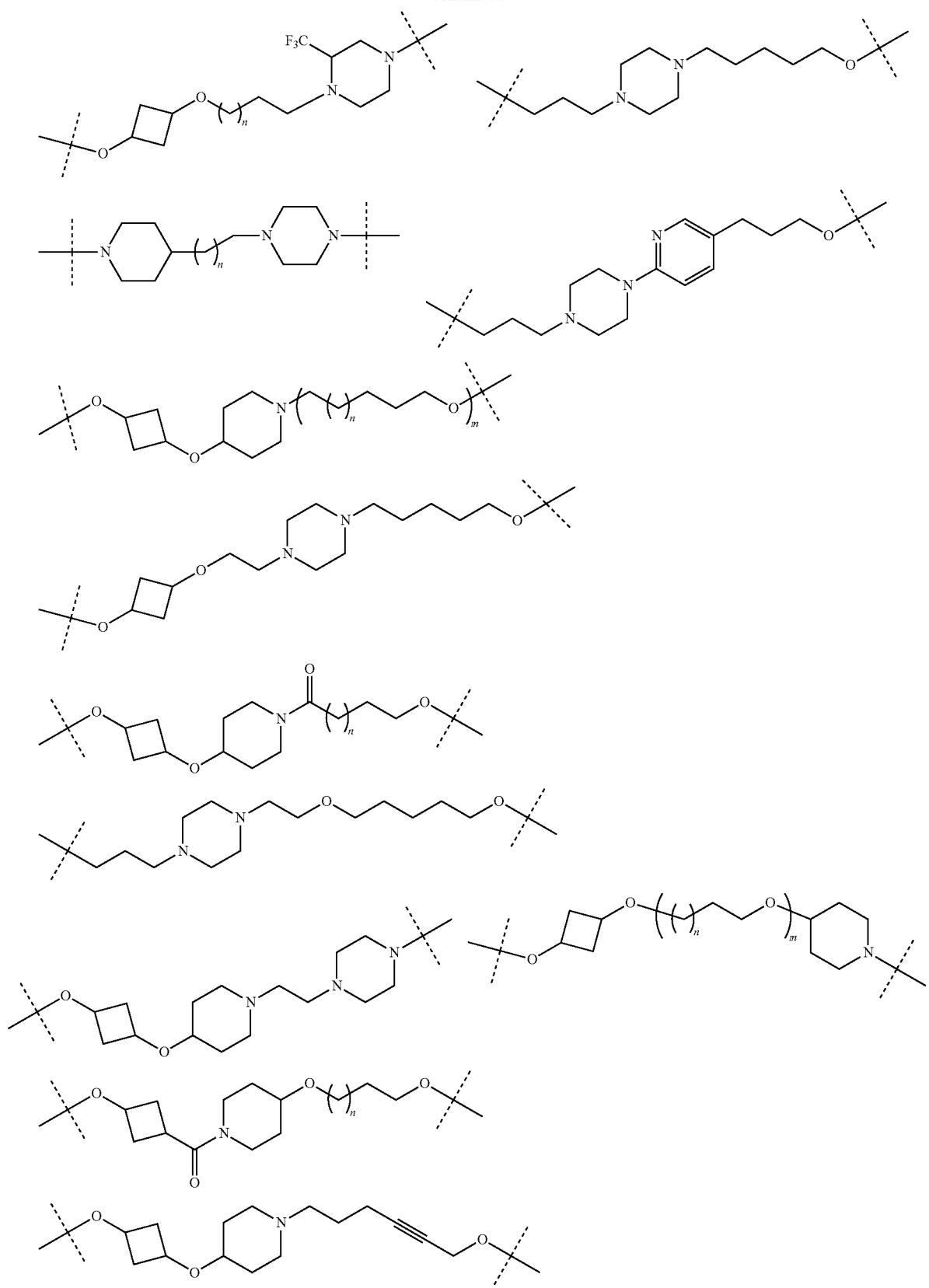

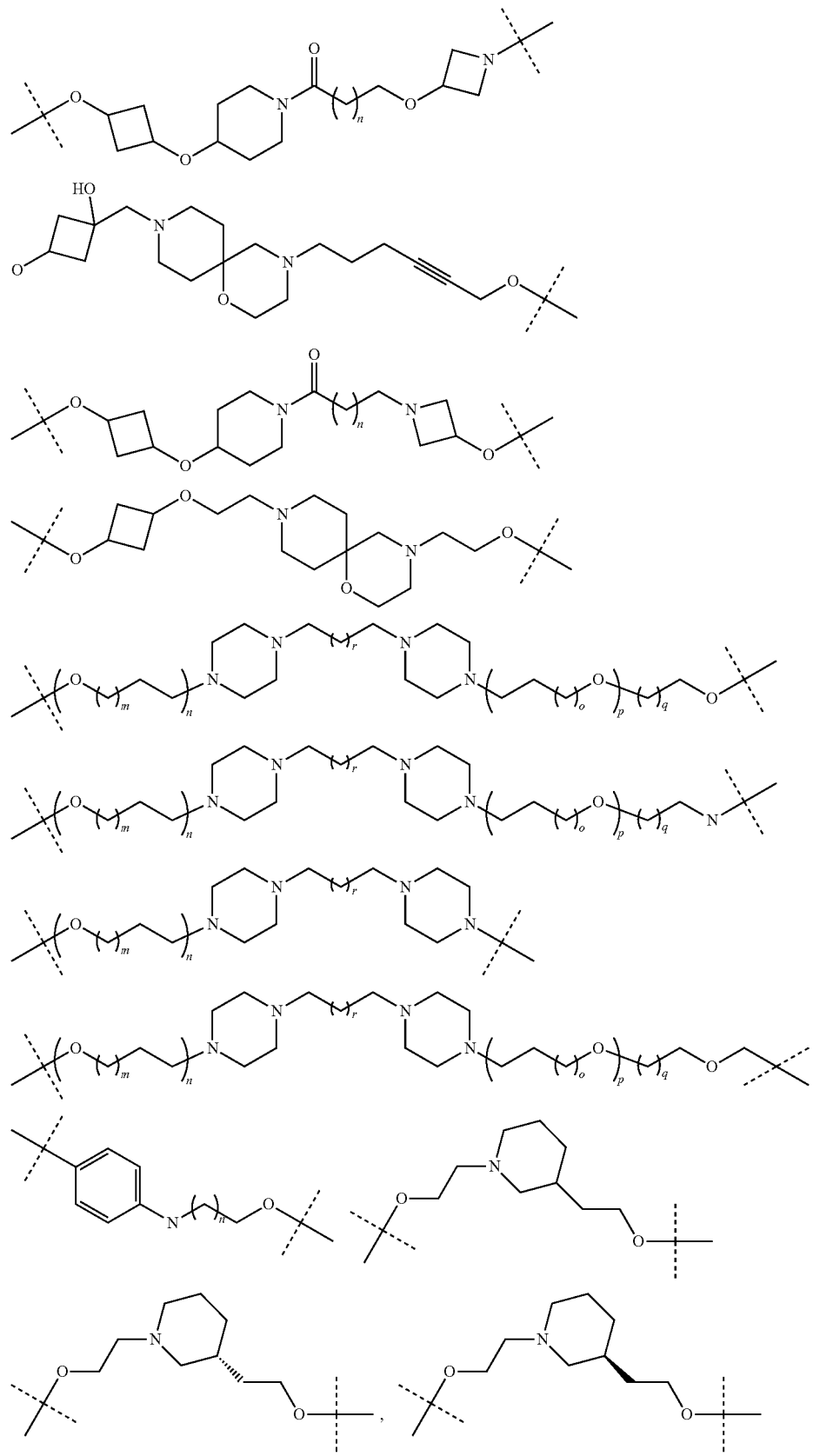

-continued
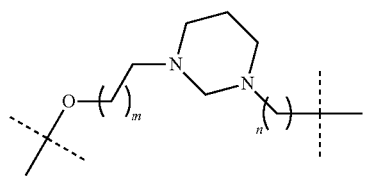
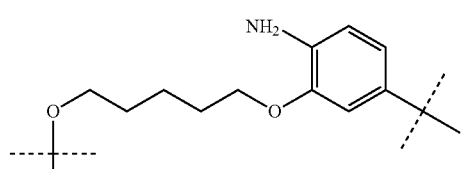
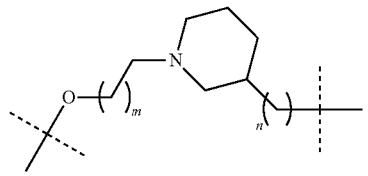
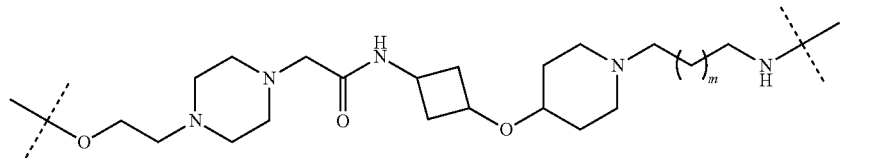
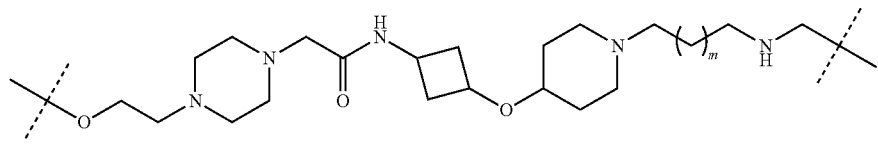
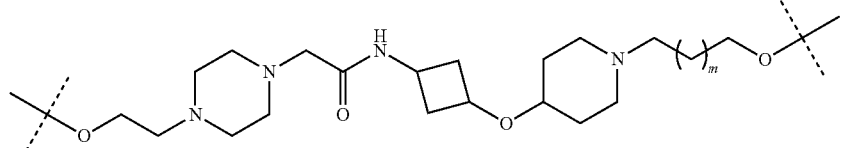
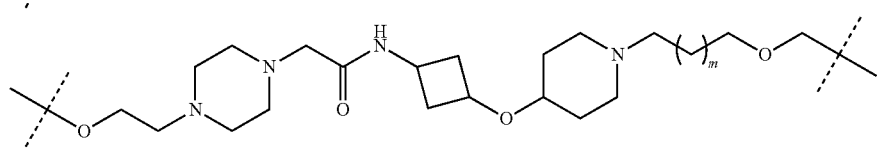
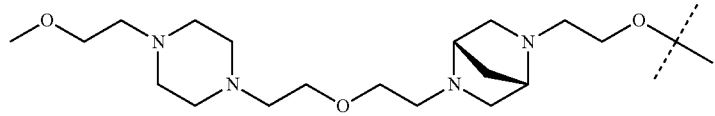
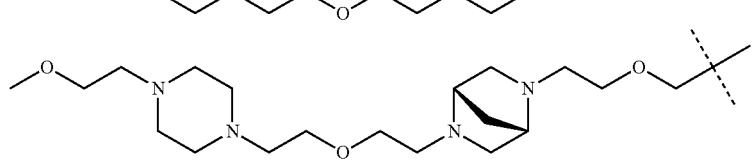
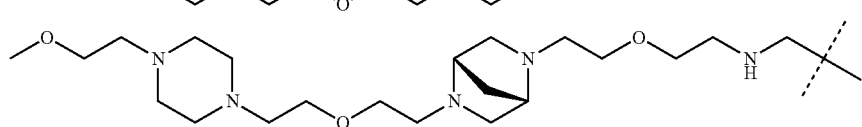
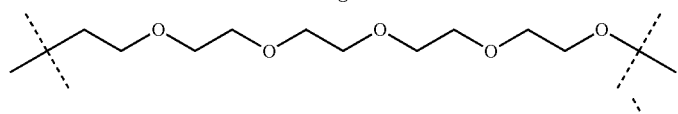
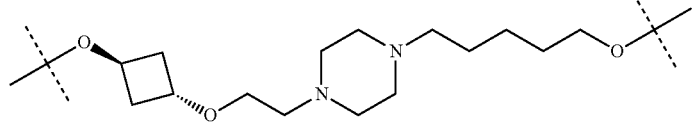

-continued
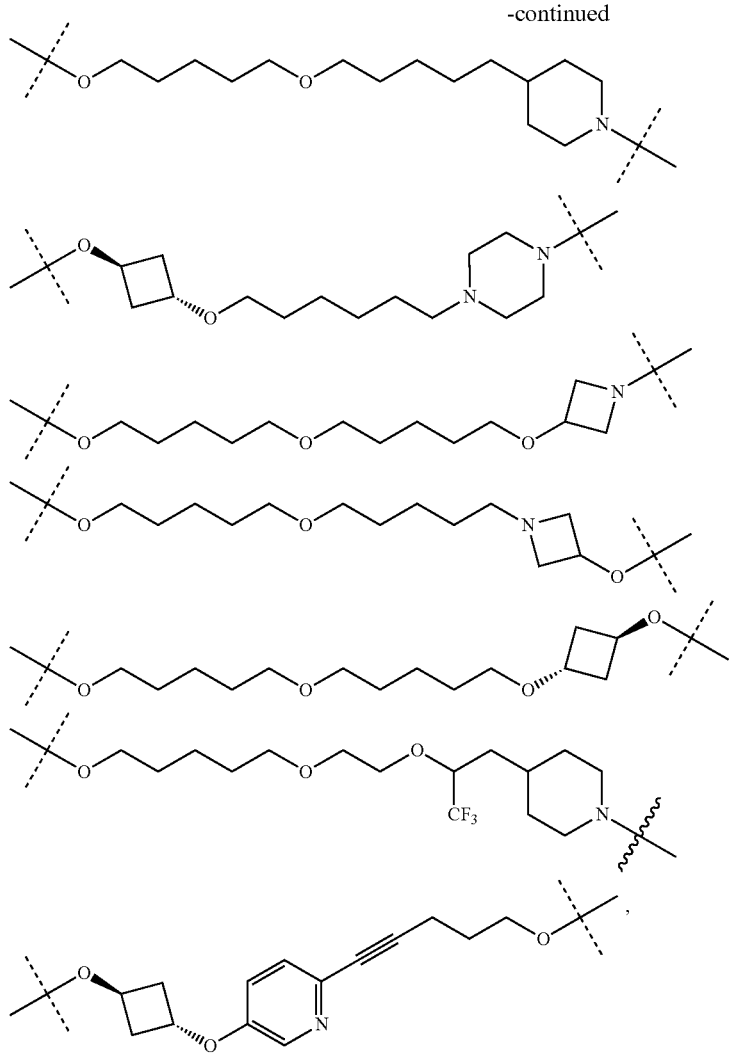
wherein at each occurrence m, n, o, p, q, and r is independently 0, 1, 2, 3, 4, 5, 6, 7, 8, 9, 10, 11, 12, 13, 14, 15, 16, 17, 18, 19, or 20.
18. The compound of claim 1, wherein the linker L is selected from the group consisting of:
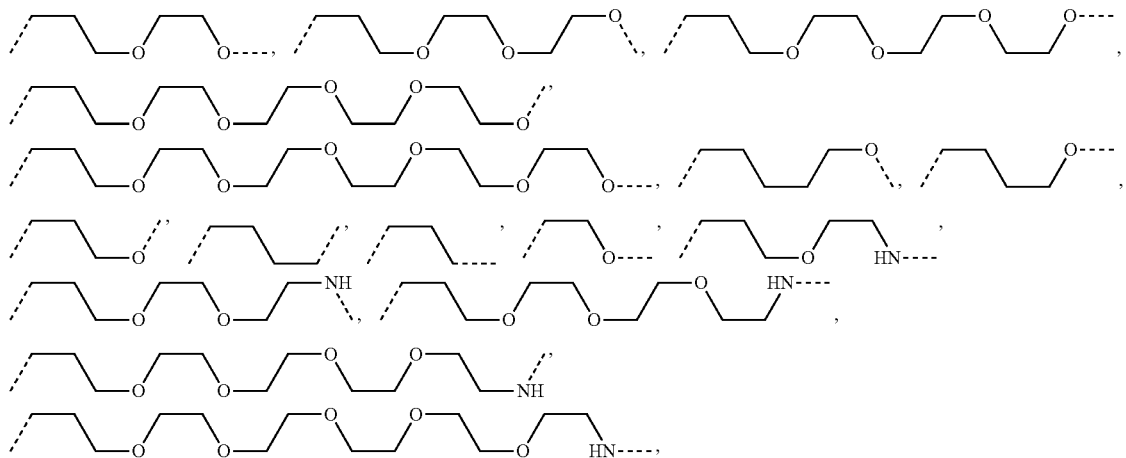

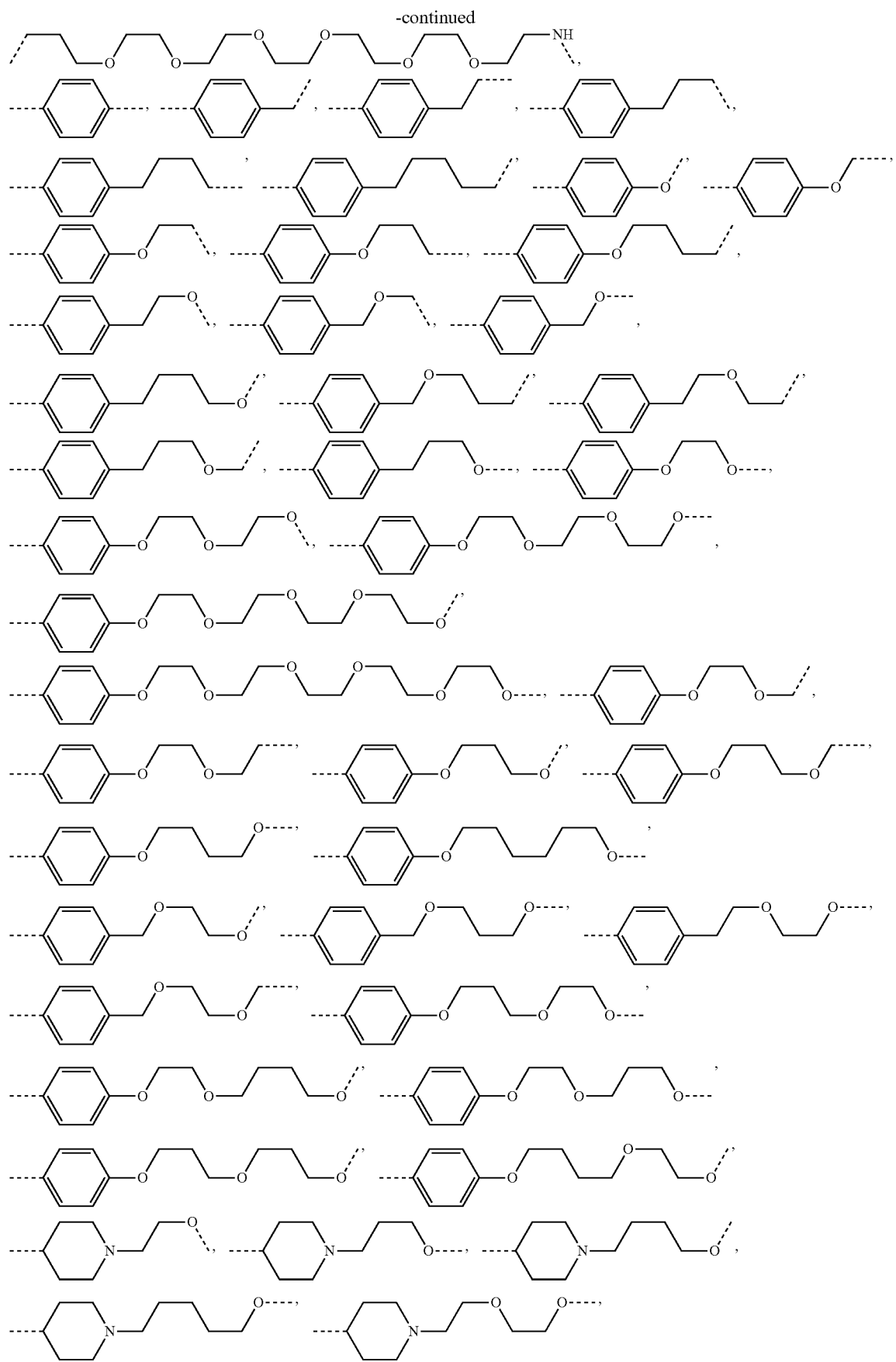

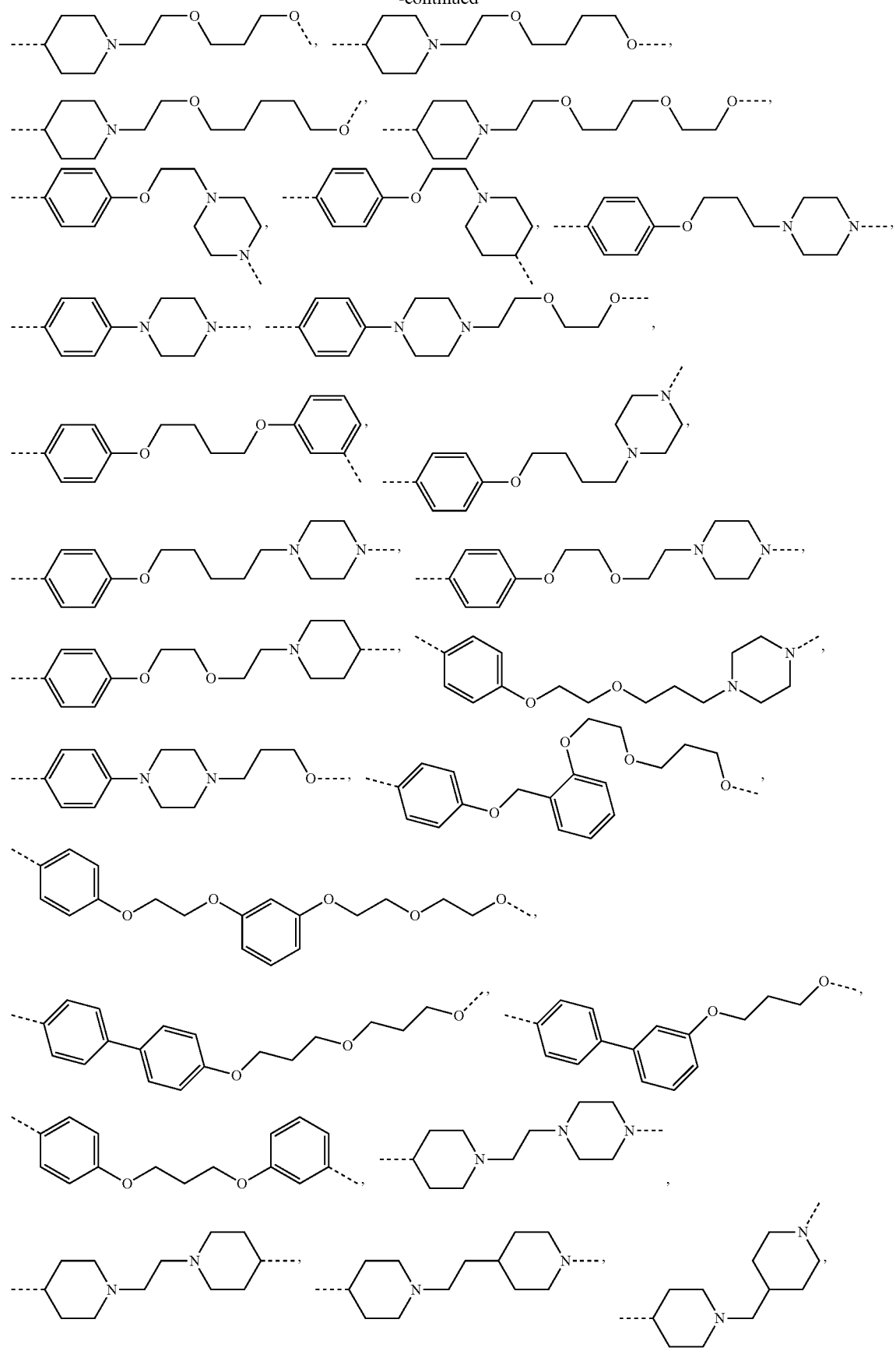

-continued
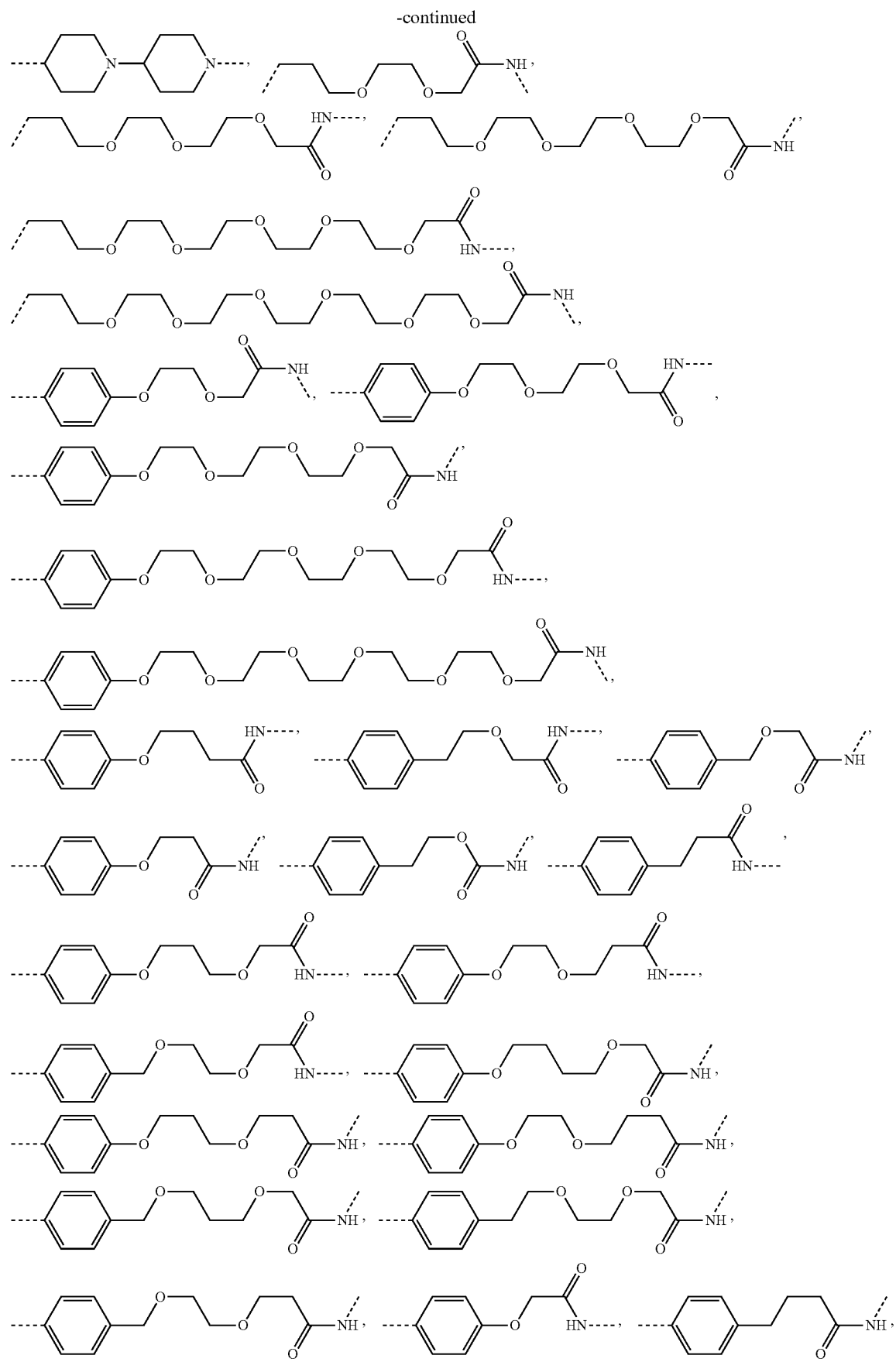

-continued
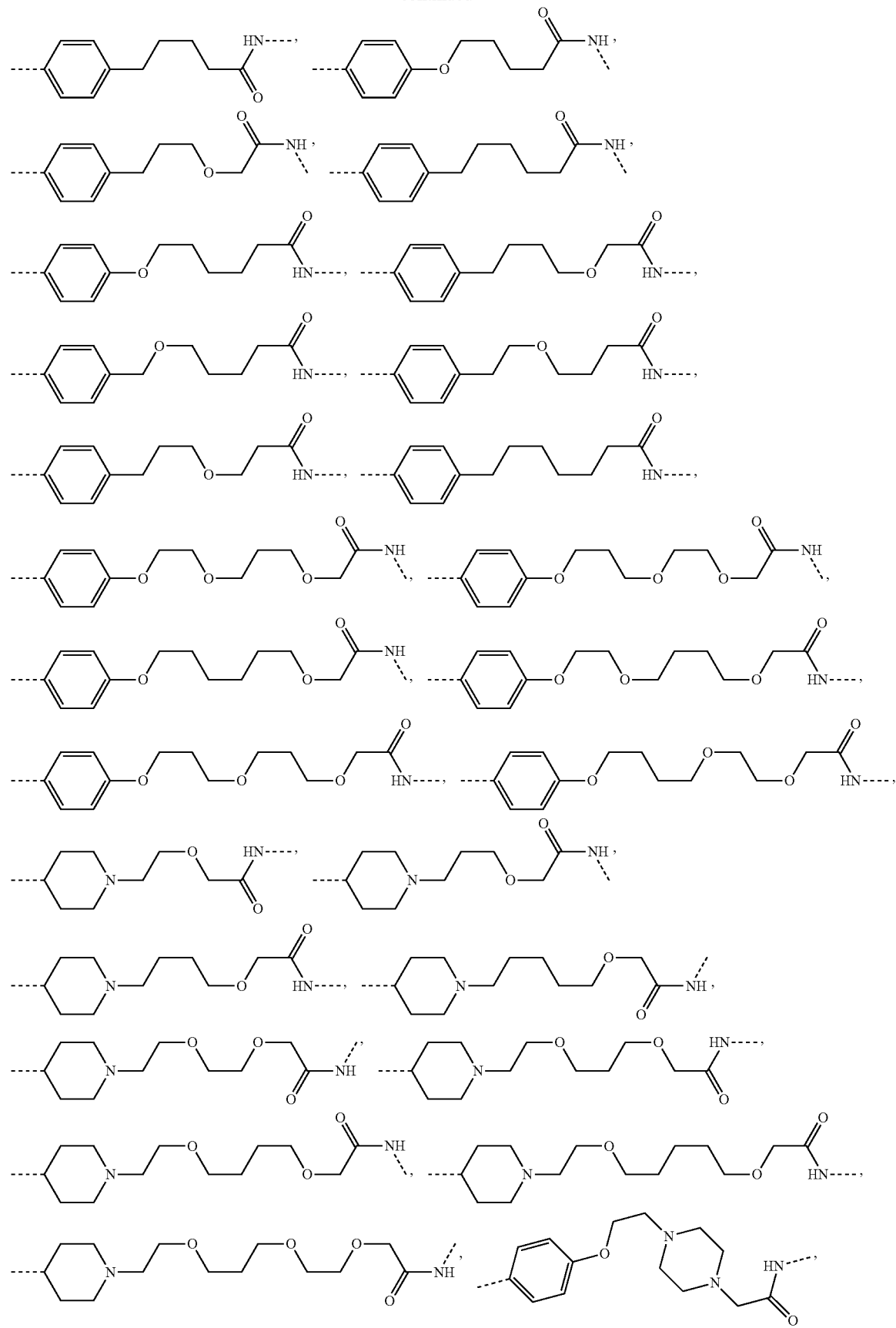

653 654
-continued
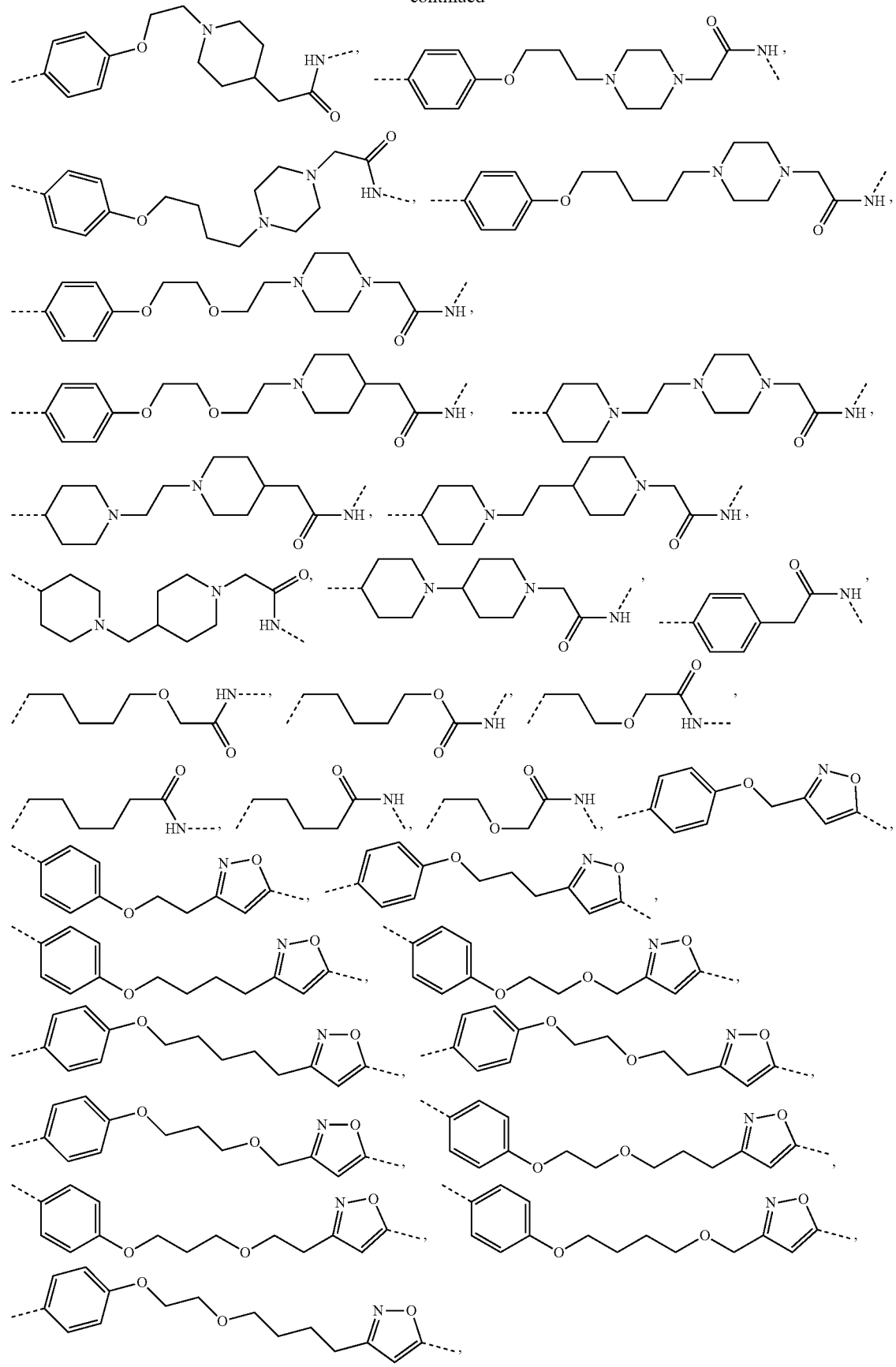

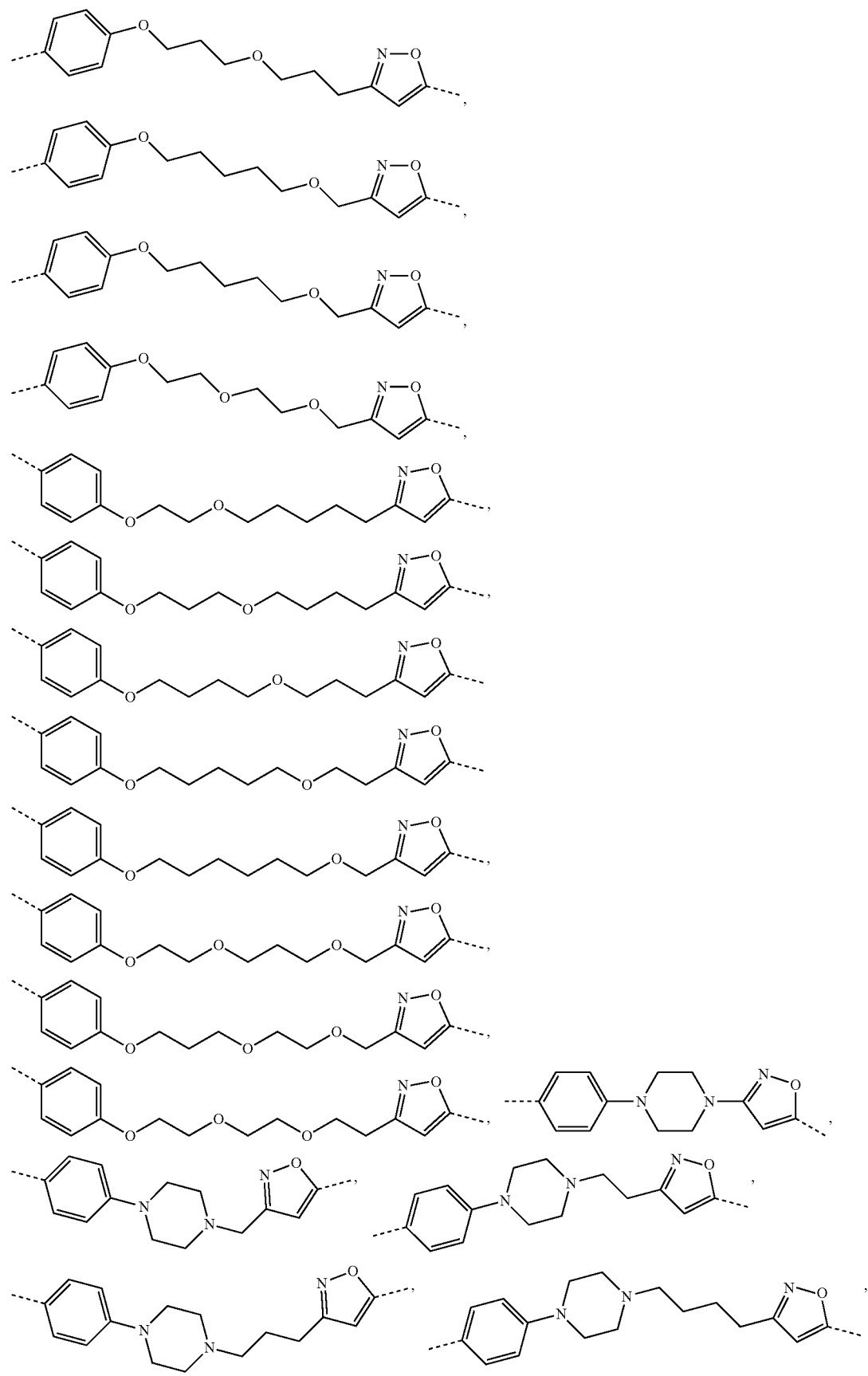

657 658
-continued
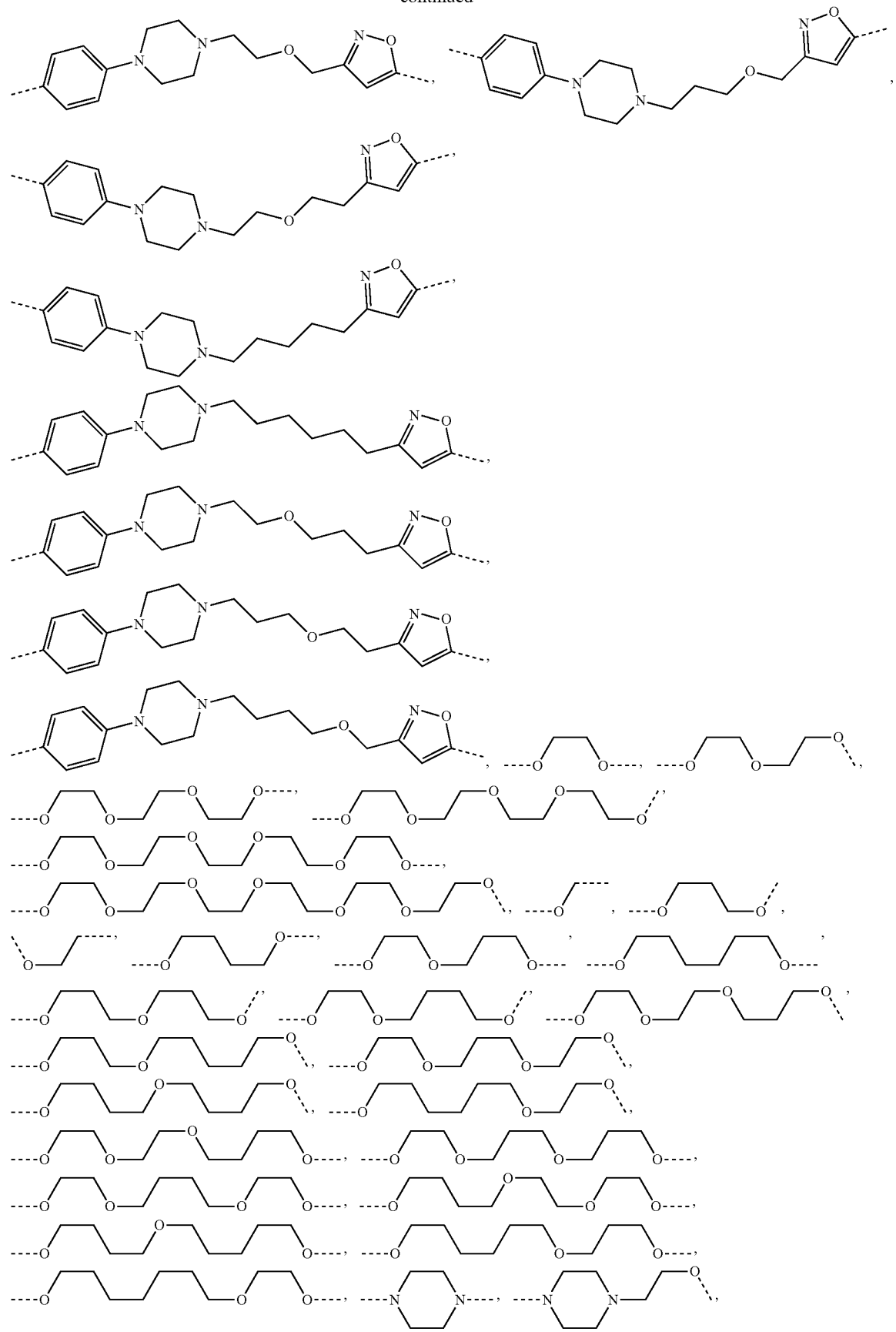

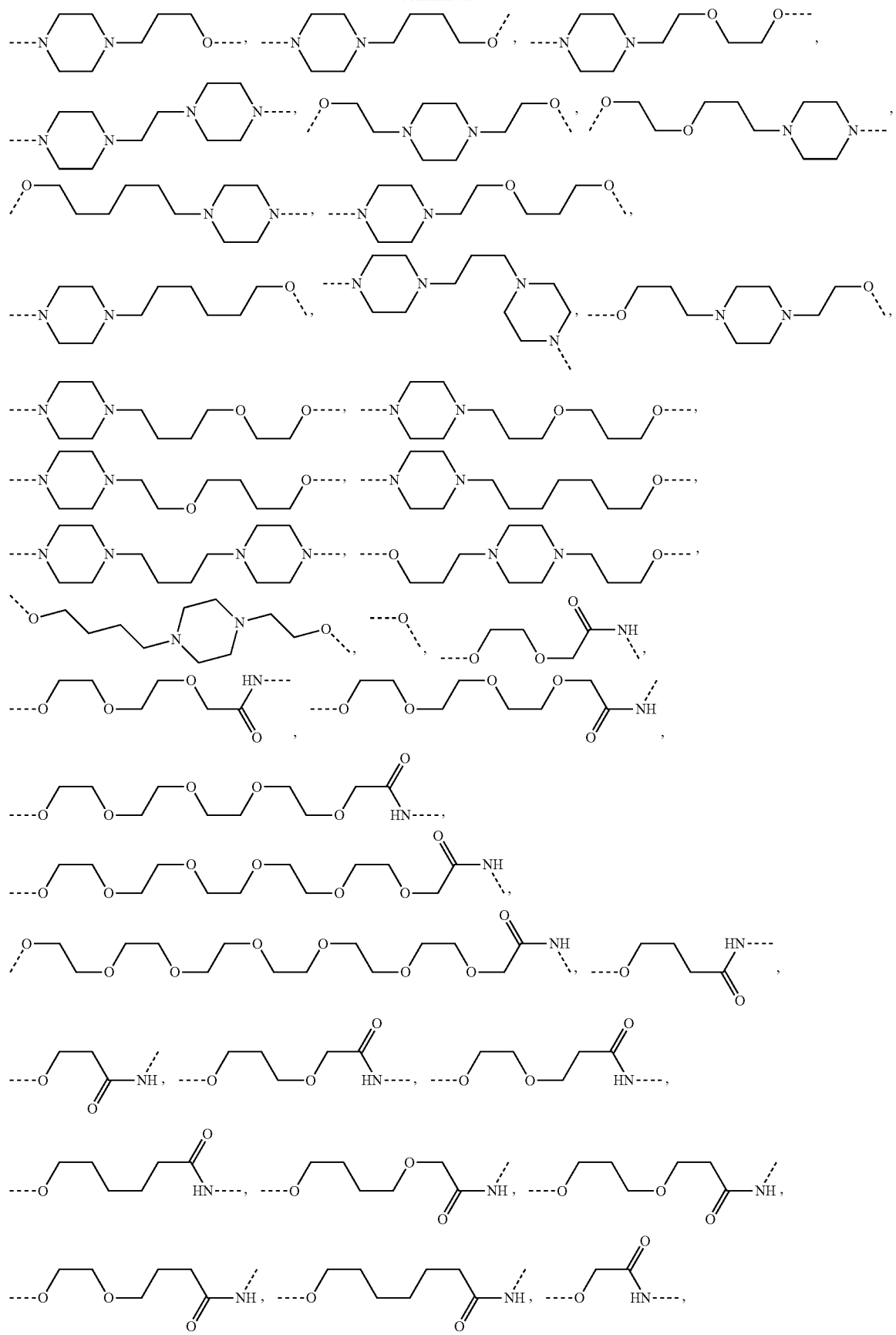

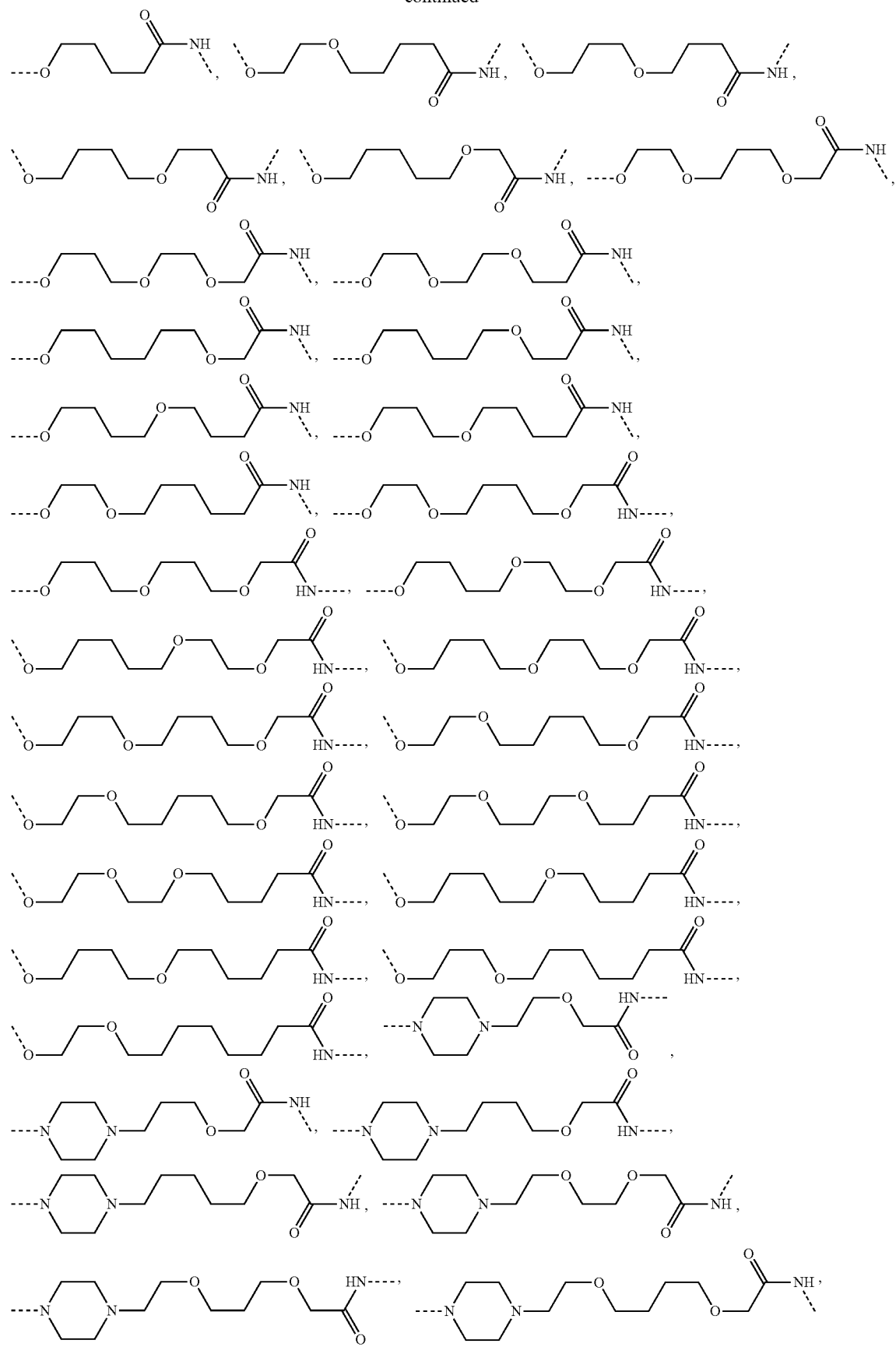

663 664
-continued
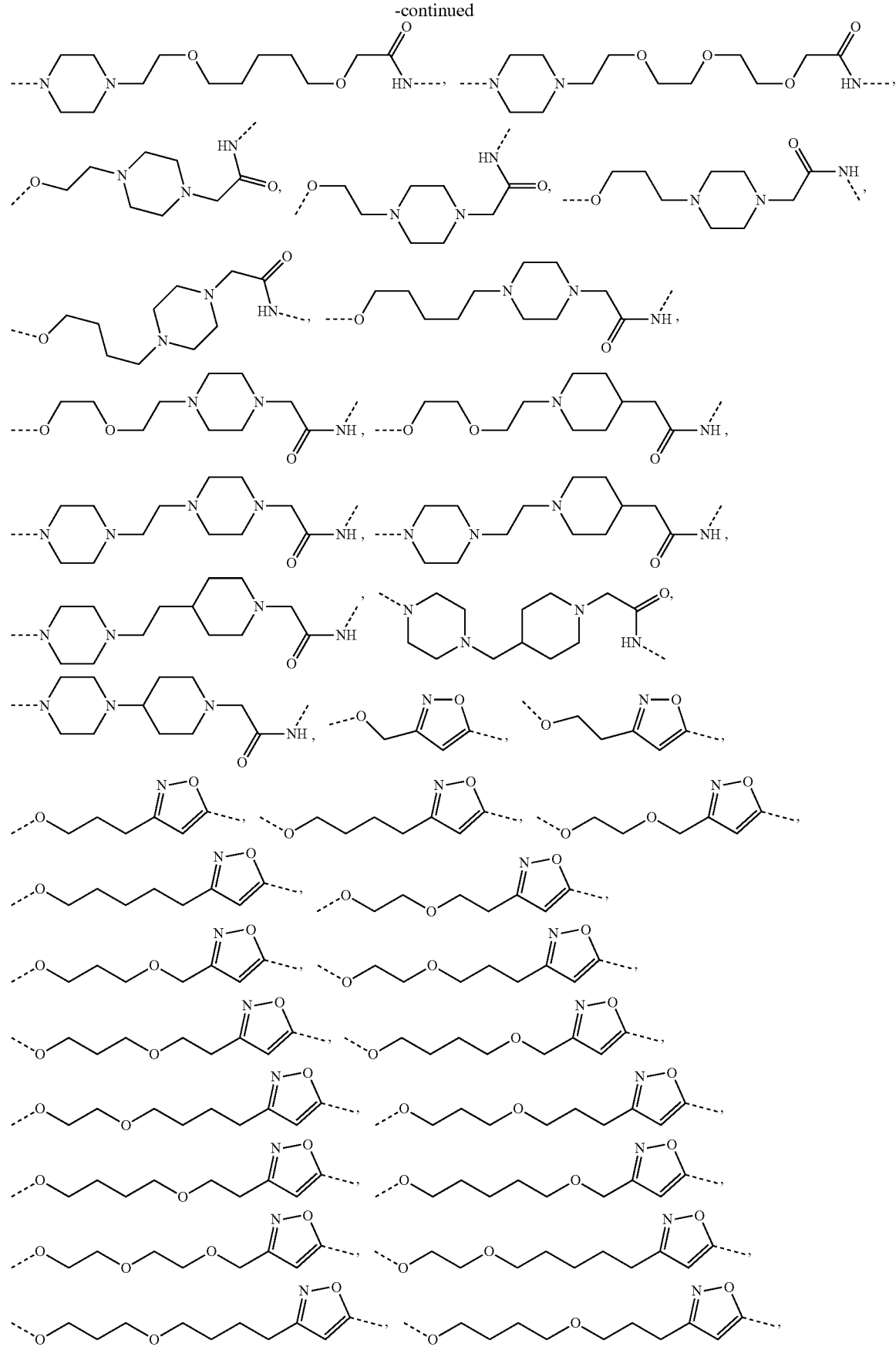

-continued

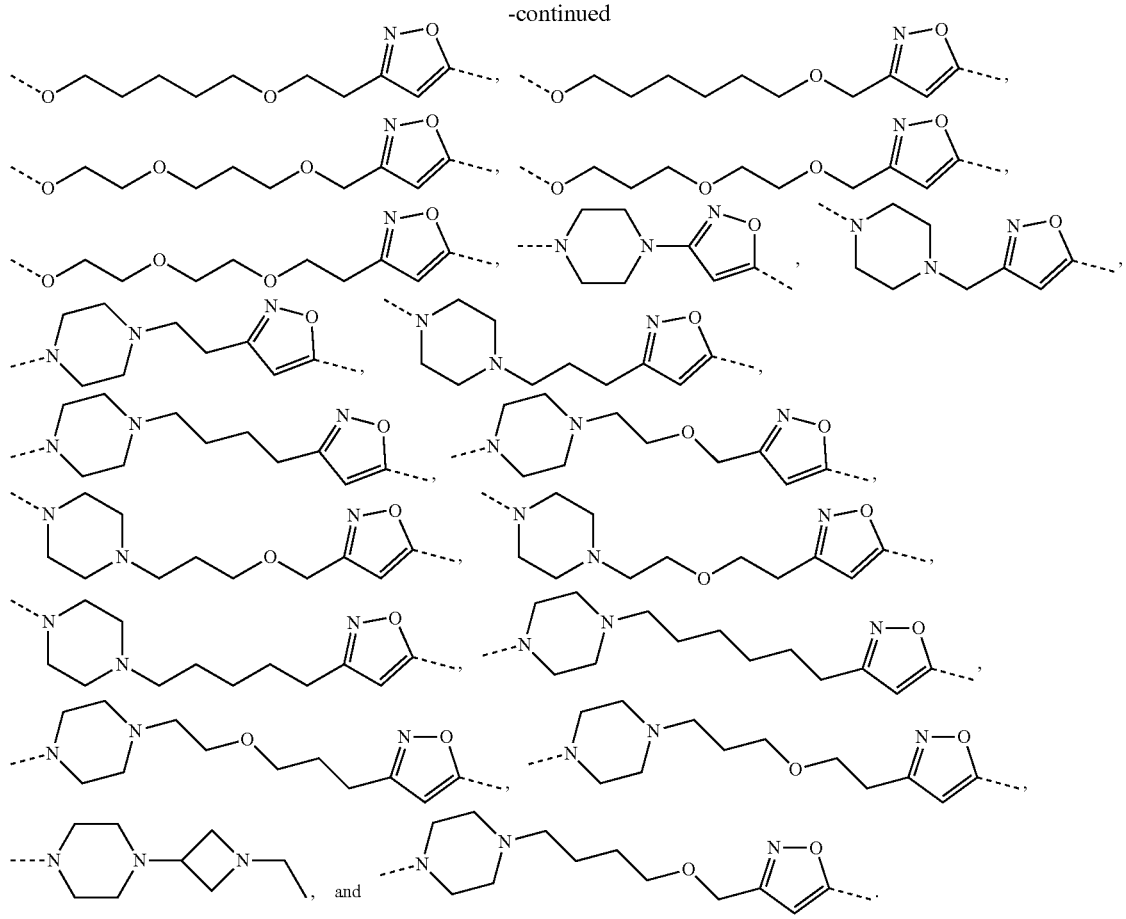

19. The compound of claim 1, wherein the linker (L) is a polyethylenoxy group optionally substituted with aryl or phenyl comprising from 1 to 10 ethylene glycol units.

20. The compound of claim 1, wherein the linker (L) has the following chemical structure:

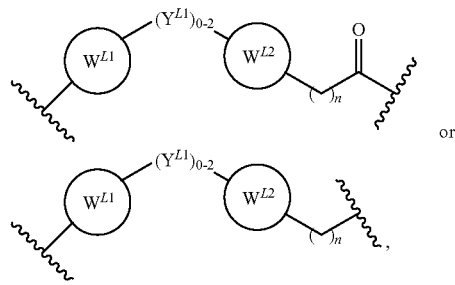

wherein:
at each occurrence $W^{L1}$ and $W^{L2}$ are each independently absent, a 4-8 membered ring with 0-4 heteroatoms, optionally substituted with $R^Q$, each $R^Q$ is independently a H, halogen, OH, CN, $CF_3$, $C_1$-$C_6$ alkyl, $C_1$-$C_6$ alkoxy, or 2 $R^Q$ groups taken together with the atom they are attached to form a 4-8 membered ring system containing 0-4 heteroatoms;
at each occurrence $Y^{L1}$ is each independently a bond, $C_1$-$C_6$ alkyl and optionally one or more C atoms are replaced with O; or $C_1$-$C_6$ alkoxy;
at each occurrence n is independently 0-10; and
at each occurrence a dashed line indicates the attachment point to the PTM or ULM moieties.

21. The compound of claim 1, wherein the linker (L) has the structure:

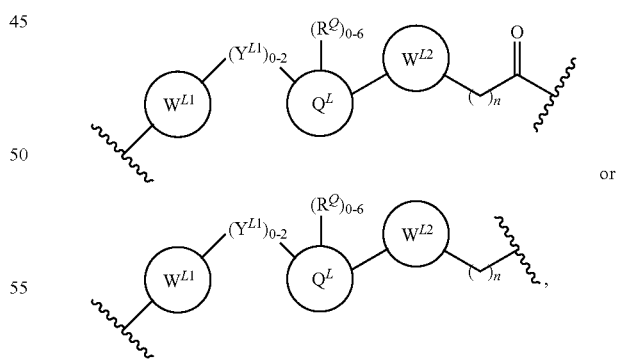

wherein:
at each occurrence $W^{L1}$ and $W^{L2}$ are each independently absent, aryl, heteroaryl, cyclic, heterocyclic, $C_{1-6}$ alkyl and optionally one or more C atoms are replaced with O, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halogen, OH, CN, $CF_3$, hydroxyl, nitro, C=CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

at each occurrence $Y^{L1}$ is independently a bond, $NR^{YL1}$, O, S, $NR^{YL2}$, $CR^{YLI}R^{YL2}$, C=O, C=S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

at each occurrence $Q^L$ is independently a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halogen, $C_{1-6}$ alkoxyl), or 2 $R^Q$ groups taken together with the atom they are attached to, form a 3-8 membered ring system containing 0-2 heteroatoms);

at each occurrence $R^{YL1}$, $R^{YL2}$ are each independently H, OH, optionally substituted $C_{1-6}$ alkyl, optionally substituted $C_{1-6}$ alkoxyl, or $R^1$ and $R^2$ together with the atom they are attached to form a 3-8 membered ring system containing 0-2 heteroatoms;

at each occurrence n is independently 0-10; and at each occurrence a dashed line indicates the attachment point to the PTM or ULM moieties.

22. The compound of claim 1, wherein the linker (L) is selected from the group consisting of:

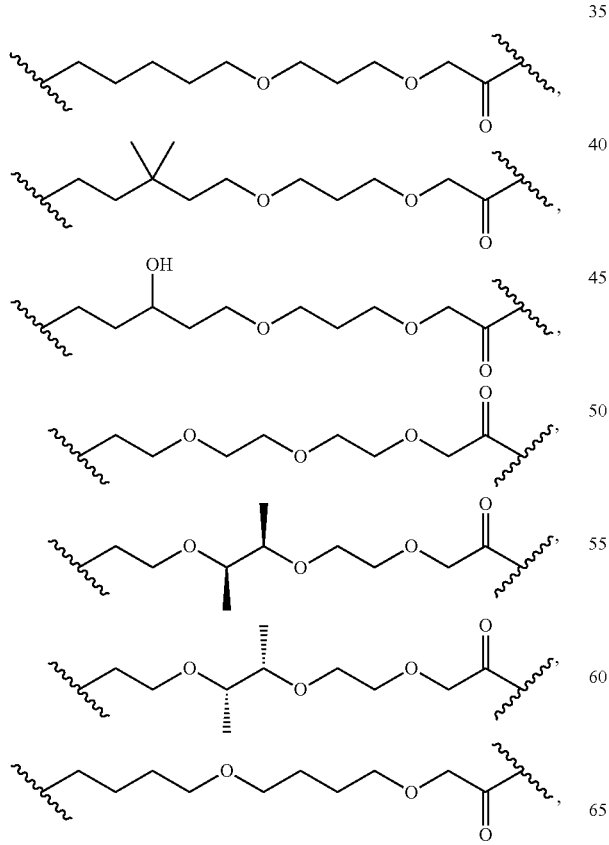

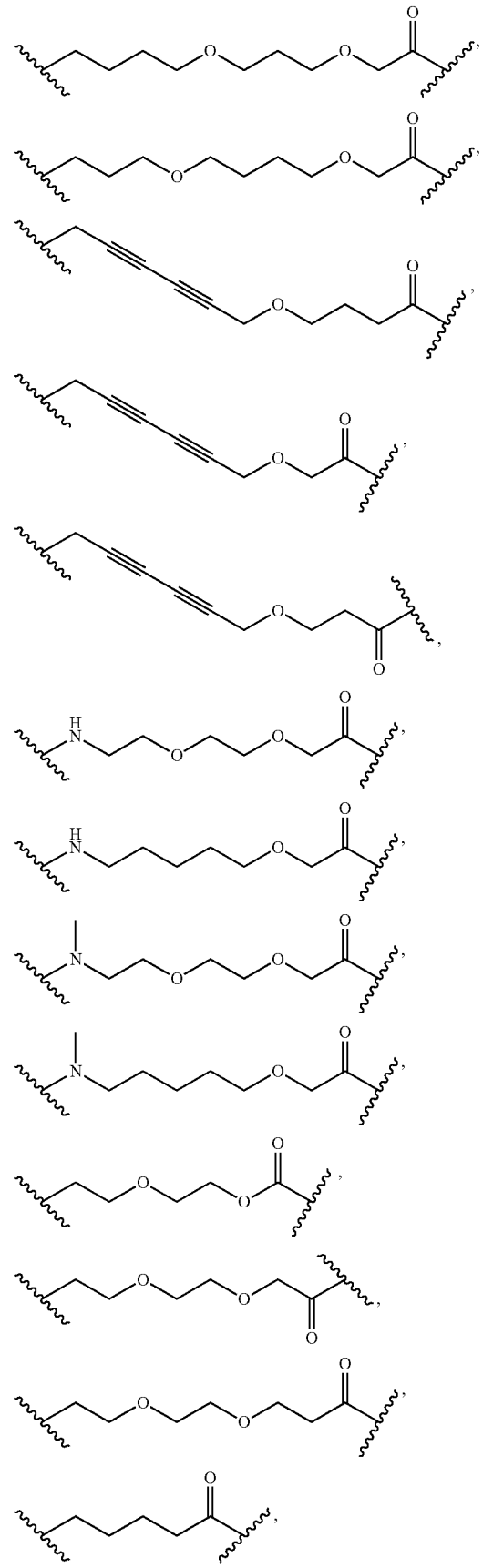

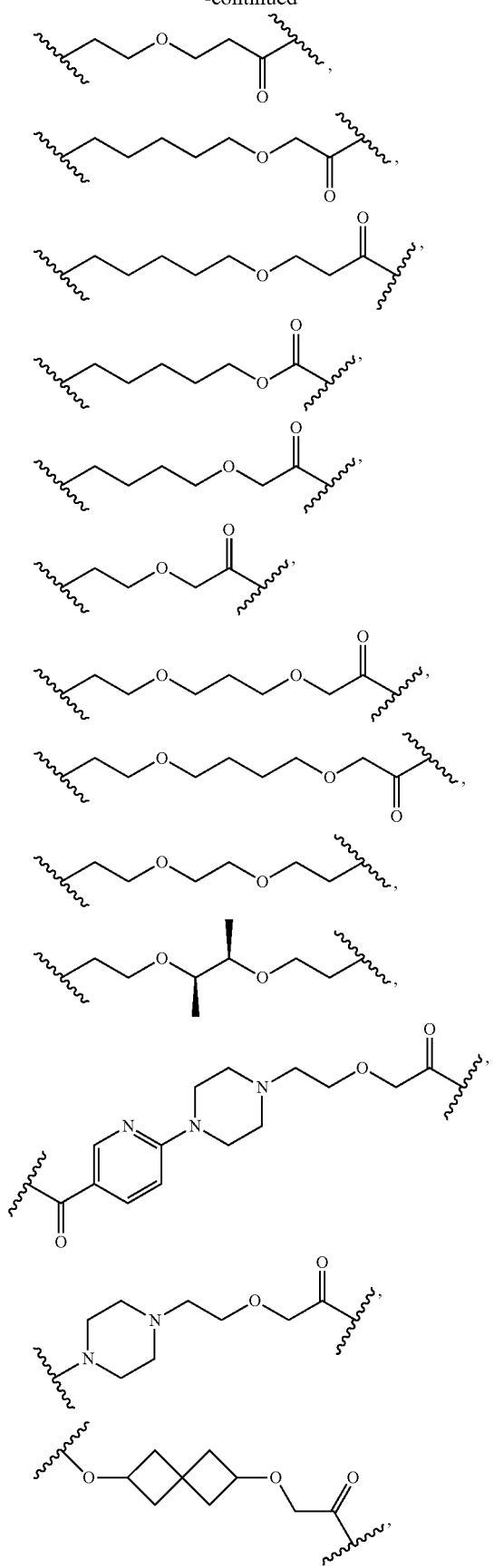
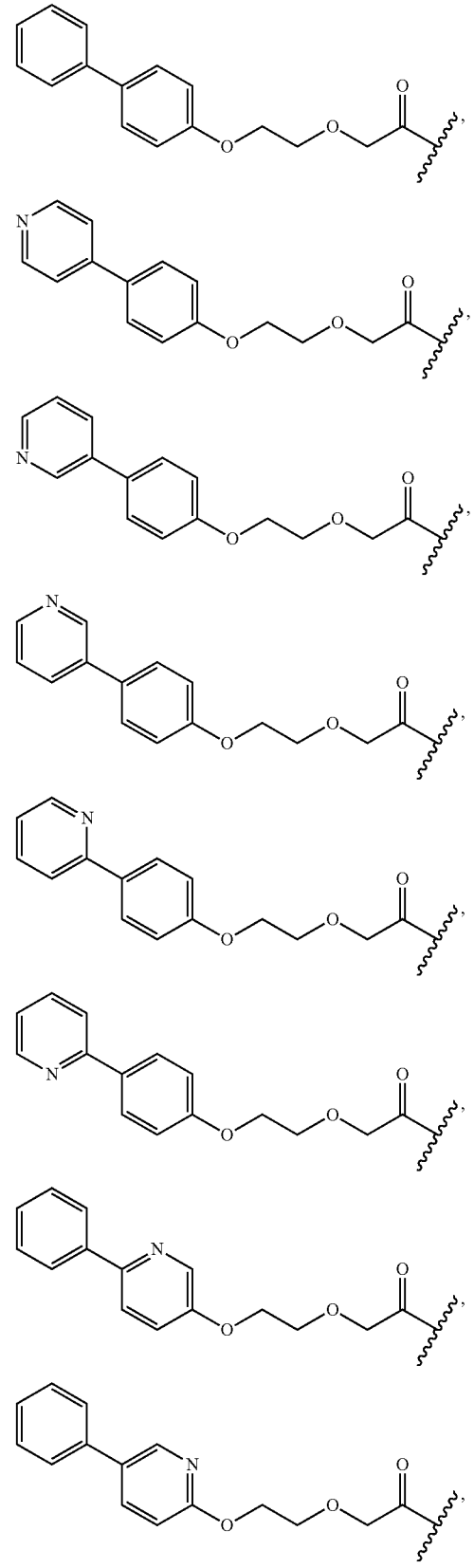

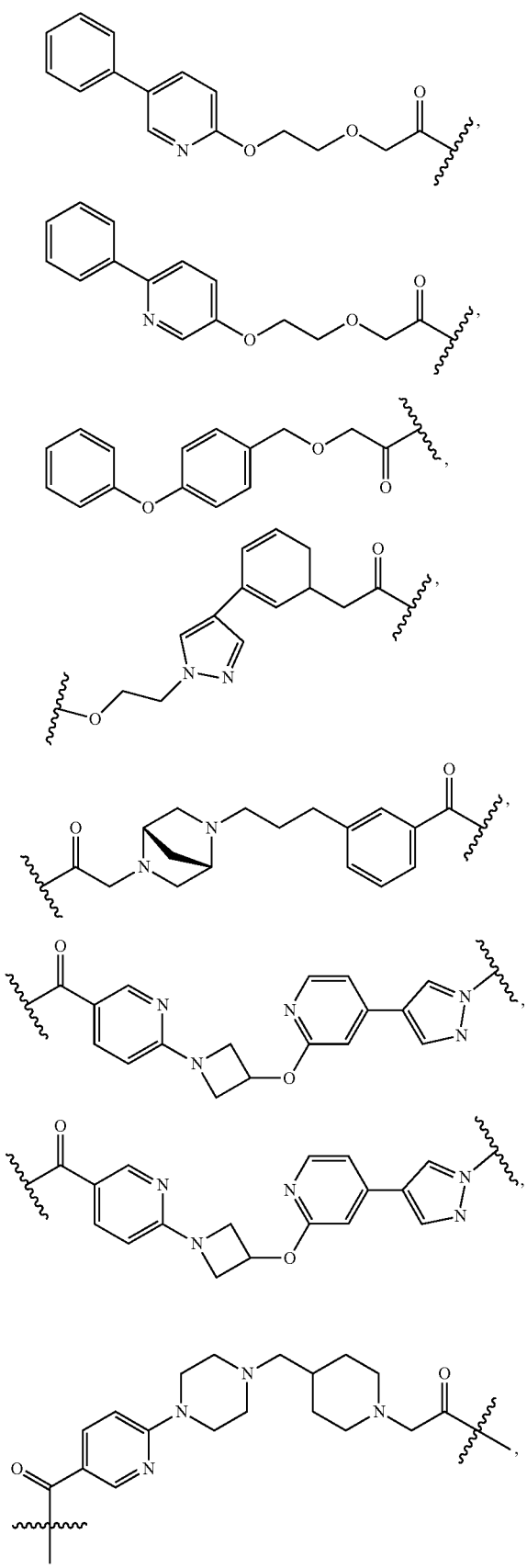
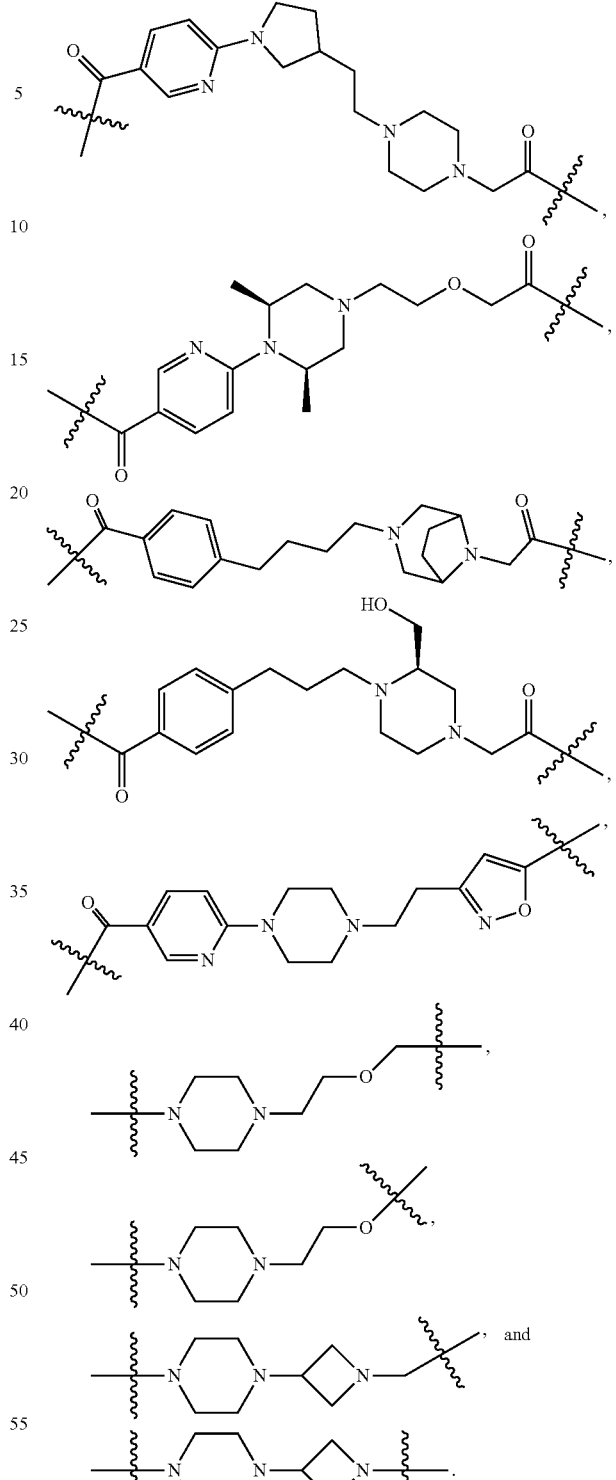
23. The compound claim 1, wherein the linker is selected from:
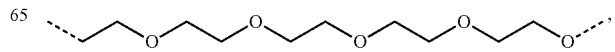

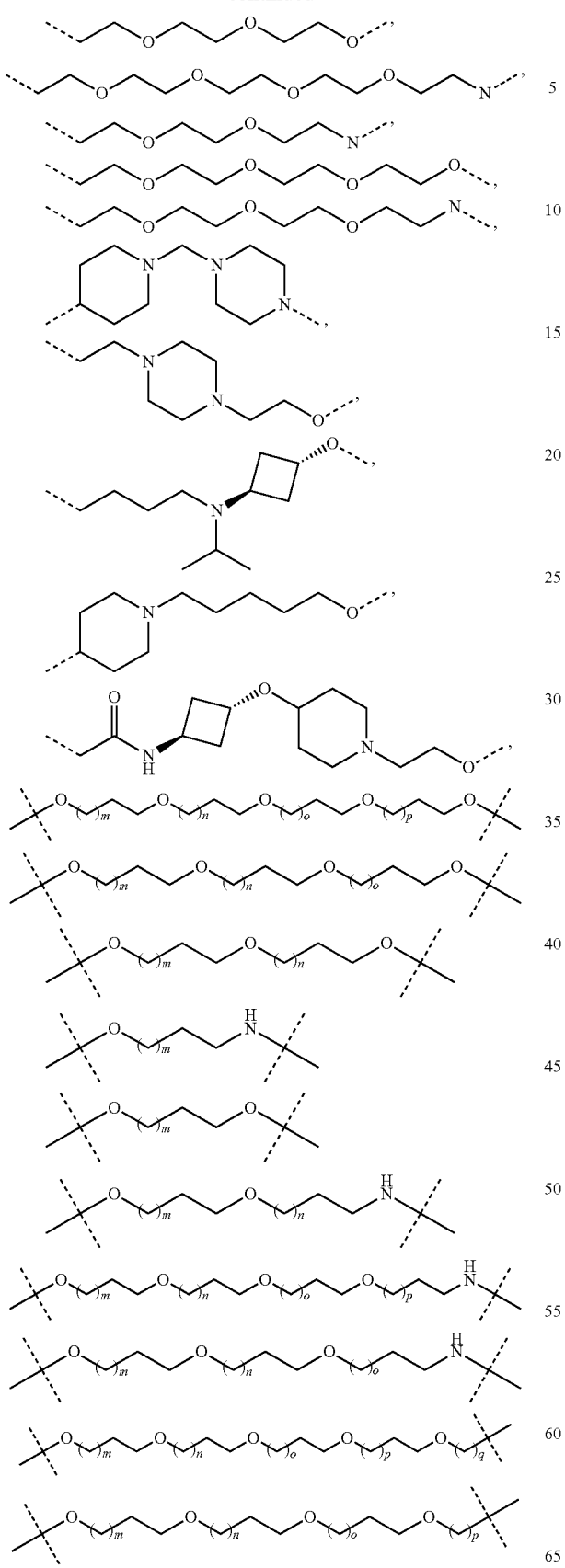

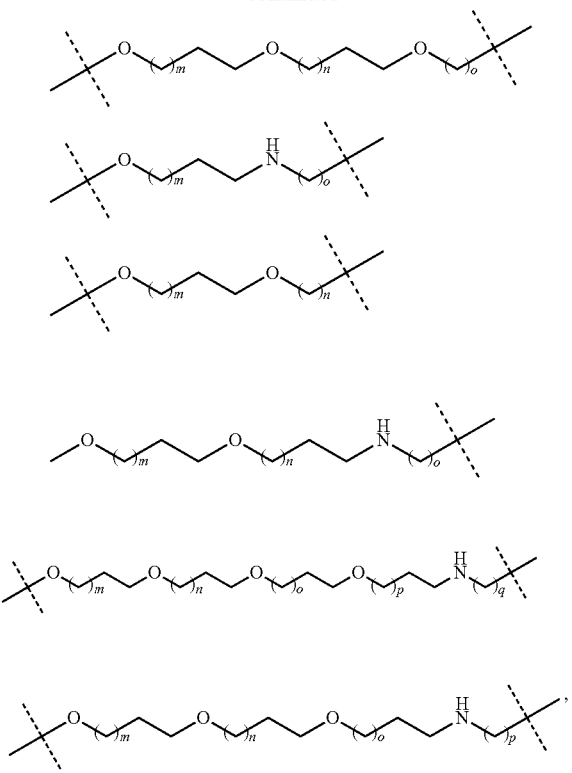

wherein at each occurrence m, n, o, p, and q are independently selected from 0, 1, 2, 3, 4, 5, 6, 7, 8, 9, or 10.

24. The compound of claim 1, wherein:
the PTM is

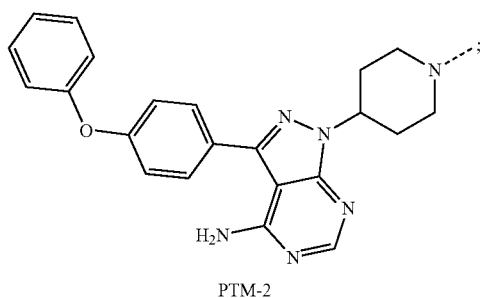

PTM-2 the linker (L) is selected from the group consisting of L-1, L-2, L-3, L-4, L-5, L-6, L-7, L-8, L-9, L-10, L-11, L-12, L-13, L-14, L-15, L-16, L-17, L-18, L-19, L-20, L-21, and L-22; and the ULM is selected from the group consisting of ULM-1, ULM-2, ULM-3, ULM-4, and ULM-5; or combinations thereof.

25. The compound of claim 1, wherein the linker (L) is selected from the group consisting of L-1, L-2, L-3, L-4, L-5, L-6, L-7, L-8, L-9, L-10, L-11, L-12, L-13, L-14, L-15, L-16, L-17, L-18, L-19, L-20, L-21, and L-22.

26. The compound of claim 1, wherein the ULM is selected from the group consisting of ULM-1, ULM-2, ULM-3, ULM-4, and ULM-5.

27. A compound selected from the group consisting of:
Compound 100
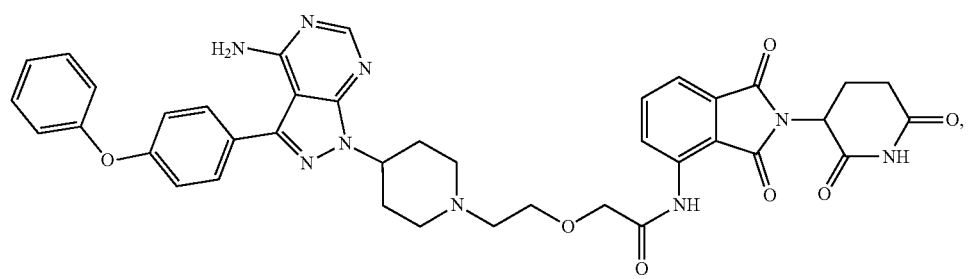
Compound 101
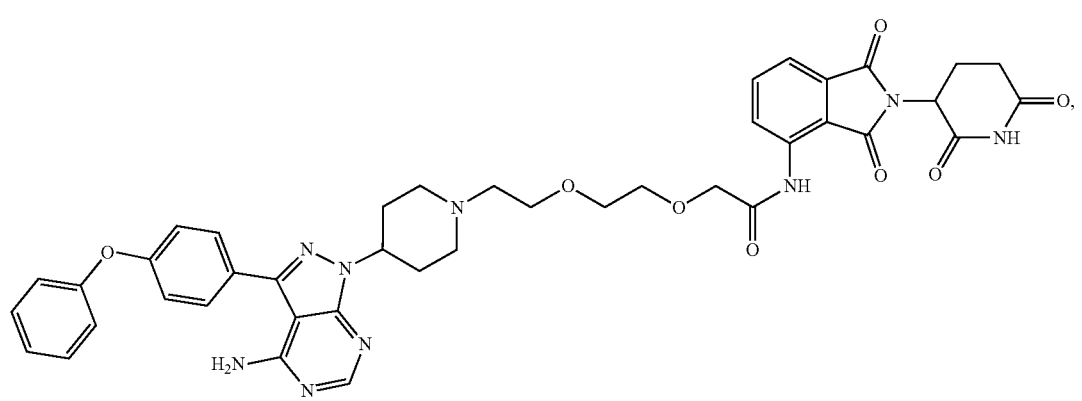
Compound 102
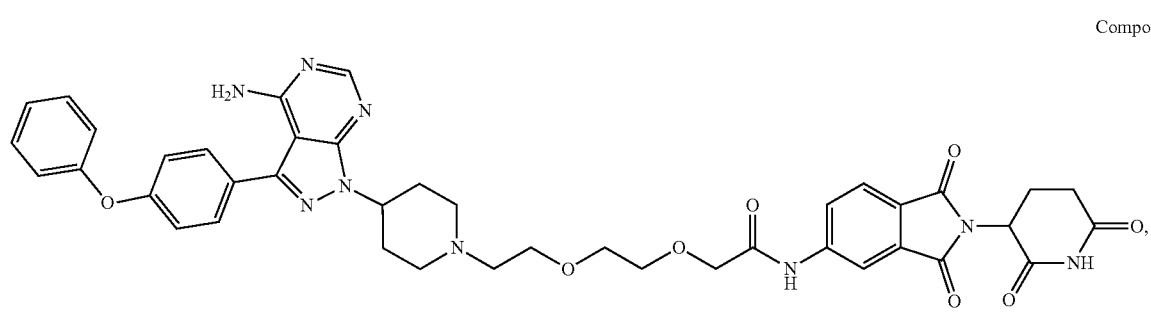
Compound 103
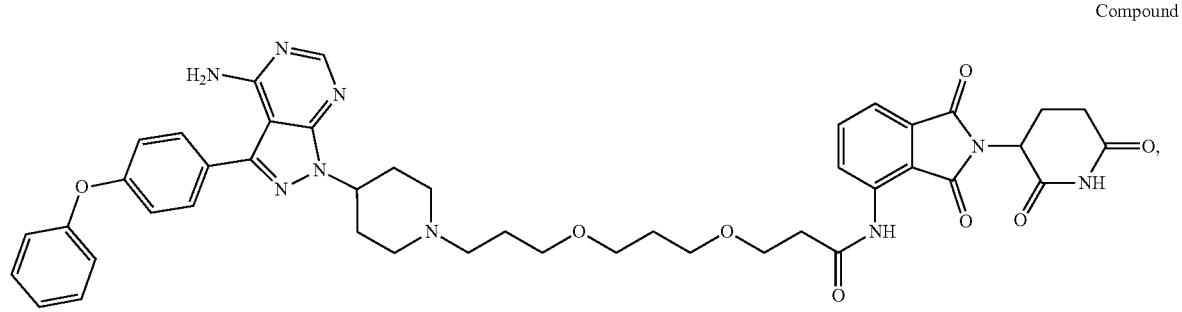

Compound 104
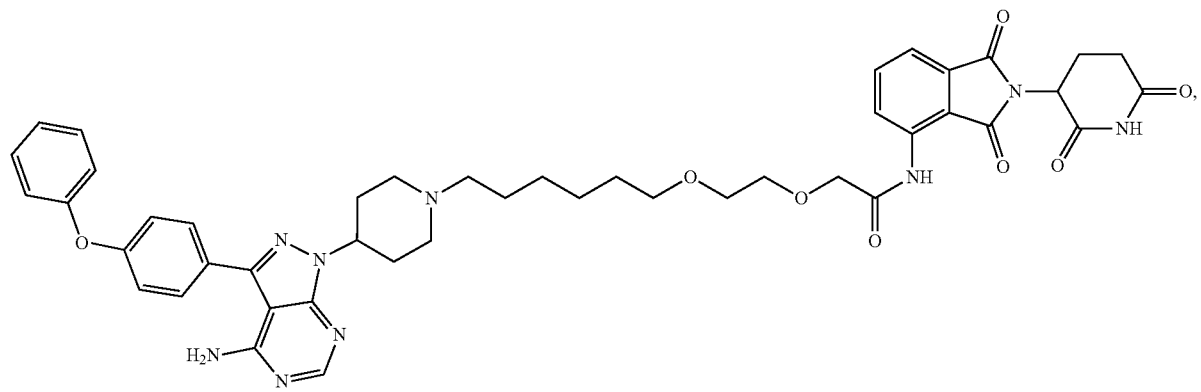
Compound 105
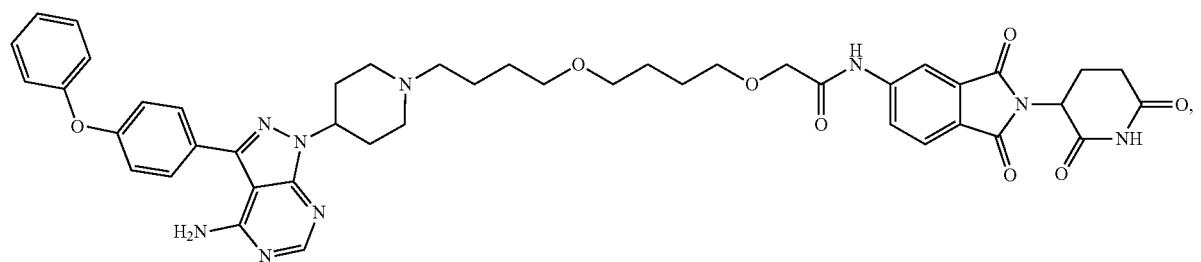
Compound 106
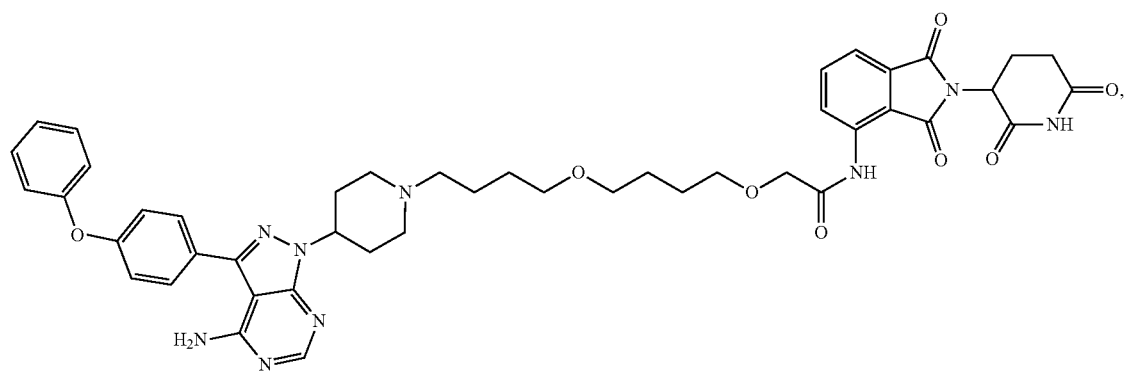
Compound 107
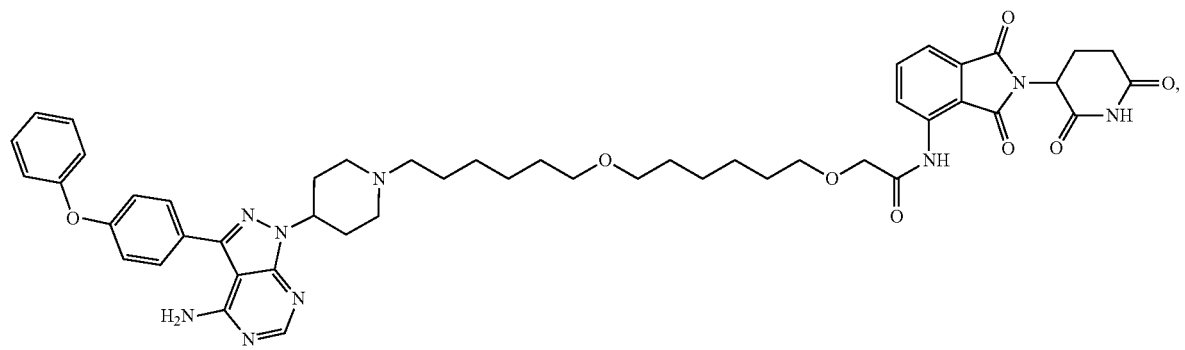

Compound 108
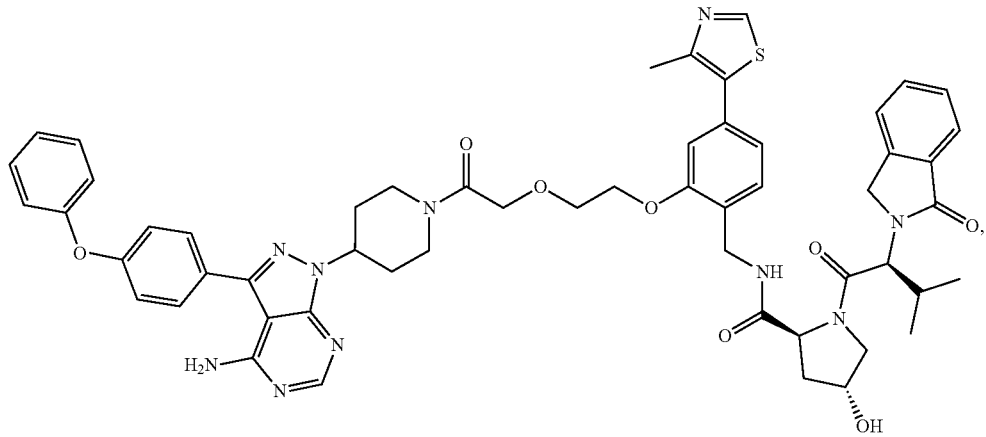
Compound 109
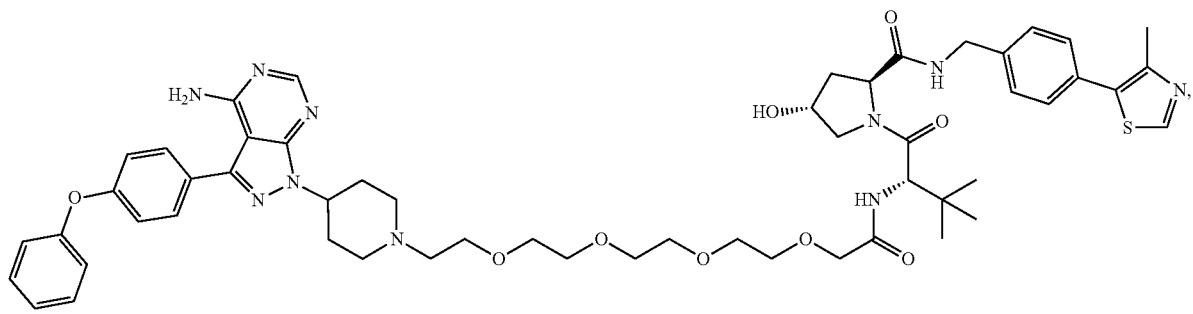
Compound 110
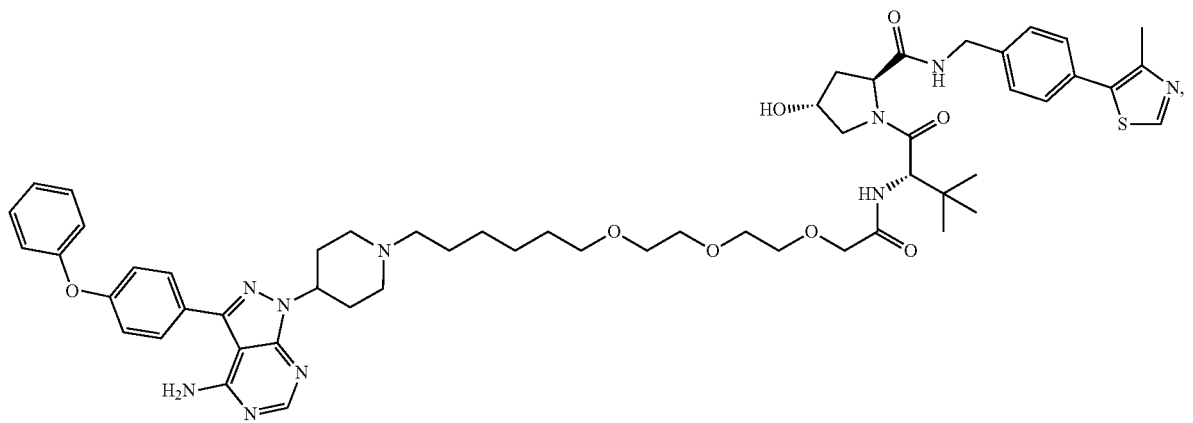
Compound 111
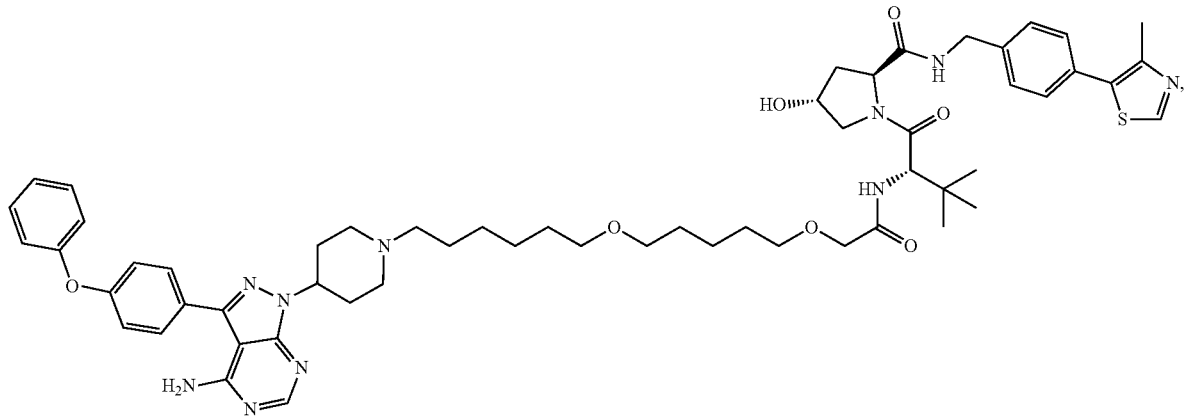

-continued
Compound 112
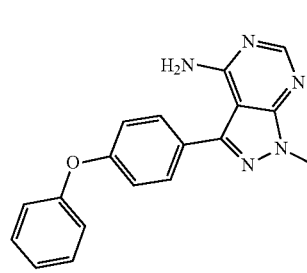 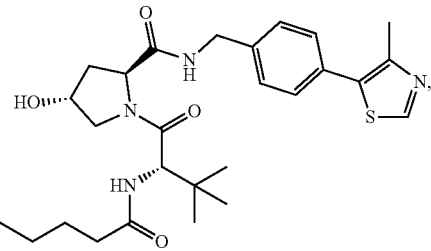
Compound 113
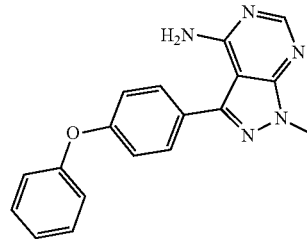 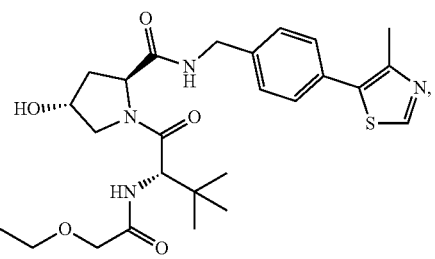
Compound 114
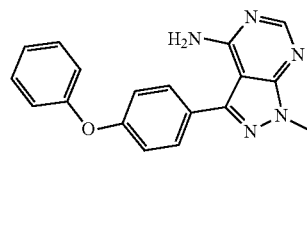 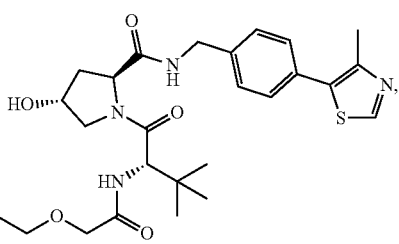
Compound 115
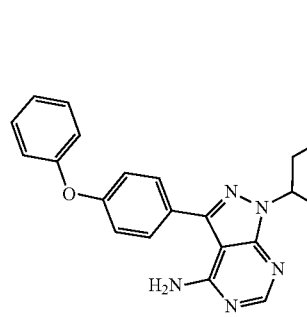 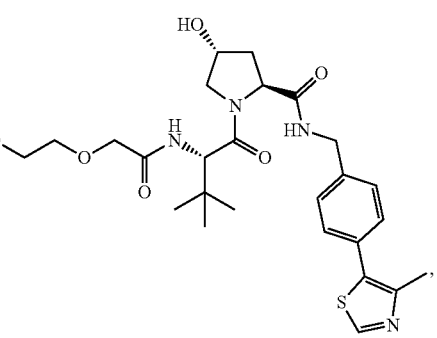
Compound 116
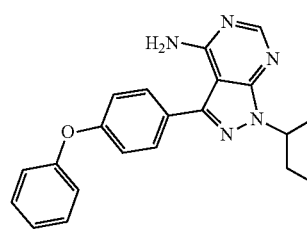 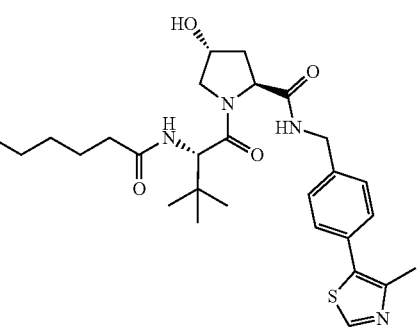

Compound 117
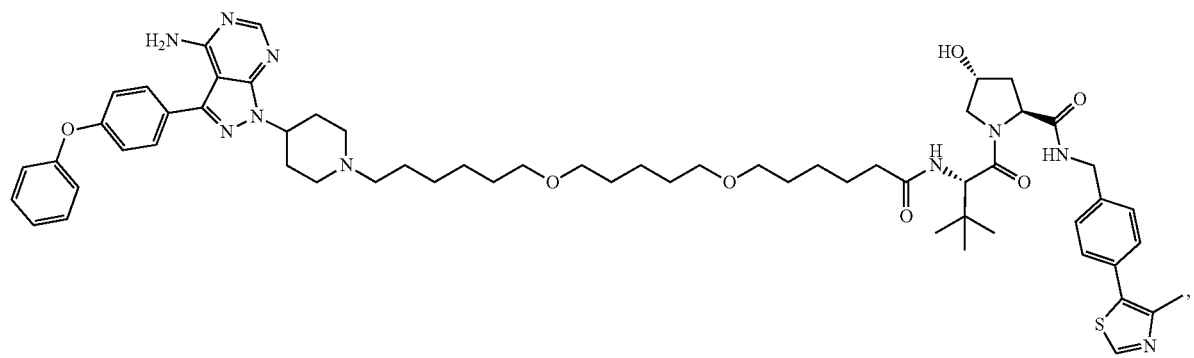
Compound 118
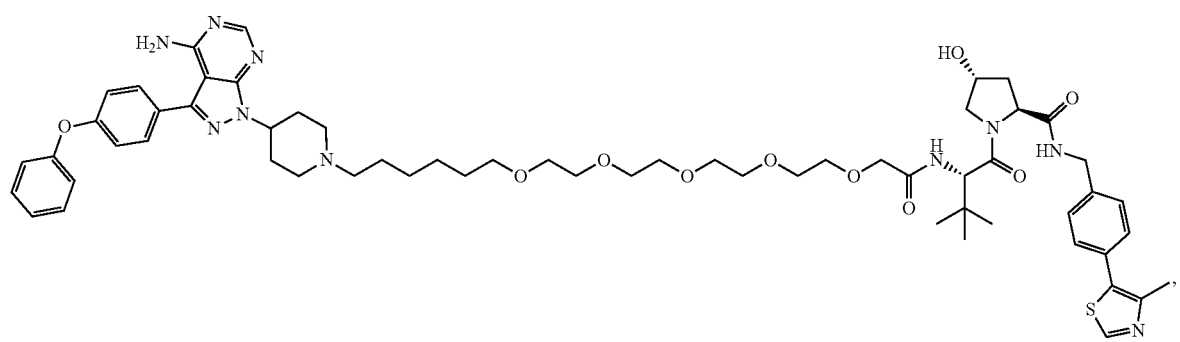
Compound 119
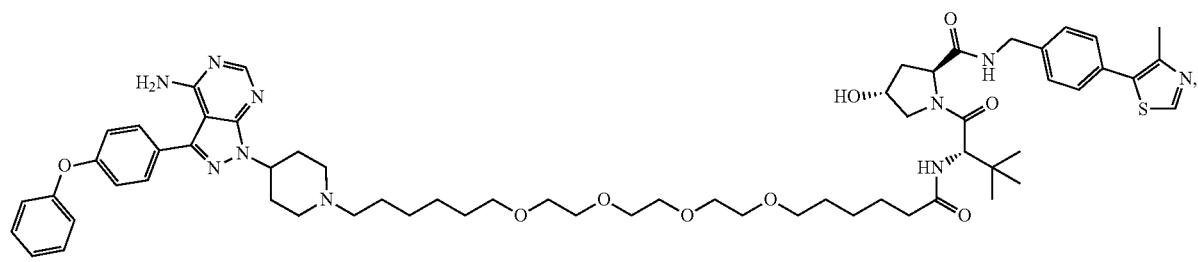
Compound 120
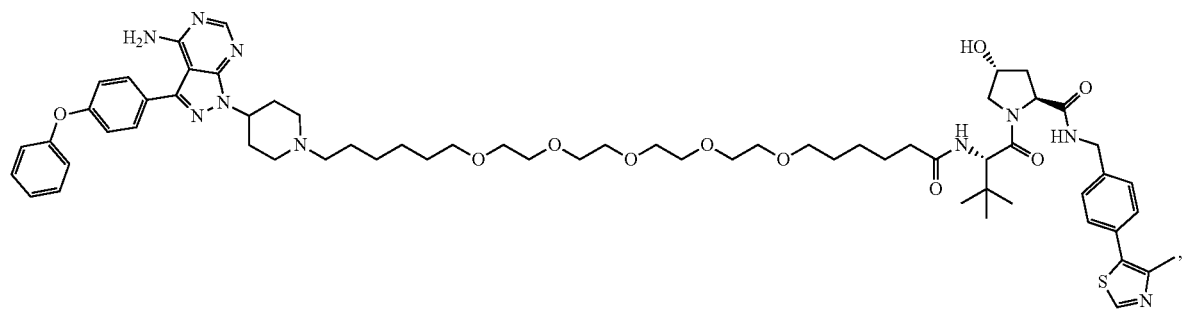

Compound 127
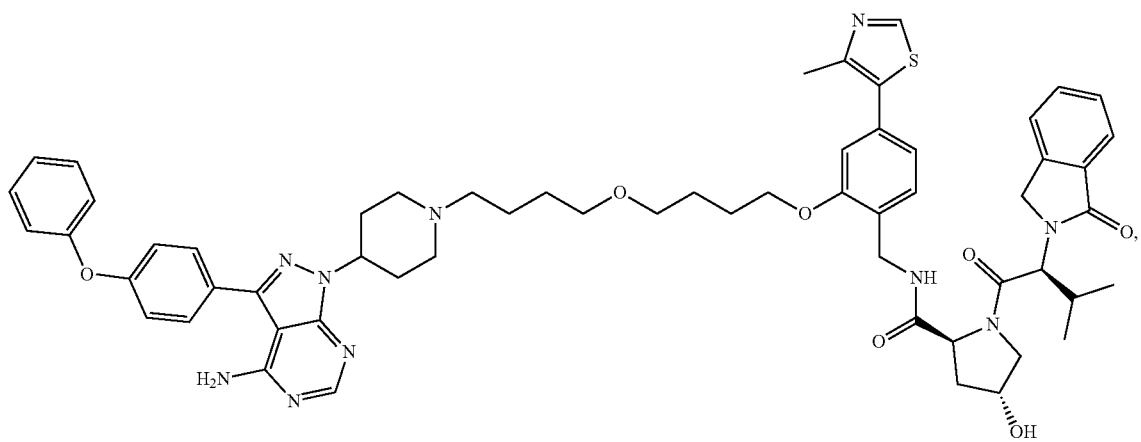
Compound 128
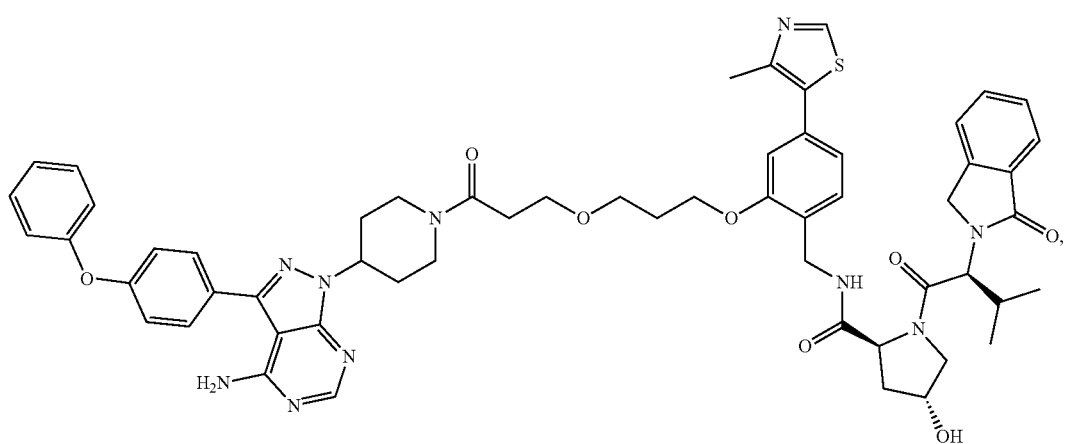
Compound 129
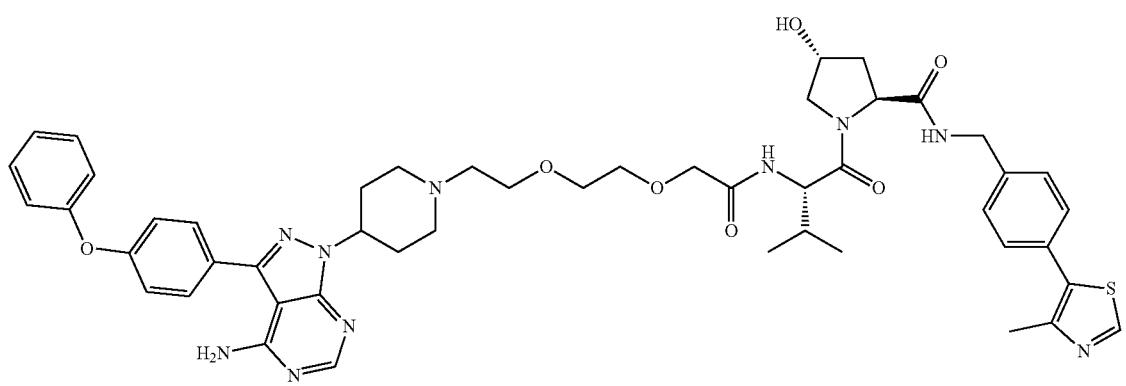
Compound 130
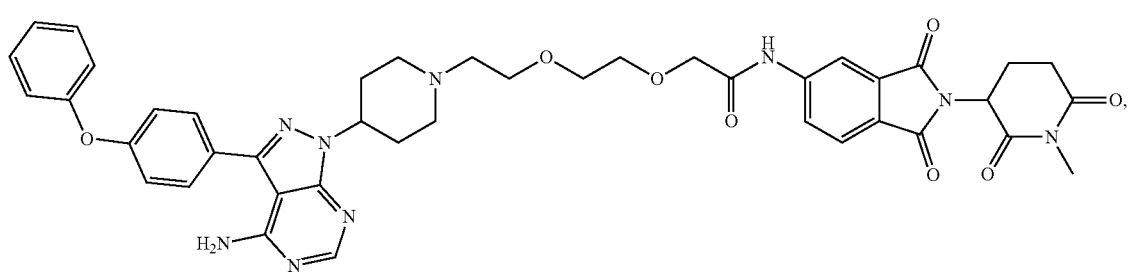

-continued

Compound 131

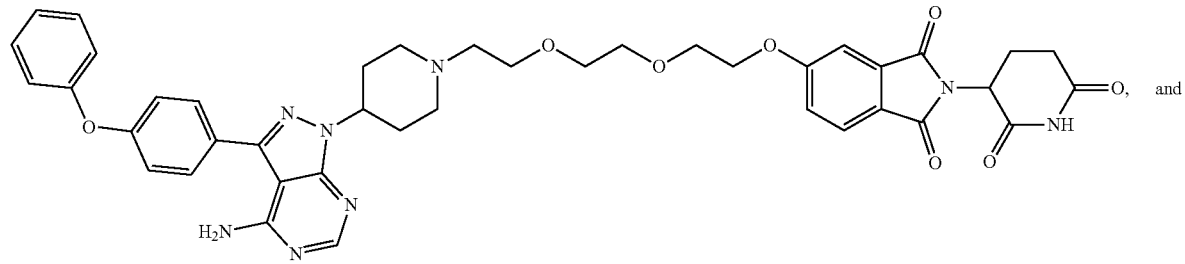

, and

Compound 135

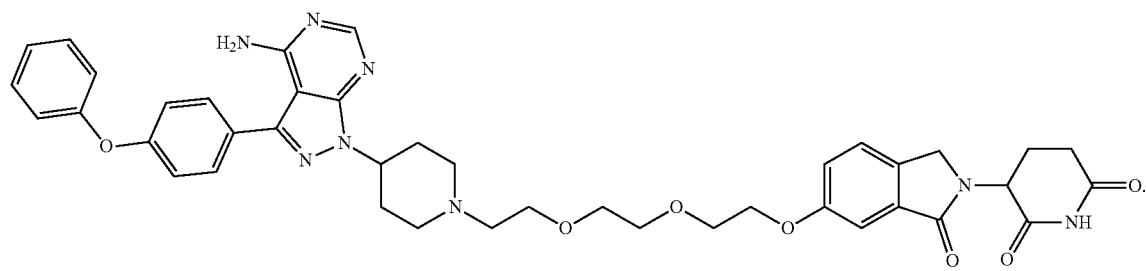

.

28. A composition comprising a therapeutically effective amount of a compound of claim 1, and a pharmaceutically acceptable carrier.

29. The composition of claim 28, wherein the composition further comprises at least one of additional bioactive agent.

30. The composition of claim 29, wherein the additional bioactive agent is an anti-cancer agent.

31. A composition comprising a pharmaceutically acceptable carrier and a therapeutically effective amount of at least one compound of claim 1 for treating a disease or disorder in a subject, the method comprising administering the composition to a subject in need thereof, wherein the compound is effective in treating or ameliorating at least one symptom of the disease or disorder.

32. The composition of claim 31, wherein the disease or disorder is associated with at least one of accumulation, aggregation, overactivation, or combinations thereof, of BTKs.

33. The composition of claim 31, wherein the disease or disorder is cancer that is associated with the accumulation, aggregation, or overactivation of BTKs.

34. The composition of claim 32, wherein the disease or disorder is leukemia, pancreatic cancer, colon cancer, colorectal cancer, lung cancer, non-small cell lung cancer, biliary tract malignancies, endometrial cancer, cervical cancer, bladder cancer, liver cancer, myeloid leukemia, and breast cancer.

35. The composition of claim 31, wherein the disease or disorder is chronic lymphocytic leukemia.

* * * * *

SEQUENCE LISTING

```
<160> NUMBER OF SEQ ID NOS: 8

<210> SEQ ID NO 1
<211> LENGTH: 57
<212> TYPE: PRT
<213> ORGANISM: Homo sapiens

<400> SEQUENCE: 1

His Glu Lys Leu Val Gln Leu Tyr Gly Val Cys Thr Lys Gln Arg Pro
1               5                   10                  15

Ile Phe Ile Ile Thr Glu Tyr Met Ala Asn Gly Cys Leu Leu Asn Tyr
            20                  25                  30

Leu Arg Glu Met Arg His Arg Phe Gln Thr Gln Gln Leu Leu Glu Met
        35                  40                  45

Cys Lys Asp Val Cys Glu Ala Met Glu
    50                  55

<210> SEQ ID NO 2
<211> LENGTH: 57
<212> TYPE: PRT
<213> ORGANISM: Homo sapiens

<400> SEQUENCE: 2

His Glu Arg Leu Val Arg Leu Tyr Ala Val Val Thr Lys Glu Pro Ile
1               5                   10                  15

Tyr Ile Val Thr Glu Tyr Met Ala Arg Gly Cys Leu Leu Asp Phe Leu
            20                  25                  30

Lys Thr Asp Glu Gly Ser Arg Leu Ser Leu Pro Arg Leu Ile Asp Met
        35                  40                  45

Ser Ala Gln Ile Ala Glu Gly Met Ala
    50                  55

<210> SEQ ID NO 3
<211> LENGTH: 57
<212> TYPE: PRT
<213> ORGANISM: Homo sapiens

<400> SEQUENCE: 3

His Pro Lys Leu Val Gln Leu Tyr Gly Val Cys Thr Gln Gln Lys Pro
1               5                   10                  15

Ile Tyr Ile Val Thr Glu Phe Met Glu Arg Gly Cys Leu Leu Asn Phe
            20                  25                  30

Leu Arg Gln Arg Gln Gly His Phe Ser Arg Asp Val Leu Leu Ser Met
        35                  40                  45

Cys Gln Asp Val Cys Glu Gly Met Glu
    50                  55

<210> SEQ ID NO 4
<211> LENGTH: 56
<212> TYPE: PRT
<213> ORGANISM: Homo sapiens
```

<400> SEQUENCE: 4

Ser Pro Tyr Val Ser Arg Leu Leu Gly Ile Cys Leu Thr Ser Thr Val
1               5                   10                  15

Gln Leu Val Thr Gln Leu Met Pro Tyr Gly Cys Leu Leu Asp His Val
            20                  25                  30

Arg Glu Asn Arg Gly Arg Leu Gly Ser Gln Asp Leu Leu Asn Trp Cys
        35                  40                  45

Met Gln Ile Ala Lys Gly Met Ser
    50                  55

<210> SEQ ID NO 5
<211> LENGTH: 56
<212> TYPE: PRT
<213> ORGANISM: Homo sapiens

<400> SEQUENCE: 5

His Ala His Ile Val Arg Leu Leu Gly Leu Cys Pro Gly Ser Ser Leu
1               5                   10                  15

Gln Leu Val Thr Gln Tyr Leu Pro Leu Gly Ser Leu Leu Asp His Val
            20                  25                  30

Arg Gln His Arg Gly Ala Leu Gly Pro Gln Leu Leu Leu Asn Trp Gly
        35                  40                  45

Val Gln Ile Ala Lys Gly Met Tyr
    50                  55

<210> SEQ ID NO 6
<211> LENGTH: 57
<212> TYPE: PRT
<213> ORGANISM: Homo sapiens

<400> SEQUENCE: 6

His Pro Lys Leu Val Gln Leu Tyr Gly Val Cys Leu Glu Gln Ala Pro
1               5                   10                  15

Ile Cys Leu Val Phe Glu Phe Met Glu His Gly Cys Leu Ser Asp Tyr
            20                  25                  30

Leu Arg Thr Gln Arg Gly Leu Phe Ala Ala Glu Thr Leu Leu Gly Met
        35                  40                  45

Cys Leu Asp Val Cys Glu Gly Met Ala
    50                  55

<210> SEQ ID NO 7
<211> LENGTH: 59
<212> TYPE: PRT
<213> ORGANISM: Homo sapiens

<400> SEQUENCE: 7

Ser Asp Phe Ile Val Lys Tyr Arg Gly Val Ser Tyr Gly Pro Gly Arg
1               5                   10                  15

Gln Ser Leu Arg Leu Val Met Glu Tyr Leu Pro Ser Gly Cys Leu Arg
            20                  25                  30

Asp Phe Leu Gln Arg His Arg Ala Arg Leu Asp Ala Ser Arg Leu Leu
        35                  40                  45

Leu Tyr Ser Ser Gln Ile Cys Lys Gly Met Glu
    50                  55

<210> SEQ ID NO 8
<211> LENGTH: 56
<212> TYPE: PRT

-continued

```
<213> ORGANISM: Homo sapiens

<400> SEQUENCE: 8

Cys Pro Tyr Ile Val Gln Cys Phe Gly Thr Phe Ile Thr Asn Thr Asp
1               5                   10                  15

Val Phe Ile Ala Met Glu Leu Met Gly Thr Cys Ala Glu Lys Leu Lys
            20                  25                  30

Lys Arg Met Gln Gly Pro Ile Pro Glu Arg Ile Leu Gly Lys Met Thr
        35                  40                  45

Val Ala Ile Val Lys Ala Leu Tyr
    50                  55
```